(12) United States Patent
Selby et al.

(10) Patent No.: US 10,597,388 B2
(45) Date of Patent: *Mar. 24, 2020

(54) PYRIDAZINONE HERBICIDES

(71) Applicant: FMC CORPORATION, Philadelphia, PA (US)

(72) Inventors: Thomas Paul Selby, Hockessin, DE (US); Nicholas Ryan Deprez, East Windsor, NJ (US); Thomas Martin Stevenson, Newark, DE (US); Andrew Edmund Taggi, New Hope, PA (US); John Robbins DeBergh, Middletown, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/115,958

(22) Filed: Aug. 29, 2018

(65) Prior Publication Data

US 2019/0016712 A1    Jan. 17, 2019

Related U.S. Application Data

(62) Division of application No. 15/307,831, filed as application No. PCT/US2015/027776 on Apr. 27, 2015, now Pat. No. 10,118,917.

(Continued)

(51) Int. Cl.
| | |
|---|---|
| *C07D 409/04* | (2006.01) |
| *C07D 405/04* | (2006.01) |
| *A01N 43/70* | (2006.01) |
| *A01N 43/90* | (2006.01) |
| *A01N 57/16* | (2006.01) |
| *A01N 47/06* | (2006.01) |
| *A01N 47/18* | (2006.01) |

(Continued)

(52) U.S. Cl.
CPC .......... *C07D 409/04* (2013.01); *A01N 41/10* (2013.01); *A01N 43/58* (2013.01); *A01N 43/70* (2013.01); *A01N 43/90* (2013.01); *A01N 47/06* (2013.01); *A01N 47/18* (2013.01); *A01N 47/36* (2013.01); *A01N 57/16* (2013.01); *A01N 57/24* (2013.01); *C07D 237/14* (2013.01); *C07D 237/16* (2013.01); *C07D 237/18* (2013.01); *C07D 307/81* (2013.01); *C07D 333/60* (2013.01); *C07D 403/04* (2013.01); *C07D 405/04* (2013.01)

(58) Field of Classification Search
CPC .. C07C 251/76; C07D 209/24; C07D 209/30; C07D 209/34; C07D 307/81; C07D 307/82; C07D 307/83; C07D 333/60; C07D 333/62; C07D 333/64; A01N 41/10; A01N 43/58; A01N 43/70; A01N 43/90; A01N 47/06; A01N 47/18; A01N 47/36; A01N 57/16; A01N 57/24

See application file for complete search history.

(56) References Cited

U.S. PATENT DOCUMENTS

| | | |
|---|---|---|
| 2010/0216642 A1 | 8/2010 | Fusaka |
| 2010/0267561 A1 | 10/2010 | Stevenson et al. |

(Continued)

FOREIGN PATENT DOCUMENTS

| | | |
|---|---|---|
| GB | 1130716 A | 10/1968 |
| WO | 2005/007632 A1 | 1/2005 |

(Continued)

OTHER PUBLICATIONS

Babichev et al., "6-Amino-1-aryl-4-pyridazinones and their derivatives", Ukrainskii Khimicheskii Zhurnal (Russian Edition), vol. 49, Issue 11, pp. 1197-1202, 1983.

*Primary Examiner* — John Pak
*Assistant Examiner* — Nathan W Schlientz
(74) *Attorney, Agent, or Firm* — Reed A. Coats

(57) ABSTRACT

Disclosed are compounds of Formula 1, including all stereoisomers, N-oxides, and salts thereof,

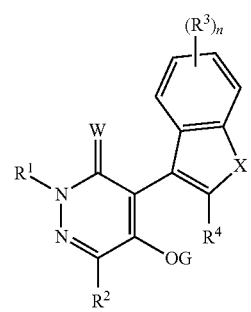

wherein
X is O, S or NR⁵; or
X is —C(R⁶)═C(R⁷)—, wherein the carbon atom bonded to R⁶ is also bonded to the carbon atom bonded to R⁴, and the carbon atom bonded to R⁷ is also bonded to the phenyl ring moiety in Formula 1;
and R¹, R², R³, R⁴, R⁵, R⁶, R⁷, G and W are as defined in the disclosure.
Also disclosed are compositions containing the compounds of Formula 1 and methods for controlling undesired vegetation comprising contacting the undesired vegetation or its environment with an effective amount of a compound or a composition of the invention.

10 Claims, No Drawings

Related U.S. Application Data

(60) Provisional application No. 61/985,895, filed on Apr. 29, 2014, provisional application No. 62/004,006, filed on May 28, 2014, provisional application No. 62/071,949, filed on Nov. 17, 2014.

(51) Int. Cl.

| | | |
|---|---|---|
| *A01N 41/10* | (2006.01) |
| *A01N 57/24* | (2006.01) |
| *A01N 43/58* | (2006.01) |
| *C07D 403/04* | (2006.01) |
| *C07D 237/14* | (2006.01) |
| *C07D 237/16* | (2006.01) |
| *C07D 237/18* | (2006.01) |
| *A01N 47/36* | (2006.01) |
| *C07D 333/60* | (2006.01) |
| *C07D 307/81* | (2006.01) |

(56) References Cited

U.S. PATENT DOCUMENTS

| | | |
|---|---|---|
| 2013/0172556 A1 | 7/2013 | Jachmann et al. |
| 2013/0281299 A1* | 10/2013 | Kuragano .............. A01N 43/58 504/237 |
| 2014/0378688 A1 | 12/2014 | Jachmann et al. |
| 2015/0031540 A1 | 1/2015 | Burton et al. |
| 2018/0312467 A1 | 11/2018 | Selby et al. |
| 2018/0332851 A1 | 11/2018 | Stevenson et al. |

FOREIGN PATENT DOCUMENTS

| | | |
|---|---|---|
| WO | 20070119434 | 10/2007 |
| WO | 20090035145 | 3/2009 |
| WO | 20090035151 | 3/2009 |
| WO | 20130050421 | 4/2013 |
| WO | 2013/160126 A1 | 10/2013 |
| WO | 2014/031971 A1 | 2/2014 |
| WO | 20150132608 | 9/2015 |
| WO | 2018/183432 A1 | 10/2018 |
| WO | 2019/005484 A1 | 1/2019 |

\* cited by examiner

PYRIDAZINONE HERBICIDES

FIELD OF THE INVENTION

This invention relates to certain pyridazinones, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1 (including all stereoisomers), N-oxides, and salts thereof, agricultural compositions containing them and their use as herbicides:

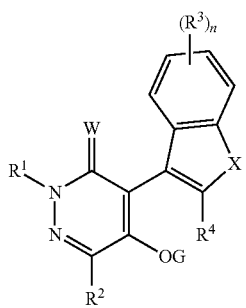

1 wherein
W is O or S;
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl; or a 5-, or 6-membered saturated or partially saturated heterocyclic ring containing ring members selected from carbon and up to 1 O and 1 S;
$R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio, $C_2$-$C_3$ alkoxycarbonyl; or phenyl optionally substituted by halogen, $C_1$-$C_4$ alkyl or $C_1$-$C_4$ haloalkyl;
X is O, S or $NR^5$; or
X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 1;
each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;
$R^4$, $R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;
$R^5$ is H, $C_1$-$C_3$ alkyl or $C_1$-$C_3$ haloalkyl;
G is $G^1$ or $W^1G^1$;
$G^1$ is H, —C(=O)$R^8$, —C(=S)$R^8$, —$CO_2R^9$, —C(=O)$SR^9$, —S(O)$_2R^8$, —CONR$^{10}$R$^{11}$, —S(O)$_2$NR$^{10}$R$^{11}$, or P(=O)$R^{12}$; or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_1$-$C_4$ alkoxyalkyl, $C_3$-$C_6$ cycloalkyl or $C_4$-$C_7$ cycloalkylalkyl; or a 5- or 6-membered heterocyclic ring;
$W^1$ is $C_1$-$C_4$ alkanediyl or $C_2$-$C_4$ alkenediyl;
$R^8$ and $R^{10}$ are independently $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl, $C_4$-$C_7$ cycloalkylalkyl; or phenyl, benzyl, or a 5- to 6-membered heterocyclic ring, each phenyl, benzyl or heterocyclic ring optionally substituted by halogen, $C_1$-$C_4$ alkyl or $C_1$-$C_4$ haloalkyl;
$R^9$ is $C_1$-$C_7$ alkyl, $C_3$-$C_7$ alkenyl, $C_3$-$C_7$ alkynyl, $C_3$-$C_7$ cycloalkyl, $C_2$-$C_7$ haloalkyl, $C_3$-$C_7$ haloalkenyl, $C_2$-$C_7$ alkoxyalkyl, $C_4$-$C_7$ cycloalkylalkyl; or phenyl, benzyl or a 5- to 6-membered heterocyclic ring, each phenyl, benzyl or heterocycling ring optionally substituted by halogen, $C_1$-$C_4$ alkyl or $C_1$-$C_4$ haloalkyl;
$R^{11}$ is H, $C_1$-$C_7$ alkyl, $C_2$-$C_7$ alkenyl, $C_2$-$C_7$ alkynyl, $C_3$-$C_7$ cycloalkyl, $C_4$-$C_7$ cycloalkylalkyl, $C_1$-$C_7$ haloalkyl or $C_2$-$C_7$ alkoxyalkyl;
$R^{12}$ is $C_1$-$C_7$ alkyl or $C_1$-$C_7$ alkoxy; and
n is 0, 1, 2, 3 or 4;
provided that when $R^4$ is H, then X is —C($R^6$)=C($R^7$)—.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating" refers reaction in which nucleophile displaces a leaving group such as halide or sulfonate from a carbon-containing radical. Unless otherwise indicated, the term "alkylating" does not limit the carbon-containing radical to alkyl.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Cyanoalkyl" denotes an alkyl group substituted with one cyano group. Examples of "cyanoalkyl" include $NCCH_2$ and $NCCH_2CH_2$ (alternatively identified as $CH_2CH_2CN$).

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkylthio", "haloalkenyl", "haloalkynyl", and the like, areis defined analogously to the term "haloalkyl". Examples of "haloalkoxy" include $CF_3O—$, $CCl_3CH_2O—$, $HCF_2CH_2CH_2O—$ and $CF_3CH_2O—$. Examples of "haloalkylthio" include $CCl_3S—$, $CF_3S—$, $CCl_3CH_2S—$ and $ClCH_2CH_2CH_2S—$. Examples of "haloalkenyl" include $(Cl)_2C$=$CHCH_2—$ and $CF_3CH_2CH$=$CHCH_2—$. Examples of "haloalkynyl" include HC≡CCHCl—, $CF_3C$≡$C—$, $CCl_3C$≡$C—$ and $FCH_2C$≡$CCH_2—$.

"Alkoxycarbonyl" denotes a straight-chain or branched alkoxy moieties bonded to a C(=O) moiety. Examples of "alkoxycarbonyl" include $CH_3OC(=O)—$, $CH_3CH_2OC(=O)—$, $CH_3CH_2CH_2OC(=O)—$, $(CH_3)_2CHOC(=O)—$ and the different butoxy- or pentoxycarbonyl isomers.

The total number of carbon atoms in a substituent group is indicated by the "$C_i$-$C_j$" prefix where i and j are numbers from 1 to 7. For example, $C_1$-$C_4$ alkylsulfonyl designates methylsulfonyl through butylsulfonyl; $C_2$ alkoxyalkyl designates $CH_3OCH_2—$; $C_3$ alkoxyalkyl designates, for example, $CH_3CH(OCH_3)—$, $CH_3OCH_2CH_2—$ or $CH_3CH_2OCH_2—$; and $C_4$ alkoxyalkyl designates the various isomers of an alkyl group substituted with an alkoxy group containing a total of four carbon atoms, examples including $CH_3CH_2CH_2OCH_2—$ and $CH_3CH_2OCH_2CH_2—$.

When a compound is substituted with a substituent bearing a subscript that indicates the number of said substituents can exceed 1, said substituents (when they exceed 1) are independently selected from the group of defined substituents, e.g., $(R^3)_n$, wherein n is 1, 2, 3 or 4. When a group contains a substituent which can be hydrogen, for example $R^2$ or $R^4$, then when this substituent is taken as hydrogen, it is recognized that this is equivalent to said group being unsubstituted. When a variable group is shown to be optionally attached to a position, for example $(R^3)_n$ wherein n may be 0, then hydrogen may be at the position even if not recited in the variable group definition. When one or more positions on a group are said to be "not substituted" or "unsubstituted", then hydrogen atoms are attached to take up any free valency.

The compounds of Formula 1 wherein G is H (i.e. a hydroxy function) are believed to be the compounds that bind to an active site on a plant enzyme or receptor causing herbicidal effect on the plant. Other compounds of Formula 1 wherein the substituent G is a group that can be transformed within plants or the environment to the hydroxy moiety provide similar herbicidal effects and are within the scope of the present invention. Therefore, G can be any derivative known in the art which does not extinguish the herbicidal activity of the compound of Formula 1 and is or can be hydrolyzed, oxidized, reduced or otherwise metabolized in plants or soil to provide the carboxylic acid function, which depending upon pH, is in the dissociated or the undissociated form. The term "ring system" denotes two or more fused rings. The term "bicyclic ring system" denotes a ring system consisting of two fused rings.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 typically exist in more than one form, and Formula 1 thus include all crystalline and noncrystalline forms of the compounds they represent. Noncrystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as an enolic function (e.g., when G is H), salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1

A compound of Formula 1 wherein W is O.

Embodiment 2

A compound of Formula 1 or Embodiment 1 wherein X is O, S or —C($R^6$)═C($R^7$)—.

Embodiment 3

A compound of Embodiment 2 wherein X is O or S.

Embodiment 4

A compound of Embodiment 3 wherein X is O.

Embodiment 5

A compound of Embodiment 3 wherein X is S.

Embodiment 6

A compound of Embodiment 2 wherein X is —C($R^6$)=C($R^7$)—.

Embodiment 7

A compound of Formula 1 or Embodiment 1 wherein X is $NR^5$.

Embodiment 7a

A compound of Embodiment 2 wherein X is O, S, —CH=CH—, —C(CH$_3$)=CH—, —CH=CF—, —CH=CCl— or —CH=C(CH$_3$)—.

Embodiment 7b

A compound of Embodiment 2 wherein X is —CH=CH—, —C(CH$_3$)=CH—, —CH=CF—, —CH=CCl— or —CH=C(CH$_3$)—

Embodiment 7c

A compound of Embodiment 2 wherein X is —CH=CH—, —CH=CF—, —CH=CCl— or —CH=C(CH$_3$)—.

Embodiment 7d

A compound of Formula 1 or any one of Embodiments 1 through 7a wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl.

Embodiment 7e

A compound of Formula 1 or any one of Embodiments 1 through 7a wherein $R^1$ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl.

Embodiment 8

A compound of Formula 1 or any one of Embodiments 1 through 7 wherein $R^1$ is $C_1$-$C_4$ alkyl, $C_3$-$C_4$ alkenyl, $C_3$-$C_4$ alkynyl, $C_3$-$C_4$ cycloalkyl, $C_2$-$C_3$ cyanoalkyl, $C_1$-$C_3$ haloalkyl or $C_2$-$C_4$ alkoxyalkyl.

Embodiment 9

A compound of Embodiment 8 wherein $R^1$ is $C_1$-$C_3$ alkyl, allyl, propargyl, CH$_2$CH$_2$CN, $C_1$-$C_2$ haloalkyl or 2-methoxyethyl.

Embodiment 10

A compound of Embodiment 9 wherein $R^1$ is methyl, ethyl, n-propyl or 2-methoxyethyl.

Embodiment 11

A compound of Embodiment 10 wherein $R^1$ is methyl or ethyl.

Embodiment 12

A compound of Embodiment 11 wherein $R^1$ is methyl.

Embodiment 12a

A compound of Formula 1 wherein $R^1$ is other than H.

Embodiment 12b

A compound of Formula 1 wherein $R^1$ is other than phenyl.

Embodiment 12c

A compound of Formula 1 wherein $R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy or $C_1$-$C_5$ alkylthio.

Embodiment 12d

A compound of Formula 1 wherein $R^2$ is H, halogen, —CN, —CHO, $C_1$-$C_7$ alkyl, $C_1$-$C_4$ alkylcarbonyl, $C_2$-$C_7$ alkylcarbonyloxy, $C_4$-$C_7$ alkylcycloalkyl, $C_1$-$C_4$ alkylsulfinyl, $C_1$-$C_4$ alkylsulfonyl, $C_1$-$C_4$ alkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl or $C_1$-$C_7$ alkoxy.

Embodiment 13

A compound of Formula 1 or any one of Embodiments 1 through 12 wherein $R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy.

Embodiment 14

A compound of Embodiment 13 wherein $R^2$ is H, halogen, $C_1$-$C_3$ alkyl, cyclopropyl, $C_1$-$C_2$ haloalkyl, methoxy or ethoxy.

Embodiment 15

A compound of Embodiment 14 wherein $R^2$ is H, methyl, ethyl, n-propyl, CF$_3$ or methoxy.

Embodiment 16

A compound of Embodiment 15 wherein $R^2$ is methyl or ethyl.

Embodiment 17

A compound of Embodiment 16 wherein $R^2$ is methyl.

Embodiment 17a

A compound of Formula 1 wherein $R^2$ is other than phenyl.

Embodiment 18

A compound of Formula 1 or any one of Embodiments 1 through 17 wherein each $R^3$ is independently halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment 19

A compound of Embodiment 18 wherein each $R^3$ is independently halogen, —CN, $C_1$-$C_2$ alkyl, —CH=$CH_2$, —C≡CH, cyclopropyl, $C_1$-$C_2$ haloalkyl or $C_1$-$C_2$ alkoxy.

Embodiment 20

A compound of Embodiment 19 wherein each $R^3$ is independently halogen, —CN, methyl, ethyl, —CH=$CH_2$, —C≡CH, cyclopropyl, $CF_3$, methoxy or ethoxy.

Embodiment 21

A compound of Embodiment 20 wherein each $R^3$ is independently halogen, —CN, methyl, ethyl, methoxy or ethoxy.

Embodiment 22

A compound of Embodiment 21 wherein each $R^3$ is independently F, Cl, Br, methyl, ethyl or methoxy.

Embodiment 23

A compound of Formula 1 or any one of Embodiments 1 through 22 wherein $R^4$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment 24

A compound of Embodiment 23 wherein $R^4$ is halogen, —CN, $C_1$-$C_2$ alkyl, —CH=$CH_2$, —C≡CH, cyclopropyl, $C_1$-$C_2$ haloalkyl or $C_1$-$C_2$ alkoxy.

Embodiment 25

A compound of Embodiment 24 wherein $R^4$ is halogen, —CN, methyl, ethyl, —CH=$CH_2$, —C≡CH, cyclopropyl, $CF_3$, methoxy or ethoxy.

Embodiment 26

A compound of Embodiment 25 wherein $R^4$ is methyl or ethyl.

Embodiment 27

A compound of Embodiment 26 wherein $R^4$ is methyl.

Embodiment 28

A compound of Formula 1 or any one of Embodiments 1 through 27 wherein $R^5$ is $C_1$-$C_2$ alkyl.

Embodiment 29

A compound of Embodiment 28 wherein $R^5$ is methyl.

Embodiment 30

A compound of Formula 1 or any one of Embodiments 1 through 29 wherein independently, $R^6$ and $R^7$ are H, halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment 31

A compound of Formula 1 or any one of Embodiments 1 through 30 wherein independently, $R^6$ and $R^7$ are H, halogen, —CN, $C_1$-$C_2$ alkyl, —CH=$CH_2$, —C≡CH, cyclopropyl, $C_1$-$C_2$ haloalkyl or $C_1$-$C_2$ alkoxy.

Embodiment 32

A compound of Formula 1 or any one of Embodiments 1 through 31 wherein independently, $R^6$ and $R^7$ are H, halogen, —CN, methyl, ethyl, —CH=$CH_2$, —C≡CH, cyclopropyl, $CF_3$, methoxy or ethoxy.

Embodiment 34a

A compound of Formula 1 or any one of Embodiments 1 through 32 wherein independently, $R^6$ and $R^7$ are H, halogen or $C_1$-$C_2$ alkyl.

Embodiment 34b

A compound of Formula 1 or any one of Embodiments 1 through 32 wherein independently, $R^6$ and $R^7$ are H or halogen.

Embodiment 34c

A compound of Formula 1 or any one of Embodiments 1 through 32 wherein $R^6$ is H and $R^7$ is halogen.

Embodiment 34d

A compound of Formula 1 or any one of Embodiments 1 through 32 wherein $R^6$ is halogen and $R^7$ is H.

Embodiment 33

A compound of Formula 1 or any one of Embodiments 1 through 32 wherein independently, $R^6$ and $R^7$ are H or $C_1$-$C_2$ alkyl.

Embodiment 34

A compound of Formula 1 or any one of Embodiments 1 through 33 wherein $R^6$ is H or methyl (i.e. $CH_3$).

Embodiment 35

A compound of Formula 1 or any one of Embodiments 1 through 34 wherein $R^7$ is H or methyl (i.e. $CH_3$).

Embodiment 36

A compound of Embodiment 34 or 35 wherein $R^6$ is H and $R^7$ is H, or $R^6$ is H and $R^7$ is $CH_3$, or $R^6$ is $CH_3$ and $R^7$ is H.

Embodiment 37

A compound of Embodiment 36 wherein $R^6$ is H and $R^7$ is H.

Embodiment 37a

A compound of Formula 1 or any one of Embodiments 1 through 37 wherein G is $G^1$.

Embodiment 37b

A compound of Formula 1 or any one of Embodiments 1 through 37a whereins $G^1$ is H, —C(=O)$R^8$, —C(=S)$R^8$, —CO$_2R^9$, —C(=O)S$R^9$, —S(O)$_2R^8$, —CONR$^{10}R^{11}$, —S(O)$_2$NR$^{10}R^{11}$ or P(=O)$R^{12}$; or $C_3$-$C_6$ cycloalkyl or $C_4$-$C_7$ cycloalkylalkyl.

Embodiment 37b

A compound of Formula 1 or any one of Embodiments 1 through 37a wherein $G^1$ is H, —C(=O)$R^8$, —C(=S)$R^8$, —CO$_2R^9$, —C(=O)S$R^9$, —S(O)$_2R^8$, —CONR$^{10}R^{11}$, —S(O)$_2$NR$^{10}R^{11}$ or P(=O)$R^{12}$; or $C_4$-$C_7$ cycloalkylalkyl.

Embodiment 38

A compound of Formula 1 or any one of Embodiments 1 through 37 wherein $G^1$ is H, —C(=O)$R^8$, —CO$_2R^9$, —S(O)$_2R^8$, —CONR$^{10}R^{11}$, —S(O)$_2$NR$^{10}R^{11}$ or P(=O)$R^{12}$.

Embodiment 39

A compound of Embodiment 38 wherein $G^1$ is H, —C(=O)$R^8$, —CO$_2R^9$, —S(O)$_2R^8$ or P(=O)$R^{12}$.

Embodiment 39a

A compound of Embodiment 39 wherein $G^1$ is H.

Embodiment 39b

A compound of Embodiment 39 wherein $G^1$ is —C(=O)$R^8$.

Embodiment 39c

A compound of Embodiment 39 wherein $G^1$ is —CO$_2R^9$.

Embodiment 39d

A compound of Embodiment 39 wherein $G^1$-S(O)$_2R^8$.

Embodiment 39e

A compound of Embodiment 39 or P(=O)$R^{12}$

Embodiment 40

A compound of Formula 1 or any one of Embodiments 1 through 39e wherein $R^8$ and $R^{10}$ are independently H, $C_1$-$C_7$ alkyl, $C_3$-$C_7$ cycloalkyl, $C_1$-$C_3$ haloalkyl or $C_2$-$C_7$ alkoxyalkyl.

Embodiment 41

A compound of Embodiment 40 wherein $R^8$ and $R^{10}$ are independently H, $C_1$-$C_7$ alkyl, $C_3$-$C_7$ cycloalkyl or $C_2$-$C_7$ alkoxyalkyl.

Embodiment 42

A compound of Embodiment 41 wherein $R^8$ and $R^{10}$ are independently $C_1$-$C_7$ alkyl or $C_2$-$C_7$ alkoxyalkyl.

Embodiment 42a

A compound of any one of Embodiments 1 through 40 wherein $R^8$ is $C_1$-$C_7$ alkyl, $C_3$-$C_7$ cycloalkyl or $C_2$-$C_7$ alkoxyalkyl.

Embodiment 42b

A compound of Embodiment 41 wherein $R^8$ is independently $C_1$-$C_3$ alkyl or $C_2$-$C_4$ alkoxyalkyl.

Embodiment 42c

A compound of Formula 1 or any one of Embodiments 1 through 37 wherein G is $WG^1$.

Embodiment 42d

A compound of Formula 1 or any one of Embodiments 1 through 42a wherein $W^1$ is $C_1$-$C_2$ alkanediyl or $C_2$-$C_3$ alkenediyl.

Embodiment 42e

A compound of Embodiment 42b wherein $W^1$ is —$CH_2$— or —CH=CH—.

Embodiment 42f

A compound of Embodiment 42c wherein $W^1$ is —$CH_2$—.

Embodiment 43

A compound of Formula 1 or any one of Embodiments 1 through 42 wherein $R^9$ is H, $C_1$-$C_7$ alkyl, $C_3$-$C_7$ cycloalkyl, $C_2$-$C_3$ haloalkyl or $C_2$-$C_7$ alkoxyalkyl.

Embodiment 44

A compound of Embodiment 43 wherein $R^9$ is H, $C_1$-$C_7$ alkyl, $C_3$-$C_7$ cycloalkyl or $C_2$-$C_7$ alkoxyalkyl.

Embodiment 45

A compound of Embodiment 44 wherein $R^9$ is $C_1$-$C_7$ alkyl or $C_2$-$C_7$ alkoxyalkyl.

Embodiment 46

A compound of Formula 1 or any one of Embodiments 1 through 45 wherein $R^{11}$ is H, $C_1$-$C_7$ alkyl, $C_3$-$C_7$ cycloalkyl, $C_1$-$C_3$ haloalkyl or $C_2$-$C_7$ alkoxyalkyl.

Embodiment 47

A compound of Embodiment 46 wherein $R^{11}$ is H, $C_1$-$C_7$ alkyl, $C_3$-$C_7$ cycloalkyl or $C_2$-$C_7$ alkoxyalkyl.

Embodiment 48

A compound of any one of Embodiments 1 through 47 wherein $R^{12}$ is $C_1$-$C_3$ alkyl or $C_1$-$C_3$ alkoxy.

Embodiment 49

A compound of Embodiment 48 wherein $R^{12}$ is $CH_3$ or $OCH_3$.

Embodiment 48

A compound of Formula 1 or any one of Embodiments 1 through 47 wherein n is 0, 1, 2 or 3.

Embodiment 49

A compound of Embodiment 48 wherein n is 0, 1 or 2.

Embodiment 50

A compound of Embodiment 48 wherein n is 1, 2 or 3.

Embodiment 51

A compound of Embodiment 49 or 50 wherein n is 1 or 2.

Embodiments of this invention, including Embodiments 1-51 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-51 above as well as any other embodiments described herein, and any combination thereof, pertain to the compositions and methods of the present invention.

Combinations of Embodiments 1-51 are illustrated by:

Embodiment A

A compound of Formula 1 wherein
W is O;
X is O, S, —CH=CH—, —C(CH$_3$)=CH—, —CH=CF—, —CH=CCl— or —CH=C(CH$_3$)—;
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl;
$R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy or $C_1$-$C_5$ alkylthio;
each $R^3$ is independently halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;
$R^4$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;
G is $G^1$;
$G^1$ is H, —C(=O)$R^8$, —C(=S)$R^8$, —CO$_2$$R^9$, —C(=O)SR$^9$, —S(O)$_2$R$^8$, —CONR$^{10}$R$^{11}$, —S(O)$_2$NR$^{10}$R$^{11}$ or P(=O)R$^{12}$; or $C_3$-$C_6$ cycloalkyl or $C_4$-$C_7$ cycloalkylalkyl;
$R^8$ and $R^{10}$ are independently H, $C_1$-$C_7$ alkyl, $C_3$-$C_7$ cycloalkyl, $C_1$-$C_3$ haloalkyl or $C_2$-$C_7$ alkoxyalkyl;
$R^9$ is H, $C_1$-$C_7$ alkyl, $C_3$-$C_7$ cycloalkyl, $C_2$-$C_3$ haloalkyl or $C_2$-$C_7$ alkoxyalkyl;
$R^{11}$ is H, $C_1$-$C_7$ alkyl, $C_3$-$C_7$ cycloalkyl, $C_1$-$C_3$ haloalkyl or $C_2$-$C_7$ alkoxyalkyl;
$R^{12}$ is $C_1$-$C_3$ alkyl or $C_1$-$C_3$ alkoxy;
and
n is 0, 1, 2 or 3.

Embodiment B

A compound of Embodiment A wherein
X is —CH=CH—, —C(CH$_3$)=CH—, —CH=CF—, —CH=CCl— or —CH=C(CH$_3$)—;
$R^1$ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl;
$R^2$ is H, halogen, —CN, —CHO, $C_1$-$C_7$ alkyl, $C_1$-$C_4$ alkylcarbonyl, $C_2$-$C_7$ alkylcarbonyloxy, $C_4$-$C_7$ alkylcycloalkyl, $C_1$-$C_4$ alkylsulfinyl, $C_1$-$C_4$ alkylsulfonyl, $C_1$-$C_4$ alkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl or $C_1$-$C_7$ alkoxy;
each $R^3$ is independently halogen, —CN, $C_1$-$C_2$ alkyl, —CH=CH$_2$, —C≡CH, cyclopropyl, $C_1$-$C_2$ haloalkyl or $C_1$-$C_2$ alkoxy;
$R^4$ is halogen, —CN, $C_1$-$C_2$ alkyl, —CH=CH$_2$, —C≡CH, cyclopropyl, $C_1$-$C_2$ haloalkyl or $C_1$-$C_2$ alkoxy;
$G^1$ is H, —C(=O)$R^8$, —CO$_2$$R^9$, —S(O)$_2$R$^8$, —CONR$^{10}$R$^{11}$, —S(O)$_2$NR$^{10}$R$^{11}$ or P(=O)R$^{12}$;
$R^8$, $R^9$ and $R^{10}$ are independently H, $C_1$-$C_7$ alkyl, $C_3$-$C_7$ cycloalkyl or $C_2$-$C_7$ alkoxyalkyl;
$R^{11}$ is H, $C_1$-$C_7$ alkyl, $C_3$-$C_7$ cycloalkyl or $C_2$-$C_7$ alkoxyalkyl; and
$R^{12}$ is $CH_3$ or $OCH_3$.

Embodiment C

A compound of Embodiment B wherein
X is —CH=CH—, —CH=CF—, —CH=CCl— or —CH=C(CH$_3$)—
$R^1$ is methyl, ethyl, n-propyl or 2-methoxyethyl;
$R^2$ is H, methyl, ethyl, n-propyl, CF$_3$ or methoxy;
each $R^3$ is independently halogen, —CN, methyl, ethyl, —CH=CH$_2$, —C≡CH, cyclopropyl, CF$_3$, methoxy or ethoxy;
$R^4$ is halogen, —CN, methyl, ethyl, —CH=CH$_2$, —C≡CH, cyclopropyl, CF$_3$, methoxy or ethoxy; $G^1$ is H, —C(=O)R$^8$, —CO$_2$R$^9$, —S(O)$_2$R$^8$ or P(=O)R$^{12}$; $R^8$ and $R^9$ are independently C$_1$-C$_7$ alkyl or C$_2$-C$_7$ alkoxyalkyl; and
n is 1 or 2.

Specific embodiments include compounds of Formula 1 selected from the group consisting of:
4-(2,5-dimethylbenzo[b]thien-3-yl)-5-hydroxy-2,6-dimethyl-3(2H)-pyridazinone (Compound 1),
5-hydroxy-2,6-dimethyl-4-(2,5,7-trimethylbenzo[b]thien-3-yl)-3(2H)-pyridazinone (Compound 2),
5-hydroxy-2,6-dimethyl-4-(2,4,6-trimethylbenzo[b]thien-3-yl)-3(2H)-pyridazinone (Compound 3),
5-hydroxy-2,6-dimethyl-4-(2-methyl-3-benzofuranyl)-3 (2H)-pyridazinone (Compound 4),
5-hydroxy-4-(5-methoxy-3-benzofuranyl)-2,6-dimethyl-3 (2H)-pyridazinone (Compound 5),
4-(5-chloro-2-methyl-3-benzofuranyl)-5-hydroxy-2,6-dimethyl-3 (2H)-pyridazinone (Compound 6),
4-(2,5-dimethyl-3-benzofuranyl)-5-hydroxy-2,6-dimethyl-3 (2H)-pyridazinone (Compound 7),
4-(2,4-dimethyl-3-benzofuranyl)-5-hydroxy-2,6-dimethyl-3 (2H)-pyridazinone (Compound 8),
4-(2,7-dimethyl-3-benzofuranyl)-5-hydroxy-2,6-dimethyl-3 (2H)-pyridazinone (Compound 9),
4-(2-ethyl-5-methyl-3-benzofuranyl)-5-hydroxy-2,6-dimethyl-3(2H)-pyridazinone (Compound 10),
5-hydroxy-2,6-dimethyl-4-(1-naphthalenyl)-3(2H)-pyridazinone (Compound 11),
5-hydroxy-2,6-dimethyl-4-(2,5,7-trimethyl-3-benzofuranyl)-3 (2H)-pyridazinone (Compound 12),
4-(5-ethyl-2-methyl-3-benzofuranyl)-5-hydroxy-2,6-dimethyl-3(2H)-pyridazinone (Compound 13),
5-(acetyloxy)-4-(2,5-dimethyl-3-benzofuranyl)-2,6-dimethyl-3(2H)-pyridazinone (Compound 14),
5-(acetyloxy)-4-(2,7-dimethyl-3-benzofuranyl)-2,6-dimethyl-3(2H)-pyridazinone (Compound 15),
5-(acetyloxy)-2,6-dimethyl-4-(2,5,7-trimethyl-3-benzofuranyl)-3(2H)-pyridazinone (Compound 16),
5-(2,5-dimethyl-3-benzofuranyl)-1,6-dihydro-1,3-dimethyl-6-oxo-4-pyridazinyl 2,2-dimethylpropanoate (Compound 17),
1,6-dihydro-1,3-dimethyl-6-oxo-5-(2,5,7-trimethyl-3-benzofuranyl)-4-pyridazinyl 2,2-dimethylpropanoate (Compound 18), and
4-(2-ethyl-4,6-dimethylbenzo[b]thien-3-yl)-5-hydroxy-2,6-dimethyl-3(2H)-pyridazinone (Compound 19).

Specific embodiments also include compounds of Formula 1 selected from the group consisting of: compound numbers 1, 3, 11, 23, 25, 27, 28, 29, 32, 42, 47, 57, 59 and 60. Compound numbers refer to compounds in Index Table A.

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention can be used for weed control in a variety of crops such as wheat, barley, maize, soybean, sunflower, cotton, oilseed rape and rice, and specialty crops such as sugarcane, citrus, fruit and nut crops. Compounds of the invention are particularly useful for selective control of weeds in cereal crops in the Family Poaceae such as maize, rice and wheat.

Embodiments of the present invention as described in the Summary of the Invention include (where Formula 1 as used in the following Embodiments includes N-oxides and salts thereof):

Embodiment P1

A compound of Formula 1 wherein W is O.

Embodiment P2

A compound of Formula 1 or Embodiment P1 wherein X is O, S or —C(R$^6$)=C(R$^7$)—.

Embodiment P3

A compound of Embodiment P2 wherein X is O or S.

Embodiment P4

A compound of Embodiment P3 wherein X is O.

Embodiment P5

A compound of Embodiment P3 wherein X is S.

Embodiment P6

A compound of Embodiment P2 wherein X is —C(R$^6$)=C(R$^7$)—.

Embodiment P7

A compound of Formula 1 or Embodiment P1 wherein X is NR$^5$.

Embodiment P8

A compound of Formula 1 or any one of Embodiments P1 through P7 wherein R$^1$ is C$_1$-C$_4$ alkyl, C$_3$-C$_4$ alkenyl, C$_3$-C$_4$ alkynyl, C$_3$-C$_4$ cycloalkyl, C$_2$-C$_3$ cyanoalkyl, C$_1$-C$_3$ haloalkyl or C$_2$-C$_4$ alkoxyalkyl.

Embodiment P9

A compound of Embodiment P8 wherein R$^1$ is C$_1$-C$_3$ alkyl, allyl, propargyl, CH$_2$CH$_2$CN, C$_1$-C$_2$ haloalkyl or 2-methoxyethyl.

Embodiment P10

A compound of Embodiment P9 wherein R$^1$ is methyl, ethyl, n-propyl or 2-methoxyethyl.

Embodiment P11

A compound of Embodiment P10 wherein R$^1$ is methyl or ethyl.

Embodiment P12

A compound of Embodiment P11 wherein $R^1$ is methyl.

Embodiment P13

A compound of Formula 1 or any one of Embodiments P1 through P12 wherein $R^2$ is H, halogen, —CN, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy.

Embodiment P14

A compound of Embodiment P13 wherein $R^2$ is H, halogen, $C_1$-$C_3$ alkyl, cyclopropyl, $C_1$-$C_2$ haloalkyl, methoxy or ethoxy.

Embodiment P15

A compound of Embodiment P14 wherein $R^2$ is H, methyl, ethyl, n-propyl, $CF_3$ or methoxy.

Embodiment P16

A compound of Embodiment P15 wherein $R^2$ is methyl or ethyl.

Embodiment P17

A compound of Embodiment P16 wherein $R^2$ is methyl.

Embodiment P18

A compound of Formula 1 or any one of Embodiments P1 through P17 wherein each $R^3$ is independently halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment P19

A compound of Embodiment P18 wherein each $R^3$ is independently halogen, —CN, $C_1$-$C_2$ alkyl, —CH=$CH_2$, —C≡CH, cyclopropyl, $C_1$-$C_2$ haloalkyl or $C_1$-$C_2$ alkoxy.

Embodiment P20

A compound of Embodiment P19 wherein each $R^3$ is independently halogen, —CN, methyl, ethyl, —CH=$CH_2$, —C≡CH, cyclopropyl, $CF_3$, methoxy or ethoxy.

Embodiment P21

A compound of Embodiment P20 wherein each $R^3$ is independently halogen, —CN, methyl, ethyl, methoxy or ethoxy.

Embodiment P22

A compound of Embodiment P21 wherein each $R^3$ is independently F, Cl, Br, methyl, ethyl or methoxy.

Embodiment P23

A compound of Formula 1 or any one of Embodiments P1 through P22 wherein $R^4$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment P24

A compound of Embodiment P23 wherein $R^4$ is halogen, —CN, $C_1$-$C_2$ alkyl, —CH=$CH_2$, —C≡CH, cyclopropyl, $C_1$-$C_2$ haloalkyl or $C_1$-$C_2$ alkoxy.

Embodiment P25

A compound of Embodiment P24 wherein $R^4$ is halogen, —CN, methyl, ethyl, —CH=$CH_2$, —C≡CH, cyclopropyl, $CF_3$, methoxy or ethoxy.

Embodiment P26

A compound of Embodiment P25 wherein $R^4$ is methyl or ethyl.

Embodiment P27

A compound of Embodiment P26 wherein $R^4$ is methyl.

Embodiment P28

A compound of Formula 1 or any one of Embodiments P1 through P27 wherein $R^5$ is $C_1$-$C_2$ alkyl.

Embodiment P29

A compound of Embodiment P28 wherein $R^5$ is methyl.

Embodiment P30

A compound of Formula 1 or any one of Embodiments P1 through P29 wherein independently, $R^6$ and $R^7$ are H, halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio.

Embodiment P31

A compound of Formula 1 or any one of Embodiments P1 through P30 wherein independently, $R^6$ and $R^7$ are H, halogen, —CN, $C_1$-$C_2$ alkyl, —CH=$CH_2$, —C≡CH, cyclopropyl, $C_1$-$C_2$ haloalkyl or $C_1$-$C_2$ alkoxy.

Embodiment P32

A compound of Formula 1 or any one of Embodiments P1 through P31 wherein independently, $R^6$ and $R^7$ are H, halogen, —CN, methyl, ethyl, —CH=$CH_2$, —C≡CH, cyclopropyl, $CF_3$, methoxy or ethoxy.

Embodiment P33

A compound of Formula 1 or any one of Embodiments P1 through P32 wherein independently, $R^6$ and $R^7$ are H or $C_1$-$C_2$ alkyl.

Embodiment P34

A compound of Formula 1 or any one of Embodiments P1 through P33 wherein $R^6$ is H or methyl (i.e. $CH_3$).

Embodiment P35

A compound of Formula 1 or any one of Embodiments P1 through P34 wherein $R^7$ is H or methyl (i.e. $CH_3$).

Embodiment P36

A compound of Embodiment P34 or 35 wherein $R^6$ is H and $R^7$ is H, or $R^6$ is H and $R^7$ is $CH_3$, or $R^6$ is $CH_3$ and $R^7$ is H.

Embodiment P37

A compound of Embodiment P36 wherein $R^6$ is H and $R^7$ is H.

Embodiment P38

A compound of Formula 1 or any one of Embodiments P1 through P37 wherein G is H, $-C(=O)R^8$, $-CO_2R^9$, $-S(O)_2R^8$, $-CONR^{10}R^{11}$ or $-S(O)_2NR^{10}R^{11}$.

Embodiment P39

A compound of Embodiment P38 wherein G is H, $-C(=O)R^8$, $-CO_2R^9$ or $-S(O)_2R^8$.

Embodiment P40

A compound of Formula 1 or any one of Embodiments P1 through P39 wherein $R^8$ and $R^{10}$ are independently H, $C_1$-$C_7$ alkyl, $C_3$-$C_7$ cycloalkyl, $C_1$-$C_3$ haloalkyl or $C_2$-$C_7$ alkoxyalkyl.

Embodiment P41

A compound of Embodiment P40 wherein $R^8$ and $R^{10}$ are independently H, $C_1$-$C_7$ alkyl, $C_3$-$C_7$ cycloalkyl or $C_2$-$C_7$ alkoxyalkyl.

Embodiment P42

A compound of Embodiment P41 wherein $R^8$ and $R^{10}$ are independently $C_1$-$C_7$ alkyl or $C_2$-$C_7$ alkoxyalkyl.

Embodiment P43

A compound of Formula 1 or any one of Embodiments 1 through 42 wherein $R^9$ is H, $C_1$-$C_7$ alkyl, $C_3$-$C_7$ cycloalkyl, $C_2$-$C_3$ haloalkyl or $C_2$-$C_7$ alkoxyalkyl.

Embodiment P44

A compound of Embodiment P43 wherein $R^9$ is H, $C_1$-$C_7$ alkyl, $C_3$-$C_7$ cycloalkyl or $C_2$-$C_7$ alkoxyalkyl.

Embodiment P45

A compound of Embodiment P44 wherein $R^9$ is $C_1$-$C_7$ alkyl or $C_2$-$C_7$ alkoxyalkyl.

Embodiment P46

A compound of Formula 1 or any one of Embodiments P1 through P45 wherein $R^{11}$ is H, $C_1$-$C_7$ alkyl, $C_3$-$C_7$ cycloalkyl, $C_1$-$C_3$ haloalkyl or $C_2$-$C_7$ alkoxyalkyl.

Embodiment P47

A compound of Embodiment P46 wherein $R^{11}$ is H, $C_1$-$C_7$ alkyl, $C_3$-$C_7$ cycloalkyl or $C_2$-$C_7$ alkoxyalkyl.

Embodiment P48

A compound of Formula 1 or any one of Embodiments P1 through P47 wherein n is 0, 1, 2 or 3.

Embodiment P49

A compound of Embodiment P48 wherein n is 0, 1 or 2.

Embodiment P50

A compound of Embodiment P48 wherein n is 1, 2 or 3.

Embodiment P51

A compound of Embodiment P49 or P50 wherein n is 1 or 2.

Embodiments of this invention, including Embodiments P1-P51 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments P1-P51 above as well as any other embodiments described herein, and any combination thereof, pertain to the compositions and methods of the present invention.

Combinations of Embodiments P1-P51 are illustrated by:

Embodiment PA

A compound of Formula 1 wherein

W is O;

X is O, S, $-CH=CH-$, $-C(CH_3)=CH-$ or $-CH=C(CH_3)-$;

$R^1$ is $C_1$-$C_4$ alkyl, $C_3$-$C_4$ alkenyl, $C_3$-$C_4$ alkynyl, $C_3$-$C_4$ cycloalkyl, $C_2$-$C_3$ cyanoalkyl, $C_1$-$C_3$ haloalkyl or $C_2$-$C_4$ alkoxyalkyl;

$R^2$ is H, halogen, $-CN$, $C_1$-$C_4$ alkyl, $C_3$-$C_5$ cycloalkyl, $C_1$-$C_3$ haloalkyl, $C_2$-$C_4$ alkoxyalkyl or $C_1$-$C_3$ alkoxy;

each $R^3$ is independently halogen, $-CN$, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;

$R^4$ is halogen, $-CN$, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;

G is H, $-C(=O)R^8$, $-CO_2R^9$, $-S(O)_2R^8$, $-CONR^{10}R^{11}$ or $-S(O)_2NR^{10}R^{11}$;

$R^8$ and $R^{10}$ are independently H, $C_1$-$C_7$ alkyl, $C_3$-$C_7$ cycloalkyl, $C_1$-$C_3$ haloalkyl or $C_2$-$C_7$ alkoxyalkyl;

$R^9$ is H, $C_1$-$C_7$ alkyl, $C_3$-$C_7$ cycloalkyl, $C_2$-$C_3$ haloalkyl or $C_2$-$C_7$ alkoxyalkyl;

$R^{11}$ is H, $C_1$-$C_7$ alkyl, $C_3$-$C_7$ cycloalkyl, $C_1$-$C_3$ haloalkyl or $C_2$-$C_7$ alkoxyalkyl; and n is 0, 1, 2 or 3.

Embodiment PB

A compound of Embodiment PA wherein
$R^1$ is $C_1$-$C_3$ alkyl, allyl, propargyl, $CH_2CH_2CN$, $C_1$-$C_2$ haloalkyl or 2-methoxyethyl;
$R^2$ is H, halogen, $C_1$-$C_3$ alkyl, cyclopropyl, $C_1$-$C_2$ haloalkyl, methoxy or ethoxy;
each $R^3$ is independently halogen, —CN, $C_1$-$C_2$ alkyl, —CH=$CH_2$, —C≡CH, cyclopropyl, $C_1$-$C_2$ haloalkyl or $C_1$-$C_2$ alkoxy;
$R^4$ is halogen, —CN, $C_1$-$C_2$ alkyl, —CH=$CH_2$, —C≡CH, cyclopropyl, $C_1$-$C_2$ haloalkyl or $C_1$-$C_2$ alkoxy;
$R^8$, $R^9$ and $R^{10}$ are independently H, $C_1$-$C_7$ alkyl, $C_3$-$C_7$ cycloalkyl or $C_2$-$C_7$ alkoxyalkyl; and
$R^{11}$ is H, $C_1$-$C_7$ alkyl, $C_3$-$C_7$ cycloalkyl or $C_2$-$C_7$ alkoxyalkyl.

Embodiment PC

A compound of Embodiment PB wherein
$R^1$ is methyl, ethyl, n-propyl or 2-methoxyethyl;
$R^2$ is H, methyl, ethyl, n-propyl, $CF_3$ or methoxy;
each $R^3$ is independently halogen, —CN, methyl, ethyl, —CH=$CH_2$, —C≡CH, cyclopropyl, $CF_3$, methoxy or ethoxy;
$R^4$ is halogen, —CN, methyl, ethyl, —CH=$CH_2$, —C≡CH, cyclopropyl, $CF_3$, methoxy or ethoxy;
G is H, —C(=O)$R^8$, —$CO_2R^9$ or —S(O)$_2R^8$;
$R^8$ and $R^9$ are independently $C_1$-$C_7$ alkyl or $C_2$-$C_7$ alkoxyalkyl; and
n is 1 or 2.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics and (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine. Of note is a compound of the invention mixed with atrazine, bromoxynil or bentazon. Also of note is a compound of the invention mixed with atrazine, bromoxynil or metribuzin.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]-benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron. Of note is a compound of the invention mixed with rimsulfuron, thifensulfuron-methyl, tribenuron, nicosulfuron, metsulfuron-methyl, flupyrsulfuron-methyl, cloransulam-methyl, pyroxsulam or florasulam. Also of note is a compound of the invention mixed with nicosulfuron, flupyrsulfuron or chlorimuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl. Of note is a compound of the invention mixed with pinoxaden or quizalofop.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate. Of particular note is a compound of the invention mixed with dicamba, fluroxypyr-meptyl, 2,4-D, halauxifen-methyl or MCPA. Also of note is a compound of the invention mixed with dicamba.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-3-alaninate) and 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione. Of note is a compound of the invention mixed with saflufenacil, flumioxazin or carfentrazone-ethyl.

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides. Of note is a compound of the invention mixed with pyroxasulfone, metolachlor, acetochlor, dimethenamid, alachlor or flufenacet. Also of note is a compound of the invention mixed with flufenacet.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-

(methylsulfonyl)-N-(1-methyl-1H-tetrazol-5-yl)-4-(trifluoromethyl)benzamide. Of note is a mixture of a compound of the invention with mesotrione, isoxaflutole, tembotrione, bicyclopyrone, topramazone or pyrasulfotole. Also of note is a compound of the invention mixed with mesotrione or pyrasulfatole.

HST (homogentisate solenesyltransererase) inhibitors (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, 7-(3, 5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

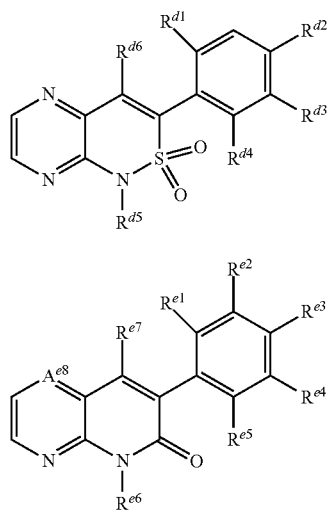

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

Cellulose biosynthesis inhibitors (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

Other herbicides (b15) include herbicides that act through a variety of different modes of action such as mitotic disruptors (e.g., flamprop-M-methyl and flamprop-M-isopropyl) organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro-[4.5]decane (MON 4660).

The compounds of Formula 1 can be prepared by general methods known in the art of synthetic organic chemistry. A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

One or more of the following methods and variations as described in Schemes 1-22 can be used to prepare compounds of Formula 1. The definitions of groups $R^1$, $R^2$, $R^3$, $R^4$, W, X and G in the compounds of Formulae 1-35 are as defined above in the Summary of the Invention unless otherwise noted. Formulae 1a, 1b and 1c are subsets of compounds of Formula 1, and all substituents for Formulae 1a-1c are as defined above for Formula 1 unless otherwise noted. Formulae 6a, 6b and 6c are subsets of compounds of Formula 6, and all substituents for Formulae 6a-6c are as defined for Formula 6 unless otherwise noted.

As shown in Scheme 1, pyridazinones of Formula 1a (a subset of compounds of Formula 1 where W is O, and G is as defined above, but other than hydrogen) can be made by reacting substituted 5-hydroxy-3(2H)-pyridazinones of Formula 1b (i.e. Formula 1 wherein W is O and G is H) with a suitable electrophilic reagent of Formula 2 (i.e. $Z^1$-G where $Z^1$ is a leaving group, alternatively known as a nucleofuge, such as a halogen) in the presence of base in an appropriate solvent. Some examples of reagent classes representing Formula 2 wherein $Z^1$ is Cl include acid chlorides (G is —(C=O)$R^8$), chloroformates (G is —$CO_2R^9$), carbamoyl chlorides (G is —$CONR^{10}R^{11}$), sulfonyl chlorides (G is —S(O)$_2R^8$) and chlorosulfonamides (G is —S(O)$_2$N$R^{10}R^{11}$). Examples of suitable bases for this reaction include, but are not limited to, potassium carbonate, sodium hydroxide, potassium hydroxide, sodium hydride or potassium tert-butoxide and, depending on the specific base used, appropriate solvents can be protic or aprotic and used anhydrous or as aqueous mixtures. Preferred solvents for this reaction include acetonitrile, methanol, ethanol, tetrahydrofuran, diethyl ether, 1,2-dimethoxyethane, dioxane, dichloromethane or N,N-dimethylformamide. The reaction can be run under a range of temperatures, with temperatures typically ranging from 0° C. to the reflux temperature of the solvent.

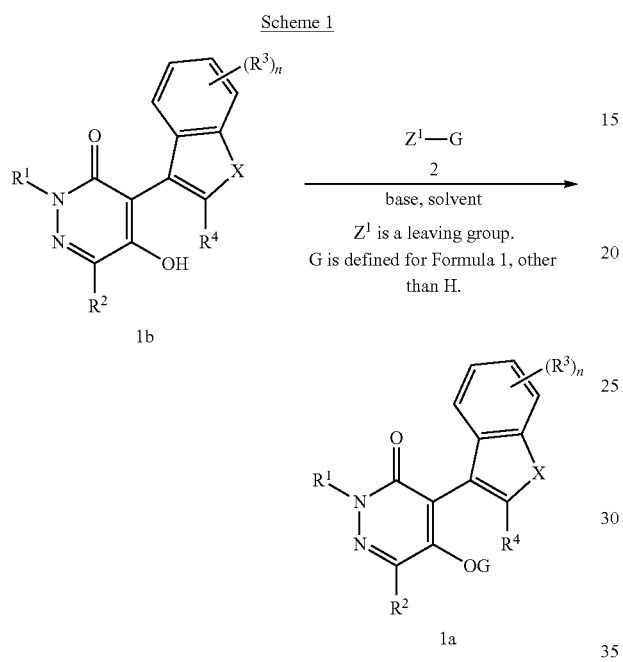

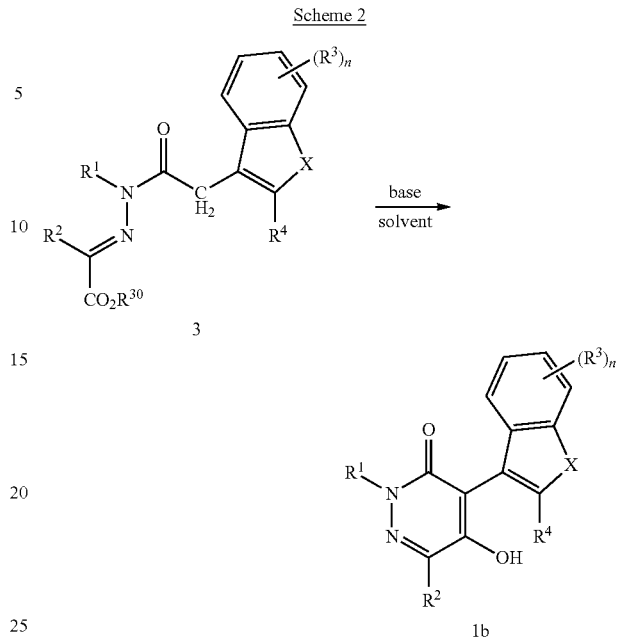

Substituted 5-hydroxy-3(2H)-pyridazinones of Formula 1b can be prepared as outlined in Scheme 2 by cyclization of hydrazide esters of Formula 3 (where $R^{30}$ is alkyl, typically methyl or ethyl) in the presence of base and solvent. Suitable bases for this reaction include but are not limited to potassium carbonate, sodium hydroxide, potassium hydroxide, sodium hydride, potassium t-butoxide or 1,8-diazabicyclo[5.4.0]undec-7-ene. Depending on the specific base used, appropriate solvents can be protic or aprotic and used anhydrous or as aqueous mixtures. Solvents for this cyclization include acetonitrile, methanol, ethanol, tetrahydrofuran, diethyl ether, dioxane, 1,2-dimethoxyethane, dichloromethane or N,N-dimethylformamide. Temperatures for this cyclization generally range from 0° C. to the reflux temperature of the solvent. Literature methods for cyclizing hydrazide ester intermediates of formula $CH_3(CO_2C_2H_5)C$=$NNCH_3C$(=$O)CH_2Ar$ (where Ar is a substituted phenyl instead of the bicyclic ring system shown in Formula 3) to the corresponding 4-aryl-5-hydroxy-pyridazinones are disclosed in U.S. Pat. Nos. 8,541,414 and 8,470,738. The same conditions reported in these patents are applicable to cyclizing hydrazone esters of Formula 3 to pyridazinones of Formula 1b. The method of Scheme 2 is illustrated by Step F of Synthesis Example 1, Step H of Synthesis Example 2 and Step H of Synthesis Example 3.

Substituted hydrazide esters of Formula 3 can be prepared as outlined in Scheme 3 by coupling a hydrazone ester of Formula 4 (where $R^{30}$ is alkyl, typically methyl or ethyl) with an acid chloride of Formula 5 in the presence of base and solvent. Preferred bases for this reaction are usually tertiary amines such as triethylamine or Hunig's base, but other bases can also be used, including N,N-dimethylaminopyridine, potassium carbonate, sodium hydroxide, potassium hydroxide, sodium hydride or potassium t-butoxide. Depending on the specific base used, appropriate solvents can be protic or aprotic where the reaction takes place under anhydrous conditions or as aqueous mixtures under Schotten-Baumann conditions. Solvents that are used for this acylation on nitrogen include acetonitrile, tetrahydrofuran, diethyl ether, dioxane, toluene, 1,2-dimethoxyethane, dichloromethane or N,N-dimethylformamide. Temperatures for this reaction can range from 0° C. to the reflux temperature of the solvent. Methods to make related hydrazide ester intermediates of formula $CH_3(CO_2C_2H_5)C$=$NNCH_3C$(=$O)Ar$ (where Ar is a substituted phenyl) have been published in the patent literature, see U.S. Pat. Nos. 8,541,414 and 8,470,738, and U.S. Patent Application Publication 2010/0267561. The procedures disclosed in these patent publications are directly applicable to making intermediates useful for preparing the present compounds as depicted in Scheme 3. The method of Scheme 3 is illustrated by Step E of Synthesis Example 1, Step G of Synthesis Example 2 and Step G of Synthesis Example 3.

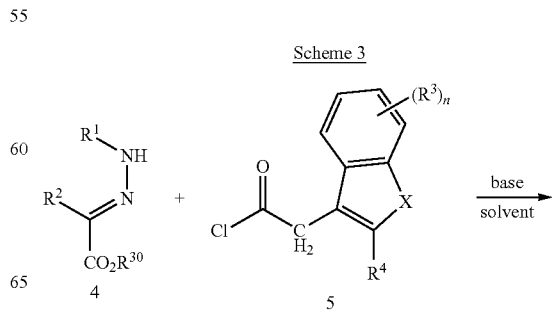

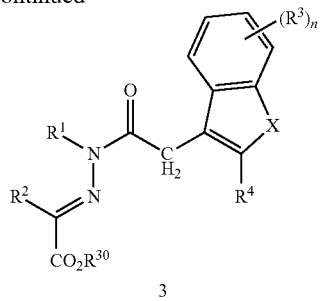

3

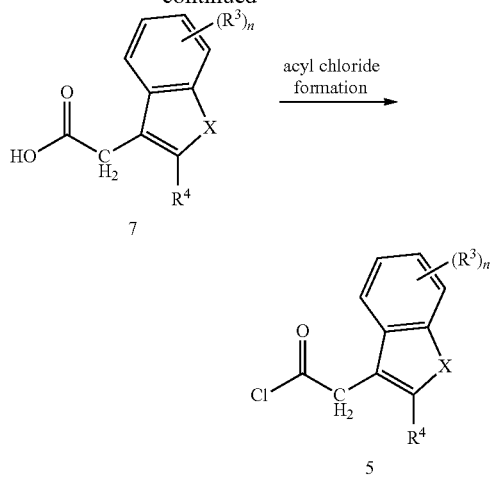

Hydrazone esters of Formula 4 are readily accessible by reaction of an appropriately substituted hydrazine of formula $R^1NHNH_2$ with a ketone or aldehyde ester of formula $R^2(C=O)CO_2R^{30}$ (where $R^{30}$ is typically methyl or ethyl) in a suitable solvent such as ethanol, methanol, acetonitrile or dioxane or dichloromethane at temperatures generally ranging from 0 to 80° C. U.S. Patent Application Publications 2007/0112038 and 2005/0256123 disclose procedures for forming the hydrazone from methylhydrazine and the keto ester $CH_3(C=O)CO_2C_2H_5$. Preparation of hydrazone esters of Formula 4 is illustrated by Step D of Synthesis Example 1.

As shown in Scheme 4, bicyclic acetyl chlorides of Formula 5 can be prepared from the corresponding bicyclic acetic acid esters of Formula 6 wherein $R^{31}$ is typically methyl or ethyl via ester hydrolysis and acid chloride formation. Standard methods for this transformation are known in the literature. For example, ester hydrolysis can be achieved by heating an alcoholic solution of an ester of Formula 6 with an aqueous solution of an alkali metal hydroxide, following by acidification with a mineral acid. The carboxylic acid of Formula 7 formed can then be converted to the corresponding acyl chloride of Formula 5 by treatment with oxalyl chloride and a catalytic amount of N,N-dimethylformamide in an inert solvent such as dichloromethane. *J. Heterocyclic Chem.* 1983, 20(6), 1697-1703; *J. Med. Chem.* 2007, 50(1), 40-64; and PCT Patent Publications WO 2005/012291, WO 98/49141 and WO 98/49158 disclose hydrolysis of benzofuran- and benzothiophene-acetate esters to the corresponding acetic acids. *Monatshefte für Chemie* 1968, 99(2) 715-720 and patent publications WO 2004046122, WO 2009/038974 and JP09077767 disclose conversion of benzofuran- and benzothiophene-acetic acids to the corresponding acid chlorides. The hydrolysis step of Scheme 4 is illustrated by Step C of Synthesis Example 1, Step F of Synthesis Example 2 and Step F of Synthesis Example 3. The acyl chloride formation step of Scheme 4 is illustrated by Step E of Synthesis Example 1, Step G of Synthesis Example 2 and Step G of Synthesis Example 3.

Scheme 4

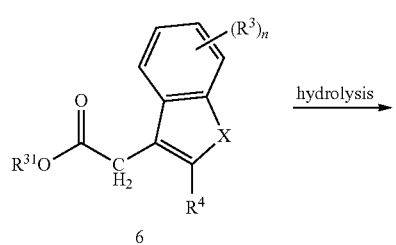

6

As shown in Scheme 5, benzofuran acetates of Formula 6a (i.e. Formula 6 wherein X is O) can be made from benzofuran-3-ones of Formula 8 via either a Wittig reaction with a (triphenylphosphoranylidine)acetate of Formula 9 wherein $R^{31}$ is typically methyl or ethyl in an inert solvent such as tetrahydrofuran or toluene or by a Wadsworth-Emmons reaction using a phosphonate acetate of Formula 10 wherein $R^{31}$ is typically methyl or ethyl in the presence of a base such as sodium hydride or potassium tert-butoxide in a suitable solvent that is generally anhydrous tetrahydrofuran or dioxane. This reaction involves migration of an initially formed exocyclic double bond (formation of a dihydrobenzofuran substituted unsaturated ester) to inside the benzofuran ring system, thereby giving rise to a benzofuran acetate of Formula 6a. Experimental conditions for a Wittig transformation are provided in PCT Patent Publication WO 2008/074752. Temperatures typically range from 0° C. to the reflux temperature of the solvent. In some cases, longer heating is required to drive migration of the exocyclic double bond in conjugation with the ester to the endocyclic position within the fully benzofuran ring system. The method of Scheme 5 is illustrated by Step E of Synthesis Example 2 and Step E of Synthesis Example 3.

Scheme 5

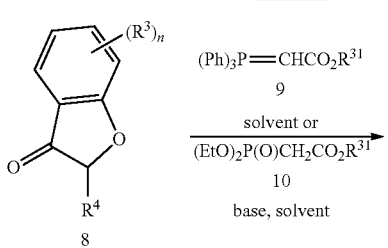

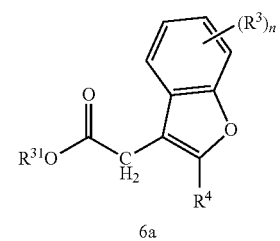

6a

As shown in Scheme 6, substituted benzofuran-3-ones of Formula 8 where $R^4$ is hydrogen or alkyl can be made by first alkylating a salicylate of Formula 11 with an α-bromo ester of Formula 12 (wherein $R^{32}$ is typically methyl or ethyl) in the presence of a base such as potassium carbonate or sodium hydride in an appropriate solvent, e.g., acetonitrile, methanol, ethanol, tetrahydrofuran, diethyl ether, 1,2-dimethoxyethane, dioxane or N,N-dimethylformamide, at temperatures ranging from 0° C. to the reflux temperature of the solvent. Next, the bis-ester of Formula 13 is treated with a metal halide or alkoxide, e.g., sodium hydride or potassium tert-butoxide, in an inert solvent such as tetrahydrofuran, dioxane, 1,2-dimethoxyethane or N,N-dimethylformamide to form the corresponding benzofuran-3-one of Formula 8. An alternative more stepwise process for converting diesters of Formula 13 to benzofuran-3-ones of Formula 8 has been reported in PCT Patent Publication WO 2008/074752 whereas the method in Scheme 5 allows for cyclization of diesters of Formula 13 followed by ester hydrolysis and decarboxylation to provide benzofuran-3-ones of Formula 8 in one convenient step. The first step of the method of Scheme 6 is illustrated by Step A of Synthesis Example 2.

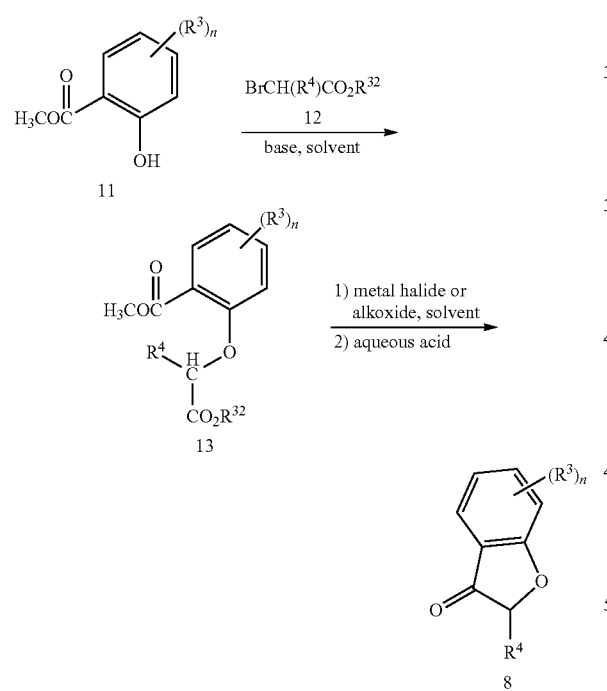

Scheme 6

$R^4$ is H or alkyl.

As illustrated in Scheme 7, substituted benzothiophenes of Formula 6b (i.e. Formula 6 wherein X is S) where $R^4$ is hydrogen or alkyl are readily accessible by cyclization of appropriately substituted phenylthio ketoesters of Formula 14, generally under acidic conditions and preferably with polyphosphoric acid (PPA) neat or in an inert generally high boiling solvent, e.g., chlorobenzene, xylene or toluene. Chlorobenzene is usually the solvent of choice and for a literature example of this cyclization using PPA in chlorobenzene, see *J. Heterocyclic Chem.* 1988, 25, 1271-1272. Also see U.S. Pat. No. 5,376,677 for published experimental detail for making benzothiophene acetates using this PPA-mediated cyclization. The method of Scheme 7 is illustrated by Step B of Synthesis Example 1.

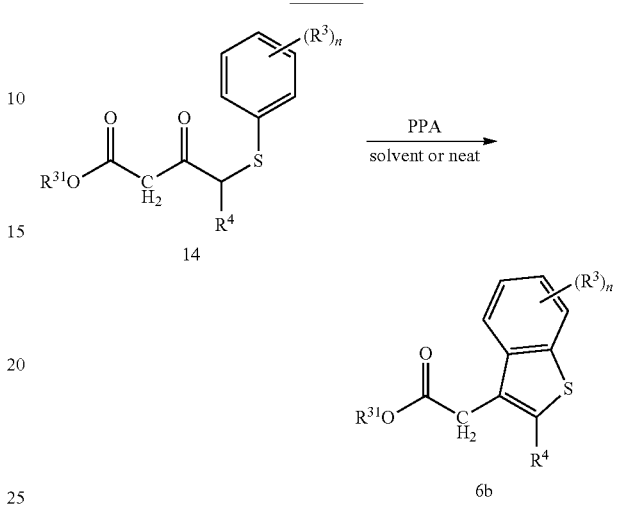

Scheme 7

As shown in Scheme 8, by methods also taught in *J. Heterocyclic Chem.* 1988, 25, 1271-1272 and U.S. Pat. No. 5,376,677, substituted 4-phenylthio-1,3-ketoesters of Formula 14, can be readily made by alkylation of thiophenols of Formula 15 with 4-bromo-1,3-ketoesters of Formula 16 (i.e. $R^4CHBr(C=O)CH_2CO_2R$ where R is generally methyl or ethyl) in the presence of base in solvent. Alkylation with an alkali or alkaline carbonate such as potassium carbonate in a polar aprotic solvent such as acetonitrile or N,N-dimethylformamide is generally preferred. The method of Scheme 8 is illustrated by Step A of Synthesis Example 1.

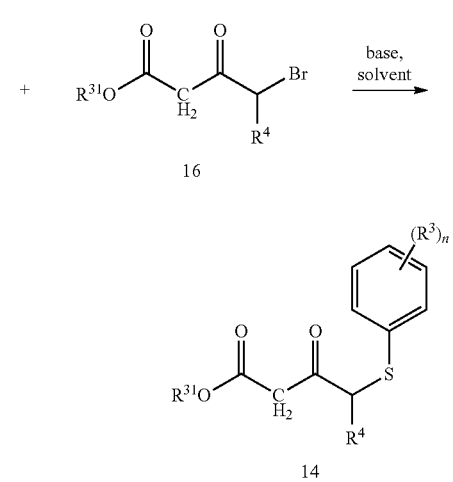

Scheme 8

As shown in Scheme 9, naphthalene acetic acid esters of Formula 6c (i.e. Formula 6 wherein X is $-C(R^6)=C(R^7)-$) can be prepared from appropriately substituted naphthalene amines of Formula 17. According to this method, amines of Formula 17 are diazotized (preferably with t-butyl nitrite in the presence of cupric chloride in acetonitrile) in the presence of 1,1-dichloroethene (18) to give the corresponding trichloroethylnaphthalenes of Formula 19. The trichloroethylnaphthalenes of Formula 19 are then heated with an appropriate alkali or alkaline earth alkoxide such as a sodium alkoxide of Formula 20, in a suitable solvent such as an alcohol of Formula 21, followed by acidification such as with concentrated sulfuric acid to provide the naphthalene acetic acid esters of Formula 6c. This method is taught in *Pest. Manag. Sci.* 2011, 67, 1499-1521 and U.S. Pat. No. 5,376,677.

N-bromosuccinimide (NBS) under free radical conditions (e.g., benzoyl peroxide as catalyst) in an inert solvent such as dichloromethane, dichloromethane or tetrachloromethane to give naphthalene methyl bromides of Formula 23. Displacement of the bromine with cyanide by reacting compounds of Formula 23 with an alkali or alkaline cyanide (e.g., potassium cyanide) affords the naphthalene acetoni- Scheme 9

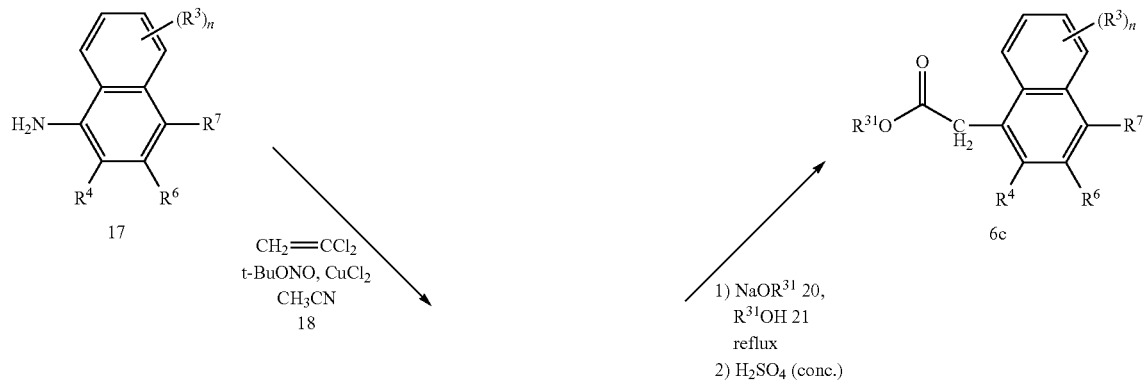

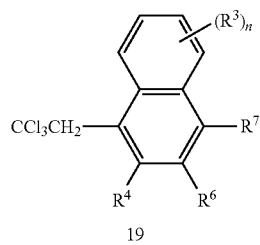

An alternative method for making naphthalene acetic acid esters of Formula 6c is outlined in Scheme 10. As taught by the method in *Pest. Manag. Sci.* 2011, 67, 1499-1521, methyl naphthalenes of Formula 22 can be brominated with triles of Formula 24 that can be hydrolyzed with esterification to the acetates of Formula 6c by heating in acidic alcohol (e.g., HCl in methanol or ethanol), generally at reflux.

Scheme 10

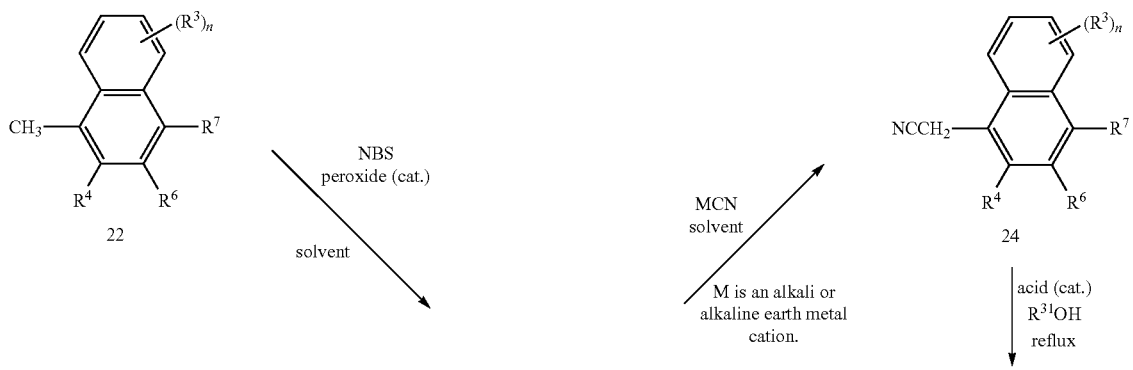

-continued

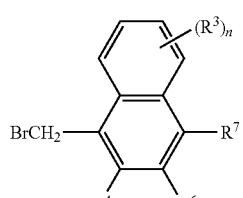

Hydrolysis of leaving groups at the 5-position of the pyridazinone ring can be accomplished as shown in Scheme 11. When the LG group is lower alkoxy, lower alkylsulfide (sulfoxide or sulfone), halide or N-linked azole, it can be removed by hydrolysis with basic reagents such as tetrabutylammonium hydroxide in solvents such as tetrahydrofuran, dimethoxyethane or dioxane at temperatures from 0 to 120° C. Other hydroxide reagents useful for this hydrolysis include potassium, lithium and sodium hydroxide (see, for example, WO 2009/086041). When the LG group is lower alkoxy, hydrolysis of the LG group can also be accomplished with dealkylation reagents such as boron tribromide or morpholine (see, for example, WO 2009/086041, WO 2013/160126 and WO 2013/050421).

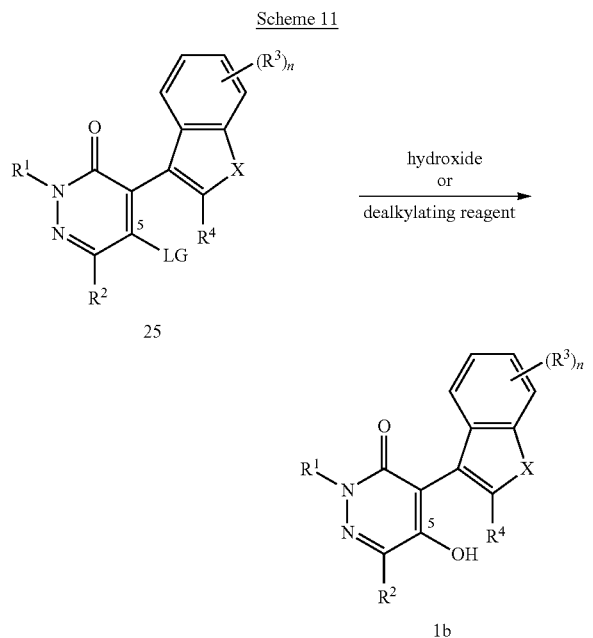

Introduction of a halogen at the 6-position of the pyridazinone can be accomplished by zincation followed by halogenation. For conditions, reagents and examples of zincation of pyridazinones, see Verhelst, T., Ph.D. thesis, University of Antwerp, 2012. Typically the pyridazinone of Formula 26 is treated in tetrahydrofuran with a solution of Zn(TMP)—LiCl or Zn(TMP)$_2$—MgCl$_2$—LiCl (commercially available) at −20 to 30° C. to form a zinc reagent. Subsequent addition of bromine or iodine provides compounds of Formula 27 (wherein R$^2$ is Br or I, respectively). This method is shown in Scheme 12. For preparation of a variety of appropriate zincation reagents, see Wunderlich, S. Ph.D. thesis, University of Munich, 2010 and references cited therein, as well as WO 2008/138946 and WO 2010/092096. Zincation at the 6-position of the pyridazinone ring can be accomplished in the presence of aromatic/heteroaromatic substituents, alkoxy substituents or halogen at the 4-position of the pyridazinone ring, or in the presence of halogen or alkoxy substituents at the 5-position of the pyridazinone ring.

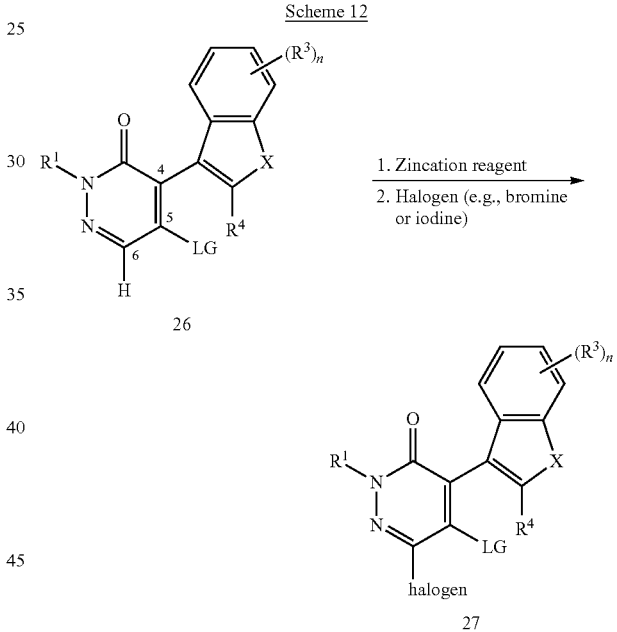

The R$^2$ substituent of compounds of Formula 28 (wherein R$^2$ is halogen or sulfonate) can be further transformed into other functional groups. Compounds wherein R$^2$ is alkyl, cycloalkyl or substituted alkyl can be prepared by transition metal catalyzed reactions of compounds of Formula 28 as shown in Scheme 13. For reviews of these types of reactions, see: E. Negishi, *Handbook of Organopalladium Chemistry for Organic Synthesis*, John Wiley and Sons, Inc., New York, 2002, N. Miyaura, *Cross-Coupling Reactions: A Practical Guide*, Springer, New York, 2002, H. C. Brown et al., *Organic Synthesis via Boranes*, Aldrich Chemical Co., Milwaukee, Vol. 3, 2002, Suzuki et al., *Chemical Reviews* 1995, 95, 2457-2483 and Molander et al., *Accounts of Chemical Research* 2007, 40, 275-286. Also see Gribble and Li editors *Palladium in Heterocyclic Chemistry Volume* 1, Pergamon Press, Amsterdam, 2000 and Gribble and Li editors *Palladium in Heterocyclic Chemistry Volume* 2, Pergamon Press, Amsterdam, 2007. For a review of Buchwald-Hartwig

Scheme 13

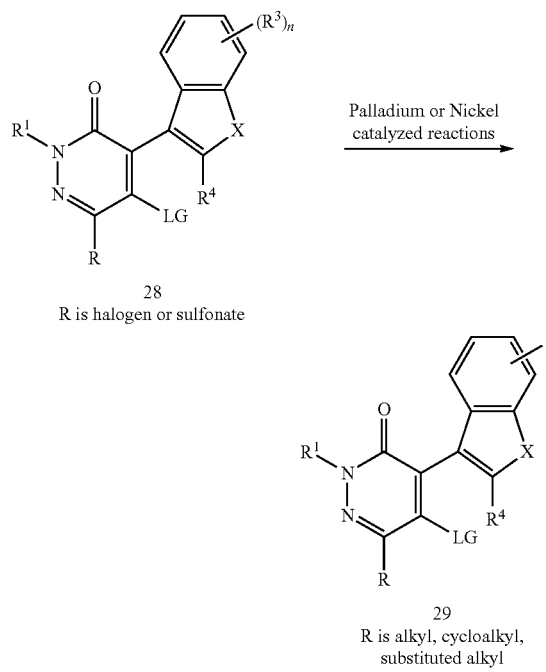

Related synthetic methods for the introduction of other functional groups at the R-position of Formula 29 are known in the art. Copper catalyzed reactions are useful for introducing the $CF_3$ group. For a comprehensive recent review of reagents for this reaction see Wu, Neumann and Beller in *Chemistry: An Asian Journal*, 2012, ASAP, and references cited therein. For introduction of a sulfur containing substitutent at this position, see methods disclosed in WO 2013/160126. For introduction of a cyano group, see WO 2014/031971. For introduction of a nitro group, see *J. Am. Chem. Soc.*, 2009, 12898. For introduction of a fluoro substituent, see *J. Am. Chem. Soc.*, 2014, 3792.

Compounds of Formula 28 can be prepared by reaction of organometallic reagents with pyridazinones of Formula 29 with a reactive group at the 4-position, as shown in Scheme 14. Depending upon the leaving group a transition metal catalyst may be desirable. When the leaving group is lower alkoxy, N-linked azole (such as pyrazole or triazole) or sulfonate, no catalyst is required, and reaction directly with a magnesium reagent can take place at the 4-position. This reaction can be done in a variety of solvents which do not react with organomagnesium reagents. Typical reaction conditions include tetrahydrofuran as the solvent, a reaction temperature of −20 to 65° C., and an excess of the organomagnesium reagent. When the reactive group at the 4-position is halogen, a transition metal catalyst and ligand are helpful. A variety of different coupling partners can be used, including boron (Suzuki Reaction), tin (Stille Reaction), and zinc (Negishi reaction); these reactions can be catalyzed by palladium and nickel catalysts with a wide variety of ligands. Conditions for these reactions are known in the art; see, for example, *Palladium-Catalyzed Coupling Reactions: Practical Aspects and Future Development* Edited by Arpad Molnar, Wiley, 2013 and references cited within. The organomagnesium reagents used in the non-catalyzed process can be prepared by direct insertion of magnesium into a carbon-halogen bond (optionally in the presence of a lithium halide), by a Grignard exchange reaction with an i-propyl-magnesium halide (optionally in the presence of a lithium halide), or by transformation of an organolithium reagent by reaction with a magnesium salt such as magnesium bromide etherate. A variety of groups which are inert toward the organomagnesium reagents can be present at $R^2$ and at the 5-position of the pyridazinone in these reactions.

Scheme 14

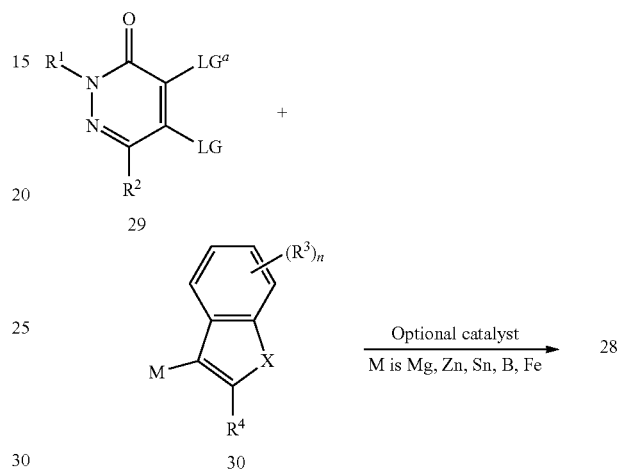

Compounds of Formula 29 are known in the art or can be prepared by methods described by Maes and Lemiere in *Comprehensive Heterocyclic Chemistry III Volume* 8, Katritsky, Ramsden, Scriven and Taylor editors and references cited therein. See also Verhelst, Ph.D. thesis University of Antwerp and references cited therein. Functional group transformations on pyridazinones are also described in Stevenson et. al. *J. Heterocyclic Chem.* 2005, 42, 427; U.S. Pat. No. 6,077,953; WO 2009/086041 and references cited therein; U.S. Pat. No. 2,782,195; WO 2013/160126; and WO 2013/050421.

Compounds of Formula 1b can also be prepared by hydrolysis of sulfonates of Formula 31 in aqueous base. Suitable bases include sodium, potassium or tetrabutylammonium hydroxide. Typical reaction temperatures range from 0 to 80° C., and typical reaction times are 1-12 hours. This method is shown in Scheme 15.

Scheme 15

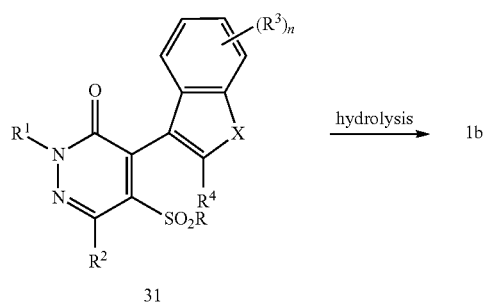

Compounds of Formula 31 can be prepared by the cyclization of compounds of Formula 32 by treatment with base.

Typical bases useful in this method include potassium, sodium or cesium carbonate. Typical solvents include acetonitrile, tetrahydrofuran or N,N-dimethylformamide. This method is shown in Scheme 16.

Scheme 16

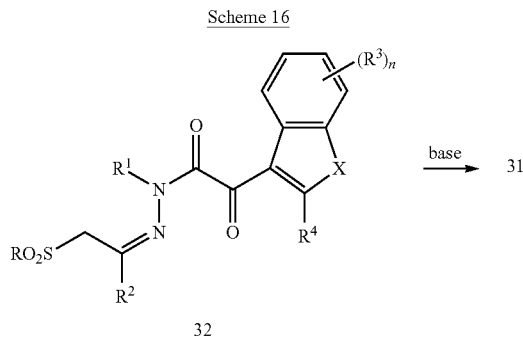

Compounds of Formula 32 can be prepared by the method shown in Scheme 17. In this method, compounds of Formula 33 are coupled with compounds of Formula 34 in the presence of a base. Bases useful in this method include triethylamine, sodium or potassium carbonate, pyridine or diisopropylethylamine.

Scheme 17

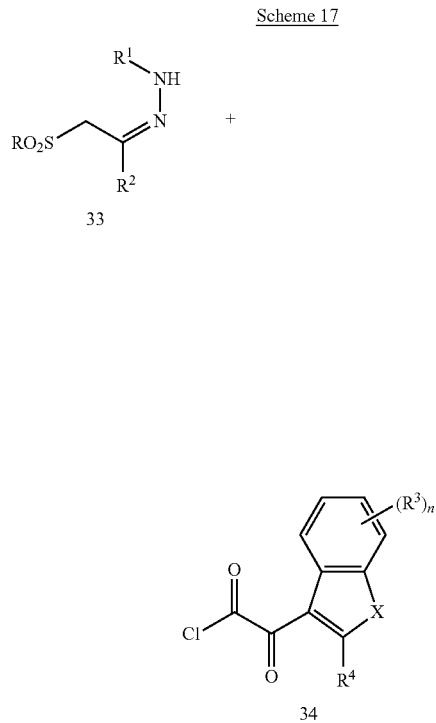

Compounds of Formula 33 can be prepared by methods known in the art.

Compounds of Formula 34 can be prepared by several methods. In one method shown in Scheme 18, compounds of Formula 35 are first treated with ClC(O)CO$_2$Me in the presence of aluminum trichloride. Subsequent hydrolysis to the carboxylic acid, followed by treatment with oxalyl chloride, provides the acyl chlorides of Formula 34.

Scheme 18

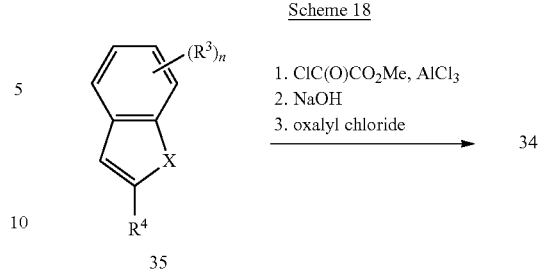

Compounds of Formula 35 are commercially available or can be prepared by methods known in the art.

As shown in Scheme 20 compounds of formula 1c can be made by rearrangement of compounds of Formula 30. This rearrangement may be carried out at temperatures between 110 and 300° C. Suitable solvents include, but are not limited to, aromatic hydrocarbons such as xylenes, diethylbenzene, and mesitylene as well as halogenated aromatics such as dichlorobenzene. Other high boiling solvents such as Dowtherm A and diglyme may be successfully employed. Many other solvents with lower boiling points can be used in conjunction with microwave heating especially when ionic liquids are added to the medium.

Scheme 20

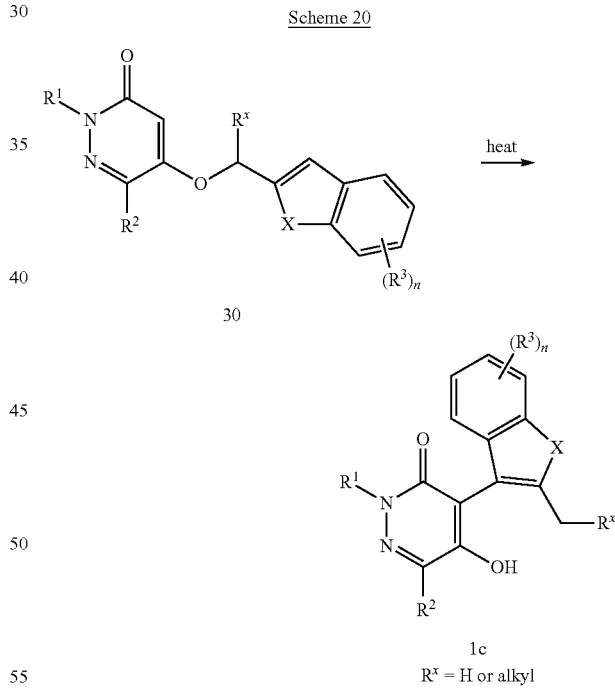

R$^x$ = H or alkyl

Compounds of Formula 30 can be prepared as shown in Scheme 21 by alkylation of pyridazinones of Formula 31 with alkyl halides of Formula 32. The reaction can be carried out in a variety of solvents such as acetone, 2-butanone, acetonitrile, dimethylacetamide, N-methylpyrrolidinone, dimethylsulfoxide and dimethylformamide. The presence of an acid acceptor such as, but not limited to, cesium carbonate, potassium carbonate, sodium carbonate, potassium hydroxide or sodium hydroxide is preferred. The leaving group Y can be halogen or sulfonate.

Scheme 21

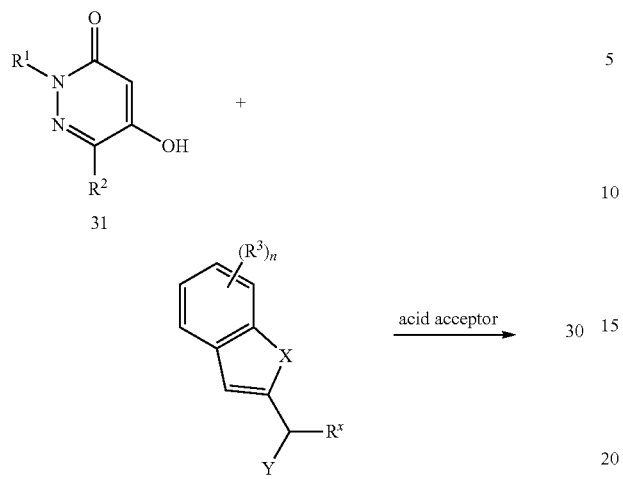

Compounds of Formula 30 may also be prepared as shown in Scheme 22 by the nucleophilic displacement reaction of pyridazinones of Formula 33 with alcohols of Formula 33. Suitable solvents include dioxanes, dimethoxyethane, tetrahydrofuran, dimethylacetamide, N-methylpyrrolidinone, dimethylsulfoxide and dimethylformamide. Suitable acid acceptors include, but are not limited to, sodium hydride, potassium hydride, potassium t-butoxide, sodium hexamethyldisilazide, potassium hexamethyldisilazide, and lithium hexamethyldisilazide.

Scheme 22

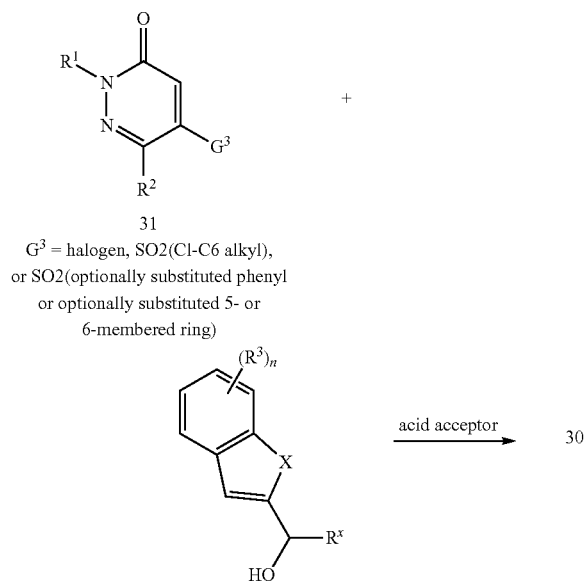

As shown in Scheme 23, pyridazinones of Formula 1a (a subset of compounds of Formula 1 where W is O) can be thionated to give the corresponding thiones of Formula 1c (i.e. Formula 1 wherein W is S) with a thionation reagent that is generally phosphorus pentasulfide in pyridine or Lawesson's reagent (2,4-bis-(4-methoxyphenyl)-1,3-dithia-2,4-diphosphetane 2,4-disulfide) in an appropriate solvent (e.g., toluene, tetrahydrofuran or dioxane) at temperatures generally ranging 0° C. to room temperature.

Scheme 23

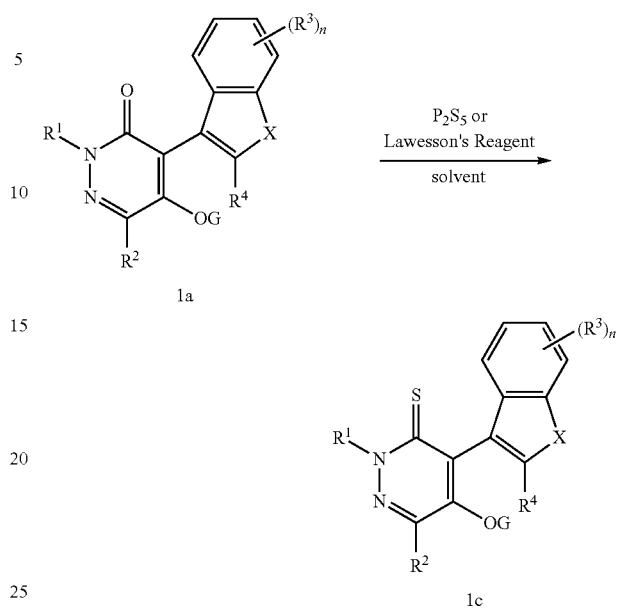

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Examples of intermediates useful in the preparation of compounds of this invention are shown in Tables I-1a through I-3d. The position(s) of the $R^3$ group(s) in Tables I-1a through I-3d is(are) based on the locant numbering shown below.

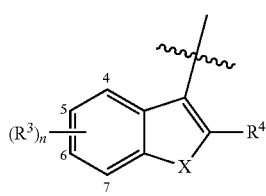

The following abbreviations are used in the Tables which follow: Me means methyl, Et means ethyl, Pr means propyl, and Ph means phenyl.

TABLE I-1a

| X is S, and R is CO₂Me. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is S, and R is CO₂Et. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is S, and R is CO₂H. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

TABLE I-1a-continued

| X is S, and R is C(O)Cl. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, and R is CO₂Me. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, and R is CO₂Et. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, and R is CO₂H. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

TABLE I-1a-continued

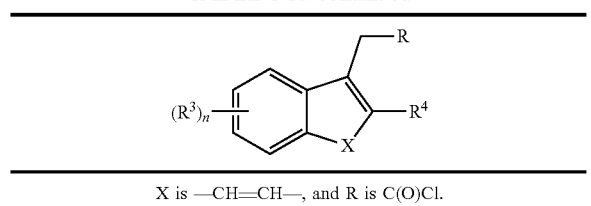

| X is —CH=CH—, and R is C(O)Cl. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CF—, and R is CO₂Me. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CF—, and R is CO₂Et. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CF—, and R is CO₂H. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

TABLE I-1a-continued

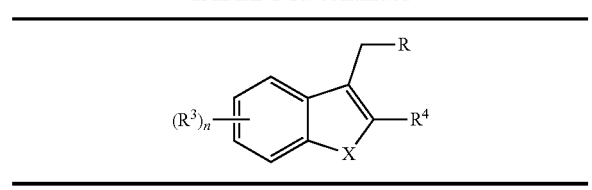

| X is —CH=CF—, and R is C(O)Cl. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

TABLE I-1b

| X is S, R¹ is Me, and R² is Me. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is S, R¹ is Me, and R² is Et. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

TABLE I-1b-continued

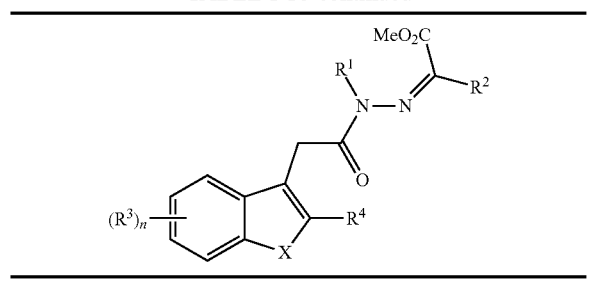

X is S, R¹ is Me, and R² is Br.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Me, and R² is I.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Me, and R² is Cl.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Me, and R² is OMe.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |

TABLE I-1b-continued

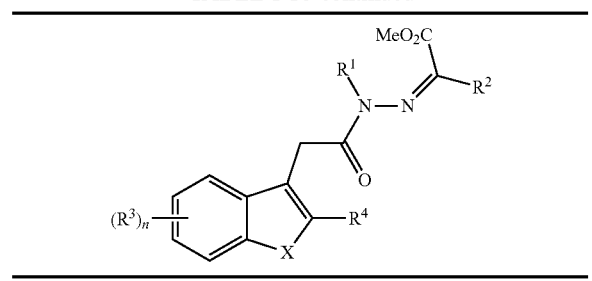

| 4,6-di-Me | Et |
| 5,7-di-Me | Et |

X is S, R¹ is Et, and R² is Me.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Et, and R² is Et.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Et, and R² is Br.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Et, and R² is I.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| — | Et |

TABLE I-1b-continued

![Structure: MeO2C-C(R2)=N-N(R1)-C(=O)-CH2- attached to benzofused heterocycle with (R3)n on benzo ring, R4 at 2-position, X as heteroatom]

| X is S, R¹ is Et, and R² is Cl. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is S, R¹ is Et, and R² is OMe. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, R¹ is Me, and R² is Me. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, R¹ is Me, and R² is Et. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, R¹ is Me, and R² is Br. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, R¹ is Me, and R² is I. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, R¹ is Me, and R² is Cl. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, R¹ is Me, and R² is OMe. | |
|---|---|
| (R³)ₙ | R⁴ |
| — | H |
| 5-Me | H |
| 4,6-di-Me | H |
| 5,7-di-Me | H |
| — | Me |
| 5-Me | Me |
| 4,6-di-Me | Me |

TABLE I-1b-continued

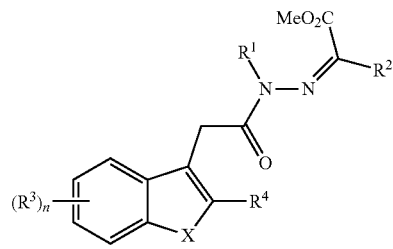

| $(R^3)_n$ | $R^4$ |
|---|---|
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is Me.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is Et.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is Br.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is I.

| $(R^3)_n$ | $R^4$ |
|---|---|
| — | H |
| 5-Me | H |
| 4,6-di-Me | H |
| 5,7-di-Me | H |
| — | Me |
| 5-Me | Me |

TABLE I-1b-continued

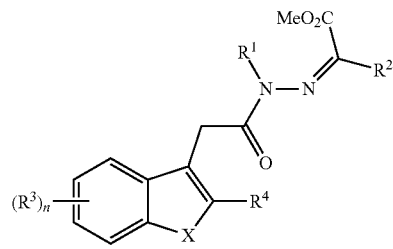

| $(R^3)_n$ | $R^4$ |
|---|---|
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is Cl.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is OMe.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CCl—, $R^1$ is Et, and $R^2$ is Me.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CCl—, $R^1$ is Et, and $R^2$ is Et.

| $(R^3)_n$ | $R^4$ |
|---|---|
| — | H |
| 5-Me | H |
| 4,6-di-Me | H |
| 5,7-di-Me | H |
| — | Me |

TABLE I-1b-continued

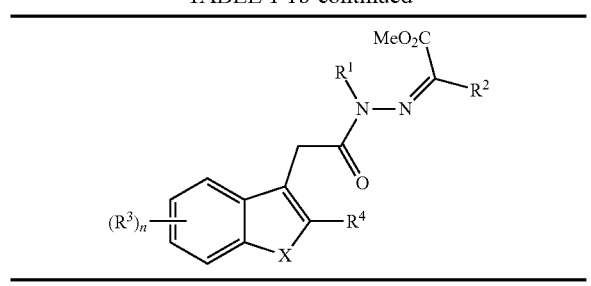

| $(R^3)_n$ | $R^4$ |
|---|---|
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CCl—, $R^1$ is Et, and $R^2$ is Br.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CCl—, $R^1$ is Et, and $R^2$ is I.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CCl—, $R^1$ is Et, and $R^2$ is Cl.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CCl—, $R^1$ is Et, and $R^2$ is OMe.

| $(R^3)_n$ | $R^4$ |
|---|---|
| — | H |
| 5-Me | H |
| 4,6-di-Me | H |
| 5,7-di-Me | H |

TABLE I-1b-continued

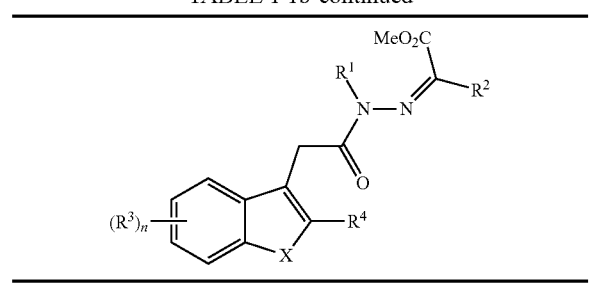

| $(R^3)_n$ | $R^4$ |
|---|---|
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

TABLE I-2a

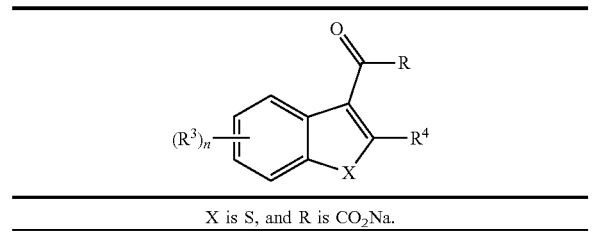

X is S, and R is $CO_2Na$.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, and R is $CO_2K$.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, and R is $CO_2H$.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |

TABLE I-2a-continued

[Structure: indole/benzofuran/benzothiophene with C(O)R at 3-position, R⁴ at 2-position, (R³)ₙ on benzene ring, X at 1-position]

| (R³)ₙ | R⁴ |
|---|---|
| 5,7-di-Me | Me |
| — | Et |
| 5-Me | Et |
| 4,6-di-Me | Et |
| 5,7-di-Me | Et |

X is S, and R is C(O)Cl.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, and R is CO₂Na.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, and R is CO₂K.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, and R is CO₂H.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, and R is C(O)Cl.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

TABLE I-2b

[Structure: indole/benzothiophene with C(O)C(O)N(R¹)—N=C(R²)CH₂SO₂Me substituent at 3-position, R⁴ at 2-position, (R³)ₙ on ring, X at 1-position]

X is S, R¹ is Me, and R² is Me.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Me, and R² is Et.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

TABLE I-2b-continued

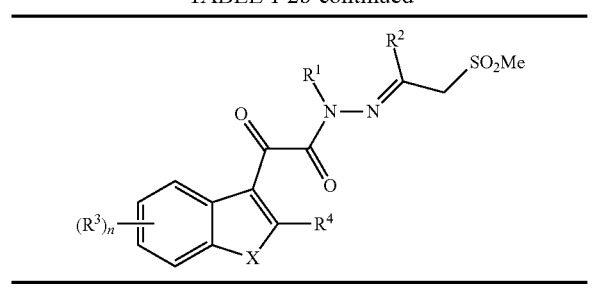

X is S, R¹ is Me, and R² is Br.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Me, and R² is I.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Me, and R² is Cl.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Me, and R² is OMe.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |

TABLE I-2b-continued

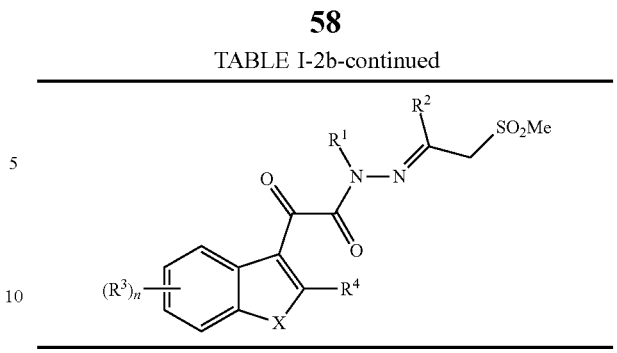

| 4,6-di-Me | Et |
| 5,7-di-Me | Et |

X is S, R¹ is Et, and R² is Me.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Et, and R² is Et.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Et, and R² is Br.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R¹ is Et, and R² is I.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |

TABLE I-2b-continued

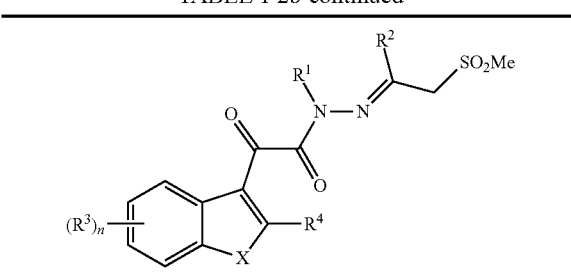

| $(R^3)_n$ | $R^4$ |
|---|---|
| 5-Me | Et |
| 4,6-di-Me | Et |
| 5,7-di-Me | Et |

| X is S, $R^1$ is Et, and $R^2$ is Cl. | |
|---|---|
| $(R^3)_n$ | $R^4$ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is S, $R^1$ is Et, and $R^2$ is OMe. | |
|---|---|
| $(R^3)_n$ | $R^4$ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, $R^1$ is Me, and $R^2$ is Me. | |
|---|---|
| $(R^3)_n$ | $R^4$ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, $R^1$ is Me, and $R^2$ is Et. | |
|---|---|
| $(R^3)_n$ | $R^4$ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |

TABLE I-2b-continued

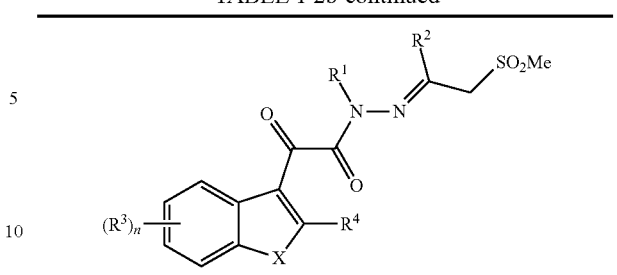

| — | Et |
| 5-Me | Et |
| 4,6-di-Me | Et |
| 5,7-di-Me | Et |

| X is —CH=CH—, $R^1$ is Me, and $R^2$ is Br. | |
|---|---|
| $(R^3)_n$ | $R^4$ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, $R^1$ is Me, and $R^2$ is I. | |
|---|---|
| $(R^3)_n$ | $R^4$ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, $R^1$ is Me, and $R^2$ is Cl. | |
|---|---|
| $(R^3)_n$ | $R^4$ |
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

| X is —CH=CH—, $R^1$ is Me, and $R^2$ is OMe. | |
|---|---|
| $(R^3)_n$ | $R^4$ |
| — | H |
| 5-Me | H |
| 4,6-di-Me | H |
| 5,7-di-Me | H |
| — | Me |
| 5-Me | Me |
| 4,6-di-Me | Me |

TABLE I-2b-continued

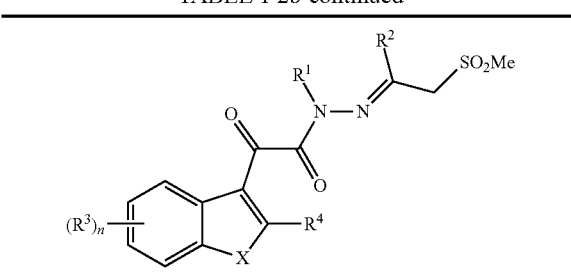

| $(R^3)_n$ | $R^4$ |
|---|---|
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is Me.

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is Et.

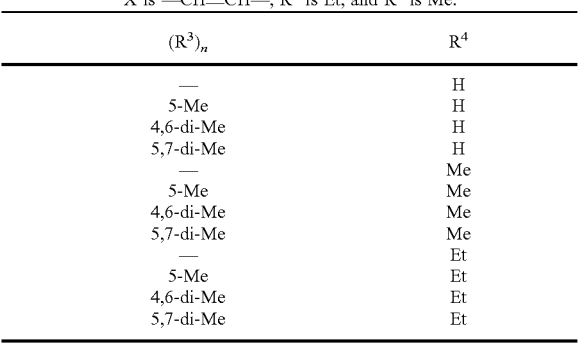

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is Br.

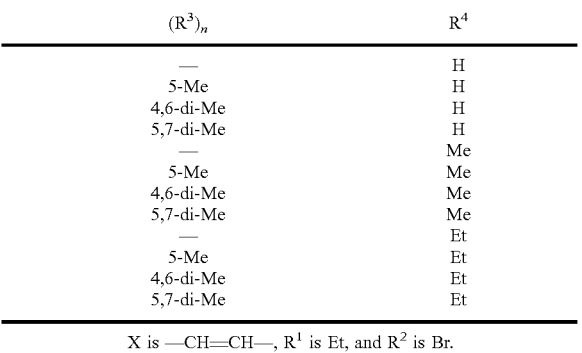

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is I.

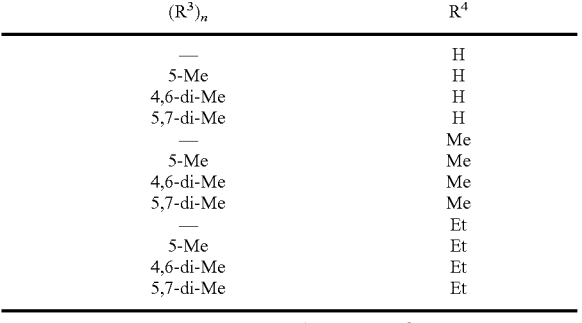

| $(R^3)_n$ | $R^4$ |
|---|---|
| — | H |
| 5-Me | H |
| 4,6-di-Me | H |
| 5,7-di-Me | H |
| — | Me |
| 5-Me | Me |

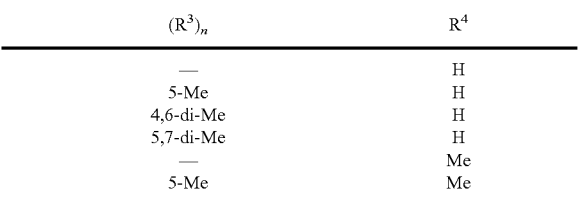

| $(R^3)_n$ | $R^4$ |
|---|---|
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is Cl.

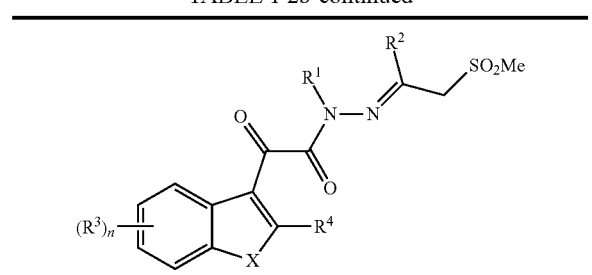

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, $R^1$ is Et, and $R^2$ is OMe.

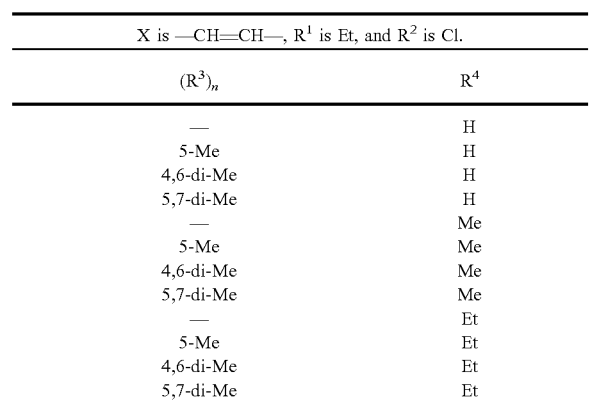

| $(R^3)_n$ | $R^4$ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

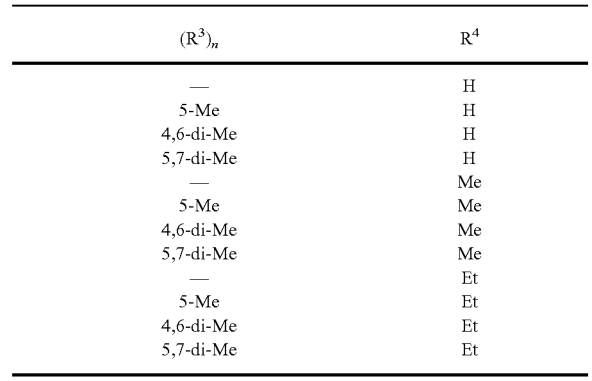

Table I-2c

Table I-2c is identical to Table I-2b, except that $R^1$ is —SO$_2$Ph.

Table I-2d

Table I-2d is identical to Table I-2b, except that $R^1$ is —SO$_2$(4-methylphenyl).

Table I-2e

Table I-2e is identical to Table I-2b, except that $R^1$ is —SO$_2$(4-chlorophenyl).

TABLE I-3a

X is S, R is Me, R¹ is Me, and R² is Me.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R is Me, R¹ is Me, and R² is Et.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R is Me, R¹ is Me, and R² is Br.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R is Me, R¹ is Me, and R² is I.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

TABLE I-3a-continued

| | Et |
| | Et |

X is S, R is Me, R¹ is Me, and R² is Cl.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R is Me, R¹ is Me, and R² is OMe.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R is Me, R¹ is Et, and R² is Me.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R is Me, R¹ is Et, and R² is Et.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |

TABLE I-3a-continued

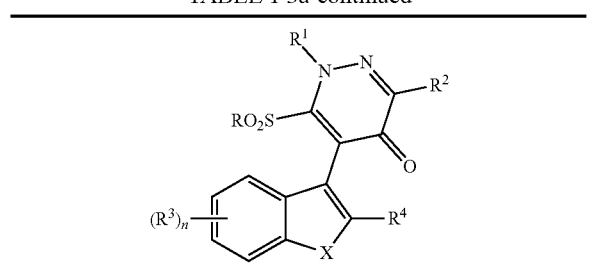

| (R³)ₙ | R⁴ |
|---|---|
| 5-Me | Et |
| 4,6-di-Me | Et |
| 5,7-di-Me | Et |

X is S, R is Me, R¹ is Et, and R² is Br.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R is Me, R¹ is Et, and R² is I.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R is Me, R¹ is Et, and R² is Cl.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is S, R is Me, R¹ is Et, and R² is OMe.

| (R³)ₙ | R⁴ |
|---|---|
| — | H |
| 5-Me | H |
| 4,6-di-Me | H |
| 5,7-di-Me | H |
| — | Me |
| 5-Me | Me |

TABLE I-3a-continued

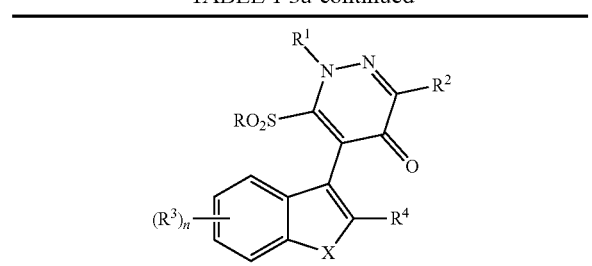

| (R³)ₙ | R⁴ |
|---|---|
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Me, and R² is Me.

| (R3)n | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Me, and R² is Et.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Me, and R² is Br.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Me, and R² is I.

| (R³)ₙ | R⁴ |
|---|---|
| — | H |
| 5-Me | H |
| 4,6-di-Me | H |
| 5,7-di-Me | H |
| — | Me |

TABLE I-3a-continued

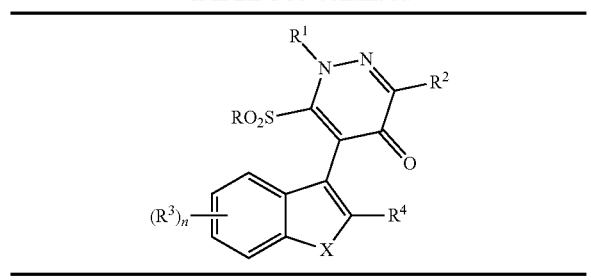

| (R³)ₙ | R⁴ |
|---|---|
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Me, and R² is Cl.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Me, and R² is OMe.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Et, and R² is Me.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Et, and R² is Et.

| (R³)ₙ | R⁴ |
|---|---|
| — | H |
| 5-Me | H |
| 4,6-di-Me | H |
| 5,7-di-Me | H |

TABLE I-3a-continued

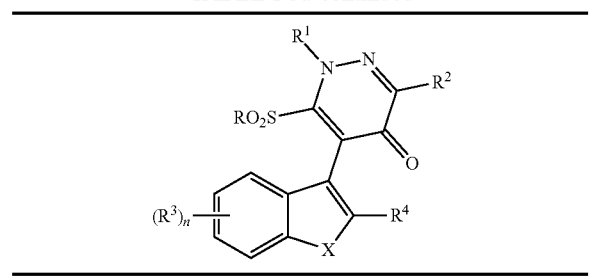

| (R³)ₙ | R⁴ |
|---|---|
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Et, and R² is Br.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Et, and R² is I.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Et, and R² is Cl.

| (R³)ₙ | R⁴ |
|---|---|
| — | H |
| 5-Me | H |
| 4,6-di-Me | H |
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

X is —CH=CH—, R is Me, R¹ is Et, and R² is OMe.

| (R³)ₙ | R⁴ |
|---|---|
| — | H |
| 5-Me | H |
| 4,6-di-Me | H |

TABLE I-3a-continued

[Structure: Pyridazinone with R¹, R², R³, R⁴, RO₂S, and X substituents on fused bicyclic ring]

| | |
|---|---|
| 5,7-di-Me | H |
| — | Me |
| 5-Me | Me |
| 4,6-di-Me | Me |
| 5,7-di-Me | Me |
| — | Et |
| 5-Me | Et |
| 4,6-di-Me | Et |
| 5,7-di-Me | Et |

Table I-3b

Table I-3b is identical to Table I-3a, except that R is phenyl.

Table I-3c

Table I-3c is identical to Table I-3a, except that R is 4-methylphenyl.

Table I-3d

Table I-3d is identical to Table I-3a, except that R is 4-chlorophenyl.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in CDCl$_3$ solution unless indicated otherwise; "s" means singlet, "d" means doublet, "t" means triplet, "q" means quartet, "m" means multiplet, and "br s" means broad singlet.

Synthesis Example 1

Preparation of 4-(2,5-dimethylbenzo[b]thien-3-yl)-5-hydroxy-2,6-dimethyl-3(2H)-pyridazinone (Compound 1)

Step A: Preparation of Ethyl 4-[(4-methylphenyl)thio]-3-oxopentanoate

To a mixture of potassium carbonate (1.11 g, 8.03 mmol) in N,N-dimethylformamide (DMF) (27 mL) at room temperature under nitrogen (i.e. under a nitrogen atmosphere) was added 4-methylbenzenethiol (0.626 g, 5.04 mmol). The mixture was cooled to 0° C., and then ethyl 4-bromo-3-oxopentanoate (1.25 g, 5.04 mmol) was added dropwise by syringe over 10 minutes. The mixture was allowed to warm to room temperature while being stirred for 16 h. Then the mixture was poured into aqueous hydrochloric acid (0.2 M, 80 mL) and extracted with diethyl ether (3×50 mL). The combined extracts were dried (MgSO$_4$) and concentrated. The crude residue was purified by flash chromatography (gradient of 0 to 10% of ethyl acetate in hexanes) to yield the title product as a yellow oil (0.82 g).

$^1$H NMR δ 7.27-7.31 (m, 2H), 7.12 (m, 2H), 4.18 (m, 2H), 3.82 (q, 1H), 3.64-3.77 (m, 2H), 2.33 (s, 3H), 1.38 (d, 3H), 1.24-1.30 (m, 3H).

Step B: Preparation of Ethyl 2,5-dimethylbenzo[b]thiophene-3-acetate

Polyphosphoric acid (1 mL) was added to chlorobenzene (anhydrous, 20 mL), and the mixture was heated to reflux under nitrogen. To the mixture was added ethyl 4-[(4-methylphenyl)thio]-3-oxopentanoate (i.e. the product of Step A) (0.82 g, 3.08 mmol) dropwise via syringe over about 30 minutes. The mixture was held at reflux for 16 h. The mixture was then cooled to room temperature, and the upper, chlorobenzene layer was decanted to a separate flask and concentrated. The crude residue was purified by flash chromatography (gradient of 0 to 10% ethyl acetate in hexanes) to yield the title product as a white solid (0.33 g).

$^1$H NMR δ 7.61 (d, 1H), 7.46 (s, 1H), 7.10-7.12 (m, 1H), 4.10-4.17 (m, 2H), 3.74 (s, 2H), 2.53 (s, 3H), 2.46 (s, 3H), 1.22-1.25 (m, 3H).

Step C: Preparation of 2,5-dimethylbenzo[b]thiophene-3-acetic Acid

Ethyl 2,5-dimethylbenzo[b]thiophene-3-acetate (i.e. the product of Step B) (0.33 g, 1.33 mmol) was dissolved in methanol (50 mL), and aqueous sodium hydroxide (2 M, 5 mL, 10 mmol) was added. The mixture was heated to reflux for 3 h. The mixture was then cooled, and the solvent was removed by rotary evaporation. To the residue was added water (50 mL), and the pH was brought to ~1 by the careful addition of concentrated hydrochloric acid. The mixture was then extracted with dichloromethane (3×50 mL), and the combined organic extracts were dried (MgSO$_4$), filtered and concentrated by rotary evaporation to yield the title product as a white solid (0.26 g).

$^1$H NMR δ 7.62 (d, 1H), 7.43 (s, 1H), 7.11 (m, 1H), 3.78 (s, 2H), 2.53 (s, 3H), 2.46 (s, 3H).

Step D: Preparation of Methyl 2-(2-methylhydrazinylidene)propanoate

To a suspension of methyl 2-oxopropanoate (17.0 mL, 169 mmol) and magnesium sulfate (20.46 g, 170 mmol) in trichloromethane (250 mL) chilled to 0° C. was added a solution of methylhydrazine (9.0 mL, 166 mmol) in trichloromethane (50 mL). The reaction mixture was then warmed to room temperature. After stirring for 24 h at room temperature, the reaction mixture was filtered. The filtrate was concentrated under reduced pressure to give the title product as a yellow solid (21.16 g) that was used directly in the next step without further purification. A portion of this sample was later purified by flash chromatography to provide an off-white solid.

$^1$H NMR δ 5.63 (br s, 1H), 3.82 (s, 3H), 3.22-3.24 (m, 3H), 1.93 (s, 3H).

Step E: Preparation of Methyl 2-[2-[2-(2,5-dimethylbenzo[b]thien-3yl)acetyl]-2-methylhydrazinylidene]propanoate To a solution of 2,5-dimethylbenzo[b]thiophene-3-acetic acid (i.e. the product of Step C) (0.26 g, 1.2 mmol) in dichloromethane (40 mL) was added oxalyl chloride (0.25 mL, 3.0 mmol) followed by a catalytic amount of DMF (3 drops). This mixture is allowed to stir for 2 h under nitrogen and then concentrated by rotary evaporation. The residue, comprising the acid chloride, was dissolved in acetonitrile (25 mL) and added dropwise over 15 min. to a mixture of methyl 2-(2-methylhydrazinylidene)propanoate (i.e. the product of Step D) (0.20 g, 1.5 mmol) and potassium carbonate (0.28 g, 2.0 mmol) in acetonitrile (20 mL) cooled to 0° C. under nitrogen. The reaction mixture was then allowed to warm to room temperature and stirred for 64 h. The solvent was removed by rotary evaporation, and water (50 mL) was added to the residue. The aqueous phase was extracted with ethyl acetate (3×50 mL), and the combined organic extracts were washed with brine (i.e. saturated aqueous sodium chloride) (50 mL), dried ($MgSO_4$), filtered and concentrated by rotary evaporation. The residue was purified by flash chromatography (gradient of 10 to 50% ethyl acetate in hexanes) to yield a white solid (0.23 g).
$^1$H NMR δ 7.55-7.61 (m, 1H), 7.45-7.46 (m, 1H), 7.04-7.09 (m, 1H), 4.08-4.17 (m, 2H), 3.88 (s, 3H), 3.34 (s, 3H), 2.51 (s, 3H), 2.42 (s, 3H), 2.20 (s, 3H).

Step F: Preparation of 4-(2,5-dimethylbenzo[b]thien-3-yl)-5-hydroxy-2,6-dimethyl-3(2H)-pyridazinone A solution of methyl 2-[2-[2-(2,5-dimethylbenzo[b]thien-3yl)acetyl]-2-methylhydrazinylidene]propanoate (i.e. the product of Step E) (0.23 g, 0.69 mmol) in DMF (anhydrous, 3 mL) was added via syringe pump over a period of 30 minutes to a tetrahydrofuran solution of potassium tert-butoxide (3.0 mL, 3 mmol) cooled to 0° C. under nitrogen. The reaction mixture was then allowed to warm to room temperature while being stirred for 1 h. The reaction mixture was poured into aqueous hydrochloric acid (0.5 M, 100 mL) and extracted with ethyl acetate (3×50 mL). The combined organic extracts were washed with brine (50 mL), dried ($MgSO_4$), filtered and concentrated by rotary evaporation to yield a crude residue (0.40 g), which was purified by flash chromatography (gradient of 0 to 40% ethyl acetate in hexanes) to yield the title product, a compound of the present invention, as a white solid (118 mg).
$^1$H NMR δ 7.60 (d, 1H), 7.09 (m, 1H), 7.02 (s, 1H), 6.91 (br s, 1H), 3.52 (s, 3H), 2.39 (s, 3H), 2.21 (s, 3H), 2.17 (s, 3H).

Synthesis Example 2

Preparation of 4-(2,5-dimethyl-3-benzofuranyl)-5-hydroxy-2,6-dimethyl-3 (2H)-pyridazinone (Compound 7)

Step A: Preparation of Methyl 2-(2-methoxy-1-methyl-2-oxoethoxy)-5-methylbenzoate A mixture of methyl 2-hydroxy-5-methylbenzoate (11.89 g, 71.5 mmol), methyl 2-bromopropanoate (13.03 g, 78.0 mmol) and potassium carbonate (29.71 g, 215 mmol) in acetone (300 mL) was heated under reflux for 18 h. The reaction mixture was then filtered, and the filtrate was concentrated by rotary evaporation to yield the title product as a white solid (18.9 g).
$^1$H NMR δ 7.61 (s, 1H), 7.15-7.24 (m, 1H), 6.70-6.84 (m, 1H), 4.73 (m, 1H), 3.89 (s, 3H), 3.74 (s, 3H), 2.30 (s, 3H), 1.63-1.65 (d, 3H).

Step B: Preparation of 2-(1-carboxyethoxy)-5-methylbenzoic Acid

A solution of methyl 2-(2-methoxy-1-methyl-2-oxoethoxy)-5-methylbenzoate (i.e. the product of Step A) (18.9 g, 71.5 mmol) in a mixture of tetrahydrofuran (100 mL), methanol (100 mL) and aqueous NaOH solution (6 M, 100 mL) was heated to reflux for 16 h. Then the reaction mixture was cooled and concentrated by rotary evaporation. The residue was dissolved in water (150 mL) and acidified with aqueous concentrated hydrochloric acid to pH<2. The aqueous phase was extracted with ethyl acetate (2×125 mL). The combined organic extracts were washed with brine, dried ($MgSO_4$), filtered and concentrated by rotary evaporation to yield the title product as a yellow solid (16.31 g), which was used in Step C without further purification.
$^1$H NMR δ 7.91 (d, 1H), 7.36 (m, 1H), 6.90 (d, 1H), 4.99 (m, 1H), 2.34 (s, 3H), 1.75-1.80 (m, 3H).

Step C: Preparation of 2,5-dimethyl-3-benzofuranyl Acetate

A mixture of 2-(1-carboxyethoxy)-5-methylbenzoic acid (i.e. the product of Step B) (16.3 g, 71 mmol), acetic anhydride (145 mL) and sodium acetate (11.93 g, 145 mmol) was heated at reflux for 3 h. After cooling, the mixture was added to water (300 mL) and extracted with dichloromethane (2×150 mL). The organic extracts were dried ($MgSO_4$) and filtered, and the filtrate was concentrated by rotary evaporation to yield the title product as a light brown oil (14.43 g), which was used in Step D without further purification.
$^1$H NMR δ 7.22-7.25 (m, 1H), 7.07-7.11 (m, 1H), 7.01-7.04 (m, 1H), 2.41 (s, 3H), 2.37 (s, 3H), 2.34 (s, 3H).

Step D: Preparation of 2,5-dimethyl-3(2H)-benzofuranone

A mixture of 2,5-dimethyl-3-benzofuranyl acetate (i.e. the product of Step C) (14.40 g, 70.5 mmol), methanol (150 mL) and aqueous hydrochloric acid (1.0 M, 40 mL, 40 mmol) was heated at reflux under nitrogen. The reaction mixture was then concentrated by rotary evaporation. The residue was diluted with water and extracted with diethyl ether (2×100 mL). The combined organic extracts were washed with water and brine, dried ($MgSO_4$), filtered and concentrated. The residue was purified by flash chromatography (gradient of 0 to 15% ethyl acetate in hexanes) to yield the title product as a white solid (7.47 g).
$^1$H NMR δ 7.41-7.46 (m, 2H), 6.99-7.02 (m, 1H), 4.60-4.64 (q, 1H), 2.35 (s, 3H), 1.50-1.54 (d, 3H).

Step E: Preparation of Methyl 2,5-dimethyl-3-benzofuranacetate

A mixture of 2,5-dimethyl-3(2H)-benzofuranone (i.e. the product of Step D) (7.45 g, 45.9 mmol), methyl 2-(triphenylphosphoranylidine)acetate (20.43 g, 61.1 mmol) and toluene (300 mL) were heated at reflux for 66 h. The reaction mixture was then concentrated by rotary evaporation, and diethyl ether (200 mL) was added to the crude residue. This mixture was filtered to remove solids, and the filtrate was concentrated by rotary evaporation to leave an oily mixture (18 g). To this residue were added methanol (40 mL) and a methanolic hydrogen chloride solution (0.5 M, 60 mL, 30 mmol), and the mixture is heated to reflux for 16 h. Then the reaction mixture was cooled and concentrated by rotary evaporation. The residue was purified by flash chromatography (gradient of 0 to 10% ethyl acetate in hexanes) to provide the title product as a yellow oil (6.75 g).

$^1$H NMR δ 7.19-7.27 (m, 2H), 6.98-7.05 (m, 1H), 3.693 (s, 3H), 3.584 (s, 2H), 2.40-2.45 (m, 6H).

Step F: Preparation of 2,5-dimethyl-3-benzofuranacetic Acid

Aqueous sodium hydroxide (5 M, 33 mL, 165 mmol) was added to a solution of methyl 2,5-dimethyl-3-benzofuranacetate (i.e. the product of Step E) (6.75 g, 30.9 mmol) in methanol (120 mL). The mixture was heated to reflux for 16 h and then cooled. The solvent was removed by rotary evaporation. To the residue was added diethyl ether (100 mL), and the resultant mixture was extracted with aqueous sodium hydroxide (1 N, 2×100 mL). The ether layer is discarded, and the combined aqueous extracts were acidified with concentrated aqueous hydrochloric acid to pH 1. The acidic aqueous mixture obtained was extracted with dichloromethane (2×125 mL). The combined organic extracts were washed with brine (100 mL), dried (MgSO$_4$), filtered and concentrated by rotary evaporation to yield the title product as a yellow solid (4.93 g), which was used in Step G without further purification.

$^1$H NMR δ 7.22-7.28 (m, 2H), 6.99-7.05 (m, 1H), 3.61 (s, 2H), 2.42 (s, 3H), 2.41 (s, 3H).

Step G: Preparation of Methyl 2-[2-[2-(2,5-dimethyl-3-benzofuranyl)acetyl]-2-methylhydrazinylidene]propanoate To a solution of 2,5-dimethyl-3-benzofuranacetic acid (i.e. the product of Step F) (4.14 g, 20.2 mmol) in dichloromethane (120 mL) was added oxalyl chloride (2.56 mL, 30.0 mmol) followed by a catalytic amount of DMF (5 drops). The resultant mixture was allowed to stir for 2 h under nitrogen and was then concentrated by rotary evaporation to leave a residue comprising the acid chloride. The residue was dissolved in acetonitrile (50 mL) and added dropwise over 25 min from an addition funnel to a mixture of methyl 2-(2-methylhydrazinylidene)propanoate (2.81 g, 21.6 mmol) and potassium carbonate (3.18 g, 23.0 mmol) in acetonitrile (30 mL) cooled to 0° C. under nitrogen. The reaction mixture was then allowed to warm to room temperature and stirred for 64 h. The solvent was removed by rotary evaporation, and water (150 mL) was added to the residue. The resultant mixture was extracted with ethyl acetate (3×80 mL), and the combined organic extracts were washed with brine (50 mL), dried (MgSO$_4$), filtered and concentrated by rotary evaporation. The residue was purified by flash chromatography (gradient of 10 to 100% ethyl acetate in hexanes) to yield the title product as a white solid (3.08 g).

$^1$H NMR δ 7.32 (m, 1H), 7.22-7.24 (m, 1H), 6.98-6.99 (m, 1H), 3.96 (s, 2H), 3.90 (s, 3H), 3.35 (s, 3H), 2.40 (m, 6H), 2.20 (s, 3H).

Step H: Preparation of 4-(2,5-dimethyl-3-benzofuranyl)-5-hydroxy-2,6-dimethyl-3 (2H)-pyridazinone A solution of methyl 2-[2-[2-(2,5-dimethyl-3-benzofuranyl)acetyl]-2-methylhydrazinylidene]propanoate (i.e. the product of Step G) (2.97 g, 9.39 mmol) anhydrous DMF (25 mL) was added over 30 min from an addition funnel to a tetrahydrofuran solution of potassium tert-butoxide (25.0 mL, 25.0 mmol) cooled to 0° C. under nitrogen. The reaction mixture was then allowed to warm to room temperature and stirred for 1 h. The reaction mixture was poured into aqueous hydrochloric acid (0.5 M, 150 mL) and extracted with ethyl acetate (3×90 mL). The combined organic extracts were washed with brine (100 mL), dried (MgSO$_4$), filtered and concentrated by rotary evaporation. The residue was purified by flash chromatography (gradient of 10 to 75% ethyl acetate in hexanes) to yield the title product, a compound of the present invention, as a white solid (790 mg).

$^1$H NMR (DMSO-d$_6$) δ 10.29 (s, 1H), 7.39 (m, 1H), 7.04 (m, 1H), 6.95-7.01 (m, 1H), 3.60 (s, 3H), 2.32 (s, 3H), 2.25 (m, 6H).

Synthesis Example 3

Preparation of 5-hydroxy-2,6-dimethyl-4-(2,5,7-trimethyl-3-benzofuranyl)-3(2H)-pyridazinone (Compound 12)

Step A: Preparation of 2,4-dimethylphenyl Propanoate

Propanoyl chloride (2.44 g, 26.4 mmol) was added dropwise to a mixture of 2,4-dimethylphenol (3.26 g, 24 mmol) and triethylamine (3.51 mL, 25 mmol) in dichloromethane (35 mL) cooled to 0° C. under nitrogen. The mixture was stirred for 16 h, and then aqueous hydrochloric acid (0.2 M, 50 mL) was added. The organic phase was separated, and the aqueous phase was extracted with dichloromethane (50 mL). The combined organic phases were washed with brine, dried (MgSO$_4$), filtered and concentrated to yield the title product as a yellow oil (3.91 g), which was used directly in the next step without further purification.

$^1$H NMR δ 7.03 (s, 1H), 6.99 (d, 1H), 6.87 (d, 1H), 2.56-2.62 (m, 2H), 2.30 (s, 3H), 2.14 (s, 3H), 1.26-1.31 (m, 3H).

Step B: Preparation of 1-(2-hydroxy-3,5-dimethylphenyl)-1-propanone

Aluminum chloride (3.10 g, 23.2 mmol) was added to 2,4-dimethylphenyl propanoate (i.e. the product of Step A) (3.91 g, 21.9 mmol), and the mixture formed was heated to 130° C. for 2 h. The mixture was then cooled to room temperature, and aqueous hydrochloric acid (1.0 M, 100 mL) was added, followed by diethyl ether (100 mL). The organic phase was separated, and the aqueous phase was extracted with diethyl ether (50 mL). The combined organic extracts were dried (MgSO$_4$), filtered and concentrated to yield the title product as a yellow crystalline solid (3.71 g), which was used directly in the next step without further purification.

$^1$H NMR δ 12.49 (s, 1H), 7.40 (s, 1H), 7.16 (s, 1H), 3.03 (m, 2H), 2.29 (s, 3H), 2.23 (s, 3H), 1.22-1.25 (m, 3H).

Step C: Preparation of 2-bromo-1-(2-hydroxy-3,5-methylphenyl)-1-propanone

To mixture of copper(II) bromide (9.30 g, 41.6 mmol) in ethyl acetate (30 mL) was added dropwise from an addition funnel a solution of 1-(2-hydroxy-3,5-dimethylphenyl)-1-propanone (i.e. the product of Step B) (3.71 g, 20.8 mmol) dissolved in trichloromethane (24 mL). The resultant mixture was heated to reflux for 16 h, then cooled to room temperature and filtered through a filter funnel packed with Celite® diatomaceous filter aid. The filtrate was concentrated, and the residue was diluted with diethyl ether (100 mL) and washed with saturated aqueous ethylenediaminetetraacetic acid disodium salt solution (100 mL). The organic phase was dried (MgSO$_4$), filtered and concentrated by rotary evaporation to yield the title product as a brown oil (5.33 g), which was used directly in the next step without further purification.

$^1$H NMR δ 12.09 (s, 1H), 7.39-7.44 (m, 1H), 7.18-7.23 (m, 1H), 5.31-5.40 (m, 1H), 2.29 (s, 3H), 2.24 (s, 3H), 1.90 (d, 3H).

Step D: Preparation of 2,5,7-trimethyl-3(2H)-benzofuranone

N,N-dimethylformamide (25 mL) and potassium carbonate (4.15 g, 30 mmol) were added to 2-bromo-1-(2-hydroxy-3,5-methylphenyl)-1-propanone (i.e. the product of Step C) (5.33 g, 20.7 mmol), and the resultant mixture was stirred at room temperature for 18 h. Then water (150 mL) was added, and the mixture was extracted with diethyl ether (3×80 mL). The combined organic extracts were washed with water, followed by brine, dried (MgSO$_4$), filtered and concentrated. The residue was purified by flash chromatography (eluted with gradient of 0 to 10% ethyl acetate in hexanes) to yield the title product as a yellow oil (2.13 g).

$^1$H NMR δ 7.26-7.28 (m, 1H), 7.24-7.26 (m, 1H), 4.59-4.64 (m, 1H), 2.32 (s, 3H), 2.29 (s, 3H), 1.52 (d, 3H).

Step E: Preparation of Methyl 2,5,7-trimethyl-3-benzofuranacetate

A mixture of 2,5,7-trimethyl-3(2H)-benzofuranone (i.e. the product of Step D) (2.07 g, 11.7 mmol), methyl 2-(triphenylphosphoranylidene)acetate (5.89 g, 17.6 mmol) and toluene (120 mL) were heated at reflux for 66 h. The reaction mixture was then concentrated by rotary evaporation, and to the residue was added diethyl ether (150 mL). The resultant mixture was filtered to remove solids, and the filtrate was concentrated by rotary evaporation to leave an oily mixture (6 g). To this residue were added methanol (100 mL) and a methanol solution of hydrogen chloride (0.5 M, 30 mL, 15 mmol). The resultant mixture was heated to reflux for 16 h and then cooled. The mixture was concentrated by rotary evaporation to leave a residue which was purified by flash chromatography (gradient of 0 to 5% ethyl acetate in hexanes) to yield the title product as a yellow oil (0.59 g), with was used without further purification in the next step.

$^1$H NMR δ 7.06 (s, 1H), 6.83 (s, 1H), 3.68 (s, 3H), 3.57 (s, 2H), 2.44 (s, 3H), 2.42 (s, 3H), 2.39 (s, 3H).

Step F: Preparation of 2,5,7-trimethyl-3-benzofuranacetic Acid

To a solution of methyl 2,5,7-trimethyl-3-benzofuranacetate (i.e. the product of Step E) (0.55 g, 2.37 mmol) in methanol (50 mL) was added aqueous sodium hydroxide (5 M, 2 mL, 10 mmol). The resultant mixture was heated to reflux for 16 h and then cooled. The solvent was removed by rotary evaporation. To the residue was added diethyl ether (100 mL), and the resultant mixture was extracted with aqueous sodium hydroxide (1 N, 2×100 mL). The ether layer was discarded, and the combined basic extracts were acidified with concentrated aqueous hydrochloric acid to a pH of 1. The acidic aqueous mixture was then extracted with dichloromethane (2×125 mL). The combined organic extracts were dried (MgSO$_4$), filtered and concentrated by rotary evaporation to yield the title product as a yellow solid (0.52 g), which was used in the next step without further purification.

$^1$H NMR δ 7.05 (s, 1H), 6.84 (s, 1H), 3.60 (s, 2H), 2.43 (s, 3H), 2.41 (s, 3H), 2.38 (s, 3H).

Step G: Preparation of 2,5,7-trimethyl-3-benzofuranacetic acid 2-(2-methoxy-1-methyl-2-oxoethylidene)-1-methylhydrazide To a solution of 2,5,7-trimethyl-3-benzofuranacetic acid (i.e. the product of Step F) (0.52 g, 2.38 mmol) in dichloromethane (80 mL) was added oxalyl chloride (0.5 mL, 6.0 mmol), followed by a catalytic amount of DMF (3 drops). The resultant mixture was allowed to stir for 2 h under nitrogen and then was concentrated by rotary evaporation. The residue, which contained 2,5,7-trimethyl-3-benzofuranacetyl chloride, was dissolved in acetonitrile (50 mL) and added dropwise over 25 min from an addition funnel to a mixture of methyl 2-(2-methylhydrazinylidene)propanoate (0.35 g, 2.7 mmol) and potassium carbonate (0.69 g, 5.0 mmol) in acetonitrile (30 mL) cooled to 0° C. under nitrogen. Then the reaction mixture was allowed to warm to room temperature and stir for 18 h. The solvent was removed by rotary evaporation, and to the residue was added water (90 mL). The resultant mixture was extracted with ethyl acetate (3×50 mL), and the combined organic extracts were washed with brine (50 mL), dried (MgSO$_4$), filtered and concentrated by rotary evaporation. The residue was purified by flash chromatography (gradient of 5 to 50% ethyl acetate in hexanes) to yield the title product as a yellow solid (0.32 g).

$^1$H NMR δ 7.14 (s, 1H), 6.80 (s, 1H), 3.95 (s, 2H), 3.90 (s, 3H), 3.35 (s, 3H), 2.42 (s, 3H), 2.41 (s, 3H), 2.36 (s, 3H), 2.19 (s, 3H).

Step H: Preparation of 5-hydroxy-2,6-dimethyl-4-(2,5,7-trimethyl-3-benzofuranyl)-3 (2H)-pyridazinone A solution of 2,5,7-trimethyl-3-benzofuranacetic acid 2-(2-methoxy-1-methyl-2-oxoethylidene)-1-methylhydrazide (i.e. the product of Step G) (0.31 g, 1.0 mmol) in N,N-dimethylformamide (anhydrous, 5 mL) was added by syringe pump over 1 h to a tetrahydrofuran solution of potassium tert-butoxide (1 M, 5.0 mL, 5.0 mmol) cooled to 0° C. under nitrogen. The reaction mixture was allowed to warm to room temperature and stirred for 1 h. The mixture was then poured into aqueous hydrochloric acid (0.5 M, 60 mL) and extracted with ethyl acetate (3×50 mL). The combined organic extracts were washed with brine (60 mL), dried (MgSO$_4$), filtered and concentrated by rotary evaporation. The resultant residue was purified by flash chromatography (gradient of 5 to 100% ethyl acetate in hexanes) to yield the title product, a compound of the present invention, as a white solid (72.3 mg).

$^1$H NMR δ 6.88 (s, 1H), 6.84 (s, 1H), 5.86 (br s, 1H), 3.74 (s, 3H), 2.48 (s, 3H), 2.38 (s, 3H), 2.36 (s, 3H), 2.34 (s, 3H).

Synthesis Example 4

Preparation of 4-(2,3-dimethyl-1-naphthalenyl)-5-hydroxy-6-methoxy-2-methyl-3(2H)-pyridazinone (Compound 46)

Step A: Preparation of 5-chloro-4,6-dimethoxy-2-methyl-3(2H)-pyridazinone 4,5-Dichloro-6-methoxy-2-methyl-3(2H)-pyridazinone (2.00 g, 9.57 mmol) and sodium methoxide (2.00 mL of a 25 wt % solution in MeOH) were combined in 1,4-dioxane (20 mL) and stirred at room temperature overnight. The solution was then concentrated to 50% volume and partitioned between water (100 mL) and ethyl acetate (100 mL). The aqueous layer was extracted with ethyl acetate (3×100 mL). The organic layers were combined, washed with brine, dried over MgSO$_4$ and concentrated. The resulting residue was absorbed onto silica gel (1 g) and purified by MPLC with a 0-100% ethyl acetate/hexane gradient through a pre-packed 40 g silica gel column. The fractions containing pure desired product were concentrated in vacuo to yield 1.78 g of the title compound as a white solid.

Step B: Preparation of 5-chloro-4-(2,3-dimethyl-1-naphthalenyl)-6-methoxy-2-methyl-3 (2H)-pyridazinone In a 2-neck 100 mL RB flask flushed with nitrogen fitted with a thermometer, 1-bromo-2,3-dimethylnaphthalene (1.41 g, 6.01 mmol) was dissolved in anhydrous tetrahydrofuran (15 mL) and cooled over a dry ice/acetone bath to −78° C. N-Butyllithium (2.4 mL of a 2.5M solution in hexane) was added dropwise over 15 minutes, and the reaction mixture was stirred at −78° C. for 5 minutes. The cooling bath was then removed and the solution was allowed to warm to −50° C. Magnesium bromide etherate (1.55 g, 6.01 mmol) was then added in one portion, and the reaction mixture was stirred and warmed to −20° C. The product of Step A (0.700 g, 4.00 mmol) was then added in one portion, and the reaction mixture was stirred and warmed to room temperature. After 1 h, the resulting green colored solution was poured into saturated aqueous $NH_4Cl$ (100 mL) and extracted into ethyl acetate (4×50 mL). The organic layers were combined, dried over $MgSO_4$ and concentrated in vacuo. The resulting residue was dissolved in dichloromethane, absorbed onto silica gel (1 g) and purified by MPLC with a gradient of 0-100% ethyl acetate/hexane through a 40 g silica gel column. The fractions containing pure desired product were combined and concentrated in vacuo to yield 0.290 g of the title compound.

Step C: Preparation of 4-(2,3-dimethyl-1-naphthalenyl)-5-hydroxy-6-methoxy-2-methyl-3 (21H)-pyridazinone The product of Step B (0.200 g, 0.608 mmol) was dissolved in 1,4-dioxane (10 mL) and treated with tetrabutylammonium hydroxide (0.800 mL of a 40 wt % solution in water). The resulting solution was heated to reflux and stirred for 2 h. The reaction mixture was then cooled to room temperature and poured into 1N HCl (50 mL) and extracted into ethyl acetate (4×20 mL). The organic layers were combined, dried over $MgSO_4$ and concentrated under reduced pressure. The crude solid was dissolved in dichloromethane and absorbed onto silica gel (1 g). Purification was performed by MPLC with a 40 to 100% ethyl actetate/hexane gradient through a 40 g silica gel column. The fractions containing desired product were combined and concentrated in vacuo to yield 0.130 g of the title compound, a compound of the invention, as a white solid.

Synthesis Example 5

Preparation of 6-chloro-4-(5-chloro-2-methylbenzo[b]thiene-2-yl)-5-hydroxy-2-methylpyridazin-3(2H)-one (Compound 91)

Step A: Preparation of 6-chloro-5-[(5-chlorobenzo[b]thien-2-yl)methoxy]-2-methylpyridazin-3 (2H)-one A slurry of N,N-dimethylformamide (20 mL) and sodium hydride (0.335 g, 8.37 mmol) was cooled over ice for 15 min under nitrogen. 5-Chloro-[b]thiophene-2-methanol (1.33 g, 6.7 mmol) was added portionwise under a blanket of nitrogen and stirred over ice for 15 min. 5,6-Dichloro-2-methyl-3(2H)-pyridazinone (1.00 g, 5.58 mol) was then added under a blanket of nitrogen. The ice bath was removed and the reaction mixture was allowed to stir at room temperature overnight. The resulting reaction mixture was then poured into a solution of saturated ammonium chloride and ice (200 mL) and extracted into diethyl ether (3×40 mL). The resulting organic layers were combined, dried over $MgSO_4$ and absorbed onto silica gel (4 g). Chromatography using a 40 g silica gel column eluting with a gradient of 0 to 100% ethyl acetate in hexanes gradient afforded the title compound as as a yellow solid. (1.00 g, 53% yield).
$^1$H NMR (500 MHz) δ 7.78-7.71 (m, 2H), 7.37-7.32 (m, 2H), 5.35 (s, 2H), 3.74 (s, 3H).

Step B: Preparation 6-chloro-4-(5-chloro-2-methylbenzo[b]thiene-2-yl)-5-hydroxy-2-methylpyridazin-3 (2H)-one 6-Chloro-5-[(5-chlorobenzo[b]thien-2-yl)methoxy]-2-methylpyridazin-3 (2H)-one (i.e. the product obtained in Step A above, 0.250 g, 0.700 mmol) was dissolved in 5 mL xylenes in a 40 mL scintillation vial and stirred at 175° C. overnight. The reaction mixture was then cooled to room temperature and 40 mL of hexane was added. The resulting precipitate was filtered, washed with hexane and dried to give the desired product as an orange solid (0.100 g).
$^1$H NMR (500 MHz) δ 7.71-7.69 (m, 1H), 7.30-7.27 (m, 1H), 7.26-7.24 (m, 1H), 3.80 (s, 3H), 2.43 (s, 3H).

By the procedures described herein together with methods known in the art, the following compounds of Tables 1 to 619 can be prepared. The following abbreviations are used in the Tables which follow: t means tertiary, s means secondary, n means normal, i means iso, Me means methyl, Et means ethyl, Pr means propyl, Bu means butyl, Bu means butyl, OMe means methoxy, CN means cyano, $S(O)_2Me$ means methylsulfonyl, and "—" means no substitution with $R^3$.

TABLE 1

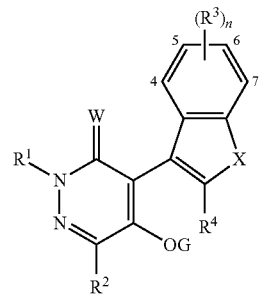

W is O, X is S, $R^1$ is Me, $R^2$ is Me, and G is H.

| $(R^3)_n$ | $R^4$ | $(R^3)_n$ | $R^4$ | $(R^3)_n$ | $R^4$ |
|---|---|---|---|---|---|
| — | H | — | Me | — | Et |
| 4-Me | H | 4-Me | Me | 4-Me | Et |

TABLE 1-continued

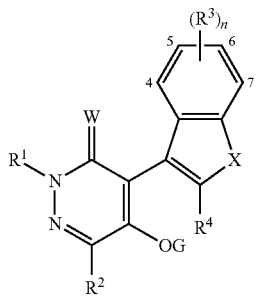

W is O, X is S, R¹ is Me, R² is Me, and G is H.

| (R³)ₙ | R⁴ | (R³)ₙ | R⁴ | (R³)ₙ | R⁴ |
|---|---|---|---|---|---|
| 5-Me | H | 5-Me | Me | 5-Me | Et |
| 6-Me | H | 6-Me | Me | 6-Me | Et |
| 7-Me | H | 7-Me | Me | 7-Me | Et |
| 4-Et | H | 4-Et | Me | 4-Et | Et |
| 5-Et | H | 5-Et | Me | 5-Et | Et |
| 6-Et | H | 6-Et | Me | 6-Et | Et |
| 7-Et | H | 7-Et | Me | 7-Et | Et |
| 4-Pr | H | 4-Pr | Me | 4-Pr | Et |
| 5-Pr | H | 5-Pr | Me | 5-Pr | Et |
| 6-Pr | H | 6-Pr | Me | 6-Pr | Et |
| 7-Pr | H | 7-Pr | Me | 7-Pr | Et |
| 4-OMe | H | 4-OMe | Me | 4-OMe | Et |
| 5-OMe | H | 5-OMe | Me | 5-OMe | Et |
| 6-OMe | H | 6-OMe | Me | 6-OMe | Et |
| 7-OMe | H | 7-OMe | Me | 7-OMe | Et |
| 4-CN | H | 4-CN | Me | 4-CN | Et |
| 5-CN | H | 5-CN | Me | 5-CN | Et |
| 6-CN | H | 6-CN | Me | 6-CN | Et |
| 7-CN | H | 7-CN | Me | 7-CN | Et |
| 4-CF₃ | H | 4-CF₃ | Me | 4-CF₃ | Et |
| 5-CF₃ | H | 5-CF₃ | Me | 5-CF₃ | Et |
| 6-CF₃ | H | 6-CF₃ | Me | 6-CF₃ | Et |
| 7-CF₃ | H | 7-CF₃ | Me | 7-CF₃ | Et |
| 4-F | H | 4-F | Me | 4-F | Et |
| 5-F | H | 5-F | Me | 5-F | Et |
| 6-F | H | 6-F | Me | 6-F | Et |
| 7-F | H | 7-F | Me | 7-F | Et |
| 4-Cl | H | 4-Cl | Me | 4-Cl | Et |
| 5-Cl | H | 5-Cl | Me | 5-Cl | Et |
| 6-Cl | H | 6-Cl | Me | 6-Cl | Et |
| 7-Cl | H | 7-Cl | Me | 7-Cl | Et |
| 4-Br | H | 4-Br | Me | 4-Br | Et |
| 5-Br | H | 5-Br | Me | 5-Br | Et |
| 6-Br | H | 6-Br | Me | 6-Br | Et |
| 7-Br | H | 7-Br | Me | 7-Br | Et |
| 4-OCHF₂ | H | 4-OCHF₂ | Me | 4-OCHF₂ | Et |
| 5OCHF₂ | H | 5OCHF₂ | Me | 5OCHF₂ | Et |
| 6-OCHF₂ | H | 6-OCHF₂ | Me | 6-OCHF₂ | Et |
| 7-OCHF₂ | H | 7-OCHF₂ | Me | 7-OCHF₂ | Et |
| 4-(C≡CH) | H | 4-(C≡CH) | Me | 4-(C≡CH) | Et |
| 5-(C≡CH) | H | 5-(C≡CH) | Me | 5-(C≡CH) | Et |
| 6-(C≡CH) | H | 6-(C≡CH) | Me | 6-(C≡CH) | Et |
| 7-(C≡CH) | H | 7-(C≡CH) | Me | 7-(C≡CH) | Et |
| 4,5-di-Me | H | 4,5-di-Me | Me | 4,5-di-Me | Et |
| 4,6-di-Me | H | 4,6-di-Me | Me | 4,6-di-Me | Et |
| 4,7-di-Me | H | 4,7-di-Me | Me | 4,7-di-Me | Et |
| 5,6-di-Me | H | 5,6-di-Me | Me | 5,6-di-Me | Et |
| 5,7-di-Me | H | 5,7-di-Me | Me | 5,7-di-Me | Et |
| 5-Cl, 7-Me | H | 5-Cl, 7-Me | Me | 5-Cl, 7-Me | Et |
| 5-Cl, 7-OMe | H | 5-Cl, 7-OMe | Me | 5-Cl, 7-OMe | Et |
| 5-F, 7-Me | H | 5-F, 7-Me | Me | 5-F, 7-Me | Et |
| 5-Me, 7-F | H | 5-Me, 7-F | Me | 5-Me, 7-F | Et |
| 5-Me, 7-Cl | H | 5-Me, 7-Cl | Me | 5-Me, 7-Cl | Et |
| 5-Me, 7-CN | H | 5-Me, 7-CN | Me | 5-Me, 7-CN | Et |
| 5-Me, 7-OMe | H | 5-Me, 7-OMe | Me | 5-Me, 7-OMe | Et |
| 5-(C≡CH), 7-Me | H | 5-(C≡CH), 7-Me | Me | 5-(C≡CH), 7-Me | Et |
| 5,7-di-F | H | 5,7-di-F | Me | 5,7-di-F | Et |
| 5,7-di-Cl | H | 5,7-di-Cl | Me | 5,7-di-Cl | Et |
| 5,7-di-Br | H | 5,7-di-Br | Me | 5,7-di-Br | Et |
| — | Pr | — | F | — | Cl |
| 4-Me | Pr | 4-Me | F | 4-Me | Cl |
| 5-Me | Pr | 5-Me | F | 5-Me | Cl |

TABLE 1-continued

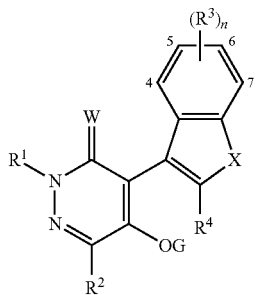

W is O, X is S, R¹ is Me, R² is Me, and G is H.

| (R³)ₙ | R⁴ | (R³)ₙ | R⁴ | (R³)ₙ | R⁴ |
|---|---|---|---|---|---|
| 6-Me | Pr | 6-Me | F | 6-Me | Cl |
| 7-Me | Pr | 7-Me | F | 7-Me | Cl |
| 4-Et | Pr | 4-Et | F | 4-Et | Cl |
| 5-Et | Pr | 5-Et | F | 5-Et | Cl |
| 6-Et | Pr | 6-Et | F | 6-Et | Cl |
| 7-Et | Pr | 7-Et | F | 7-Et | Cl |
| 4-Pr | Pr | 4-Pr | F | 4-Pr | Cl |
| 5-Pr | Pr | 5-Pr | F | 5-Pr | Cl |
| 6-Pr | Pr | 6-Pr | F | 6-Pr | Cl |
| 7-Pr | Pr | 7-Pr | F | 7-Pr | Cl |
| 4-OMe | Pr | 4-OMe | F | 4-OMe | Cl |
| 5-OMe | Pr | 5-OMe | F | 5-OMe | Cl |
| 6-OMe | Pr | 6-OMe | F | 6-OMe | Cl |
| 7-OMe | Pr | 7-OMe | F | 7-OMe | Cl |
| 4-CN | Pr | 4-CN | F | 4-CN | Cl |
| 5-CN | Pr | 5-CN | F | 5-CN | Cl |
| 6-CN | Pr | 6-CN | F | 6-CN | Cl |
| 7-CN | Pr | 7-CN | F | 7-CN | Cl |
| 4-CF₃ | Pr | 4-CF₃ | F | 4-CF₃ | Cl |
| 5-CF₃ | Pr | 5-CF₃ | F | 5-CF₃ | Cl |
| 6-CF₃ | Pr | 6-CF₃ | F | 6-CF₃ | Cl |
| 7-CF₃ | Pr | 7-CF₃ | F | 7-CF₃ | Cl |
| 4-F | Pr | 4-F | F | 4-F | Cl |
| 5-F | Pr | 5-F | F | 5-F | Cl |
| 6-F | Pr | 6-F | F | 6-F | Cl |
| 7-F | Pr | 7-F | F | 7-F | Cl |
| 4-Cl | Pr | 4-Cl | F | 4-Cl | Cl |
| 5-Cl | Pr | 5-Cl | F | 5-Cl | Cl |
| 6-Cl | Pr | 6-Cl | F | 6-Cl | Cl |
| 7-Cl | Pr | 7-Cl | F | 7-Cl | Cl |
| 4-Br | Pr | 4-Br | F | 4-Br | Cl |
| 5-Br | Pr | 5-Br | F | 5-Br | Cl |
| 6-Br | Pr | 6-Br | F | 6-Br | Cl |
| 7-Br | Pr | 7-Br | F | 7-Br | Cl |
| 4-OCHF₂ | Pr | 4-OCHF₂ | F | 4-OCHF₂ | Cl |
| 5OCHF₂ | Pr | 5OCHF₂ | F | 5OCHF₂ | Cl |
| 6-OCHF₂ | Pr | 6-OCHF₂ | F | 6-OCHF₂ | Cl |
| 7-OCHF₂ | Pr | 7-OCHF₂ | F | 7-OCHF₂ | Cl |
| 4-(C≡CH) | Pr | 4-(C≡CH) | F | 4-(C≡CH) | Cl |
| 5-(C≡CH) | Pr | 5-(C≡CH) | F | 5-(C≡CH) | Cl |
| 6-(C≡CH) | Pr | 6-(C≡CH) | F | 6-(C≡CH) | Cl |
| 7-(C≡CH) | Pr | 7-(C≡CH) | F | 7-(C≡CH) | Cl |
| 4,5-di-Me | Pr | 4,5-di-Me | F | 4,5-di-Me | Cl |
| 4,6-di-Me | Pr | 4,6-di-Me | F | 4,6-di-Me | Cl |
| 4,7-di-Me | Pr | 4,7-di-Me | F | 4,7-di-Me | Cl |
| 5,6-di-Me | Pr | 5,6-di-Me | F | 5,6-di-Me | Cl |
| 5,7-di-Me | Pr | 5,7-di-Me | F | 5,7-di-Me | Cl |
| 5-Cl, 7-Me | Pr | 5-Cl, 7-Me | F | 5-Cl, 7-Me | Cl |
| 5-Cl, 7-OMe | Pr | 5-Cl, 7-OMe | F | 5-Cl, 7-OMe | Cl |
| 5-F, 7-Me | Pr | 5-F, 7-Me | F | 5-F, 7-Me | Cl |
| 5-Me, 7-F | Pr | 5-Me, 7-F | F | 5-Me, 7-F | Cl |
| 5-Me, 7-Cl | Pr | 5-Me, 7-Cl | F | 5-Me, 7-Cl | Cl |
| 5-Me, 7-CN | Pr | 5-Me, 7-CN | F | 5-Me, 7-CN | Cl |
| 5-Me, 7-OMe | Pr | 5-Me, 7-OMe | F | 5-Me, 7-OMe | Cl |
| 5-(C≡CH), 7-Me | Pr | 5-(C≡CH), 7-Me | F | 5-(C≡CH), 7-Me | Cl |
| 5,7-di-F | Pr | 5,7-di-F | F | 5,7-di-F | Cl |
| 5,7-di-Cl | Pr | 5,7-di-Cl | F | 5,7-di-Cl | Cl |
| 5,7-di-Br | Pr | 5,7-di-Br | F | 5,7-di-Br | Cl |
| — | Br | — | CN | — | C≡CH |
| 4-Me | Br | 4-Me | CN | 4-Me | C≡CH |
| 5-Me | Br | 5-Me | CN | 5-Me | C≡CH |
| 6-Me | Br | 6-Me | CN | 6-Me | C≡CH |

TABLE 1-continued

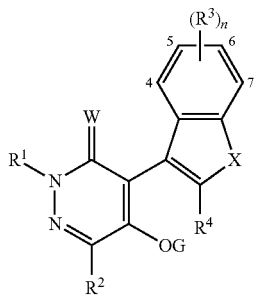

W is O, X is S, R¹ is Me, R² is Me, and G is H.

| $(R^3)_n$ | $R^4$ | $(R^3)_n$ | $R^4$ | $(R^3)_n$ | $R^4$ |
|---|---|---|---|---|---|
| 7-Me | Br | 7-Me | CN | 7-Me | C≡CH |
| 4-Et | Br | 4-Et | CN | 4-Et | C≡CH |
| 5-Et | Br | 5-Et | CN | 5-Et | C≡CH |
| 6-Et | Br | 6-Et | CN | 6-Et | C≡CH |
| 7-Et | Br | 7-Et | CN | 7-Et | C≡CH |
| 4-Pr | Br | 4-Pr | CN | 4-Pr | C≡CH |
| 5-Pr | Br | 5-Pr | CN | 5-Pr | C≡CH |
| 6-Pr | Br | 6-Pr | CN | 6-Pr | C≡CH |
| 7-Pr | Br | 7-Pr | CN | 7-Pr | C≡CH |
| 4-OMe | Br | 4-OMe | CN | 4-OMe | C≡CH |
| 5-OMe | Br | 5-OMe | CN | 5-OMe | C≡CH |
| 6-OMe | Br | 6-OMe | CN | 6-OMe | C≡CH |
| 7-OMe | Br | 7-OMe | CN | 7-OMe | C≡CH |
| 4-CN | Br | 4-CN | CN | 4-CN | C≡CH |
| 5-CN | Br | 5-CN | CN | 5-CN | C≡CH |
| 6-CN | Br | 6-CN | CN | 6-CN | C≡CH |
| 7-CN | Br | 7-CN | CN | 7-CN | C≡CH |
| 4-CF$_3$ | Br | 4-CF$_3$ | CN | 4-CF$_3$ | C≡CH |
| 5-CF$_3$ | Br | 5-CF$_3$ | CN | 5-CF$_3$ | C≡CH |
| 6-CF$_3$ | Br | 6-CF$_3$ | CN | 6-CF$_3$ | C≡CH |
| 7-CF$_3$ | Br | 7-CF$_3$ | CN | 7-CF$_3$ | C≡CH |
| 4-F | Br | 4-F | CN | 4-F | C≡CH |
| 5-F | Br | 5-F | CN | 5-F | C≡CH |
| 6-F | Br | 6-F | CN | 6-F | C≡CH |
| 7-F | Br | 7-F | CN | 7-F | C≡CH |
| 4-Cl | Br | 4-Cl | CN | 4-Cl | C≡CH |
| 5-Cl | Br | 5-Cl | CN | 5-Cl | C≡CH |
| 6-Cl | Br | 6-Cl | CN | 6-Cl | C≡CH |
| 7-Cl | Br | 7-Cl | CN | 7-Cl | C≡CH |
| 4-Br | Br | 4-Br | CN | 4-Br | C≡CH |
| 5-Br | Br | 5-Br | CN | 5-Br | C≡CH |
| 6-Br | Br | 6-Br | CN | 6-Br | C≡CH |
| 7-Br | Br | 7-Br | CN | 7-Br | C≡CH |
| 4-OCHF$_2$ | Br | 4-OCHF$_2$ | CN | 4-OCHF$_2$ | C≡CH |
| 5-OCHF$_2$ | Br | 5-OCHF$_2$ | CN | 5-OCHF$_2$ | C≡CH |
| 6-OCHF$_2$ | Br | 6-OCHF$_2$ | CN | 6-OCHF$_2$ | C≡CH |
| 7-OCHF$_2$ | Br | 7-OCHF$_2$ | CN | 7-OCHF$_2$ | C≡CH |
| 4-(C≡CH) | Br | 4-(C≡CH) | CN | 4-(C≡CH) | C≡CH |
| 5-(C≡CH) | Br | 5-(C≡CH) | CN | 5-(C≡CH) | C≡CH |
| 6-(C≡CH) | Br | 6-(C≡CH) | CN | 6-(C≡CH) | C≡CH |
| 7-(C≡CH) | Br | 7-(C≡CH) | CN | 7-(C≡CH) | C≡CH |
| 4,5-di-Me | Br | 4,5-di-Me | CN | 4,5-di-Me | C≡CH |
| 4,6-di-Me | Br | 4,6-di-Me | CN | 4,6-di-Me | C≡CH |
| 4,7-di-Me | Br | 4,7-di-Me | CN | 4,7-di-Me | C≡CH |
| 5,6-di-Me | Br | 5,6-di-Me | CN | 5,6-di-Me | C≡CH |
| 5,7-di-Me | Br | 5,7-di-Me | CN | 5,7-di-Me | C≡CH |
| 5-Cl, 7-Me | Br | 5-Cl, 7-Me | CN | 5-Cl, 7-Me | C≡CH |
| 5-Cl, 7-OMe | Br | 5-Cl, 7-OMe | CN | 5-Cl, 7-OMe | C≡CH |
| 5-F, 7-Me | Br | 5-F, 7-Me | CN | 5-F, 7-Me | C≡CH |
| 5-Me, 7-F | Br | 5-Me, 7-F | CN | 5-Me, 7-F | C≡CH |
| 5-Me, 7-Cl | Br | 5-Me, 7-Cl | CN | 5-Me, 7-Cl | C≡CH |
| 5-Me, 7-CN | Br | 5-Me, 7-CN | CN | 5-Me, 7-CN | C≡CH |
| 5-Me, 7-OMe | Br | 5-Me, 7-OMe | CN | 5-Me, 7-OMe | C≡CH |
| 5-(C≡CH), 7-Me | Br | 5-(C≡CH), 7-Me | CN | 5-(C≡CH), 7-Me | C≡CH |
| 5,7-di-F | Br | 5,7-di-F | CN | 5,7-di-F | C≡CH |
| 5,7-di-Cl | Br | 5,7-di-Cl | CN | 5,7-di-Cl | C≡CH |
| 5,7-di-Br | Br | 5,7-di-Br | CN | 5,7-di-Br | C≡CH |
| — | OMe | — | OCHF$_2$ | — | SMe |
| 4-Me | OMe | 4-Me | OCHF$_2$ | 4-Me | SMe |
| 5-Me | OMe | 5-Me | OCHF$_2$ | 5-Me | SMe |
| 6-Me | OMe | 6-Me | OCHF$_2$ | 6-Me | SMe |
| 7-Me | OMe | 7-Me | OCHF$_2$ | 7-Me | SMe |

TABLE 1-continued

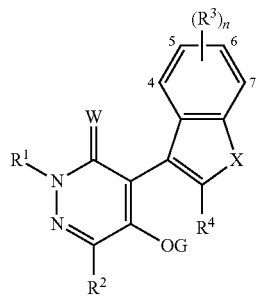

W is O, X is S, R¹ is Me, R² is Me, and G is H.

| (R³)ₙ | R⁴ | (R³)ₙ | R⁴ | (R³)ₙ | R⁴ |
|---|---|---|---|---|---|
| 4-Et | OMe | 4-Et | OCHF₂ | 4-Et | SMe |
| 5-Et | OMe | 5-Et | OCHF₂ | 5-Et | SMe |
| 6-Et | OMe | 6-Et | OCHF₂ | 6-Et | SMe |
| 7-Et | OMe | 7-Et | OCHF₂ | 7-Et | SMe |
| 4-Pr | OMe | 4-Pr | OCHF₂ | 4-Pr | SMe |
| 5-Pr | OMe | 5-Pr | OCHF₂ | 5-Pr | SMe |
| 6-Pr | OMe | 6-Pr | OCHF₂ | 6-Pr | SMe |
| 7-Pr | OMe | 7-Pr | OCHF₂ | 7-Pr | SMe |
| 4-OMe | OMe | 4-OMe | OCHF₂ | 4-OMe | SMe |
| 5-OMe | OMe | 5-OMe | OCHF₂ | 5-OMe | SMe |
| 6-OMe | OMe | 6-OMe | OCHF₂ | 6-OMe | SMe |
| 7-OMe | OMe | 7-OMe | OCHF₂ | 7-OMe | SMe |
| 4-CN | OMe | 4-CN | OCHF₂ | 4-CN | SMe |
| 5-CN | OMe | 5-CN | OCHF₂ | 5-CN | SMe |
| 6-CN | OMe | 6-CN | OCHF₂ | 6-CN | SMe |
| 7-CN | OMe | 7-CN | OCHF₂ | 7-CN | SMe |
| 4-CF₃ | OMe | 4-CF₃ | OCHF₂ | 4-CF₃ | SMe |
| 5-CF₃ | OMe | 5-CF₃ | OCHF₂ | 5-CF₃ | SMe |
| 6-CF₃ | OMe | 6-CF₃ | OCHF₂ | 6-CF₃ | SMe |
| 7-CF₃ | OMe | 7-CF₃ | OCHF₂ | 7-CF₃ | SMe |
| 4-F | OMe | 4-F | OCHF₂ | 4-F | SMe |
| 5-F | OMe | 5-F | OCHF₂ | 5-F | SMe |
| 6-F | OMe | 6-F | OCHF₂ | 6-F | SMe |
| 7-F | OMe | 7-F | OCHF₂ | 7-F | SMe |
| 4-Cl | OMe | 4-Cl | OCHF₂ | 4-Cl | SMe |
| 5-Cl | OMe | 5-Cl | OCHF₂ | 5-Cl | SMe |
| 6-Cl | OMe | 6-Cl | OCHF₂ | 6-Cl | SMe |
| 7-Cl | OMe | 7-Cl | OCHF₂ | 7-Cl | SMe |
| 4-Br | OMe | 4-Br | OCHF₂ | 4-Br | SMe |
| 5-Br | OMe | 5-Br | OCHF₂ | 5-Br | SMe |
| 6-Br | OMe | 6-Br | OCHF₂ | 6-Br | SMe |
| 7-Br | OMe | 7-Br | OCHF₂ | 7-Br | SMe |
| 4-OCHF₂ | OMe | 4-OCHF₂ | OCHF₂ | 4-OCHF₂ | SMe |
| 5OCHF₂ | OMe | 5OCHF₂ | OCHF₂ | 5OCHF₂ | SMe |
| 6-OCHF₂ | OMe | 6-OCHF₂ | OCHF₂ | 6-OCHF₂ | SMe |
| 7-OCHF₂ | OMe | 7-OCHF₂ | OCHF₂ | 7-OCHF₂ | SMe |
| 4-(C≡CH) | OMe | 4-(C≡CH) | OCHF₂ | 4-(C≡CH) | SMe |
| 5-(C≡CH) | OMe | 5-(C≡CH) | OCHF₂ | 5-(C≡CH) | SMe |
| 6-(C≡CH) | OMe | 6-(C≡CH) | OCHF₂ | 6-(C≡CH) | SMe |
| 7-(C≡CH) | OMe | 7-(C≡CH) | OCHF₂ | 7-(C≡CH) | SMe |
| 4,5-di-Me | OMe | 4,5-di-Me | OCHF₂ | 4,5-di-Me | SMe |
| 4,6-di-Me | OMe | 4,6-di-Me | OCHF₂ | 4,6-di-Me | SMe |
| 4,7-di-Me | OMe | 4,7-di-Me | OCHF₂ | 4,7-di-Me | SMe |
| 5,6-di-Me | OMe | 5,6-di-Me | OCHF₂ | 5,6-di-Me | SMe |
| 5,7-di-Me | OMe | 5,7-di-Me | OCHF₂ | 5,7-di-Me | SMe |
| 5-Cl, 7-Me | OMe | 5-Cl, 7-Me | OCHF₂ | 5-Cl, 7-Me | SMe |
| 5-Cl, 7-OMe | OMe | 5-Cl, 7-OMe | OCHF₂ | 5-Cl, 7-OMe | SMe |
| 5-F, 7-Me | OMe | 5-F, 7-Me | OCHF₂ | 5-F, 7-Me | SMe |
| 5-Me, 7-F | OMe | 5-Me, 7-F | OCHF₂ | 5-Me, 7-F | SMe |
| 5-Me, 7-Cl | OMe | 5-Me, 7-Cl | OCHF₂ | 5-Me, 7-Cl | SMe |
| 5-Me, 7-CN | OMe | 5-Me, 7-CN | OCHF₂ | 5-Me, 7-CN | SMe |
| 5-Me, 7-OMe | OMe | 5-Me, 7-OMe | OCHF₂ | 5-Me, 7-OMe | SMe |
| 5-(C≡CH), 7-Me | OMe | 5-(C≡CH), 7-Me | OCHF₂ | 5-(C≡CH), 7-Me | SMe |
| 5,7-di-F | OMe | 5,7-di-F | OCHF₂ | 5,7-di-F | SMe |
| 5,7-di-Cl | OMe | 5,7-di-Cl | OCHF₂ | 5,7-di-Cl | SMe |
| 5,7-di-Br | OMe | 5,7-di-Br | OCHF₂ | 5,7-di-Br | SMe |
| — | SCHF₂ | — | SCF₃ | | |
| 4-Me | SCHF₂ | 4-Me | SCF₃ | | |
| 5-Me | SCHF₂ | 5-Me | SCF₃ | | |
| 6-Me | SCHF₂ | 6-Me | SCF₃ | | |
| 7-Me | SCHF₂ | 7-Me | SCF₃ | | |
| 4-Et | SCHF₂ | 4-Et | SCF₃ | | |

TABLE 1-continued

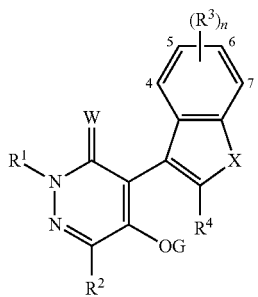

W is O, X is S, R¹ is Me, R² is Me, and G is H.

| (R³)ₙ | R⁴ | (R³)ₙ | R⁴ | (R³)ₙ | R⁴ |
|---|---|---|---|---|---|
| 5-Et | SCHF₂ | 5-Et | SCF₃ | | |
| 6-Et | SCHF₂ | 6-Et | SCF₃ | | |
| 7-Et | SCHF₂ | 7-Et | SCF₃ | | |
| 4-Pr | SCHF₂ | 4-Pr | SCF₃ | | |
| 5-Pr | SCHF₂ | 5-Pr | SCF₃ | | |
| 6-Pr | SCHF₂ | 6-Pr | SCF₃ | | |
| 7-Pr | SCHF₂ | 7-Pr | SCF₃ | | |
| 4-OMe | SCHF₂ | 4-OMe | SCF₃ | | |
| 5-OMe | SCHF₂ | 5-OMe | SCF₃ | | |
| 6-OMe | SCHF₂ | 6-OMe | SCF₃ | | |
| 7-OMe | SCHF₂ | 7-OMe | SCF₃ | | |
| 4-CN | SCHF₂ | 4-CN | SCF₃ | | |
| 5-CN | SCHF₂ | 5-CN | SCF₃ | | |
| 6-CN | SCHF₂ | 6-CN | SCF₃ | | |
| 7-CN | SCHF₂ | 7-CN | SCF₃ | | |
| 4-CF₃ | SCHF₂ | 4-CF₃ | SCF₃ | | |
| 5-CF₃ | SCHF₂ | 5-CF₃ | SCF₃ | | |
| 6-CF₃ | SCHF₂ | 6-CF₃ | SCF₃ | | |
| 7-CF₃ | SCHF₂ | 7-CF₃ | SCF₃ | | |
| 4-F | SCHF₂ | 4-F | SCF₃ | | |
| 5-F | SCHF₂ | 5-F | SCF₃ | | |
| 6-F | SCHF₂ | 6-F | SCF₃ | | |
| 7-F | SCHF₂ | 7-F | SCF₃ | | |
| 4-Cl | SCHF₂ | 4-Cl | SCF₃ | | |
| 5-Cl | SCHF₂ | 5-Cl | SCF₃ | | |
| 6-Cl | SCHF₂ | 6-Cl | SCF₃ | | |
| 7-Cl | SCHF₂ | 7-Cl | SCF₃ | | |
| 4-Br | SCHF₂ | 4-Br | SCF₃ | | |
| 5-Br | SCHF₂ | 5-Br | SCF₃ | | |
| 6-Br | SCHF₂ | 6-Br | SCF₃ | | |
| 7-Br | SCHF₂ | 7-Br | SCF₃ | | |
| 4-OCHF₂ | SCHF₂ | 4-OCHF₂ | SCF₃ | | |
| 5OCHF₂ | SCHF₂ | 5OCHF₂ | SCF₃ | | |
| 6-OCHF₂ | SCHF₂ | 6-OCHF₂ | SCF₃ | | |
| 7-OCHF₂ | SCHF₂ | 7-OCHF₂ | SCF₃ | | |
| 4-(C≡CH) | SCHF₂ | 4-(C≡CH) | SCF₃ | | |
| 5-(C≡CH) | SCHF₂ | 5-(C≡CH) | SCF₃ | | |
| 6-(C≡CH) | SCHF₂ | 6-(C≡CH) | SCF₃ | | |
| 7-(C≡CH) | SCHF₂ | 7-(C≡CH) | SCF₃ | | |
| 4,5-di-Me | SCHF₂ | 4,5-di-Me | SCF₃ | | |
| 4,6-di-Me | SCHF₂ | 4,6-di-Me | SCF₃ | | |
| 4,7-di-Me | SCHF₂ | 4,7-di-Me | SCF₃ | | |
| 5,6-di-Me | SCHF₂ | 5,6-di-Me | SCF₃ | | |
| 5,7-di-Me | SCHF₂ | 5,7-di-Me | SCF₃ | | |
| 5-Cl, 7-Me | SCHF₂ | 5-Cl, 7-Me | SCF₃ | | |
| 5-Cl, 7-OMe | SCHF₂ | 5-Cl, 7-OMe | SCF₃ | | |
| 5-F, 7-Me | SCHF₂ | 5-F, 7-Me | SCF₃ | | |
| 5-Me, 7-F | SCHF₂ | 5-Me, 7-F | SCF₃ | | |
| 5-Me, 7-Cl | SCHF₂ | 5-Me, 7-Cl | SCF₃ | | |
| 5-Me, 7-CN | SCHF₂ | 5-Me, 7-CN | SCF₃ | | |
| 5-Me, 7-OMe | SCHF₂ | 5-Me, 7-OMe | SCF₃ | | |
| 5-(C≡CH), 7-Me | SCHF₂ | 5-(C≡CH), 7-Me | SCF₃ | | |
| 5,7-di-F | SCHF₂ | 5,7-di-F | SCF₃ | | |
| 5,7-di-Cl | SCHF₂ | 5,7-di-Cl | SCF₃ | | |
| 5,7-di-Br | SCHF₂ | 5,7-di-Br | SCF₃ | | |

Table 2 is constructed in the same manner except that the Row Heading "W is O, X is S, $R^1$ is Me, $R^2$ is Me, and G is H." is replaced with the Row Heading listed for Table 2 below (i.e. "W is O, X is S, $R^1$ is Me, $R^2$ is Me, and G is C(O)Me."). Therefore the first entry in Table 2 is a compound of Formula 1 wherein W is O, X is S, $R^1$ is Me, $R^2$ is Me, $(R^3)_n$ is "-" (i.e. n is 0; no substitution with $R^3$), $R^4$ is H, and G is C(O)Me. Tables 3 through 627 are constructed similarly.

| Table | Row Heading |
|---|---|
| 2 | W is O, X is S, $R^1$ is Me, $R^2$ is Me, and G is C(O)Me. |
| 3 | W is O, X is S, $R^1$ is Me, $R^2$ is Me, and G is C(O)Et. |
| 4 | W is O, X is S, $R^1$ is Me, $R^2$ is Me, and G is C(O)-i-Pr. |
| 5 | W is O, X is S, $R^1$ is Me, $R^2$ is Me, and G is C(O)-t-Bu. |
| 6 | W is O, X is S, $R^1$ is Me, $R^2$ is Me, and G is $CO_2$Me. |
| 7 | W is O, X is S, $R^1$ is Me, $R^2$ is Me, and G is $CO_2$Et. |
| 8 | W is O, X is S, $R^1$ is Me, $R^2$ is Me, and G is $CO_2$-i-Pr. |
| 9 | W is O, X is S, $R^1$ is Me, $R^2$ is Me, and G is $CO_2$-t-Bu. |
| 10 | W is O, X is S, $R^1$ is Me, $R^2$ is Me, and G is $SO_2$Me. |
| 11 | W is O, X is S, $R^1$ is Me, $R^2$ is H, and G is C(O)Me. |
| 12 | W is O, X is S, $R^1$ is Me, $R^2$ is H, and G is C(O)Et. |
| 13 | W is O, X is S, $R^1$ is Me, $R^2$ is H, and G is C(O)-i-Pr. |
| 14 | W is O, X is S, $R^1$ is Me, $R^2$ is H, and G is C(O)-t-Bu. |
| 15 | W is O, X is S, $R^1$ is Me, $R^2$ is H, and G is $CO_2$Me. |
| 16 | W is O, X is S, $R^1$ is Me, $R^2$ is H, and G is $CO_2$Et. |
| 17 | W is O, X is S, $R^1$ is Me, $R^2$ is H, and G is $CO_2$-i-Pr. |
| 18 | W is O, X is S, $R^1$ is Me, $R^2$ is H, and G is $CO_2$-t-Bu. |
| 19 | W is O, X is S, $R^1$ is Me, $R^2$ is H, and G is $SO_2$Me. |
| 20 | W is O, X is S, $R^1$ is Me, $R^2$ is Et, and G is C(O)Me. |
| 21 | W is O, X is S, $R^1$ is Me, $R^2$ is Et, and G is C(O)Et. |
| 22 | W is O, X is S, $R^1$ is Me, $R^2$ is Et, and G is C(O)-i-Pr. |
| 23 | W is O, X is S, $R^1$ is Me, $R^2$ is Et, and G is C(O)-t-Bu. |
| 24 | W is O, X is S, $R^1$ is Me, $R^2$ is Et, and G is $CO_2$Me. |
| 25 | W is O, X is S, $R^1$ is Me, $R^2$ is Et, and G is $CO_2$Et. |
| 26 | W is O, X is S, $R^1$ is Me, $R^2$ is Et, and G is $CO_2$-i-Pr. |
| 27 | W is O, X is S, $R^1$ is Me, $R^2$ is Et, and G is $CO_2$-t-Bu. |
| 28 | W is O, X is S, $R^1$ is Me, $R^2$ is Et, and G is $SO_2$Me. |
| 29 | W is O, X is S, $R^1$ is Me, $R^2$ is Pr, and G is C(O)Me. |
| 30 | W is O, X is S, $R^1$ is Me, $R^2$ is Pr, and G is C(O)Et. |
| 31 | W is O, X is S, $R^1$ is Me, $R^2$ is Pr, and G is C(O)-i-Pr. |
| 32 | W is O, X is S, $R^1$ is Me, $R^2$ is Pr, and G is C(O)-t-Bu. |
| 33 | W is O, X is S, $R^1$ is Me, $R^2$ is Pr, and G is $CO_2$Me. |
| 34 | W is O, X is S, $R^1$ is Me, $R^2$ is Pr, and G is $CO_2$Et. |
| 35 | W is O, X is S, $R^1$ is Me, $R^2$ is Pr, and G is $CO_2$-i-Pr. |
| 36 | W is O, X is S, $R^1$ is Me, $R^2$ is Pr, and G is $CO_2$-t-Bu. |
| 37 | W is O, X is S, $R^1$ is Me, $R^2$ is Pr, and G is $SO_2$Me. |
| 38 | W is O, X is S, $R^1$ is Me, $R^2$ is $CF_3$, and G is C(O)Me. |
| 39 | W is O, X is S, $R^1$ is Me, $R^2$ is $CF_3$, and G is C(O)Et. |
| 40 | W is O, X is S, $R^1$ is Me, $R^2$ is $CF_3$, and G is C(O)-i-Pr. |
| 41 | W is O, X is S, $R^1$ is Me, $R^2$ is $CF_3$, and G is C(O)-t-Bu. |
| 42 | W is O, X is S, $R^1$ is Me, $R^2$ is $CF_3$, and G is $CO_2$Me. |
| 43 | W is O, X is S, $R^1$ is Me, $R^2$ is $CF_3$, and G is $CO_2$Et. |
| 44 | W is O, X is S, $R^1$ is Me, $R^2$ is $CF_3$, and G is $CO_2$-i-Pr. |
| 45 | W is O, X is S, $R^1$ is Me, $R^2$ is $CF_3$, and G is $CO_2$-t-Bu. |
| 46 | W is O, X is S, $R^1$ is Me, $R^2$ is $CF_3$, and G is $SO_2$Me. |
| 47 | W is O, X is S, $R^1$ is Me, $R^2$ is Cl, and G is C(O)Me. |
| 48 | W is O, X is S, $R^1$ is Me, $R^2$ is Cl, and G is C(O)Et. |
| 49 | W is O, X is S, $R^1$ is Me, $R^2$ is Cl, and G is C(O)-i-Pr. |
| 50 | W is O, X is S, $R^1$ is Me, $R^2$ is Cl, and G is C(O)-t-Bu. |
| 51 | W is O, X is S, $R^1$ is Me, $R^2$ is Cl, and G is $CO_2$Me. |
| 52 | W is O, X is S, $R^1$ is Me, $R^2$ is Cl, and G is $CO_2$Et. |
| 53 | W is O, X is S, $R^1$ is Me, $R^2$ is Cl, and G is $CO_2$-i-Pr. |
| 54 | W is O, X is S, $R^1$ is Me, $R^2$ is Cl, and G is $CO_2$-t-Bu. |
| 55 | W is O, X is S, $R^1$ is Me, $R^2$ is Cl, and G is $SO_2$Me. |
| 56 | W is O, X is S, $R^1$ is Me, $R^2$ is Br, and G is C(O)Me. |
| 57 | W is O, X is S, $R^1$ is Me, $R^2$ is Br, and G is C(O)Et. |
| 58 | W is O, X is S, $R^1$ is Me, $R^2$ is Br, and G is C(O)-i-Pr. |
| 59 | W is O, X is S, $R^1$ is Me, $R^2$ is Br, and G is C(O)-t-Bu. |
| 60 | W is O, X is S, $R^1$ is Me, $R^2$ is Br, and G is $CO_2$Me. |
| 61 | W is O, X is S, $R^1$ is Me, $R^2$ is Br, and G is $CO_2$Et. |
| 62 | W is O, X is S, $R^1$ is Me, $R^2$ is Br, and G is $CO_2$-i-Pr. |
| 63 | W is O, X is S, $R^1$ is Me, $R^2$ is Br, and G is $CO_2$-t-Bu. |
| 64 | W is O, X is S, $R^1$ is Me, $R^2$ is Br, and G is $SO_2$Me. |
| 65 | W is O, X is S, $R^1$ is Me, $R^2$ is I, and G is C(O)Me. |
| 66 | W is O, X is S, $R^1$ is Me, $R^2$ is I, and G is C(O)Et. |
| 67 | W is O, X is S, $R^1$ is Me, $R^2$ is I, and G is C(O)-i-Pr. |
| 68 | W is O, X is S, $R^1$ is Me, $R^2$ is I, and G is C(O)-t-Bu. |
| 69 | W is O, X is S, $R^1$ is Me, $R^2$ is I, and G is $CO_2$Me. |
| 70 | W is O, X is S, $R^1$ is Me, $R^2$ is I, and G is $CO_2$Et. |
| 71 | W is O, X is S, $R^1$ is Me, $R^2$ is I, and G is $CO_2$-i-Pr. |
| 72 | W is O, X is S, $R^1$ is Me, $R^2$ is I, and G is $CO_2$-t-Bu. |
| 73 | W is O, X is S, $R^1$ is Me, $R^2$ is I, and G is $SO_2$Me. |
| 74 | W is O, X is S, $R^1$ is Me, $R^2$ is OMe, and G is C(O)Me. |
| 75 | W is O, X is S, $R^1$ is Me, $R^2$ is OMe, and G is C(O)Et. |
| 76 | W is O, X is S, $R^1$ is Me, $R^2$ is OMe, and G is C(O)-i-Pr. |
| 77 | W is O, X is S, $R^1$ is Me, $R^2$ is OMe, and G is C(O)-t-Bu. |
| 78 | W is O, X is S, $R^1$ is Me, $R^2$ is OMe, and G is $CO_2$Me. |
| 79 | W is O, X is S, $R^1$ is Me, $R^2$ is OMe, and G is $CO_2$Et. |
| 80 | W is O, X is S, $R^1$ is Me, $R^2$ is OMe, and G is $CO_2$-i-Pr. |
| 81 | W is O, X is S, $R^1$ is Me, $R^2$ is OMe, and G is $CO_2$-t-Bu. |
| 82 | W is O, X is S, $R^1$ is Me, $R^2$ is OMe, and G is $SO_2$Me. |
| 83 | W is O, X is S, $R^1$ is Me, $R^2$ is OEt, and G is C(O)Me. |
| 84 | W is O, X is S, $R^1$ is Me, $R^2$ is OEt, and G is C(O)Et. |
| 85 | W is O, X is S, $R^1$ is Me, $R^2$ is OEt, and G is C(O)-i-Pr. |
| 86 | W is O, X is S, $R^1$ is Me, $R^2$ is OEt, and G is C(O)-t-Bu. |
| 87 | W is O, X is S, $R^1$ is Me, $R^2$ is OEt, and G is $CO_2$Me. |
| 88 | W is O, X is S, $R^1$ is Me, $R^2$ is OEt, and G is $CO_2$Et. |
| 89 | W is O, X is S, $R^1$ is Me, $R^2$ is OEt, and G is $CO_2$-i-Pr. |
| 90 | W is O, X is S, $R^1$ is Me, $R^2$ is OEt, and G is $CO_2$-t-Bu. |
| 91 | W is O, X is S, $R^1$ is Me, $R^2$ is OEt, and G is $SO_2$Me. |
| 92 | W is O, X is S, $R^1$ is Et, $R^2$ is Me, and G is C(O)Me. |
| 93 | W is O, X is S, $R^1$ is Et, $R^2$ is Me, and G is C(O)Et. |
| 94 | W is O, X is S, $R^1$ is Et, $R^2$ is Me, and G is C(O)-i-Pr. |
| 95 | W is O, X is S, $R^1$ is Et, $R^2$ is Me, and G is C(O)-t-Bu. |
| 96 | W is O, X is S, $R^1$ is Et, $R^2$ is Me, and G is $CO_2$Me. |
| 97 | W is O, X is S, $R^1$ is Et, $R^2$ is Me, and G is $CO_2$Et. |
| 98 | W is O, X is S, $R^1$ is Et, $R^2$ is Me, and G is $CO_2$-i-Pr. |
| 99 | W is O, X is S, $R^1$ is Et, $R^2$ is Me, and G is $CO_2$-t-Bu. |
| 100 | W is O, X is S, $R^1$ is Et, $R^2$ is Me, and G is $SO_2$Me. |
| 101 | W is O, X is S, $R^1$ is Et, $R^2$ is H, and G is C(O)Me. |
| 102 | W is O, X is S, $R^1$ is Et, $R^2$ is H, and G is C(O)Et. |
| 103 | W is O, X is S, $R^1$ is Et, $R^2$ is H, and G is C(O)-i-Pr. |
| 104 | W is O, X is S, $R^1$ is Et, $R^2$ is H, and G is C(O)-t-Bu. |
| 105 | W is O, X is S, $R^1$ is Et, $R^2$ is H, and G is $CO_2$Me. |
| 106 | W is O, X is S, $R^1$ is Et, $R^2$ is H, and G is $CO_2$Et. |
| 107 | W is O, X is S, $R^1$ is Et, $R^2$ is H, and G is $CO_2$-i-Pr. |
| 108 | W is O, X is S, $R^1$ is Et, $R^2$ is H, and G is $CO_2$-t-Bu. |
| 109 | W is O, X is S, $R^1$ is Et, $R^2$ is H, and G is $SO_2$Me. |
| 110 | W is O, X is S, $R^1$ is Et, $R^2$ is Et, and G is C(O)Me. |
| 111 | W is O, X is S, $R^1$ is Et, $R^2$ is Et, and G is C(O)Et. |
| 112 | W is O, X is S, $R^1$ is Et, $R^2$ is Et, and G is C(O)-i-Pr. |
| 113 | W is O, X is S, $R^1$ is Et, $R^2$ is Et, and G is C(O)-t-Bu. |
| 114 | W is O, X is S, $R^1$ is Et, $R^2$ is Et, and G is $CO_2$Me. |
| 115 | W is O, X is S, $R^1$ is Et, $R^2$ is Et, and G is $CO_2$Et. |
| 116 | W is O, X is S, $R^1$ is Et, $R^2$ is Et, and G is $CO_2$-i-Pr. |
| 117 | W is O, X is S, $R^1$ is Et, $R^2$ is Et, and G is $CO_2$-t-Bu. |
| 118 | W is O, X is S, $R^1$ is Et, $R^2$ is Et, and G is $SO_2$Me. |
| 119 | W is O, X is S, $R^1$ is Et, $R^2$ is Pr, and G is C(O)Me. |
| 120 | W is O, X is S, $R^1$ is Et, $R^2$ is Pr, and G is C(O)Et. |
| 121 | W is O, X is S, $R^1$ is Et, $R^2$ is Pr, and G is C(O)-i-Pr. |
| 122 | W is O, X is S, $R^1$ is Et, $R^2$ is Pr, and G is C(O)-t-Bu. |
| 123 | W is O, X is S, $R^1$ is Et, $R^2$ is Pr, and G is $CO_2$Me. |
| 124 | W is O, X is S, $R^1$ is Et, $R^2$ is Pr, and G is $CO_2$Et. |
| 125 | W is O, X is S, $R^1$ is Et, $R^2$ is Pr, and G is $CO_2$-i-Pr. |
| 126 | W is O, X is S, $R^1$ is Et, $R^2$ is Pr, and G is $CO_2$-t-Bu. |
| 127 | W is O, X is S, $R^1$ is Et, $R^2$ is Pr, and G is $SO_2$Me. |
| 128 | W is O, X is S, $R^1$ is Et, $R^2$ is $CF_3$, and G is C(O)Me. |
| 129 | W is O, X is S, $R^1$ is Et, $R^2$ is $CF_3$, and G is C(O)Et. |
| 130 | W is O, X is S, $R^1$ is Et, $R^2$ is $CF_3$, and G is C(O)-i-Pr. |
| 131 | W is O, X is S, $R^1$ is Et, $R^2$ is $CF_3$, and G is C(O)-t-Bu. |
| 132 | W is O, X is S, $R^1$ is Et, $R^2$ is $CF_3$, and G is $CO_2$Me. |
| 133 | W is O, X is S, $R^1$ is Et, $R^2$ is $CF_3$, and G is $CO_2$Et. |
| 134 | W is O, X is S, $R^1$ is Et, $R^2$ is $CF_3$, and G is $CO_2$-i-Pr. |
| 135 | W is O, X is S, $R^1$ is Et, $R^2$ is $CF_3$, and G is $CO_2$-t-Bu. |
| 136 | W is O, X is S, $R^1$ is Et, $R^2$ is $CF_3$, and G is $SO_2$Me. |
| 137 | W is O, X is S, $R^1$ is Et, $R^2$ is Cl, and G is C(O)Me. |
| 138 | W is O, X is S, $R^1$ is Et, $R^2$ is Cl, and G is C(O)Et. |
| 139 | W is O, X is S, $R^1$ is Et, $R^2$ is Cl, and G is C(O)-i-Pr. |
| 140 | W is O, X is S, $R^1$ is Et, $R^2$ is Cl, and G is C(O)-t-Bu. |
| 141 | W is O, X is S, $R^1$ is Et, $R^2$ is Cl, and G is $CO_2$Me. |
| 142 | W is O, X is S, $R^1$ is Et, $R^2$ is Cl, and G is $CO_2$Et. |
| 143 | W is O, X is S, $R^1$ is Et, $R^2$ is Cl, and G is $CO_2$-i-Pr. |
| 144 | W is O, X is S, $R^1$ is Et, $R^2$ is Cl, and G is $CO_2$-t-Bu. |
| 145 | W is O, X is S, $R^1$ is Et, $R^2$ is Cl, and G is $SO_2$Me. |

| Table | Row Heading |
|---|---|
| 146 | W is O, X is S, $R^1$ is Et, $R^2$ is Br, and G is C(O)Me. |
| 147 | W is O, X is S, $R^1$ is Et, $R^2$ is Br, and G is C(O)Et. |
| 148 | W is O, X is S, $R^1$ is Et, $R^2$ is Br, and G is C(O)-i-Pr. |
| 149 | W is O, X is S, $R^1$ is Et, $R^2$ is Br, and G is C(O)-t-Bu. |
| 150 | W is O, X is S, $R^1$ is Et, $R^2$ is Br, and G is $CO_2Me$. |
| 151 | W is O, X is S, $R^1$ is Et, $R^2$ is Br, and G is $CO_2Et$. |
| 152 | W is O, X is S, $R^1$ is Et, $R^2$ is Br, and G is $CO_2$-i-Pr. |
| 153 | W is O, X is S, $R^1$ is Et, $R^2$ is Br, and G is $CO_2$-t-Bu. |
| 154 | W is O, X is S, $R^1$ is Et, $R^2$ is Br, and G is $SO_2Me$. |
| 155 | W is O, X is S, $R^1$ is Et, $R^2$ is I, and G is C(O)Me. |
| 156 | W is O, X is S, $R^1$ is Et, $R^2$ is I, and G is C(O)Et. |
| 157 | W is O, X is S, $R^1$ is Et, $R^2$ is I, and G is C(O)-i-Pr. |
| 158 | W is O, X is S, $R^1$ is Et, $R^2$ is I, and G is C(O)-t-Bu. |
| 159 | W is O, X is S, $R^1$ is Et, $R^2$ is I, and G is $CO_2Me$. |
| 160 | W is O, X is S, $R^1$ is Et, $R^2$ is I, and G is $CO_2Et$. |
| 161 | W is O, X is S, $R^1$ is Et, $R^2$ is I, and G is $CO_2$-i-Pr. |
| 162 | W is O, X is S, $R^1$ is Et, $R^2$ is I, and G is $CO_2$-t-Bu. |
| 163 | W is O, X is S, $R^1$ is Et, $R^2$ is I, and G is $SO_2Me$. |
| 164 | W is O, X is S, $R^1$ is Et, $R^2$ is OMe, and G is C(O)Me. |
| 165 | W is O, X is S, $R^1$ is Et, $R^2$ is OMe, and G is C(O)Et. |
| 166 | W is O, X is S, $R^1$ is Et, $R^2$ is OMe, and G is C(O)-i-Pr. |
| 167 | W is O, X is S, $R^1$ is Et, $R^2$ is OMe, and G is C(O)-t-Bu. |
| 168 | W is O, X is S, $R^1$ is Et, $R^2$ is OMe, and G is $CO_2Me$. |
| 169 | W is O, X is S, $R^1$ is Et, $R^2$ is OMe, and G is $CO_2Et$. |
| 170 | W is O, X is S, $R^1$ is Et, $R^2$ is OMe, and G is $CO_2$-i-Pr. |
| 171 | W is O, X is S, $R^1$ is Et, $R^2$ is OMe, and G is $CO_2$-t-Bu. |
| 172 | W is O, X is S, $R^1$ is Et, $R^2$ is OMe, and G is $SO_2Me$. |
| 173 | W is O, X is S, $R^1$ is Et, $R^2$ is OEt, and G is C(O)Me. |
| 174 | W is O, X is S, $R^1$ is Et, $R^2$ is OEt, and G is C(O)Et. |
| 175 | W is O, X is S, $R^1$ is Et, $R^2$ is OEt, and G is C(O)-i-Pr. |
| 176 | W is O, X is S, $R^1$ is Et, $R^2$ is OEt, and G is C(O)-t-Bu. |
| 177 | W is O, X is S, $R^1$ is Et, $R^2$ is OEt, and G is $CO_2Me$. |
| 178 | W is O, X is S, $R^1$ is Et, $R^2$ is OEt, and G is $CO_2Et$. |
| 179 | W is O, X is S, $R^1$ is Et, $R^2$ is OEt, and G is $CO_2$-i-Pr. |
| 180 | W is O, X is S, $R^1$ is Et, $R^2$ is OEt, and G is $CO_2$-t-Bu. |
| 181 | W is O, X is S, $R^1$ is Et, $R^2$ is OEt, and G is $SO_2Me$. |
| 182 | W is O, X is S, $R^1$ is Pr, $R^2$ is Me, and G is C(O)Me. |
| 183 | W is O, X is S, $R^1$ is Pr, $R^2$ is Me, and G is C(O)Et. |
| 184 | W is O, X is S, $R^1$ is Pr, $R^2$ is Me, and G is C(O)-i-Pr. |
| 185 | W is O, X is S, $R^1$ is Pr, $R^2$ is Me, and G is C(O)-t-Bu. |
| 186 | W is O, X is S, $R^1$ is Pr, $R^2$ is Me, and G is $CO_2Me$. |
| 187 | W is O, X is S, $R^1$ is Pr, $R^2$ is Me, and G is $CO_2Et$. |
| 188 | W is O, X is S, $R^1$ is Pr, $R^2$ is Me, and G is $CO_2$-i-Pr. |
| 189 | W is O, X is S, $R^1$ is Pr, $R^2$ is Me, and G is $CO_2$-t-Bu. |
| 190 | W is O, X is S, $R^1$ is Pr, $R^2$ is Me, and G is $SO_2Me$. |
| 191 | W is O, X is S, $R^1$ is Pr, $R^2$ is H, and G is C(O)Me. |
| 192 | W is O, X is S, $R^1$ is Pr, $R^2$ is H, and G is C(O)Et. |
| 193 | W is O, X is S, $R^1$ is Pr, $R^2$ is H, and G is C(O)-i-Pr. |
| 194 | W is O, X is S, $R^1$ is Pr, $R^2$ is H, and G is C(O)-t-Bu. |
| 195 | W is O, X is S, $R^1$ is Pr, $R^2$ is H, and G is $CO_2Me$. |
| 196 | W is O, X is S, $R^1$ is Pr, $R^2$ is H, and G is $CO_2Et$. |
| 197 | W is O, X is S, $R^1$ is Pr, $R^2$ is H, and G is $CO_2$-i-Pr. |
| 198 | W is O, X is S, $R^1$ is Pr, $R^2$ is H, and G is $CO_2$-t-Bu. |
| 199 | W is O, X is S, $R^1$ is Pr, $R^2$ is H, and G is $SO_2Me$. |
| 200 | W is O, X is S, $R^1$ is Pr, $R^2$ is Et, and G is C(O)Me. |
| 201 | W is O, X is S, $R^1$ is Pr, $R^2$ is Et, and G is C(O)Et. |
| 202 | W is O, X is S, $R^1$ is Pr, $R^2$ is Et, and G is C(O)-i-Pr. |
| 203 | W is O, X is S, $R^1$ is Pr, $R^2$ is Et, and G is C(O)-t-Bu. |
| 204 | W is O, X is S, $R^1$ is Pr, $R^2$ is Et, and G is $CO_2Me$. |
| 205 | W is O, X is S, $R^1$ is Pr, $R^2$ is Et, and G is $CO_2Et$. |
| 206 | W is O, X is S, $R^1$ is Pr, $R^2$ is Et, and G is $CO_2$-i-Pr. |
| 207 | W is O, X is S, $R^1$ is Pr, $R^2$ is Et, and G is $CO_2$-t-Bu. |
| 208 | W is O, X is S, $R^1$ is Pr, $R^2$ is Et, and G is $SO_2Me$. |
| 209 | W is O, X is S, $R^1$ is Pr, $R^2$ is Pr, and G is C(O)Me. |
| 210 | W is O, X is S, $R^1$ is Pr, $R^2$ is Pr, and G is C(O)Et. |
| 211 | W is O, X is S, $R^1$ is Pr, $R^2$ is Pr, and G is C(O)-i-Pr. |
| 212 | W is O, X is S, $R^1$ is Pr, $R^2$ is Pr, and G is C(O)-t-Bu. |
| 213 | W is O, X is S, $R^1$ is Pr, $R^2$ is Pr, and G is $CO_2Me$. |
| 214 | W is O, X is S, $R^1$ is Pr, $R^2$ is Pr, and G is $CO_2Et$. |
| 215 | W is O, X is S, $R^1$ is Pr, $R^2$ is Pr, and G is $CO_2$-i-Pr. |
| 216 | W is O, X is S, $R^1$ is Pr, $R^2$ is Pr, and G is $CO_2$-t-Bu. |
| 217 | W is O, X is S, $R^1$ is Pr, $R^2$ is Pr, and G is $SO_2Me$. |
| 218 | W is O, X is S, $R^1$ is Pr, $R^2$ is $CF_3$, and G is C(O)Me. |
| 219 | W is O, X is S, $R^1$ is Pr, $R^2$ is $CF_3$, and G is C(O)Et. |
| 220 | W is O, X is S, $R^1$ is Pr, $R^2$ is $CF_3$, and G is C(O)-i-Pr. |
| 221 | W is O, X is S, $R^1$ is Pr, $R^2$ is $CF_3$, and G is C(O)-t-Bu. |
| 222 | W is O, X is S, $R^1$ is Pr, $R^2$ is $CF_3$, and G is $CO_2Me$. |
| 223 | W is O, X is S, $R^1$ is Pr, $R^2$ is $CF_3$, and G is $CO_2Et$. |
| 224 | W is O, X is S, $R^1$ is Pr, $R^2$ is $CF_3$, and G is $CO_2$-i-Pr. |
| 225 | W is O, X is S, $R^1$ is Pr, $R^2$ is $CF_3$, and G is $CO_2$-t-Bu. |
| 226 | W is O, X is S, $R^1$ is Pr, $R^2$ is $CF_3$, and G is $SO_2Me$. |
| 227 | W is O, X is S, $R^1$ is Pr, $R^2$ is Cl, and G is C(O)Me. |
| 228 | W is O, X is S, $R^1$ is Pr, $R^2$ is Cl, and G is C(O)Et. |
| 229 | W is O, X is S, $R^1$ is Pr, $R^2$ is Cl, and G is C(O)-i-Pr. |
| 230 | W is O, X is S, $R^1$ is Pr, $R^2$ is Cl, and G is C(O)-t-Bu. |
| 231 | W is O, X is S, $R^1$ is Pr, $R^2$ is Cl, and G is $CO_2Me$. |
| 232 | W is O, X is S, $R^1$ is Pr, $R^2$ is Cl, and G is $CO_2Et$. |
| 233 | W is O, X is S, $R^1$ is Pr, $R^2$ is Cl, and G is $CO_2$-i-Pr. |
| 234 | W is O, X is S, $R^1$ is Pr, $R^2$ is Cl, and G is $CO_2$-t-Bu. |
| 235 | W is O, X is S, $R^1$ is Pr, $R^2$ is Cl, and G is $SO_2Me$. |
| 236 | W is O, X is S, $R^1$ is Pr, $R^2$ is Br, and G is C(O)Me. |
| 237 | W is O, X is S, $R^1$ is Pr, $R^2$ is Br, and G is C(O)Et. |
| 238 | W is O, X is S, $R^1$ is Pr, $R^2$ is Br, and G is C(O)-i-Pr. |
| 239 | W is O, X is S, $R^1$ is Pr, $R^2$ is Br, and G is C(O)-t-Bu. |
| 240 | W is O, X is S, $R^1$ is Pr, $R^2$ is Br, and G is $CO_2Me$. |
| 241 | W is O, X is S, $R^1$ is Pr, $R^2$ is Br, and G is $CO_2Et$. |
| 242 | W is O, X is S, $R^1$ is Pr, $R^2$ is Br, and G is $CO_2$-i-Pr. |
| 243 | W is O, X is S, $R^1$ is Pr, $R^2$ is Br, and G is CO2-t-Bu. |
| 244 | W is O, X is S, $R^1$ is Pr, $R_2$ is Br, and G is SO2Me. |
| 245 | W is O, X is S, $R^1$ is Pr, $R^2$ is I, and G is C(O)Me. |
| 246 | W is O, X is S, $R^1$ is Pr, $R^2$ is I, and G is C(O)Et. |
| 247 | W is O, X is S, $R^1$ is Pr, $R^2$ is I, and G is C(O)-i-Pr. |
| 248 | W is O, X is S, $R^1$ is Pr, $R^2$ is I, and G is C(O)-t-Bu. |
| 249 | W is O, X is S, $R^1$ is Pr, $R^2$ is I, and G is $CO_2Me$. |
| 250 | W is O, X is S, $R^1$ is Pr, $R^2$ is I, and G is $CO_2Et$. |
| 251 | W is O, X is S, $R^1$ is Pr, $R^2$ is I, and G is $CO_2$-i-Pr. |
| 252 | W is O, X is S, $R^1$ is Pr, $R^2$ is I, and G is $CO_2$-t-Bu. |
| 253 | W is O, X is S, $R^1$ is Pr, $R^2$ is I, and G is $SO_2Me$. |
| 254 | W is O, X is S, $R^1$ is Pr, $R^2$ is OMe, and G is C(O)Me. |
| 255 | W is O, X is S, $R^1$ is Pr, $R^2$ is OMe, and G is C(O)Et. |
| 256 | W is O, X is S, $R^1$ is Pr, $R^2$ is OMe, and G is C(O)-i-Pr. |
| 257 | W is O, X is S, $R^1$ is Pr, $R^2$ is OMe, and G is C(O)-t-Bu. |
| 258 | W is O, X is S, $R^1$ is Pr, $R^2$ is OMe, and G is $CO_2Me$. |
| 259 | W is O, X is S, $R^1$ is Pr, $R^2$ is OMe, and G is $CO_2Et$. |
| 260 | W is O, X is S, $R^1$ is Pr, $R^2$ is OMe, and G is $CO_2$-i-Pr. |
| 261 | W is O, X is S, $R^1$ is Pr, $R^2$ is OMe, and G is $CO_2$-t-Bu. |
| 262 | W is O, X is S, $R^1$ is Pr, $R^2$ is OMe, and G is $SO_2Me$. |
| 263 | W is O, X is S, $R^1$ is Pr, $R^2$ is OEt, and G is C(O)Me. |
| 264 | W is O, X is S, $R^1$ is Pr, $R^2$ is OEt, and G is C(O)Et. |
| 265 | W is O, X is S, $R^1$ is Pr, $R^2$ is OEt, and G is C(O)-i-Pr. |
| 266 | W is O, X is S, $R^1$ is Pr, $R^2$ is OEt, and G is C(O)-t-Bu. |
| 267 | W is O, X is S, $R^1$ is Pr, $R^2$ is OEt, and G is $CO_2Me$. |
| 268 | W is O, X is S, $R^1$ is Pr, $R^2$ is OEt, and G is $CO_2Et$. |
| 269 | W is O, X is S, $R^1$ is Pr, $R^2$ is OEt, and G is $CO_2$-i-Pr. |
| 270 | W is O, X is S, $R^1$ is Pr, $R^2$ is OEt, and G is $CO_2$-t-Bu. |
| 271 | W is O, X is S, $R^1$ is Pr, $R^2$ is OEt, and G is $SO_2Me$. |
| 272 | W is O, X is —CH=CH—, $R^1$ is Me, $R^2$ is Me, and G is C(O)Me. |
| 273 | W is O, X is —CH=CH—, $R^1$ is Me, $R^2$ is Me, and G is C(O)Et. |
| 274 | W is O, X is —CH=CH—, $R^1$ is Me, $R^2$ is Me, and G is C(O)-i-Pr. |
| 275 | W is O, X is —CH=CH—, $R^1$ is Me, $R^2$ is Me, and G is C(O)-t-Bu. |
| 276 | W is O, X is —CH=CH—, $R^1$ is Me, $R^2$ is Me, and G is $CO_2Me$. |
| 277 | W is O, X is —CH=CH—, $R^1$ is Me, $R^2$ is Me, and G is $CO_2Et$. |
| 278 | W is O, X is —CH=CH—, $R^1$ is Me, $R^2$ is Me, and G is $CO_2$-i-Pr. |
| 279 | W is O, X is —CH=CH—, $R^1$ is Me, $R^2$ is Me, and G is $CO_2$-t-Bu. |
| 280 | W is O, X is —CH=CH—, $R^1$ is Me, $R^2$ is Me, and G is $SO_2Me$. |
| 281 | W is O, X is —CH=CH—, $R^1$ is Me, $R^2$ is H, and G is C(O)Me. |
| 282 | W is O, X is —CH=CH—, $R^1$ is Me, $R^2$ is H, and G is C(O)Et. |
| 283 | W is O, X is —CH=CH—, $R^1$ is Me, $R^2$ is H, and G is C(O)-i-Pr. |
| 284 | W is O, X is —CH=CH—, $R^1$ is Me, $R^2$ is H, and G is C(O)-t-Bu. |
| 285 | W is O, X is —CH=CH—, $R^1$ is Me, $R^2$ is H, and G is $CO_2Me$. |

| Table | Row Heading |
|---|---|
| 286 | W is O, X is —CH=CH—, $R^1$ is Me, $R^2$ is H, and G is $CO_2Et$. |
| 287 | W is O, X is —CH=CH—, $R^1$ is Me, $R^2$ is H, and G is $CO_2$-i-Pr. |
| 288 | W is O, X is —CH=CH—, $R^1$ is Me, $R^2$ is H, and G is $CO_2$-t-Bu. |
| 289 | W is O, X is —CH=CH—, $R^1$ is Me, $R^2$ is H, and G is $SO_2Me$. |
| 290 | W is O, X is —CH=CH—, $R^1$ is Me, $R^2$ is Et, and G is C(O)Me. |
| 291 | W is O, X is —CH=CH—, $R^1$ is Me, $R^2$ is Et, and G is C(O)Et. |
| 292 | W is O, X is —CH=CH—, $R^1$ is Me, $R^2$ is Et, and G is C(O)-i-Pr. |
| 293 | W is O, X is —CH=CH—, $R^1$ is Me, $R^2$ is Et, and G is C(O)-t-Bu. |
| 294 | W is O, X is —CH=CH—, $R^1$ is Me, $R^2$ is Et, and G is $CO_2Me$. |
| 295 | W is O, X is —CH=CH—, $R^1$ is Me, $R^2$ is Et, and G is $CO_2Et$. |
| 296 | W is O, X is —CH=CH—, $R^1$ is Me, $R^2$ is Et, and G is $CO_2$-i-Pr. |
| 297 | W is O, X is —CH=CH—, $R^1$ is Me, $R^2$ is Et, and G is $CO_2$-t-Bu. |
| 298 | W is O, X is —CH=CH—, $R^1$ is Me, $R^2$ is Et, and G is $SO_2Me$. |
| 299 | W is O, X is —CH=CH—, $R^1$ is Me, $R^2$ is Pr, and G is C(O)Me. |
| 300 | W is O, X is —CH=CH—, $R^1$ is Me, $R^2$ is Pr, and G is C(O)Et. |
| 301 | W is O, X is —CH=CH—, $R^1$ is Me, $R^2$ is Pr, and G is C(O)-i-Pr. |
| 302 | W is O, X is —CH=CH—, $R^1$ is Me, $R^2$ is Pr, and G is C(O)-t-Bu. |
| 303 | W is O, X is —CH=CH—, $R^1$ is Me, $R^2$ is Pr, and G is $CO_2Me$. |
| 304 | W is O, X is —CH=CH—, $R^1$ is Me, $R^2$ is Pr, and G is $CO_2Et$. |
| 305 | W is O, X is —CH=CH—, $R^1$ is Me, $R^2$ is Pr, and G is $CO_2$-i-Pr. |
| 306 | W is O, X is —CH=CH—, $R^1$ is Me, $R^2$ is Pr, and G is $CO_2$-t-Bu. |
| 307 | W is O, X is —CH=CH—, $R^1$ is Me, $R^2$ is Pr, and G is $SO_2Me$. |
| 308 | W is O, X is —CH=CH—, $R^1$ is Me, $R^2$ is $CF_3$, and G is C(O)Me. |
| 309 | W is O, X is —CH=CH—, $R^1$ is Me, $R^2$ is $CF_3$, and G is C(O)Et. |
| 310 | W is O, X is —CH=CH—, $R^1$ is Me, $R^2$ is $CF_3$, and G is C(O)-i-Pr. |
| 311 | W is O, X is —CH=CH—, $R^1$ is Me, $R^2$ is $CF_3$, and G is C(O)-t-Bu. |
| 312 | W is O, X is —CH=CH—, $R^1$ is Me, $R^2$ is $CF_3$, and G is $CO_2Me$. |
| 313 | W is O, X is —CH=CH—, $R^1$ is Me, $R^2$ is $CF_3$, and G is $CO_2Et$. |
| 314 | W is O, X is —CH=CH—, $R^1$ is Me, $R^2$ is $CF_3$, and G is $CO_2$-i-Pr. |
| 315 | W is O, X is —CH=CH—, $R^1$ is Me, $R^2$ is $CF_3$, and G is $CO_2$-t-Bu. |
| 316 | W is O, X is —CH=CH—, $R^1$ is Me, $R^2$ is $CF_3$, and G is $SO_2Me$. |
| 317 | W is O, X is —CH=CH—, $R^1$ is Me, $R^2$ is Cl, and G is C(O)Me. |
| 318 | W is O, X is —CH=CH—, $R^1$ is Me, $R^2$ is Cl, and G is C(O)Et. |
| 319 | W is O, X is —CH=CH—, $R^1$ is Me, $R^2$ is Cl, and G is C(O)-i-Pr. |
| 320 | W is O, X is —CH=CH—, $R^1$ is Me, $R^2$ is Cl, and G is C(O)-t-Bu. |
| 321 | W is O, X is —CH=CH—, $R^1$ is Me, $R^2$ is Cl, and G is $CO_2Me$. |
| 322 | W is O, X is —CH=CH—, $R^1$ is Me, $R^2$ is Cl, and G is $CO_2Et$. |
| 323 | W is O, X is —CH=CH—, $R^1$ is Me, $R^2$ is Cl, and G is $CO_2$-i-Pr. |
| 324 | W is O, X is —CH=CH—, $R^1$ is Me, $R^2$ is Cl, and G is $CO_2$-t-Bu. |
| 325 | W is O, X is —CH=CH—, $R^1$ is Me, $R^2$ is Cl, and G is $SO_2Me$. |
| 326 | W is O, X is —CH=CH—, $R^1$ is Me, $R^2$ is Br, and G is C(O)Me. |
| 327 | W is O, X is —CH=CH—, $R^1$ is Me, $R^2$ is Br, and G is C(O)Et. |
| 328 | W is O, X is —CH=CH—, $R^1$ is Me, $R^2$ is Br, and G is C(O)-i-Pr. |
| 329 | W is O, X is —CH=CH—, $R^1$ is Me, $R^2$ is Br, and G is C(O)-t-Bu. |
| 330 | W is O, X is —CH=CH—, $R^1$ is Me, $R^2$ is Br, and G is $CO_2Me$. |
| 331 | W is O, X is —CH=CH—, $R^1$ is Me, $R^2$ is Br, and G is $CO_2Et$. |
| 332 | W is O, X is —CH=CH—, $R^1$ is Me, $R^2$ is Br, and G is $CO_2$-i-Pr. |
| 333 | W is O, X is —CH=CH—, $R^1$ is Me, $R^2$ is Br, and G is $CO_2$-t-Bu. |
| 334 | W is O, X is —CH=CH—, $R^1$ is Me, $R^2$ is Br, and G is $SO_2Me$. |
| 335 | W is O, X is —CH=CH—, $R^1$ is Me, $R^2$ is I, and G is C(O)Me. |
| 336 | W is O, X is —CH=CH—, $R^1$ is Me, $R^2$ is I, and G is C(O)Et. |
| 337 | W is O, X is —CH=CH—, $R^1$ is Me, $R^2$ is I, and G is C(O)-i-Pr. |
| 338 | W is O, X is —CH=CH—, $R^1$ is Me, $R^2$ is I, and G is C(O)-t-Bu. |
| 339 | W is O, X is —CH=CH—, $R^1$ is Me, $R^2$ is I, and G is $CO_2Me$. |
| 340 | W is O, X is —CH=CH—, $R^1$ is Me, $R^2$ is I, . and G is $CO_2Et$ |
| 341 | W is O, X is —CH=CH—, $R^1$ is Me, $R^2$ is I, and G is $CO_2$-i-Pr. |
| 342 | W is O, X is —CH=CH—, $R^1$ is Me, $R^2$ is I, and G is $CO_2$-t-Bu. |
| 343 | W is O, X is —CH=CH—, $R^1$ is Me, $R^2$ is I, and G is $SO_2Me$. |
| 344 | W is O, X is —CH=CH—, $R^1$ is Me, $R^2$ is OMe, and G is C(O)Me. |
| 345 | W is O, X is —CH=CH—, $R^1$ is Me, $R^2$ is OMe, and G is C(O)Et. |
| 346 | W is O, X is —CH=CH—, $R^1$ is Me, $R^2$ is OMe, and G is C(O)-i-Pr. |
| 347 | W is O, X is —CH=CH—, $R^1$ is Me, $R^2$ is OMe, and G is C(O)-t-Bu. |
| 348 | W is O, X is —CH=CH—, $R^1$ is Me, $R^2$ is OMe, and G is $CO_2Me$. |
| 349 | W is O, X is —CH=CH—, $R^1$ is Me, $R^2$ is OMe, and G is $CO_2Et$. |
| 350 | W is O, X is —CH=CH—, $R^1$ is Me, $R^2$ is OMe, and G is $CO_2$-i-Pr. |
| 351 | W is O, X is —CH=CH—, $R^1$ is Me, $R^2$ is OMe, and G is $CO_2$-t-Bu. |
| 352 | W is O, X is —CH=CH—, $R^1$ is Me, $R^2$ is OMe, and G is $SO_2Me$. |
| 353 | W is O, X is —CH=CH—, $R^1$ is Me, $R^2$ is OEt, and G is C(O)Me. |
| 354 | W is O, X is —CH=CH—, $R^1$ is Me, $R^2$ is OEt, and G is C(O)Et. |
| 355 | W is O, X is —CH=CH—, $R^1$ is Me, $R^2$ is OEt, and G is C(O)-i-Pr. |
| 356 | W is O, X is —CH=CH—, $R^1$ is Me, $R^2$ is OEt, and G is C(O)-t-Bu. |
| 357 | W is O, X is —CH=CH—, $R^1$ is Me, $R^2$ is OEt, and G is $CO_2Me$. |
| 358 | W is O, X is —CH=CH—, $R^1$ is Me, $R^2$ is OEt, and G is $CO_2Et$. |
| 359 | W is O, X is —CH=CH—, $R^1$ is Me, $R^2$ is OEt, and G is $CO_2$-i-Pr. |
| 360 | W is O, X is —CH=CH—, $R^1$ is Me, $R^2$ is OEt, and G is $CO_2$-t-Bu. |
| 361 | W is O, X is —CH=CH—, $R^1$ is Me, $R^2$ is OEt, and G is $SO_2Me$. |

| Table | Row Heading |
|---|---|
| 362 | W is O, X is —CH=CH—, $R^1$ is Et, $R^2$ is Me, and G is C(O)Me. |
| 363 | W is O, X is —CH=CH—, $R^1$ is Et, $R^2$ is Me, and G is C(O)Et. |
| 364 | W is O, X is —CH=CH—, $R^1$ is Et, $R^2$ is Me, and G is C(O)-i-Pr. |
| 365 | W is O, X is —CH=CH—, $R^1$ is Et, $R^2$ is Me, and G is C(O)-t-Bu. |
| 366 | W is O, X is —CH=CH—, $R^1$ is Et, $R^2$ is Me, and G is $CO_2$Me. |
| 367 | W is O, X is —CH=CH—, $R^1$ is Et, $R^2$ is Me, and G is $CO_2$Et. |
| 368 | W is O, X is —CH=CH—, $R^1$ is Et, $R^2$ is Me, and G is $CO_2$-i-Pr. |
| 369 | W is O, X is —CH=CH—, $R^1$ is Et, $R^2$ is Me, and G is $CO_2$-t-Bu. |
| 370 | W is O, X is —CH=CH—, $R^1$ is Et, $R^2$ is Me, and G is $SO_2$Me. |
| 371 | W is O, X is —CH=CH—, $R^1$ is Et, $R^2$ is H, and G is C(O)Me. |
| 372 | W is O, X is —CH=CH—, $R^1$ is Et, $R^2$ is H, and G is C(O)Et. |
| 373 | W is O, X is —CH=CH—, $R^1$ is Et, $R^2$ is H, and G is C(O)-i-Pr. |
| 374 | W is O, X is —CH=CH—, $R^1$ is Et, $R^2$ is H, and G is C(O)-t-Bu. |
| 375 | W is O, X is —CH=CH—, $R^1$ is Et, $R^2$ is H, and G is $CO_2$Me. |
| 376 | W is O, X is —CH=CH—, $R^1$ is Et, $R^2$ is H, and G is $CO_2$Et. |
| 377 | W is O, X is —CH=CH—, $R^1$ is Et, $R^2$ is H, and G is $CO_2$-i-Pr. |
| 378 | W is O, X is —CH=CH—, $R^1$ is Et, $R^2$ is H, and G is $CO_2$-t-Bu. |
| 379 | W is O, X is —CH=CH—, $R^1$ is Et, $R^2$ is H, and G is $SO_2$Me. |
| 380 | W is O, X is —CH=CH—, $R^1$ is Et, $R^2$ is Et, and G is C(O)Me. |
| 381 | W is O, X is —CH=CH—, $R^1$ is Et, $R^2$ is Et, and G is C(O)Et. |
| 382 | W is O, X is —CH=CH—, $R^1$ is Et, $R^2$ is Et, and G is C(O)-i-Pr. |
| 383 | W is O, X is —CH=CH—, $R^1$ is Et, $R^2$ is Et, and G is C(O)-t-Bu. |
| 384 | W is O, X is —CH=CH—, $R^1$ is Et, $R^2$ is Et, and G is $CO_2$Me. |
| 385 | W is O, X is —CH=CH—, $R^1$ is Et, $R^2$ is Et, and G is $CO_2$Et. |
| 386 | W is O, X is —CH=CH—, $R^1$ is Et, $R^2$ is Et, and G is $CO_2$-i-Pr. |
| 387 | W is O, X is —CH=CH—, $R^1$ is Et, $R^2$ is Et, and G is $CO_2$-t-Bu. |
| 388 | W is O, X is —CH=CH—, $R^1$ is Et, $R^2$ is Et, and G is $SO_2$Me. |
| 389 | W is O, X is —CH=CH—, $R^1$ is Et, $R^2$ is Pr, and G is C(O)Me. |
| 390 | W is O, X is —CH=CH—, $R^1$ is Et, $R^2$ is Pr, and G is C(O)Et. |
| 391 | W is O, X is —CH=CH—, $R^1$ is Et, $R^2$ is Pr, and G is C(O)-i-Pr. |
| 392 | W is O, X is —CH=CH—, $R^1$ is Et, $R^2$ is Pr, and G is C(O)-t-Bu. |
| 393 | W is O, X is —CH=CH—, $R^1$ is Et, $R^2$ is Pr, and G is $CO_2$Me. |
| 394 | W is O, X is —CH=CH—, $R^1$ is Et, $R^2$ is Pr, and G is $CO_2$Et. |
| 395 | W is O, X is —CH=CH—, $R^1$ is Et, $R^2$ is Pr, and G is $CO_2$-i-Pr. |
| 396 | W is O, X is —CH=CH—, $R^1$ is Et, $R^2$ is Pr, and G is $CO_2$-t-Bu. |
| 397 | W is O, X is —CH=CH—, $R^1$ is Et, $R^2$ is Pr, and G is $SO_2$Me. |
| 398 | W is O, X is —CH=CH—, $R^1$ is Et, $R^2$ is $CF_3$, and G is C(O)Me. |
| 399 | W is O, X is —CH=CH—, $R^1$ is Et, $R^2$ is $CF_3$, and G is C(O)Et. |
| 400 | W is O, X is —CH=CH—, $R^1$ is Et, $R^2$ is $CF_3$, and G is C(O)-i-Pr. |
| 401 | W is O, X is —CH=CH—, $R^1$ is Et, $R^2$ is $CF_3$, and G is C(O)-t-Bu. |
| 402 | W is O, X is —CH=CH—, $R^1$ is Et, $R^2$ is $CF_3$, and G is $CO_2$Me. |
| 403 | W is O, X is —CH=CH—, $R^1$ is Et, $R^2$ is $CF_3$, and G is $CO_2$Et. |
| 404 | W is O, X is —CH=CH—, $R^1$ is Et, $R^2$ is $CF_3$, and G is $CO_2$-i-Pr. |
| 405 | W is O, X is —CH=CH—, $R^1$ is Et, $R^2$ is $CF_3$, and G is $CO_2$-t-Bu. |
| 406 | W is O, X is —CH=CH—, $R^1$ is Et, $R^2$ is $CF_3$, and G is $SO_2$Me. |
| 407 | W is O, X is —CH=CH—, $R^1$ is Et, $R^2$ is Cl, and G is C(O)Me. |
| 408 | W is O, X is —CH=CH—, $R^1$ is Et, $R^2$ is Cl, and G is C(O)Et. |
| 409 | W is O, X is —CH=CH—, $R^1$ is Et, $R^2$ is Cl, and G is C(O)-i-Pr. |
| 410 | W is O, X is —CH=CH—, $R^1$ is Et, $R^2$ is Cl, and G is C(O)-t-Bu. |
| 411 | W is O, X is —CH=CH—, $R^1$ is Et, $R^2$ is Cl, and G is $CO_2$Me. |
| 412 | W is O, X is —CH=CH—, $R^1$ is Et, $R^2$ is Cl, and G is $CO_2$Et. |
| 413 | W is O, X is —CH=CH—, $R^1$ is Et, $R^2$ is Cl, and G is $CO_2$-i-Pr. |
| 414 | W is O, X is —CH=CH—, $R^1$ is Et, $R^2$ is Cl, and G is $CO_2$-t-Bu. |
| 415 | W is O, X is —CH=CH—, $R^1$ is Et, $R^2$ is Cl, and G is $SO_2$Me. |
| 416 | W is O, X is —CH=CH—, $R^1$ is Et, $R^2$ is Br, and G is C(O)Me. |
| 417 | W is O, X is —CH=CH—, $R^1$ is Et, $R^2$ is Br, and G is C(O)Et. |
| 418 | W is O, X is —CH=CH—, $R^1$ is Et, $R^2$ is Br, and G is C(O)-i-Pr. |
| 419 | W is O, X is —CH=CH—, $R^1$ is Et, $R^2$ is Br, and G is C(O)-t-Bu. |
| 420 | W is O, X is —CH=CH—, $R^1$ is Et, $R^2$ is Br, and G is $CO_2$Me. |
| 421 | W is O, X is —CH=CH—, $R^1$ is Et, $R^2$ is Br, and G is $CO_2$Et. |
| 422 | W is O, X is —CH=CH—, $R^1$ is Et, $R^2$ is Br, and G is $CO_2$-i-Pr. |
| 423 | W is O, X is —CH=CH—, $R^1$ is Et, $R^2$ is Br, and G is $CO_2$-t-Bu. |
| 424 | W is O, X is —CH=CH—, $R^1$ is Et, $R^2$ is Br, and G is $SO_2$Me. |
| 425 | W is O, X is —CH=CH—, $R^1$ is Et, $R^2$ is I, and G is C(O)Me. |
| 426 | W is O, X is —CH=CH—, $R^1$ is Et, $R^2$ is I, and G is C(O)Et. |
| 427 | W is O, X is —CH=CH—, $R^1$ is Et, $R^2$ is I, and G is C(O)-i-Pr. |
| 428 | W is O, X is —CH=CH—, $R^1$ is Et, $R^2$ is I, and G is C(O)-t-Bu. |
| 429 | W is O, X is —CH=CH—, $R^1$ is Et, $R^2$ is I, and G is $CO_2$Me. |
| 430 | W is O, X is —CH=CH—, $R^1$ is Et, $R^2$ is I, and G is $CO_2$Et. |
| 431 | W is O, X is —CH=CH—, $R^1$ is Et, $R^2$ is I, and G is $CO_2$-i-Pr. |
| 432 | W is O, X is —CH=CH—, $R^1$ is Et, $R^2$ is I, and G is $CO_2$-t-Bu. |
| 433 | W is O, X is —CH=CH—, $R^1$ is Et, $R^2$ is I, and G is $SO_2$Me. |
| 434 | W is O, X is —CH=CH—, $R^1$ is Et, $R^2$ is OMe, and G is C(O)Me. |
| 435 | W is O, X is —CH=CH—, $R^1$ is Et, $R^2$ is OMe, and G is C(O)Et. |
| 436 | W is O, X is —CH=CH—, $R^1$ is Et, $R^2$ is OMe, and G is C(O)-i-Pr. |
| 437 | W is O, X is —CH=CH—, $R^1$ is Et, $R^2$ is OMe, and G is C(O)-t-Bu. |

| Table | Row Heading |
|---|---|
| 438 | W is O, X is —CH=CH—, R¹ is Et, R² is OMe, and G is CO₂Me. |
| 439 | W is O, X is —CH=CH—, R¹ is Et, R² is OMe, and G is CO₂Et. |
| 440 | W is O, X is —CH=CH—, R¹ is Et, R² is OMe, and G is CO₂-i-Pr. |
| 441 | W is O, X is —CH=CH—, R¹ is Et, R² is OMe, and G is CO₂-t-Bu. |
| 442 | W is O, X is —CH=CH—, R¹ is Et, R² is OMe, and G is SO₂Me. |
| 443 | W is O, X is —CH=CH—, R¹ is Et, R² is OEt, and G is C(O)Me. |
| 444 | W is O, X is —CH=CH—, R¹ is Et, R² is OEt, and G is C(O)Et. |
| 445 | W is O, X is —CH=CH—, R¹ is Et, R² is OEt, and G is C(O)-i-Pr. |
| 446 | W is O, X is —CH=CH—, R¹ is Et, R² is OEt, and G is C(O)-t-Bu. |
| 447 | W is O, X is —CH=CH—, R¹ is Et, R² is OEt, and G is CO₂Me. |
| 448 | W is O, X is —CH=CH—, R¹ is Et, R² is OEt, and G is CO₂Et. |
| 449 | W is O, X is —CH=CH—, R¹ is Et, R² is OEt, and G is CO₂-i-Pr. |
| 450 | W is O, X is —CH=CH—, R¹ is Et, R² is OEt, and G is CO₂-t-Bu. |
| 451 | W is O, X is —CH=CH—, R¹ is Et, R² is OEt, and G is SO₂Me. |
| 452 | W is O, X is —CH=CH—, R¹ is Pr, R² is Me, and G is C(O)Me. |
| 453 | W is O, X is —CH=CH—, R¹ is Pr, R² is Me, and G is C(O)Et. |
| 454 | W is O, X is —CH=CH—, R¹ is Pr, R² is Me, and G is C(O)-i-Pr. |
| 455 | W is O, X is —CH=CH—, R¹ is Pr, R² is Me, and G is C(O)-t-Bu. |
| 456 | W is O, X is —CH=CH—, R¹ is Pr, R² is Me, and G is CO₂Me. |
| 457 | W is O, X is —CH=CH—, R¹ is Pr, R² is Me, and G is CO₂Et. |
| 458 | W is O, X is —CH=CH—, R¹ is Pr, R² is Me, and G is CO₂-i-Pr. |
| 459 | W is O, X is —CH=CH—, R¹ is Pr, R² is Me, and G is CO₂-t-Bu. |
| 460 | W is O, X is —CH=CH—, R¹ is Pr, R² is Me, and G is SO₂Me. |
| 461 | W is O, X is —CH=CH—, R¹ is Pr, R² is H, and G is C(O)Me. |
| 462 | W is O, X is —CH=CH—, R¹ is Pr, R² is H, and G is C(O)Et. |
| 463 | W is O, X is —CH=CH—, R¹ is Pr, R² is H, and G is C(O)-i-Pr. |
| 464 | W is O, X is —CH=CH—, R¹ is Pr, R² is H, and G is C(O)-t-Bu. |
| 465 | W is O, X is —CH=CH—, R¹ is Pr, R² is H, and G is CO₂Me. |
| 466 | W is O, X is —CH=CH—, R¹ is Pr, R² is H, and G is CO₂Et. |
| 467 | W is O, X is —CH=CH—, R¹ is Pr, R² is H, and G is CO₂-i-Pr. |
| 468 | W is O, X is —CH=CH—, R¹ is Pr, R² is H, and G is CO₂-t-Bu. |
| 469 | W is O, X is —CH=CH—, R¹ is Pr, R² is H, and G is SO₂Me. |
| 470 | W is O, X is —CH=CH—, R¹ is Pr, R² is Et, and G is C(O)Me. |
| 471 | W is O, X is —CH=CH—, R¹ is Pr, R² is Et, and G is C(O)Et. |
| 472 | W is O, X is —CH=CH—, R¹ is Pr, R² is Et, and G is C(O)-i-Pr. |
| 473 | W is O, X is —CH=CH—, R¹ is Pr, R² is Et, and G is C(O)-t-Bu. |
| 474 | W is O, X is —CH=CH—, R¹ is Pr, R² is Et, and G is CO₂Me. |
| 475 | W is O, X is —CH=CH—, R¹ is Pr, R² is Et, and G is CO₂Et. |
| 476 | W is O, X is —CH=CH—, R¹ is Pr, R² is Et, and G is CO₂-i-Pr. |
| 477 | W is O, X is —CH=CH—, R¹ is Pr, R² is Et, and G is CO₂-t-Bu. |
| 478 | W is O, X is —CH=CH—, R¹ is Pr, R² is Et, and G is SO₂Me. |
| 479 | W is O, X is —CH=CH—, R¹ is Pr, R² is Pr, and G is C(O)Me. |
| 480 | W is O, X is —CH=CH—, R¹ is Pr, R² is Pr, and G is C(O)Et. |
| 481 | W is O, X is —CH=CH—, R¹ is Pr, R² is Pr, and G is C(O)-i-Pr. |
| 482 | W is O, X is —CH=CH—, R¹ is Pr, R² is Pr, and G is C(O)-t-Bu. |
| 483 | W is O, X is —CH=CH—, R¹ is Pr, R² is Pr, and G is CO₂Me. |
| 484 | W is O, X is —CH=CH—, R¹ is Pr, R² is Pr, and G is CO₂Et. |
| 485 | W is O, X is —CH=CH—, R¹ is Pr, R² is Pr, and G is CO₂-i-Pr. |
| 486 | W is O, X is —CH=CH—, R¹ is Pr, R² is Pr, and G is CO₂-t-Bu. |
| 487 | W is O, X is —CH=CH—, R¹ is Pr, R² is Pr, and G is SO₂Me. |
| 488 | W is O, X is —CH=CH—, R¹ is Pr, R² is CF₃, and G is C(O)Me. |
| 489 | W is O, X is —CH=CH—, R¹ is Pr, R² is CF₃, and G is C(O)Et. |
| 490 | W is O, X is —CH=CH—, R¹ is Pr, R² is CF₃, and G is C(O)-i-Pr. |
| 491 | W is O, X is —CH=CH—, R¹ is Pr, R² is CF₃, and G is C(O)-t-Bu. |
| 492 | W is O, X is —CH=CH—, R¹ is Pr, R² is CF₃, and G is CO₂Me. |
| 493 | W is O, X is —CH=CH—, R¹ is Pr, R² is CF₃, and G is CO₂Et. |
| 494 | W is O, X is —CH=CH—, R¹ is Pr, R² is CF₃, and G is CO₂-i-Pr. |
| 495 | W is O, X is —CH=CH—, R¹ is Pr, R² is CF₃, and G is CO₂-t-Bu. |
| 496 | W is O, X is —CH=CH—, R¹ is Pr, R² is CF₃, and G is SO₂Me. |
| 497 | W is O, X is —CH=CH—, R¹ is Pr, R² is Cl, and G is C(O)Me. |
| 498 | W is O, X is —CH=CH—, R¹ is Pr, R² is Cl, and G is C(O)Et. |
| 499 | W is O, X is —CH=CH—, R¹ is Pr, R² is Cl, and G is C(O)-i-Pr. |
| 500 | W is O, X is —CH=CH—, R¹ is Pr, R² is Cl, and G is C(O)-t-Bu. |
| 501 | W is O, X is —CH=CH—, R¹ is Pr, R² is Cl, and G is CO₂Me. |
| 502 | W is O, X is —CH=CH—, R¹ is Pr, R² is Cl, and G is CO₂Et. |
| 503 | W is O, X is —CH=CH—, R¹ is Pr, R² is Cl, and G is CO₂-i-Pr. |
| 504 | W is O, X is —CH=CH—, R¹ is Pr, R² is Cl, and G is CO₂-t-Bu. |
| 505 | W is O, X is —CH=CH—, R¹ is Pr, R² is Cl, and G is SO₂Me. |
| 506 | W is O, X is —CH=CH—, R¹ is Pr, R² is Br, and G is C(O)Me. |
| 507 | W is O, X is —CH=CH—, R¹ is Pr, R² is Br, and G is C(O)Et. |
| 508 | W is O, X is —CH=CH—, R¹ is Pr, R² is Br, and G is C(O)-i-Pr. |
| 509 | W is O, X is —CH=CH—, R¹ is Pr, R² is Br, and G is C(O)-t-Bu. |
| 510 | W is O, X is —CH=CH—, R¹ is Pr, R² is Br, and G is CO₂Me. |
| 511 | W is O, X is —CH=CH—, R¹ is Pr, R² is Br, and G is CO₂Et. |
| 512 | W is O, X is —CH=CH—, R¹ is Pr, R² is Br, and G is CO₂-i-Pr. |
| 513 | W is O, X is —CH=CH—, R¹ is Pr, R² is Br, and G is CO₂-t-Bu. |

| Table | Row Heading |
|---|---|
| 514 | W is O, X is —CH=CH—, $R^1$ is Pr, $R^2$ is Br, and G is $SO_2Me$. |
| 515 | W is O, X is —CH=CH—, $R^1$ is Pr, $R^2$ is I, and G is C(O)Me. |
| 516 | W is O, X is —CH=CH—, $R^1$ is Pr, $R^2$ is I, and G is C(O)Et. |
| 517 | W is O, X is —CH=CH—, $R^1$ is Pr, $R^2$ is I, and G is C(O)-i-Pr. |
| 518 | W is O, X is —CH=CH—, $R^1$ is Pr, $R^2$ is I, and G is C(O)-t-Bu. |
| 519 | W is O, X is —CH=CH—, $R^1$ is Pr, $R^2$ is I, and G is $CO_2Me$. |
| 520 | W is O, X is —CH=CH—, $R^1$ is Pr, $R^2$ is I, and G is $CO_2Et$. |
| 521 | W is O, X is —CH=CH—, $R^1$ is Pr, $R^2$ is I, and G is $CO_2$-i-Pr. |
| 522 | W is O, X is —CH=CH—, $R^1$ is Pr, $R^2$ is I, and G is $CO_2$-t-Bu. |
| 523 | W is O, X is —CH=CH—, $R^1$ is Pr, $R^2$ is I, and G is $SO_2Me$. |
| 524 | W is O, X is —CH=CH—, $R^1$ is Pr, $R^2$ is OMe, and G is C(O)Me. |
| 525 | W is O, X is —CH=CH—, $R^1$ is Pr, $R^2$ is OMe, and G is C(O)Et. |
| 526 | W is O, X is —CH=CH—, $R^1$ is Pr, $R^2$ is OMe, and G is C(O)-i-Pr. |
| 527 | W is O, X is —CH=CH—, $R^1$ is Pr, $R^2$ is OMe, and G is C(O)-t-Bu. |
| 528 | W is O, X is —CH=CH—, $R^1$ is Pr, $R^2$ is OMe, and G is $CO_2Me$. |
| 529 | W is O, X is —CH=CH—, $R^1$ is Pr, $R^2$ is OMe, and G is $CO_2Et$. |
| 530 | W is O, X is —CH=CH—, $R^1$ is Pr, $R^2$ is OMe, and G is $CO_2$-i-Pr. |
| 531 | W is O, X is —CH=CH—, $R^1$ is Pr, $R^2$ is OMe, and G is $CO_2$-t-Bu. |
| 532 | W is O, X is —CH=CH—, $R^1$ is Pr, $R^2$ is OMe, and G is $SO_2Me$. |
| 533 | W is O, X is —CH=CH—, $R^1$ is Pr, $R^2$ is OEt, and G is C(O)Me. |
| 534 | W is O, X is —CH=CH—, $R^1$ is Pr, $R^2$ is OEt, and G is C(O)Et. |
| 535 | W is O, X is —CH=CH—, $R^1$ is Pr, $R^2$ is OEt, and G is C(O)-i-Pr. |
| 536 | W is O, X is —CH=CH—, $R^1$ is Pr, $R^2$ is OEt, and G is C(O)-t-Bu. |
| 537 | W is O, X is —CH=CH—, $R^1$ is Pr, $R^2$ is OEt, and G is $CO_2Me$. |
| 538 | W is O, X is —CH=CH—, $R^1$ is Pr, $R^2$ is OEt, and G is $CO_2Et$. |
| 539 | W is O, X is —CH=CH—, $R^1$ is Pr, $R^2$ is OEt, and G is $CO_2$-i-Pr. |
| 540 | W is O, X is —CH=CH—, $R^1$ is Pr, $R^2$ is OEt, and G is $CO_2$-t-Bu. |
| 541 | W is O, X is —CH=CH—, $R^1$ is Pr, $R^2$ is OEt, and G is $SO_2Me$. |
| 542 | W is O, X is S, $R^1$ is $CH_2CF_3$, $R^2$ is Me, and G is H. |
| 543 | W is O, X is S, $R^1$ is $CH_2CF_3$, $R^2$ is Me, and G is C(O)Me. |
| 544 | W is O, X is S, $R^1$ is $CH_2CF_3$, $R^2$ is Me, and G is $CO_2Me$. |
| 545 | W is O, X is S, $R^1$ is $CH_2CF_3$, $R^2$ is Br, and G is H. |
| 546 | W is O, X is S, $R^1$ is $CH_2CF_3$, $R^2$ is Br, and G is C(O)Me. |
| 547 | W is O, X is S, $R^1$ is $CH_2CF_3$, $R^2$ is Br, and G is $CO_2Me$. |
| 548 | W is O, X is S, $R^1$ is $CH_2CH_2CN$, $R^2$ is Me, and G is H. |
| 549 | W is O, X is S, $R^1$ is $CH_2CH_2CN$, $R^2$ is Me, and G is C(O)Me. |
| 550 | W is O, X is S, $R^1$ is $CH_2CH_2CN$, $R^2$ is Me, and G is $CO_2Me$. |
| 551 | W is O, X is S, $R^1$ is $CH_2CH_2CN$, $R^2$ is Br, and G is H. |
| 552 | W is O, X is S, $R^1$ is $CH_2CH_2CN$, $R^2$ is Br, and G is C(O)Me. |
| 553 | W is O, X is S, $R^1$ is $CH_2CH_2CN$, $R^2$ is Br, and G is $CO_2Me$. |
| 554 | W is O, X is —CH=CH—, $R^1$ is $CH_2CF_3$, $R^2$ is Me, and G is H. |
| 555 | W is O, X is —CH=CH—, $R^1$ is $CH_2CF_3$, $R^2$ is Me, and G is C(O)Me. |
| 556 | W is O, X is —CH=CH—, $R^1$ is $CH_2CF_3$, $R^2$ is Me, and G is $CO_2Me$. |
| 557 | W is O, X is —CH=CH—, $R^1$ is $CH_2CF_3$, $R^2$ is Br, and G is H. |
| 558 | W is O, X is —CH=CH—, $R^1$ is $CH_2CF_3$, $R^2$ is Br, and G is C(O)Me. |
| 559 | W is O, X is —CH=CH—, $R^1$ is $CH_2CF_3$, $R^2$ is Br, and G is $CO_2Me$. |
| 560 | W is O, X is —CH=CH—, $R^1$ is $CH_2CH_2CN$, $R^2$ is Me, and G is H. |
| 561 | W is O, X is —CH=CH—, $R^1$ is $CH_2CH_2CN$, $R^2$ is Me, and G is C(O)Me. |
| 562 | W is O, X is —CH=CH—, $R^1$ is $CH_2CH_2CN$, $R^2$ is Me, and G is $CO_2Me$. |
| 563 | W is O, X is —CH=CH—, $R^1$ is $CH_2CH_2CN$, $R^2$ is Br, and G is H. |
| 564 | W is O, X is —CH=CH—, $R^1$ is $CH_2CH_2CN$, $R^2$ is Br, and G is C(O)Me. |
| 565 | W is O, X is —CH=CH—, $R^1$ is $CH_2CH_2CN$, $R^2$ is Br, and G is $CO_2Me$. |
| 566 | W is O, X is O, $R^1$ is Me, $R^2$ is Me, and G is H. |
| 567 | W is O, X is O, $R^1$ is Me, $R^2$ is Me, and G is C(O)Me. |
| 568 | W is O, X is O, $R^1$ is Me, $R^2$ is Me, and G is $CO_2Me$. |
| 569 | W is O, X is O, $R^1$ is Me, $R^2$ is Br, and G is H. |
| 570 | W is O, X is O, $R^1$ is Me, $R^2$ is Br, and G is C(O)Me. |
| 571 | W is O, X is O, $R^1$ is Me, $R^2$ is Br, and G is $CO_2Me$. |
| 572 | W is O, X is —CH=C(Me)—, $R^1$ is Me, $R^2$ is Me, and G is H. |
| 573 | W is O, X is —CH=C(Me)—, $R^1$ is Me, $R^2$ is Me, and G is C(O)Me. |
| 574 | W is O, X is —CH=C(Me)—, $R^1$ is Me, $R^2$ is Me, and G is $CO_2Me$. |
| 575 | W is O, X is —CH=C(Me)—, $R^1$ is Me, $R^2$ is Br, and G is H. |
| 576 | W is O, X is —CH=C(Me)—, $R^1$ is Me, $R^2$ is Br, and G is C(O)Me. |
| 577 | W is O, X is —CH=C(Me)—, $R^1$ is Me, $R^2$ is Br, and G is $CO_2Me$. |
| 578 | W is O, X is N(Me), $R^1$ is Me, $R^2$ is Me, and G is H. |
| 579 | W is O, X is N(Me), $R^1$ is Me, $R^2$ is Me, and G is C(O)Me. |
| 580 | W is O, X is N(Me), $R^1$ is Me, $R^2$ is Me, and G is $CO_2Me$. |
| 581 | W is O, X is N(Me), $R^1$ is Me, $R^2$ is Br, and G is H. |
| 582 | W is O, X is N(Me), $R^1$ is Me, $R^2$ is Br, and G is C(O)Me. |
| 583 | W is O, X is N(Me), $R^1$ is Me, $R^2$ is Br, and G is $CO_2Me$. |
| 584 | W is O, X is —CH=C(F)—, $R^1$ is Me, $R^2$ is Me, and G is H. |
| 585 | W is O, X is —CH=C(F)—, $R^1$ is Me, $R^2$ is Me, and G is C(O)Me. |
| 586 | W is O, X is —CH=C(F)—, $R^1$ is Me, $R^2$ is Me, and G is $CO_2Me$. |
| 587 | W is O, X is —CH=C(F)—, $R^1$ is Me, $R^2$ is Br, and G is H. |
| 588 | W is O, X is —CH=C(F)—, $R^1$ is Me, $R^2$ is Br, and G is C(O)Me. |
| 589 | W is O, X is —CH=C(F)—, $R^1$ is Me, $R^2$ is Br, and G is $CO_2Me$. |
| 590 | W is O, X is —CH=C(Cl)—, $R^1$ is Me, $R^2$ is Me, and G is H. |
| 591 | W is O, X is —CH=C(Cl)—, $R^1$ is Me, $R^2$ is Me, and G is C(O)Me. |
| 592 | W is O, X is —CH=C(Cl)—, $R^1$ is Me, $R^2$ is Me, and G is $CO_2Me$. |

-continued

| Table | Row Heading |
|---|---|
| 593 | W is O, X is —CH═C(Cl)—, $R^1$ is Me, $R^2$ is Br, and G is H. |
| 594 | W is O, X is —CH═C(Cl)—, $R^1$ is Me, $R^2$ is Br, and G is C(O)Me. |
| 595 | W is O, X is —CH═C(Cl)—, $R^1$ is Me, $R^2$ is Br, and G is $CO_2Me$. |
| 596 | W is O, X is —CH═C(OMe)—, $R^1$ is Me, $R^2$ is Me, and G is H. |
| 597 | W is O, X is —CH═C(OMe)—, $R^1$ is Me, $R^2$ is Me, and G is C(O)Me. |
| 598 | W is O, X is —CH═C(OMe)—, $R^1$ is Me, $R^2$ is Me, and G is $CO_2Me$. |
| 599 | W is O, X is —CH═C(OMe)—, $R^1$ is Me, $R^2$ is Br, and G is H. |
| 600 | W is O, X is —CH═C(OMe)—, $R^1$ is Me, $R^2$ is Br, and G is C(O)Me. |
| 601 | W is O, X is —CH═C(OMe)—, $R^1$ is Me, $R^2$ is Br, and G is $CO_2Me$. |
| 602 | W is O, X is —CH═C(CN)—, $R^1$ is Me, $R^2$ is Me, and G is H. |
| 603 | W is O, X is —CH═C(CN)—, $R^1$ is Me, $R^2$ is Me, and G is C(O)Me. |
| 604 | W is O, X is —CH═C(CN)—, $R^1$ is Me, $R^2$ is Me, and G is $CO_2Me$. |
| 605 | W is O, X is —CH═C(CN)—, $R^1$ is Me, $R^2$ is Br, and G is H. |
| 606 | W is O, X is —CH═C(CN)—, $R^1$ is Me, $R^2$ is Br, and G is C(O)Me. |
| 607 | W is O, X is —CH═C(CN)—, $R^1$ is Me, $R^2$ is Br, and G is CO2Me. |
| 608 | W is S, X is S, $R^1$ is Me, $R^2$ is Me, and G is H. |
| 609 | W is S, X is S, $R^1$ is Me, $R^2$ is Me, and G is C(O)Me. |
| 610 | W is S, X is S, $R^1$ is Me, $R^2$ is Me, and G is $CO_2Me$. |
| 611 | W is S, X is S, $R^1$ is Me, $R^2$ is Br, and G is H. |
| 612 | W is S, X is S, $R^1$ is Me, $R^2$ is Br, and G is C(O)Me. |
| 613 | W is S, X is S, $R^1$ is Me, $R^2$ is Br, and G is $CO_2Me$. |
| 614 | W is S, X is —CH═CH—, $R^1$ is Me, $R^2$ is Me, and G is H. |
| 615 | W is S, X is —CH═CH—, $R^1$ is Me, $R^2$ is Me, and G is C(O)Me. |
| 616 | W is S, X is —CH═CH—, $R^1$ is Me, $R^2$ is Me, and G is $CO_2Me$. |
| 617 | W is S, X is —CH═CH—, $R^1$ is Me, $R^2$ is Br, and G is H. |
| 618 | W is S, X is —CH═CH—, $R^1$ is Me, $R^2$ is Br, and G is C(O)Me. |
| 619 | W is S, X is —CH═CH—, $R^1$ is Me, $R^2$ is Br, and G is $CO_2Me$. |
| 620 | W is O, X is —CH═CH—, $R^1$ is $CH_3$, $R^2$ is Me, and G is H. |
| 621 | W is S, X is —CH═CH—, $R^1$ is $CH_3$, $R^2$ is Me, and G is H. |
| 622 | W is O, X is —CH═CH—, $R^1$ is $CH_2CH_3$, $R^2$ is Me, and G is H. |
| 623 | W is S, X is —CH═CH—, $R^1$ is $CH_2CH_3$, $R^2$ is Me, and G is H. |
| 624 | W is O, X is —CH═CH—, $R^1$ is $CH_3$, $R^2$ is Et, and G is H. |
| 625 | W is S, X is —CH═CH—, $R^1$ is $CH_3$, $R^2$ is Et, and G is H. |
| 626 | W is O, X is —CH═CH—, $R^1$ is $CH_2CH_3$, $R^2$ is Et, and G is H. |
| 627 | W is S, X is —CH═CH—, $R^1$ is $CH_2CH_3$, $R^2$ is Et, and G is H. |

Formulation/Utility

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following non-limiting Examples are illustrative of the invention. Percentages are by weight except where otherwise indicated.

Example A

| High Strength Concentrate | |
|---|---|
| Compound 1 | 98.5% |
| silica aerogel | 0.5% |
| synthetic amorphous fine silica | 1.0% |

Example B

| Wettable Powder | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 1 | 10.0% |
| attapulgite granules (low volatile matter, 0.71/0.30 mm; U.S.S. No. 25-50 sieves) | 90.0% |

Example D

| Extruded Pellet | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 1 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 1 | 5.0% |
| polyvinylpyrrolidone-vinyl acetate copolymer | 30.0% |

-continued

Microemulsion

| | |
|---|---|
| alkylpolyglycoside | 30.0% |
| glyceryl monooleate | 15.0% |
| water | 20.0% |

Example G

Suspension Concentrate

| | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

Emulsion in Water

| | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

Oil Dispersion

| | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except the "Compound 1" is replaced with "Compound 2", "Compound 3", "Compound 4", "Compound 5", "Compound 6", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24", "Compound 25", "Compound 26", "Compound 27", "Compound 28", "Compound 29", "Compound 30", "Compound 31", "Compound 32", "Compound 33", "Compound 34", "Compound 35", "Compound 36", "Compound 37", "Compound 38", "Compound 39", "Compound 40", "Compound 41", "Compound 42", "Compound 43", "Compound 44", "Compound 45", "Compound 46", "Compound 47", "Compound 48", "Compound 49", "Compound 50", "Compound 51", "Compound 52", "Compound 53", "Compound 54", "Compound 55", "Compound 56", "Compound 57", "Compound 58", "Compound 59", "Compound 60", "Compound 61", "Compound 62", "Compound 63", "Compound 64", "Compound 65", "Compound 66", "Compound 67", "Compound 68", "Compound 69", "Compound 70", "Compound 71", "Compound 72", "Compound 73", "Compound 74", "Compound 75", "Compound 76", "Compound 77", "Compound 78", "Compound 79", "Compound 80", "Compound 81", "Compound 82", "Compound 83", "Compound 84", "Compound 85", "Compound 86", "Compound 87", "Compound 88", "Compound 89", "Compound 90", "Compound 91", "Compound 92", "Compound 93", "Compound 94", "Compound 95", "Compound 96", "Compound 97", "Compound 98", "Compound 99", "Compound 100", "Compound 101", "Compound 102", "Compound 103", "Compound 104", "Compound 105", "Compound 106", "Compound 107", "Compound 108", "Compound 109", "Compound 110", "Compound 111", "Compound 112", "Compound 113", "Compound 114", "Compound 115", "Compound 116", "Compound 117", "Compound 118", "Compound 119", "Compound 120", "Compound 121", "Compound 122", "Compound 123", "Compound 124", "Compound 125", "Compound 126", "Compound 127", "Compound 128", "Compound 129", "Compound 130", "Compound 131", "Compound 132", "Compound 133", "Compound 134", "Compound 135", "Compound 136", "Compound 137", "Compound 138", "Compound 139", "Compound 140", "Compound 141", "Compound 142", "Compound 143", "Compound 144", "Compound 145", "Compound 146", "Compound 147", "Compound 148", "Compound 149", "Compound 150", "Compound 151", "Compound 152", "Compound 153", "Compound 154", "Compound 155", "Compound 156", "Compound 157", "Compound 158", "Compound 159", "Compound 160", "Compound 161", "Compound 162", "Compound 163", "Compound 164", "Compound 165", "Compound 166", "Compound 167", "Compound 168", "Compound 169", "Compound 170", "Compound 171", "Compound 172", "Compound 173", "Compound 174", "Compound 175", "Compound 176", "Compound 177", "Compound 178", "Compound 179", "Compound 180", "Compound 181", "Compound 182", "Compound 183", "Compound 184", "Compound 185", "Compound 186", "Compound 187" or "Compound 188".

Test results indicate that the compounds of the present invention are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), *sorghum*, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. "tol." means "tolerance". A hyphen "-" means the entry is not available.

| | Trait Description |
|---|---|
| T1 | Glyphosate tolerance |
| T2 | High lauric acid oil |
| T3 | Glufosinate tolerance |
| T4 | Phytate breakdown |
| T5 | Oxynil tolerance |
| T6 | Disease resistance |
| T7 | Insect resistance |
| T9 | Modified flower color |
| T11 | ALS herbicide tol. |
| T12 | Dicamba tolerance |
| T13 | Anti-allergy |
| T14 | Salt tolerance |
| T15 | Cold tolerance |
| T16 | Imidazolinone herbicide tol. |
| T17 | Modified alpha-amylase |
| T18 | Pollination control |
| T19 | 2,4-D tolerance |
| T20 | Increased lysine |
| T21 | Drought tolerance |
| T22 | Delayed ripening/senescence |
| T23 | Modified product quality |
| T24 | High cellulose |
| T25 | Modified starch/carbohydrate |
| T26 | Insect & disease resistance |
| T27 | High tryptophan |
| T28 | Erect leaves semidwarf |
| T29 | Semidwarf |
| T30 | Low iron tolerance |
| T31 | Modified oil/fatty acid |
| T32 | HPPD tolerance |
| T33 | High oil |
| T34 | Aryloxyalkanoate tol. |
| T35 | Mesotrione tolerance |
| T36 | Reduced nicotine |
| T37 | Modified product |

Exhibit C

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |

-continued

| Crop | Event Name | Exhibit C Event Code | Trait(s) | Gene(s) |
|---|---|---|---|---|
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1Ac | GTL-GMF311-7 | T7 | cry1Ab-Ac |
| Cotton | GHB119 | BCS-GH005-8 | T7 | cry2Ae |
| Cotton | GHB614 | BCS-GH002-5 | Ti | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | Ti | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |

Exhibit C -continued

| Crop | Event Name | Event Code | Trait(s) | Gene(s) |
|---|---|---|---|---|
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |

Exhibit C

| Crop | Event Name | Event Code | Trait(s) | Gene(s) |
|---|---|---|---|---|
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92 /130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DA568416-4 | DA568416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DA544406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*), **Polish (*B. rapa*), # Eggplant

Although most typically, compounds of the invention are used to control undesired vegetation, contact of desired vegetation in the treated locus with compounds of the invention may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron, vemolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3

(2H)-pyridazinone), 5-[[(2,6-difluorophenyl)methoxy]methyl]-4,5-dihydro-5-methyl-3-(3-methyl-2-thienyl)isoxazole (previously methioxolin), 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione, 4-(4-fluorophenyl)-6-[(2-hydroxy-6-oxo-1-cyclohexen-1-yl)carbonyl]-2-methyl-1,2,4-triazine-3,5 (2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U. K., 2003 and *The BioPesticide Manual*, 2nd Edition, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is generally between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Table A1 lists specific combinations of a Component (a) with Component (b) illustrative of the mixtures, compositions and methods of the present invention. Compound No. (Compound Number) (i.e. Compound 1) in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:384-6:1. The remaining lines of Table A1 are to be construed similarly.

TABLE A1

| Component (a) (Compound No.) | Component (b) | Typical Weight Ratio | More Typical Weight Ratio | Most Typical Weight Ratio |
|---|---|---|---|---|
| 1 | 2,4-D | 1:384-6:1 | 1:128-2:1 | 1:12-1:2 |
| 1 | Acetochlor | 1:1536-2:1 | 1:512-1:2 | 1:48-1:6 |
| 1 | Acifluorfen | 1:192-12:1 | 1:64-4:1 | 1:6-2:1 |
| 1 | Aclonifen | 1:1714-2:1 | 1:571-1:3 | 1:53-1:6 |
| 1 | Alachlor | 1:1536-2:1 | 1:512-1:2 | 1:48-1:6 |
| 1 | Ametiyn | 1:768-3:1 | 1:256-1:1 | 1:24-1:3 |
| 1 | Amicarbazone | 1:384-6:1 | 1:128-2:1 | 1:12-1:2 |
| 1 | Amidosulfuron | 1:13-168:1 | 1:4-56:1 | 2:1-21:1 |
| 1 | Aminocyclopyrachlor | 1:96-24:1 | 1:32-8:1 | 1:3-3:1 |
| 1 | Aminopyralid | 1:41-56:1 | 1:13-19:1 | 1:1-7:1 |
| 1 | Amitrole | 1:1536-2:1 | 1:512-1:2 | 1:48-1:6 |
| 1 | Anilofos | 1:192-12:1 | 1:64-4:1 | 1:6-2:1 |
| 1 | Asulam | 1:1920-2:1 | 1:640-1:3 | 1:60-1:7 |
| 1 | Atrazine | 1:384-6:1 | 1:128-2:1 | 1:12-1:2 |
| 1 | Azimsulfuron | 1:13-168:1 | 1:4-56:1 | 2:1-21:1 |
| 1 | Beflubutamid | 1:685-4:1 | 1:228-2:1 | 1:21-1:3 |
| 1 | Benfuresate | 1:1234-2:1 | 1:411-1:2 | 1:38-1:5 |
| 1 | Bensulfuron-methyl | 1:51-45:1 | 1:17-15:1 | 1:1-6:1 |
| 1 | Bentazone | 1:384-6:1 | 1:128-2:1 | 1:12-1:2 |
| 1 | Benzobicyclon | 1:171-14:1 | 1:57-5:1 | 1:5-2:1 |
| 1 | Benzofenap | 1:514-5:1 | 1:171-2:1 | 1:16-1:2 |
| 1 | Bicyclopyrone | 1:85-27:1 | 1:28-9:1 | 1:2-4:1 |
| 1 | Bifenox | 1:514-5:1 | 1:171-2:1 | 1:16-1:2 |
| 1 | Bispyribac-sodium | 1:20-112:1 | 1:6-38:1 | 1:1-14:1 |
| 1 | Bromacil | 1:768-3:1 | 1:256-1:1 | 1:24-1:3 |
| 1 | Bromobutide | 1:768-3:1 | 1:256-1:1 | 1:24-1:3 |
| 1 | Bromoxynil | 1:192-12:1 | 1:64-4:1 | 1:6-2:1 |
| 1 | Butachlor | 1:1536-2:1 | 1:512-1:2 | 1:48-1:6 |
| 1 | Butafenacil | 1:85-27:1 | 1:28-9:1 | 1:2-4:1 |
| 1 | Butylate | 1:3085-1:2 | 1:1028-1:5 | 1:96-1:11 |
| 1 | Carfenstrole | 1:384-6:1 | 1:128-2:1 | 1:12-1:2 |
| 1 | Carfentrazone-ethyl | 1:257-9:1 | 1:85-3:1 | 1:8-2:1 |
| 1 | Chlorimuron-ethyl | 1:17-135:1 | 1:5-45:1 | 1:1-17:1 |
| 1 | Chlorotoluron | 1:1536-2:1 | 1:512-1:2 | 1:48-1:6 |
| 1 | Chlorsulfuron | 1:13-168:1 | 1:4-56:1 | 2:1-21:1 |
| 1 | Cincosulfuron | 1:34-68:1 | 1:11-23:1 | 1:1-9:1 |
| 1 | Cinidon-ethyl | 1:768-3:1 | 1:256-1:1 | 1:24-1:3 |
| 1 | Cinmethylin | 1:68-34:1 | 1:22-12:1 | 1:2-5:1 |
| 1 | Clacyfos | 1:384-6:1 | 1:128-2:1 | 1:12-1:2 |
| 1 | Clethodim | 1:96-24:1 | 1:32-8:1 | 1:3-3:1 |
| 1 | Clodinafop-propargyl | 1:41-56:1 | 1:13-19:1 | 1:1-7:1 |
| 1 | Clomazone | 1:768-3:1 | 1:256-1:1 | 1:24-1:3 |
| 1 | Clomeprop | 1:342-7:1 | 1:114-3:1 | 1:10-1:2 |
| 1 | Clopyralid | 1:384-6:1 | 1:128-2:1 | 1:12-1:2 |
| 1 | Cloransulam-methyl | 1:24-96:1 | 1:8-32:1 | 1:1-12:1 |
| 1 | Cumyluron | 1:768-3:1 | 1:256-1:1 | 1:24-1:3 |
| 1 | Cyanazine | 1:768-3:1 | 1:256-1:1 | 1:24-1:3 |
| 1 | Cyclopyrimorate | 1:34-68:1 | 1:11-23:1 | 1:1-9:1 |
| 1 | Cyclosulfamuron | 1:34-68:1 | 1:11-23:1 | 1:1-9:1 |
| 1 | Cycloxydim | 1:192-12:1 | 1:64-4:1 | 1:6-2:1 |
| 1 | Cyhalofop | 1:51-45:1 | 1:17-15:1 | 1:1-6:1 |
| 1 | Daimuron | 1:384-6:1 | 1:128-2:1 | 1:12-1:2 |
| 1 | Desmedipham | 1:644-4:1 | 1:214-2:1 | 1:20-1:3 |
| 1 | Dicamba | 1:384-6:1 | 1:128-2:1 | 1:12-1:2 |
| 1 | Dichlobenil | 1:2742-1:2 | 1:914-1:4 | 1:85-1:10 |
| 1 | Dichlorprop | 1:1851-2:1 | 1:617-1:3 | 1:57-1:7 |
| 1 | Diclofop-methyl | 1:768-3:1 | 1:256-1:1 | 1:24-1:3 |
| 1 | Diclosulam | 1:20-112:1 | 1:6-38:1 | 1:1-14:1 |
| 1 | Difenzoquat | 1:576-4:1 | 1:192-2:1 | 1:18-1:2 |
| 1 | Diflufenican | 1:1714-2:1 | 1:571-1:3 | 1:53-1:6 |
| 1 | Diflufenzopyr | 1:24-96:1 | 1:8-32:1 | 1:1-12:1 |
| 1 | Dimethachlor | 1:1536-2:1 | 1:512-1:2 | 1:48-1:6 |
| 1 | Dimethametiyn | 1:384-6:1 | 1:128-2:1 | 1:12-1:2 |
| 1 | Dimethenamid-P | 1:768-3:1 | 1:256-1:1 | 1:24-1:3 |
| 1 | Dithiopyr | 1:384-6:1 | 1:128-2:1 | 1:12-1:2 |
| 1 | Diuron | 1:768-3:1 | 1:256-1:1 | 1:24-1:3 |
| 1 | EPTC | 1:1536-2:1 | 1:512-1:2 | 1:48-1:6 |
| 1 | Esprocarb | 1:2742-1:2 | 1:914-1:4 | 1:85-1:10 |
| 1 | Ethalfluralin | 1:768-3:1 | 1:256-1:1 | 1:24-1:3 |

TABLE A1-continued

| Component (a) (Compound No.) | Component (b) | Typical Weight Ratio | More Typical Weight Ratio | Most Typical Weight Ratio |
|---|---|---|---|---|
| 1 | Ethametsulfuron-methyl | 1:34-68:1 | 1:11-23:1 | 1:1-9:1 |
| 1 | Ethoxyfen | 1:17-135:1 | 1:5-45:1 | 1:1-17:1 |
| 1 | Ethoxysulfuron | 1:41-56:1 | 1:13-19:1 | 1:1-7:1 |
| 1 | Etobenzanid | 1:514-5:1 | 1:171-2:1 | 1:16-1:2 |
| 1 | Fenoxaprop-ethyl | 1:240-10:1 | 1:80-4:1 | 1:7-2:1 |
| 1 | Fenoxasulfone | 1:171-14:1 | 1:57-5:1 | 1:5-2:1 |
| 1 | Fenquinotrione | 1:85-27:1 | 1:28-9:1 | 1:2-4:1 |
| 1 | Fentrazamide | 1:34-68:1 | 1:11-23:1 | 1:1-9:1 |
| 1 | Flazasulfuron | 1:34-68:1 | 1:11-23:1 | 1:1-9:1 |
| 1 | Florasulam | 1:5-420:1 | 1:1-140:1 | 5:1-53:1 |
| 1 | Fluazifop-butyl | 1:384-6:1 | 1:128-2:1 | 1:12-1:2 |
| 1 | Flucarbazone | 1:17-135:1 | 1:5-45:1 | 1:1-17:1 |
| 1 | Flucetosulfuron | 1:17-135:1 | 1:5-45:1 | 1:1-17:1 |
| 1 | Flufenacet | 1:514-5:1 | 1:171-2:1 | 1:16-1:2 |
| 1 | Flumetsulam | 1:48-48:1 | 1:16-16:1 | 1:1-6:1 |
| 1 | Flumiclorac-pentyl | 1:20-112:1 | 1:6-38:1 | 1:1-14:1 |
| 1 | Flumioxazin | 1:51-45:1 | 1:17-15:1 | 1:1-6:1 |
| 1 | Fluometuron | 1:768-3:1 | 1:256-1:1 | 1:24-1:3 |
| 1 | Flupyrsulfuron-methyl | 1:6-336:1 | 1:2-112:1 | 4:1-42:1 |
| 1 | Fluridone | 1:768-3:1 | 1:256-1:1 | 1:24-1:3 |
| 1 | Fluroxypyr | 1:192-12:1 | 1:64-4:1 | 1:6-2:1 |
| 1 | Flurtamone | 1:1714-2:1 | 1:571-1:3 | 1:53-1:6 |
| 1 | Fluthiacet-methyl | 1:96-42:1 | 1:32-14:1 | 1:1-6:1 |
| 1 | Fomesafen | 1:192-12:1 | 1:64-4:1 | 1:6-2:1 |
| 1 | Foramsulfuron | 1:27-84:1 | 1:9-28:1 | 1:1-11:1 |
| 1 | Glufosinate | 1:576-4:1 | 1:192-2:1 | 1:18-1:2 |
| 1 | Glyphosate | 1:576-4:1 | 1:192-2:1 | 1:18-1:2 |
| 1 | Halosulfuron-methyl | 1:34-68:1 | 1:11-23:1 | 1:1-9:1 |
| 1 | Halauxifen | 1:41-56:1 | 1:13-19:1 | 1:1-7:1 |
| 1 | Halauxifen methyl | 1:41-56:1 | 1:13-19:1 | 1:1-7:1 |
| 1 | Haloxyfop-methyl | 1:68-34:1 | 1:22-12:1 | 1:2-5:1 |
| 1 | Hexazinone | 1:384-6:1 | 1:128-2:1 | 1:12-1:2 |
| 1 | Imazamox | 1:27-84:1 | 1:9-28:1 | 1:1-11:1 |
| 1 | Imazapic | 1:41-56:1 | 1:13-19:1 | 1:1-7:1 |
| 1 | Imazapyr | 1:171-14:1 | 1:57-5:1 | 1:5-2:1 |
| 1 | Imazaquin | 1:68-34:1 | 1:22-12:1 | 1:2-5:1 |
| 1 | Imazethabenz-methyl | 1:342-7:1 | 1:114-3:1 | 1:10-1:2 |
| 1 | Imazethapyr | 1:48-48:1 | 1:16-16:1 | 1:1-6:1 |
| 1 | Imazosulfuron | 1:54-42:1 | 1:18-14:1 | 1:1-6:1 |
| 1 | Indanofan | 1:685-4:1 | 1:228-2:1 | 1:21-1:3 |
| 1 | Indaziflam | 1:51-45:1 | 1:17-15:1 | 1:1-6:1 |
| 1 | Iodosulfuron-methyl | 1:6-336:1 | 1:2-112:1 | 4:1-42:1 |
| 1 | Ioxynil | 1:384-6:1 | 1:128-2:1 | 1:12-1:2 |
| 1 | Ipfencarbazone | 1:171-14:1 | 1:57-5:1 | 1:5-2:1 |
| 1 | Isoproturon | 1:768-3:1 | 1:256-1:1 | 1:24-1:3 |
| 1 | Isoxaben | 1:576-4:1 | 1:192-2:1 | 1:18-1:2 |
| 1 | Isoxaflutole | 1:120-20:1 | 1:40-7:1 | 1:3-3:1 |
| 1 | Lactofen | 1:85-27:1 | 1:28-9:1 | 1:2-4:1 |
| 1 | Lenacil | 1:768-3:1 | 1:256-1:1 | 1:24-1:3 |
| 1 | Linuron | 1:768-3:1 | 1:256-1:1 | 1:24-1:3 |
| 1 | MCPA | 1:384-6:1 | 1:128-2:1 | 1:12-1:2 |
| 1 | MCPB | 1:576-4:1 | 1:192-2:1 | 1:18-1:2 |
| 1 | Mecoprop | 1:1536-2:1 | 1:512-1:2 | 1:48-1:6 |
| 1 | Mefenacet | 1:768-3:1 | 1:256-1:1 | 1:24-1:3 |
| 1 | Mefluidide | 1:384-6:1 | 1:128-2:1 | 1:12-1:2 |
| 1 | Mesosulfuron-methyl | 1:10-224:1 | 1:3-75:1 | 3:1-28:1 |
| 1 | Mesotrione | 1:85-27:1 | 1:28-9:1 | 1:2-4:1 |
| 1 | Metamifop | 1:85-27:1 | 1:28-9:1 | 1:2-4:1 |
| 1 | Metazachlor | 1:768-3:1 | 1:256-1:1 | 1:24-1:3 |
| 1 | Metazosulfuron | 1:51-45:1 | 1:17-15:1 | 1:1-6:1 |
| 1 | Methabenzthiazuron | 1:1536-2:1 | 1:512-1:2 | 1:48-1:6 |
| 1 | Metolachlor | 1:1536-2:1 | 1:512-1:2 | 1:48-1:6 |
| 1 | Metosulam | 1:17-135:1 | 1:5-45:1 | 1:1-17:1 |
| 1 | Metribuzin | 1:384-6:1 | 1:128-2:1 | 1:12-1:2 |
| 1 | Metsulfuron-methyl | 1:4-560:1 | 1:1-187:1 | 7:1-70:1 |
| 1 | Molinate | 1:2057-2:1 | 1:685-1:3 | 1:64-1:8 |
| 1 | Napropamide | 1:768-3:1 | 1:256-1:1 | 1:24-1:3 |
| 1 | Napropamide-M | 1:384-6:1 | 1:128-2:1 | 1:12-1:2 |
| 1 | Naptalam | 1:384-6:1 | 1:128-2:1 | 1:12-1:2 |

TABLE A1-continued

| Component (a) (Compound No.) | Component (b) | Typical Weight Ratio | More Typical Weight Ratio | Most Typical Weight Ratio |
|---|---|---|---|---|
| 1 | Nicosulfuron | 1:24-96:1 | 1:8-32:1 | 1:1-12:1 |
| 1 | Norflurazon | 1:2304-1:1 | 1:768-1:3 | 1:72-1:8 |
| 1 | Orbencarb | 1:2742-1:2 | 1:914-1:4 | 1:85-1:10 |
| 1 | Orthosulfamuron | 1:41-56:1 | 1:13-19:1 | 1:1-7:1 |
| 1 | Ofyzalin | 1:1028-3:1 | 1:342-1:2 | 1:32-1:4 |
| 1 | Oxadiargyl | 1:768-3:1 | 1:256-1:1 | 1:24-1:3 |
| 1 | Oxadiazon | 1:1097-3:1 | 1:365-1:2 | 1:34-1:4 |
| 1 | Oxasulfuron | 1:54-42:1 | 1:18-14:1 | 1:1-6:1 |
| 1 | Oxaziclomefone | 1:85-27:1 | 1:28-9:1 | 1:2-4:1 |
| 1 | Oxyfluorfen | 1:768-3:1 | 1:256-1:1 | 1:24-1:3 |
| 1 | Paraquat | 1:384-6:1 | 1:128-2:1 | 1:12-1:2 |
| 1 | Pendimethalin | 1:768-3:1 | 1:256-1:1 | 1:24-1:3 |
| 1 | Penoxsulam | 1:20-112:1 | 1:6-38:1 | 1:1-14:1 |
| 1 | Penthoxamid | 1:768-3:1 | 1:256-1:1 | 1:24-1:3 |
| 1 | Pentoxazone | 1:205-12:1 | 1:68-4:1 | 1:6-2:1 |
| 1 | Phenmedipham | 1:205-12:1 | 1:68-4:1 | 1:6-2:1 |
| 1 | Picloram | 1:192-12:1 | 1:64-4:1 | 1:6-2:1 |
| 1 | Picolinafen | 1:68-34:1 | 1:22-12:1 | 1:2-5:1 |
| 1 | Pinoxaden | 1:51-45:1 | 1:17-15:1 | 1:1-6:1 |
| 1 | Pretilachlor | 1:384-6:1 | 1:128-2:1 | 1:12-1:2 |
| 1 | Primisulfuron-methyl | 1:17-135:1 | 1:5-45:1 | 1:1-17:1 |
| 1 | Prodiamine | 1:768-3:1 | 1:256-1:1 | 1:24-1:3 |
| 1 | Profoxydim | 1:85-27:1 | 1:28-9:1 | 1:2-4:1 |
| 1 | Prometiyn | 1:768-3:1 | 1:256-1:1 | 1:24-1:3 |
| 1 | Propachlor | 1:2304-1:1 | 1:768-1:3 | 1:72-1:8 |
| 1 | Propanil | 1:768-3:1 | 1:256-1:1 | 1:24-1:3 |
| 1 | Propaquizafop | 1:96-24:1 | 1:32-8:1 | 1:3-3:1 |
| 1 | Propoxycarbazone | 1:34-68:1 | 1:11-23:1 | 1:1-9:1 |
| 1 | Propyrisulfuron | 1:34-68:1 | 1:11-23:1 | 1:1-9:1 |
| 1 | Propyzamide | 1:768-3:1 | 1:256-1:1 | 1:24-1:3 |
| 1 | Prosulfocarb | 1:2400-1:2 | 1:800-1:4 | 1:75-1:9 |
| 1 | Prosulfuron | 1:13-168:1 | 1:4-56:1 | 2:1-21:1 |
| 1 | Pyraclonil | 1:85-27:1 | 1:28-9:1 | 1:2-4:1 |
| 1 | Pyraflufen-ethyl | 1:10-224:1 | 1:3-75:1 | 3:1-28:1 |
| 1 | Pyrasulfotole | 1:27-84:1 | 1:9-28:1 | 1:1-11:1 |
| 1 | Pyrazolynate | 1:1714-2:1 | 1:571-1:3 | 1:53-1:6 |
| 1 | Pyrazosulfuron-ethyl | 1:20-112:1 | 1:6-38:1 | 1:1-14:1 |
| 1 | Pyrazoxyfen | 1:10-224:1 | 1:3-75:1 | 3:1-28:1 |
| 1 | Pyribenzoxim | 1:20-112:1 | 1:6-38:1 | 1:1-14:1 |
| 1 | Pyributicarb | 1:768-3:1 | 1:256-1:1 | 1:24-1:3 |
| 1 | Pyridate | 1:576-4:1 | 1:192-2:1 | 1:18-1:2 |
| 1 | Pyriftalid | 1:20-112:1 | 1:6-38:1 | 1:1-14:1 |
| 1 | Pyriminobac-methyl | 1:41-56:1 | 1:13-19:1 | 1:1-7:1 |
| 1 | Pyrimisulfan | 1:34-68:1 | 1:11-23:1 | 1:1-9:1 |
| 1 | Pyrithiobac | 1:48-48:1 | 1:16-16:1 | 1:1-6:1 |
| 1 | Pyroxasulfone | 1:171-14:1 | 1:57-5:1 | 1:5-2:1 |
| 1 | Pyroxsulam | 1:10-224:1 | 1:3-75:1 | 3:1-28:1 |
| 1 | Quinclorac | 1:384-6:1 | 1:128-2:1 | 1:12-1:2 |
| 1 | Quizalofop-ethyl | 1:85-27:1 | 1:28-9:1 | 1:2-4:1 |
| 1 | Rimsulfuron | 1:27-84:1 | 1:9-28:1 | 1:1-11:1 |
| 1 | Saflufenacil | 1:51-45:1 | 1:17-15:1 | 1:1-6:1 |
| 1 | Sethoxydim | 1:192-12:1 | 1:64-4:1 | 1:6-2:1 |
| 1 | Simazine | 1:768-3:1 | 1:256-1:1 | 1:24-1:3 |
| 1 | Sulcotrione | 1:240-10:1 | 1:80-4:1 | 1:7-2:1 |
| 1 | Sulfentrazone | 1:294-8:1 | 1:98-3:1 | 1:9-1:2 |
| 1 | Sulfometuron-methyl | 1:68-34:1 | 1:22-12:1 | 1:2-5:1 |
| 1 | Sulfosulfuron | 1:17-135:1 | 1:5-45:1 | 1:1-17:1 |
| 1 | Tebuthiuron | 1:768-3:1 | 1:256-1:1 | 1:24-1:3 |
| 1 | Tefufyltrione | 1:85-27:1 | 1:28-9:1 | 1:2-4:1 |
| 1 | Tembotrione | 1:63-37:1 | 1:21-13:1 | 1:1-5:1 |
| 1 | Tepraloxydim | 1:51-45:1 | 1:17-15:1 | 1:1-6:1 |
| 1 | Terbacil | 1:576-4:1 | 1:192-2:1 | 1:18-1:2 |
| 1 | Terbuthylazine | 1:1714-2:1 | 1:571-1:3 | 1:53-1:6 |
| 1 | Terbutiyn | 1:384-6:1 | 1:128-2:1 | 1:12-1:2 |
| 1 | Thenylchlor | 1:171-14:1 | 1:57-5:1 | 1:5-2:1 |
| 1 | Thiazopyr | 1:768-3:1 | 1:256-1:1 | 1:24-1:3 |
| 1 | Thiencarbazone | 1:6-336:1 | 1:2-112:1 | 4:1-42:1 |
| 1 | Thifensulfuron-methyl | 1:10-224:1 | 1:3-75:1 | 3:1-28:1 |
| 1 | Tiafenacil | 1:85-27:1 | 1:28-9:1 | 1:2-4:1 |
| 1 | Thiobencath | 1:1536-2:1 | 1:512-1:2 | 1:48-1:6 |

TABLE A1-continued

| Component (a) (Compound No.) | Component (b) | Typical Weight Ratio | More Typical Weight Ratio | Most Typical Weight Ratio |
|---|---|---|---|---|
| 1 | Topramezone | 1:13-168:1 | 1:4-56:1 | 2:1-21:1 |
| 1 | Tralkoxydim | 1:137-17:1 | 1:45-6:1 | 1:4-3:1 |
| 1 | Triallate | 1:1536-2:1 | 1:512-1:2 | 1:48-1:6 |
| 1 | Triasulfuron | 1:10-224:1 | 1:3-75:1 | 3:1-28:1 |
| 1 | Triaziflam | 1:342-7:1 | 1:114-3:1 | 1:10-1:2 |
| 1 | Tribenuron-methyl | 1:6-336:1 | 1:2-112:1 | 4:1-42:1 |
| 1 | Triclopyr | 1:384-6:1 | 1:128-2:1 | 1:12-1:2 |
| 1 | Trifloxysulfuron | 1:5-420:1 | 1:1-140:1 | 5:1-53:1 |
| 1 | Trifluralin | 1:576-4:1 | 1:192-2:1 | 1:18-1:2 |
| 1 | Triflusulfuron-methyl | 1:34-68:1 | 1:11-23:1 | 1:1-9:1 |
| 1 | Tritosulfuron | 1:27-84:1 | 1:9-28:1 | 1:1-11:1 |

Table A2 is constructed the same as Table A1 above except that entries below the "Component (a)" column heading are replaced with the respective Component (a) Column Entry shown below. Compound No. in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D. Tables A3 through A60 are constructed similarly.

| Table Number | Component (a) Column Entries |
|---|---|
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |
| A9 | Compound 9 |
| A10 | Compound 10 |
| A11 | Compound 11 |
| A12 | Compound 12 |
| A13 | Compound 13 |
| A14 | Compound 14 |
| A15 | Compound 15 |
| A16 | Compound 16 |
| A17 | Compound 17 |
| A18 | Compound 18 |
| A19 | Compound 19 |
| A20 | Compound 20 |
| A21 | Compound 21 |
| A22 | Compound 22 |
| A23 | Compound 23 |
| A24 | Compound 24 |
| A25 | Compound 25 |
| A26 | Compound 26 |
| A27 | Compound 27 |
| A28 | Compound 28 |
| A29 | Compound 29 |
| A30 | Compound 30 |
| A31 | Compound 31 |
| A32 | Compound 32 |
| A33 | Compound 33 |

-continued

| Table Number | Component (a) Column Entries |
|---|---|
| A34 | Compound 34 |
| A35 | Compound 35 |
| A36 | Compound 36 |
| A37 | Compound 37 |
| A38 | Compound 38 |
| A39 | Compound 39 |
| A40 | Compound 40 |
| A41 | Compound 41 |
| A42 | Compound 42 |
| A43 | Compound 43 |
| A44 | Compound 44 |
| A45 | Compound 45 |
| A46 | Compound 46 |
| A47 | Compound 47 |
| A48 | Compound 48 |
| A49 | Compound 49 |
| A50 | Compound 50 |
| A51 | Compound 51 |
| A52 | Compound 52 |
| A53 | Compound 53 |
| A54 | Compound 54 |
| A55 | Compound 55 |
| A56 | Compound 56 |
| A57 | Compound 57 |
| A58 | Compound 58 |
| A59 | Compound 59 |
| A60 | Compound 60 |
| A61 | Compound 61 |
| A62 | Compound 62 |
| A63 | Compound 63 |
| A64 | Compound 64 |
| A65 | Compound 65 |
| A66 | Compound 66 |
| A67 | Compound 67 |
| A68 | Compound 68 |
| A69 | Compound 69 |
| A70 | Compound 70 |
| A71 | Compound 71 |
| A72 | Compound 72 |
| A73 | Compound 73 |
| A74 | Compound 74 |
| A75 | Compound 75 |
| A76 | Compound 76 |
| A77 | Compound 77 |
| A78 | Compound 78 |
| A79 | Compound 79 |

| Table Number | Component (a) Column Entries |
|---|---|
| A80 | Compound 80 |
| A81 | Compound 81 |
| A82 | Compound 82 |
| A83 | Compound 83 |
| A84 | Compound 84 |
| A85 | Compound 85 |
| A86 | Compound 86 |
| A87 | Compound 87 |
| A88 | Compound 88 |
| A89 | Compound 89 |
| A90 | Compound 90 |
| A91 | Compound 91 |
| A92 | Compound 92 |
| A93 | Compound 93 |
| A94 | Compound 94 |
| A95 | Compound 95 |
| A96 | Compound 96 |
| A97 | Compound 97 |
| A98 | Compound 98 |
| A99 | Compound 99 |
| A100 | Compound 100 |
| A101 | Compound 101 |
| A102 | Compound 102 |
| A103 | Compound 103 |
| A104 | Compound 104 |
| A105 | Compound 105 |
| A106 | Compound 106 |
| A107 | Compound 107 |
| A108 | Compound 108 |
| A109 | Compound 109 |
| A110 | Compound 110 |
| A111 | Compound 111 |
| A112 | Compound 112 |
| A113 | Compound 113 |
| A114 | Compound 114 |
| A115 | Compound 115 |
| A116 | Compound 116 |
| A117 | Compound 117 |
| A118 | Compound 118 |
| A119 | Compound 119 |
| A120 | Compound 120 |
| A121 | Compound 121 |
| A122 | Compound 122 |
| A123 | Compound 123 |
| A124 | Compound 124 |
| A125 | Compound 125 |
| A126 | Compound 126 |
| A127 | Compound 127 |
| A128 | Compound 128 |
| A129 | Compound 129 |
| A130 | Compound 130 |
| A131 | Compound 131 |
| A132 | Compound 132 |
| A133 | Compound 133 |
| A134 | Compound 134 |
| A135 | Compound 135 |
| A136 | Compound 136 |
| A137 | Compound 137 |
| A138 | Compound 138 |
| A139 | Compound 139 |
| A140 | Compound 140 |
| A141 | Compound 141 |
| A142 | Compound 142 |
| A143 | Compound 143 |
| A144 | Compound 144 |
| A145 | Compound 145 |
| A146 | Compound 146 |
| A147 | Compound 147 |
| A148 | Compound 148 |
| A149 | Compound 149 |
| A150 | Compound 150 |
| A151 | Compound 151 |
| A152 | Compound 152 |
| A153 | Compound 153 |
| A154 | Compound 154 |
| A155 | Compound 155 |
| A156 | Compound 156 |
| A157 | Compound 157 |
| A158 | Compound 158 |
| A159 | Compound 159 |
| A160 | Compound 160 |
| A161 | Compound 161 |
| A162 | Compound 162 |
| A163 | Compound 163 |
| A164 | Compound 164 |
| A165 | Compound 165 |
| A166 | Compound 166 |
| A167 | Compound 167 |
| A168 | Compound 168 |
| A169 | Compound 169 |
| A170 | Compound 170 |
| A171 | Compound 171 |
| A172 | Compound 172 |
| A173 | Compound 173 |
| A174 | Compound 174 |
| A175 | Compound 175 |
| A176 | Compound 176 |
| A177 | Compound 177 |
| A178 | Compound 178 |
| A179 | Compound 179 |
| A180 | Compound 180 |
| A181 | Compound 181 |
| A182 | Compound 182 |
| A183 | Compound 183 |
| A184 | Compound 184 |
| A185 | Compound 185 |
| A186 | Compound 186 |
| A187 | Compound 187 |
| A188 | Compound 188 |

The following Tests demonstrate the control efficacy of the compounds of this invention against specific weeds. The weed control afforded by the compounds is not limited, however, to these species. See Index Table A for compound descriptions. The following abbreviations are used in the Index Table which follows: t is tertiary, Me is methyl, morph is morpholinyl, Bn is benzyl and Bu is butyl. The abbreviation "Cmpd. No." stands for "Compound Number". The abbreviation "Ex." stands for "Example" and is followed by a number indicating in which example the compound is prepared. Mass spectra are reported with an estimated precision within ±0.5 Da as the molecular weight of the highest isotopic abundance parent ion (M+1) formed by addition of $H^+$ (molecular weight of 1) to the molecule observed by using atmospheric pressure chemical ionization (AP+).

INDEX TABLE A

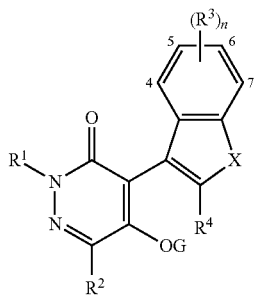

| Cmpd. No. | R¹ | R² | X | (R³)ₙ | R⁴ | G | m.p. (° C.) | M + 1 | NMR |
|---|---|---|---|---|---|---|---|---|---|
| 1 (Ex. 1) | Me | Me | S | 5-Me | Me | H | | 301.5 | ** |
| 2 | Me | Me | S | 5,7-di-Me | Me | H | | | * |
| 3 | Me | Me | S | 4,6-di-Me | Me | H | 224-227 | 315.5 | * |
| 4 | Me | Me | O | — | Me | H | 238-240 | 271.5 | * |
| 5 | Me | Me | O | 5-OMe | Me | H | | 301.5 | * |
| 6 | Me | Me | O | 5-Cl | Me | H | | | * |
| 7 (Ex. 2) | Me | Me | O | 5-Me | Me | H | | | ** |
| 8 | Me | Me | O | 4-Me | Me | H | | | * |
| 9 | Me | Me | O | 7-Me | Me | H | | 285.5 | * |
| 10 | Me | Me | O | 5-Me | Et | H | | 299.5 | * |
| 11 | Me | Me | —CH=CH— | — | H | H | | 267 | * |
| 12 (Ex. 3) | Me | Me | O | 5,7-di-Me | Me | H | | | ** |
| 13 | Me | Me | O | 5-Et | Me | H | | | * |
| 14 | Me | Me | O | 5-Me | Me | —C(=O)Me | | | * |
| 15 | Me | Me | O | 7-Me | Me | —C(=O)Me | | | * |
| 16 | Me | Me | O | 5,7-di-Me | Me | —C(=O)Me | | 341.0 | * |
| 17 | Me | Me | O | 5-Me | Me | —C(=O)-t-Bu | | 369.0 | * |
| 18 | Me | Me | O | 5,7-di-Me | Me | —C(=O)-t-Bu | | 383.0 | * |
| 19 | Me | Me | S | 4,6-di-Me | Et | H | | | * |
| 20 | Me | Br | —CH=CH— | — | H | H | | 332 | |
| 21 | Me | Me | —CH=C(Me)— | — | Me | H | | | * |
| 22 | Me | Me | S | 5-Br | Me | H | | 367 | |
| 23 | Me | Br | —CH=CH— | — | Me | H | | 343 | |
| 24 | Me | H | —CH=CF— | — | H | H | | | * |
| 25 | Me | Me | S | 5-Me | Me | —C(=O)Me | | | * |
| 26 | Me | Me | S | 5-Me | Me | —C(=O)-t-Bu | | 385.4 | |
| 27 | Me | Me | S | 5,7-di-Me | Me | —C(=O)Me | 140-145 | | |
| 28 | Me | Me | S | 5,7-di-Me | Me | —C(=O)Et | 134-137 | | |
| 29 | Me | I | —CH=CH— | — | Me | H | | 393 | |
| 30 | Me | OMe | —CH=CH— | 5-Me | Me | H | | 311 | |
| 31 | Me | Me | N(Me) | 5-Me | Me | H | 94-98 | | |
| 32 | Me | Me | —CH=CH— | — | Et | H | 226-229 | | |
| 33 | Me | OMe | S | — | Me | H | | 303 | |
| 34 | Me | Me | —C(Me)=CH— | — | Me | H | | 295 | |
| 35 | Me | Me | S | 5-Cl, 7-Me | Me | H | | 335 | |
| 36 | Me | OMe | —CH=CH— | — | Me | —C(=O)O-i-Pr | | | * |
| 37 | Me | Me | —CH=CH— | — | Et | —C(=O)OEt | | 367.6 | |
| 38 | Me | Me | —CH=CH— | — | Et | —C(=O)-c-Pr | | 363.6 | |
| 39 | Me | Me | —CH=CH— | — | Et | —C(=O)O-i-Pr | 112-116 | | |
| 40 | Me | Me | —CH=CH— | — | OMe | H | | 297 | |
| 41 | Me | Me | —CH=CF— | — | H | H | | | * |
| 42 | Me | Me | S | 5-Me | Me | —C(=O)Et | 125-130 | | |
| 43 | Me | Me | S | 5,7-di-Me | Me | —C(=O)-t-Bu | | 399.4 | |
| 44 | Me | Me | S | 4,6-di-Me | Me | —C(=O)Me | | 357 | |
| 45 | Me | Me | S | 4,6-di-Me | Me | —C(=O)-t-Bu | | 399 | |
| 46 (Ex. 4) | Me | OMe | —C(Me)=CH— | — | Me | H | | 311 | |
| 47 | Me | Me | S | 5-Me | Et | H | 203-205 | | |
| 48 | Me | H | S | — | Me | H | | 273 | |
| 49 | Me | H | —CH=CH— | — | H | H | | 251.5# | |
| 50 | Me | H | —CH=C(Me)— | — | H | H | | 267 | |

-continued

INDEX TABLE A

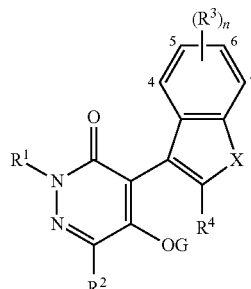

| Cmpd. No. | R¹ | R² | X | (R³)ₙ | R⁴ | G | m.p. (° C.) | M + 1 | NMR |
|---|---|---|---|---|---|---|---|---|---|
| 51 | Me | H | —CH═C(Me)— | — | Me | H | | | * |
| 52 | Me | Br | —CH═C(Me)— | — | H | H | | 347.4 | |
| 53 | Me | Me | S | 5-OMe | Me | H | 187-189 | | |
| 54 | Me | OMe | —CH═CH— | — | Me | H | | 297 | |
| 55 | Me | OMe | —CH═CH— | — | H | H | | 283 | |
| 56 | Me | H | —CH═CH— | — | Me | H | 249-251 | | |
| 57 | Me | Me | S | 5,7-di-Me | Et | H | 200-202 | | |
| 58 | Me | Me | —CH═C(OMe)— | — | H | H | | 297 | |
| 59 | Me | Me | —CH═CH— | — | Me | H | 269-273 | | |
| 60 | Me | Me | —CH═CH— | 5-Me | Me | H | 230-233 | | |
| 61 | Me | Ph | O | 5-Me | Me | H | 259-263 | | |
| 62 | Me | Me | —CH═C(Cl)— | — | H | —C(═O)Et | | | * |
| 63 | Me | Me | —CH═C(Cl)— | — | H | —C(═O)OMe | | 359 | |
| 64 | Et | Et | O | 5-Me | Me | H | 215-219 | | |
| 65 | Me | Me | S | — | Me | H | 225-228 | | |
| 66 | Me | Me | S | 5-Me | Me | —C(═O)O-i-Pr | 128-129 | | |
| 67 | Me | Me | S | 5,7-di-Me | Me | —C(═O)O-i-Pr | 123-125 | | |
| 68 | Me | Me | O | 5-OEt | Et | H | 170-174 | | |
| 69 | Me | Me | —CH═CH— | 5-Me | H | H | | 282 | |
| 70 | Me | Me | —CH═CH— | 5-I | H | H | | 393 | |
| 71 | Me | Me | —CH═CH— | 5-c-Pr | H | H | | 307 | |
| 72 | Me | Me | —CH═CH— | — | Me | —C(═O)O-i-Pr | 230-235 | | |
| 73 | Me | Me | —CH═CH— | — | Me | —C(═O)OEt | 146-150 | | |
| 74 | Me | Me | N(Me) | 5-Cl | Me | H | 314-318 | | |
| 75 | Me | Me | —CH═C(Br)— | — | H | H | 285-289 | | |
| 76 | Me | Me | —CH═CH— | — | Me | —C(═O)-c-Pr | | 349 | |
| 77 | Me | Et | O | 5-Cl | Me | H | 242-248 | | |
| 78 | Me | Me | —CH═CH— | — | Me | —C(═O)Et | | | * |
| 79 | Me | Me | S | 5-Me | Br | H | | 367.2 | |
| 80 | Me | Me | S | 5-Me | Me | —C(═O)OMe | | 359.5 | |
| 81 | Me | Me | S | 5,7-di-Me | Me | —C(═O)OMe | | 373.5 | |
| 82 | Me | Me | S | 5-Me | Me | —C(═O)OEt | | 373.5 | |
| 83 | Me | Me | S | 5,7-di-Me | Me | —C(═O)OEt | | 387.5 | |
| 84 | Me | Me | S | 5-Me | Me | —C(═O)CH₂CH₂Cl | | 407.4 | |
| 85 | Me | Me | S | 5,7-di-Me | Me | —C(═O)OCH₂CH₂Cl | | 421.4 | |
| 86 | Me | OMe | —CH═CH— | — | CF₂H | H | | 331# | |
| 87 | Me | Me | S | 5-Me | Me | —C(═O)OCH₂C═CH | | 383.3 | |
| 88 | Me | Me | S | 5,7-di-Me | Me | —C(═O)CH₂C═CH | | 397.3 | |
| 89 | Me | Cl | S | — | Me | H | | 307 | |
| 90 | Me | Me | —CH═CF— | — | H | —C(═O)Me | | | * |
| 91 (Ex. 5) | Me | Cl | S | 5-Cl | Me | H | | | ** |
| 92 | Me | Me | —CH═CH— | 5-OEt | H | H | | 309 | |
| 93 | Me | Me | —CH═CH— | 5-OCF₂H | H | H | | 333 | |

INDEX TABLE A

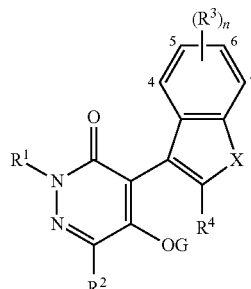

| Cmpd. No. | R¹ | R² | X | (R³)ₙ | R⁴ | G | m.p. (° C.) | M + 1 | NMR |
|---|---|---|---|---|---|---|---|---|---|
| 94 | Me | Cl | S | — | Me | —C(=O)O-i-Pr | | | * |
| 95 | Me | Me | NMe | — | Cl | H | 237-239 | | |
| 96 | Me | Me | —CH=CH— | 5-OEt | H | H | | 297 | |
| 97 | Me | H | S | — | Me | —C(=O)OMe | | 331 | |
| 98 | Me | CN | —CH=CH— | — | Me | —C(=O)Me | | | * |
| 99 | Me | Me | —CH=CMe— | — | Me | —C(=O)Me | | | * |
| 100 | Me | OMe | S | 5-Cl | Me | H | | 337 | |
| 101 | Me | Cl | S | 5-Cl | Me | —C(=O)OMe | | | * |
| 102 | Me | CF₃ | —CH=CH— | — | Me | H | | 335 | |
| 103 | Me | Me | —CH=CH— | 5-Me | Et | H | 186-189 | | |
| 104 | Me | Me | S | 5-Cl | Me | H | 254-257 | | |
| 105 | Me | Me | S | 5-Me | Me | —C(=O)-n-Pr | 115-117 | | |
| 106 | Me | Me | S | 5,7-di-Me | Me | —C(=O)-n-Pr | 113-115 | | |
| 107 | Me | Me | S | 5-Me | Et | —C(=O)-n-Pr | 80-82 | | |
| 108 | Me | Me | S | 5-Cl | Me | —C(=O)Me | 203-206 | | |
| 109 | Me | Me | S | 5-Cl | Me | —C(=O)Et | 125-127 | | |
| 110 | Me | Me | —CH=CH— | 6-Me | Me | H | | 295 | |
| 111 | Me | Cl | S | 5-Cl | Me | —C(=O)Et | | | * |
| 112 | Me | OMe | S | 5-Cl | Me | —C(=O)OMe | | 395 | |
| 113 | Me | Me | —CH=CF— | — | H | —C(=O)Et— | | | * |
| 114 | Me | Cl | S | 5-Cl | Me | —SO₂Me | | | * |
| 115 | Me | Me | —CF=CH— | — | H | —SO₂Me | | 363 | |
| 116 | Me | Cl | S | 5-Cl | Me | —C(=O)Me | | | * |
| 117 | Me | Et | O | — | Me | H | 210-215 | | |
| 118 | Me | Et | O | 5-Me | Me | H | 334-338 | | |
| 119 | Me | i-Pr | O | 5-Me | Me | H | 245-250 | | |
| 120 | Me | H | S | — | Me | —C(=O)Me | | | * |
| 121 | Me | Me | S | 5-CF₃ | Me | H | | 355 | |
| 122 | Me | OMe | S | 5-Cl | Me | —C(=O)Me | | | * |
| 123 | Me | Me | —CH=CF— | — | H | —C(=O)CH₂CF₃ | | | * |
| 124 | Me | Me | —CH=CH— | 5-OC(=O)Me | H | —C(=O)Me | | | * |
| 125 | Me | Cl | —CH=CH— | — | Me | H | | 301 | |
| 126 | Me | Me | —CH=CH— | 5-Br | H | H | | 347 | |
| 127 | Me | Me | —CH=CH— | 5-CN | H | H | | 292 | |
| 128 | Me | CN | —CH=CH— | — | Me | —C(=O)-t-Bu | | | * |
| 129 | Me | Br | —CH=CH— | — | Me | —C(=O)Me | | | * |
| 130 | Me | Me | —CH=CF— | — | H | —C(=O)OMe | | | * |
| 131 | Me | OMe | S | 5-Cl | Me | —C(=O)Et | | | * |
| 132 | Me | Me | S | 5-CF₃ | Me | —C(=O)Me | | | * |
| 133 | Me | Me | —CH=CBr— | — | H | —C(=O)Et | 117-120 | | |
| 134 | Me | Me | —CH=CBr— | — | H | —C(=O)Et | 120-124 | | |
| 135 | Me | OMe | S | 5-Cl | Me | —SO₂Me | | 415 | |
| 136 | Me | OMe | —CH=CH— | — | Me | —(C=O)OMe | | 355 | |
| 137 | Me | Br | —CH=CH— | — | Me | —C(=O)OMe | | | * |
| 138 | Me | OMe | —CH=CH— | — | Me | —C(=O)Me | | | * |
| 139 | Me | Me | —CH=CCl— | — | H | H | | 301 | |
| 140 | Me | Cl | S | 5-CF₃ | Me | H | | 375 | |

-continued

INDEX TABLE A

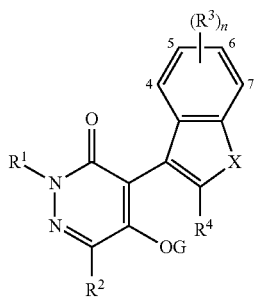

| Cmpd. No. | R¹ | R² | X | (R³)ₙ | R⁴ | G | m.p. (° C.) | M + 1 | NMR |
|---|---|---|---|---|---|---|---|---|---|
| 141 | Me | OMe | S | — | Me | —C(=O)Me | | | * |
| 142 | Me | H | —CH=CH— | — | Me | —SO₂Me | | 345 | |
| 143 | Me | H | —CH=CH— | — | Me | —C(=O)OMe | | 325 | |
| 144 | Me | Me | —CH=CH— | 5-Cl | Me | H | 280-284 | | |
| 145 | Me | Me | —CH=CBr— | — | H | —C(=O)OMe | | 403 | |
| 146 | Me | Me | —CH=CH— | — | CF₃ | —C(=O)OEt | 115-118 | | |
| 147 | Me | Me | —CH=CH— | — | CF₃ | —C(=O)Et | 132-135 | | |
| 148 | Me | Me | —CH=CH— | — | CF₃ | —C(=O)Me | 181-184 | | |
| 149 | Me | Me | —CH=CH— | — | CF₃ | —C(=O)OMe | 130-133 | | |
| 150 | Me | Me | —CH=CH— | 5-C≡CH | H | H | 291 | | |
| 151 | Me | Me | —CH=CH— | 5-F,7-Me | Me | H | 319.1 | | |
| 152 | Me | Cl | S | 5-CF₃ | Me | —C(=)Me | | | * |
| 153 | Me | Me | —CH=CMe— | — | Me | —C(=O)Me | | | * |
| 154 | Me | Me | —CH=CMe— | — | Me | —SO₂Me | | 373 | |
| 155 | Me | Br | —CH=CH— | — | Me | —SO₂Me | | | * |
| 156 | Me | Br | —CH=CH— | — | Me | —C(=O)Et | | | * |
| 157 | Me | Me | —CH=CCl— | — | H | —C(=O)Me | | 343 | |
| 158 | Me | Me | —CH=CCl— | — | H | —SO₂CF₃ | ? | 433 | |
| 159 | Me | Me | —CH=CCl— | — | H | —C(=O)CF₃ | | | * |
| 160 | Me | Me | S | 5-Me | Me | —CH₂CN | | 340 | |
| 161 | Me | Me | —CH=CH— | 5-NO₂ | Me | H | | 312 | |
| 162 | Me | Me | —CH=CH— | — | NO₂ | —C(=O)OMe | 162-166 | | |
| 163 | Me | Me | —CH=CH— | — | NO₂ | —C(=O)-t-Bu | 239-243 | | |
| 164 | Me | Me | —CH=CH— | — | NO₂ | —C(=O)Me | 189-193 | | |
| 165 | Me | Me | —CH=CH— | — | NO₂ | H | 264-268 | | |
| 166 | Me | Me | —CH=CH— | — | NO₂ | —C(=O)OEt | 147-150 | | |
| 167 | Me | Me | —CH=CH— | — | NO₂ | —C(=O)-c-Pr | 165-170 | | |
| 168 | Bn | Me | —CH=CH— | — | H | H | | 343 | |
| 169 | H | Me | —CH=CH— | — | H | H | | 253 | |
| 170 | Me | Me | S | — | Me | —C(=O)-N-morph | 168-171 | | |
| 171 | Me | Me | —CH=CH— | — | H | —C(=O)CH₂SMe | | | * |
| 172 | CH₂CO₂Me | Me | —CH=CH— | — | H | H | | 325 | |
| 173 | H | Me | —CH=CH— | — | H | —CH₂CF₂H | | 317 | |
| 174 | Me | Me | S | 5,7-di-Me | Me | —C(=O)-N-morph | | 428 | |
| 175 | H | Me | —CH=CH— | — | H | —CF₂H | | 303 | |
| 176 | Me | Br | —CH=CH— | — | Me | —C(=O)-N-morph | | | * |
| 177 | Me | NO₂ | —CH=CH— | — | Me | H | | 312 | |
| 178 | Me | Me | —CH=CH— | — | H | —CH₂C(=O)Me | | 323 | |
| 179 | Me | Me | —CH=CH— | — | H | —CH₂C≡CH | | 305 | |
| 180 | Me | Me | —CH=CH— | — | H | —CH₂CH=CHPh | | 383 | |
| 181 | Me | Me | —CH=CH— | — | H | —CH₂C(=O)-c-Pr | | 349 | |
| 182 | Me | Me | —CH=CH— | — | H | —CH₂C(=O)OMe | | 339 | |
| 183 | Me | Me | —CH=CH— | — | H | —C(=O)CH=CHPh | | 397 | |
| 184 | Me | Me | —CH=CH— | — | H | —CH₂C(=O)Ph | | 385 | |
| 185 | Me | Me | —CH=CCl— | — | H | —SO₂N(Me)₂ | | 408 | |
| 186 | Me | Me | —CH=CCl— | — | H | —P(=O)(OMe)₂ | | 410 | |

INDEX TABLE A

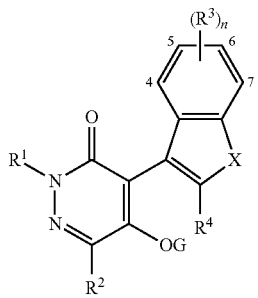

| Cmpd. No. | R¹ | R² | X | (R³)ₙ | R⁴ | G | m.p. (° C.) | M + 1 | NMR |
|---|---|---|---|---|---|---|---|---|---|
| 187 | Me | Me | —CH=CCl— | — | H | —P(=O)(Me)2 | | 377 | |
| 188 | Me | Me | S | 5,7-di-Me | Me | —CH₂CN | | 354 | |

*See Index Table B for ¹H NMR data.
**See Synthesis Example for ¹H NMR data.
M−1 peak.

INDEX TABLE B

| Cmpd. No. | ¹H NMR Data (CDCl₃ solution unless indicated otherwise)ᵃ |
|---|---|
| 2 | δ 6.93 (s, 1H), 6.90 (s, 1H), 6.41 (br s, 1H), 3.60 (s, 3H), 2.47 (s, 3H), 2.36 (s, 3H), 2.25-2.29 (m, 6H) |
| 3 | δ 7.40 (s, 1H), 6.83 (s, 1H), 6.10 (br s, 1H), 3.66 (s, 3H), 2.38 (s, 3H), 2.28 (s, 3H), 2.21 (s, 3H), 2.13 (s, 3H). |
| 4 | (DMSO-d₆) δ 10.33 (s, 1H), 7.52 (d, 1H), 7.14-7.27 (m, 3H), 3.60 (s, 3H), 2.28 (s, 3H), 2.25 (s, 3H). |
| 5 | δ 7.34 (d, 1H), 6.84-6.87 (m, 1H), 6.65-6.66 (d, 1H), 3.79 (s, 3H), 3.75 (s, 3H), 2.36 (s, 3H), 2.35 (s, 3H). |
| 6 | δ 7.35-7.39 (m, 1H), 7.20-7.24 (m, 2H), 6.08 (br s, 1H), 3.72 (s, 3H), 2.36 (s, 3H), 2.32 (s, 3H). |
| 8 | δ 7.28-7.30 (d, 1H), 7.13-7.16 (m, 1H), 6.93-6.96 (m, 1H), 5.65-5.80 (br s, 1H), 3.77 (s, 3H), 2.35 (s, 3H), 2.31 (s, 3H), 2.23 (s, 3H). |
| 9 | (DMSO-d₆) δ 10.26 (s, 1H), 6.99-7.07 (m, 3H), 3.60 (s, 3H), 2.48 (s, 3H), 2.28 (s, 3H), 2.25 (s, 3H). |
| 10 | (DMSO-d₆) δ 10.28-10.30 (br s, 1H), 7.39-7.42 (m, 1H), 7.03-7.07 (m, 1H), 6.96-6.98 (m, 1H), 3.60 (s, 3H), 2.55-2.62 (m, 2H), 2.34 (s, 3H), 2.25 (s, 3H), 1.18-1.23 (m, 3H). |
| 11 | (DMSO-d₆) δ 10.11 (br s, 1H), 8.10-7.93 (m, 2H), 7.58-7.40 (m, 4H), 7.35-7.31 (m, 1H), 3.60 (s, 3H), 2.27 (s, 3H). |
| 13 | δ 7.35 (d, 1H), 7.08-7.13 (m, 1H), 7.00-7.05 (m, 1H), 5.99-6.03 (m, 1H), 3.72 (s, 3H), 2.70 (m, 2H), 2.35 (s, 3H), 2.32 (s, 3H), 1.17-1.29 (m, 3H). |
| 14 | δ 7.27-7.29 (m, 1H), 7.06-7.07 (m, 1H), 7.01 (m, 1H), 3.83 (s, 3H), 2.38-2.40 (m, 6H), 2.29 (s, 3H), 1.89 (s, 3H). |
| 15 | δ 7.07-7.11 (m, 2H), 7.00-7.02 (m, 1H), 3.84 (s, 3H), 2.50 (s, 3H), 2.42 (s, 3H), 2.29 (s, 3H), 1.89 (s, 3H). |
| 16 | δ 6.88 (s, 1H), 6.83 (s, 1H), 3.84 (s, 3H), 2.45 (s, 3H), 2.39 (s, 3H), 2.35 (s, 3H), 2.29 (s, 3H), 1.91 (s, 3H). |
| 17 | δ 7.26 (d, 1H), 7.02 (d, 1H), 7.00 (d, 1H), 3.84 (s, 3H), 2.37 (d, 6H), 2.26 (s, 3H) 0.93 (br s, 9H). |
| 18 | δ 6.83 (s, 1H), 6.81 (s, 1H), 3.83 (s, 3H), 2.44 (s, 3H), 2.37 (s, 3H), 2.34 (s, 3H), 2.25 (s, 3H), 0.94 (br s, 9H). |
| 19 | δ 7.45 (s, 1H), 6.86 (s, 1H), 5.62 (s, 1H), 3.74 (s, 3H), 2.55-2.71 (m, 2H), 2.39 (s, 3H), 2.32 (s,3H), 2.18 (s, 3H), 1.20-1.29 (m, 3H). |
| 21 | δ 8.03 (m, 1H), 7.61-7.49 (m, 3H), 7.32 (s, 1H), 5.23 (br s, 1H), 3.79 (s, 1H), 2.71 (s, 1H), 2.36 (s, 3H), 2.26 (s, 3H). |
| 24 | δ 8.17 (m, 1H), 7.75 (s, 1H), 7.62-7.52 (m, 3H), 7.38 (m, 1H), 7.25 (m, 1H), 5.69 (br s, 1H), 3.81 (s, 3H). |
| 25 | δ 8.17 (m, 1H), 7.62-7.52 (m, 3H), 7.37 (m, 1H), 7.26 (m, 1H) 5.49 (s, 1H), 3.77 (s, 3H), 2.36 (s, 3H). |
| 36 | δ 7.82-7.78 (m, 2H), 7.45-7.35 (m, 4H), 4.72-4.64 (m, 1H), 3.97 (s, 3H), 3.78 (s, 3H), 2.30 (s, 3H), 1.10 (m, 3H), 1.03 (m, 3H). |
| 41 | δ 8.18 (m, 1H), 7.62-7.54 (m, 3H), 7.36 (m, 1H), 7.25 (m, 2H), 5.48 (s, 1H), 3.77 (s, 3H), 2.36 (s, 3H). |
| 51 | δ 8.04 (m, 1H), 7.73 (s, 1H), 7.53-7.45 (m, 2H), 7.31 (s, 1H), 5.60 (br s, 1H) 3.83 (s, 3H), 2.70 (s, 3H), 2.26 (s, 3H). |
| 62 | δ 8.28-8.35 (m, 1H), 7.57-7.65 (m, 2H), 7.47-7.56 (m, 2H), 7.20-7.29 (m, 1H), 3.85 (s, 3H), 2.29 (s, 3H), 1.96-2.19 (m, 2H), 0.62-0.85 (m, 3H). |
| 78 | (500 MHz) δ 7.88 (s, 1H), 7.81 (s, 1H), 7.79 (s, 1H), 7.44-7.33 (m, 4H), 3.91-3.88 (m, 3H), 2.29 (s, 3H), 2.02 (m, 2H), 0.76 (s, 1H), 0.64 (m, 3H). |
| 90 | (500 MHz) δ 8.15-8.14 (m, 1H), 7.65-7.51 (m, 4H), 7.29-7.27 (m, 1H), 7.20-7.16 (m, 1H), 3.85 (s, 3H), 2.31 (s, 3H), 1.84 (s, 3H). |
| 95 | (500 MHz) δ 7.75-7.72 (m, 1H), 7.33-7.26 (m, 3H), 4.66-4.63 (m, 1H), 3.87 (s, 3H), 2.43 (s, 3H), 1.07-1.00 (m, 6H). |
| 99 | δ 7.81-7.87 (m, 2H), 7.38-7.45 (m, 3H), 7.30-7.34 (m, 1H), 3.96 (s, 3H), 2.28 (s, 3H), 1.85 (s, 3H). |
| 100 | (500 MHz) δ 7.78-7.76 (m, 1H), 7.71 (s, 1H), 7.42-7.31 (m, 2H), 7.23-7.22 (m, 1H), 3.84 (s, 3H), 2.52 (s, 3H), 2.48 (s, 3H), 2.18 (s, 3H). |
| 102 | (500 MHz) δ 7.67-7.66 (m, 1H), 7.27-7.24 (m, 2H), 3.88 (s, 3H), 3.69 (s, 3H), 2.43 (s, 3H). |
| 112 | (500 MHz) δ 7.67-7.65 (m, 1H), 7.46-7.27 (m, 2H), 3.87 (s, 3H), 2.42 (s, 3H), 2.35-2.13 (m, 2H), 0.86-0.83 (m, 3H). |
| 114 | (500 MHz) δ 8.15-8.13 (m, 1H), 7.60-7.49 (m, 3H), 7.33-7.27 (m, 1H), 7.21-7.16 (m, 1H), 3.85 (s, 3H), 2.29 (s, 3H), 2.13-2.02 (m, 2H), 0.78-0.75 (m, 3H). |
| 115 | (500 MHz) δ 7.69-7.68 (m, 1H), 7.31-7.27 (m, 2H), 3.88 (s, 3H), 2.58 (s, 3H), 2.48 (s, 3H). |
| 117 | (500 MHz) δ 7.67-7.65 (m, 1H), 7.26-7.24 (m, 2H), 3.87 (s, 3H), 2.42 (s, 3H), 1.96 (s, 3H). |
| 121 | (500 MHz) δ 7.84 (s, 1H), 7.79-7.69 (m, 1H), 7.30-7.26 (m, 3H), 3.88 (s, 3H), 2.43 (s, 3H), 1.90 (s, 3H). |
| 123 | (500 MHz) δ 7.65-7.64 (m, 1H), 7.28-7.27 (m, 1H), 7.24-7.22 (m, 1H), 3.93 (s, 3H), 3.77 (s, 3H), 2.42 (s, 3H), 1.98 (s, 3H). |
| 124 | (500 MHz) δ 8.16-8.15 (m, 1H), 7.60-7.45 (m, 3H), 7.29-7.26 (m, 2H), 7.20-7.17 (m, 1H), 3.87 (s, 3H), 3.00-2.82 (m, 2H), 2.31 (s, 3H). |

INDEX TABLE B-continued

| Cmpd. No. | ¹H NMR Data (CDCl₃ solution unless indicated otherwise)[a] |
|---|---|
| 125 | δ 7.84-7.94 (m, 2H), 7.46-7.55 (m, 1H), 7.33-7.40 (m, 1H), 7.23-7.30 (m, 1H), 7.16-7.21 (m, 1H), 3.85 (s, 3H), 2.31 (s, 3H), 2.29 (s, 3H), 1.82 (s, 3H). |
| 129 | δ 7.78-7.85 (m, 2H), 7.36-7.45 (m, 3H), 7.29-7.35 (m, 1H), 3.98 (s, 3H), 2.29 (s, 3H), 0.72 (s, 9H). |
| 130 | δ 7.82, (m, 2H), 7.29 (m, 4H), 3.88 (s, 1H), 2.30 (s, 3H) 1.80 (s, 3H). |
| 131 | (500 MHz) δ 8.24-8.13 (m, 1H), 7.60-7.52 (m, 3H), 7.34-7.30 (m, 1H), 7.26-7.18 (m, 1H), 3.88 (s, 3H), 3.61 (s, 3H), 2.37 (s, 3H). |
| 132 | (500 MHz) δ 7.65-7.63 (m, 1H), 7.35-7.27 (m, 1H), 7.26-7.19 (m, 1H), 3.93 (s, 3H), 3.77 (s, 3H), 2.42 (s, 3H), 2.29-2.19 (m, 2H), 0.89-0.86 (m, 3H). |
| 133 | (500 MHz) δ 7.89-7.83 (m, 1H), 7.54-7.48 (m, 2H), 3.86 (s, 3H), 2.45 (s, 3H), 2.32 (s, 3H), 1.81 (s, 3H). |
| 138 | (500 MHz) δ 7.84-7.82 (m, 2H), 7.45-7.35 (m, 4H), 3.90 (s, 3H), 3.58 (s, 3H), 2.30 (s, 3H). |
| 139 | (500 MHz) δ 7.81-7.79 (m, 2H), 7.44-7.36 (m, 4H), 3.95 (s, 3H), 3.78 (s, 3H), 2.30 (s, 3H), 1.85 (s, 3H). |
| 142 | (500 MHz) δ 7.75-7.73 (m, 1H), 7.29-7.23 (m, 3H), 3.93 (s, 3H), 3.76 (s, 3H), 2.42 (s, 3H), 1.94 (s, 3H). |
| 153 | (500 MHz) δ 7.93-7.83 (m, 1H), 7.53-7.52 (m, 2H), 3.88 (s, 3H), 2.46 (s, 3H), 1.93 (s, 3H). |
| 154 | (500 MHz) δ 7.97-7.95 (m, 1H), 7.48-7.34 (m, 3H), 7.29-7.26 (m, 1H), 3.85 (s, 3H), 2.74 (s, 3H), 2.30 (s, 3H), 2.24 (s, 3H), 1.71 (s, 3H). |
| 156 | (500 MHz) δ 7.89-7.87 (m, 2H), 7.48-7.38 (m, 4H), 3.90 (s, 3H), 2.37 (s, 3H), 2.07 (s, 3H). |
| 157 | (500 MHz) δ 7.86-7.76 (m, 2H), 7.44-7.35 (m, 4H), 3.90 (s, 3H), 2.30 (s, 3H), 2.09-2.03 (m, 2H), 0.65-0.62 (m, 3H). |
| 160 | δ 8.31-8.37 (m, 1H), 7.59-7.68 (m, 2H), 7.49-7.56 (m, 1H), 7.42-7.48 (m, 1H), 7.19-7.25 (m, 1H), 3.93 (s, 3H), 2.37 (s, 3H). |
| 175 | (500 MHz) δ 8.17-8.10 (m, 1H), 7.59-7.45 (m, 3H), 7.31-7.27 (m, 1H), 7.23-7.14 (m, 1H), 3.86 (s, 3H), 2.95-2.88 (m, 2H), 2.33 (s, 3H), 1.67 (s, 3H). |
| 180 | (500 MHz) δ 7.89-7.77 (m, 2H), 7.50-7.33 (m, 4H), 3.90 (s, 3H), 3.26-2.86 (m, 6H), 2.33 (s, 3H). |

[a]¹H NMR data are in ppm downfield from tetramethylsilane. Couplings are designated by (s)-singlet, (d)-doublet, (t)-triplet, (m)-multiplet, (br s)-broad singlet.

Biological Examples of the Invention

Test A

Seeds of plant species selected from barnyardgrass (*Echinochloa crus-galli*), kochia (*Kochia scoparia*), ragweed (common ragweed, *Ambrosia elatior*), ryegrass, Italian (Italian ryegrass, *Lolium multiflorum*), crabgrass, large (large crabgrass, *Digitaria sanguinalis*), foxtail, giant (giant foxtail, *Setaria faberii*), morningglory (*Ipomoea* spp.), pigweed (*Amaranthus retroflexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant.

At the same time, plants selected from these crop and weed species and also blackgrass (*Alopecurus myosuroides*), and *galium* (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 1000 g ai/ha | Compounds | | | | | | | | | | | | | |
|---|---|---|---|---|---|---|---|---|---|---|---|---|---|---|
| | 1 | 3 | 4 | 5 | 6 | 7 | 10 | 11 | 13 | 32 | 60 | 178 | 179 | 180 |
| Postemergence | | | | | | | | | | | | | | |
| Barnyardgrass | 90 | 50 | 70 | 40 | 70 | 90 | 90 | 80 | 80 | 90 | 90 | 0 | 10 | 0 |
| Blackgrass | — | — | — | — | — | — | — | — | 30 | 90 | 90 | 30 | 40 | 30 |
| Corn | 40 | 0 | 0 | 0 | 0 | 10 | 20 | 50 | 20 | 50 | 50 | 0 | 10 | 0 |
| Crabgrass, Large | 90 | 10 | 50 | 80 | 50 | 50 | 70 | 70 | — | — | — | — | — | — |
| Foxtail, Giant | 80 | 10 | 80 | 80 | 70 | 90 | 80 | 90 | 80 | 90 | 90 | 0 | 10 | 0 |
| *Galium* | — | — | — | — | — | — | — | — | 70 | 100 | 100 | 70 | 90 | 80 |
| *Kochia* | — | — | — | — | — | — | — | — | 30 | 100 | 100 | 10 | 10 | 40 |
| Morningglory | 100 | 90 | 70 | 70 | 40 | 100 | 100 | 90 | — | — | — | — | — | — |
| Pigweed | 100 | 0 | 50 | 10 | 50 | 100 | 90 | 90 | 20 | 100 | 100 | 70 | 0 | 50 |
| Ragweed | — | — | — | — | — | — | — | — | 30 | 100 | 100 | 60 | 40 | 0 |
| Ryegrass, Italian | — | — | — | — | — | — | — | — | 70 | 100 | 100 | 70 | 70 | 70 |
| Velvetleaf | 100 | 70 | 60 | — | — | 100 | 100 | 100 | — | — | — | — | — | — |
| Wheat | 0 | 0 | 0 | 0 | 20 | 20 | 0 | 60 | 20 | 100 | 70 | 0 | 0 | 0 |

| 1000 g ai/ha | Compounds | | | |
|---|---|---|---|---|
| | 181 | 182 | 183 | 184 |
| Postemergence | | | | |
| Barnyardgrass | 0 | 0 | 40 | 20 |
| Blackgrass | 20 | 10 | 80 | 30 |
| Corn | 0 | 0 | 10 | 0 |
| Crabgrass, Large | — | — | — | — |
| Foxtail, Giant | 0 | 0 | 70 | 20 |
| *Galium* | 80 | 50 | 90 | 90 |
| *Kochia* | 0 | 0 | 90 | 80 |
| Morningglory | — | — | — | — |

TABLE A-continued

|  |  |  |  |  |  |
|---|---|---|---|---|---|
| Pigweed | 30 | 0 | 90 | 80 |  |
| Ragweed | 30 | 30 | 70 | 30 |  |
| Ryegrass, Italian | 80 | 0 | 100 | 80 |  |
| Velvetleaf | — | — | — | — |  |
| Wheat | 0 | 0 | 0 | 0 |  |

| Compounds |
|---|

| 500 g ai/ha | 2 | 8 | 9 | 12 | 14 | 15 | 16 | 17 | 18 | 19 | 20 | 21 | 22 | 23 |
|---|---|---|---|---|---|---|---|---|---|---|---|---|---|---|
| Postemergence |
| Barnyardgrass | 80 | 0 | 90 | 40 | 70 | 90 | 90 | 0 | 40 | 80 | 100 | 90 | 50 | 90 |
| Blackgrass | — | — | — | 50 | 30 | 50 | 30 | 40 | 20 | 0 | 40 | 90 | 70 | 80 |
| Corn | 20 | 0 | 0 | 0 | 20 | 20 | 0 | 0 | 20 | 0 | 30 | 60 | 0 | 50 |
| Crabgrass, Large | 70 | 30 | 50 | — | — | — | — | — | — | — | — | — | — | — |
| Foxtail, Giant | 90 | 30 | 90 | 70 | 70 | 90 | 80 | 0 | 20 | 60 | 100 | 100 | 90 | 90 |
| Galium | — | — | — | 90 | 90 | 90 | 100 | 60 | 60 | 80 | 100 | 100 | 100 | 100 |
| Kochia | — | — | — | 60 | 90 | 50 | 60 | 0 | 0 | 0 | 100 | 100 | 100 | 100 |
| Morningglory | 100 | 10 | 80 | — | — | — | — | — | — | — | — | — | — | — |
| Pigweed | 100 | 80 | 0 | 50 | 80 | 0 | 40 | 0 | 0 | 0 | 100 | 100 | 100 | 100 |
| Ragweed | — | — | — | 70 | 90 | 50 | 70 | 0 | 0 | 0 | 100 | 100 | 100 | 100 |
| Ryegrass, Italian | — | — | — | 70 | 80 | 90 | 80 | 60 | 50 | 0 | 100 | 100 | 100 | 100 |
| Velvetleaf | 100 | 60 | 10 | — | — | — | — | — | — | — | — | — | — | — |
| Wheat | 20 | 0 | 0 | 0 | 0 | 0 | 0 | 0 | 0 | 0 | 30 | 60 | 0 | 80 |

| Compounds |
|---|

| 500 g ai/ha | 24 | 25 | 26 | 27 | 28 | 29 | 30 | 31 | 33 | 34 | 35 | 36 | 37 | 38 |
|---|---|---|---|---|---|---|---|---|---|---|---|---|---|---|
| Postemergence |
| Barnyardgrass | 50 | 90 | 30 | 90 | 90 | 80 | 30 | 10 | 90 | 90 | 90 | 80 | 90 | 40 |
| Blackgrass | 50 | 90 | 70 | 90 | 90 | 80 | 60 | 20 | 40 | 90 | 80 | 80 | 100 | 60 |
| Corn | 0 | 20 | 0 | 20 | 20 | 40 | 0 | 0 | 10 | 0 | 30 | 40 | 40 | 10 |
| Crabgrass, Large | — | — | — | — | — | — | — | — | — | — | — | — | — | — |
| Foxtail, Giant | 60 | 90 | 60 | 90 | 90 | 90 | 60 | 10 | 90 | 90 | 90 | 90 | 90 | 50 |
| Galium | 100 | 100 | 90 | 100 | 100 | 90 | 90 | 70 | 100 | 100 | 100 | 100 | 100 | 100 |
| Kochia | 80 | 100 | 90 | 90 | 90 | 90 | 80 | 0 | 100 | 80 | 100 | 100 | 90 | 80 |
| Morningglory | — | — | — | — | — | — | — | — | — | — | — | — | — | — |
| Pigweed | 90 | 100 | 90 | 100 | 90 | 100 | 90 | 40 | 70 | 90 | 90 | 90 | 100 | 50 |
| Ragweed | 60 | 100 | 90 | 100 | 100 | 100 | 70 | 20 | 90 | 100 | 80 | 90 | 90 | 70 |
| Ryegrass, Italian | 90 | 100 | 90 | 100 | 100 | 100 | 60 | 0 | 70 | 100 | 100 | 80 | 100 | 50 |
| Velvetleaf | — | — | — | — | — | — | — | — | — | — | — | — | — | — |
| Wheat | 70 | 0 | 0 | 0 | 0 | 60 | 10 | 0 | 0 | 40 | 40 | 30 | 80 | 20 |

| Compounds |
|---|

| 500 g ai/ha | 39 | 40 | 41 | 42 | 43 | 44 | 45 | 46 | 47 | 48 | 49 | 50 | 51 | 52 |
|---|---|---|---|---|---|---|---|---|---|---|---|---|---|---|
| Postemergence |
| Barnyardgrass | 10 | 60 | 90 | 90 | 30 | 0 | 0 | 80 | 80 | 50 | 20 | 0 | 80 | 50 |
| Blackgrass | 70 | 80 | 90 | 90 | 80 | 0 | 0 | 70 | 70 | 30 | 30 | 10 | 60 | 30 |
| Corn | 0 | 10 | 70 | 20 | 0 | 0 | 0 | 0 | 10 | 0 | 0 | 0 | 0 | 20 |
| Crabgrass, Large | — | — | — | — | — | — | — | — | — | — | — | — | — | — |
| Foxtail, Giant | 60 | 80 | 100 | 100 | 70 | 0 | 0 | 80 | 80 | 60 | 20 | 0 | 80 | 50 |
| Galium | 100 | 100 | 100 | 100 | 90 | 70 | 0 | 90 | 100 | 90 | 80 | 80 | 100 | 100 |
| Kochia | 30 | 90 | 100 | 100 | 10 | 0 | 0 | 40 | 90 | 80 | 10 | 20 | 90 | 100 |
| Morningglory | — | — | — | — | — | — | — | — | — | — | — | — | — | — |
| Pigweed | 80 | 100 | 90 | 100 | 10 | 0 | 0 | 90 | 100 | 70 | 40 | 50 | 90 | 30 |
| Ragweed | 90 | 90 | 100 | 100 | 0 | 0 | 0 | 90 | 100 | 20 | 10 | 20 | 70 | 100 |
| Ryegrass, Italian | 60 | 90 | 100 | 100 | 60 | 0 | 0 | 80 | 80 | 60 | 50 | 40 | 90 | 80 |
| Velvetleaf | — | — | — | — | — | — | — | — | — | — | — | — | — | — |
| Wheat | 10 | 50 | 80 | 20 | 0 | 0 | 0 | 20 | 0 | 0 | 0 | 0 | 0 | 0 |

| Compounds |
|---|

| 500 g ai/ha | 53 | 54 | 55 | 56 | 57 | 58 | 59 | 61 | 62 | 63 | 64 | 65 | 66 | 67 |
|---|---|---|---|---|---|---|---|---|---|---|---|---|---|---|
| Postemergence |
| Barnyardgrass | 20 | 90 | 90 | 60 | 100 | 0 | 90 | 0 | 90 | 90 | 0 | 90 | 90 | 70 |
| Blackgrass | 30 | 40 | 80 | 50 | 60 | 50 | 100 | 0 | 80 | 80 | 0 | 70 | 80 | 80 |
| Corn | 0 | 30 | 20 | 10 | 30 | 0 | 60 | 0 | 30 | 40 | 0 | 0 | 0 | 0 |
| Crabgrass, Large | — | — | — | — | — | — | — | — | — | — | — | — | — | — |
| Foxtail, Giant | 30 | 90 | 90 | 60 | 90 | 10 | 100 | 0 | 90 | 90 | 0 | 90 | 90 | 90 |
| Galium | 80 | 100 | 100 | 100 | 100 | 100 | 100 | 0 | 100 | 100 | 0 | 100 | 90 | 90 |
| Kochia | 80 | 100 | 100 | 100 | 100 | 90 | 100 | 0 | 100 | 100 | 0 | 90 | 90 | 30 |
| Morningglory | — | — | — | — | — | — | — | — | — | — | — | — | — | — |

TABLE A-continued

| | | | | | | | | | | | | | | |
|---|---|---|---|---|---|---|---|---|---|---|---|---|---|---|
| Pigweed | 70 | 100 | 90 | 90 | 100 | 20 | 100 | 0 | 100 | 100 | 0 | 90 | 90 | 20 |
| Ragweed | 70 | 100 | 100 | 90 | 100 | 60 | 100 | 0 | 100 | 100 | 0 | 90 | 90 | 70 |
| Ryegrass, Italian | 70 | 100 | 100 | 100 | 90 | 80 | 100 | 0 | 100 | 100 | 0 | 100 | 100 | 90 |
| Velvetleaf | — | — | — | — | — | — | — | — | — | — | — | — | — | — |
| Wheat | 20 | 20 | 0 | 50 | 10 | 20 | 100 | 0 | 50 | 40 | 0 | 0 | 0 | 0 |

| | Compounds | | | | | | | | | | | | | |
|---|---|---|---|---|---|---|---|---|---|---|---|---|---|---|
| 500 g ai/ha | 68 | 69 | 70 | 71 | 72 | 73 | 74 | 75 | 76 | 77 | 78 | 79 | 80 | 81 |
| | Postemergence | | | | | | | | | | | | | |
| Barnyardgrass | 80 | 40 | 10 | 20 | 60 | 90 | 10 | 60 | 30 | 0 | 30 | 80 | 80 | 90 |
| Blackgrass | 10 | 40 | 30 | 40 | 90 | 90 | 40 | 70 | 10 | 0 | 80 | 80 | 80 | 90 |
| Corn | 0 | 0 | 0 | 20 | 40 | 60 | 0 | 20 | 0 | 0 | 0 | 0 | 0 | 0 |
| Crabgrass, Large | — | — | — | — | — | — | — | — | — | — | — | — | — | — |
| Foxtail, Giant | 50 | 40 | 25 | 20 | 90 | 100 | 20 | 50 | 20 | 0 | 70 | 80 | 80 | 100 |
| Galium | 0 | 90 | 90 | 90 | 100 | 100 | 20 | 100 | 80 | 60 | 100 | 90 | 90 | 100 |
| Kochia | 0 | 80 | 60 | 70 | 90 | 100 | 30 | 90 | 40 | 10 | 90 | 90 | 90 | 100 |
| Morningglory | — | — | — | — | — | — | — | — | — | — | — | — | — | — |
| Pigweed | 0 | 90 | 80 | 80 | 90 | 100 | 50 | 50 | 20 | 0 | 90 | 90 | 90 | 100 |
| Ragweed | 0 | 80 | 70 | 70 | 90 | 100 | 10 | 90 | 20 | 0 | 80 | 90 | 90 | 100 |
| Ryegrass, Italian | 0 | 90 | 80 | 90 | 100 | 100 | 0 | 100 | 80 | 60 | 100 | 90 | 90 | 100 |
| Velvetleaf | — | — | — | — | — | — | — | — | — | — | — | — | — | — |
| Wheat | 0 | 0 | 0 | 20 | 70 | 90 | 0 | 20 | 0 | 0 | 60 | 0 | 0 | 0 |

| | Compounds | | | | | | | | | | | | | |
|---|---|---|---|---|---|---|---|---|---|---|---|---|---|---|
| 500 g ai/ha | 82 | 83 | 84 | 85 | 86 | 87 | 88 | 89 | 90 | 91 | 92 | 93 | 94 | 95 |
| | Postemergence | | | | | | | | | | | | | |
| Barnyardgrass | 50 | 90 | 40 | 80 | 10 | 80 | 90 | 80 | 100 | 90 | 0 | 20 | 40 | 10 |
| Blackgrass | 70 | 100 | 80 | 90 | 30 | 80 | 90 | 60 | 90 | 60 | 20 | 0 | 30 | 10 |
| Corn | 0 | 0 | 0 | 0 | 0 | 0 | 0 | 0 | 30 | 30 | 0 | 30 | 0 | 0 |
| Crabgrass, Large | — | — | — | — | — | — | — | — | — | — | — | — | — | — |
| Foxtail, Giant | 70 | 100 | 80 | 90 | 70 | 80 | 100 | 80 | 100 | 100 | 0 | 10 | 50 | 0 |
| Galium | 90 | 100 | 90 | 100 | 100 | 90 | 100 | 90 | 100 | 100 | 30 | 90 | 90 | 60 |
| Kochia | 80 | 100 | 80 | 70 | 80 | 90 | 100 | 90 | 100 | 90 | 70 | 30 | 60 | 10 |
| Morningglory | — | — | — | — | — | — | — | — | — | — | — | — | — | — |
| Pigweed | 80 | 100 | 90 | 100 | 90 | 90 | 100 | 90 | 100 | 100 | 30 | 60 | 70 | 0 |
| Ragweed | 70 | 100 | 90 | 90 | 80 | 90 | 100 | 90 | 100 | 100 | 0 | 50 | 60 | 10 |
| Ryegrass, Italian | 80 | 100 | 80 | 90 | 50 | 80 | 100 | 90 | 100 | 100 | 0 | 90 | 50 | 50 |
| Velvetleaf | — | — | — | — | — | — | — | — | — | — | — | — | — | — |
| Wheat | 0 | 20 | 0 | 0 | 0 | 0 | 0 | 0 | 30 | 30 | 0 | 20 | 20 | 0 |

| | Compounds | | | | | | | | | | | | | |
|---|---|---|---|---|---|---|---|---|---|---|---|---|---|---|
| 500 g ai/ha | 96 | 97 | 98 | 99 | 100 | 101 | 102 | 103 | 104 | 105 | 106 | 107 | 108 | 109 |
| | Postemergence | | | | | | | | | | | | | |
| Barnyardgrass | 20 | 90 | 90 | 90 | 30 | 30 | 90 | 90 | 100 | 90 | 90 | 100 | 90 | 90 |
| Blackgrass | 20 | 90 | 30 | 80 | 70 | 40 | 70 | 90 | 90 | 90 | 90 | 90 | 90 | 90 |
| Corn | 0 | 70 | 20 | 40 | 20 | 20 | 20 | 60 | 20 | 30 | 20 | 30 | 0 | 30 |
| Crabgrass, Large | — | — | — | — | — | — | — | — | — | — | — | — | — | — |
| Foxtail, Giant | 20 | 100 | 100 | 90 | 80 | 50 | 90 | 90 | 100 | 90 | 90 | 90 | 90 | 90 |
| Galium | 50 | 100 | 100 | 100 | 100 | 90 | 100 | 100 | 100 | 100 | 100 | 100 | 100 | 100 |
| Kochia | 70 | 100 | 60 | 70 | 100 | 30 | 40 | 90 | 100 | 90 | 90 | 90 | 100 | 90 |
| Morningglory | — | — | — | — | — | — | — | — | — | — | — | — | — | — |
| Pigweed | 70 | 100 | 100 | 90 | 90 | 70 | 90 | 100 | 90 | 90 | 90 | 90 | 100 | 90 |
| Ragweed | 50 | 100 | 100 | 100 | 90 | 80 | 100 | 100 | 100 | 90 | 90 | 100 | 100 | 100 |
| Ryegrass, Italian | 60 | 100 | 100 | 100 | 100 | 50 | 80 | 100 | 100 | 100 | 90 | 100 | 100 | 100 |
| Velvetleaf | — | — | — | — | — | — | — | — | — | — | — | — | — | — |
| Wheat | 0 | 80 | 30 | 30 | 20 | 20 | 20 | 20 | 20 | 20 | 20 | 20 | 20 | 30 |

| | Compounds | | | | | | | | | | | | | |
|---|---|---|---|---|---|---|---|---|---|---|---|---|---|---|
| 500 g ai/ha | 110 | 111 | 112 | 113 | 114 | 115 | 116 | 117 | 118 | 119 | 120 | 121 | 122 | 123 |
| | Postemergence | | | | | | | | | | | | | |
| Barnyardgrass | 10 | 90 | 20 | 90 | 90 | 90 | 90 | 40 | 0 | 0 | 10 | 50 | 30 | 70 |
| Blackgrass | 60 | 70 | 80 | 90 | 60 | 70 | 70 | 0 | 0 | 0 | 10 | 50 | 40 | 50 |
| Corn | 20 | 20 | 30 | 70 | 30 | 20 | 30 | 0 | 0 | 0 | 0 | 20 | 20 | 20 |
| Crabgrass, Large | — | — | — | — | — | — | — | — | — | — | — | — | — | — |
| Foxtail, Giant | 10 | 100 | 50 | 90 | 90 | 90 | 100 | 20 | 0 | 0 | 10 | 80 | 60 | 60 |
| Galium | 90 | 100 | 90 | 100 | 100 | 100 | 100 | 0 | 0 | 0 | 70 | 90 | 70 | 90 |
| Kochia | 70 | 90 | 30 | 100 | 60 | 90 | 60 | 10 | 0 | 0 | 30 | 80 | 70 | 70 |
| Morningglory | — | — | — | — | — | — | — | — | — | — | — | — | — | — |

TABLE A-continued

| | | | | | | | | | | | | | |
|---|---|---|---|---|---|---|---|---|---|---|---|---|---|
| Pigweed | 90 | 100 | 30 | 100 | 90 | 90 | 100 | 20 | 0 | 0 | 50 | 90 | 70 | 70 |
| Ragweed | 100 | 100 | 80 | 100 | 80 | 100 | 100 | 0 | 0 | 0 | 10 | 90 | 60 | 90 |
| Ryegrass, Italian | 90 | 100 | 100 | 100 | 90 | 100 | 100 | 0 | 0 | 0 | 80 | 100 | 70 | 100 |
| Velvetleaf | — | — | — | — | — | — | — | — | — | — | — | — | — | — |
| Wheat | 40 | 30 | 30 | 70 | 40 | 30 | 50 | 0 | 0 | 0 | 0 | 20 | 0 | 20 |

| | Compounds | | | | | | | | | | | | |
|---|---|---|---|---|---|---|---|---|---|---|---|---|---|
| 500 g ai/ha | 124 | 125 | 126 | 127 | 128 | 129 | 130 | 131 | 132 | 133 | 134 | 135 | 136 | 137 |
| | Postemergence | | | | | | | | | | | | |
| Barnyardgrass | 30 | 90 | 60 | 50 | 80 | 100 | 90 | 20 | 30 | 90 | 60 | 0 | 100 | 100 |
| Blackgrass | 0 | 80 | 70 | 50 | 20 | 100 | 70 | 50 | 50 | 60 | 70 | 30 | 90 | 100 |
| Corn | 0 | 30 | 20 | 10 | 0 | 80 | 30 | 10 | 10 | 50 | 50 | 20 | 30 | 70 |
| Crabgrass, Large | — | — | — | — | — | — | — | — | — | — | — | — | — | — |
| Foxtail, Giant | 0 | 90 | 60 | 60 | 70 | 100 | 90 | 80 | 80 | 90 | 80 | 0 | 100 | 100 |
| Galium | 30 | 90 | 100 | 100 | 70 | 100 | 100 | 100 | 100 | 100 | 100 | 90 | 100 | 100 |
| Kochia | 0 | 100 | 90 | 80 | 0 | 90 | 100 | 80 | 80 | 100 | 100 | 0 | 100 | 100 |
| Morningglory | — | — | — | — | — | — | — | — | — | — | — | — | — | — |
| Pigweed | 0 | 100 | 100 | 100 | 90 | 100 | 100 | 90 | 90 | 100 | 100 | 20 | 100 | 100 |
| Ragweed | 0 | 100 | 90 | 80 | 30 | 100 | 100 | 90 | 100 | 100 | 100 | 60 | 100 | 100 |
| Ryegrass, Italian | 0 | 100 | 100 | 90 | 50 | 100 | 100 | 90 | 100 | 100 | 100 | 70 | 100 | 100 |
| Velvetleaf | — | — | — | — | — | — | — | — | — | — | — | — | — | — |
| Wheat | 0 | 80 | 20 | 20 | 0 | 80 | 30 | 20 | 20 | 30 | 30 | 0 | 30 | 90 |

| | Compounds | | | | | | | | | | | | |
|---|---|---|---|---|---|---|---|---|---|---|---|---|---|
| 500 g ai/ha | 138 | 139 | 140 | 141 | 142 | 143 | 144 | 145 | 146 | 147 | 148 | 149 | 150 | 151 |
| | Postemergence | | | | | | | | | | | | |
| Barnyardgrass | 100 | 100 | 90 | 50 | 20 | 60 | 100 | 90 | 30 | 40 | 30 | 20 | 30 | 90 |
| Blackgrass | 90 | 90 | 50 | 50 | 20 | 60 | 100 | 80 | 70 | 90 | 80 | 70 | 50 | 90 |
| Corn | 20 | 40 | 30 | 0 | 0 | 20 | 90 | 60 | 30 | 0 | 0 | 30 | 0 | 30 |
| Crabgrass, Large | — | — | — | — | — | — | — | — | — | — | — | — | — | — |
| Foxtail, Giant | 100 | 100 | 90 | 70 | 20 | 60 | 100 | 80 | 70 | 80 | 70 | 80 | 30 | 90 |
| Galium | 100 | 100 | 90 | 90 | 80 | 100 | 100 | 100 | 90 | 100 | 90 | 100 | 80 | 100 |
| Kochia | 100 | 100 | 70 | 30 | 20 | 90 | 100 | 100 | 100 | 100 | 90 | 100 | 70 | 100 |
| Morningglory | — | — | — | — | — | — | — | — | — | — | — | — | — | — |
| Pigweed | 100 | 100 | 90 | 30 | 50 | 90 | 100 | 100 | 90 | 90 | 90 | 100 | 80 | 100 |
| Ragweed | 100 | 100 | 100 | 40 | 20 | 70 | 100 | 100 | 100 | 90 | 90 | 90 | 30 | 90 |
| Ryegrass, Italian | 100 | 100 | 100 | 90 | 90 | 100 | 100 | 100 | 100 | 100 | 90 | 100 | 90 | 100 |
| Velvetleaf | — | — | — | — | — | — | — | — | — | — | — | — | — | — |
| Wheat | 20 | 30 | 70 | 0 | 0 | 50 | 100 | 30 | 70 | 80 | 60 | 70 | 20 | 20 |

| | Compounds | | | | | | | | | | | | |
|---|---|---|---|---|---|---|---|---|---|---|---|---|---|
| 500 g ai/ha | 152 | 153 | 154 | 155 | 156 | 157 | 158 | 159 | 160 | 161 | 162 | 163 | 164 | 165 |
| | Postemergence | | | | | | | | | | | | |
| Barnyardgrass | 40 | 90 | 90 | 80 | 90 | 80 | 50 | 80 | 20 | 80 | 50 | 0 | 20 | 30 |
| Blackgrass | 30 | 90 | 90 | 70 | 90 | 70 | 60 | 70 | 20 | 90 | 40 | 20 | 40 | 50 |
| Corn | 0 | 80 | 40 | 20 | 30 | 40 | 0 | 40 | 0 | 30 | 0 | 0 | 20 | 20 |
| Crabgrass, Large | — | — | — | — | — | — | — | — | — | — | — | — | — | — |
| Foxtail, Giant | 50 | 90 | 90 | 90 | 90 | 80 | 60 | 80 | 20 | 80 | 40 | 0 | 30 | 50 |
| Galium | 70 | 100 | 100 | 90 | 100 | 100 | 90 | 100 | 90 | 100 | 100 | 60 | 100 | 100 |
| Kochia | 40 | 90 | 50 | 80 | 100 | 100 | 100 | 100 | 60 | 90 | 90 | 20 | 90 | 90 |
| Morningglory | — | — | — | — | — | — | — | — | — | — | — | — | — | — |
| Pigweed | 60 | 100 | 90 | 100 | 100 | 100 | 100 | 80 | 90 | 90 | 90 | 20 | 80 | 80 |
| Ragweed | 90 | 90 | 80 | 100 | 100 | 100 | 100 | 100 | 80 | 90 | 100 | 0 | 100 | 90 |
| Ryegrass, Italian | 90 | 100 | 100 | 90 | 100 | 100 | 100 | 100 | 90 | 100 | 90 | 70 | 90 | 90 |
| Velvetleaf | — | — | — | — | — | — | — | — | — | — | — | — | — | — |
| Wheat | 50 | 30 | 20 | 50 | 60 | 50 | 0 | 30 | 0 | 20 | 20 | 0 | 0 | 0 |

| | Compounds | | | | | | | | | | | | |
|---|---|---|---|---|---|---|---|---|---|---|---|---|---|
| 500 g ai/ha | 166 | 167 | 168 | 169 | 170 | 171 | 172 | 173 | 174 | 175 | 176 | 177 | 185 | 186 |
| | Postemergence | | | | | | | | | | | | |
| Barnyardgrass | 20 | 20 | 40 | 20 | 10 | 90 | 70 | 0 | 10 | 0 | 10 | 0 | 30 | 100 |
| Blackgrass | 30 | 40 | 30 | 20 | 10 | 90 | 30 | 0 | 0 | 20 | 30 | 0 | 20 | 80 |
| Corn | 20 | 20 | 20 | 30 | 0 | 40 | 0 | 0 | 0 | 20 | 0 | 0 | 30 | 30 |
| Crabgrass, Large | — | — | — | — | — | — | — | — | — | — | — | — | — | — |
| Foxtail, Giant | 40 | 40 | 40 | 30 | 10 | 90 | 80 | 0 | 10 | 0 | 10 | 0 | 20 | 90 |
| Galium | 90 | 90 | 30 | 70 | 80 | 100 | 40 | 0 | 80 | 0 | 100 | 0 | 90 | 100 |
| Kochia | 70 | 70 | 20 | 100 | 70 | 100 | 20 | 0 | 0 | 0 | 70 | 0 | 100 | 100 |
| Morningglory | — | — | — | — | — | — | — | — | — | — | — | — | — | — |

TABLE A-continued

| | | | | | | | | | | | | | |
|---|---|---|---|---|---|---|---|---|---|---|---|---|---|
| Pigweed | 80 | 80 | 40 | 70 | 80 | 100 | 30 | 0 | 60 | 0 | 90 | 0 | 90 | 100 |
| Ragweed | 70 | 70 | 0 | 80 | 80 | 100 | 0 | 0 | 20 | 0 | 100 | 0 | 50 | 100 |
| Ryegrass, Italian | 90 | 80 | 60 | 100 | 50 | 100 | 60 | 0 | 40 | 30 | 100 | 0 | 80 | 100 |
| Velvetleaf | — | — | — | — | — | — | — | — | — | — | — | — | — | — |
| Wheat | 20 | 0 | 20 | 30 | 0 | 70 | 20 | 0 | 0 | 20 | 0 | 0 | 0 | 40 |

| | Compounds | |
|---|---|---|
| 500 g ai/ha | 187 | 188 |

Postemergence

| | | |
|---|---|---|
| Barnyardgrass | 80 | 20 |
| Blackgrass | 70 | 60 |
| Corn | 30 | 0 |
| Crabgrass, Large | — | — |
| Foxtail, Giant | 80 | 80 |
| *Galium* | 100 | 90 |
| *Kochia* | 100 | 20 |
| Morningglory | — | — |
| Pigweed | 90 | 80 |
| Ragweed | 100 | 50 |
| Ryegrass, Italian | 100 | 80 |
| Velvetleaf | — | — |
| Wheat | 30 | 0 |

| | Compounds | | | | | | | | | | | | |
|---|---|---|---|---|---|---|---|---|---|---|---|---|---|
| 125 g ai/ha | 2 | 8 | 9 | 12 | 14 | 15 | 16 | 17 | 18 | 19 | 20 | 21 | 22 | 23 |

Postemergence

| | | | | | | | | | | | | | | |
|---|---|---|---|---|---|---|---|---|---|---|---|---|---|---|
| Barnyardgrass | 30 | 0 | 10 | 0 | 10 | 70 | 20 | 0 | 0 | 20 | 30 | 90 | 30 | 80 |
| Blackgrass | — | — | — | 20 | 20 | 0 | 10 | 10 | 0 | 0 | 30 | 90 | 50 | 70 |
| Corn | 0 | 0 | 0 | 0 | 0 | 0 | 0 | 0 | 0 | 0 | 20 | 50 | 0 | 40 |
| Crabgrass, Large | 50 | 0 | 10 | — | — | — | — | — | — | — | — | — | — | — |
| Foxtail, Giant | 80 | 0 | 10 | 10 | 10 | 70 | 20 | 0 | 0 | 20 | 30 | 100 | 60 | 90 |
| *Galium* | — | — | — | 60 | 80 | 70 | 90 | 50 | 40 | 30 | 90 | 100 | 90 | 100 |
| *Kochia* | — | — | — | 0 | 80 | 50 | 50 | 0 | 0 | 0 | 90 | 100 | 100 | 100 |
| Morningglory | 100 | 0 | 40 | — | — | — | — | — | — | — | — | — | — | — |
| Pigweed | 100 | 70 | 0 | 30 | 60 | 0 | 30 | 0 | 0 | 0 | 100 | 100 | 100 | 100 |
| Ragweed | — | — | — | 10 | 70 | 50 | 30 | 0 | 0 | 0 | 80 | 100 | 90 | 90 |
| Ryegrass, Italian | — | — | — | 60 | 60 | 50 | 50 | 50 | 10 | 0 | 100 | 100 | 80 | 100 |
| Velvetleaf | 100 | 60 | 0 | — | — | — | — | — | — | — | — | — | — | — |
| Wheat | 20 | 0 | 0 | 0 | 0 | 0 | 0 | 0 | 0 | 0 | 20 | 10 | 0 | 50 |

| | Compounds | | | | | | | | | | | | |
|---|---|---|---|---|---|---|---|---|---|---|---|---|---|
| 125 g ai/ha | 24 | 25 | 26 | 27 | 28 | 29 | 30 | 31 | 33 | 34 | 35 | 36 | 37 | 38 |

Postemergence

| | | | | | | | | | | | | | | |
|---|---|---|---|---|---|---|---|---|---|---|---|---|---|---|
| Barnyardgrass | 40 | 20 | 10 | 90 | 80 | 70 | 0 | 0 | 40 | 30 | 50 | 50 | 60 | 0 |
| Blackgrass | 30 | 60 | 30 | 90 | 90 | 70 | 20 | 0 | 10 | 80 | 70 | 60 | 60 | 50 |
| Corn | 0 | 0 | 0 | 0 | 0 | 10 | 0 | 0 | 0 | 0 | 0 | 20 | 0 | 0 |
| Crabgrass, Large | — | — | — | — | — | — | — | — | — | — | — | — | — | — |
| Foxtail, Giant | 10 | 90 | 10 | 90 | 90 | 80 | 0 | 0 | 40 | 30 | 90 | 80 | 80 | 0 |
| *Galium* | 80 | 100 | 70 | 100 | 100 | 90 | 70 | 20 | 90 | 90 | 100 | 100 | 100 | 80 |
| *Kochia* | 70 | 100 | 80 | 70 | 70 | 80 | 60 | 0 | 90 | 70 | 80 | 90 | 60 | 30 |
| Morningglory | — | — | — | — | — | — | — | — | — | — | — | — | — | — |
| Pigweed | 70 | 90 | 80 | 90 | 90 | 90 | 90 | 20 | 40 | 90 | 80 | 90 | 100 | 50 |
| Ragweed | 30 | 100 | 60 | 100 | 80 | 90 | 40 | 0 | 90 | 90 | 50 | 90 | 90 | 40 |
| Ryegrass, Italian | 70 | 100 | 60 | 100 | 90 | 90 | 70 | 0 | 50 | 100 | 80 | 70 | 90 | 0 |
| Velvetleaf | — | — | — | — | — | — | — | — | — | — | — | — | — | — |
| Wheat | 30 | 0 | 0 | 0 | 0 | 40 | 10 | 0 | 0 | 20 | 20 | 20 | 40 | 10 |

| | Compounds | | | | | | | | | | | | |
|---|---|---|---|---|---|---|---|---|---|---|---|---|---|
| 125 g ai/ha | 39 | 40 | 41 | 42 | 43 | 44 | 45 | 46 | 47 | 48 | 49 | 50 | 51 | 52 |

Postemergence

| | | | | | | | | | | | | | | |
|---|---|---|---|---|---|---|---|---|---|---|---|---|---|---|
| Barnyardgrass | 0 | 10 | 30 | 30 | 0 | 0 | 0 | 20 | 40 | 10 | 0 | 0 | 20 | 10 |
| Blackgrass | 30 | 60 | 70 | 80 | 30 | 0 | 0 | 20 | 60 | 0 | 10 | 0 | 30 | 20 |
| Corn | 0 | 0 | 20 | 0 | 0 | 0 | 0 | 0 | 0 | 0 | 0 | 0 | 0 | 0 |
| Crabgrass, Large | — | — | — | — | — | — | — | — | — | — | — | — | — | — |
| Foxtail, Giant | 0 | 60 | 70 | 90 | 0 | 0 | 0 | 50 | 80 | 50 | 0 | 0 | 50 | 40 |
| *Galium* | 90 | 90 | 80 | 100 | 50 | 30 | 0 | 70 | 90 | 90 | 50 | 60 | 90 | 100 |
| *Kochia* | 30 | 80 | 100 | 100 | 0 | 0 | 0 | 30 | 90 | 70 | 0 | 0 | 70 | 40 |
| Morningglory | — | — | — | — | — | — | — | — | — | — | — | — | — | — |

TABLE A-continued

| | | | | | | | | | | | | | | |
|---|---|---|---|---|---|---|---|---|---|---|---|---|---|---|
| Pigweed | 50 | 80 | 60 | 90 | 0 | 0 | 0 | 70 | 100 | 60 | 20 | 20 | 70 | 10 |
| Ragweed | 50 | 70 | 70 | 100 | 0 | 0 | 0 | 80 | 100 | 0 | 0 | 0 | 70 | 90 |
| Ryegrass, Italian | 90 | 90 | 100 | 100 | 40 | 0 | 0 | 30 | 70 | 50 | 30 | 20 | 60 | 70 |
| Velvetleaf | — | — | — | — | — | — | — | — | — | — | — | — | — | — |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 53 | 54 | 55 | 56 | 57 | 58 | 59 | 61 | 62 | 63 | 64 | 65 | 66 | 67 |
| | Postemergence | | | | | | | | | | | | | |
| Barnyardgrass | 0 | 30 | 60 | 10 | 90 | 0 | 80 | 0 | 70 | 60 | 0 | 20 | 20 | 20 |
| Blackgrass | 0 | 20 | 70 | 30 | 30 | 20 | 90 | 0 | 70 | 70 | 0 | 20 | 60 | 70 |
| Corn | 0 | 20 | 0 | 0 | 20 | 0 | 20 | 0 | 10 | 0 | 0 | 0 | 0 | 0 |
| Crabgrass, Large | — | — | — | — | — | — | — | — | — | — | — | — | — | — |
| Foxtail, Giant | 0 | 60 | 70 | 20 | 80 | 0 | 90 | 0 | 80 | 70 | 0 | 20 | 70 | 80 |
| *Galium* | 60 | 100 | 100 | 90 | 100 | 70 | 100 | 0 | 100 | 100 | 0 | 90 | 90 | 80 |
| *Kochia* | 70 | 100 | 90 | 90 | 80 | 20 | 100 | 0 | 100 | 100 | 0 | 90 | 90 | 20 |
| Morningglory | — | — | — | — | — | — | — | — | — | — | — | — | — | — |
| Pigweed | 60 | 90 | 70 | 80 | 100 | 0 | 100 | 0 | 100 | 100 | 0 | 80 | 80 | 20 |
| Ragweed | 60 | 100 | 90 | 70 | 100 | 0 | 90 | 0 | 100 | 100 | 0 | 50 | 70 | 50 |
| Ryegrass, Italian | 40 | 60 | 100 | 90 | 70 | 60 | 100 | 0 | 100 | 100 | 0 | 90 | 90 | 70 |
| Velvetleaf | — | — | — | — | — | — | — | — | — | — | — | — | — | — |
| Wheat | 0 | 20 | 0 | 10 | 0 | 0 | 50 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 68 | 69 | 70 | 71 | 72 | 73 | 74 | 75 | 76 | 77 | 78 | 79 | 80 | 81 |
| | Postemergence | | | | | | | | | | | | | |
| Barnyardgrass | 70 | 10 | 0 | 0 | 20 | 40 | 0 | 0 | 0 | 0 | 20 | 50 | 70 | 30 |
| Blackgrass | 0 | 30 | 10 | 30 | 70 | 90 | 20 | 50 | 0 | 0 | 30 | 70 | 80 | 90 |
| Corn | 0 | 0 | 0 | 0 | 20 | 20 | 0 | 0 | 0 | 0 | 0 | 0 | 0 | 0 |
| Crabgrass, Large | — | — | — | — | — | — | — | — | — | — | — | — | — | — |
| Foxtail, Giant | 10 | 10 | 30 | 0 | 30 | 90 | 0 | 50 | 0 | 0 | 20 | 70 | 80 | 90 |
| *Galium* | 0 | 80 | 70 | 70 | 90 | 100 | 10 | 90 | 70 | 20 | 80 | 90 | 90 | 100 |
| *Kochia* | 0 | 60 | 50 | 50 | 60 | 90 | 30 | 80 | 20 | 0 | 50 | 80 | 90 | 60 |
| Morningglory | — | — | — | — | — | — | — | — | — | — | — | — | — | — |
| Pigweed | 0 | 80 | 80 | 70 | 90 | 100 | 40 | 30 | 10 | 0 | 60 | 90 | 90 | 100 |
| Ragweed | 0 | 80 | 40 | 70 | 70 | 90 | 0 | 60 | 0 | 0 | 40 | 90 | 80 | 90 |
| Ryegrass, Italian | 0 | 80 | 60 | 30 | 100 | 100 | 0 | 90 | 40 | 20 | 80 | 80 | 80 | 100 |
| Velvetleaf | — | — | — | — | — | — | — | — | — | — | — | — | — | — |
| Wheat | 0 | 0 | 0 | 0 | 20 | 40 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 82 | 83 | 84 | 85 | 86 | 87 | 88 | 89 | 90 | 91 | 92 | 93 | 94 | 95 |
| | Postemergence | | | | | | | | | | | | | |
| Barnyardgrass | 30 | 40 | 20 | 30 | 30 | 40 | 30 | 40 | 80 | 90 | 0 | 0 | 0 | 0 |
| Blackgrass | 70 | 90 | 70 | 90 | 10 | 80 | 90 | 30 | 70 | 30 | 0 | 0 | 0 | 0 |
| Corn | 0 | 0 | 0 | 0 | 0 | 0 | 0 | 0 | 20 | 20 | 0 | 0 | 0 | 0 |
| Crabgrass, Large | — | — | — | — | — | — | — | — | — | — | — | — | — | — |
| Foxtail, Giant | 50 | 90 | 50 | 90 | 50 | 70 | 90 | 70 | 80 | 90 | 0 | 0 | 30 | 0 |
| *Galium* | 90 | 100 | 90 | 90 | 90 | 90 | 100 | 90 | 100 | 100 | 10 | 70 | 80 | 20 |
| *Kochia* | 30 | 70 | 70 | 30 | 70 | 90 | 70 | 80 | 100 | 70 | 60 | 20 | 30 | 0 |
| Morningglory | — | — | — | — | — | — | — | — | — | — | — | — | — | — |
| Pigweed | 60 | 100 | 80 | 90 | 90 | 80 | 100 | 80 | 100 | 90 | 20 | 30 | 30 | 0 |
| Ragweed | 70 | 90 | 80 | 90 | 80 | 80 | 90 | 80 | 100 | 100 | 0 | 0 | 10 | 0 |
| Ryegrass, Italian | 70 | 90 | 70 | 90 | 0 | 80 | 100 | 80 | 100 | 90 | 0 | 40 | 30 | 10 |
| Velvetleaf | — | — | — | — | — | — | — | — | — | — | — | — | — | — |
| Wheat | 0 | 0 | 0 | 0 | 0 | 0 | 0 | 0 | 20 | 20 | 0 | 0 | 0 | 0 |

| | Compounds | | | | | | | | | | | | | |
|---|---|---|---|---|---|---|---|---|---|---|---|---|---|---|
| 125 g ai/ha | 96 | 97 | 98 | 99 | 100 | 101 | 102 | 103 | 104 | 105 | 106 | 107 | 108 | 109 |
| | Postemergence | | | | | | | | | | | | | |
| Barnyardgrass | 0 | 30 | 90 | 20 | 30 | 0 | 40 | 40 | 70 | 50 | 70 | 60 | 30 | 30 |
| Blackgrass | 0 | 90 | 30 | 60 | 40 | 20 | 20 | 70 | 90 | 80 | 90 | 80 | 80 | 80 |
| Corn | 0 | 10 | 20 | 20 | 0 | 0 | 20 | 20 | 0 | 0 | 0 | 0 | 0 | 0 |
| Crabgrass, Large | — | — | — | — | — | — | — | — | — | — | — | — | — | — |
| Foxtail, Giant | 0 | 80 | 90 | 40 | 80 | 30 | 70 | 90 | 80 | 70 | 90 | 70 | 60 | 70 |
| *Galium* | 20 | 100 | 100 | 100 | 90 | 70 | 100 | 100 | 100 | 100 | 100 | 100 | 100 | 100 |
| *Kochia* | 60 | 90 | 30 | 30 | 70 | 20 | 20 | 50 | 90 | 90 | 70 | 80 | 90 | 90 |
| Morningglory | — | — | — | — | — | — | — | — | — | — | — | — | — | — |

TABLE A-continued

| | | | | | | | | | | | | | | |
|---|---|---|---|---|---|---|---|---|---|---|---|---|---|---|
| Pigweed | 60 | 90 | 100 | 70 | 80 | 30 | 90 | 90 | 90 | 90 | 90 | 90 | 90 | 90 |
| Ragweed | 0 | 90 | 100 | 100 | 90 | 60 | 100 | 100 | 100 | 90 | 90 | 90 | 70 | 80 |
| Ryegrass, Italian | 20 | 100 | 90 | 100 | 90 | 30 | 20 | 100 | 100 | 100 | 90 | 60 | 100 | 100 |
| Velvetleaf | — | — | — | — | — | — | — | — | — | — | — | — | — | — |
| Wheat | 0 | 20 | 30 | 20 | 0 | 0 | 20 | 0 | 20 | 0 | 0 | 30 | 0 | 20 |

Compounds

| 125 g ai/ha | 110 | 111 | 112 | 113 | 114 | 115 | 116 | 117 | 118 | 119 | 120 | 121 | 122 | 123 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 0 | 40 | 20 | 40 | 20 | 20 | 20 | 0 | 0 | 0 | 0 | 30 | 20 | 40 |
| Blackgrass | 20 | 30 | 40 | 90 | 20 | 20 | 30 | 0 | 0 | 0 | 0 | 20 | 30 | 30 |
| Corn | 0 | 0 | 0 | 20 | 0 | 0 | 0 | 0 | 0 | 0 | 0 | 20 | 0 | 0 |
| Crabgrass, Large | — | — | — | — | — | — | — | — | — | — | — | — | — | — |
| Foxtail, Giant | 0 | 70 | 20 | 40 | 70 | 20 | 70 | 0 | 0 | 0 | 0 | 60 | 40 | 50 |
| Galium | 70 | 90 | 70 | 100 | 90 | 80 | 70 | 0 | 0 | 0 | 40 | 70 | 60 | 80 |
| Kochia | 50 | 40 | 20 | 100 | 30 | 70 | 30 | 0 | 0 | 0 | 0 | 70 | 40 | 70 |
| Morningglory | — | — | — | — | — | — | — | — | — | — | — | — | — | — |
| Pigweed | 70 | 100 | 20 | 90 | 90 | 70 | 70 | 0 | 0 | 0 | 20 | 90 | 30 | 60 |
| Ragweed | 60 | 70 | 60 | 90 | 70 | 80 | 70 | 0 | 0 | 0 | 0 | 90 | 50 | 50 |
| Ryegrass, Italian | 70 | 90 | 80 | 100 | 90 | 100 | 90 | 0 | 0 | 0 | 20 | 90 | 50 | 90 |
| Velvetleaf | — | — | — | — | — | — | — | — | — | — | — | — | — | — |
| Wheat | 0 | 20 | 20 | 30 | 20 | 20 | 20 | 0 | 0 | 0 | 0 | 0 | 0 | 0 |

Compounds

| 125 g ai/ha | 124 | 125 | 126 | 127 | 128 | 129 | 130 | 131 | 132 | 133 | 134 | 135 | 136 | 137 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 20 | 90 | 30 | 10 | 50 | 90 | 60 | 0 | 0 | 20 | 20 | 0 | 20 | 70 |
| Blackgrass | 0 | 70 | 60 | 20 | 0 | 60 | 60 | 30 | 30 | 60 | 60 | 0 | 60 | 90 |
| Corn | 0 | 20 | 0 | 0 | 0 | 10 | 0 | 0 | 0 | 10 | 20 | 0 | 30 | 30 |
| Crabgrass, Large | — | — | — | — | — | — | — | — | — | — | — | — | — | — |
| Foxtail, Giant | 0 | 90 | 20 | 10 | 50 | 90 | 70 | 50 | 60 | 20 | 20 | 0 | 90 | 100 |
| Galium | 0 | 90 | 100 | 90 | 40 | 100 | 100 | 70 | 80 | 100 | 100 | 60 | 100 | 100 |
| Kochia | 0 | 100 | 90 | 70 | 0 | 70 | 100 | 60 | 50 | 90 | 100 | 0 | 100 | 100 |
| Morningglory | — | — | — | — | — | — | — | — | — | — | — | — | — | — |
| Pigweed | 0 | 100 | 90 | 90 | 70 | 90 | 100 | 60 | 60 | 90 | 90 | 0 | 90 | 100 |
| Ragweed | 0 | 90 | 90 | 60 | 10 | 100 | 70 | 100 | 100 | 100 | 100 | 30 | 100 | 100 |
| Ryegrass, Italian | 0 | 100 | 90 | 80 | 20 | 100 | 100 | 90 | 100 | 100 | 100 | 40 | 90 | 100 |
| Velvetleaf | — | — | — | — | — | — | — | — | — | — | — | — | — | — |
| Wheat | 0 | 50 | 0 | 0 | 0 | 20 | 0 | 0 | 0 | 20 | 30 | 0 | 0 | 50 |

Compounds

| 125 g ai/ha | 138 | 139 | 140 | 141 | 142 | 143 | 144 | 145 | 146 | 147 | 148 | 149 | 150 | 151 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 20 | 20 | 50 | 20 | 10 | 20 | 100 | 20 | 0 | 10 | 10 | 20 | 0 | 70 |
| Blackgrass | 80 | 60 | 30 | 0 | 10 | 40 | 90 | 40 | 20 | 60 | 60 | 30 | 0 | 90 |
| Corn | 0 | 30 | 20 | 0 | 0 | 0 | 60 | 20 | 0 | 0 | 0 | 20 | 0 | 0 |
| Crabgrass, Large | — | — | — | — | — | — | — | — | — | — | — | — | — | — |
| Foxtail, Giant | 90 | 70 | 40 | 20 | 10 | 20 | 100 | 20 | 10 | 30 | 30 | 40 | 0 | 80 |
| Galium | 100 | 100 | 70 | 70 | 70 | 90 | 100 | 100 | 80 | 90 | 90 | 90 | 30 | 100 |
| Kochia | 100 | 100 | 30 | 10 | 0 | 70 | 100 | 100 | 70 | 80 | 80 | 80 | 40 | 70 |
| Morningglory | — | — | — | — | — | — | — | — | — | — | — | — | — | — |
| Pigweed | 90 | 60 | 70 | 0 | 20 | 90 | 100 | 100 | 90 | 90 | 90 | 90 | 40 | 90 |
| Ragweed | 100 | 100 | 90 | 60 | 0 | 70 | 100 | 100 | 90 | 90 | 90 | 90 | 0 | 90 |
| Ryegrass, Italian | 90 | 100 | 70 | 70 | 80 | 80 | 100 | 100 | 70 | 90 | 90 | 70 | 40 | 100 |
| Velvetleaf | — | — | — | — | — | — | — | — | — | — | — | — | — | — |
| Wheat | 0 | 30 | 20 | 0 | 0 | 0 | 90 | 20 | 0 | 20 | 20 | 20 | 0 | 0 |

Compounds

| 125 g ai/ha | 152 | 153 | 154 | 155 | 156 | 157 | 158 | 159 | 160 | 161 | 162 | 163 | 164 | 165 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 20 | 90 | 90 | 30 | 70 | 50 | 10 | 40 | 10 | 20 | 20 | 0 | 20 | 20 |
| Blackgrass | 20 | 90 | 70 | 60 | 60 | 60 | 50 | 70 | 10 | 80 | 20 | 0 | 20 | 20 |
| Corn | 0 | 0 | 0 | 0 | 0 | 0 | 0 | 20 | 0 | 0 | 20 | 0 | 0 | 0 |
| Crabgrass, Large | — | — | — | — | — | — | — | — | — | — | — | — | — | — |
| Foxtail, Giant | 30 | 90 | 90 | 80 | 90 | 60 | 30 | 50 | 10 | 80 | 20 | 0 | 20 | 20 |
| Galium | 60 | 100 | 100 | 90 | 100 | 100 | 80 | 100 | 70 | 80 | 90 | 30 | 80 | 100 |
| Kochia | 30 | 40 | 20 | 70 | 80 | 100 | 90 | 100 | 30 | 60 | 70 | 0 | 60 | 60 |
| Morningglory | — | — | — | — | — | — | — | — | — | — | — | — | — | — |

TABLE A-continued

| | | | | | | | | | | | | | | |
|---|---|---|---|---|---|---|---|---|---|---|---|---|---|---|
| Pigweed | 50 | 80 | 90 | 90 | 90 | 90 | 80 | 60 | 80 | 50 | 80 | 0 | 80 | 80 |
| Ragweed | 70 | 80 | 80 | 100 | 90 | 100 | 90 | 100 | 70 | 80 | 80 | 0 | 70 | 90 |
| Ryegrass, Italian | 30 | 100 | 90 | 90 | 90 | 100 | 90 | 100 | 30 | 100 | 60 | 20 | 70 | 80 |
| Velvetleaf | — | — | — | — | — | — | — | — | — | — | — | — | — | — |
| Wheat | 30 | 0 | 0 | 30 | 30 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 166 | 167 | 168 | 169 | 170 | 171 | 172 | 173 | 174 | 175 | 176 | 177 | 185 | 186 |

Postemergence

| | | | | | | | | | | | | | | |
|---|---|---|---|---|---|---|---|---|---|---|---|---|---|---|
| Barnyardgrass | 10 | 20 | 0 | 0 | 0 | 40 | 40 | 0 | 0 | 0 | 0 | 0 | 10 | 70 |
| Blackgrass | 10 | 20 | 20 | 10 | 0 | 80 | 20 | 0 | 0 | 0 | 30 | 0 | 0 | 40 |
| Corn | 20 | 0 | 0 | 0 | 0 | 20 | 0 | 0 | 0 | 0 | 0 | 0 | 0 | 20 |
| Crabgrass, Large | — | — | — | — | — | — | — | — | — | — | — | — | — | — |
| Foxtail, Giant | 10 | 20 | 30 | 0 | 0 | 40 | 40 | 0 | 0 | 0 | 0 | 0 | 0 | 70 |
| *Galium* | 70 | 70 | 0 | 30 | 40 | 90 | 20 | 0 | 30 | 0 | 90 | 0 | 70 | 100 |
| *Kochia* | 50 | 50 | 20 | 40 | 0 | 100 | 0 | 0 | 0 | 0 | 30 | 0 | 70 | 100 |
| Morningglory | — | — | — | — | — | — | — | — | — | — | — | — | — | — |
| Pigweed | 40 | 70 | 0 | 20 | 70 | 90 | 0 | 0 | 40 | 0 | 30 | 0 | 50 | 100 |
| Ragweed | 30 | 60 | 0 | 0 | 40 | 100 | 0 | 0 | 20 | 0 | 40 | 0 | 10 | 100 |
| Ryegrass, Italian | 40 | 70 | 60 | 70 | 0 | 100 | 20 | 0 | 10 | 20 | 30 | 0 | 70 | 100 |
| Velvetleaf | — | — | — | — | — | — | — | — | — | — | — | — | — | — |
| Wheat | 0 | 0 | 0 | 0 | 0 | 30 | 20 | 0 | 0 | 0 | 0 | 0 | 0 | 0 |

| | Compounds | |
|---|---|---|
| 125 g ai/ha | 187 | 188 |

Postemergence

| | | |
|---|---|---|
| Barnyardgrass | 30 | 10 |
| Blackgrass | 40 | 10 |
| Corn | 0 | 0 |
| Crabgrass, Large | — | — |
| Foxtail, Giant | 50 | 20 |
| *Galium* | 90 | 70 |
| *Kochia* | 90 | 10 |
| Morningglory | — | — |
| Pigweed | 70 | 50 |
| Ragweed | 100 | 20 |
| Ryegrass, Italian | 100 | 20 |
| Velvetleaf | — | — |
| Wheat | 0 | 0 |

| | Compounds | | | |
|---|---|---|---|---|
| 1000 g ai/ha | 181 | 182 | 183 | 184 |

Preemergence

| | | | | |
|---|---|---|---|---|
| Barnyardgrass | 0 | 0 | 40 | 10 |
| Corn | — | — | — | — |
| Crabgrass, Large | — | — | — | — |
| Foxtail, Giant | 0 | 0 | 60 | 30 |
| *Kochia* | 10 | 0 | 70 | 20 |
| Morningglory | — | — | — | — |
| Pigweed | 30 | 0 | 90 | 90 |
| Ragweed | 10 | 0 | 80 | 70 |
| Ryegrass, Italian | 60 | 0 | 90 | 90 |
| Velvetleaf | — | — | — | — |
| Wheat | — | — | — | — |

| | Compounds | | | | | | | | | | | |
|---|---|---|---|---|---|---|---|---|---|---|---|---|
| 1000 g ai/ha | 1 | 3 | 4 | 5 | 6 | 7 | 10 | 11 | 13 | 32 | 60 | 178 | 179 | 180 |

Preemergence

| | | | | | | | | | | | | | | |
|---|---|---|---|---|---|---|---|---|---|---|---|---|---|---|
| Barnyardgrass | 90 | 80 | 100 | 90 | 100 | 100 | 100 | 90 | 60 | 100 | 80 | 0 | 0 | 0 |
| Corn | 0 | 0 | 10 | 0 | 30 | 30 | 10 | 20 | — | — | — | — | — | — |
| Crabgrass, Large | 90 | 80 | 80 | 90 | — | 90 | 90 | 80 | — | — | — | — | — | — |
| Foxtail, Giant | 100 | 60 | 80 | 80 | 50 | 90 | 100 | 90 | 50 | 100 | 90 | 0 | 30 | 10 |
| *Kochia* | — | — | — | — | — | — | — | — | 20 | 100 | 80 | 0 | 30 | 0 |
| Morningglory | 90 | 80 | 60 | 0 | 10 | 80 | 90 | 90 | — | — | — | — | — | — |
| Pigweed | 100 | 0 | 70 | 0 | — | 100 | 100 | 100 | 0 | 100 | 100 | 0 | 80 | 40 |
| Ragweed | — | — | — | — | — | — | — | — | 0 | 90 | 100 | 0 | 50 | 40 |

TABLE A-continued

| | | | | | | | | | | | | | | |
|---|---|---|---|---|---|---|---|---|---|---|---|---|---|---|
| Ryegrass, Italian | — | — | — | — | — | — | — | — | 60 | 100 | 100 | 60 | 30 | 50 |
| Velvetleaf | 100 | 70 | 40 | 0 | 20 | 80 | 90 | 80 | — | — | — | — | — | — |
| Wheat | 0 | 0 | 0 | 0 | 0 | 0 | 0 | 50 | — | — | — | — | — | — |

| | Compounds | | | | | | | | | | | | | |
|---|---|---|---|---|---|---|---|---|---|---|---|---|---|---|
| 500 g ai/ha | 2 | 8 | 9 | 12 | 14 | 15 | 16 | 17 | 18 | 19 | 20 | 21 | 22 | 23 |
| | Preemergence | | | | | | | | | | | | | |
| Barnyardgrass | 80 | 0 | 100 | 80 | 40 | 90 | 70 | 0 | 0 | 90 | 90 | 100 | 70 | 90 |
| Corn | 10 | 0 | 0 | — | — | — | — | — | — | — | — | — | — | — |
| Crabgrass, Large | 100 | 60 | 90 | — | — | — | — | — | — | — | — | — | — | — |
| Foxtail, Giant | 100 | 60 | 100 | 90 | 10 | 70 | 30 | 0 | 0 | 0 | 90 | 100 | 90 | 90 |
| *Kochia* | — | — | — | 10 | 50 | 0 | 30 | 0 | 0 | 0 | 100 | 90 | 100 | 100 |
| Morningglory | 100 | 0 | 0 | — | — | — | — | — | — | — | — | — | — | — |
| Pigweed | 100 | 100 | 0 | 60 | 90 | 0 | 70 | 0 | 0 | 0 | 100 | 100 | 100 | 100 |
| Ragweed | — | — | — | 30 | 30 | 30 | 0 | 10 | 0 | 20 | 90 | 100 | 90 | 90 |
| Ryegrass, Italian | — | — | — | 50 | — | 100 | 80 | 40 | 20 | 0 | 100 | 100 | 100 | 90 |
| Velvetleaf | 90 | 30 | 0 | — | — | — | — | — | — | — | — | — | — | — |
| Wheat | 0 | 0 | 0 | — | — | — | — | — | — | — | — | — | — | — |

| | Compounds | | | | | | | | | | | | |
|---|---|---|---|---|---|---|---|---|---|---|---|---|---|
| 500 g ai/ha | 24 | 25 | 26 | 27 | 28 | 29 | 30 | 31 | 33 | 34 | 35 | 36 | 37 | 38 |
| | Preemergence | | | | | | | | | | | | |
| Barnyardgrass | 60 | 90 | 10 | 100 | 90 | 90 | 10 | 0 | 90 | 80 | 90 | 30 | 90 | 10 |
| Corn | — | — | — | — | — | — | — | — | — | — | — | — | — | — |
| Crabgrass, Large | — | — | — | — | — | — | — | — | — | — | — | — | — | — |
| Foxtail, Giant | 80 | 90 | 50 | 100 | 100 | 90 | 60 | 0 | 70 | 90 | 100 | 90 | 90 | 40 |
| *Kochia* | 50 | 100 | 30 | 90 | 90 | 100 | 40 | 0 | 80 | 60 | 70 | 80 | 80 | 40 |
| Morningglory | — | — | — | — | — | — | — | — | — | — | — | — | — | — |
| Pigweed | 90 | 100 | 100 | 100 | 100 | 100 | 90 | 0 | 20 | 100 | 90 | 100 | 100 | 80 |
| Ragweed | 0 | 100 | 40 | 100 | 90 | 90 | 70 | 30 | 100 | 90 | 80 | 90 | 90 | 70 |
| Ryegrass, Italian | 80 | 100 | 70 | 100 | 100 | 90 | 50 | 0 | 60 | 100 | 90 | 70 | 100 | 70 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | |
|---|---|---|---|---|---|---|---|---|---|---|---|---|---|
| 500 g ai/ha | 39 | 40 | 41 | 42 | 43 | 44 | 45 | 46 | 47 | 48 | 49 | 50 | 51 | 52 |
| | Preemergence | | | | | | | | | | | | |
| Barnyardgrass | 10 | 50 | 90 | 100 | 10 | 0 | 0 | 60 | 90 | 0 | 0 | 0 | 90 | 70 |
| Corn | — | — | — | — | — | — | — | — | — | — | — | — | — | — |
| Crabgrass, Large | — | — | — | — | — | — | — | — | — | — | — | — | — | — |
| Foxtail, Giant | 60 | 70 | 90 | 100 | 50 | 0 | 0 | 90 | 80 | 10 | 10 | 0 | 90 | 60 |
| *Kochia* | 0 | 80 | 100 | 100 | 20 | 0 | 0 | 30 | 90 | 10 | 0 | 0 | 30 | 80 |
| Morningglory | — | — | — | — | — | — | — | — | — | — | — | — | — | — |
| Pigweed | 80 | 100 | 100 | 100 | 10 | 0 | 0 | 100 | 100 | 30 | 40 | 0 | 100 | 60 |
| Ragweed | 70 | 80 | 90 | 100 | 10 | 10 | 0 | 80 | 90 | 60 | 10 | 0 | 80 | 80 |
| Ryegrass, Italian | 50 | 100 | 100 | 100 | 70 | 0 | 0 | 50 | 90 | 60 | 30 | 10 | 90 | 80 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | |
|---|---|---|---|---|---|---|---|---|---|---|---|---|---|
| 500 g ai/ha | 53 | 54 | 55 | 56 | 57 | 58 | 59 | 61 | 62 | 63 | 64 | 65 | 66 | 67 |
| | Preemergence | | | | | | | | | | | | |
| Barnyardgrass | 20 | 90 | 90 | 50 | 100 | 20 | 100 | 0 | 90 | 90 | 0 | 90 | 70 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 50 | 100 | 100 | 70 | 100 | 0 | 100 | 0 | 90 | 70 | 0 | 90 | 90 | 100 |
| *Kochia* | 70 | 100 | 100 | 90 | 100 | 80 | 90 | 0 | 90 | 100 | 0 | 90 | 70 | 20 |
| Morningglory | — | — | — | — | — | — | — | — | — | — | — | — | — | — |
| Pigweed | 70 | 100 | 100 | 100 | 100 | 20 | 100 | 0 | 100 | 100 | 0 | 100 | 100 | 100 |
| Ragweed | 50 | 100 | 100 | 90 | 100 | 80 | 100 | 0 | 90 | 90 | 0 | 80 | 90 | 80 |
| Ryegrass, Italian | 50 | 100 | 100 | 100 | 100 | 100 | 100 | 0 | 100 | 100 | 0 | 100 | 100 | 100 |
| Velvetleaf | — | — | — | — | — | — | — | — | — | — | — | — | — | — |
| Wheat | — | — | — | — | — | — | — | — | — | — | — | — | — | — |

TABLE A-continued

| | Compounds | | | | | | | | | | | | | |
|---|---|---|---|---|---|---|---|---|---|---|---|---|---|---|
| 500 g ai/ha | 68 | 69 | 70 | 71 | 72 | 73 | 74 | 75 | 76 | 77 | 78 | 79 | 80 | 81 |
| | Preemergence | | | | | | | | | | | | | |
| Barnyardgrass | 40 | 60 | 30 | 20 | 100 | 100 | 0 | 80 | 30 | 10 | 70 | 70 | 90 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 50 | 50 | 30 | 50 | 100 | 100 | 0 | 90 | 20 | 10 | 60 | 90 | 90 | 100 |
| Kochia | 0 | 90 | 40 | 20 | 100 | 100 | 0 | 90 | 0 | 0 | 100 | 90 | 90 | 100 |
| Morningglory | — | — | — | — | — | — | — | — | — | — | — | — | — | — |
| Pigweed | 0 | 100 | 100 | 100 | 100 | 100 | 50 | 100 | 50 | 0 | 100 | 100 | 100 | 100 |
| Ragweed | 20 | 80 | 80 | 20 | 90 | 90 | 0 | 90 | 50 | 0 | 90 | 80 | 90 | 100 |
| Ryegrass, Italian | 0 | 100 | 90 | 70 | 100 | 100 | 0 | 100 | 70 | 40 | 100 | 100 | 100 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 500 g ai/ha | 82 | 83 | 84 | 85 | 86 | 87 | 88 | 89 | 90 | 91 | 92 | 93 | 94 | 95 |
| | Preemergence | | | | | | | | | | | | | |
| Barnyardgrass | 70 | 100 | 60 | 100 | 40 | 80 | 100 | 60 | 100 | 100 | 0 | 0 | 40 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 100 | 90 | 100 | 70 | 100 | 100 | 80 | 100 | 100 | 0 | 0 | 50 | 0 |
| Kochia | 90 | 100 | 80 | 30 | 40 | 90 | 100 | 90 | 100 | 100 | 20 | 30 | 70 | 10 |
| Morningglory | — | — | — | — | — | — | — | — | — | — | — | — | — | — |
| Pigweed | 100 | 100 | 90 | 100 | 100 | 100 | 100 | 100 | 100 | 100 | 0 | 90 | 90 | 20 |
| Ragweed | 80 | 100 | 90 | 90 | 90 | 80 | 90 | 90 | 100 | 90 | 0 | 20 | 80 | 20 |
| Ryegrass, Italian | 90 | 100 | 90 | 100 | 40 | 100 | 100 | 90 | 100 | 90 | 0 | 40 | 50 | 60 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 500 g ai/ha | 96 | 97 | 98 | 99 | 100 | 101 | 102 | 103 | 104 | 105 | 106 | 107 | 108 | 109 |
| | Preemergence | | | | | | | | | | | | | |
| Barnyardgrass | 0 | 100 | 100 | 90 | 20 | 30 | 60 | 90 | 100 | 100 | 100 | 100 | 100 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 100 | 100 | 80 | 90 | 60 | 90 | 100 | 100 | 100 | 100 | 100 | 100 | 100 |
| Kochia | 30 | 100 | 40 | 70 | 70 | 40 | 30 | 40 | 100 | 100 | 90 | 90 | 100 | 100 |
| Morningglory | — | — | — | — | — | — | — | — | — | — | — | — | — | — |
| Pigweed | 90 | 100 | 100 | 100 | 100 | 90 | 100 | 100 | 100 | 100 | 100 | 100 | 100 | 100 |
| Ragweed | 0 | 100 | 90 | 80 | 80 | 40 | 90 | 100 | 100 | 100 | 100 | 100 | 100 | 100 |
| Ryegrass, Italian | 40 | 100 | 90 | 100 | 100 | 100 | 60 | 100 | 100 | 100 | 100 | 100 | 100 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 500 g ai/ha | 110 | 111 | 112 | 113 | 114 | 115 | 116 | 117 | 118 | 119 | 120 | 121 | 122 | 123 |
| | Preemergence | | | | | | | | | | | | | |
| Barnyardgrass | 20 | 100 | 20 | 100 | 80 | 50 | 100 | 50 | 30 | 0 | 30 | 50 | 30 | 80 |
| Corn | — | — | — | — | — | — | — | — | — | — | — | — | — | — |
| Crabgrass, Large | — | — | — | — | — | — | — | — | — | — | — | — | — | — |
| Foxtail, Giant | 40 | 100 | 60 | 100 | 90 | 50 | 100 | 30 | 20 | 0 | 20 | 80 | 70 | 70 |
| Kochia | 100 | 100 | 80 | 100 | 100 | 90 | 100 | 0 | 0 | 0 | 0 | 30 | 70 | 100 |
| Morningglory | — | — | — | — | — | — | — | — | — | — | — | — | — | — |
| Pigweed | 100 | 100 | 100 | 100 | 100 | 100 | 90 | 30 | 10 | 0 | 70 | 100 | 100 | 100 |
| Ragweed | 40 | 90 | 80 | 90 | 90 | 90 | 90 | 0 | 0 | 0 | 30 | 80 | 80 | 70 |
| Ryegrass, Italian | 80 | 100 | 100 | 100 | 90 | 100 | 100 | 0 | 0 | 0 | 30 | 90 | 90 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 500 g ai/ha | 124 | 125 | 126 | 127 | 128 | 129 | 130 | 131 | 132 | 133 | 134 | 135 | 136 | 137 |
| | Preemergence | | | | | | | | | | | | | |
| Barnyardgrass | 0 | 90 | 80 | 40 | 90 | 100 | 100 | 40 | 70 | 50 | 90 | 0 | 80 | 100 |
| Corn | — | — | — | — | — | — | — | — | — | — | — | — | — | — |

TABLE A-continued

| | | | | | | | | | | | | | | |
|---|---|---|---|---|---|---|---|---|---|---|---|---|---|---|
| Crabgrass, Large | — | — | — | — | — | — | — | — | — | — | — | — | — | — |
| Foxtail, Giant | 0 | 100 | 70 | 60 | 90 | 100 | 90 | 90 | 90 | 70 | 90 | 30 | 100 | 100 |
| *Kochia* | 20 | 90 | 90 | 90 | 0 | 90 | 100 | 20 | 90 | 100 | 100 | 0 | 90 | 100 |
| Morningglory | — | — | — | — | — | — | — | — | — | — | — | — | — | — |
| Pigweed | 0 | 100 | 100 | 100 | 100 | 100 | 100 | 100 | 100 | 100 | 100 | 70 | 100 | 100 |
| Ragweed | 0 | 90 | 80 | 70 | 70 | 90 | 90 | 60 | 90 | 100 | 90 | 60 | 90 | 100 |
| Ryegrass, Italian | 30 | 100 | 100 | 90 | 30 | 100 | 100 | 90 | 90 | 100 | 100 | 60 | 100 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 500 g ai/ha | 138 | 139 | 140 | 141 | 142 | 143 | 144 | 145 | 146 | 147 | 148 | 149 | 150 | 151 |
| | Preemergence | | | | | | | | | | | | | |
| Barnyardgrass | 100 | 100 | 70 | 90 | 70 | 80 | 100 | 90 | 50 | 60 | 60 | 70 | 10 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 100 | 80 | 70 | 60 | 70 | 100 | 90 | 50 | 40 | 50 | 90 | 30 | 100 |
| *Kochia* | 100 | 100 | 30 | 60 | 0 | 70 | 100 | 100 | 70 | 80 | 90 | 90 | 20 | 100 |
| Morningglory | — | — | — | — | — | — | — | — | — | — | — | — | — | — |
| Pigweed | 100 | 100 | 100 | 60 | 50 | 100 | 100 | 100 | 100 | 100 | 100 | 100 | 100 | 100 |
| Ragweed | 100 | 100 | 90 | 60 | 40 | 90 | 100 | 100 | 80 | 90 | 80 | 90 | 30 | 90 |
| Ryegrass, Italian | 100 | 100 | 90 | 80 | 80 | 100 | 100 | 100 | 80 | 100 | 100 | 90 | 70 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 500 g ai/ha | 152 | 153 | 154 | 155 | 156 | 157 | 158 | 159 | 160 | 161 | 162 | 163 | 164 | 165 |
| | Preemergence | | | | | | | | | | | | | |
| Barnyardgrass | 40 | 100 | 100 | 80 | 100 | 90 | 60 | 80 | 10 | 60 | 20 | 0 | 20 | 30 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 100 | 100 | 90 | 90 | 80 | 40 | 80 | 30 | 70 | 40 | 0 | 40 | 40 |
| *Kochia* | 70 | 90 | 20 | 90 | 100 | 100 | 40 | 100 | 20 | 30 | 90 | 0 | 100 | 100 |
| Morningglory | — | — | — | — | — | — | — | — | — | — | — | — | — | — |
| Pigweed | 90 | 100 | 100 | 100 | 100 | 100 | 100 | 100 | 100 | 100 | 90 | 70 | 100 | 90 |
| Ragweed | 100 | 90 | 90 | 90 | 90 | 90 | 80 | 80 | 80 | 90 | 90 | 0 | 90 | 90 |
| Ryegrass, Italian | 100 | 100 | 100 | 90 | 100 | 100 | 80 | 100 | 80 | 100 | 100 | 50 | 100 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 500 g ai/ha | 166 | 167 | 168 | 169 | 170 | 171 | 172 | 173 | 174 | 175 | 176 | 177 | 185 | 186 |
| | Preemergence | | | | | | | | | | | | | |
| Barnyardgrass | 10 | 20 | 20 | 30 | 0 | 100 | 50 | 0 | 0 | 0 | 10 | 0 | 50 | 80 |
| Corn | — | — | — | — | — | — | — | — | — | — | — | — | — | — |
| Crabgrass, Large | — | — | — | — | — | — | — | — | — | — | — | — | — | — |
| Foxtail, Giant | 30 | 20 | 40 | 30 | 0 | 100 | 90 | 0 | 10 | 0 | 10 | 0 | 30 | 70 |
| *Kochia* | 90 | 100 | 0 | 90 | 0 | 100 | 0 | 0 | 0 | 20 | 20 | 0 | 10 | 100 |
| Morningglory | — | — | — | — | — | — | — | — | — | — | — | — | — | — |
| Pigweed | 90 | 100 | 0 | 100 | 100 | 100 | 0 | 0 | 20 | 60 | 90 | 0 | 60 | 100 |
| Ragweed | 90 | 80 | 0 | 20 | 20 | 90 | 0 | 0 | 0 | 20 | 70 | 0 | 40 | 80 |
| Ryegrass, Italian | 90 | 100 | 40 | 100 | 40 | 100 | 20 | 0 | 0 | 20 | 90 | 0 | 40 | 100 |
| Velvetleaf | — | — | — | — | — | — | — | — | — | — | — | — | — | — |
| Wheat | — | — | — | — | — | — | — | — | — | — | — | — | — | — |

| | Compounds | |
|---|---|---|
| 500 g ai/ha | 187 | 188 |
| | Preemergence | |
| Barnyardgrass | 90 | 30 |
| Corn | — | — |
| Crabgrass, Large | — | — |
| Foxtail, Giant | 70 | 90 |
| *Kochia* | 100 | 20 |
| Morningglory | — | — |
| Pigweed | 100 | 90 |
| Ragweed | 80 | 30 |
| Ryegrass, Italian | 100 | 80 |
| Velvetleaf | — | — |

TABLE A-continued

|  |  |  |  |  |  |  |  |  |  |  |  |  |  |
|---|---|---|---|---|---|---|---|---|---|---|---|---|---|
| Wheat |  |  | — |  |  | — |  |  |  |  |  |  |  |
| Barnyardgrass |  |  | 70 |  |  | 10 |  |  |  |  |  |  |  |
| Corn |  |  | — |  |  | — |  |  |  |  |  |  |  |
| Crabgrass, Large |  |  | — |  |  | — |  |  |  |  |  |  |  |
| Foxtail, Giant |  |  | 20 |  |  | 10 |  |  |  |  |  |  |  |
| Kochia |  |  | 60 |  |  | 20 |  |  |  |  |  |  |  |
| Morningglory |  |  | — |  |  | — |  |  |  |  |  |  |  |
| Pigweed |  |  | 90 |  |  | 60 |  |  |  |  |  |  |  |
| Ragweed |  |  | 70 |  |  | 10 |  |  |  |  |  |  |  |
| Ryegrass, Italian |  |  | 100 |  |  | 20 |  |  |  |  |  |  |  |
| Velvetleaf |  |  | — |  |  | — |  |  |  |  |  |  |  |
| Wheat |  |  | — |  |  | — |  |  |  |  |  |  |  |

| | Compounds | | | | | | | | | | | | |
|---|---|---|---|---|---|---|---|---|---|---|---|---|---|
| 125 g ai/ha | 2 | 8 | 9 | 12 | 14 | 15 | 16 | 17 | 18 | 19 | 20 | 21 | 22 | 23 |
| | Preemergence | | | | | | | | | | | | |
| Barnyardgrass | 50 | 0 | 50 | 20 | 0 | 20 | 10 | 0 | 0 | 30 | 30 | 90 | 10 | 90 |
| Corn | 0 | 0 | 0 | — | — | — | — | — | — | — | — | — | — | — |
| Crabgrass, Large | 90 | 10 | 20 | — | — | — | — | — | — | — | — | — | — | — |
| Foxtail, Giant | 100 | 40 | 70 | 20 | 0 | 10 | 0 | 0 | 0 | 0 | 40 | 90 | 70 | 90 |
| Kochia | — | — | — | 0 | 10 | 0 | 0 | 0 | 0 | 0 | 80 | 30 | 70 | 80 |
| Morningglory | 80 | 0 | 0 | — | — | — | — | — | — | — | — | — | — | — |
| Pigweed | 100 | 70 | 0 | 10 | 70 | 0 | 0 | 0 | 0 | 0 | 80 | 100 | 100 | 100 |
| Ragweed | — | — | — | 0 | 0 | 0 | 0 | 0 | 0 | 0 | 30 | 100 | 90 | 90 |
| Ryegrass, Italian | — | — | — | 20 | 30 | 50 | 30 | 10 | 0 | 0 | 90 | 100 | 100 | 80 |
| Velvetleaf | 80 | 0 | 0 | — | — | — | — | — | — | — | — | — | — | — |
| Wheat | 0 | 0 | 0 | — | — | — | — | — | — | — | — | — | — | — |

| | Compounds | | | | | | | | | | | | |
|---|---|---|---|---|---|---|---|---|---|---|---|---|---|
| 125 g ai/ha | 24 | 25 | 26 | 27 | 28 | 29 | 30 | 31 | 33 | 34 | 35 | 36 | 37 | 38 |
| | Preemergence | | | | | | | | | | | | |
| Barnyardgrass | 30 | 30 | 0 | 90 | 90 | 70 | 0 | 0 | 20 | 20 | 60 | 0 | 30 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 60 | 90 | 30 | 90 | 100 | 80 | 0 | 0 | 50 | 40 | 90 | 80 | 70 | 0 |
| Kochia | 30 | 90 | 30 | 40 | 50 | 60 | 0 | 0 | 30 | 30 | 40 | 10 | 30 | 40 |
| Morningglory | — | — | — | — | — | — | — | — | — | — | — | — | — | — |
| Pigweed | 70 | 100 | 80 | 100 | 100 | 100 | 80 | 0 | 20 | 90 | 60 | 100 | 100 | 0 |
| Ragweed | 0 | 90 | 20 | 90 | 90 | 90 | 0 | 0 | 80 | 80 | 70 | 80 | 80 | 0 |
| Ryegrass, Italian | 80 | 100 | 30 | 100 | 100 | 80 | 30 | 0 | 20 | 100 | 90 | 70 | 90 | 40 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | |
|---|---|---|---|---|---|---|---|---|---|---|---|---|---|
| 125 g ai/ha | 39 | 40 | 41 | 42 | 43 | 44 | 45 | 46 | 47 | 48 | 49 | 50 | 51 | 52 |
| | Preemergence | | | | | | | | | | | | |
| Barnyardgrass | 0 | 10 | 20 | 80 | 0 | 0 | 0 | 20 | 70 | 0 | 0 | 0 | 30 | 50 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 40 | 70 | 80 | 0 | 0 | 0 | 50 | 70 | 0 | 0 | 0 | 50 | 40 |
| Kochia | 0 | 50 | 90 | 80 | 50 | 0 | 0 | 30 | 10 | 0 | 0 | 0 | 0 | 0 |
| Morningglory | — | — | — | — | — | — | — | — | — | — | — | — | — | — |
| Pigweed | 80 | 90 | 100 | 100 | 0 | 0 | 0 | 30 | 70 | 30 | 0 | 0 | 70 | 10 |
| Ragweed | 10 | 30 | 80 | 90 | 0 | 0 | 0 | 50 | 80 | 10 | 0 | 0 | 30 | 20 |
| Ryegrass, Italian | 40 | 60 | 100 | 100 | 10 | 0 | 0 | 30 | 60 | 20 | 0 | 0 | 50 | 80 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | |
|---|---|---|---|---|---|---|---|---|---|---|---|---|---|
| 125 g ai/ha | 53 | 54 | 55 | 56 | 57 | 58 | 59 | 61 | 62 | 63 | 64 | 65 | 66 | 67 |
| | Preemergence | | | | | | | | | | | | |
| Barnyardgrass | 0 | 40 | 90 | 10 | 100 | 0 | 80 | 0 | 50 | 80 | 0 | 60 | 20 | 30 |
| Corn | — | — | — | — | — | — | — | — | — | — | — | — | — | — |
| Crabgrass, Large | — | — | — | — | — | — | — | — | — | — | — | — | — | — |
| Foxtail, Giant | 50 | 60 | 80 | 30 | 100 | 0 | 90 | 0 | 50 | 40 | 0 | 60 | 60 | 80 |
| Kochia | 50 | 50 | 70 | 40 | 100 | 20 | 90 | 0 | 90 | 100 | 0 | 60 | 60 | 20 |
| Morningglory | — | — | — | — | — | — | — | — | — | — | — | — | — | — |
| Pigweed | 50 | 100 | 70 | 60 | 100 | 0 | 100 | 0 | 100 | 100 | 0 | 100 | 100 | 90 |

TABLE A-continued

| | | | | | | | | | | | | | | |
|---|---|---|---|---|---|---|---|---|---|---|---|---|---|---|
| Ragweed | 0 | 90 | 90 | 80 | 90 | 70 | 90 | 0 | 70 | 80 | 0 | 70 | 80 | 80 |
| Ryegrass, Italian | 10 | 30 | 100 | 100 | 90 | 70 | 90 | 0 | 100 | 100 | 0 | 90 | 90 | 90 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 68 | 69 | 70 | 71 | 72 | 73 | 74 | 75 | 76 | 77 | 78 | 79 | 80 | 81 |
| | Preemergence | | | | | | | | | | | | | |
| Barnyardgrass | 10 | 10 | 0 | 0 | 10 | 40 | 0 | 40 | 0 | 0 | 0 | 50 | 70 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 10 | 10 | 0 | 0 | 70 | 90 | 0 | 50 | 0 | 0 | 20 | 90 | 80 | 100 |
| Kochia | 0 | 20 | 10 | 0 | 50 | 50 | 0 | 80 | 0 | 0 | 20 | 70 | 90 | 30 |
| Morningglory | — | — | — | — | — | — | — | — | — | — | — | — | — | — |
| Pigweed | 0 | 90 | 60 | 30 | 100 | 100 | 30 | 100 | 20 | 0 | 60 | 100 | 90 | 100 |
| Ragweed | 0 | 80 | 70 | 0 | 90 | 90 | 0 | 70 | 0 | 0 | 60 | 80 | 80 | 90 |
| Ryegrass, Italian | 0 | 70 | 60 | 0 | 100 | 100 | 0 | 100 | 50 | 10 | 100 | 80 | 90 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | |
|---|---|---|---|---|---|---|---|---|---|---|---|---|---|
| 125 g ai/ha | 82 | 83 | 84 | 85 | 86 | 87 | 88 | 89 | 90 | 91 | 92 | 93 | 94 | 95 |
| | Preemergence | | | | | | | | | | | | |
| Barnyardgrass | 40 | 70 | 20 | 70 | 0 | 50 | 90 | 50 | 60 | 90 | 0 | 0 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 70 | 100 | 70 | 100 | 20 | 80 | 100 | 50 | 50 | 80 | 0 | 0 | 20 | 0 |
| Kochia | 70 | 30 | 70 | 0 | 0 | 80 | 60 | 70 | 70 | 60 | 0 | 0 | 30 | 0 |
| Morningglory | — | — | — | — | — | — | — | — | — | — | — | — | — | — |
| Pigweed | 100 | 100 | 90 | 100 | 80 | 100 | 100 | 100 | 100 | 100 | 0 | 20 | 70 | 0 |
| Ragweed | 80 | 90 | 80 | 90 | 40 | 70 | 90 | 80 | 90 | 80 | 0 | 0 | 50 | 0 |
| Ryegrass, Italian | 80 | 100 | 70 | 100 | 0 | 90 | 100 | 80 | 100 | 90 | 0 | 20 | 20 | 10 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | |
|---|---|---|---|---|---|---|---|---|---|---|---|---|---|
| 125 g ai/ha | 96 | 97 | 98 | 99 | 100 | 101 | 102 | 103 | 104 | 105 | 106 | 107 | 108 | 109 |
| | Preemergence | | | | | | | | | | | | |
| Barnyardgrass | 0 | 20 | 40 | 60 | 20 | 0 | 40 | 40 | 80 | 20 | 80 | 70 | 20 | 20 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 60 | 90 | 50 | 70 | 30 | 70 | 80 | 70 | 90 | 100 | 70 | 90 | 90 |
| Kochia | 0 | 80 | 20 | 20 | 30 | 0 | 10 | 20 | 100 | 100 | 20 | 20 | 90 | 100 |
| Morningglory | — | — | — | — | — | — | — | — | — | — | — | — | — | — |
| Pigweed | 30 | 100 | 100 | 100 | 100 | 90 | 80 | 100 | 100 | 100 | 100 | 100 | 100 | 100 |
| Ragweed | 0 | 90 | 60 | 80 | 40 | 40 | 90 | 90 | 90 | 100 | 90 | 90 | 90 | 100 |
| Ryegrass, Italian | 0 | 100 | 20 | 100 | 90 | 60 | 60 | 90 | 100 | 100 | 100 | 80 | 100 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | |
|---|---|---|---|---|---|---|---|---|---|---|---|---|---|
| 125 g ai/ha | 110 | 111 | 112 | 113 | 114 | 115 | 116 | 117 | 118 | 119 | 120 | 121 | 122 | 123 |
| | Preemergence | | | | | | | | | | | | |
| Barnyardgrass | 0 | 70 | 10 | 70 | 30 | 10 | 70 | 0 | 0 | 0 | 0 | 20 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 10 | 80 | 50 | 70 | 40 | 30 | 80 | 0 | 0 | 0 | 0 | 80 | 30 | 70 |
| Kochia | 0 | 60 | 20 | 90 | 30 | 30 | 30 | 0 | 0 | 0 | 0 | 0 | 30 | 50 |
| Morningglory | — | — | — | — | — | — | — | — | — | — | — | — | — | — |
| Pigweed | 90 | 90 | 90 | 100 | 100 | 70 | 90 | 0 | 0 | 0 | 0 | 100 | 100 | 100 |
| Ragweed | 30 | 80 | 40 | 70 | 80 | 40 | 90 | 0 | 0 | 0 | 0 | 60 | — | 60 |
| Ryegrass, Italian | 20 | 90 | 90 | 100 | 80 | 100 | 80 | 0 | 0 | 0 | 30 | 80 | 70 | 90 |
| Velvetleaf | — | — | — | — | — | — | — | — | — | — | — | — | — | — |
| Wheat | — | — | — | — | — | — | — | — | — | — | — | — | — | — |

TABLE A-continued

| | Compounds | | | | | | | | | | | | | |
|---|---|---|---|---|---|---|---|---|---|---|---|---|---|---|
| 125 g ai/ha | 124 | 125 | 126 | 127 | 128 | 129 | 130 | 131 | 132 | 133 | 134 | 135 | 136 | 137 |
| | Preemergence | | | | | | | | | | | | | |
| Barnyardgrass | 0 | 70 | 40 | 10 | 50 | 90 | 30 | 0 | 0 | 20 | 20 | 0 | 10 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 90 | 10 | 50 | 80 | 90 | 30 | 80 | 70 | 40 | 50 | 20 | 80 | 90 |
| Kochia | 0 | 60 | 50 | 0 | 0 | 70 | 60 | 0 | 60 | 40 | 70 | 0 | 60 | 30 |
| Morningglory | — | — | — | — | — | — | — | — | — | — | — | — | — | — |
| Pigweed | 0 | 100 | 100 | 70 | 90 | 100 | 90 | 80 | 90 | 80 | 100 | 30 | 100 | 100 |
| Ragweed | 0 | 80 | 70 | 30 | 70 | 90 | 60 | 40 | 80 | 90 | 80 | 30 | 80 | 90 |
| Ryegrass, Italian | 0 | 100 | 90 | 60 | 10 | 100 | 100 | 90 | 90 | 100 | 100 | 20 | 90 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 138 | 139 | 140 | 141 | 142 | 143 | 144 | 145 | 146 | 147 | 148 | 149 | 150 | 151 |
| | Preemergence | | | | | | | | | | | | | |
| Barnyardgrass | 10 | 20 | 50 | 50 | 10 | 20 | 90 | 20 | 0 | 30 | 10 | 0 | 0 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 60 | 50 | 30 | 10 | 20 | 100 | 30 | 0 | 10 | 20 | 30 | 0 | 90 |
| Kochia | 40 | 100 | 0 | 0 | 0 | 10 | 100 | 90 | 20 | 50 | 30 | 40 | 0 | 30 |
| Morningglory | — | — | — | — | — | — | — | — | — | — | — | — | — | — |
| Pigweed | 100 | 100 | 50 | 40 | 60 | 80 | 100 | 90 | 100 | 90 | 100 | 100 | 80 | 100 |
| Ragweed | 90 | 90 | 70 | 60 | 20 | 10 | 90 | 80 | 80 | 80 | 80 | 80 | 0 | 90 |
| Ryegrass, Italian | 100 | 100 | 70 | 70 | 50 | 70 | 100 | 100 | 80 | 70 | 80 | 90 | 20 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 152 | 153 | 154 | 155 | 156 | 157 | 158 | 159 | 160 | 161 | 162 | 163 | 164 | 165 |
| | Preemergence | | | | | | | | | | | | | |
| Barnyardgrass | 40 | 100 | 70 | 50 | 70 | 70 | 10 | 50 | 10 | 10 | 10 | 0 | 10 | 10 |
| Corn | — | — | — | — | — | — | — | — | — | — | — | — | — | — |
| Crabgrass, Large | — | — | — | — | — | — | — | — | — | — | — | — | — | — |
| Foxtail, Giant | 40 | 100 | 90 | 60 | 80 | 50 | 10 | 60 | 10 | 10 | 10 | 0 | 10 | 10 |
| Kochia | 30 | 80 | 0 | 20 | 50 | 100 | 30 | 100 | 20 | 0 | 60 | 0 | 60 | 60 |
| Morningglory | — | — | — | — | — | — | — | — | — | — | — | — | — | — |
| Pigweed | 90 | 100 | 100 | 100 | 100 | 100 | 10 | 100 | 50 | 100 | 80 | 30 | 80 | 100 |
| Ragweed | 80 | 80 | 80 | 90 | 90 | 60 | 50 | 80 | 30 | 90 | 50 | 0 | 50 | 50 |
| Ryegrass, Italian | 90 | 100 | 90 | 70 | 90 | 100 | 80 | 100 | 20 | 100 | 40 | 10 | 60 | 40 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 166 | 167 | 168 | 169 | 170 | 171 | 172 | 173 | 174 | 175 | 176 | 177 | 185 | 186 |
| | Preemergence | | | | | | | | | | | | | |
| Barnyardgrass | 10 | 10 | 0 | 0 | 0 | 70 | 20 | 0 | 0 | 0 | 0 | 0 | 0 | 40 |
| Corn | — | — | — | — | — | — | — | — | — | — | — | — | — | — |
| Crabgrass, Large | — | — | — | — | — | — | — | — | — | — | — | — | — | — |
| Foxtail, Giant | 10 | 10 | 0 | 0 | 0 | 50 | 60 | 0 | 0 | 0 | 0 | 0 | 0 | 50 |
| Kochia | 30 | 60 | 0 | 20 | 0 | 100 | 0 | 0 | 0 | 0 | 0 | 0 | 0 | 80 |
| Morningglory | — | — | — | — | — | — | — | — | — | — | — | — | — | — |
| Pigweed | 80 | 100 | 0 | 50 | 30 | 90 | 0 | 0 | 0 | 0 | 0 | 0 | 20 | 100 |
| Ragweed | 70 | 70 | 0 | 0 | 0 | 70 | 0 | 0 | 0 | 20 | 0 | 0 | 0 | 70 |
| Ryegrass, Italian | 40 | 80 | 0 | 80 | 0 | 100 | 0 | 0 | 0 | 20 | 0 | 0 | 0 | 100 |
| Velvetleaf | — | — | — | — | — | — | — | — | — | — | — | — | — | — |
| Wheat | — | — | — | — | — | — | — | — | — | — | — | — | — | — |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

TABLE B

| 250 g ai/ha | Compounds | | | | | | | | | | | | | |
|---|---|---|---|---|---|---|---|---|---|---|---|---|---|---|
| Flood | 1 | 2 | 3 | 4 | 5 | 7 | 8 | 9 | 10 | 11 | 12 | 13 | 14 | 15 |
| Barnyardgrass | 0 | 30 | 0 | 0 | 0 | 20 | 30 | 0 | 0 | 0 | 0 | 0 | 0 | 0 |
| Ducksalad | 20 | 80 | 20 | 0 | 45 | 60 | 20 | 0 | 30 | 0 | 30 | 0 | 0 | 20 |
| Rice | 0 | 35 | 0 | 0 | 0 | 0 | 0 | 0 | 0 | 0 | 0 | 0 | 0 | 0 |
| Sedge, Umbrella | 0 | 85 | 0 | 0 | 75 | 60 | 70 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 16 | 17 | 18 | 19 | 20 | 21 | 22 | 23 | 24 | 25 | 26 | 27 | 28 | 29 |
| Barnyardgrass | 0 | 0 | 0 | 0 | 0 | 70 | 0 | 0 | 0 | 30 | 0 | 30 | 60 | 0 |
| Ducksalad | 30 | 0 | 30 | 0 | 50 | 0 | 0 | 75 | 0 | 20 | 0 | 30 | 80 | 55 |
| Rice | 0 | 0 | 0 | 0 | 0 | 55 | 0 | 0 | 0 | 0 | 0 | 40 | 40 | 0 |
| Sedge, Umbrella | 0 | 0 | 0 | 0 | 50 | 65 | 0 | 95 | 0 | 60 | 0 | 80 | 95 | 60 |

| 250 g ai/ha | Compounds | | | | | | | | | | | | | |
|---|---|---|---|---|---|---|---|---|---|---|---|---|---|---|
| Flood | 31 | 32 | 33 | 34 | 35 | 36 | 41 | 42 | 43 | 44 | 45 | 46 | 47 | 48 |
| Barnyardgrass | 0 | 0 | 0 | 0 | 0 | 0 | 30 | 0 | 0 | 0 | 0 | 0 | 0 | 0 |
| Ducksalad | 0 | 0 | 0 | 0 | 75 | 30 | 40 | 0 | 0 | 0 | 0 | 0 | 0 | 0 |
| Rice | 0 | 0 | 0 | 0 | 0 | 20 | 0 | 0 | 0 | 0 | 0 | 0 | 0 | 0 |
| Sedge, Umbrella | 0 | 0 | 0 | 0 | 65 | 70 | 40 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 49 | 50 | 51 | 53 | 54 | 55 | 56 | 57 | 58 | 59 | 60 | 62 | 63 | 65 |
| Barnyardgrass | 0 | 0 | 0 | 0 | 0 | 0 | 0 | 0 | 0 | 0 | 35 | 20 | 0 | 0 |
| Ducksalad | 0 | 0 | 0 | 0 | 0 | 0 | 0 | 0 | 0 | 0 | 20 | 20 | 30 | 0 |
| Rice | 0 | 0 | 0 | 0 | 0 | 0 | 0 | 0 | 0 | 0 | 35 | 0 | 0 | 0 |
| Sedge, Umbrella | 0 | 0 | 0 | 0 | 0 | 0 | 0 | 0 | 0 | 0 | 30 | 75 | 65 | 0 |

| 250 g ai/ha | Compounds | | | | | | | | | | | | | |
|---|---|---|---|---|---|---|---|---|---|---|---|---|---|---|
| Flood | 66 | 67 | 68 | 72 | 73 | 74 | 75 | 79 | 81 | 82 | 83 | 84 | 85 | 86 |
| Barnyardgrass | 0 | 0 | 0 | 0 | 0 | 0 | 0 | 0 | 60 | 0 | 60 | 0 | 50 | 0 |
| Ducksalad | 0 | 0 | 0 | 0 | 0 | 0 | 0 | 0 | 70 | 0 | 70 | 0 | 50 | 20 |
| Rice | 0 | 0 | 0 | 0 | 0 | 0 | 15 | 0 | 60 | 0 | 30 | 0 | 50 | 15 |
| Sedge, Umbrella | 0 | 0 | 30 | 0 | 0 | 0 | 0 | 0 | 80 | 0 | 90 | 0 | 80 | 60 |

| 250 g ai/ha | Compounds | | | | | | | | | | | | | |
|---|---|---|---|---|---|---|---|---|---|---|---|---|---|---|
| Flood | 87 | 88 | 89 | 91 | 92 | 93 | 94 | 98 | 99 | 100 | 101 | 102 | 103 | 110 |
| Barnyardgrass | 0 | 50 | 0 | 0 | 0 | 0 | 0 | 45 | 0 | 0 | 0 | 0 | 30 | 0 |
| Ducksalad | 0 | 50 | 65 | 0 | 0 | 0 | 0 | 75 | 0 | 0 | 0 | 0 | 0 | 0 |
| Rice | 0 | 40 | 0 | 0 | 0 | 0 | 0 | 30 | 0 | 0 | 0 | 0 | 0 | 0 |
| Sedge, Umbrella | 0 | 80 | 40 | 40 | 40 | 50 | 0 | 60 | 0 | 0 | 0 | 50 | 50 | 0 |

| 250 g ai/ha | Compounds | | | | | | | | | | | | | |
|---|---|---|---|---|---|---|---|---|---|---|---|---|---|---|
| Flood | 111 | 112 | 113 | 114 | 115 | 116 | 117 | 118 | 119 | 121 | 122 | 123 | 124 | 125 |
| Barnyardgrass | 0 | 0 | 0 | 0 | 0 | 0 | 0 | 0 | 0 | 0 | 0 | 20 | 0 | 0 |
| Ducksalad | 75 | 0 | 0 | 50 | 0 | 50 | 0 | 0 | 0 | 0 | 0 | 30 | 0 | 80 |
| Rice | 0 | 0 | 0 | 0 | 0 | 0 | 0 | 0 | 0 | 0 | 0 | 15 | 0 | 0 |
| Sedge, Umbrella | 75 | 0 | 0 | 70 | 0 | 70 | 0 | 0 | 0 | 0 | 0 | 70 | 0 | 75 |

| 250 g ai/ha | Compounds | | | | | | | | | | | | | |
|---|---|---|---|---|---|---|---|---|---|---|---|---|---|---|
| Flood | 126 | 127 | 128 | 130 | 131 | 132 | 133 | 134 | 135 | 136 | 137 | 138 | 139 | 143 |
| Barnyardgrass | 0 | 0 | 0 | 0 | 0 | 0 | 0 | 0 | 0 | 0 | 25 | 0 | 0 | 0 |
| Ducksalad | 30 | 0 | 30 | 0 | 0 | 0 | 0 | 0 | 0 | 0 | 40 | 0 | 0 | 0 |

TABLE B-continued

| | | | | | | | | | | | | | | |
|---|---|---|---|---|---|---|---|---|---|---|---|---|---|---|
| Rice | 0 | 0 | 0 | 0 | 0 | 0 | 20 | 0 | 0 | 0 | 0 | 0 | 0 | 0 |
| Sedge, Umbrella | 0 | 0 | 0 | 0 | 0 | 0 | 0 | 0 | 0 | 0 | 65 | 0 | 0 | 0 |

| 250 g ai/ha | Compounds | | | | | | | | | | | | | |
|---|---|---|---|---|---|---|---|---|---|---|---|---|---|---|
| Flood | 144 | 145 | 146 | 147 | 148 | 149 | 150 | 151 | 152 | 153 | 154 | 155 | 156 | 157 |
| Barnyardgrass | 30 | 0 | 0 | 0 | 0 | 0 | 0 | 45 | 0 | 0 | 50 | 0 | 0 | 20 |
| Ducksalad | 40 | 0 | 0 | 0 | 0 | 0 | 0 | 40 | 0 | 0 | 60 | 50 | 60 | 0 |
| Rice | 30 | 0 | 0 | 0 | 0 | 0 | 0 | 20 | 0 | 0 | 50 | 20 | 0 | 0 |
| Sedge, Umbrella | 0 | 0 | 0 | 0 | 0 | 0 | 0 | 70 | 0 | 0 | 80 | 65 | 75 | 75 |

| 250 g ai/ha | Compounds | | | | | | | | | | | | | |
|---|---|---|---|---|---|---|---|---|---|---|---|---|---|---|
| Flood | 158 | 159 | 160 | 162 | 163 | 164 | 165 | 166 | 167 | 168 | 169 | 170 | 171 | 172 |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 40 | 0 | 0 | 0 | 0 |
| Rice | 20 | 0 | 0 | 0 | 0 | 0 | 0 | 0 | 0 | 0 | 0 | 0 | 0 | 0 |
| Sedge, Umbrella | 65 | 50 | 0 | 0 | 0 | 0 | 0 | 0 | 0 | 0 | 0 | 60 | 60 | 0 |

| 250 g ai/ha | Compounds | | | | | | | | | | | | | |
|---|---|---|---|---|---|---|---|---|---|---|---|---|---|---|
| Flood | 173 | 174 | 175 | 176 | 177 | 179 | 180 | 181 | 183 | 184 | 185 | 186 | 187 | 188 |
| Barnyardgrass | 0 | 0 | 0 | 0 | 0 | 0 | 0 | 0 | 0 | 0 | 0 | 15 | 0 | 0 |
| Ducksalad | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 20 | 0 |
| Sedge, Umbrella | 0 | 0 | 0 | 0 | 0 | 0 | 0 | 0 | 0 | 0 | 0 | 40 | 0 | 0 |

Test C

Seeds of plant species selected from blackgrass (*Alopecurus myosuroides*), ryegrass, Italian (Italian ryegrass, *Lolium multiflorum*), wheat (winter wheat, *Triticum aestivum*), galium (catchweed bedstraw, *Galium aparine*), corn (*Zea mays*), large crabgrass, large (large crabgrass, *Digitaria sanguinalis*), foxtail, giant (giant foxtail, *Setaria faberii*), johnsongrass (*Sorghum halepense*), lambsquarters (*Chenopodium album*), morningglory (*Ipomoea coccinea*), nutsedge, yellow (yellow nutsedge, *Cyperus esculentus*), pigweed (*Amaranthus retroflexus*), ragweed (common ragweed, *Ambrosia elatior*), soybean (*Glycine max*), barnyardgrass (*Echinochloa crus-galli*), oilseed rape (*Brassica napus*), waterhemp (common waterhemp, *Amaranthus rudis*), and velvetleaf (*Abutilon theophrasti*) were planted into a blend of loam soil and sand and treated preemergence with test chemicals formulated in a non-phytotoxic solvent mixture which included a surfactant.

At the same time, plants selected from these crop and weed species and also chickweed (common chickweed, *Stellaria media*), kochia (*Kochia scoparia*), and oat, wild (wild oat, *Avena fatua*), were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of test chemicals formulated in the same manner. Plants ranged in height from 2 to 18 cm (1- to 4-leaf stage) for postemergence treatments. Treated plants and controls were maintained in a greenhouse for 13 to 15 d, after which time all species were compared to controls and visually evaluated. Plant response ratings, summarized in Table C, are based on a scale of 0 to 100 where 0 is no effect and 100 is complete control. A dash (-) response means no test result.

TABLE C

| 250 g ai/ha Post-emergence | Compounds | | | | | | | | | | | | | |
|---|---|---|---|---|---|---|---|---|---|---|---|---|---|---|
| | 1 | 2 | 10 | 11 | 14 | 16 | 20 | 21 | 22 | 23 | 25 | 26 | 27 | 28 |
| Barnyardgrass | 5 | 20 | 98 | 15 | 60 | 90 | 45 | 90 | 15 | 85 | 25 | 35 | 50 | 40 |
| Blackgrass | 75 | 80 | 15 | 75 | 20 | 40 | 45 | 95 | 20 | 85 | 80 | 75 | 90 | 90 |
| Chickweed | 100 | 98 | 90 | 90 | 90 | 90 | 100 | 100 | 98 | 100 | 100 | 100 | 100 | 95 |
| Corn | 40 | 10 | 5 | 0 | 5 | 0 | 10 | 20 | 5 | 25 | 10 | 5 | 15 | 15 |
| Crabgrass, Large | 35 | 10 | 75 | 10 | 35 | 30 | 30 | 55 | 5 | 45 | 20 | 25 | 45 | 45 |
| Foxtail, Giant | 90 | 95 | 90 | 30 | 50 | 80 | 80 | 95 | 35 | 90 | 85 | 65 | 95 | 95 |
| *Galium* | 95 | 98 | 85 | 90 | 90 | 80 | 100 | 100 | 95 | 100 | 95 | 95 | 100 | 100 |
| Johnsongrass | 15 | 5 | 25 | 5 | 5 | 5 | 10 | 35 | 5 | 40 | 10 | 5 | 10 | 30 |
| *Kochia* | 100 | 75 | 95 | 100 | 90 | 25 | 100 | 100 | 95 | 100 | 100 | 100 | 90 | 100 |
| Lambsquarters | 100 | 100 | 98 | 90 | 90 | 20 | 100 | 98 | 90 | 98 | 98 | 98 | 98 | 100 |
| Morningglory | 100 | 100 | 100 | 98 | 100 | 40 | 100 | 100 | 100 | 100 | 100 | 100 | 100 | 100 |
| Nutsedge, Yellow | — | 98 | — | 45 | — | — | 95 | 90 | 65 | 85 | 90 | 25 | 95 | 90 |

TABLE C-continued

| | | | | | | | | | | | | | |
|---|---|---|---|---|---|---|---|---|---|---|---|---|---|
| Oat, Wild | 100 | 85 | 25 | 70 | 45 | 40 | 40 | 100 | 80 | 100 | 95 | 90 | 100 | 100 |
| Oilseed Rape | 40 | 75 | 0 | 0 | 0 | 0 | 25 | 100 | 75 | 10 | 5 | 5 | 70 | 70 |
| Pigweed | 100 | 98 | 95 | 95 | 90 | 50 | 100 | 98 | 98 | 98 | 98 | 95 | 90 | 90 |
| Ragweed | 95 | 98 | 98 | 95 | 98 | 30 | 100 | 95 | 100 | 98 | 95 | 90 | 90 | 90 |
| Ryegrass, Italian | 98 | 90 | 55 | 90 | 85 | 70 | 90 | 95 | 90 | 95 | 95 | 90 | 90 | 95 |
| Soybean | 5 | 5 | 0 | 0 | 5 | 0 | 0 | 20 | 0 | 15 | 10 | 10 | 0 | 5 |
| Velvetleaf | 100 | 100 | 70 | 80 | 40 | 35 | 100 | 90 | 80 | 90 | 98 | 70 | 95 | 90 |
| Waterhemp | 100 | 100 | 90 | 95 | 40 | 5 | 90 | 80 | 90 | 98 | 98 | 95 | 90 | 85 |
| Wheat | 15 | 5 | 0 | 5 | 5 | 0 | 0 | 35 | 0 | 30 | 5 | 5 | 5 | 5 |

| 250 g ai/ha Post- | Compounds | | | | | | | | | | | | | |
|---|---|---|---|---|---|---|---|---|---|---|---|---|---|---|
| emergence | 29 | 32 | 33 | 34 | 36 | 37 | 41 | 42 | 47 | 51 | 52 | 54 | 56 | 57 |
| Barnyardgrass | 40 | 90 | 80 | 35 | 40 | 90 | 60 | 40 | 90 | 20 | 10 | 20 | 10 | 98 |
| Blackgrass | 75 | 80 | 10 | 60 | 20 | 85 | 60 | 70 | 30 | 10 | 30 | 40 | 40 | 25 |
| Chickweed | 100 | 100 | 95 | 95 | 95 | 95 | 100 | 100 | 98 | 95 | 100 | 100 | 70 | 100 |
| Corn | 20 | 40 | 20 | 5 | 5 | 30 | 20 | 5 | 5 | 0 | 0 | 10 | 0 | 10 |
| Crabgrass, Large | 40 | 70 | 25 | 25 | 35 | 35 | 35 | 20 | 35 | 10 | 10 | 55 | 20 | 35 |
| Foxtail, Giant | 80 | 90 | 70 | 35 | 80 | 85 | 65 | 80 | 85 | 35 | 35 | 90 | 50 | 95 |
| *Galium* | 100 | 100 | 95 | 95 | 95 | 95 | 100 | 95 | 90 | 95 | 100 | 98 | 90 | 100 |
| Johnsongrass | 25 | 35 | 40 | 5 | 5 | 35 | 35 | 25 | 25 | 0 | 15 | 10 | 10 | 10 |
| *Kochia* | 85 | 95 | 50 | 85 | 90 | 80 | 100 | 100 | 98 | 75 | 70 | 95 | 100 | 95 |
| Lambsquarters | 90 | 100 | 100 | 100 | 100 | 100 | 98 | 98 | 85 | — | 98 | 100 | 85 | 90 |
| Morningglory | 100 | 100 | 98 | 98 | 100 | 98 | 98 | 100 | 100 | 75 | 100 | 100 | 50 | 100 |
| Nutsedge, Yellow | 75 | 85 | 65 | 85 | 65 | 60 | 80 | 95 | 90 | 90 | 95 | 70 | 60 | 90 |
| Oat, Wild | 95 | 100 | 45 | 90 | 85 | 90 | 95 | 95 | 50 | 10 | 0 | 85 | 40 | 60 |
| Oilseed Rape | 0 | 90 | 50 | 20 | 90 | 50 | 0 | 0 | 10 | 5 | 0 | 70 | 0 | 5 |
| Pigweed | 98 | 95 | 80 | 98 | 100 | 95 | 95 | 98 | 98 | 85 | 55 | 100 | 90 | 100 |
| Ragweed | 95 | 98 | 98 | 95 | 95 | 98 | 100 | 100 | 100 | 25 | 98 | 98 | 60 | 95 |
| Ryegrass, Italian | 95 | 95 | 75 | 90 | 80 | 90 | 90 | 95 | 30 | 70 | 60 | 80 | 90 | 60 |
| Soybean | 25 | 35 | 0 | 5 | 15 | 25 | 15 | 15 | 15 | 0 | 0 | 10 | 0 | 5 |
| Velvetleaf | 90 | 85 | 85 | 90 | 95 | 90 | 90 | 95 | 95 | 70 | 100 | 100 | 70 | 100 |
| Waterhemp | 98 | 98 | 75 | 98 | 98 | 98 | 85 | 95 | 100 | — | 55 | 95 | 90 | 100 |
| Wheat | 10 | 40 | 0 | 0 | 5 | 35 | 5 | 0 | 0 | 0 | 0 | 0 | 5 | 5 |

| 250 g ai/ha Post- | Compounds | | | | | | | | | | | | | |
|---|---|---|---|---|---|---|---|---|---|---|---|---|---|---|
| emergence | 59 | 60 | 65 | 66 | 67 | 69 | 72 | 73 | 75 | 78 | 79 | 80 | 81 | 82 |
| Barnyardgrass | 70 | 65 | 50 | 35 | 45 | 55 | 65 | 60 | 20 | 25 | 40 | 35 | 60 | 30 |
| Blackgrass | 90 | 90 | 40 | 60 | 80 | 70 | 90 | 90 | 35 | 30 | 50 | 50 | 90 | 40 |
| Chickweed | 98 | 98 | 90 | 95 | 95 | 100 | 90 | 95 | 95 | 80 | 90 | 98 | 95 | 98 |
| Corn | 50 | 35 | 5 | 25 | 20 | 10 | 25 | 60 | 10 | 0 | 35 | 5 | 0 | 5 |
| Crabgrass, Large | 60 | 65 | 25 | 45 | 40 | 30 | 60 | 75 | 20 | 10 | 35 | 35 | 55 | 30 |
| Foxtail, Giant | 90 | 90 | 60 | 80 | 85 | 25 | 85 | 85 | 10 | 25 | 90 | 90 | 90 | 80 |
| *Galium* | 98 | 100 | 90 | 95 | 90 | 98 | 95 | 95 | 90 | 95 | 95 | 95 | 95 | 95 |
| Johnsongrass | 35 | 45 | 5 | 15 | 10 | 15 | 45 | 50 | 10 | 5 | 10 | 15 | 70 | 10 |
| *Kochia* | 90 | 100 | 100 | 98 | 80 | 98 | 90 | 100 | 95 | 90 | 90 | 90 | 80 | 90 |
| Lambsquarters | 98 | 100 | 100 | 100 | 100 | 98 | 95 | 98 | 100 | 100 | 100 | 100 | 100 | 100 |
| Morningglory | 100 | 100 | 95 | 100 | 100 | 98 | 100 | 95 | 75 | 65 | 98 | 98 | 98 | 100 |
| Nutsedge, Yellow | 95 | 95 | 65 | 85 | 85 | 65 | 85 | 90 | 70 | 60 | 85 | 95 | 90 | 85 |
| Oat, Wild | 98 | 95 | 70 | 90 | 100 | 85 | 95 | 95 | 35 | 60 | 90 | 95 | 95 | 90 |
| Oilseed Rape | 55 | 80 | 5 | 0 | 75 | 0 | 85 | 85 | 80 | 5 | 80 | 80 | 45 | 75 |
| Pigweed | 98 | 98 | 100 | 100 | 85 | 95 | 98 | 98 | 98 | 80 | 98 | 95 | 90 | 90 |
| Ragweed | 98 | 100 | 90 | 100 | 95 | 98 | 90 | 90 | 100 | 75 | 98 | 98 | 85 | 95 |
| Ryegrass, Italian | 95 | 95 | 85 | 85 | 85 | 95 | 90 | 90 | 85 | 90 | 85 | 85 | 90 | 85 |
| Soybean | 25 | 50 | 10 | 5 | 10 | 35 | 30 | 45 | 10 | 20 | 5 | 20 | 0 | 10 |
| Velvetleaf | 95 | 95 | 75 | 95 | 98 | 98 | 95 | 90 | 85 | 60 | 90 | 90 | 90 | 90 |

TABLE C-continued

| | | | | | | | | | | | | | | |
|---|---|---|---|---|---|---|---|---|---|---|---|---|---|---|
| Waterhemp | 100 | 98 | 85 | 100 | 70 | 100 | 85 | 100 | 100 | 90 | 95 | 95 | 80 | 98 |
| Wheat | 15 | 15 | 0 | 0 | 0 | 0 | 35 | 40 | 0 | 10 | 0 | 15 | 0 | 5 |

| 250 g ai/ha Post-emergence | Compounds | | | | | | | | | | | | | |
|---|---|---|---|---|---|---|---|---|---|---|---|---|---|---|
| | 83 | 84 | 85 | 87 | 88 | 89 | 90 | 91 | 97 | 98 | 99 | 100 | 102 | 104 |
| Barnyardgrass | 45 | 40 | 50 | 45 | 60 | 40 | 70 | 65 | 35 | 98 | 35 | 40 | 40 | 55 |
| Blackgrass | 90 | 60 | 90 | 65 | 90 | 5 | 40 | 30 | 0 | 70 | 65 | 25 | 10 | 55 |
| Chickweed | 100 | 100 | 100 | 98 | 100 | 100 | 98 | 100 | 60 | 100 | 90 | 95 | 98 | 100 |
| Corn | 10 | 10 | 5 | 5 | 15 | 5 | 25 | 20 | 5 | 15 | 10 | 10 | 10 | 30 |
| Crabgrass, Large | 55 | 30 | 45 | 35 | 55 | 10 | 75 | 40 | 25 | 70 | 50 | 15 | 15 | 55 |
| Foxtail, Giant | 90 | 85 | 90 | 85 | 90 | 30 | 75 | 80 | 5 | 100 | 50 | 90 | 75 | 85 |
| Galium | 100 | 95 | 100 | 98 | 100 | 95 | 95 | 98 | 90 | 98 | 98 | 95 | 95 | 98 |
| Johnsongrass | 10 | 20 | 25 | 10 | 5 | 5 | 20 | 10 | 5 | 10 | 5 | 10 | 10 | 5 |
| Kochia | 80 | 95 | 70 | 95 | 85 | 100 | 100 | 98 | 85 | 80 | 95 | 95 | 50 | 100 |
| Lambsquarters | 98 | 98 | 100 | 100 | 98 | 100 | 100 | 100 | 60 | 100 | 98 | 98 | 100 | 100 |
| Morningglory | 98 | 100 | 100 | 100 | 98 | 98 | 100 | 100 | 30 | 100 | 100 | 100 | 100 | 100 |
| Nutsedge, Yellow | 90 | 90 | 90 | 85 | 85 | 75 | 85 | 85 | 5 | 60 | 85 | 50 | 75 | 75 |
| Oat, Wild | 95 | 90 | 90 | 90 | 100 | 40 | 95 | 90 | 10 | 100 | 95 | 95 | 25 | 90 |
| Oilseed Rape | 70 | 50 | 15 | 20 | 80 | 0 | 5 | 90 | 35 | 25 | 55 | 90 | 30 | 98 |
| Pigweed | 90 | 100 | 90 | 98 | 90 | 95 | 100 | 100 | 75 | 100 | 95 | 100 | 100 | 100 |
| Ragweed | 85 | 95 | 90 | 100 | 90 | 98 | 100 | 100 | 35 | 100 | 100 | 98 | 100 | 100 |
| Ryegrass, Italian | 95 | 85 | 95 | 85 | 90 | 80 | 90 | 95 | 55 | 85 | 95 | 95 | 30 | 90 |
| Soybean | 10 | 5 | 15 | 5 | 25 | 0 | 70 | 20 | 5 | 25 | 5 | 5 | 10 | 10 |
| Velvetleaf | 90 | 98 | 95 | 90 | 90 | 80 | 98 | 100 | 30 | 100 | 100 | 65 | 100 | 90 |
| Waterhemp | 80 | 90 | 85 | 90 | 90 | 50 | 100 | 80 | 10 | 100 | 98 | 98 | 85 | 95 |
| Wheat | 0 | 0 | 0 | 0 | 0 | 0 | 30 | 5 | 0 | 30 | 10 | 5 | 5 | 10 |

| 250 g ai/ha Post-emergence | Compounds | | | | | | | | | | | | | |
|---|---|---|---|---|---|---|---|---|---|---|---|---|---|---|
| | 105 | 106 | 107 | 108 | 109 | 111 | 113 | 114 | 115 | 121 | 123 | 125 | 126 | 127 |
| Barnyardgrass | 20 | 40 | 90 | 60 | 65 | 40 | 45 | 40 | 45 | 30 | 70 | 70 | 50 | 25 |
| Blackgrass | 60 | 75 | 30 | 55 | 80 | 35 | 60 | 15 | 35 | 50 | 45 | 80 | 40 | 35 |
| Chickweed | 100 | 98 | 98 | 98 | 100 | 98 | 100 | 98 | 90 | 98 | 98 | 95 | 100 | 95 |
| Corn | 30 | 10 | 15 | 30 | 50 | 10 | 15 | 0 | 15 | 5 | 20 | 5 | 25 | 10 |
| Crabgrass, Large | 30 | 30 | 65 | 40 | 60 | 25 | 70 | 25 | 25 | 40 | 75 | 60 | 30 | 25 |
| Foxtail, Giant | 85 | 95 | 75 | 85 | 85 | 85 | 70 | 85 | 35 | 85 | 80 | 98 | 25 | 40 |
| Galium | 100 | 100 | 98 | 95 | 100 | 95 | 95 | 95 | 95 | 95 | 95 | 95 | 98 | 90 |
| Johnsongrass | 0 | 10 | 20 | 5 | 5 | 10 | 20 | 15 | 20 | 5 | 25 | 20 | 25 | 15 |
| Kochia | 100 | 80 | 90 | 100 | 100 | 95 | 100 | 95 | 90 | 95 | 95 | 98 | 90 | 95 | 90 |
| Lambsquarters | 100 | 98 | 98 | 98 | 100 | 100 | 100 | 100 | 98 | 100 | 100 | 100 | 95 | 98 |
| Morningglory | 100 | 98 | 100 | 100 | 100 | 100 | 100 | 100 | 100 | 98 | 100 | 100 | 98 | 98 |
| Nutsedge, Yellow | 90 | 80 | 85 | 75 | 80 | 75 | 95 | 35 | 80 | 75 | 90 | 90 | 85 | 70 |
| Oat, Wild | 90 | 90 | 35 | 90 | 90 | 98 | 90 | 85 | 90 | 90 | 95 | 95 | 85 | 60 |
| Oilseed Rape | 75 | 95 | 45 | 95 | 95 | 100 | 0 | 80 | 0 | 55 | 5 | 10 | 85 | 100 |
| Pigweed | 98 | 90 | 98 | 98 | 100 | 98 | 98 | 95 | 90 | 98 | 98 | 98 | 95 | 95 |
| Ragweed | 100 | 98 | 98 | 100 | 100 | 100 | 100 | 100 | 98 | 98 | 98 | 98 | 95 | 90 |
| Ryegrass, Italian | 80 | 35 | 90 | 90 | 90 | 95 | 95 | 95 | 95 | 90 | 95 | 95 | 90 | 90 |
| Soybean | 40 | 10 | 10 | 15 | 25 | 10 | 55 | 5 | 65 | 0 | 65 | 10 | 35 | 35 |
| Velvetleaf | 100 | 100 | 100 | 100 | 100 | 90 | 98 | 85 | 65 | 80 | 95 | 98 | 95 | 55 |
| Waterhemp | 98 | 80 | 90 | 98 | 100 | 70 | 100 | 45 | 90 | 70 | 100 | 100 | 100 | 95 |
| Wheat | 5 | 5 | 0 | 10 | 35 | 25 | 15 | 15 | 5 | 0 | 20 | 35 | 5 | 30 |

| 250 g ai/ha Post-emergence | Compounds | | | | | | | | | | | | | |
|---|---|---|---|---|---|---|---|---|---|---|---|---|---|---|
| | 129 | 130 | 132 | 133 | 134 | 136 | 137 | 138 | 139 | 145 | 153 | 154 | 161 | 162 |
| Barnyardgrass | 85 | 55 | 25 | 35 | 55 | 40 | 65 | 40 | 60 | 70 | 90 | 95 | 55 | 25 |

TABLE C-continued

| | | | | | | | | | | | | | | |
|---|---|---|---|---|---|---|---|---|---|---|---|---|---|---|
| Blackgrass | 80 | 60 | 45 | 30 | 98 | 45 | 0 | 80 | 10 | 90 | 90 | 85 | 65 | 40 |
| Chickweed | 100 | 100 | 95 | — | — | — | — | — | — | — | 98 | 95 | 80 | 95 |
| Corn | 30 | 15 | 10 | 5 | 15 | 10 | 20 | 15 | 15 | 10 | 10 | 5 | 40 | 0 |
| Crabgrass, Large | 60 | 60 | 25 | 20 | 40 | 35 | 35 | 25 | 40 | 20 | 75 | 75 | 20 | 10 |
| Foxtail, Giant | 95 | 70 | 75 | 55 | 45 | 90 | 95 | 80 | 60 | 55 | 95 | 95 | 35 | 40 |
| *Galium* | 100 | 98 | 95 | 100 | 100 | 95 | 95 | 95 | 100 | 100 | 98 | 95 | 95 | 98 |
| Johnsongrass | 25 | 20 | 10 | 10 | 25 | 5 | 15 | 20 | 25 | 20 | 15 | 20 | 25 | 10 |
| *Kochia* | 95 | 100 | 95 | 100 | 100 | 100 | 100 | 100 | 100 | 100 | 85 | 80 | 90 | 90 |
| Lambsquarters | 98 | 100 | 100 | 100 | 100 | 100 | 100 | 98 | 100 | 100 | 95 | 95 | 85 | 95 |
| Morningglory | 100 | 100 | 98 | 95 | 100 | 100 | 100 | 100 | 100 | 100 | 100 | 100 | 98 | 90 |
| Nutsedge, Yellow | 95 | 85 | 85 | 98 | 90 | 85 | 90 | 80 | 85 | 95 | 90 | 80 | 50 | 30 |
| Oat, Wild | 98 | 95 | 90 | 95 | 95 | 90 | 90 | 90 | 90 | 100 | 95 | 90 | 90 | 70 |
| Oilseed Rape | 5 | 0 | 40 | 98 | 100 | 98 | 98 | 98 | 95 | 90 | 90 | 95 | 90 | 0 |
| Pigweed | 98 | 90 | 65 | 95 | 100 | 98 | 100 | 98 | 98 | 100 | 85 | 85 | 98 | 90 |
| Ragweed | 95 | 98 | 98 | 5 | 30 | 5 | 40 | 5 | 0 | 25 | 90 | 90 | 85 | 90 |
| Ryegrass, Italian | 95 | 95 | 95 | 5 | 40 | 35 | 60 | 70 | 60 | 40 | 95 | 95 | 90 | 80 |
| Soybean | 25 | 50 | 20 | 40 | 85 | 15 | 20 | 25 | 60 | 70 | 5 | 25 | 40 | 0 |
| Velvetleaf | 100 | 98 | 75 | 100 | 100 | 98 | 95 | 98 | 100 | 100 | 95 | 90 | 100 | 70 |
| Waterhemp | 98 | 98 | 75 | 100 | 100 | 100 | 90 | 100 | 100 | 100 | 90 | 70 | 95 | 65 |
| Wheat | 55 | 15 | 0 | 80 | 90 | 90 | 95 | 90 | 90 | 90 | 10 | 5 | 15 | 10 |

| 250 g ai/ha Postemergence | Compounds | | | |
|---|---|---|---|---|
| | 164 | 165 | 171 | 176 |
| Barnyardgrass | 35 | 25 | 60 | 20 |
| Blackgrass | 45 | 25 | 55 | 0 |
| Chickweed | 98 | 98 | 95 | — |
| Corn | 5 | 5 | 20 | 5 |
| Crabgrass, Large | 10 | 20 | 55 | 30 |
| Foxtail, Giant | 30 | 25 | 75 | 40 |
| *Galium* | 100 | 100 | 95 | 60 |
| Johnsongrass | 10 | 15 | 20 | 10 |
| *Kochia* | 95 | 90 | 98 | 100 |
| Lambsquarters | 98 | 98 | 100 | 90 |
| Morningglory | 90 | 95 | 100 | 100 |
| Nutsedge, Yellow | 40 | 35 | — | 5 |
| Oat, Wild | 80 | 70 | 95 | 35 |
| Oilseed Rape | 0 | 5 | 30 | 95 |
| Pigweed | 85 | 85 | 100 | 75 |
| Ragweed | 90 | 85 | 100 | 0 |
| Ryegrass, Italian | 85 | 70 | 95 | 10 |
| Soybean | 5 | 15 | 50 | 10 |
| Velvetleaf | 70 | 50 | 100 | 80 |
| Waterhemp | 75 | 75 | 100 | 55 |
| Wheat | 20 | 15 | 20 | 40 |

| 125 g ai/ha Postemergence | Compounds | | | | | | | | | | | | |
|---|---|---|---|---|---|---|---|---|---|---|---|---|---|
| | 1 | 2 | 10 | 11 | 14 | 16 | 20 | 21 | 22 | 23 | 25 | 26 | 27 | 28 |
| Barnyardgrass | 5 | 15 | 90 | 5 | 55 | 70 | 30 | 75 | 10 | 75 | 20 | 30 | 25 | 35 |
| Blackgrass | 60 | 85 | 10 | 30 | 5 | 5 | 10 | 90 | 20 | 70 | 60 | 60 | 85 | 80 |
| Chickweed | 98 | 95 | 90 | 85 | 90 | 90 | 100 | 100 | 95 | 100 | 100 | 100 | 100 | 98 |
| Corn | 5 | 5 | 5 | 0 | 0 | 0 | 5 | 20 | 5 | 10 | 5 | 5 | 0 | 5 |
| Crabgrass, Large | 25 | 15 | 65 | 0 | 30 | 20 | 10 | 40 | 5 | 35 | 20 | 20 | 30 | 40 |
| Foxtail, Giant | 60 | 90 | 50 | 10 | 50 | 70 | 45 | 90 | 40 | 85 | 70 | 40 | 90 | 85 |

TABLE C-continued

| | | | | | | | | | | | | | | |
|---|---|---|---|---|---|---|---|---|---|---|---|---|---|---|
| Galium | 95 | 98 | 70 | 90 | 80 | 85 | 100 | 100 | 95 | 100 | 100 | 95 | 100 | 100 |
| Johnsongrass | 0 | 5 | 5 | 5 | 0 | 0 | 10 | 20 | 5 | 10 | 5 | 5 | — | — |
| Kochia | 95 | 65 | 95 | 100 | 90 | 20 | 90 | 95 | 95 | 100 | 100 | 90 | 90 | 95 |
| Lambs-quarters | 100 | 98 | 65 | 90 | 80 | 40 | 100 | 95 | 90 | 95 | 98 | 90 | 90 | 100 |
| Morning-glory | 100 | 100 | 100 | 90 | 100 | 60 | 100 | 100 | 100 | 100 | 100 | 100 | 100 | 100 |
| Nutsedge, Yellow | — | 98 | — | 30 | — | — | 85 | 90 | 65 | 85 | 90 | 20 | — | 85 |
| Oat, Wild | 85 | 90 | 5 | 60 | 40 | 10 | 25 | 98 | 80 | 100 | 90 | 95 | 95 | 100 |
| Oilseed Rape | 5 | 70 | 0 | 0 | 0 | 10 | 5 | 100 | 90 | 45 | 20 | 5 | 80 | 5 |
| Pigweed | 98 | 90 | 70 | 90 | 70 | 30 | 98 | 95 | 90 | 98 | 95 | 98 | 85 | 90 |
| Ragweed | 95 | 95 | 70 | 95 | 50 | 0 | 95 | 90 | 90 | 95 | 95 | 85 | 85 | 85 |
| Ryegrass, Italian | 95 | 85 | 20 | 90 | 65 | 60 | 80 | 95 | 90 | 95 | 90 | 90 | 90 | 90 |
| Soybean | 5 | 50 | 0 | 0 | 5 | 0 | 35 | 10 | 0 | 10 | 10 | 10 | 0 | 0 |
| Velvetleaf | 95 | 100 | 40 | 45 | 40 | 20 | 85 | 85 | 80 | 85 | 85 | 60 | 90 | 85 |
| Waterhemp | 100 | 85 | 50 | 95 | 50 | 5 | 60 | 85 | 75 | 85 | 95 | 85 | 10 | 85 |
| Wheat | 10 | 5 | 0 | 5 | 5 | 0 | 0 | 35 | 5 | 35 | 0 | 0 | 5 | 0 |

| 125 g ai/ha Post-emergence | Compounds | | | | | | | | | | | | |
|---|---|---|---|---|---|---|---|---|---|---|---|---|---|
| | 29 | 32 | 33 | 34 | 36 | 37 | 40 | 41 | 42 | 47 | 51 | 52 | 54 | 56 |
| Barnyardgrass | 40 | 65 | 50 | 35 | 35 | 60 | 25 | 40 | 30 | 85 | 10 | 5 | 55 | 5 |
| Blackgrass | 60 | 80 | 5 | 35 | 5 | 80 | 45 | 50 | 60 | 30 | 0 | 30 | 60 | 5 |
| Chickweed | 100 | 100 | 90 | 90 | 95 | 90 | 90 | 90 | 100 | 98 | 70 | 98 | 95 | 55 |
| Corn | 30 | 30 | 5 | 5 | 5 | 20 | 20 | 10 | 5 | 10 | 0 | 0 | 5 | 0 |
| Crabgrass, Large | 50 | 75 | 20 | 20 | 25 | 25 | 10 | 25 | 20 | 40 | 10 | 5 | 35 | 5 |
| Foxtail, Giant | 60 | 80 | 60 | 25 | 70 | 60 | 20 | 30 | 35 | 75 | 15 | 10 | 75 | 0 |
| Galium | 100 | 100 | 95 | 95 | 95 | 95 | 90 | 100 | 100 | 90 | 90 | 100 | 98 | 90 |
| Johnsongrass | — | 15 | 5 | 5 | 5 | 5 | 5 | 10 | — | 20 | 0 | 10 | 10 | 5 |
| Kochia | 75 | 90 | 40 | 60 | 55 | 5 | 0 | 100 | 100 | 95 | 50 | 5 | 90 | 90 |
| Lambs-quarters | 85 | 98 | 98 | 95 | 98 | 95 | 80 | 95 | 100 | 98 | 65 | 75 | 100 | 85 |
| Morning-glory | 100 | 100 | 95 | 95 | 98 | 98 | 80 | 100 | 100 | 100 | 75 | 100 | 98 | 50 |
| Nutsedge, Yellow | — | 80 | 45 | 85 | 55 | 65 | 20 | 65 | — | 80 | 85 | 90 | 55 | 50 |
| Oat, Wild | 85 | 100 | 40 | 90 | 65 | 90 | 60 | 90 | 90 | 30 | 5 | 0 | 60 | 20 |
| Oilseed Rape | 5 | 60 | 30 | 50 | 50 | 40 | 5 | 5 | 10 | 5 | 5 | 0 | 40 | 0 |
| Pigweed | 98 | 90 | 65 | 80 | 95 | 95 | 85 | 75 | 98 | 98 | 70 | 10 | 98 | 85 |
| Ragweed | 95 | 98 | 90 | 95 | 95 | 98 | 85 | 95 | 98 | 98 | 5 | 80 | 95 | 60 |
| Ryegrass, Italian | 85 | 90 | 70 | 90 | 60 | 90 | 80 | 90 | 90 | 25 | 60 | 45 | 85 | 65 |
| Soybean | 20 | 30 | 0 | 15 | 5 | 15 | 30 | 20 | 10 | 10 | 0 | 0 | 10 | 0 |
| Velvetleaf | 85 | 85 | 75 | 100 | 95 | 85 | 20 | 85 | 85 | 95 | 50 | 55 | 98 | 15 |
| Waterhemp | 80 | 85 | 65 | 90 | 95 | 80 | 80 | 90 | 98 | 100 | 80 | 10 | 95 | 95 |
| Wheat | 30 | 25 | 0 | 10 | 0 | 30 | 10 | 30 | 0 | 0 | 0 | 0 | 0 | 5 |

| 125 g ai/ha Post-emergence | Compounds | | | | | | | | | | | | |
|---|---|---|---|---|---|---|---|---|---|---|---|---|---|
| | 57 | 59 | 60 | 65 | 66 | 67 | 69 | 72 | 73 | 75 | 78 | 79 | 80 | 81 |
| Barnyardgrass | 95 | 55 | 35 | 35 | 30 | 35 | 35 | 50 | 55 | 15 | 30 | 30 | 35 | 35 |
| Blackgrass | 5 | 85 | 85 | 10 | 40 | 65 | 30 | 80 | 90 | 20 | 5 | 35 | 40 | 90 |
| Chickweed | 95 | 98 | 95 | 90 | 95 | 95 | 95 | 90 | 95 | 95 | 70 | 90 | 95 | 95 |
| Corn | 5 | 65 | 30 | 5 | 5 | 10 | 5 | 20 | 20 | 10 | 10 | 25 | 5 | 10 |
| Crabgrass, Large | 30 | 25 | 50 | 20 | 35 | 35 | 25 | 35 | 60 | 5 | 10 | 30 | 30 | 40 |
| Foxtail, Giant | 85 | 85 | 70 | 35 | 65 | 80 | 10 | 75 | 75 | 5 | 20 | 75 | 70 | 90 |
| Galium | 95 | 98 | 100 | 90 | 95 | 95 | 98 | 95 | 95 | 90 | 80 | 95 | 95 | 95 |
| Johnsongrass | 5 | 25 | 55 | 5 | 5 | 5 | 10 | 5 | 40 | 5 | 5 | 10 | 5 | 5 |
| Kochia | 70 | 85 | 100 | 90 | 90 | 35 | 95 | 90 | 90 | 95 | 85 | 90 | 90 | 80 |
| Lambs-quarters | 95 | 98 | 95 | 95 | 100 | 90 | 100 | 90 | 95 | 100 | 75 | 98 | 98 | 98 |
| Morning-glory | 100 | 100 | 100 | 95 | 100 | 100 | 95 | 95 | 95 | 100 | 65 | 100 | 100 | 100 |
| Nutsedge, Yellow | 90 | 95 | 90 | 60 | 85 | 80 | 70 | 70 | 80 | 50 | 35 | 80 | 85 | 90 |

TABLE C-continued

| | | | | | | | | | | | | | | |
|---|---|---|---|---|---|---|---|---|---|---|---|---|---|---|
| Oat, Wild | 45 | 90 | 95 | 50 | 90 | 90 | 80 | 90 | 95 | 40 | 60 | 85 | 90 | 95 |
| Oilseed Rape | 0 | 40 | 85 | 0 | 10 | 75 | 50 | 20 | 70 | 90 | 0 | 70 | 60 | 85 |
| Pigweed | 85 | 95 | 95 | 98 | 100 | 80 | 90 | 95 | 95 | 100 | 75 | 98 | 95 | 85 |
| Ragweed | 85 | 95 | 98 | 80 | 90 | 98 | 95 | 95 | 90 | 100 | 60 | 98 | 98 | 70 |
| Ryegrass, Italian | 50 | 90 | 95 | 85 | 85 | 85 | 95 | 90 | 90 | 85 | 85 | 85 | 85 | 90 |
| Soybean | 0 | 10 | 40 | 5 | 10 | 5 | 20 | 15 | 25 | 35 | 5 | 5 | 5 | 5 |
| Velvetleaf | 100 | 90 | 90 | 65 | 85 | 85 | 85 | 85 | 85 | 85 | 35 | 90 | 55 | 90 |
| Waterhemp | 85 | 98 | 98 | 75 | 90 | 75 | 95 | 85 | 85 | 100 | 80 | 80 | 85 | 85 |
| Wheat | 0 | 10 | 30 | 0 | 0 | 0 | 0 | 5 | 35 | 0 | 5 | 0 | 10 | 0 |

| 125 g ai/ha Post-emergence | Compounds | | | | | | | | | | | | | |
|---|---|---|---|---|---|---|---|---|---|---|---|---|---|---|
| | 82 | 83 | 84 | 85 | 87 | 88 | 89 | 90 | 91 | 97 | 98 | 99 | 100 | 102 |
| Barnyardgrass | 25 | 30 | 25 | 40 | 35 | 40 | 20 | 50 | 45 | 15 | 98 | 35 | 30 | 35 |
| Blackgrass | 35 | 90 | 55 | 90 | 60 | 90 | 0 | 25 | 10 | 0 | 50 | 50 | 5 | 5 |
| Chickweed | 90 | 95 | 95 | 95 | 95 | 100 | 100 | 95 | 100 | 15 | 100 | 90 | 95 | 95 |
| Corn | 10 | 10 | 30 | 0 | 30 | 20 | 10 | 10 | 10 | 0 | 15 | 10 | 5 | 10 |
| Crabgrass, Large | 20 | 40 | 20 | 40 | 25 | 55 | 5 | 35 | 25 | 10 | 45 | 30 | 25 | 20 |
| Foxtail, Giant | 60 | 85 | 65 | 90 | 75 | 90 | 20 | 55 | 75 | 5 | 98 | 30 | 75 | 60 |
| Galium | 95 | 100 | 95 | 100 | 95 | 100 | 95 | 95 | 98 | 85 | 98 | 98 | 95 | 95 |
| Johnsongrass | 10 | 5 | 10 | 50 | 5 | 5 | 0 | 10 | 5 | 0 | 10 | 10 | 5 | 0 |
| Kochia | 90 | 65 | 90 | 60 | 90 | 100 | 90 | 100 | 90 | 70 | 60 | 90 | 95 | 20 |
| Lambsquarters | 98 | 85 | 98 | 100 | 98 | 95 | 100 | 98 | 100 | 50 | 100 | 85 | 98 | 70 |
| Morningglory | 100 | 100 | 98 | 100 | 100 | 98 | 98 | 100 | 100 | 30 | 100 | 100 | 100 | 100 |
| Nutsedge, Yellow | 85 | 85 | 85 | 95 | 80 | 80 | 70 | 90 | 45 | 0 | 50 | 75 | 20 | 60 |
| Oat, Wild | 90 | 90 | 90 | 95 | 85 | 100 | 30 | 90 | 90 | 5 | 95 | 90 | 85 | 10 |
| Oilseed Rape | 50 | 45 | 50 | 10 | 50 | 60 | 0 | 0 | 95 | 0 | 10 | 60 | 10 | 5 |
| Pigweed | 90 | 90 | 95 | 85 | 90 | 90 | 80 | 95 | 100 | 60 | 100 | 98 | 100 | 95 |
| Ragweed | 95 | 90 | 98 | 85 | 95 | 85 | 90 | 95 | 95 | 25 | 98 | 95 | 95 | 100 |
| Ryegrass, Italian | 85 | 90 | 85 | 90 | 85 | 90 | 75 | 90 | 95 | 50 | 65 | 95 | 90 | 25 |
| Soybean | 5 | 0 | 10 | 0 | 10 | 5 | 0 | 55 | 10 | 5 | 25 | 5 | 5 | 10 |
| Velvetleaf | 95 | 90 | 85 | 85 | 90 | 85 | 75 | 98 | 98 | 10 | 75 | 98 | 40 | 100 |
| Waterhemp | 90 | 60 | 95 | 85 | 90 | 85 | 50 | 100 | 75 | 5 | 100 | 95 | 95 | 80 |
| Wheat | 5 | 0 | 5 | 0 | 0 | 0 | 0 | 10 | 10 | 0 | 15 | 10 | 0 | 5 |

| 125 g ai/ha Post-emergence | Compounds | | | | | | | | | | | | | |
|---|---|---|---|---|---|---|---|---|---|---|---|---|---|---|
| | 104 | 105 | 106 | 107 | 108 | 109 | 111 | 113 | 114 | 115 | 121 | 123 | 125 | 126 |
| Barnyardgrass | 45 | 25 | 20 | 40 | 40 | 55 | 45 | 35 | 40 | 35 | 25 | 40 | 80 | 35 |
| Blackgrass | 50 | 50 | 60 | 5 | 35 | 50 | 20 | 45 | 5 | 20 | 15 | 45 | 60 | 10 |
| Chickweed | 100 | 98 | 95 | 95 | 95 | 95 | 100 | 98 | 98 | 90 | 90 | 90 | 95 | 95 |
| Corn | 50 | 30 | 10 | 20 | 25 | 35 | 15 | 10 | 0 | 5 | 5 | 20 | 5 | 20 |
| Crabgrass, Large | 35 | 20 | 30 | 35 | 25 | 60 | 25 | 25 | 20 | 20 | 20 | 30 | 40 | 30 |
| Foxtail, Giant | 75 | 75 | 90 | 70 | 75 | 80 | 70 | 30 | 50 | 20 | 70 | 35 | 95 | 15 |
| Galium | 98 | 95 | 95 | 100 | 95 | 100 | 95 | 95 | 95 | 95 | 95 | 95 | 95 | 98 |
| Johnsongrass | 5 | 0 | 10 | 0 | 5 | 5 | 15 | 10 | 5 | 10 | 5 | 20 | 20 | 15 |
| Kochia | 95 | 95 | 80 | 90 | 95 | 100 | 90 | 95 | 90 | 90 | 95 | 95 | 90 | 95 |
| Lambsquarters | 100 | 100 | 95 | 90 | 98 | 100 | 100 | 100 | 100 | 90 | 98 | 100 | 98 | 95 |
| Morningglory | 100 | 100 | 100 | 98 | 98 | 100 | 100 | 100 | 95 | 100 | 98 | 100 | 98 | |
| Nutsedge, Yellow | 60 | 75 | 90 | 75 | 70 | 80 | 65 | 85 | 25 | 65 | 85 | 85 | 85 | 70 |
| Oat, Wild | 90 | 90 | 90 | 40 | 90 | 90 | 90 | 90 | 65 | 80 | 80 | 90 | 95 | 90 |
| Oilseed Rape | 95 | 60 | 85 | 80 | 85 | 95 | 95 | 0 | 40 | 0 | 85 | 0 | 5 | 60 |
| Pigweed | 100 | 100 | 90 | 98 | 98 | 100 | 90 | 95 | 95 | 70 | 90 | 80 | 98 | 95 |
| Ragweed | 98 | 98 | 75 | 98 | 98 | 100 | 98 | 98 | 98 | 95 | 95 | 95 | 98 | 95 |
| Ryegrass, Italian | 90 | 90 | 90 | 60 | 90 | 90 | 95 | 95 | 80 | 95 | 90 | 90 | 95 | 90 |
| Soybean | 10 | 10 | 0 | 20 | 15 | 30 | 5 | 40 | 0 | 20 | 0 | 20 | 10 | 20 |
| Velvetleaf | 98 | 90 | 90 | 95 | 100 | 98 | 98 | 90 | 55 | 70 | 75 | 85 | 95 | 98 |

TABLE C-continued

| | | | | | | | | | | | | | | |
|---|---|---|---|---|---|---|---|---|---|---|---|---|---|---|
| Waterhemp | 100 | 100 | 75 | 95 | 90 | 90 | 55 | 90 | 55 | 90 | 75 | 100 | 98 | 95 |
| Wheat | 5 | 5 | 0 | 0 | 5 | 10 | 15 | 5 | 5 | 0 | 25 | 15 | 30 | 0 |

| 125 g ai/ha Post-emergence | Compounds | | | | | | | | | | | | | |
|---|---|---|---|---|---|---|---|---|---|---|---|---|---|---|
| | 127 | 129 | 130 | 132 | 133 | 134 | 136 | 137 | 138 | 139 | 143 | 145 | 153 | 154 |
| Barnyardgrass | 25 | 70 | 35 | 25 | 45 | 40 | 35 | 50 | 30 | 40 | 30 | 30 | 70 | 90 |
| Blackgrass | 5 | 60 | 55 | 25 | 70 | 50 | 30 | 0 | 50 | 60 | 20 | 30 | 90 | 60 |
| Chickweed | 90 | 100 | 98 | 95 | — | — | — | — | — | — | 80 | — | 98 | 90 |
| Corn | 5 | 30 | 5 | 5 | 5 | 10 | 10 | 10 | 15 | 15 | 5 | 5 | 25 | 5 |
| Crabgrass, Large | 10 | 35 | 15 | 10 | 5 | 15 | 25 | 35 | 20 | 30 | 30 | 10 | 50 | 70 |
| Foxtail, Giant | 25 | 85 | 40 | 60 | 40 | 35 | 70 | 80 | 65 | 30 | 20 | 25 | 90 | 95 |
| *Galium* | 85 | 100 | 95 | 95 | 98 | 100 | 90 | 90 | 95 | 100 | 90 | 98 | 98 | 95 |
| Johnsongrass | 10 | 15 | 5 | 5 | 20 | 5 | 5 | 15 | 20 | 15 | 20 | 20 | 10 | 20 |
| *Kochia* | 95 | 90 | 100 | 95 | 100 | 100 | 100 | 100 | 100 | 100 | 60 | 100 | 80 | 60 |
| Lambsquarters | 85 | 95 | 100 | 100 | 100 | 100 | 95 | 98 | 95 | 100 | 75 | 100 | 95 | 90 |
| Morningglory | 85 | 100 | 85 | 95 | 100 | 100 | 100 | 100 | 98 | 100 | 70 | 100 | 98 | 98 |
| Nutsedge, Yellow | 60 | 85 | 80 | 75 | 95 | 95 | 75 | 85 | 75 | 70 | 35 | 85 | 95 | 85 |
| Oat, Wild | 55 | 100 | 85 | 70 | 95 | 95 | 85 | 90 | 80 | 90 | 60 | 95 | 95 | 90 |
| Oilseed Rape | 25 | 5 | 0 | 5 | 98 | 100 | 98 | 98 | 98 | 98 | 5 | 95 | 90 | 98 |
| Pigweed | 90 | 98 | 90 | 70 | 100 | 100 | 85 | 98 | 90 | 98 | 75 | 75 | 85 | 90 |
| Ragweed | 60 | 95 | 98 | 95 | 5 | 5 | 0 | 30 | 5 | 0 | 70 | 5 | 95 | 85 |
| Ryegrass, Italian | 80 | 95 | 95 | 95 | 35 | 20 | 30 | 30 | 10 | 35 | 90 | 30 | 95 | 90 |
| Soybean | 30 | 20 | 25 | 0 | 75 | 70 | 10 | 15 | 10 | 65 | 20 | 55 | 10 | 20 |
| Velvetleaf | 25 | 95 | 98 | 65 | 100 | 100 | 90 | 90 | 95 | 95 | 50 | 98 | 90 | 85 |
| Waterhemp | 85 | 85 | 80 | 80 | 100 | 100 | 95 | 85 | 98 | 100 | 90 | 100 | 90 | 85 |
| Wheat | 5 | 40 | 10 | 0 | 55 | 65 | 45 | 90 | 80 | 60 | 15 | 85 | 10 | 10 |

| 125 g ai/ha Post-emergence | Compounds | | | | | |
|---|---|---|---|---|---|---|
| | 161 | 162 | 164 | 165 | 171 | 176 |
| Barnyardgrass | 45 | 25 | 30 | 25 | 40 | 10 |
| Blackgrass | 60 | 30 | 40 | 20 | 40 | 0 |
| Chickweed | 70 | 95 | 95 | 95 | 90 | — |
| Corn | 15 | 0 | 5 | 0 | 10 | 0 |
| Crabgrass, Large | 5 | 10 | 10 | 20 | 40 | 20 |
| Foxtail, Giant | 10 | 15 | 15 | 15 | 50 | 35 |
| *Galium* | 95 | 95 | 100 | 98 | 95 | 60 |
| Johnsongrass | 20 | 5 | 5 | 10 | 15 | 5 |
| *Kochia* | 80 | 90 | 90 | 85 | 98 | 95 |
| Lambsquarters | 80 | 90 | 85 | 85 | 98 | 80 |
| Morningglory | 95 | 85 | 90 | 85 | 100 | 98 |
| Nutsedge, Yellow | 20 | 30 | 25 | 25 | 75 | 5 |
| Oat, Wild | 80 | 70 | 70 | 65 | 90 | 10 |
| Oilseed Rape | 95 | 0 | 0 | 0 | 0 | 95 |
| Pigweed | 90 | 85 | 85 | 75 | 90 | 50 |
| Ragweed | 95 | 75 | 85 | 75 | 100 | 0 |
| Ryegrass, Italian | 90 | 70 | 80 | 55 | 95 | 0 |
| Soybean | 40 | 0 | 10 | 15 | 60 | 15 |
| Velvetleaf | 90 | 30 | 25 | 20 | 100 | 75 |
| Waterhemp | 85 | 70 | 70 | 75 | 98 | 60 |
| Wheat | 10 | 5 | 10 | 10 | 30 | 10 |

| 62 g ai/ha Post-emergence | Compounds | | | | | | | | | | | | | |
|---|---|---|---|---|---|---|---|---|---|---|---|---|---|---|
| | 1 | 2 | 10 | 11 | 14 | 16 | 20 | 21 | 22 | 23 | 25 | 26 | 27 | 28 |
| Barnyardgrass | 5 | 10 | 90 | 0 | 5 | 70 | 10 | 45 | 5 | 60 | 20 | 25 | 20 | 25 |
| Blackgrass | 50 | 65 | 0 | 15 | 0 | 5 | 10 | 90 | 0 | 60 | 55 | 55 | 70 | 70 |
| Chickweed | 95 | 95 | 90 | 65 | 90 | 80 | 98 | 100 | 90 | 100 | 98 | 95 | 100 | 95 |

TABLE C-continued

| | | | | | | | | | | | | | | |
|---|---|---|---|---|---|---|---|---|---|---|---|---|---|---|
| Corn | 25 | 5 | 0 | 0 | 0 | 0 | 5 | 65 | 5 | 30 | 5 | 10 | 5 | 5 |
| Crabgrass, Large | 10 | 15 | 30 | 0 | 5 | 20 | 10 | 35 | 5 | 20 | 15 | 20 | 25 | 20 |
| Foxtail, Giant | 15 | 65 | 60 | 5 | 45 | 60 | 25 | 80 | 15 | 65 | 35 | 25 | 75 | 80 |
| *Galium* | 95 | 95 | 50 | 90 | 55 | 80 | 100 | 100 | 90 | 100 | 95 | 95 | 100 | 100 |
| Johnsongrass | 0 | 5 | 0 | 0 | 0 | 0 | 10 | 20 | 5 | 5 | 5 | 5 | 0 | 5 |
| *Kochia* | 95 | 55 | 85 | 95 | 85 | 0 | 80 | 90 | 95 | 95 | 95 | 70 | 80 | 70 |
| Lambsquarters | 100 | 85 | 80 | 90 | 80 | 60 | 85 | 90 | 85 | 95 | 95 | 85 | 85 | 98 |
| Morningglory | 100 | 100 | 90 | 80 | 85 | 50 | 100 | 100 | 100 | 100 | 100 | 100 | 100 | 98 |
| Nutsedge, Yellow | — | 95 | — | 15 | — | — | 65 | 90 | 50 | 70 | 75 | 10 | 80 | 85 |
| Oat, Wild | 70 | 80 | 5 | 45 | 30 | 5 | 5 | 98 | 50 | 95 | 70 | 80 | 95 | 95 |
| Oilseed Rape | 0 | 70 | 0 | 0 | 0 | 0 | 0 | 80 | 15 | 15 | 0 | 0 | 70 | 60 |
| Pigweed | 95 | 60 | 60 | 90 | 70 | 30 | 90 | 95 | 75 | 98 | 90 | 85 | 80 | 85 |
| Ragweed | 95 | 80 | 30 | 40 | 90 | 0 | 85 | 90 | 75 | 90 | 85 | 70 | 75 | 75 |
| Ryegrass, Italian | 90 | 75 | 5 | 70 | 60 | 50 | 60 | 95 | 70 | 90 | 85 | 90 | 85 | 85 |
| Soybean | 0 | 0 | 0 | 0 | 0 | 0 | 0 | 0 | 0 | 10 | 0 | 5 | 0 | 0 |
| Velvetleaf | 85 | 100 | 45 | 5 | 20 | 5 | 25 | 85 | 50 | 85 | 80 | 30 | 85 | 85 |
| Waterhemp | 95 | 65 | 45 | 80 | 10 | 5 | 40 | 75 | 70 | 55 | 95 | 85 | 60 | 75 |
| Wheat | 0 | 0 | 0 | 0 | 0 | 0 | 0 | 5 | 0 | 30 | 0 | 0 | 0 | 0 |

| 62 g ai/ha Post- | Compounds | | | | | | | | | | | | | |
|---|---|---|---|---|---|---|---|---|---|---|---|---|---|---|
| emergence | 29 | 32 | 33 | 34 | 35 | 36 | 37 | 40 | 41 | 42 | 47 | 51 | 52 | 54 |
| Barnyardgrass | 25 | 30 | 25 | 25 | 20 | 25 | 20 | 15 | 35 | 30 | 55 | 5 | 5 | 30 |
| Blackgrass | 50 | 60 | 0 | 10 | 45 | 5 | 40 | 15 | 35 | 35 | 20 | 0 | 10 | 5 |
| Chickweed | 95 | 95 | 90 | 90 | 95 | 95 | 90 | 60 | 95 | 100 | 90 | 55 | 90 | 95 |
| Corn | 10 | 20 | 5 | 5 | 5 | 0 | 10 | 0 | 5 | 5 | 5 | 0 | 0 | 0 |
| Crabgrass, Large | 20 | 30 | 20 | 10 | 20 | 30 | 20 | 5 | 10 | 15 | 30 | 5 | 0 | 25 |
| Foxtail, Giant | 35 | 50 | 40 | 20 | 75 | 55 | 35 | 15 | 15 | 30 | 65 | 5 | 5 | 55 |
| *Galium* | 95 | 100 | 90 | 95 | 95 | 95 | 95 | 85 | 100 | 90 | 90 | 90 | 100 | 98 |
| Johnsongrass | 5 | 25 | 5 | 5 | 20 | 5 | 5 | 5 | 10 | 5 | 10 | 0 | 10 | 5 |
| *Kochia* | 60 | 50 | 5 | 45 | 40 | 55 | 0 | 80 | 100 | 100 | 90 | 15 | 0 | 90 |
| Lambsquarters | 85 | 90 | 95 | 90 | 70 | 98 | 90 | 70 | 95 | 95 | 85 | 50 | 60 | 95 |
| Morningglory | 100 | 100 | 95 | 98 | 100 | 98 | 95 | 65 | 95 | 100 | 100 | 55 | 100 | 98 |
| Nutsedge, Yellow | 35 | 80 | 15 | 60 | 85 | 40 | 40 | 15 | 65 | 75 | 70 | 70 | 80 | 35 |
| Oat, Wild | 55 | 90 | 30 | 85 | 60 | 60 | 80 | 50 | 90 | 90 | 10 | 5 | 0 | 50 |
| Oilseed Rape | 0 | 60 | 55 | 30 | 10 | 40 | 20 | 30 | 0 | 5 | 0 | 5 | 0 | 80 |
| Pigweed | 95 | 90 | 50 | 85 | 55 | 85 | 100 | 65 | 75 | 95 | 90 | 65 | 5 | 95 |
| Ragweed | 90 | 90 | 95 | 98 | 40 | 90 | 95 | 75 | 85 | 85 | 98 | 5 | 65 | 95 |
| Ryegrass, Italian | 80 | 90 | 45 | 80 | 55 | 60 | 85 | 65 | 90 | 90 | 10 | 50 | 40 | 80 |
| Soybean | 10 | 25 | 0 | 5 | 5 | 0 | 5 | 60 | 15 | 5 | 10 | 0 | 0 | 5 |
| Velvetleaf | 80 | 70 | 60 | 80 | 100 | 85 | 70 | 10 | 65 | 85 | 90 | 20 | 25 | 90 |
| Waterhemp | 80 | 80 | 30 | 85 | 45 | 95 | 80 | 65 | 75 | 85 | 75 | 50 | 10 | 90 |
| Wheat | 5 | 15 | 0 | 5 | 5 | 0 | 0 | 10 | 0 | 0 | 0 | 0 | 0 | 50 |

| 62 g ai/ha Post- | Compounds | | | | | | | | | | | | | |
|---|---|---|---|---|---|---|---|---|---|---|---|---|---|---|
| emergence | 56 | 57 | 59 | 60 | 65 | 66 | 67 | 69 | 72 | 73 | 75 | 78 | 79 | 80 |
| Barnyardgrass | 5 | 95 | 30 | 25 | 15 | 20 | 35 | 35 | 40 | 40 | 25 | 25 | 25 | 30 |
| Blackgrass | 5 | 5 | 80 | 60 | 5 | 15 | 60 | 20 | 70 | 85 | 5 | 5 | 10 | 35 |
| Chickweed | 10 | 95 | 98 | 95 | 90 | 95 | 95 | 90 | 90 | 90 | 90 | 60 | 90 | 95 |
| Corn | 0 | 5 | 45 | 25 | 5 | 0 | 5 | 0 | 10 | 20 | 5 | 0 | 0 | 5 |
| Crabgrass, Large | 5 | 20 | 20 | 35 | 20 | 30 | 35 | 25 | 25 | 35 | 10 | 5 | 25 | 25 |
| Foxtail, Giant | 0 | 70 | 60 | 60 | 20 | 55 | 75 | 10 | 70 | 65 | 5 | 5 | 60 | 55 |
| *Galium* | 85 | 95 | 98 | 100 | 85 | 95 | 95 | 95 | 95 | 90 | 90 | 80 | 95 | 95 |
| Johnsongrass | 0 | 5 | 5 | 35 | 5 | 5 | 5 | 10 | 5 | 5 | 5 | 5 | 5 | 5 |

TABLE C-continued

| | | | | | | | | | | | | | | |
|---|---|---|---|---|---|---|---|---|---|---|---|---|---|---|
| Kochia | 90 | 65 | 85 | 90 | 90 | 90 | 30 | 90 | 85 | 90 | 85 | 70 | 90 | 90 |
| Lambs-quarters | 50 | 70 | 95 | 90 | 95 | 100 | 95 | 90 | 85 | 95 | 100 | 70 | 95 | 95 |
| Morning-glory | 50 | 100 | 100 | 98 | 85 | 95 | 95 | 95 | 90 | 90 | 100 | 40 | 100 | 100 |
| Nutsedge, Yellow | 5 | 90 | 85 | 85 | 50 | 70 | 70 | 65 | 60 | 80 | 20 | 25 | 80 | 80 |
| Oat, Wild | 10 | 35 | 75 | 95 | 35 | 80 | 85 | 60 | 95 | 90 | 35 | 50 | 60 | 90 |
| Oilseed Rape | 0 | 0 | 50 | 5 | 0 | 10 | 50 | 10 | 35 | 70 | 70 | 0 | 25 | 50 |
| Pigweed | 75 | 80 | 95 | 85 | 90 | 98 | 85 | 85 | 90 | 85 | 95 | 60 | 98 | 90 |
| Ragweed | 0 | 90 | 95 | 90 | 85 | 85 | 75 | 90 | 90 | 90 | 85 | 20 | 95 | 90 |
| Ryegrass, Italian | 60 | 30 | 90 | 90 | 80 | 80 | 80 | 90 | 90 | 90 | 80 | 65 | 60 | 85 |
| Soybean | 0 | 0 | 15 | 20 | 5 | 10 | 5 | 25 | 15 | 15 | 35 | 0 | 0 | 15 |
| Velvetleaf | 0 | 95 | 85 | 85 | 20 | 75 | 85 | 80 | 85 | 85 | 50 | 10 | 85 | 90 |
| Waterhemp | 75 | 65 | 90 | 90 | 75 | 90 | 70 | 90 | 65 | 75 | 100 | 90 | 90 | 80 |
| Wheat | 0 | 0 | 20 | 5 | 0 | 0 | 0 | 0 | 30 | 30 | 0 | 5 | 0 | 5 |

| 62 g ai/ha Post-emergence | Compounds | | | | | | | | | | | | | |
|---|---|---|---|---|---|---|---|---|---|---|---|---|---|---|
| | 81 | 82 | 83 | 84 | 85 | 87 | 88 | 89 | 90 | 91 | 97 | 98 | 99 | 100 |
| Barnyardgrass | 35 | 25 | 25 | 20 | 45 | 25 | 40 | 15 | 35 | 30 | 5 | 85 | 25 | 25 |
| Blackgrass | 85 | 35 | 80 | 35 | 80 | 35 | 80 | 0 | 15 | 5 | 0 | 30 | 30 | 5 |
| Chickweed | 90 | 90 | 95 | 90 | 95 | 90 | 100 | 95 | 90 | 98 | 0 | 100 | 90 | 90 |
| Corn | 5 | 30 | 5 | 20 | 0 | 5 | 0 | 5 | 10 | 0 | 0 | 0 | 5 | 10 |
| Crabgrass, Large | 35 | 20 | 25 | 10 | 30 | 10 | 20 | 5 | 15 | 20 | 5 | 25 | 20 | 15 |
| Foxtail, Giant | 85 | 25 | 85 | 55 | 85 | 55 | 85 | 10 | 25 | 45 | 5 | 95 | 15 | 45 |
| Galium | 95 | 95 | 90 | 95 | 100 | 95 | 100 | 95 | 95 | 90 | 80 | 95 | 95 | 95 |
| Johnsongrass | 5 | 5 | 5 | 5 | 15 | 5 | 5 | 0 | 10 | 5 | 0 | 5 | 10 | 0 |
| Kochia | 75 | 90 | 60 | 90 | 70 | 90 | 50 | 90 | 100 | 90 | 0 | 20 | 85 | 90 |
| Lambs-quarters | 95 | 98 | 85 | 90 | 98 | 98 | 85 | 90 | 98 | 100 | 20 | 100 | 75 | 90 |
| Morning-glory | 100 | 100 | 90 | 98 | 98 | 98 | 100 | 95 | 100 | 100 | 40 | 100 | 95 | 100 |
| Nutsedge, Yellow | 85 | 80 | 80 | 85 | 85 | 80 | 85 | 60 | 80 | 40 | 0 | 15 | 55 | 25 |
| Oat, Wild | 90 | 85 | 90 | 90 | 90 | 90 | 95 | 10 | 70 | 70 | 5 | 80 | 70 | 70 |
| Oilseed Rape | 65 | 40 | 0 | 45 | 10 | 50 | 5 | 0 | 0 | 90 | 0 | 0 | 5 | 60 |
| Pigweed | 85 | 90 | 85 | 90 | 85 | 90 | 85 | 75 | 80 | 90 | 50 | 100 | 75 | 85 |
| Ragweed | 75 | 98 | 85 | 90 | 85 | 95 | 85 | 90 | 85 | 98 | 10 | 98 | 90 | 95 |
| Ryegrass, Italian | 85 | 85 | 90 | 80 | 90 | 80 | 90 | 75 | 90 | 80 | 30 | 45 | 90 | 90 |
| Soybean | 0 | 10 | 0 | 5 | 0 | 0 | 0 | 0 | 50 | 5 | 0 | 10 | 5 | 5 |
| Velvetleaf | 85 | 80 | 90 | 90 | 85 | 85 | 85 | 75 | 75 | 75 | 20 | 70 | 85 | 50 |
| Waterhemp | 60 | 98 | 85 | 85 | 65 | 80 | 85 | 40 | 100 | 50 | 5 | 100 | 75 | 90 |
| Wheat | 0 | 0 | 0 | 0 | 0 | 0 | 0 | 0 | 10 | 5 | 0 | 10 | 0 | 0 |

| 62 g ai/ha Post-emergence | Compounds | | | | | | | | | | | | | |
|---|---|---|---|---|---|---|---|---|---|---|---|---|---|---|
| | 102 | 104 | 105 | 106 | 107 | 108 | 109 | 111 | 113 | 114 | 115 | 121 | 123 | 125 |
| Barnyardgrass | 20 | 35 | 25 | 15 | 50 | 35 | 30 | 30 | 35 | 35 | 20 | 20 | 25 | 40 |
| Blackgrass | 5 | 35 | 40 | 50 | 5 | 35 | 25 | 5 | 25 | 0 | 10 | 15 | 35 | 45 |
| Chickweed | 95 | 98 | 95 | 98 | 90 | 90 | 95 | 98 | 90 | 95 | 75 | 90 | 90 | 95 |
| Corn | 0 | 80 | 15 | 10 | 10 | 40 | 15 | 10 | 10 | 0 | 5 | 5 | 15 | 0 |
| Crabgrass, Large | 10 | 30 | 30 | 40 | 20 | 10 | 40 | 20 | 15 | 20 | 20 | 5 | 35 | 35 |
| Foxtail, Giant | 35 | 70 | 50 | 75 | 55 | 40 | 50 | 45 | 25 | 20 | 15 | 50 | 20 | 90 |
| Galium | 95 | 95 | 98 | 95 | 95 | 98 | 100 | 95 | 95 | 95 | 90 | 90 | 95 | 95 |
| Johnsongrass | 0 | 5 | 0 | 10 | 0 | 0 | 5 | 10 | 10 | 5 | 10 | 5 | 10 | 5 |
| Kochia | 0 | 95 | 95 | 85 | 85 | 95 | 95 | 85 | 98 | 90 | 90 | 90 | 95 | 90 |
| Lambs-quarters | 70 | 98 | 85 | 90 | 90 | 95 | 100 | 100 | 98 | 95 | 90 | 95 | 98 | 98 |
| Morning-glory | 100 | 100 | 98 | 98 | 98 | 100 | 98 | 100 | 100 | 100 | 85 | 98 | 90 | 95 |
| Nutsedge, Yellow | 55 | 45 | 70 | 85 | 80 | 60 | 50 | 40 | 70 | 10 | 60 | 40 | 75 | 85 |
| Oat, Wild | 5 | 90 | 60 | 90 | 20 | 90 | 80 | 70 | 90 | 60 | 60 | 90 | 85 | 90 |

TABLE C-continued

| | | | | | | | | | | | | | | |
|---|---|---|---|---|---|---|---|---|---|---|---|---|---|---|
| Oilseed Rape | 0 | 70 | 30 | 80 | 55 | 90 | 90 | 10 | 0 | 85 | 0 | 60 | 0 | 0 |
| Pigweed | 80 | 98 | 98 | 80 | 95 | 95 | 95 | 90 | 75 | 85 | 70 | 85 | 80 | 95 |
| Ragweed | 95 | 90 | 95 | 85 | 90 | 95 | 95 | 90 | 95 | 90 | 85 | 90 | 90 | 98 |
| Ryegrass, Italian | 5 | 90 | 90 | 90 | 50 | 90 | 90 | 90 | 95 | 70 | 90 | 90 | 90 | 90 |
| Soybean | 10 | 0 | 0 | 0 | 5 | 5 | 15 | 5 | 30 | 0 | 20 | 0 | 10 | 5 |
| Velvetleaf | 75 | 85 | 85 | 85 | 98 | 85 | 80 | 80 | 95 | 55 | 25 | 35 | 75 | 90 |
| Waterhemp | 60 | 90 | 100 | 80 | 85 | 85 | 85 | 45 | 90 | 55 | 75 | 65 | 90 | 95 |
| Wheat | 0 | 5 | 0 | 0 | 0 | 5 | 5 | 10 | 15 | 5 | 5 | 5 | 5 | 15 |

| 62 g ai/ha Post-emergence | Compounds | | | | | | | | | | | | | |
|---|---|---|---|---|---|---|---|---|---|---|---|---|---|---|
| | 126 | 127 | 129 | 130 | 132 | 133 | 134 | 136 | 137 | 138 | 139 | 143 | 145 | 151 |
| Barnyardgrass | 30 | 20 | 65 | 30 | 30 | 30 | 20 | 25 | 40 | 25 | 20 | 25 | 15 | 50 |
| Blackgrass | 5 | 5 | 40 | 35 | 5 | 35 | 45 | 5 | 0 | 5 | 50 | 5 | 0 | 35 |
| Chickweed | 90 | 90 | 98 | 95 | 90 | — | — | — | — | — | — | 70 | — | 98 |
| Corn | 10 | 0 | 20 | 5 | 5 | 5 | 10 | 5 | 15 | 0 | 0 | 0 | 5 | 25 |
| Crabgrass, Large | 20 | 5 | 30 | 15 | 15 | 5 | 10 | 20 | 30 | 20 | 10 | 10 | 10 | 40 |
| Foxtail, Giant | 15 | 5 | 75 | 20 | 40 | 25 | 25 | 45 | 60 | 60 | 30 | 5 | 25 | 75 |
| *Galium* | 95 | 80 | 100 | 95 | 95 | 95 | 95 | 90 | 90 | 90 | 95 | 90 | 95 | 95 |
| Johnsongrass | 10 | 5 | 15 | 5 | 5 | 10 | 10 | 5 | 10 | 10 | 5 | 25 | 10 | 20 |
| *Kochia* | 90 | 85 | 60 | 95 | 90 | 100 | 100 | 95 | 100 | 95 | 100 | 60 | 98 | 30 |
| Lambsquarters | 95 | 80 | 95 | 98 | 90 | 98 | 98 | 90 | 90 | 90 | 95 | 60 | 98 | 98 |
| Morningglory | 95 | 75 | 100 | 80 | 80 | 100 | 100 | 98 | 98 | 100 | 100 | 65 | 98 | 98 |
| Nutsedge, Yellow | 60 | 35 | 75 | 75 | 55 | 90 | 80 | 55 | 85 | 65 | 75 | 40 | 90 | 85 |
| Oat, Wild | 80 | 20 | 90 | 80 | 60 | 90 | 90 | 75 | 70 | 80 | 90 | 55 | 95 | 90 |
| Oilseed Rape | 80 | 0 | 0 | 0 | 10 | 98 | 100 | 98 | 98 | 98 | 95 | 0 | 98 | 20 |
| Pigweed | 90 | 85 | 95 | 70 | 55 | 98 | 100 | 80 | 98 | 85 | 95 | 65 | 100 | 70 |
| Ragweed | 90 | 55 | 90 | 90 | 95 | 0 | 5 | 0 | 20 | 0 | 0 | 30 | 0 | 85 |
| Ryegrass, Italian | 85 | 75 | 90 | 90 | 85 | 10 | 15 | 10 | 30 | 5 | 10 | 60 | 15 | 85 |
| Soybean | 10 | 10 | 10 | 15 | 0 | 40 | 70 | 10 | 10 | 10 | 55 | 15 | 40 | 25 |
| Velvetleaf | 85 | 30 | 95 | 70 | 40 | 90 | 90 | 95 | 90 | 90 | 80 | 25 | 90 | 65 |
| Waterhemp | 90 | 85 | 70 | 85 | 60 | 100 | 100 | 80 | 65 | 95 | 100 | 55 | 100 | 75 |
| Wheat | 0 | 5 | 35 | 5 | 0 | 35 | 50 | 45 | 90 | 40 | 55 | 35 | 50 | 0 |

| 62 g ai/ha Post-emergence | Compounds | | | | | | | |
|---|---|---|---|---|---|---|---|---|
| | 153 | 154 | 161 | 162 | 164 | 165 | 171 | 176 |
| Barnyardgrass | 60 | 85 | 35 | 20 | 25 | 15 | 35 | 5 |
| Blackgrass | 85 | 65 | 40 | 15 | 15 | 15 | 30 | 0 |
| Chickweed | 95 | 90 | 70 | 90 | 90 | 90 | 90 | — |
| Corn | 35 | 5 | 5 | 0 | 0 | 0 | 0 | 10 |
| Crabgrass, Large | 50 | 70 | 5 | 5 | 5 | 5 | 20 | 5 |
| Foxtail, Giant | 85 | 90 | 5 | 15 | 10 | 5 | 25 | 15 |
| *Galium* | 95 | 95 | 80 | 90 | 95 | 85 | 95 | 5 |
| Johnsongrass | 5 | 5 | 5 | 5 | 5 | 5 | 5 | 5 |
| *Kochia* | 70 | 50 | 70 | 80 | 85 | 40 | 95 | 90 |
| Lambsquarters | 90 | 85 | 90 | 95 | 85 | 75 | 95 | 80 |
| Morningglory | 100 | 98 | 90 | 85 | 85 | 70 | 100 | 85 |
| Nutsedge, Yellow | 90 | 60 | 10 | 25 | 20 | 30 | 75 | 5 |
| Oat, Wild | 95 | 80 | 50 | 60 | 45 | 45 | 90 | 5 |
| Oilseed Rape | 90 | 90 | 70 | 0 | 0 | 0 | 0 | 95 |
| Pigweed | 75 | 85 | 80 | 80 | 80 | 70 | 80 | 30 |
| Ragweed | 90 | 75 | 80 | 85 | 80 | 55 | 100 | 0 |
| Ryegrass, Italian | 95 | 90 | 80 | 70 | 60 | 50 | 95 | 0 |
| Soybean | 10 | 20 | 30 | 0 | 0 | 10 | 30 | 10 |
| Velvetleaf | 85 | 85 | 65 | 15 | 60 | 25 | 70 | 25 |

TABLE C-continued

| | | | | | | | | | |
|---|---|---|---|---|---|---|---|---|---|
| Waterhemp | 65 | 80 | 90 | 65 | 70 | 70 | 95 | 40 | |
| Wheat | 20 | 5 | 0 | 10 | 5 | 5 | 15 | 5 | |

| 31 g ai/ha Post-emergence | Compounds | | | | | | | | | | | | | |
|---|---|---|---|---|---|---|---|---|---|---|---|---|---|---|
| | 1 | 2 | 10 | 11 | 14 | 16 | 20 | 21 | 22 | 23 | 25 | 26 | 27 | 28 |
| Barnyardgrass | 0 | 10 | 35 | 0 | 5 | 5 | 5 | 35 | 5 | 40 | 15 | 20 | 15 | 20 |
| Blackgrass | 20 | 45 | 0 | 5 | 0 | 0 | 5 | 80 | 0 | 50 | 30 | 50 | 50 | 50 |
| Chickweed | 95 | 95 | 90 | 60 | 90 | 75 | 90 | 95 | 90 | 100 | 90 | 95 | 95 | 95 |
| Corn | 0 | 0 | 0 | 0 | 0 | 0 | 5 | 5 | 0 | 10 | 5 | 0 | 0 | 5 |
| Crabgrass, Large | 20 | 10 | 10 | 0 | 5 | 5 | 5 | 30 | 0 | 5 | 5 | 5 | 5 | 25 |
| Foxtail, Giant | 35 | 20 | 70 | 5 | 20 | 55 | 0 | 55 | 10 | 30 | 35 | 15 | 60 | 60 |
| *Galium* | 90 | 95 | 5 | 75 | 50 | 60 | 98 | 98 | 90 | 95 | 90 | 90 | 100 | 100 |
| Johnsongrass | 0 | 5 | 0 | 0 | 0 | 0 | 5 | 10 | 5 | 5 | 0 | 5 | 10 | 5 |
| *Kochia* | 95 | 50 | 60 | 85 | 85 | 0 | 50 | 80 | 90 | 95 | 95 | 80 | 75 | 70 |
| Lambsquarters | 85 | 85 | 50 | 80 | 80 | 10 | 80 | 85 | 70 | 85 | 90 | 75 | 85 | 85 |
| Morningglory | 100 | 100 | 55 | 70 | 65 | 45 | 100 | 85 | 100 | 100 | 100 | 98 | 100 | 95 |
| Nutsedge, Yellow | — | 80 | — | 5 | — | — | 45 | 85 | 35 | 60 | 65 | 5 | 85 | 75 |
| Oat, Wild | 50 | 75 | 5 | 40 | 10 | 5 | 0 | 90 | 40 | 85 | 60 | 60 | 85 | 95 |
| Oilseed Rape | 0 | 65 | 0 | 0 | 0 | 0 | 0 | 65 | 5 | 5 | 0 | 0 | 5 | 5 |
| Pigweed | 95 | 80 | 55 | 50 | 55 | 40 | 75 | 70 | 85 | 90 | 90 | 75 | 55 | 60 |
| Ragweed | 90 | 80 | 5 | 0 | 15 | 0 | 80 | 85 | 70 | 85 | 90 | 15 | 70 | 65 |
| Ryegrass, Italian | 80 | 60 | 5 | 70 | 40 | 10 | 55 | 90 | 60 | 85 | 70 | 85 | 80 | 80 |
| Soybean | 0 | 0 | 0 | 0 | 0 | 0 | 0 | 0 | 0 | 5 | 0 | 5 | 0 | 0 |
| Velvetleaf | 80 | 100 | 40 | 0 | 10 | 5 | 25 | 75 | 20 | 70 | 70 | 5 | 80 | 70 |
| Waterhemp | 95 | 65 | 40 | 80 | 5 | 5 | 70 | 40 | 75 | 80 | 75 | 75 | 65 | 60 |
| Wheat | 0 | 0 | 0 | 0 | 0 | 0 | 0 | 0 | 0 | 10 | 0 | 0 | 0 | 0 |

| 31 g ai/ha Post-emergence | Compounds | | | | | | | | | | | | | |
|---|---|---|---|---|---|---|---|---|---|---|---|---|---|---|
| | 29 | 32 | 33 | 34 | 35 | 36 | 37 | 40 | 41 | 42 | 47 | 51 | 52 | 54 |
| Barnyardgrass | 15 | 10 | 25 | 20 | 20 | 15 | 25 | 5 | 25 | 20 | 15 | 5 | 5 | 15 |
| Blackgrass | 40 | 30 | 0 | 10 | 15 | 5 | 35 | 5 | 30 | 30 | 0 | 0 | 0 | 15 |
| Chickweed | 95 | 90 | 85 | 90 | 95 | 80 | 90 | 55 | 95 | 90 | 90 | 50 | 95 | 95 |
| Corn | 0 | 0 | 0 | 0 | 5 | 0 | 0 | 0 | 5 | 0 | 0 | 0 | 0 | 0 |
| Crabgrass, Large | 10 | 10 | 10 | 5 | 20 | 25 | 10 | 5 | 5 | 10 | 20 | 0 | 0 | 20 |
| Foxtail, Giant | 30 | 15 | 20 | 10 | 50 | 30 | 25 | 5 | 15 | 25 | 50 | 5 | 0 | 20 |
| *Galium* | 90 | 90 | 90 | 90 | 90 | 90 | 90 | 80 | 100 | 95 | 80 | 85 | 90 | 95 |
| Johnsongrass | 0 | 5 | 0 | 5 | 20 | 0 | 0 | 0 | 5 | 5 | 10 | 0 | 5 | 5 |
| *Kochia* | 60 | 50 | 20 | 10 | 30 | 50 | 0 | 70 | 100 | 90 | 75 | 0 | 0 | 50 |
| Lambsquarters | 80 | 85 | 90 | 90 | 80 | 90 | 90 | 70 | 90 | 85 | 85 | 5 | 55 | 95 |
| Morningglory | 85 | 90 | 85 | 85 | 100 | 90 | 90 | 55 | 95 | 75 | 100 | 5 | 98 | 95 |
| Nutsedge, Yellow | 25 | 55 | 5 | 45 | 75 | 20 | 20 | 0 | 65 | 65 | 40 | 35 | 60 | 10 |
| Oat, Wild | 60 | 70 | 35 | 80 | 40 | 50 | 60 | 35 | 55 | 75 | 5 | 0 | 0 | 45 |
| Oilseed Rape | 0 | 10 | 40 | 30 | — | 40 | 40 | 5 | 0 | 0 | 0 | 0 | 0 | 70 |
| Pigweed | 95 | 75 | 30 | 90 | 60 | 70 | 85 | 35 | 65 | 85 | 90 | 60 | 30 | 85 |
| Ragweed | 80 | 85 | 85 | 85 | 25 | 90 | 90 | 45 | 70 | 90 | 80 | 10 | 55 | 90 |
| Ryegrass, Italian | 70 | 85 | 30 | 80 | 35 | 55 | 80 | 50 | 80 | 65 | 0 | 35 | 10 | 50 |
| Soybean | 0 | 15 | 0 | 5 | 0 | 0 | 10 | 5 | 15 | 0 | 0 | 0 | 0 | 5 |
| Velvetleaf | 35 | 10 | 10 | 50 | 100 | 65 | 20 | 5 | 30 | 45 | 70 | 5 | 5 | 45 |
| Waterhemp | 70 | 70 | 25 | 85 | 25 | 85 | 85 | 65 | 75 | 75 | 90 | 30 | 10 | 85 |
| Wheat | 5 | 5 | 0 | 5 | 0 | 0 | 30 | 10 | 10 | 0 | 0 | 0 | 0 | 0 |

TABLE C-continued

| 31 g ai/ha Post-emergence | Compounds | | | | | | | | | | | | | |
|---|---|---|---|---|---|---|---|---|---|---|---|---|---|---|
| | 56 | 57 | 59 | 60 | 65 | 66 | 67 | 69 | 72 | 73 | 75 | 78 | 79 | 80 |
| Barnyardgrass | 0 | 90 | 20 | 20 | 10 | 15 | 25 | 25 | 35 | 25 | 25 | 15 | 20 | 25 |
| Blackgrass | 0 | 5 | 65 | 50 | 5 | 10 | 40 | 15 | 60 | 40 | 5 | 0 | 5 | 15 |
| Chickweed | 5 | 90 | 90 | 90 | 55 | 90 | 90 | 90 | 90 | 90 | 95 | 30 | 90 | 90 |
| Corn | 0 | 0 | 5 | 10 | 5 | 0 | 5 | 0 | 5 | 5 | 5 | 0 | 0 | 0 |
| Crabgrass, Large | 0 | 10 | 15 | 15 | 5 | 25 | 35 | 5 | 10 | 30 | 5 | 5 | 20 | 10 |
| Foxtail, Giant | 0 | 70 | 45 | 45 | 10 | 40 | 70 | 5 | 50 | 40 | 5 | 15 | 35 | 25 |
| *Galium* | 80 | 95 | 95 | 100 | 85 | 90 | 90 | 90 | 80 | 90 | 90 | 70 | 95 | 90 |
| Johnsongrass | 0 | 5 | 5 | 5 | 5 | 5 | 5 | 5 | 5 | 5 | 5 | 5 | 5 | 5 |
| *Kochia* | 70 | 50 | 95 | 90 | 90 | 90 | 0 | 90 | 60 | 90 | 90 | 45 | 50 | 90 |
| Lambsquarters | 0 | 70 | 90 | 85 | 90 | 90 | 85 | 85 | 85 | 90 | 100 | 40 | 85 | 95 |
| Morningglory | 35 | 95 | 95 | 90 | 75 | 90 | 95 | 90 | 80 | 75 | 98 | 20 | 100 | 100 |
| Nutsedge, Yellow | 0 | 90 | 65 | 85 | 25 | 65 | 65 | 40 | 30 | 80 | 25 | 0 | 85 | 65 |
| Oat, Wild | 5 | 20 | 80 | 85 | 25 | 55 | 80 | 45 | 85 | 75 | 40 | 35 | 50 | 90 |
| Oilseed Rape | 0 | 0 | 5 | 5 | 0 | 0 | 40 | 40 | 40 | 10 | 70 | 0 | 20 | 5 |
| Pigweed | 80 | 60 | 90 | 85 | 90 | 95 | 100 | 70 | 85 | 80 | 85 | 50 | 90 | 85 |
| Ragweed | 0 | 60 | 90 | 85 | 55 | 85 | 70 | 70 | 80 | 85 | 95 | 10 | 90 | 98 |
| Ryegrass, Italian | 40 | 25 | 85 | 90 | 65 | 60 | 80 | 85 | 85 | 85 | 80 | 55 | 50 | 80 |
| Soybean | 0 | 0 | 0 | 15 | 5 | 0 | 5 | 10 | 10 | 0 | 20 | 0 | 0 | 0 |
| Velvetleaf | 0 | 90 | 80 | 40 | 10 | 55 | 70 | 40 | 45 | 40 | 70 | 0 | 75 | 70 |
| Waterhemp | 55 | 50 | 85 | 65 | 60 | 98 | 60 | 85 | 70 | 75 | 100 | 75 | 85 | 85 |
| Wheat | 0 | 0 | 0 | 5 | 0 | 0 | 0 | 0 | 30 | 10 | 0 | 0 | 0 | 0 |

| 31 g ai/ha Post-emergence | Compounds | | | | | | | | | | | | | |
|---|---|---|---|---|---|---|---|---|---|---|---|---|---|---|
| | 81 | 82 | 83 | 84 | 85 | 87 | 88 | 89 | 90 | 91 | 97 | 98 | 99 | 100 |
| Barnyardgrass | 25 | 20 | 25 | 10 | 25 | 25 | 35 | 5 | 30 | 25 | 0 | 60 | 25 | 10 |
| Blackgrass | 60 | 10 | 40 | 10 | 70 | 10 | 40 | 0 | 10 | 0 | 0 | 5 | 20 | 5 |
| Chickweed | 90 | 90 | 90 | 90 | 90 | 90 | 95 | 90 | 90 | 95 | 0 | 95 | 90 | 90 |
| Corn | 0 | 35 | 5 | 0 | 0 | 5 | 0 | 5 | 5 | 0 | 0 | 5 | 0 | 5 |
| Crabgrass, Large | 25 | 10 | 20 | 5 | 35 | 5 | 25 | 0 | 5 | 15 | 0 | 10 | 20 | 5 |
| Foxtail, Giant | 80 | 35 | 75 | 40 | 75 | 35 | 80 | 5 | 20 | 10 | 5 | 90 | 5 | 20 |
| *Galium* | 90 | 90 | 90 | 90 | 95 | 90 | 95 | 90 | 90 | 90 | 45 | 95 | 90 | 90 |
| Johnsongrass | 5 | 5 | 5 | 0 | 5 | 0 | 5 | 0 | 5 | 0 | 0 | 0 | 5 | 0 |
| *Kochia* | 40 | 90 | 40 | 85 | 30 | 90 | 30 | 85 | 95 | 75 | 0 | 0 | 20 | 80 |
| Lambsquarters | 95 | 90 | 95 | 90 | 85 | 95 | 85 | 85 | 95 | 98 | 0 | 98 | 75 | 80 |
| Morningglory | 95 | 100 | 98 | 90 | 98 | 98 | 95 | 90 | 100 | 100 | 10 | 100 | 75 | 100 |
| Nutsedge, Yellow | 70 | 65 | 85 | 80 | 75 | 70 | 65 | 40 | 70 | 20 | 0 | 10 | 30 | 5 |
| Oat, Wild | 85 | 55 | 90 | 85 | 90 | 85 | 90 | 5 | 70 | 50 | 5 | 70 | 60 | 50 |
| Oilseed Rape | 45 | 35 | 50 | 5 | 5 | 10 | 20 | 0 | 0 | 60 | 0 | 0 | 0 | 30 |
| Pigweed | 80 | 85 | 80 | 85 | 85 | 75 | 65 | 80 | 75 | 98 | 20 | 100 | 75 | 75 |
| Ragweed | 70 | 90 | 70 | 85 | 75 | 90 | 80 | 80 | 85 | 75 | 0 | 100 | 70 | 98 |
| Ryegrass, Italian | 85 | 80 | 80 | 80 | 85 | 80 | 80 | 45 | 85 | 60 | 10 | 40 | 85 | 65 |
| Soybean | 0 | 10 | 0 | 0 | 0 | 0 | 0 | 0 | 40 | 0 | 0 | 5 | 0 | 0 |
| Velvetleaf | 75 | 70 | 85 | 60 | 75 | 75 | 75 | 25 | 35 | 50 | 0 | 55 | 35 | 20 |
| Waterhemp | 60 | 85 | 85 | 80 | 85 | 85 | 60 | 30 | 85 | 50 | 5 | 98 | 75 | 85 |
| Wheat | 0 | 0 | 0 | 0 | 0 | 0 | 0 | 0 | 5 | 0 | 0 | 10 | 0 | 0 |

| 31 g ai/ha Post-emergence | Compounds | | | | | | | | | | | | | |
|---|---|---|---|---|---|---|---|---|---|---|---|---|---|---|
| | 102 | 104 | 105 | 106 | 107 | 108 | 109 | 111 | 113 | 114 | 115 | 121 | 123 | 125 |
| Barnyardgrass | 20 | 20 | 10 | 15 | 35 | 20 | 25 | 10 | 25 | 30 | 10 | 20 | 20 | 35 |

TABLE C-continued

| | | | | | | | | | | | | | | |
|---|---|---|---|---|---|---|---|---|---|---|---|---|---|---|
| Blackgrass | 0 | 15 | 15 | 45 | 0 | 15 | 20 | 0 | 15 | 0 | 0 | 0 | 15 | 20 |
| Chickweed | 95 | 90 | 90 | 95 | 90 | 90 | 80 | 95 | 90 | 90 | 80 | 90 | 90 | 95 |
| Corn | 0 | 5 | 10 | 0 | 5 | 5 | 0 | 5 | 5 | 0 | 5 | 0 | 10 | 5 |
| Crabgrass, Large | 5 | 20 | 20 | 25 | 15 | 5 | 35 | 10 | 5 | 10 | 10 | 10 | 10 | 25 |
| Foxtail, Giant | 20 | 50 | 40 | 70 | 15 | 30 | 45 | 15 | 20 | 10 | 5 | 20 | 20 | 70 |
| *Galium* | 90 | 95 | 95 | 95 | 95 | 90 | 98 | 95 | 95 | 95 | 85 | 90 | 95 | 95 |
| Johnson-grass | 0 | 10 | 5 | 5 | 0 | 0 | 0 | 10 | 0 | 5 | 5 | 0 | 5 | 5 |
| *Kochia* | 0 | 95 | 95 | 70 | 70 | 90 | 95 | 80 | 95 | 30 | 70 | 90 | 95 | 85 |
| Lambsquarters | 75 | 90 | 85 | 85 | 85 | 90 | 95 | 90 | 98 | 95 | 70 | 90 | 95 | 90 |
| Morning-glory | 100 | 98 | 100 | 100 | 95 | 98 | 95 | 100 | 98 | 95 | 55 | 98 | 95 | 95 |
| Nutsedge, Yellow | 20 | 55 | 55 | 65 | 80 | 30 | 45 | 35 | 70 | 10 | 40 | 45 | 55 | 35 |
| Oat, Wild | 5 | 80 | 60 | 50 | 20 | 80 | 80 | 55 | 90 | 40 | 55 | 65 | 70 | 85 |
| Oilseed Rape | 0 | 85 | 5 | 60 | 25 | 80 | 70 | 80 | 0 | 15 | 0 | 70 | 0 | 0 |
| Pigweed | 75 | 95 | 85 | 70 | 85 | 90 | 95 | 85 | 65 | 80 | 30 | 75 | 65 | 95 |
| Ragweed | 95 | 85 | 90 | 80 | 85 | 90 | 80 | 98 | 90 | 90 | 60 | 75 | 75 | 95 |
| Ryegrass, Italian | 0 | 90 | 85 | 85 | 40 | 90 | 90 | 85 | 90 | 60 | 90 | 85 | 90 | 85 |
| Soybean | 0 | 0 | 5 | 0 | 0 | 10 | 0 | 0 | 15 | 0 | 10 | 0 | 10 | 0 |
| Velvetleaf | 30 | 50 | 75 | 80 | 75 | 70 | 75 | 40 | 70 | 25 | 15 | 10 | 65 | 85 |
| Waterhemp | 25 | 70 | 80 | 65 | 75 | 85 | 80 | 40 | 85 | 25 | 65 | 60 | 80 | 85 |
| Wheat | 0 | 0 | 0 | 0 | 0 | 0 | 0 | 10 | 5 | 0 | 0 | 5 | 5 | 0 |

| 31 g ai/ha Post-emergence | Compounds | | | | | | | | | | | | | |
|---|---|---|---|---|---|---|---|---|---|---|---|---|---|---|
| | 126 | 127 | 129 | 130 | 132 | 133 | 134 | 136 | 137 | 138 | 139 | 143 | 144 | 145 |
| Barnyardgrass | 25 | 10 | 50 | 30 | 15 | 15 | 10 | 15 | 25 | 25 | 25 | 20 | 65 | 20 |
| Blackgrass | 5 | 0 | 35 | 30 | 5 | 45 | 50 | 10 | 0 | 5 | 20 | 5 | 35 | 5 |
| Chickweed | 90 | 50 | 98 | 90 | 90 | — | — | — | — | — | — | 45 | — | — |
| Corn | 10 | 0 | 0 | 5 | 0 | 5 | 5 | 0 | 5 | 0 | 5 | 5 | 30 | 10 |
| Crabgrass, Large | 10 | 0 | 20 | 10 | 15 | 0 | 5 | 10 | 30 | 15 | 20 | 10 | 30 | 15 |
| Foxtail, Giant | 5 | 5 | 60 | 20 | 30 | 25 | 15 | 35 | 45 | 35 | 20 | 5 | 70 | 20 |
| *Galium* | 90 | 75 | 95 | 95 | 90 | 90 | 95 | 90 | 85 | 90 | 95 | 65 | 95 | 90 |
| Johnson-grass | 10 | 5 | 10 | 5 | 0 | 5 | 10 | 5 | 10 | 10 | 5 | 10 | 10 | 10 |
| *Kochia* | 90 | 40 | 50 | 95 | 85 | 98 | 95 | 95 | 100 | 90 | 95 | 30 | 98 | 95 |
| Lambsquarters | 80 | 70 | 95 | 90 | 90 | 95 | 100 | 90 | 90 | 90 | 98 | 50 | 90 | 98 |
| Morning-glory | 95 | 65 | 98 | 75 | 65 | 100 | 98 | 98 | 100 | 98 | 98 | 50 | 98 | 95 |
| Nutsedge, Yellow | 35 | 10 | 60 | 55 | 30 | 75 | 75 | 15 | 65 | 45 | 55 | 10 | 75 | 70 |
| Oat, Wild | 60 | 10 | 85 | 60 | 40 | 90 | 90 | 50 | 70 | 50 | 90 | 40 | 90 | 95 |
| Oilseed Rape | 60 | 0 | 0 | 0 | 5 | 95 | 95 | 95 | 95 | 95 | 95 | 0 | 95 | 98 |
| Pigweed | 85 | 70 | 95 | 50 | 50 | 80 | 80 | 75 | 90 | 80 | 80 | 50 | 90 | 70 |
| Ragweed | 85 | 10 | 90 | 85 | 65 | 0 | 0 | 0 | 10 | 0 | 0 | 0 | 35 | 0 |
| Ryegrass, Italian | 80 | 50 | 70 | 90 | 80 | 5 | 5 | 5 | 10 | 5 | 5 | 55 | 70 | 5 |
| Soybean | 5 | 0 | 0 | 10 | 0 | 55 | 75 | 5 | 10 | 10 | 45 | 0 | 25 | 40 |
| Velvetleaf | 30 | 20 | 85 | 75 | 30 | 85 | 80 | 75 | 85 | 85 | 70 | 20 | 85 | 85 |
| Waterhemp | 75 | 70 | 75 | 70 | 40 | 95 | 98 | 80 | 85 | 90 | 98 | 40 | 95 | 95 |
| Wheat | 0 | 0 | 10 | 0 | 0 | 25 | 30 | 35 | 75 | 60 | 45 | 5 | 95 | 40 |

| 31 g ai/ha Post-emergence | Compounds | | | | | | | | |
|---|---|---|---|---|---|---|---|---|---|
| | 151 | 153 | 154 | 161 | 162 | 164 | 165 | 171 | 176 |
| Barnyardgrass | 40 | 40 | 70 | 20 | 10 | 10 | 10 | 15 | 5 |
| Blackgrass | 45 | 80 | 60 | 10 | 10 | 5 | 5 | 5 | 0 |
| Chickweed | 95 | 90 | 90 | 65 | 90 | 80 | 70 | 90 | — |
| Corn | 20 | 20 | 15 | 0 | 0 | 0 | 0 | 0 | 0 |
| Crabgrass, Large | 35 | 55 | 65 | 0 | 0 | 0 | 0 | 5 | 10 |
| Foxtail, Giant | 60 | 80 | 85 | 0 | 5 | 5 | 0 | 10 | 5 |

TABLE C-continued

| | | | | | | | | | |
|---|---|---|---|---|---|---|---|---|---|
| *Galium* | 95 | 95 | 95 | 80 | 90 | 90 | 85 | 95 | 0 |
| Johnson-grass | 10 | 10 | 5 | 10 | 5 | 5 | 0 | 5 | 5 |
| *Kochia* | 60 | 40 | 50 | 70 | 70 | 60 | 45 | 95 | 90 |
| Lambs-quarters | 95 | 85 | 90 | 80 | 85 | 70 | 70 | 90 | 60 |
| Morning-glory | 98 | 98 | 95 | 90 | 60 | 80 | 75 | 90 | 85 |
| Nutsedge, Yellow | 80 | 85 | 70 | 5 | 20 | 20 | 20 | 50 | 5 |
| Oat, Wild | 70 | 90 | 55 | 60 | 50 | 35 | 40 | 65 | 0 |
| Oilseed Rape | 65 | 90 | 75 | 50 | 0 | 0 | 0 | 0 | 95 |
| Pigweed | 75 | 85 | 65 | 80 | 75 | 70 | 75 | 60 | 20 |
| Ragweed | 60 | 70 | 70 | 70 | 70 | 70 | 40 | 75 | 0 |
| Ryegrass, Italian | 60 | 90 | 80 | 70 | 60 | 50 | 40 | 90 | 0 |
| Soybean | 5 | 5 | 10 | 15 | 0 | 0 | 10 | 10 | 5 |
| Velvetleaf | 60 | 85 | 70 | 45 | 5 | 25 | 20 | 35 | 0 |
| Waterhemp | 55 | 70 | 75 | 85 | 45 | 60 | 65 | 75 | 20 |
| Wheat | 0 | 15 | 0 | 0 | 0 | 5 | 5 | 0 | 0 |

| 16 g ai/ha Post-emergence | Compounds | | | | |
|---|---|---|---|---|---|
| | 35 | 40 | 143 | 144 | 151 |
| Barnyard-grass | 10 | 5 | 15 | 35 | 30 |
| Blackgrass | 5 | 5 | 0 | 20 | 40 |
| Chickweed | 90 | 50 | 30 | — | 95 |
| Corn | 0 | 0 | 0 | 5 | 25 |
| Crabgrass, Large | 5 | 5 | 5 | 25 | 30 |
| Foxtail, Giant | 35 | 5 | 5 | 60 | 40 |
| *Galium* | 90 | 30 | 60 | 90 | 95 |
| Johnson-grass | 15 | 0 | 10 | 10 | 5 |
| *Kochia* | 30 | 20 | 0 | 98 | 10 |
| Lambs-quarters | 75 | 50 | 10 | 90 | 80 |
| Morning-glory | 100 | 5 | 30 | 98 | 98 |
| Nutsedge, Yellow | 60 | 0 | 10 | 60 | 55 |
| Oat, Wild | 30 | 5 | 30 | 90 | 50 |
| Oilseed Rape | 0 | 0 | 60 | 95 | 50 |
| Pigweed | 25 | 15 | 50 | 85 | 55 |
| Ragweed | 0 | 25 | 0 | 35 | 35 |
| Ryegrass, Italian | 30 | 10 | 45 | 45 | 40 |
| Soybean | 0 | 35 | 0 | 25 | 5 |
| Velvetleaf | 75 | 5 | 30 | 90 | 60 |
| Waterhemp | 30 | 20 | 25 | 90 | 55 |
| Wheat | 0 | 0 | 0 | 95 | 0 |

| 8 g ai/ha Post-emergence | Compounds | | |
|---|---|---|---|
| | 35 | 144 | 151 |
| Barnyard-grass | 10 | 25 | 25 |
| Blackgrass | 0 | 30 | 10 |
| Chickweed | 90 | — | 90 |
| Corn | 0 | 0 | 20 |
| Crabgrass, Large | 5 | 20 | 5 |
| Foxtail, Giant | 25 | 50 | 20 |
| *Galium* | 90 | 90 | 95 |
| Johnson-grass | 10 | 10 | 5 |
| *Kochia* | — | 90 | 0 |
| Lambs-quarters | 35 | 90 | 80 |
| Morning-glory | 100 | 95 | 95 |

TABLE C-continued

|  |  |  |  |  |
|---|---|---|---|---|
| Nutsedge, Yellow | | 45 | 60 | 55 |
| Oat, Wild | | 10 | 90 | 35 |
| Oilseed Rape | | 0 | 95 | 30 |
| Pigweed | | 35 | 85 | 65 |
| Ragweed | | 0 | 10 | 10 |
| Ryegrass, Italian | | 10 | 35 | 40 |
| Soybean | | 0 | 40 | 0 |
| Velvetleaf | | 60 | 70 | 15 |
| Waterhemp | | 0 | 90 | 30 |
| Wheat | | 0 | 90 | 0 |

| | 4 g ai/ha Post-emergence | Compound 144 |
|---|---|---|
| | Barnyardgrass | 15 |
| | Blackgrass | 30 |
| | Corn | 0 |
| | Crabgrass, Large | 20 |
| | Foxtail, Giant | 45 |
| | *Galium* | 80 |
| | Johnsongrass | 20 |
| | *Kochia* | 90 |
| | Lambsquarters | 80 |
| | Morningglory | 90 |
| | Nutsedge, Yellow | 10 |
| | Oat, Wild | 80 |
| | Oilseed Rape | 85 |
| | Pigweed | 80 |
| | Ragweed | 10 |
| | Ryegrass, Italian | 20 |
| | Soybean | 45 |
| | Velvetleaf | 50 |
| | Waterhemp | 90 |
| | Wheat | 90 |

| 250 g ai/ha Pre-emergence | Compounds | | | | | | | | | | | | | |
|---|---|---|---|---|---|---|---|---|---|---|---|---|---|---|
| | 1 | 2 | 10 | 11 | 20 | 21 | 22 | 23 | 25 | 27 | 28 | 29 | 32 | 34 |
| Barnyardgrass | 90 | 98 | 5 | 80 | 85 | 100 | 60 | 85 | 85 | 90 | 95 | 90 | 100 | 75 |
| Blackgrass | 90 | 95 | 0 | 85 | 80 | 90 | 45 | 90 | 90 | 90 | 90 | 85 | 90 | 90 |
| Corn | 5 | 10 | 5 | 0 | 35 | 65 | 35 | 65 | 10 | 0 | 15 | 45 | 35 | 0 |
| Crabgrass, Large | 100 | 95 | 0 | 40 | 60 | 100 | 35 | 95 | 90 | 98 | 85 | 90 | 100 | 30 |
| Foxtail, Giant | 100 | 100 | 0 | 90 | 85 | 100 | 85 | 100 | 100 | 100 | 100 | 95 | 85 | 70 |
| *Galium* | 100 | 100 | 45 | 95 | 95 | 100 | 95 | 100 | 98 | 95 | 95 | 98 | 98 | 100 |
| Johnsongrass | 5 | 5 | 0 | 0 | 10 | 50 | 0 | 35 | 20 | 25 | 10 | 20 | 45 | 20 |
| Lambsquarters | 100 | 100 | 30 | 100 | 90 | 100 | 90 | 95 | 95 | 98 | 90 | 90 | 90 | 75 |
| Morningglory | 100 | 100 | 55 | 100 | 100 | 100 | 100 | 98 | 100 | 100 | 100 | 98 | 98 | 95 |
| Nutsedge, Yellow | 75 | 95 | 0 | 30 | 95 | 85 | 70 | 90 | 80 | 95 | 70 | 85 | 60 | 65 |
| Oilseed Rape | 20 | 65 | 0 | 0 | 20 | 100 | 80 | 100 | 35 | 98 | 90 | 70 | 100 | 90 |
| Pigweed | 100 | 100 | 30 | 100 | 100 | 100 | 100 | 100 | 100 | 100 | 100 | 100 | 100 | 100 |
| Ragweed | 98 | 98 | 5 | 90 | 75 | 100 | 100 | 90 | 95 | 95 | 90 | 90 | 98 | 95 |
| Ryegrass, Italian | 100 | 98 | 80 | 100 | 95 | 95 | 95 | 95 | 95 | 95 | 95 | 90 | 95 | 95 |
| Soybean | 0 | 0 | 0 | 0 | 30 | 20 | 5 | 55 | 5 | 0 | 50 | 0 | 55 | 5 |
| Velvetleaf | 98 | 100 | 50 | 90 | 100 | 98 | 98 | 100 | 98 | 98 | 95 | 100 | 90 | 98 |
| Waterhemp | 100 | 100 | 90 | 100 | 100 | 100 | 100 | 100 | 100 | 100 | 100 | 100 | 100 | 100 |
| Wheat | 20 | 10 | 0 | 10 | 30 | 40 | 0 | 90 | 5 | 10 | 10 | 50 | 70 | 25 |

TABLE C-continued

| 250 g ai/ha Pre-emergence | Compounds | | | | | | | | | | | | |
|---|---|---|---|---|---|---|---|---|---|---|---|---|---|
| | 36 | 37 | 41 | 42 | 47 | 54 | 57 | 59 | 60 | 66 | 67 | 69 | 72 | 73 |
| Barnyardgrass | 70 | 80 | 95 | 80 | 100 | 85 | 100 | 95 | 90 | 70 | 80 | 75 | 80 | 85 |
| Blackgrass | 30 | 90 | 90 | 90 | 90 | 80 | 80 | 98 | 90 | 30 | 60 | 35 | 90 | 90 |
| Corn | 0 | 20 | 40 | 35 | 5 | 0 | 35 | 65 | 45 | 0 | 0 | 5 | 20 | 25 |
| Crabgrass, Large | 65 | 25 | 70 | 85 | 95 | 60 | 100 | 100 | 95 | 85 | 65 | 10 | 85 | 75 |
| Foxtail, Giant | 85 | 85 | 85 | 100 | 100 | 90 | 100 | 100 | 100 | 85 | 100 | 60 | 85 | 95 |
| *Galium* | 100 | 100 | 98 | 98 | 98 | 100 | 98 | 98 | 100 | 98 | 90 | 98 | 95 | 98 |
| Johnsongrass | 5 | 0 | 35 | 30 | 0 | 10 | 0 | 65 | 60 | 65 | 30 | 35 | 85 | 55 |
| Lambsquarters | 80 | 90 | 90 | 90 | 100 | 80 | 100 | 95 | 90 | 98 | 85 | 95 | 90 | 90 |
| Morningglory | 95 | 98 | 98 | 98 | 95 | 98 | 100 | 100 | 100 | 90 | 90 | 90 | 90 | 95 |
| Nutsedge, Yellow | 65 | 60 | 80 | 80 | 85 | 70 | 95 | 90 | 85 | 65 | 70 | 90 | 70 | 95 |
| Oilseed Rape | 95 | 90 | 100 | 20 | 10 | 100 | 60 | 95 | 90 | 5 | 20 | 40 | 80 | 85 |
| Pigweed | 100 | 100 | 100 | 100 | 100 | 100 | 100 | 100 | 100 | 100 | 100 | 85 | 100 | 98 |
| Ragweed | 95 | 98 | 100 | 100 | 100 | 100 | 100 | 100 | 95 | 95 | 98 | 95 | 95 | 98 |
| Ryegrass, Italian | 85 | 95 | 95 | 90 | 50 | 90 | 85 | 100 | 95 | 90 | 90 | 90 | 90 | 90 |
| Soybean | 20 | 65 | 55 | 5 | 30 | 20 | 0 | 25 | 75 | 0 | 0 | 5 | 0 | 0 |
| Velvetleaf | 90 | 90 | 98 | 98 | 100 | 95 | 100 | 100 | 98 | 85 | 75 | 90 | 85 | 85 |
| Waterhemp | 100 | 100 | 100 | 100 | 100 | 100 | 100 | 100 | 100 | 100 | 85 | 95 | 90 | 95 |
| Wheat | 0 | 45 | 65 | 5 | 0 | 0 | 5 | 85 | 70 | 40 | 0 | 5 | 40 | 60 |

| 250 g ai/ha Pre-emergence | Compounds | | | | | | | | | | | | |
|---|---|---|---|---|---|---|---|---|---|---|---|---|---|
| | 75 | 79 | 80 | 81 | 82 | 83 | 84 | 85 | 87 | 88 | 89 | 90 | 91 | 97 |
| Barnyardgrass | 85 | 85 | 85 | 98 | 90 | 90 | 85 | 90 | 85 | 100 | 65 | 95 | 95 | 35 |
| Blackgrass | 30 | 85 | 90 | 90 | 80 | 90 | 85 | 90 | 90 | 90 | 45 | 55 | 60 | 5 |
| Corn | 10 | 5 | 25 | 30 | 25 | 10 | 0 | 10 | 10 | 20 | 0 | 30 | 25 | 0 |
| Crabgrass, Large | 50 | 30 | 75 | 98 | 80 | 85 | 85 | 85 | 85 | 80 | 75 | 85 | 85 | 60 |
| Foxtail, Giant | 75 | 95 | 98 | 100 | 100 | 100 | 100 | 100 | 95 | 100 | 75 | 95 | 98 | 55 |
| *Galium* | 98 | 98 | 95 | 95 | 95 | 95 | 98 | 95 | 98 | 98 | 98 | — | 98 | 90 |
| Johnsongrass | 10 | 30 | 35 | 98 | 40 | 70 | 30 | 40 | 40 | 60 | 5 | 65 | 25 | 0 |
| Lambsquarters | 90 | 100 | 98 | 95 | 98 | 100 | 100 | 100 | 100 | 90 | 90 | 100 | 100 | 25 |
| Morningglory | 100 | 98 | 98 | 95 | 95 | 98 | 95 | 98 | 95 | 100 | 90 | 98 | 98 | 30 |
| Nutsedge, Yellow | 75 | 90 | 80 | 95 | 90 | 95 | 80 | 80 | 80 | 95 | 90 | 90 | 90 | 0 |
| Oilseed Rape | 98 | 30 | 0 | 95 | 85 | 50 | 80 | 90 | 80 | 30 | 90 | 90 | 100 | 0 |
| Pigweed | 100 | 100 | 100 | 100 | 100 | 100 | 100 | 100 | 100 | 95 | 100 | 100 | 100 | 65 |
| Ragweed | 100 | 100 | 100 | 98 | 95 | 95 | 98 | 98 | 90 | 98 | 90 | 95 | 100 | 10 |
| Ryegrass, Italian | 90 | 90 | 90 | 90 | 90 | 90 | 95 | 90 | 90 | 90 | 90 | 95 | 95 | 30 |
| Soybean | 55 | 0 | 0 | 0 | 0 | 0 | 0 | 0 | 0 | 100 | 5 | 100 | 20 | 20 |
| Velvetleaf | 98 | 95 | 95 | 98 | 90 | 90 | 90 | 90 | 90 | 85 | 85 | 95 | 100 | 30 |
| Waterhemp | 100 | 100 | 100 | 100 | 100 | 100 | 100 | 100 | 100 | 98 | 75 | 100 | 85 | 20 |
| Wheat | 5 | 0 | 0 | 0 | 0 | 0 | 0 | 5 | 0 | 10 | 0 | 40 | 40 | 0 |

| 250 g ai/ha Pre-emergence | Compounds | | | | | | | | | | | | |
|---|---|---|---|---|---|---|---|---|---|---|---|---|---|
| | 99 | 102 | 104 | 105 | 106 | 107 | 108 | 109 | 111 | 113 | 114 | 116 | 121 | 125 |
| Barnyardgrass | 85 | 85 | 80 | 90 | 95 | 98 | 85 | 80 | 85 | 95 | 95 | 95 | 60 | 98 |
| Blackgrass | 90 | 70 | 60 | 90 | 85 | 10 | 85 | 90 | 20 | 60 | 10 | 35 | 60 | 90 |
| Corn | 30 | 30 | 10 | 25 | 20 | 15 | 15 | 0 | 15 | 35 | 5 | 25 | 5 | 55 |
| Crabgrass, Large | 80 | 55 | 60 | 80 | 80 | 85 | 70 | 80 | 80 | 90 | 80 | 90 | 35 | 98 |
| Foxtail, Giant | 90 | 90 | 100 | 100 | 100 | 98 | 95 | 90 | — | — | — | — | 95 | 100 |

TABLE C-continued

| | | | | | | | | | | | | | | |
|---|---|---|---|---|---|---|---|---|---|---|---|---|---|---|
| Galium | 98 | 95 | 98 | 98 | 95 | 95 | 95 | 90 | 100 | 98 | 100 | 100 | 100 | 100 |
| Johnson-grass | 20 | 0 | 30 | 60 | 15 | 20 | 20 | 65 | 20 | 30 | 0 | 10 | 10 | 70 |
| Lambs-quarters | 95 | 100 | 95 | 95 | 100 | 95 | 100 | 100 | 95 | 100 | 95 | 95 | 100 | 100 |
| Morning-glory | 95 | 98 | 98 | 95 | 98 | 98 | 98 | 98 | 98 | 100 | 90 | 98 | 90 | 98 |
| Nutsedge, Yellow | 90 | 75 | 85 | 85 | 90 | 90 | 80 | 80 | 90 | 85 | 95 | 95 | 50 | 90 |
| Oilseed Rape | 98 | 35 | 95 | 10 | 90 | 80 | 90 | 90 | 100 | 90 | 100 | 100 | 85 | 100 |
| Pigweed | 100 | 100 | 100 | 100 | 100 | 100 | 100 | 100 | 100 | 100 | 100 | 100 | 100 | 100 |
| Ragweed | 95 | 100 | 100 | 100 | 95 | 100 | 98 | 100 | 98 | 95 | 98 | 100 | 98 | 100 |
| Ryegrass, Italian | 100 | 70 | 95 | 95 | 90 | 30 | 95 | 95 | 95 | 95 | 95 | 90 | 100 | 95 |
| Soybean | 20 | 5 | 0 | 0 | 0 | 15 | 0 | 0 | 0 | 80 | — | 5 | 0 | 35 |
| Velvetleaf | 95 | 100 | 90 | 95 | 90 | 90 | 90 | 90 | 100 | 100 | 100 | 100 | 95 | 100 |
| Waterhemp | 100 | 85 | 100 | 100 | 90 | 98 | 100 | 100 | 85 | 98 | 80 | 100 | 100 | 100 |
| Wheat | 65 | 25 | 0 | 5 | 0 | 5 | 10 | 15 | 40 | 50 | 35 | 15 | 15 | 90 |

| 250 g ai/ha Pre-emergence | Compounds | | | | | | | | | | | | | |
|---|---|---|---|---|---|---|---|---|---|---|---|---|---|---|
| | 129 | 131 | 132 | 133 | 134 | 136 | 137 | 138 | 139 | 145 | 152 | 153 | 154 | 161 |
| Barnyard-grass | 90 | 35 | 45 | 95 | 90 | 95 | 100 | 98 | 95 | 95 | 70 | 100 | 95 | 30 |
| Blackgrass | 80 | 90 | 50 | 50 | 75 | 90 | 90 | 90 | 90 | 60 | 35 | 95 | 90 | 45 |
| Corn | 40 | 15 | 10 | 10 | 5 | 5 | 55 | 15 | 15 | 15 | 15 | 65 | 5 | 5 |
| Crabgrass, Large | 85 | 80 | 40 | 65 | 60 | 95 | 80 | 80 | 50 | 55 | 10 | 100 | 100 | 40 |
| Foxtail, Giant | 98 | 98 | 98 | 90 | 80 | 98 | 100 | 100 | 95 | 95 | 90 | 100 | 100 | 80 |
| Galium | 98 | 95 | 98 | 100 | 98 | 100 | 100 | 98 | 100 | 98 | 100 | 100 | 100 | 95 |
| Johnson-grass | 25 | 20 | 25 | 40 | 5 | 10 | 20 | 20 | 25 | 5 | 5 | 70 | 75 | 10 |
| Lambs-quarters | 90 | 95 | 100 | 95 | 100 | 100 | 95 | 100 | 98 | 100 | 98 | 98 | 95 | 80 |
| Morning-glory | 98 | 95 | 90 | 95 | 100 | 98 | 98 | 98 | 98 | 100 | 90 | 98 | 90 | 85 |
| Nutsedge, Yellow | 95 | 75 | 75 | 95 | 90 | 80 | 95 | 90 | 90 | 90 | 85 | 95 | 85 | 60 |
| Oilseed Rape | 90 | 80 | 90 | 90 | 98 | 100 | 90 | 100 | 100 | 98 | 100 | 100 | 98 | 90 |
| Pigweed | 100 | 100 | 100 | 100 | 100 | 100 | 100 | 100 | 100 | 100 | 100 | 100 | 100 | 100 |
| Ragweed | 95 | 98 | 100 | 98 | 98 | 100 | 100 | 95 | 100 | 90 | 90 | 100 | 95 | 85 |
| Ryegrass, Italian | 95 | 95 | 95 | 100 | 100 | 90 | 100 | 95 | 100 | 100 | 90 | 95 | 90 | 85 |
| Soybean | 20 | 0 | 0 | 80 | 75 | 20 | 30 | 15 | 80 | 80 | 10 | 45 | 20 | 100 |
| Velvetleaf | 98 | 95 | 95 | 100 | 100 | 100 | 100 | 100 | 100 | 100 | 75 | 90 | 85 | 80 |
| Waterhemp | 100 | 100 | 98 | 100 | 100 | 100 | 98 | 100 | 100 | 100 | 75 | 100 | 100 | 95 |
| Wheat | 85 | 20 | 50 | 40 | 40 | 45 | 90 | 5 | 10 | 5 | 85 | 50 | 30 | 0 |

| 250 g ai/ha Pre-emergence | Compound 171 |
|---|---|
| Barnyard-grass | 95 |
| Blackgrass | 90 |
| Corn | 40 |
| Crabgrass, Large | 80 |
| Foxtail, Giant | — |
| Galium | 100 |
| Johnson-grass | 35 |
| Lambs-quarters | 100 |
| Morning-glory | 98 |
| Nutsedge, Yellow | 90 |
| Oilseed Rape | 90 |
| Pigweed | 100 |
| Ragweed | 98 |
| Ryegrass, Italian | 95 |

TABLE C-continued

|  |  |
|---|---|
| Soybean | 70 |
| Velvetleaf | 100 |
| Waterhemp | 100 |
| Wheat | 70 |

| 125 g ai/ha Pre-emergence | Compounds | | | | | | | | | | | | | |
|---|---|---|---|---|---|---|---|---|---|---|---|---|---|---|
| | 1 | 2 | 10 | 11 | 20 | 21 | 22 | 23 | 25 | 27 | 28 | 29 | 32 | 34 |
| Barnyardgrass | 25 | 95 | 5 | 10 | 60 | 100 | 5 | 85 | 70 | 90 | 90 | 80 | 85 | 65 |
| Blackgrass | 90 | 95 | 0 | 50 | 40 | 90 | 40 | 90 | 90 | 90 | 90 | 85 | 90 | 85 |
| Corn | 0 | 0 | 0 | 0 | 5 | 40 | 0 | 30 | 0 | 5 | 30 | 0 | 0 | 10 |
| Crabgrass, Large | 80 | 98 | 0 | 40 | 15 | 85 | 0 | 75 | 95 | 95 | 80 | 55 | 70 | 25 |
| Foxtail, Giant | 100 | 98 | 0 | 50 | 65 | 100 | 55 | 85 | 90 | 100 | 100 | 90 | 85 | 75 |
| *Galium* | 95 | 100 | 5 | 90 | 95 | 98 | 95 | 100 | 95 | 95 | 95 | 98 | 100 | 90 |
| Johnsongrass | 5 | 5 | 0 | 0 | 0 | 35 | 0 | 35 | 5 | 5 | 5 | 25 | 10 | 0 |
| Lambsquarters | 100 | 100 | — | 100 | 85 | 98 | 90 | 95 | 85 | 95 | 85 | 80 | 85 | 80 |
| Morningglory | 100 | 98 | 25 | 100 | 98 | 100 | 100 | 95 | 95 | 100 | 98 | 95 | 98 | 85 |
| Nutsedge, Yellow | 70 | 70 | 0 | 10 | 95 | 85 | 70 | 85 | 70 | 90 | 85 | 85 | 45 | 35 |
| Oilseed Rape | — | 65 | 0 | 0 | 0 | 100 | 5 | 90 | 5 | 98 | 85 | 5 | 90 | 90 |
| Pigweed | 100 | 100 | 10 | 100 | 100 | 100 | 100 | 100 | 100 | 98 | 100 | 100 | 100 | 100 |
| Ragweed | 100 | 100 | 0 | 80 | 70 | 100 | 90 | 95 | 98 | 100 | 95 | 85 | 95 | 90 |
| Ryegrass, Italian | 100 | 98 | 25 | 100 | 95 | 90 | 95 | 95 | 95 | 90 | 95 | 90 | 95 | 85 |
| Soybean | 0 | 0 | 0 | 0 | 30 | 0 | 0 | 5 | 0 | 10 | 0 | 0 | 40 | 0 |
| Velvetleaf | 100 | 100 | 10 | 90 | 100 | 98 | 75 | 100 | 90 | 85 | 90 | 100 | 85 | 85 |
| Waterhemp | 100 | 100 | 100 | 100 | 100 | 100 | 100 | 100 | 100 | 100 | 85 | 100 | 100 | 100 |
| Wheat | 5 | 0 | 0 | 0 | 35 | 30 | 0 | 90 | 0 | 0 | 0 | 45 | 50 | 5 |

| 125 g ai/ha Pre-emergence | Compounds | | | | | | | | | | | | | |
|---|---|---|---|---|---|---|---|---|---|---|---|---|---|---|
| | 36 | 37 | 41 | 42 | 47 | 54 | 57 | 59 | 60 | 66 | 67 | 69 | 72 | 73 |
| Barnyardgrass | 65 | 70 | 85 | 60 | 85 | 65 | 100 | 90 | 85 | 40 | 40 | 20 | 55 | 70 |
| Blackgrass | 20 | 90 | 85 | 90 | 40 | 55 | 70 | 90 | 90 | 35 | 40 | 60 | 70 | 85 |
| Corn | 0 | 0 | 5 | 10 | 0 | 10 | 0 | 50 | 30 | 0 | 0 | 0 | 0 | 5 |
| Crabgrass, Large | 20 | 20 | 65 | 80 | 60 | 75 | 98 | 85 | 85 | 75 | 10 | 10 | 65 | 75 |
| Foxtail, Giant | 85 | 85 | 85 | 90 | 85 | 75 | 90 | 98 | 100 | 80 | 98 | 25 | 85 | 85 |
| *Galium* | 100 | 95 | 98 | 95 | 98 | 100 | 95 | 98 | 98 | 95 | 90 | 90 | 95 | 95 |
| Johnsongrass | 5 | 5 | 35 | 5 | 0 | 5 | 0 | 45 | 40 | 55 | 10 | 30 | 80 | 35 |
| Lambsquarters | 85 | 85 | 100 | 85 | 100 | 80 | 100 | 95 | 95 | 85 | 85 | 90 | 85 | 80 |
| Morningglory | 90 | 90 | 95 | 98 | 100 | 95 | 100 | 100 | 98 | 80 | 80 | 85 | 90 | 90 |
| Nutsedge, Yellow | 20 | 40 | 75 | 40 | 75 | 25 | 90 | 85 | 85 | 30 | 55 | 25 | 60 | 50 |
| Oilseed Rape | 60 | 60 | 40 | 5 | 0 | 90 | 30 | 95 | 90 | 0 | 0 | 0 | 80 | 90 |
| Pigweed | 100 | 100 | 100 | 100 | 100 | 100 | 100 | 100 | 100 | 100 | 95 | 100 | 98 | 100 |
| Ragweed | 95 | 95 | 95 | 95 | 98 | 95 | 100 | 100 | 95 | 90 | 100 | 90 | 100 | 95 |
| Ryegrass, Italian | 35 | 90 | 95 | 90 | 45 | 80 | 70 | 100 | 95 | 80 | 85 | 90 | 90 | 90 |
| Soybean | 30 | 20 | 50 | 0 | 10 | 0 | 0 | 15 | 65 | 0 | 0 | 5 | 0 | 0 |
| Velvetleaf | 85 | 85 | 95 | 90 | 100 | 90 | 95 | 98 | 95 | 70 | 60 | 75 | 80 | 85 |
| Waterhemp | 100 | 95 | 100 | 100 | 100 | 100 | 100 | 100 | 100 | 100 | 65 | 100 | 90 | 90 |
| Wheat | 0 | 5 | 50 | 0 | 0 | 0 | 0 | 75 | 45 | 0 | 0 | 0 | 30 | 35 |

| 125 g ai/ha Pre-emergence | Compounds | | | | | | | | | | | | | |
|---|---|---|---|---|---|---|---|---|---|---|---|---|---|---|
| | 75 | 79 | 80 | 81 | 82 | 83 | 84 | 85 | 87 | 88 | 89 | 90 | 91 | 97 |
| Barnyardgrass | 50 | 65 | 75 | 80 | 70 | 85 | 60 | 80 | 65 | 85 | 25 | 75 | 20 | 0 |
| Blackgrass | 30 | 60 | 80 | 90 | 65 | 80 | 90 | 90 | 85 | 90 | 40 | 50 | 60 | 0 |
| Corn | 0 | 5 | 10 | 20 | 20 | 0 | 0 | 0 | 0 | 0 | 0 | 5 | 10 | 0 |

TABLE C-continued

| | | | | | | | | | | | | | | |
|---|---|---|---|---|---|---|---|---|---|---|---|---|---|---|
| Crabgrass, Large | 25 | 20 | 40 | 90 | 70 | 70 | 70 | 80 | 80 | 80 | 25 | 75 | 50 | 0 |
| Foxtail, Giant | 70 | 85 | 85 | 98 | 90 | 100 | 90 | 100 | 90 | 98 | 65 | 90 | 90 | 5 |
| *Galium* | 90 | 95 | 95 | 95 | 90 | 95 | 95 | 95 | 98 | 98 | 98 | — | 98 | 0 |
| Johnsongrass | 20 | 40 | 30 | 45 | 60 | 60 | 5 | 65 | 40 | 60 | 0 | 60 | 0 | 0 |
| Lambsquarters | 85 | 100 | 90 | 85 | 98 | 95 | 100 | 90 | 85 | 90 | 98 | 85 | 80 | 20 |
| Morningglory | 95 | 98 | 90 | 90 | 95 | 95 | 95 | 95 | 95 | 95 | 85 | 98 | 90 | 20 |
| Nutsedge, Yellow | 65 | 90 | 80 | 80 | 60 | 85 | 70 | 75 | 85 | 95 | 80 | 85 | 80 | 0 |
| Oilseed Rape | 90 | 30 | 50 | 40 | 0 | 50 | 80 | 40 | 85 | 10 | 30 | 50 | 100 | 0 |
| Pigweed | 100 | 100 | 100 | 95 | 100 | 100 | 100 | 100 | 100 | 95 | 100 | 100 | 100 | 65 |
| Ragweed | 90 | 98 | 95 | 95 | 90 | 95 | 95 | 98 | 95 | 95 | 80 | 85 | 90 | 0 |
| Ryegrass, Italian | 90 | 90 | 90 | 90 | 85 | 90 | 85 | 90 | 90 | 90 | 90 | 95 | 95 | 30 |
| Soybean | 45 | 5 | 0 | 0 | 0 | 0 | 0 | 0 | 100 | 0 | 0 | 10 | 10 | 10 |
| Velvetleaf | 90 | 95 | 90 | 85 | 85 | 85 | 85 | 85 | 90 | 85 | 90 | 95 | 85 | 20 |
| Waterhemp | 100 | 100 | 100 | 90 | 100 | 100 | 100 | 90 | 100 | 95 | 40 | 100 | 65 | 10 |
| Wheat | 10 | 0 | 0 | 0 | 0 | 0 | 0 | 0 | 0 | 0 | 0 | 35 | 30 | 0 |

| 125 g ai/ha Pre-emergence | Compounds | | | | | | | | | | | | | |
|---|---|---|---|---|---|---|---|---|---|---|---|---|---|---|
| | 99 | 102 | 104 | 105 | 106 | 107 | 108 | 109 | 111 | 113 | 114 | 116 | 121 | 125 |
| Barnyardgrass | 55 | 30 | 40 | 60 | 85 | 80 | 35 | 70 | 55 | 65 | 60 | 70 | 55 | 90 |
| Blackgrass | 90 | 45 | 30 | 55 | 90 | 10 | 60 | 85 | 5 | 55 | 5 | 30 | 45 | 55 |
| Corn | 10 | 20 | 15 | 5 | 10 | 10 | 5 | 0 | 0 | 20 | 5 | 60 | 0 | 20 |
| Crabgrass, Large | 60 | 30 | 55 | 75 | 75 | 75 | 65 | 70 | 85 | 75 | 75 | 50 | 10 | 75 |
| Foxtail, Giant | 65 | 85 | 75 | 90 | 100 | 85 | 85 | 85 | — | — | — | — | 90 | 98 |
| *Galium* | 98 | 95 | 90 | 95 | 95 | 90 | 95 | 90 | 100 | 98 | 100 | 100 | 98 | 100 |
| Johnsongrass | 0 | 0 | 20 | 20 | 5 | 10 | 30 | 40 | 0 | 20 | 0 | 0 | 0 | 60 |
| Lambsquarters | 100 | 85 | 95 | 90 | 100 | 95 | 90 | 90 | 90 | 90 | 90 | 90 | 98 | 100 |
| Morningglory | 90 | 85 | 100 | 100 | 98 | 95 | 98 | 90 | 95 | 98 | 75 | 85 | 85 | 95 |
| Nutsedge, Yellow | 60 | 75 | 75 | 40 | 80 | 70 | 70 | 90 | 75 | 85 | 65 | 85 | 20 | 95 |
| Oilseed Rape | 90 | 10 | 85 | 10 | 30 | 20 | 90 | 85 | 100 | 60 | 100 | 95 | 30 | 85 |
| Pigweed | 100 | 98 | 100 | 100 | 100 | 100 | 100 | 100 | 98 | 100 | 100 | 100 | 90 | 100 |
| Ragweed | 95 | 90 | 95 | 98 | 95 | 85 | 98 | 95 | 90 | 85 | 95 | 95 | 98 | 98 |
| Ryegrass, Italian | 100 | 50 | 90 | 90 | 85 | 35 | 90 | 90 | 85 | 90 | 90 | 70 | 95 | 95 |
| Soybean | 5 | 5 | 0 | 0 | 0 | 0 | 0 | 0 | 0 | 65 | 20 | 0 | 0 | 30 |
| Velvetleaf | 90 | 85 | 90 | 90 | 85 | 85 | 85 | 80 | 95 | 98 | 85 | 100 | 85 | 100 |
| Waterhemp | 98 | 75 | 100 | 100 | 80 | 95 | 100 | 100 | 75 | 98 | 65 | 80 | 85 | 100 |
| Wheat | 30 | — | 5 | 10 | 0 | 0 | 15 | 10 | 20 | 35 | 5 | 5 | 10 | 90 |

| 125 g ai/ha Pre-emergence | Compounds | | | | | | | | | | | | | |
|---|---|---|---|---|---|---|---|---|---|---|---|---|---|---|
| | 129 | 131 | 132 | 133 | 134 | 136 | 137 | 138 | 139 | 145 | 152 | 153 | 154 | 161 |
| Barnyardgrass | 100 | 10 | 35 | 50 | 70 | 90 | 90 | 90 | 75 | 75 | 30 | 100 | 90 | 10 |
| Blackgrass | 70 | 40 | 40 | 50 | 40 | 70 | 30 | 40 | 60 | 60 | 30 | 95 | 85 | 5 |
| Corn | 15 | 5 | 0 | 10 | 10 | 0 | 10 | 5 | 10 | 0 | 10 | 40 | 5 | 5 |
| Crabgrass, Large | 75 | 60 | 10 | 35 | 40 | 60 | 70 | 70 | 20 | 55 | 10 | 98 | 90 | 20 |
| Foxtail, Giant | 95 | 90 | 85 | 75 | 70 | 100 | 95 | 100 | 85 | 75 | 65 | 100 | 100 | 25 |
| *Galium* | 100 | 95 | 90 | 100 | 98 | 100 | 98 | 98 | 100 | 100 | 95 | 100 | 98 | 95 |
| Johnsongrass | 10 | 0 | 55 | 30 | 5 | 20 | 20 | 30 | 35 | 5 | 0 | 65 | 50 | 0 |
| Lambsquarters | 85 | 85 | 85 | 95 | 100 | 100 | 100 | 100 | 95 | 100 | 90 | 100 | 85 | 65 |
| Morningglory | 90 | 85 | 95 | 90 | 95 | 98 | 90 | 98 | 95 | 98 | 75 | 98 | 85 | 75 |
| Nutsedge, Yellow | 90 | 65 | 45 | 70 | 95 | 70 | 90 | 95 | 85 | 95 | 55 | 80 | 70 | 55 |

TABLE C-continued

| | | | | | | | | | | | | | | |
|---|---|---|---|---|---|---|---|---|---|---|---|---|---|---|
| Oilseed Rape | 90 | 85 | 30 | 90 | 90 | 90 | 50 | 90 | 98 | 90 | 95 | 98 | 98 | 90 |
| Pigweed | 98 | 100 | 100 | 100 | 100 | 100 | 100 | 100 | 100 | 100 | 100 | 100 | 100 | 98 |
| Ragweed | 95 | 98 | 95 | 95 | 95 | 100 | 95 | 98 | 95 | 85 | 75 | 98 | 90 | 30 |
| Ryegrass, Italian | 95 | 95 | 95 | 100 | 100 | 85 | 100 | 90 | 100 | 100 | 90 | 90 | 90 | 85 |
| Soybean | 5 | 0 | 0 | 65 | 65 | 10 | 40 | 20 | 60 | 75 | 5 | 20 | 5 | 0 |
| Velvetleaf | 98 | 85 | 90 | 90 | 90 | 100 | 100 | 98 | 100 | 95 | 65 | 95 | 85 | 50 |
| Waterhemp | 100 | 98 | 95 | 95 | 98 | 98 | 95 | 98 | 100 | 98 | 85 | 95 | 95 | 75 |
| Wheat | 55 | 20 | 20 | 10 | 15 | 45 | 90 | 5 | 15 | 0 | 25 | 30 | 0 | 0 |

| 125 g ai/ha Pre-emergence | Compound 171 |
|---|---|
| Barnyardgrass | 75 |
| Blackgrass | 45 |
| Corn | 0 |
| Crabgrass, Large | 60 |
| Foxtail, Giant | — |
| *Galium* | 98 |
| Johnsongrass | 10 |
| Lambsquarters | 95 |
| Morningglory | 95 |
| Nutsedge, Yellow | 70 |
| Oilseed Rape | 50 |
| Pigweed | 100 |
| Ragweed | 95 |
| Ryegrass, Italian | 95 |
| Soybean | 55 |
| Velvetleaf | 95 |
| Waterhemp | 100 |
| Wheat | 45 |

| 62 g ai/ha Pre-emergence | Compounds | | | | | | | | | | | | | |
|---|---|---|---|---|---|---|---|---|---|---|---|---|---|---|
| | 1 | 2 | 10 | 11 | 20 | 21 | 22 | 23 | 25 | 27 | 28 | 29 | 32 | 34 |
| Barnyardgrass | 5 | 70 | 5 | 0 | 30 | 100 | 5 | 85 | 30 | 80 | 75 | 35 | 65 | 55 |
| Blackgrass | 90 | 90 | 0 | 40 | 5 | 90 | 20 | 85 | 85 | 90 | 90 | 50 | 90 | 50 |
| Corn | 0 | 0 | 0 | 0 | 0 | 15 | 0 | 0 | 0 | 0 | 0 | 0 | 0 | 0 |
| Crabgrass, Large | 40 | 55 | 0 | 0 | 15 | 85 | 0 | 45 | 75 | 80 | 60 | 5 | 35 | 10 |
| Foxtail, Giant | 75 | 100 | 0 | 35 | 30 | 100 | 15 | 85 | 85 | 100 | 100 | 75 | 80 | 65 |
| *Galium* | 100 | 100 | 5 | 90 | 100 | 98 | 90 | 100 | 95 | 95 | 95 | 95 | 95 | 95 |
| Johnsongrass | 5 | 0 | 0 | 0 | 0 | 10 | 0 | 5 | 0 | 5 | 0 | 5 | 0 | 0 |
| Lambsquarters | 95 | 100 | 0 | 100 | 85 | 98 | 45 | 85 | 85 | 95 | 85 | 80 | 70 | 90 |
| Morningglory | 100 | 100 | 0 | 100 | 98 | 98 | 85 | 90 | 95 | 98 | 98 | 95 | 90 | 80 |
| Nutsedge, Yellow | 35 | 45 | 0 | 5 | 85 | 85 | 45 | 90 | 30 | 90 | 75 | 80 | 45 | 25 |
| Oilseed Rape | 5 | 20 | 0 | 0 | 0 | 100 | 5 | 90 | 0 | 95 | 20 | 0 | 90 | 25 |
| Pigweed | 100 | 100 | 0 | 100 | 100 | 100 | 100 | 100 | 100 | 100 | 100 | 100 | 100 | 100 |
| Ragweed | 80 | 100 | 0 | 50 | 45 | 100 | 75 | 85 | 95 | 100 | 90 | 85 | 90 | 80 |
| Ryegrass, Italian | 100 | 98 | 0 | 95 | 95 | 90 | 90 | 90 | 95 | 90 | 90 | 90 | 90 | 85 |
| Soybean | 0 | 0 | 0 | 0 | 20 | 0 | 0 | 0 | 0 | 25 | 0 | 10 | 10 |
| Velvetleaf | 90 | 95 | 0 | 10 | 90 | 90 | 60 | 90 | 85 | 85 | 85 | 90 | 85 | 80 |
| Waterhemp | 100 | 100 | 0 | 100 | 100 | 95 | 80 | 100 | 100 | 85 | 75 | 100 | 100 | 100 |
| Wheat | 0 | 0 | 0 | 0 | 0 | 5 | 0 | 85 | 0 | 0 | 0 | 5 | 45 | 0 |

TABLE C-continued

| 62 g ai/ha Pre-emergence | Compounds | | | | | | | | | | | | | |
|---|---|---|---|---|---|---|---|---|---|---|---|---|---|---|
| | 35 | 36 | 37 | 41 | 42 | 47 | 54 | 57 | 59 | 60 | 66 | 67 | 69 | 72 |
| Barnyardgrass | 25 | 25 | 30 | 40 | 30 | 20 | 35 | 90 | 70 | 40 | 20 | 20 | 5 | 20 |
| Blackgrass | 55 | 30 | 30 | 80 | 85 | 30 | 55 | 60 | 90 | 90 | 30 | 30 | 30 | 50 |
| Corn | 0 | 0 | 0 | 0 | 0 | 0 | 10 | — | 20 | 10 | 0 | 0 | 0 | 0 |
| Crabgrass, Large | 5 | 20 | 5 | 35 | 70 | 30 | 40 | 35 | 70 | 75 | 65 | 70 | 5 | 80 |
| Foxtail, Giant | 85 | 75 | 75 | 80 | 80 | 50 | 80 | 80 | 95 | 85 | 75 | 80 | 5 | 70 |
| Galium | 95 | 100 | 90 | 100 | 90 | 95 | 95 | 90 | 95 | 95 | 90 | 90 | 90 | 90 |
| Johnsongrass | 10 | 5 | 0 | 50 | 0 | 0 | 0 | 0 | 25 | 20 | 25 | 20 | 10 | 25 |
| Lambsquarters | 100 | 80 | 60 | 90 | 80 | 100 | 85 | 100 | 90 | 85 | 85 | 80 | 100 | 65 |
| Morningglory | 98 | 80 | 80 | 95 | 98 | 100 | 90 | 100 | 100 | 98 | 85 | 80 | 85 | 85 |
| Nutsedge, Yellow | 40 | 20 | 20 | 75 | 60 | 45 | 5 | 30 | 80 | 45 | 35 | 20 | 35 | 10 |
| Oilseed Rape | 90 | 60 | 40 | 50 | 0 | 0 | 90 | 0 | 80 | 85 | 0 | 0 | 0 | 35 |
| Pigweed | 80 | 100 | 98 | 100 | 100 | 100 | 100 | 100 | 100 | 100 | 100 | 90 | 100 | 98 |
| Ragweed | 40 | 90 | 90 | 85 | 90 | 85 | 90 | 95 | 95 | 90 | 85 | 85 | 70 | 90 |
| Ryegrass, Italian | 70 | 30 | 85 | 95 | 90 | 20 | 50 | 65 | 100 | 95 | 50 | 40 | 90 | 90 |
| Soybean | 0 | 0 | 30 | 20 | 0 | 0 | 90 | 0 | 0 | 45 | 0 | 0 | 0 | 0 |
| Velvetleaf | 85 | 80 | 80 | 90 | 90 | 90 | 85 | 80 | 90 | 85 | 60 | 35 | 55 | 45 |
| Waterhemp | 50 | 100 | 95 | 95 | 98 | 98 | 100 | 98 | 100 | 100 | 90 | 80 | 95 | 90 |
| Wheat | 5 | 0 | 0 | 5 | 0 | 0 | 0 | 0 | 60 | 40 | 0 | 0 | 0 | 0 |

| 62 g ai/ha Pre-emergence | Compounds | | | | | | | | | | | | | |
|---|---|---|---|---|---|---|---|---|---|---|---|---|---|---|
| | 73 | 75 | 79 | 80 | 81 | 82 | 83 | 84 | 85 | 87 | 88 | 89 | 90 | 91 |
| Barnyardgrass | 25 | 25 | 15 | 65 | 70 | 55 | 70 | 25 | 60 | 35 | 40 | 15 | 65 | 15 |
| Blackgrass | 80 | 30 | 50 | 80 | 80 | 60 | 80 | 60 | 85 | 30 | 90 | 40 | 40 | 30 |
| Corn | 0 | 5 | 0 | 10 | 10 | 0 | 0 | 0 | 10 | 10 | 0 | 0 | 0 | 10 |
| Crabgrass, Large | 30 | 10 | 25 | 15 | 75 | 20 | 65 | 10 | 85 | 65 | 80 | 0 | 70 | 20 |
| Foxtail, Giant | 70 | 45 | 85 | 85 | 98 | 85 | 100 | 75 | 98 | 80 | 90 | 60 | 75 | 65 |
| Galium | 98 | 90 | 95 | 95 | 95 | 90 | 90 | 95 | 90 | 95 | 98 | 98 | — | 98 |
| Johnsongrass | 10 | 20 | 35 | 5 | 5 | 65 | 75 | 5 | 30 | 25 | 70 | 75 | 55 | 0 |
| Lambsquarters | 70 | 100 | 95 | 90 | 90 | 90 | 85 | 85 | 90 | 80 | 85 | 85 | 80 | 25 |
| Morningglory | 90 | 85 | 95 | 90 | 85 | 90 | 90 | 90 | 90 | 90 | 90 | 85 | 85 | 85 |
| Nutsedge, Yellow | 35 | 40 | 45 | 25 | 70 | 60 | 90 | 40 | 85 | 35 | 75 | 75 | 45 | 45 |
| Oilseed Rape | 85 | 70 | 35 | 30 | 5 | 0 | 0 | 0 | 85 | 30 | 20 | 0 | 35 | 98 |
| Pigweed | 100 | 100 | 100 | 100 | 95 | 100 | 100 | 100 | 100 | 100 | 100 | 100 | 100 | 98 |
| Ragweed | 95 | 85 | 95 | 95 | 95 | 90 | 100 | 95 | 90 | 90 | 85 | 80 | 90 | 75 |
| Ryegrass, Italian | 90 | 90 | 90 | 70 | 90 | 85 | 90 | 85 | 85 | 90 | 90 | 80 | 95 | 70 |
| Soybean | 0 | 20 | 0 | 0 | 100 | 100 | 0 | 0 | 0 | 0 | 10 | 0 | 0 | 10 |
| Velvetleaf | 80 | 85 | 85 | 85 | 65 | 80 | 70 | 65 | 80 | 85 | 70 | 80 | 90 | 70 |
| Waterhemp | 90 | 100 | 100 | 100 | 85 | 100 | 90 | 100 | 80 | 100 | 100 | 50 | 90 | 60 |
| Wheat | 20 | 0 | 0 | 0 | 0 | 0 | 0 | 0 | 0 | 0 | 0 | 0 | 0 | 5 |

| 62 g ai/ha Pre-emergence | Compounds | | | | | | | | | | | | | |
|---|---|---|---|---|---|---|---|---|---|---|---|---|---|---|
| | 97 | 99 | 102 | 104 | 105 | 106 | 107 | 108 | 109 | 111 | 113 | 114 | 116 | 121 |
| Barnyardgrass | 0 | 15 | 10 | 25 | 30 | 45 | 45 | 35 | 35 | 20 | 35 | 10 | 30 | 10 |
| Blackgrass | 0 | 70 | 50 | 15 | 50 | 50 | 5 | 0 | 30 | 5 | 50 | 5 | 5 | 45 |
| Corn | 0 | 20 | 10 | 0 | 0 | 0 | 0 | 10 | 0 | 0 | 0 | 5 | 0 | 0 |
| Crabgrass, Large | 0 | 35 | 5 | 55 | 50 | 70 | 30 | 70 | 65 | 5 | 35 | 5 | 20 | 10 |
| Foxtail, Giant | 5 | 35 | 75 | 85 | 80 | 95 | 80 | 85 | 85 | — | — | — | — | 55 |

TABLE C-continued

| | | | | | | | | | | | | | | |
|---|---|---|---|---|---|---|---|---|---|---|---|---|---|---|
| *Galium* | 0 | — | — | 85 | 90 | 90 | 90 | 90 | 90 | 80 | 90 | 98 | 85 | 90 |
| Johnson-grass | 0 | 0 | 0 | 20 | 20 | 5 | 0 | 5 | 30 | 0 | 10 | 0 | 0 | 0 |
| Lambs-quarters | 0 | 80 | 85 | 85 | 85 | 90 | 100 | 90 | 90 | 95 | 85 | 98 | 98 | 80 |
| Morning-glory | 30 | 85 | 75 | 95 | 90 | 90 | 85 | 90 | 85 | 70 | 95 | 55 | 80 | 55 |
| Nutsedge, Yellow | 0 | 70 | 70 | 45 | 45 | 70 | 50 | 80 | 70 | 20 | 70 | 40 | 35 | 25 |
| Oilseed Rape | 0 | 40 | 10 | 30 | 5 | 0 | 0 | 90 | 85 | 98 | 0 | 98 | 80 | 85 |
| Pigweed | 35 | 100 | 85 | 100 | 100 | 98 | 100 | 100 | 100 | 90 | 75 | 90 | 100 | 98 |
| Ragweed | 0 | 90 | 75 | 90 | 90 | 90 | 90 | 90 | 90 | 75 | 95 | 75 | 90 | 95 |
| Ryegrass, Italian | 5 | 90 | 25 | 85 | 90 | 70 | 35 | 85 | 90 | 90 | 95 | 85 | 30 | 90 |
| Soybean | 10 | 0 | 5 | 0 | 0 | 0 | 0 | 0 | 0 | — | 45 | 0 | 0 | 0 |
| Velvetleaf | 0 | 75 | 85 | 80 | 85 | 60 | 60 | 75 | 75 | 70 | 95 | 60 | 85 | 75 |
| Waterhemp | 10 | 100 | 65 | 90 | 95 | 75 | 75 | 90 | 90 | 65 | 100 | 75 | 70 | 95 |
| Wheat | 0 | 0 | 5 | 5 | 10 | 0 | 0 | 10 | 10 | 5 | 30 | 0 | 0 | 0 |

| 62 g ai/ha Pre-emergence | Compounds | | | | | | | | | | | | | |
|---|---|---|---|---|---|---|---|---|---|---|---|---|---|---|
| | 125 | 129 | 131 | 132 | 133 | 134 | 136 | 137 | 138 | 139 | 145 | 151 | 152 | 153 |
| Barnyardgrass | 70 | 70 | 0 | 5 | 40 | 40 | 50 | 85 | 55 | 55 | 35 | 85 | 5 | 100 |
| Blackgrass | 55 | 30 | 40 | 45 | 60 | 40 | 80 | 40 | 55 | 55 | 30 | 65 | 5 | 90 |
| Corn | 0 | 5 | 0 | 0 | 5 | 0 | 5 | 10 | 5 | 0 | 0 | 10 | 10 | 0 |
| Crabgrass, Large | 45 | 25 | 20 | 0 | 30 | 30 | 5 | 20 | 40 | 30 | 50 | 70 | 0 | 100 |
| Foxtail, Giant | 100 | 90 | 85 | 70 | 65 | 75 | 85 | 85 | 85 | 65 | 60 | 98 | 35 | 100 |
| *Galium* | 100 | 98 | 90 | 90 | 95 | 98 | 98 | 98 | 98 | 90 | 98 | 95 | 45 | 98 |
| Johnson-grass | 55 | 5 | 0 | 10 | 35 | 5 | 5 | 5 | 15 | 35 | 5 | 25 | 0 | 50 |
| Lambs-quarters | 100 | 80 | 70 | 60 | 90 | 90 | 90 | 100 | 95 | 90 | 90 | 85 | 75 | 100 |
| Morning-glory | 95 | 90 | 55 | 65 | 85 | 90 | 95 | 85 | 90 | 90 | 80 | 98 | 40 | 90 |
| Nutsedge, Yellow | 95 | 85 | 35 | 35 | 55 | 45 | 35 | 85 | 60 | 60 | 85 | 95 | 20 | 85 |
| Oilseed Rape | 0 | 50 | 40 | 85 | 85 | 90 | 30 | 90 | 90 | 98 | 90 | 98 | 85 | 100 |
| Pigweed | 100 | 98 | 100 | 100 | 100 | 100 | 100 | 100 | 98 | 98 | 98 | 100 | 100 | 100 |
| Ragweed | 100 | 85 | 95 | 85 | 75 | 95 | 98 | 95 | 100 | 90 | 65 | 85 | 40 | 95 |
| Ryegrass, Italian | 95 | 90 | 80 | 90 | 95 | 100 | 55 | 95 | 90 | 100 | 100 | 90 | 50 | 95 |
| Soybean | 5 | 0 | 0 | 0 | 55 | 45 | 10 | 20 | 0 | 35 | 55 | 10 | 5 | 10 |
| Velvetleaf | 100 | 85 | 55 | 60 | 90 | 90 | 95 | 100 | 90 | 85 | 85 | 75 | 40 | 90 |
| Waterhemp | 100 | 95 | 98 | 85 | 100 | 98 | 100 | 98 | 100 | 100 | 98 | 45 | 85 | 95 |
| Wheat | 45 | 50 | 0 | 40 | 0 | 0 | 10 | 80 | 35 | 10 | 0 | 0 | 10 | 10 |

| 62 g ai/ha Pre-emergence | Compounds | | |
|---|---|---|---|
| | 154 | 161 | 171 |
| Barnyardgrass | 80 | 0 | 35 |
| Blackgrass | 50 | 0 | 40 |
| Corn | 5 | 5 | 0 |
| Crabgrass, Large | 85 | 30 | 45 |
| Foxtail, Giant | 95 | 25 | — |
| *Galium* | 95 | 70 | 90 |
| Johnson-grass | 45 | 0 | 5 |
| Lambs-quarters | 60 | 40 | 95 |
| Morning-glory | 85 | 40 | 90 |
| Nutsedge, Yellow | 20 | 20 | 55 |
| Oilseed Rape | 85 | 20 | 5 |
| Pigweed | 95 | 98 | 60 |
| Ragweed | 95 | 15 | 80 |
| Ryegrass, | 55 | 40 | 95 |

TABLE C-continued

|  |  |  |  |
|---|---|---|---|
| Italian |  |  |  |
| Soybean | 5 | 0 | 0 |
| Velvetleaf | 60 | 40 | 90 |
| Waterhemp | 85 | 70 | 95 |
| Wheat | 0 | 0 | 5 |

| 31 g ai/ha Pre-emergence | Compounds | | | | | | | | | | | | | |
|---|---|---|---|---|---|---|---|---|---|---|---|---|---|---|
|  | 1 | 2 | 10 | 11 | 20 | 21 | 22 | 23 | 25 | 27 | 28 | 29 | 32 | 34 |
| Barnyardgrass | 5 | 35 | 0 | 0 | 5 | 80 | 5 | 10 | 0 | 55 | 45 | 10 | 20 | 60 |
| Blackgrass | 60 | 85 | 0 | 35 | 0 | 90 | 5 | 45 | 85 | 85 | 85 | 50 | 70 | 5 |
| Corn | 0 | 0 | 0 | 0 | 0 | 0 | 0 | 0 | 0 | 0 | 0 | 0 | 0 | 0 |
| Crabgrass, Large | 35 | 55 | 0 | 0 | 10 | 35 | 0 | 5 | 70 | 55 | 25 | 5 | 0 | 0 |
| Foxtail, Giant | 55 | 80 | 0 | 0 | 5 | 100 | 5 | 30 | 75 | 100 | 85 | 75 | 55 | 0 |
| *Galium* | 90 | 95 | 0 | 85 | 90 | 98 | 90 | 98 | 90 | 90 | 95 | 95 | 90 | 95 |
| Johnsongrass | 0 | 0 | 0 | 0 | 0 | 10 | 0 | 5 | 0 | 0 | 0 | 10 | 0 | 0 |
| Lambsquarters | 80 | 100 | 0 | 70 | 80 | 90 | 25 | 85 | 80 | 70 | 65 | 75 | 80 | 80 |
| Morningglory | 95 | 98 | 0 | 100 | 85 | 95 | 30 | 85 | 85 | 85 | 80 | 80 | 80 | 70 |
| Nutsedge, Yellow | 40 | 30 | 0 | 0 | 80 | 75 | 55 | 40 | 40 | 70 | 50 | 15 | 25 | 25 |
| Oilseed Rape | 0 | 0 | 0 | 0 | 0 | 90 | 0 | 50 | 0 | 5 | 0 | 0 | 25 | 10 |
| Pigweed | 100 | 100 | 0 | 0 | 100 | 100 | 60 | 100 | 100 | 98 | 100 | 100 | 100 | 100 |
| Ragweed | 90 | 65 | 0 | 15 | 35 | 95 | 30 | 85 | 80 | 80 | 70 | 80 | 85 | 80 |
| Ryegrass, Italian | 95 | 95 | 0 | 90 | 75 | 90 | 90 | 85 | 90 | 85 | 85 | 90 | 85 | 45 |
| Soybean | 0 | 0 | 0 | 0 | 0 | 0 | 0 | 0 | 0 | 0 | 0 | 0 | 0 | 10 |
| Velvetleaf | 70 | 75 | 0 | 0 | 60 | 85 | 10 | 85 | 80 | 70 | 55 | 85 | 75 | 70 |
| Waterhemp | 100 | 75 | 10 | 90 | 90 | 90 | 75 | 100 | 100 | 80 | 70 | 100 | 98 | 85 |
| Wheat | 0 | 0 | 0 | 0 | 0 | 0 | 0 | 75 | 0 | 0 | 0 | 0 | 15 | 0 |

| 31 g ai/ha Pre-emergence | Compounds | | | | | | | | | | | | | |
|---|---|---|---|---|---|---|---|---|---|---|---|---|---|---|
|  | 35 | 36 | 37 | 41 | 42 | 47 | 54 | 57 | 59 | 60 | 66 | 67 | 69 | 72 |
| Barnyardgrass | 5 | 10 | 10 | 10 | 0 | 5 | 15 | 5 | 30 | 10 | 0 | 5 | 0 | 10 |
| Blackgrass | 50 | 0 | 10 | 70 | 40 | 0 | 50 | 30 | 85 | 90 | 10 | 60 | 30 | 40 |
| Corn | 0 | 0 | 0 | 0 | 0 | 0 | 0 | 0 | 0 | 0 | 0 | 0 | 0 | 0 |
| Crabgrass, Large | 5 | 70 | 5 | 30 | 55 | 0 | 40 | 0 | 25 | 20 | 75 | 10 | 0 | 60 |
| Foxtail, Giant | 60 | 75 | 65 | 45 | 75 | 15 | 70 | 45 | 80 | 75 | 70 | 75 | 0 | 60 |
| *Galium* | 90 | 100 | 100 | 90 | 90 | 90 | 95 | 80 | 98 | 90 | 90 | 70 | 50 | 90 |
| Johnsongrass | 10 | 0 | 0 | 0 | 0 | 0 | 0 | 0 | 5 | 5 | 10 | 10 | 20 | 0 |
| Lambsquarters | 20 | 70 | 85 | 75 | 85 | 100 | 80 | 100 | 70 | 80 | 80 | 80 | 10 | 60 |
| Morningglory | 25 | 80 | 70 | 85 | 85 | 90 | 80 | 100 | 98 | 85 | 80 | 70 | 70 | 75 |
| Nutsedge, Yellow | 20 | 10 | 0 | 60 | 55 | 35 | 5 | 10 | 80 | 45 | 35 | 10 | 5 | 10 |
| Oilseed Rape | 90 | 50 | 0 | 5 | 0 | 0 | 70 | 0 | 65 | 30 | 0 | 0 | 0 | 30 |
| Pigweed | 75 | 90 | 98 | 75 | 100 | 100 | 100 | 100 | 100 | 100 | 100 | 75 | 100 | 90 |
| Ragweed | 5 | 85 | 85 | 85 | 90 | 50 | 90 | 70 | 90 | 80 | 75 | 60 | 60 | 85 |
| Ryegrass, Italian | 65 | 30 | 50 | 95 | 85 | 0 | 55 | 45 | 100 | 90 | 55 | 30 | 85 | 90 |
| Soybean | 0 | 100 | 0 | 0 | 35 | 0 | 0 | 0 | 0 | 0 | 0 | 0 | 0 | 80 |
| Velvetleaf | 40 | 55 | 25 | 85 | 85 | 65 | 80 | 50 | 85 | 75 | 15 | 10 | 35 | 30 |
| Waterhemp | 40 | 100 | 90 | 85 | 80 | 100 | 98 | 90 | 95 | 100 | 85 | 70 | 85 | 75 |
| Wheat | 0 | 0 | 0 | 0 | 0 | 0 | 0 | 0 | 60 | 10 | 0 | 0 | 0 | 0 |

| 31 g ai/ha Pre-emergence | Compounds | | | | | | | | | | | | | |
|---|---|---|---|---|---|---|---|---|---|---|---|---|---|---|
|  | 73 | 75 | 79 | 80 | 81 | 82 | 83 | 84 | 85 | 87 | 88 | 89 | 90 | 91 |
| Barnyardgrass | 10 | 5 | 10 | 10 | 30 | 10 | 50 | 5 | 35 | 5 | 35 | 5 | 35 | 0 |

TABLE C-continued

| | | | | | | | | | | | | | |
|---|---|---|---|---|---|---|---|---|---|---|---|---|---|
| Blackgrass | 50 | 20 | 20 | 70 | 60 | 50 | 70 | 60 | 50 | 40 | 55 | 5 | 25 | 0 |
| Corn | 0 | 0 | 0 | 0 | 0 | 0 | 0 | 0 | 0 | 0 | 0 | 0 | 0 | 0 |
| Crabgrass, Large | 0 | 75 | 25 | 10 | 90 | 25 | 75 | 10 | 80 | 10 | 55 | 20 | 35 | 0 |
| Foxtail, Giant | 55 | 5 | 65 | 70 | 80 | 60 | 85 | 70 | 90 | 70 | 85 | 10 | 75 | 5 |
| *Galium* | 90 | 90 | 95 | 90 | 90 | 90 | 90 | 90 | 90 | 95 | 90 | 95 | — | 95 |
| Johnsongrass | 0 | 0 | 10 | 5 | 25 | 45 | 65 | 5 | 40 | 5 | 50 | 0 | 50 | 0 |
| Lambsquarters | 75 | 65 | 100 | 90 | 75 | 85 | 80 | 60 | 85 | 55 | 60 | 40 | 75 | 10 |
| Morningglory | 85 | 70 | 90 | 85 | 80 | 85 | 85 | 85 | 85 | 85 | 85 | 80 | 85 | 25 |
| Nutsedge, Yellow | 0 | 15 | 25 | 20 | 60 | 35 | 85 | 15 | 70 | 10 | 40 | 60 | 55 | 10 |
| Oilseed Rape | 90 | 30 | 0 | 0 | 0 | 0 | 0 | 0 | 5 | 30 | 20 | 0 | 30 | 80 |
| Pigweed | 95 | 85 | 100 | 100 | 98 | 95 | 100 | 100 | 100 | 75 | 90 | 95 | 100 | 70 |
| Ragweed | 85 | 80 | 90 | 90 | 85 | 85 | 85 | 85 | 80 | 90 | 90 | 30 | 80 | 35 |
| Ryegrass, Italian | 75 | 90 | 20 | 35 | 80 | 80 | 90 | 80 | 85 | 35 | 85 | 20 | 90 | 30 |
| Soybean | 0 | 0 | 0 | 0 | 0 | 0 | 30 | 0 | 0 | 0 | 0 | 0 | 0 | 0 |
| Velvetleaf | 25 | 35 | 80 | 55 | 35 | 65 | 35 | 40 | 50 | 55 | 10 | 70 | 85 | 55 |
| Waterhemp | 85 | 100 | 100 | 100 | 85 | 100 | 60 | 100 | 60 | 100 | 100 | 75 | 75 | 25 |
| Wheat | 0 | 0 | 0 | 0 | 0 | 0 | 0 | 0 | 0 | 0 | 0 | 0 | 5 | 0 |

| 31 g ai/ha Pre-emergence | Compounds | | | | | | | | | | | | |
|---|---|---|---|---|---|---|---|---|---|---|---|---|---|
| | 97 | 99 | 102 | 104 | 105 | 106 | 107 | 108 | 109 | 111 | 113 | 114 | 116 | 121 |
| Barnyardgrass | 0 | 5 | 5 | 10 | 0 | 25 | 15 | 5 | 10 | 10 | 10 | 5 | 5 | 5 |
| Blackgrass | 0 | 50 | 0 | 5 | 20 | 10 | 0 | 10 | 35 | 0 | 10 | 0 | 0 | 10 |
| Corn | 5 | 5 | 5 | 5 | 0 | 0 | 0 | 5 | 5 | 0 | 0 | 0 | 0 | 0 |
| Crabgrass, Large | 0 | 30 | 0 | 40 | 20 | 70 | 30 | 5 | 40 | 5 | 0 | 0 | 0 | 0 |
| Foxtail, Giant | 0 | 40 | 30 | 75 | 60 | 85 | 60 | 65 | 65 | — | — | — | — | 20 |
| *Galium* | 0 | — | — | 90 | 85 | 90 | 90 | 90 | 90 | 80 | 100 | 98 | 60 | 90 |
| Johnsongrass | 0 | 0 | 0 | 10 | 10 | 5 | 0 | 0 | 0 | 0 | 0 | 0 | 0 | 0 |
| Lambsquarters | 0 | 25 | 70 | 85 | 95 | 90 | 90 | 85 | 80 | 90 | 90 | 90 | 65 | 60 |
| Morningglory | 25 | 80 | 45 | 80 | 85 | 85 | 80 | 80 | 85 | 50 | 85 | 25 | 55 | 25 |
| Nutsedge, Yellow | 0 | 20 | 15 | 30 | 40 | 60 | 30 | 35 | 40 | 0 | 55 | 10 | 0 | 10 |
| Oilseed Rape | 0 | 0 | 0 | 5 | 0 | 0 | 0 | 5 | 5 | 0 | 0 | 30 | 85 | 0 |
| Pigweed | 5 | 95 | 75 | 100 | 98 | 98 | 100 | 100 | 100 | 98 | 70 | 98 | 95 | 100 |
| Ragweed | 0 | 70 | 70 | 85 | 90 | 85 | 75 | 75 | 95 | 60 | 65 | 55 | 85 | 35 |
| Ryegrass, Italian | 5 | 90 | 15 | 55 | 40 | 50 | 15 | 60 | 70 | 10 | 95 | 40 | 5 | 75 |
| Soybean | 15 | 0 | 0 | 0 | 0 | 0 | 75 | 0 | 0 | — | 0 | 0 | — | 0 |
| Velvetleaf | 0 | 60 | 65 | 40 | 60 | 40 | 30 | 50 | 60 | 65 | 60 | 45 | 70 | 60 |
| Waterhemp | 0 | 85 | 75 | 75 | 90 | 70 | 75 | 75 | 80 | 50 | 85 | 50 | 55 | 70 |
| Wheat | 0 | 0 | 0 | 5 | 0 | 15 | 0 | 0 | 0 | 0 | 0 | 0 | 0 | 0 |

| 31 g ai/ha Pre-emergence | Compounds | | | | | | | | | | | | |
|---|---|---|---|---|---|---|---|---|---|---|---|---|---|
| | 125 | 129 | 131 | 132 | 133 | 134 | 136 | 137 | 138 | 139 | 144 | 145 | 151 | 152 |
| Barnyardgrass | 55 | 15 | 0 | 0 | 0 | 5 | 25 | 35 | 30 | 20 | 35 | 10 | 70 | 5 |
| Blackgrass | 50 | 5 | 0 | 20 | 30 | 20 | 70 | 30 | 45 | 50 | 90 | 10 | 60 | 5 |
| Corn | 0 | 0 | 0 | 0 | 5 | 0 | 0 | 0 | 5 | 0 | 0 | 0 | 10 | 15 |
| Crabgrass, Large | 40 | 5 | 0 | 0 | 0 | 5 | 0 | 20 | 0 | 5 | 60 | 5 | 30 | 0 |
| Foxtail, Giant | 95 | 85 | 35 | 40 | 30 | 25 | 75 | 65 | 80 | 35 | 90 | 35 | 85 | 0 |
| *Galium* | 100 | 95 | 85 | 90 | 95 | 100 | 90 | 98 | 95 | 90 | 100 | 90 | 95 | 50 |
| Johnsongrass | 40 | 5 | 0 | 15 | 5 | 0 | 5 | 0 | 10 | 5 | 60 | 10 | 0 | 0 |
| Lambsquarters | 90 | 85 | 60 | 50 | 90 | 75 | 95 | 90 | 95 | 100 | 100 | 90 | 80 | 50 |
| Morningglory | 90 | 85 | 35 | 40 | 45 | 75 | 80 | 70 | 80 | 85 | 90 | 75 | 90 | 10 |

TABLE C-continued

| | | | | | | | | | | | | | | |
|---|---|---|---|---|---|---|---|---|---|---|---|---|---|---|
| Nutsedge, Yellow | 65 | 55 | 10 | 10 | 20 | 30 | 5 | 55 | 5 | 65 | 40 | 35 | 70 | 5 |
| Oilseed Rape | 85 | 5 | 20 | 70 | 5 | 55 | 10 | 0 | 85 | 20 | 70 | 5 | 98 | 50 |
| Pigweed | 100 | 100 | 60 | 100 | 100 | 75 | 100 | 100 | 100 | 70 | 100 | 70 | 100 | 80 |
| Ragweed | 95 | 70 | 65 | 70 | 70 | 70 | 95 | 80 | 95 | 75 | 98 | 55 | 90 | 85 |
| Ryegrass, Italian | 85 | 90 | 10 | 45 | 90 | 98 | 50 | 85 | 55 | 95 | 100 | 100 | 90 | 10 |
| Soybean | 0 | 0 | 0 | 0 | 5 | 40 | 10 | 30 | 0 | 25 | 5 | 0 | 20 | 0 |
| Velvetleaf | 95 | 70 | 0 | 60 | 55 | 75 | 75 | 80 | 85 | 60 | 90 | 40 | 60 | 15 |
| Waterhemp | 98 | 90 | 95 | 90 | 80 | 90 | 98 | 85 | 95 | 100 | 100 | 85 | 35 | 20 |
| Wheat | 40 | 35 | 0 | 25 | 0 | 0 | 0 | 15 | 0 | 0 | 90 | 0 | 0 | 0 |

| 31 g ai/ha Pre-emergence | Compounds | | | |
|---|---|---|---|---|
| | 153 | 154 | 161 | 171 |
| Barnyardgrass | 85 | 65 | 0 | 5 |
| Blackgrass | 90 | 5 | 5 | 30 |
| Corn | 0 | 5 | 0 | 0 |
| Crabgrass, Large | 80 | 70 | 30 | 0 |
| Foxtail, Giant | 98 | 85 | 10 | — |
| *Galium* | 95 | 98 | 80 | 90 |
| Johnsongrass | 25 | 10 | 0 | 0 |
| Lambsquarters | 95 | 15 | 0 | 98 |
| Morningglory | 95 | 45 | 10 | 85 |
| Nutsedge, Yellow | 80 | 0 | 0 | 45 |
| Oilseed Rape | 95 | 80 | 10 | 0 |
| Pigweed | 100 | 55 | 75 | 70 |
| Ragweed | 95 | 80 | 40 | 65 |
| Ryegrass, Italian | 90 | 40 | 5 | 90 |
| Soybean | 20 | 0 | 0 | — |
| Velvetleaf | 85 | 40 | 0 | 70 |
| Waterhemp | 80 | 30 | 20 | 85 |
| Wheat | 0 | 0 | 0 | 0 |

| 16 g ai/ha Pre-emergence | Compounds | | |
|---|---|---|---|
| | 35 | 144 | 151 |
| Barnyardgrass | 5 | 5 | 20 |
| Blackgrass | 40 | 70 | 60 |
| Corn | 0 | 0 | 30 |
| Crabgrass, Large | 0 | 25 | 10 |
| Foxtail, Giant | 25 | 75 | 75 |
| *Galium* | 90 | 95 | 95 |
| Johnsongrass | 0 | 25 | 0 |
| Lambsquarters | 5 | 65 | 80 |
| Morningglory | 25 | 80 | 90 |
| Nutsedge, Yellow | 20 | 25 | 30 |
| Oilseed Rape | 5 | 5 | 85 |
| Pigweed | 75 | 100 | 95 |
| Ragweed | 0 | 95 | 85 |
| Ryegrass, Italian | 50 | 100 | 50 |
| Soybean | 0 | 0 | 0 |
| Velvetleaf | 0 | 85 | 55 |
| Waterhemp | 40 | 100 | 10 |
| Wheat | 0 | 70 | 0 |

TABLE C-continued

| 8 g ai/ha Pre-emergence | Compounds | | |
|---|---|---|---|
| | 35 | 144 | 151 |
| Barnyardgrass | 0 | 0 | 5 |
| Blackgrass | 5 | 55 | 30 |
| Corn | 0 | 0 | 20 |
| Crabgrass, Large | 0 | 5 | 0 |
| Foxtail, Giant | 5 | 60 | 40 |
| *Galium* | 90 | 95 | 98 |
| Johnsongrass | 0 | 25 | 0 |
| Lambsquarters | 5 | 35 | 60 |
| Morningglory | 10 | 60 | 80 |
| Nutsedge, Yellow | 0 | 5 | 40 |
| Oilseed Rape | 0 | 0 | 85 |
| Pigweed | 40 | 100 | 70 |
| Ragweed | 0 | 90 | 55 |
| Ryegrass, Italian | 40 | 95 | 15 |
| Soybean | 0 | 0 | 0 |
| Velvetleaf | 0 | 70 | 40 |
| Waterhemp | — | 100 | 5 |
| Wheat | 0 | 55 | 0 |

| 4 g ai/ha Pre-emergence | Compound 144 |
|---|---|
| Barnyardgrass | 0 |
| Blackgrass | 30 |
| Corn | 0 |
| Crabgrass, Large | 0 |
| Foxtail, Giant | 30 |
| *Galium* | 90 |
| Johnsongrass | 0 |
| Lambsquarters | 25 |
| Morningglory | 25 |
| Nutsedge, Yellow | 5 |
| Oilseed Rape | 0 |
| Pigweed | 75 |
| Ragweed | 70 |
| Ryegrass, Italian | 80 |
| Soybean | 10 |
| Velvetleaf | 25 |
| Waterhemp | 80 |
| Wheat | 0 |

Test D

Seeds of plant species selected from bluegrass (annual bluegrass, *Poa annua*), blackgrass (*Alopecurus myosuroides*), Canada thistle (*Cirsium arvense*), canarygrass (*Phalaris minor*), chickweed (common chickweed, *Stellaria media*), geranium, cutleaf (cutleaf geranium, *Geranium dissectum*), galium (catchweed bedstraw, *Galium aparine*), bromegrass, downy (downy bromegrass, *Bromus tectorum*), field poppy (*Papaver rhoeas*), field violet (*Viola arvensis*), foxtail, green (green foxtail, *Setaria viridis*), deadnettle (henbit deadnettle, *Lamium amplexicaule*), ryegrass, Italian (Italian ryegrass, *Lolium multiflorum*), kochia (*Kochia scoparia*), lambsquarters (*Chenopodium album*), oilseed rape (*Brassica napus*), pigweed (*Amaranthus retroflexus*), chamomile (scentless chamomile, *Matricaria inodora*), Russian thistle (*Salsola kali*), speedwell (bird's-eye speedwell, *Veronica persica*), barley, spring (spring barley, *Hordeum vulgare*), wheat, spring (spring wheat, *Triticum aestivum*), buckwheat, wild (wild buckwheat, *Polygonum convolvulus*), mustard, wild (wild mustard, *Sinapis arvensis*), oat, wild (wild oat, *Avena fatua*), radish, wild (wild radish, *Raphanus raphanistrum*), windgrass (*Apera spicaventi*), barley, winter (winter barley, *Hordeum vulgare*), and wheat, winter (winter wheat, *Triticum aestivum*) were planted into a silt loam soil and treated preemergence with test chemicals formulated in a non-phytotoxic solvent mixture which included a surfactant.

At the same time, these species were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of the test chemicals formulated in the same manner. Plants ranged in height from 2 to 18 cm (1- to 4-leaf stage). Treated plants and controls were maintained in a controlled growth environment for 14 to 21 d after which time all species were compared to controls and visually evaluated. Plant response ratings, summarized in Table D, are based on a scale of 0 to 100 where 0 is no effect and 100 is complete control. A dash (-) response means no test result.

TABLE D

| 250 g ai/ha Post-emergence | Compounds | | | | | | | | | | | | | |
|---|---|---|---|---|---|---|---|---|---|---|---|---|---|---|
| | 1 | 2 | 11 | 20 | 21 | 22 | 23 | 25 | 27 | 28 | 34 | 35 | 36 | 41 |
| Barley, Spring | 10 | 5 | 10 | 0 | 30 | 15 | 30 | 10 | 10 | 10 | 5 | 15 | 10 | 20 |
| Barley, Winter | 10 | 10 | 40 | 0 | 40 | 5 | 30 | 10 | 5 | 5 | 20 | 15 | 10 | 35 |
| Blackgrass | 80 | 90 | 70 | 60 | 90 | 70 | 80 | 80 | 90 | 85 | 75 | 85 | 70 | 75 |
| Bluegrass | 5 | 15 | 15 | 40 | 50 | 25 | 40 | 40 | 40 | 50 | 20 | 40 | 35 | 35 |
| Bromegrass, Downy | 20 | 20 | 50 | 15 | 80 | 25 | 75 | 65 | 70 | 70 | 70 | 30 | 65 | 45 |
| Buckwheat, Wild | 100 | 100 | 95 | 100 | 100 | 100 | 100 | 100 | 100 | 100 | 100 | 100 | 100 | 100 |
| Canada Thistle | — | — | — | — | — | — | — | — | — | — | — | — | — | — |
| Canarygrass | 70 | 75 | 55 | 55 | 95 | 65 | 90 | 85 | 90 | 85 | 85 | 80 | 80 | 80 |
| Chamomile | 100 | 100 | 90 | 100 | 100 | 100 | 100 | 100 | 100 | 95 | 100 | 100 | 100 | 100 |
| Chickweed | 100 | 100 | 100 | 100 | 100 | 100 | 100 | 100 | 100 | 100 | 100 | 100 | 100 | 100 |
| Deadnettle | 70 | 60 | 100 | 65 | 100 | 70 | 85 | 45 | 60 | 70 | 100 | 80 | 100 | 100 |
| Field Poppy | 95 | 100 | 100 | 100 | 100 | 100 | 100 | 100 | 100 | 100 | 100 | 100 | 100 | 95 |
| Field Violet | 95 | 80 | 90 | 45 | 100 | 95 | 75 | 95 | 85 | 90 | 95 | 98 | 90 | 100 |
| Foxtail, Green | 85 | 100 | 70 | 70 | 95 | 75 | 90 | 75 | 80 | 90 | 70 | 95 | 90 | 65 |
| *Galium* | 100 | 100 | 90 | 100 | 100 | 98 | 100 | 100 | 100 | 100 | 100 | 100 | 100 | 100 |
| *Geranium*, Cutleaf | — | — | — | — | — | — | — | — | — | — | — | — | — | — |
| *Kochia* | 100 | 70 | 100 | 100 | 85 | 100 | 80 | 100 | 75 | 75 | 95 | 70 | 100 | 100 |
| Lambsquarters | 100 | 100 | 85 | 95 | 95 | 98 | 80 | 95 | 85 | 90 | 100 | 98 | 100 | 85 |
| Mustard, Wild | 65 | 55 | 95 | 100 | 100 | 100 | 100 | 85 | 75 | 70 | 100 | 100 | 100 | 100 |
| Oat, Wild | 95 | 100 | 98 | 75 | 100 | 100 | 95 | 90 | 98 | 95 | 95 | 98 | 95 | 85 |
| Oilseed Rape | 60 | 70 | 55 | 5 | 100 | 100 | 85 | 60 | 85 | 85 | 90 | 100 | 100 | 55 |
| Pigweed | 100 | 95 | 100 | 100 | 98 | 100 | 100 | 100 | 95 | 90 | 100 | 98 | 100 | 85 |
| Radish, Wild | 60 | 60 | 85 | 65 | 100 | 85 | 100 | 75 | 90 | 95 | 95 | 100 | 100 | 95 |
| Russian Thistle | — | — | — | 98 | 85 | 85 | 80 | 90 | 70 | 85 | 85 | 95 | 90 | 75 |
| Ryegrass, Italian | 85 | 90 | 90 | 90 | 80 | 90 | 85 | 90 | 85 | 85 | 95 | 90 | 90 | 90 |
| Speedwell | 70 | 90 | 100 | 100 | 100 | 100 | 95 | 80 | 100 | 100 | 100 | 100 | 100 | 100 |
| Wheat, Spring | 15 | 25 | 25 | 20 | 50 | 15 | 60 | 20 | 20 | 20 | 45 | 30 | 10 | 40 |
| Wheat, Winter | 5 | 10 | 25 | 25 | 40 | 15 | 70 | 20 | 10 | 15 | 25 | 20 | 15 | 35 |
| Windgrass | 70 | 70 | 20 | 40 | 85 | 55 | 85 | 85 | 90 | 85 | 75 | 85 | 75 | 75 |

| 250 g ai/ha Post-emergence | Compounds | | | | | | | | | | | | | |
|---|---|---|---|---|---|---|---|---|---|---|---|---|---|---|
| | 42 | 47 | 52 | 54 | 57 | 59 | 60 | 66 | 67 | 69 | 72 | 73 | 75 | 79 |
| Barley, Spring | 10 | 0 | 0 | 10 | 10 | 60 | 50 | 15 | 20 | 5 | 15 | 40 | 0 | 10 |
| Barley, Winter | 10 | 15 | 0 | 30 | 25 | 60 | 50 | 5 | 10 | 5 | 35 | 35 | 5 | 5 |
| Blackgrass | 85 | 65 | 40 | 75 | 75 | 85 | 90 | 75 | 95 | 65 | 80 | 90 | 70 | 50 |
| Bluegrass | 35 | 15 | 30 | 35 | 15 | 75 | 60 | 35 | 30 | 25 | 55 | 65 | 15 | 15 |
| Bromegrass, Downy | 70 | 5 | 10 | 75 | 35 | 85 | 80 | 70 | 70 | 40 | 75 | 85 | 30 | 20 |
| Buckwheat, Wild | 100 | 100 | 100 | 100 | 100 | 100 | 100 | 100 | 100 | 98 | 100 | 100 | 100 | 100 |
| Canada Thistle | — | — | — | — | — | — | — | — | — | 98 | — | — | — | — |
| Canarygrass | 80 | 0 | 0 | 75 | 25 | 90 | 90 | 85 | 95 | 75 | 85 | 90 | 50 | 45 |
| Chamomile | 100 | — | 100 | 100 | 100 | 100 | 100 | 100 | 100 | 80 | 100 | 100 | 100 | 100 |
| Chickweed | 100 | 100 | 100 | 100 | 100 | 100 | 100 | 100 | 100 | 98 | 100 | 100 | 100 | 100 |
| Deadnettle | 55 | 30 | 35 | 100 | 100 | 100 | 95 | 40 | 60 | 80 | 100 | 100 | 100 | 40 |

TABLE D-continued

| | | | | | | | | | | | | | | |
|---|---|---|---|---|---|---|---|---|---|---|---|---|---|---|
| Field Poppy | 100 | 100 | 100 | 100 | 100 | 100 | 100 | 95 | 100 | 80 | 100 | 100 | 100 | 98 |
| Field Violet | 90 | — | 75 | 90 | 85 | 95 | 85 | 95 | 95 | 98 | 95 | 90 | 100 | 95 |
| Foxtail, Green | 80 | 80 | 40 | 80 | 90 | 85 | 75 | 98 | 100 | 15 | 75 | 80 | 60 | 80 |
| *Galium* | 100 | 80 | 100 | 100 | 98 | 100 | 100 | 100 | 100 | 100 | 100 | 100 | 100 | 100 |
| *Geranium*, Cutleaf | — | — | — | — | — | — | — | — | — | 65 | — | — | — | — |
| *Kochia* | 100 | 100 | 65 | 100 | 75 | 100 | 95 | 100 | 50 | 98 | 100 | 100 | 100 | 95 |
| Lambs-quarters | 90 | 70 | 90 | 100 | 85 | 95 | 80 | 100 | 100 | 100 | 100 | 100 | 100 | 100 |
| Mustard, Wild | 80 | 25 | 100 | 100 | 40 | 100 | 100 | 70 | 65 | 80 | 100 | 100 | 100 | 50 |
| Oat, Wild | 95 | 40 | 15 | 90 | 85 | 98 | 100 | 100 | 100 | 85 | 98 | 100 | 80 | 85 |
| Oilseed Rape | 70 | 70 | 80 | 100 | 65 | 90 | 80 | 75 | 90 | 20 | 90 | 95 | 100 | 30 |
| Pigweed | 100 | 100 | 80 | 100 | 100 | 100 | 100 | 100 | 100 | 100 | 100 | 100 | 100 | 100 |
| Radish, Wild | 65 | 20 | 85 | 100 | 90 | 100 | 95 | 45 | 95 | 75 | 95 | 100 | 100 | 65 |
| Russian Thistle | 90 | — | 55 | 100 | — | 85 | 85 | 80 | 85 | 70 | 85 | 85 | 85 | 65 |
| Ryegrass, Italian | 85 | 45 | 80 | 95 | 85 | 90 | 95 | 98 | 100 | 85 | 100 | 98 | 98 | 90 |
| Speedwell | 45 | 50 | 100 | 100 | 100 | 100 | 100 | 75 | 100 | 100 | 80 | 100 | 100 | 65 |
| Wheat, Spring | 20 | 15 | 5 | 25 | 10 | 80 | 55 | 5 | 5 | 0 | 70 | 85 | 15 | 5 |
| Wheat, Winter | 15 | 5 | 15 | 30 | 15 | 80 | 40 | 0 | 0 | 0 | 60 | 75 | 0 | 0 |
| Windgrass | 98 | 15 | 5 | 75 | 15 | 85 | 98 | 100 | 90 | 55 | 85 | 85 | 65 | 65 |

| 250 g ai/ha Post-emergence | Compounds | | | | | | | | | | | | | |
|---|---|---|---|---|---|---|---|---|---|---|---|---|---|---|
| | 80 | 81 | 82 | 83 | 84 | 85 | 87 | 88 | 90 | 104 | 105 | 108 | 109 | 126 |
| Barley, Spring | 25 | 10 | 5 | 10 | 10 | 20 | 5 | 15 | 40 | 15 | 15 | 20 | 25 | 10 |
| Barley, Winter | 15 | 10 | 0 | 15 | 0 | 10 | 5 | 10 | 35 | 15 | 15 | 15 | 20 | 0 |
| Blackgrass | 90 | 85 | 80 | 80 | 85 | 90 | 90 | 95 | 65 | 70 | 65 | 75 | 75 | 45 |
| Bluegrass | 45 | 40 | 35 | 25 | 35 | 40 | 45 | 35 | 30 | 30 | 25 | 35 | 45 | 15 |
| Bromegrass, Downy | 75 | 75 | 60 | 70 | 75 | 60 | 65 | 65 | 55 | 65 | 65 | 65 | 75 | 25 |
| Buckwheat, Wild | 100 | 100 | 100 | 100 | 100 | 100 | 100 | 100 | 100 | 100 | 100 | 100 | 100 | 100 |
| Canada Thistle | — | — | — | — | — | — | — | — | 98 | — | — | — | — | 100 |
| Canarygrass | 90 | 100 | 85 | 90 | 80 | 90 | 90 | 95 | 75 | 85 | 80 | 80 | 90 | 75 |
| Chamomile | 100 | 100 | 100 | 100 | 100 | 85 | 100 | 95 | 100 | 100 | 100 | 100 | 100 | 100 |
| Chickweed | 100 | 100 | 100 | 100 | 100 | 100 | 100 | 100 | 100 | 100 | 100 | 100 | 100 | 100 |
| Deadnettle | 50 | 60 | 35 | 60 | 40 | 45 | 60 | 45 | 100 | 85 | 30 | 90 | 95 | 85 |
| Field Poppy | 100 | 100 | 100 | 100 | 100 | 95 | 100 | 100 | 90 | 80 | 80 | 75 | 85 | 85 |
| Field Violet | 100 | 100 | 100 | 100 | 100 | 90 | 100 | 80 | 100 | 98 | 100 | 100 | 100 | 100 |
| Foxtail, Green | 95 | 100 | 90 | 100 | 95 | 85 | 90 | 80 | 75 | 90 | 80 | 95 | 85 | 25 |
| *Galium* | 100 | 100 | 100 | 100 | 100 | 100 | 100 | 100 | 100 | 100 | 100 | 100 | 100 | 100 |
| *Geranium*, Cutleaf | — | — | — | — | — | — | — | — | 95 | — | — | — | — | 90 |
| *Kochia* | 100 | 95 | 100 | 90 | 100 | 75 | 95 | 70 | 100 | 100 | 100 | 100 | 100 | 100 |
| Lambs-quarters | 100 | 100 | 100 | 100 | 100 | 95 | 100 | 90 | 100 | 100 | 95 | 100 | 100 | 100 |
| Mustard, Wild | 100 | 80 | 70 | 70 | 75 | 80 | 60 | 75 | 100 | 90 | 75 | 100 | 100 | 100 |
| Oat, Wild | 100 | 98 | 95 | 95 | 100 | 100 | 100 | 100 | 100 | 100 | 100 | 100 | 100 | 90 |
| Oilseed Rape | 75 | 85 | 80 | 95 | 75 | 80 | 75 | 80 | 70 | 95 | 60 | 100 | 85 | 85 |
| Pigweed | 100 | 100 | 100 | 100 | 100 | 85 | 100 | 90 | 100 | 100 | 100 | 100 | 100 | 98 |
| Radish, Wild | 65 | 100 | 60 | 100 | 45 | 80 | 60 | 85 | 95 | 95 | 70 | 90 | 100 | 95 |
| Russian Thistle | 80 | 90 | 85 | 85 | 85 | 90 | 75 | 85 | 90 | 85 | 50 | 90 | 90 | 85 |
| Ryegrass, Italian | 100 | 95 | 90 | 90 | 100 | 90 | 98 | 95 | 100 | 95 | 95 | 100 | 100 | 90 |
| Speedwell | 80 | 100 | 85 | 100 | 80 | 100 | 80 | 100 | 100 | 70 | 75 | 80 | 100 | 100 |
| Wheat, Spring | 30 | 20 | 5 | 20 | 10 | 20 | 10 | 35 | 50 | 30 | 25 | 30 | 30 | 5 |
| Wheat, Winter | 15 | 5 | 0 | 10 | 0 | 10 | 5 | 5 | 40 | 25 | 20 | 20 | 35 | 0 |
| Windgrass | 98 | 95 | 85 | 95 | 85 | 85 | 100 | 85 | 90 | 85 | 85 | 85 | 90 | 55 |

TABLE D-continued

| 250 g ai/ha Post-emergence | Compounds | |
|---|---|---|
| | 129 | 153 |
| Barley, Spring | 30 | 30 |
| Barley, Winter | 35 | 25 |
| Blackgrass | 75 | 80 |
| Bluegrass | 30 | 40 |
| Bromegrass, Downy | 80 | 70 |
| Buckwheat, Wild | 100 | 100 |
| Canada Thistle | 100 | 100 |
| Canarygrass | 80 | 85 |
| Chamomile | 100 | 100 |
| Chickweed | 100 | 100 |
| Deadnettle | 95 | 90 |
| Field Poppy | 98 | 100 |
| Field Violet | 75 | 100 |
| Foxtail, Green | 95 | 85 |
| *Galium* | 100 | 100 |
| *Geranium*, Cutleaf | 75 | 98 |
| *Kochia* | 85 | 35 |
| Lambs-quarters | 100 | 75 |
| Mustard, Wild | 100 | 100 |
| Oat, Wild | 100 | 98 |
| Oilseed Rape | 70 | 98 |
| Pigweed | 100 | 85 |
| Radish, Wild | 98 | 100 |
| Russian Thistle | 90 | 55 |
| Ryegrass, Italian | 90 | 90 |
| Speedwell | 75 | 100 |
| Wheat, Spring | 70 | 50 |
| Wheat, Winter | 55 | 35 |
| Windgrass | 90 | 75 |

| 125 g ai/ha Post-emergence | Compounds | | | | | | | | | | | | | |
|---|---|---|---|---|---|---|---|---|---|---|---|---|---|---|
| | 1 | 2 | 11 | 20 | 21 | 22 | 23 | 25 | 27 | 28 | 34 | 35 | 36 | 41 |
| Barley, Spring | 5 | 5 | 10 | 0 | 10 | 15 | 25 | 0 | 5 | 5 | 0 | 10 | 0 | 10 |
| Barley, Winter | 5 | 15 | 25 | 0 | 30 | 0 | 25 | 0 | 5 | 5 | 0 | 0 | 5 | 5 |
| Blackgrass | 70 | 80 | 70 | 50 | 85 | 45 | 75 | 80 | 90 | 85 | 70 | 75 | 45 | 70 |
| Bluegrass | 5 | 5 | 5 | 30 | 35 | 25 | 35 | 30 | 30 | 35 | 15 | 35 | 40 | 25 |
| Bromegrass, Downy | 10 | 10 | 25 | 10 | 75 | 25 | 60 | 50 | 55 | 40 | 40 | 25 | 55 | 35 |
| Buckwheat, Wild | 100 | 100 | 60 | 100 | 100 | 100 | 100 | 100 | 100 | 100 | 100 | 100 | 100 | 95 |
| Canada Thistle | — | — | — | — | — | — | — | — | — | — | — | — | — | — |
| Canarygrass | 50 | 55 | 30 | 45 | 85 | 40 | 85 | 80 | 85 | 80 | 75 | 70 | 55 | 80 |
| Chamomile | 85 | 90 | 75 | 100 | 100 | 85 | 85 | 100 | 95 | 90 | 100 | 100 | 100 | 80 |
| Chickweed | 90 | 100 | 80 | 100 | 100 | 98 | 100 | 100 | 100 | 100 | 100 | 100 | 100 | 95 |
| Deadnettle | 35 | 60 | 100 | 55 | 95 | 45 | 75 | 20 | 30 | 35 | 100 | 20 | 100 | 80 |
| Field Poppy | 100 | 100 | 80 | 100 | 100 | 100 | 100 | 100 | 100 | 100 | 100 | 100 | 90 | 75 |
| Field Violet | 90 | 75 | 75 | 25 | 100 | 75 | 75 | 85 | 75 | 85 | 95 | 75 | 90 | 90 |
| Foxtail, Green | 75 | 95 | 65 | 40 | 85 | 70 | 80 | 70 | 80 | 85 | 55 | 95 | 80 | 50 |
| *Galium* | 95 | 100 | 90 | 100 | 100 | 98 | 100 | 100 | 100 | 100 | 100 | 95 | 100 | 100 |
| *Geranium*, Cutleaf | — | — | — | — | — | — | — | — | — | — | — | — | — | — |
| *Kochia* | 95 | 65 | 85 | 85 | 75 | 100 | 75 | 100 | 55 | 50 | 85 | 65 | 100 | 85 |
| Lambs-quarters | 90 | 95 | 80 | 90 | 90 | 95 | 75 | 90 | 85 | 90 | 100 | 98 | 100 | 75 |

TABLE D-continued

| | | | | | | | | | | | | | | |
|---|---|---|---|---|---|---|---|---|---|---|---|---|---|---|
| Mustard, Wild | 40 | 40 | 75 | 100 | 100 | 100 | 100 | 70 | 30 | 70 | 100 | 100 | 100 | 100 |
| Oat, Wild | 80 | 90 | 85 | 60 | 85 | 85 | 95 | 90 | 90 | 90 | 95 | 85 | 85 | 85 |
| Oilseed Rape | 35 | 55 | 20 | 5 | 100 | 95 | 65 | 45 | 70 | 65 | 75 | 100 | 95 | 25 |
| Pigweed | 100 | 85 | 95 | 100 | 90 | 98 | 85 | 95 | 95 | 100 | 100 | 85 | 100 | 80 |
| Radish, Wild | 30 | 65 | 60 | 70 | 100 | 100 | 100 | 65 | 85 | 85 | 90 | 100 | 100 | 90 |
| Russian Thistle | — | — | — | 80 | 80 | 75 | 75 | 80 | 70 | 80 | 80 | 85 | 85 | 75 |
| Ryegrass, Italian | 85 | 85 | 85 | 80 | 85 | 85 | 85 | 85 | 85 | 80 | 95 | 80 | 90 | 85 |
| Speedwell | 60 | 80 | 100 | 100 | 100 | 65 | 75 | 25 | 100 | 100 | 100 | 80 | 100 | 100 |
| Wheat, Spring | 10 | 10 | 25 | 15 | 40 | 10 | 60 | 15 | 10 | 10 | 15 | 25 | 0 | 30 |
| Wheat, Winter | 0 | 5 | 15 | 15 | 35 | 15 | 55 | 5 | 5 | 5 | 15 | 15 | 5 | 25 |
| Windgrass | 50 | 55 | 15 | 30 | 85 | 35 | 75 | 85 | 80 | 85 | 65 | 70 | 70 | 60 |

| 125 g ai/ha Post-emergence | Compounds | | | | | | | | | | | | | |
|---|---|---|---|---|---|---|---|---|---|---|---|---|---|---|
| | 42 | 47 | 52 | 54 | 57 | 59 | 60 | 66 | 67 | 69 | 72 | 73 | 75 | 79 |
| Barley, Spring | 5 | 0 | 5 | 0 | 10 | 40 | 40 | 5 | 10 | 0 | 10 | 30 | 0 | 5 |
| Barley, Winter | 0 | 15 | 0 | 5 | 25 | 45 | 40 | 0 | 5 | 5 | 30 | 20 | 0 | 0 |
| Blackgrass | 80 | 35 | 15 | 70 | 55 | 85 | 85 | 75 | 85 | 35 | 75 | 80 | 65 | 40 |
| Bluegrass | 20 | 10 | 30 | 25 | 15 | 55 | 35 | 30 | 20 | 15 | 40 | 55 | 15 | 10 |
| Bromegrass, Downy | 40 | 5 | 0 | 55 | 25 | 70 | 65 | 65 | 65 | 20 | 65 | 70 | 15 | 10 |
| Buckwheat, Wild | 100 | 90 | 100 | 100 | 85 | 100 | 100 | 100 | 100 | 95 | 100 | 100 | 100 | 100 |
| Canada Thistle | — | — | — | — | — | — | — | — | — | 100 | — | — | — | — |
| Canarygrass | 80 | 0 | 0 | 65 | 15 | 90 | 85 | 70 | 85 | 70 | 80 | 80 | 30 | 40 |
| Chamomile | 100 | — | 100 | 100 | 100 | 85 | 100 | 100 | 100 | 80 | 85 | 90 | 85 | 100 |
| Chickweed | 100 | 95 | 90 | 100 | 100 | 100 | 100 | 100 | 100 | 90 | 100 | 100 | 100 | 100 |
| Deadnettle | 35 | 30 | 35 | 100 | 85 | 90 | 95 | 35 | 40 | 75 | 100 | 100 | 95 | 20 |
| Field Poppy | 100 | 100 | 90 | 100 | 100 | 95 | 85 | 95 | 100 | 70 | 100 | 100 | 100 | 95 |
| Field Violet | 90 | — | 75 | 95 | 75 | 95 | 100 | 95 | 90 | 85 | 95 | 90 | 95 | 85 |
| Foxtail, Green | 65 | 70 | 10 | 70 | 75 | 75 | 65 | 90 | 100 | 15 | 70 | 75 | 55 | 75 |
| *Galium* | 100 | 75 | 98 | 100 | 90 | 100 | 100 | 100 | 100 | 90 | 100 | 100 | 95 | 100 |
| *Geranium*, Cutleaf | — | — | — | — | — | — | — | — | — | 55 | — | — | — | — |
| *Kochia* | 95 | 95 | 55 | 100 | 65 | 95 | 90 | 100 | 40 | 95 | 100 | 100 | 100 | 85 |
| Lambsquarters | 85 | 70 | 75 | 95 | 75 | 90 | 80 | 100 | 100 | 95 | 90 | 100 | 100 | 90 |
| Mustard, Wild | 70 | 15 | 90 | 100 | 30 | 100 | 98 | 55 | 40 | 80 | 100 | 100 | 100 | 40 |
| Oat, Wild | 85 | 20 | 5 | 90 | 65 | 95 | 95 | 100 | 100 | 80 | 95 | 95 | 85 | 80 |
| Oilseed Rape | 60 | 55 | 65 | 100 | 65 | 85 | 75 | 65 | 85 | 10 | 80 | 75 | 95 | 20 |
| Pigweed | 90 | 100 | 75 | 100 | 100 | 100 | 100 | 100 | 85 | 98 | 100 | 100 | 100 | 100 |
| Radish, Wild | 20 | 5 | 80 | 100 | 100 | 100 | 95 | 30 | 70 | 60 | 90 | 100 | 100 | 0 |
| Russian Thistle | 85 | — | 45 | 90 | — | 85 | 80 | 75 | 75 | 50 | 80 | 80 | 85 | 55 |
| Ryegrass, Italian | 85 | 30 | 75 | 90 | 75 | 90 | 90 | 95 | 98 | 80 | 95 | 95 | 95 | 85 |
| Speedwell | 45 | 40 | 100 | 100 | 25 | 100 | 90 | 70 | 75 | 100 | 100 | 100 | 100 | 35 |
| Wheat, Spring | 15 | 15 | 0 | 15 | 10 | 70 | 40 | 0 | 0 | 0 | 60 | 70 | 5 | 0 |
| Wheat, Winter | 10 | 10 | 15 | 25 | 10 | 55 | 35 | 0 | 0 | 0 | 50 | 65 | 0 | 0 |
| Windgrass | 90 | 15 | 5 | 70 | 10 | 80 | 90 | 85 | 90 | 35 | 80 | 75 | 40 | 35 |

| 125 g ai/ha Post-emergence | Compounds | | | | | | | | | | | | | |
|---|---|---|---|---|---|---|---|---|---|---|---|---|---|---|
| | 80 | 81 | 82 | 83 | 84 | 85 | 87 | 88 | 90 | 104 | 105 | 108 | 109 | 126 |
| Barley, Spring | 15 | 0 | 0 | 5 | 5 | 15 | 0 | 5 | 35 | 10 | 10 | 15 | 10 | 10 |
| Barley, Winter | 5 | 0 | 0 | 0 | 5 | 5 | 5 | 5 | 25 | 10 | 10 | 10 | 5 | 0 |
| Blackgrass | 90 | 80 | 75 | 75 | 85 | 90 | 85 | 90 | 55 | 65 | 65 | 65 | 65 | 30 |
| Bluegrass | 35 | 30 | 30 | 15 | 30 | 25 | 45 | 30 | 25 | 20 | 20 | 25 | 25 | 15 |
| Bromegrass, Downy | 70 | 65 | 60 | 50 | 65 | 35 | 65 | 35 | 40 | 55 | 25 | 40 | 60 | 20 |
| Buckwheat, Wild | 100 | 100 | 100 | 100 | 100 | 100 | 100 | 100 | 100 | 100 | 100 | 100 | 100 | 100 |

TABLE D-continued

| | | | | | | | | | | | | | | |
|---|---|---|---|---|---|---|---|---|---|---|---|---|---|---|
| Canada Thistle | — | — | — | — | — | — | — | — | 100 | — | — | — | — | 98 |
| Canarygrass | 85 | 95 | 75 | 80 | 80 | 85 | 85 | 85 | 75 | 80 | 75 | 80 | 80 | 45 |
| Chamomile | 100 | 100 | 100 | 100 | 100 | 90 | 100 | 95 | 98 | 95 | 100 | 95 | 95 | 98 |
| Chickweed | 100 | 100 | 95 | 100 | 90 | 100 | 100 | 100 | 98 | 100 | 100 | 100 | 100 | 100 |
| Deadnettle | 35 | 35 | 25 | 55 | 20 | 40 | 35 | 35 | 100 | 70 | 20 | 75 | 70 | 80 |
| Field Poppy | 100 | 100 | 95 | 100 | 90 | 80 | 85 | 100 | 75 | 75 | 80 | 65 | 75 | 75 |
| Field Violet | 95 | 100 | 100 | 100 | 100 | 75 | 100 | 80 | 100 | 95 | 95 | 100 | 100 | 90 |
| Foxtail, Green | 90 | 95 | 85 | 90 | 85 | 85 | 80 | 80 | 70 | 85 | 75 | 75 | 75 | 25 |
| *Galium* | 95 | 100 | 100 | 100 | 100 | 100 | 100 | 100 | 100 | 100 | 95 | 100 | 100 | 100 |
| *Geranium*, Cutleaf | — | — | — | — | — | — | — | — | 75 | — | — | — | — | 80 |
| *Kochia* | 100 | 90 | 100 | 80 | 100 | 70 | 90 | 60 | 100 | 100 | 95 | 100 | 100 | 95 |
| Lambsquarters | 100 | 100 | 95 | 100 | 95 | 95 | 100 | 90 | 100 | 100 | 90 | 100 | 95 | 100 |
| Mustard, Wild | 70 | 60 | 40 | 65 | 70 | 30 | 25 | 25 | 100 | 85 | 40 | 95 | 90 | 90 |
| Oat, Wild | 100 | 95 | 95 | 90 | 98 | 95 | 98 | 100 | 98 | 95 | 95 | 100 | 95 | 80 |
| Oilseed Rape | 65 | 75 | 60 | 75 | 70 | 70 | 65 | 75 | 15 | 90 | 25 | 75 | 75 | 75 |
| Pigweed | 100 | 100 | 100 | 100 | 95 | 85 | 100 | 75 | 95 | 100 | 100 | 100 | 100 | 98 |
| Radish, Wild | 50 | 95 | 50 | 100 | 55 | 75 | 30 | 85 | 75 | 90 | 20 | 85 | 90 | 75 |
| Russian Thistle | 80 | 90 | 75 | 80 | 75 | 80 | 65 | 80 | 75 | 65 | 50 | 75 | 75 | 80 |
| Ryegrass, Italian | 98 | 95 | 90 | 90 | 98 | 85 | 95 | 90 | 95 | 95 | 90 | 95 | 95 | 90 |
| Speedwell | 85 | 95 | 85 | 75 | 75 | 80 | 75 | 85 | 100 | 55 | 65 | 70 | 75 | 100 |
| Wheat, Spring | 15 | 0 | 0 | 5 | 0 | 15 | 5 | 5 | 40 | 20 | 20 | 20 | 25 | 0 |
| Wheat, Winter | 5 | 5 | 0 | 5 | 0 | 0 | 0 | 5 | 40 | 20 | 10 | 20 | 25 | 0 |
| Windgrass | 95 | 90 | 80 | 90 | 80 | 80 | 85 | 85 | 70 | 85 | 80 | 75 | 80 | 30 |

| 125 g ai/ha Post-emergence | Compounds | |
|---|---|---|
| | 129 | 153 |
| Barley, Spring | 30 | 15 |
| Barley, Winter | 30 | 10 |
| Blackgrass | 60 | 75 |
| Bluegrass | 20 | 30 |
| Bromegrass, Downy | 65 | 65 |
| Buckwheat, Wild | 100 | 100 |
| Canada Thistle | 100 | 100 |
| Canarygrass | 75 | 80 |
| Chamomile | 100 | 100 |
| Chickweed | 100 | 85 |
| Deadnettle | 70 | 80 |
| Field Poppy | 80 | 100 |
| Field Violet | 70 | 95 |
| Foxtail, Green | 85 | 85 |
| *Galium* | 100 | 100 |
| *Geranium*, Cutleaf | 75 | 90 |
| *Kochia* | 80 | 30 |
| Lambsquarters | 95 | 65 |
| Mustard, Wild | 98 | 100 |
| Oat, Wild | 95 | 90 |
| Oilseed Rape | 15 | 85 |
| Pigweed | 100 | 80 |
| Radish, Wild | 80 | 100 |
| Russian Thistle | 85 | 45 |
| Ryegrass, Italian | 90 | 90 |
| Speedwell | 65 | 90 |
| Wheat, Spring | 50 | 40 |

TABLE D-continued

|  | | | | | | | | | | | | | |
|---|---|---|---|---|---|---|---|---|---|---|---|---|---|
| Wheat, Winter | | | | | 40 | | | | | 25 | | | |
| Windgrass | | | | | 55 | | | | | 65 | | | |

| 62 g ai/ha Post-emergence | Compounds | | | | | | | | | | | | |
|---|---|---|---|---|---|---|---|---|---|---|---|---|---|
|  | 1 | 2 | 11 | 20 | 21 | 22 | 23 | 25 | 27 | 28 | 34 | 35 | 36 | 41 |
| Barley, Spring | 5 | 0 | 0 | 0 | 5 | 0 | 15 | 0 | 0 | 5 | 0 | 0 | 0 | 5 |
| Barley, Winter | 5 | 10 | 20 | 0 | 10 | 0 | 15 | 0 | 0 | 0 | 0 | 0 | 0 | 5 |
| Blackgrass | 50 | 70 | 40 | 40 | 85 | 20 | 70 | 75 | 80 | 80 | 40 | 65 | 35 | 65 |
| Bluegrass | 5 | 10 | 5 | 25 | 30 | 15 | 35 | 20 | 25 | 30 | 15 | 25 | 15 | 30 |
| Bromegrass, Downy | 10 | 10 | 15 | 10 | 60 | 10 | 45 | 25 | 25 | 25 | 30 | 25 | 20 | 20 |
| Buckwheat, Wild | 75 | 95 | 45 | 100 | 100 | 98 | 100 | 100 | 100 | 100 | 100 | 100 | 100 | 90 |
| Canada Thistle | — | — | — | — | — | — | — | — | — | — | — | — | — | — |
| Canarygrass | 35 | 40 | 20 | 30 | 80 | 35 | 75 | 80 | 80 | 75 | 65 | 30 | 40 | 70 |
| Chamomile | 75 | 80 | 65 | 95 | 95 | 80 | 85 | 95 | 90 | 90 | 80 | 100 | 95 | 75 |
| Chickweed | 80 | 95 | 90 | 100 | 100 | 95 | 100 | 98 | 100 | 100 | 100 | 100 | 100 | 98 |
| Deadnettle | 35 | 60 | 100 | 35 | 100 | 10 | 65 | 10 | 5 | 35 | 100 | 20 | 100 | 100 |
| Field Poppy | 95 | 95 | 85 | 60 | 100 | 85 | 100 | 80 | 100 | 90 | 100 | 100 | 70 | 80 |
| Field Violet | 75 | 85 | 65 | 15 | 95 | 70 | 45 | 75 | 70 | 75 | 100 | 75 | 85 | 90 |
| Foxtail, Green | 65 | 80 | 25 | 35 | 80 | 45 | 75 | 65 | 80 | 75 | 45 | 90 | 45 | 55 |
| *Galium* | 90 | 100 | 85 | 75 | 100 | 90 | 100 | 100 | 100 | 100 | 100 | 98 | 100 | 100 |
| *Geranium*, Cutleaf | — | — | — | — | — | — | — | — | — | — | — | — | — | — |
| *Kochia* | 85 | 60 | 75 | 65 | 45 | 95 | 75 | 95 | 55 | 40 | 85 | 20 | 95 | 95 |
| Lambs-quarters | 90 | 90 | 80 | 85 | 85 | 85 | 75 | 90 | 85 | 85 | 95 | 100 | 95 | 65 |
| Mustard, Wild | 30 | 35 | 70 | 100 | 100 | 95 | 95 | 40 | 40 | 45 | 85 | 100 | 100 | 100 |
| Oat, Wild | 70 | 80 | 75 | 25 | 85 | 85 | 75 | 80 | 85 | 85 | 85 | 90 | 80 | 80 |
| Oilseed Rape | 15 | 45 | 15 | 0 | 100 | 30 | 60 | 30 | 65 | 65 | 70 | 98 | 85 | 5 |
| Pigweed | 90 | 80 | 65 | 100 | 85 | 95 | 75 | 100 | 85 | 90 | 100 | 80 | 100 | 80 |
| Radish, Wild | 20 | 55 | 30 | 40 | 100 | 75 | 75 | 35 | 75 | 100 | 85 | 100 | 90 | 80 |
| Russian Thistle | — | — | — | 75 | 75 | 70 | 75 | 75 | 75 | 75 | 80 | 75 | 85 | 70 |
| Ryegrass, Italian | 75 | 80 | 85 | 70 | 80 | 80 | 80 | 85 | 85 | 80 | 95 | 75 | 80 | 85 |
| Speedwell | 55 | 65 | 100 | 15 | 100 | 60 | 100 | 15 | 70 | 85 | 75 | 75 | 90 | 100 |
| Wheat, Spring | 0 | 0 | 15 | 15 | 30 | 10 | 50 | 0 | 5 | 5 | 10 | 20 | 0 | 20 |
| Wheat, Winter | 0 | 0 | 15 | 10 | 25 | 5 | 40 | 0 | 5 | 5 | 25 | 15 | 0 | 20 |
| Windgrass | 25 | 25 | 10 | 30 | 80 | 20 | 70 | 75 | 75 | 80 | 50 | 65 | 50 | 55 |

| 62 g ai/ha Post-emergence | Compounds | | | | | | | | | | | | |
|---|---|---|---|---|---|---|---|---|---|---|---|---|---|
|  | 42 | 47 | 52 | 54 | 57 | 59 | 60 | 66 | 67 | 69 | 72 | 73 | 75 | 79 |
| Barley, Spring | 0 | 0 | 0 | 0 | 10 | 30 | 25 | 0 | 5 | 0 | 5 | 25 | 0 | 5 |
| Barley, Winter | 0 | 10 | 0 | 0 | 30 | 30 | 25 | 0 | 0 | 0 | 20 | 15 | 0 | 0 |
| Blackgrass | 75 | 25 | 15 | 40 | 45 | 80 | 80 | 70 | 75 | 30 | 70 | 70 | 20 | 20 |
| Bluegrass | 20 | 10 | 5 | 15 | 15 | 40 | 25 | 25 | 15 | 15 | 35 | 30 | 10 | 10 |
| Bromegrass, Downy | 20 | 0 | 0 | 55 | 20 | 70 | 55 | 60 | 60 | 15 | 55 | 55 | 0 | 5 |
| Buckwheat, Wild | 95 | 75 | 100 | 100 | 85 | 100 | 95 | 100 | 100 | 70 | 100 | 100 | 100 | 100 |
| Canada Thistle | — | — | — | — | — | — | — | — | — | 100 | — | — | — | — |
| Canarygrass | 75 | 0 | 0 | 55 | 5 | 80 | 80 | 65 | 85 | 25 | 50 | 70 | 15 | 20 |
| Chamomile | 70 | — | 100 | 100 | 100 | 80 | 80 | 90 | 100 | 70 | 80 | 85 | 90 | 95 |
| Chickweed | 100 | 95 | 100 | 100 | 100 | 98 | 100 | 85 | 100 | 80 | 100 | 95 | 100 | 95 |
| Deadnettle | 25 | 20 | 25 | 100 | 90 | 80 | 75 | 15 | 30 | 65 | 90 | 90 | 90 | 15 |
| Field Poppy | 85 | 100 | 80 | 100 | 100 | 75 | 75 | 85 | 100 | 70 | 90 | 100 | 100 | 85 |
| Field Violet | 80 | — | 65 | 75 | 70 | 80 | 95 | 95 | 80 | 80 | 95 | 95 | 100 | 75 |
| Foxtail, Green | 50 | 60 | 5 | 65 | 75 | 70 | 40 | 80 | 90 | 10 | 65 | 70 | 25 | 70 |
| *Galium* | 100 | 75 | 95 | 100 | 90 | 100 | 100 | 100 | 100 | 85 | 100 | 100 | 95 | 100 |
| *Geranium*, Cutleaf | — | — | — | — | — | — | — | — | — | 30 | — | — | — | — |

TABLE D-continued

| | | | | | | | | | | | | | | |
|---|---|---|---|---|---|---|---|---|---|---|---|---|---|---|
| *Kochia* | 90 | 70 | 20 | 95 | 55 | 95 | 85 | 95 | 35 | 85 | 95 | 80 | 100 | 80 |
| Lambs-quarters | 85 | 50 | 75 | 95 | 75 | 85 | 80 | 95 | 100 | 95 | 95 | 95 | 100 | 80 |
| Mustard, Wild | 70 | 0 | 75 | 100 | 30 | 100 | 75 | 40 | 35 | 35 | 100 | 100 | 100 | 20 |
| Oat, Wild | 85 | 15 | 5 | 85 | 25 | 90 | 90 | 95 | 98 | 75 | 85 | 95 | 70 | 70 |
| Oilseed Rape | 50 | 20 | 5 | 95 | 25 | 70 | 70 | 20 | 80 | 10 | 70 | 70 | 95 | 5 |
| Pigweed | 90 | 75 | 40 | 100 | 85 | 85 | 95 | 100 | 80 | 80 | 100 | 100 | 100 | 100 |
| Radish, Wild | 10 | 10 | 65 | 100 | 100 | 95 | 75 | 25 | 65 | 20 | 80 | 95 | 100 | 0 |
| Russian Thistle | 75 | — | 35 | 80 | — | 80 | 80 | 80 | 60 | 20 | 75 | 80 | 80 | 55 |
| Ryegrass, Italian | 80 | 10 | 50 | 85 | 50 | 90 | 90 | 95 | 90 | 75 | 95 | 85 | 95 | 75 |
| Speedwell | 50 | 10 | 85 | 100 | 15 | 100 | 80 | 70 | 75 | 85 | 75 | 100 | 100 | 30 |
| Wheat, Spring | 10 | 10 | 0 | 0 | 10 | 45 | 35 | 0 | 0 | 0 | 50 | 55 | 0 | 0 |
| Wheat, Winter | 5 | 5 | 10 | 5 | 10 | 40 | 30 | 0 | 0 | 0 | 35 | 35 | 0 | 0 |
| Windgrass | 75 | 10 | 5 | 45 | 10 | 80 | 85 | 80 | 85 | 15 | 75 | 70 | 15 | 20 |

| 62 g ai/ha Post-emergence | Compounds | | | | | | | | | | | | |
|---|---|---|---|---|---|---|---|---|---|---|---|---|---|
| | 80 | 81 | 82 | 83 | 84 | 85 | 87 | 88 | 90 | 104 | 105 | 108 | 109 | 126 |
| Barley, Spring | 10 | 0 | 5 | 5 | 0 | 0 | 0 | 0 | 25 | 10 | 5 | 10 | 5 | 0 |
| Barley, Winter | 0 | 0 | 0 | 0 | 0 | 0 | 0 | 0 | 15 | 10 | 10 | 5 | 0 | 5 |
| Blackgrass | 80 | 75 | 70 | 70 | 75 | 80 | 75 | 85 | 35 | 40 | 25 | 45 | 30 | 20 |
| Bluegrass | 35 | 20 | 20 | 10 | 20 | 20 | 25 | 25 | 15 | 10 | 10 | 10 | 15 | 10 |
| Bromegrass, Downy | 65 | 35 | 45 | 35 | 65 | 30 | 65 | 25 | 30 | 30 | 20 | 30 | 30 | 10 |
| Buckwheat, Wild | 100 | 100 | 100 | 100 | 80 | 100 | 100 | 85 | 90 | 95 | 95 | 100 | 95 | 100 |
| Canada Thistle | — | — | — | — | — | — | — | — | 100 | — | — | — | — | 100 |
| Canarygrass | 80 | 85 | 55 | 75 | 65 | 85 | 80 | 80 | 45 | 65 | 50 | 50 | 55 | 35 |
| Chamomile | 95 | 100 | 100 | 100 | 98 | 75 | 100 | 100 | 75 | 85 | 85 | 85 | 85 | 95 |
| Chickweed | 100 | 100 | 90 | 100 | 90 | 100 | 90 | 95 | 90 | 100 | 90 | 100 | 100 | 98 |
| Deadnettle | 25 | 35 | 10 | 25 | 10 | 15 | 15 | 15 | 80 | 50 | 10 | 50 | 50 | 70 |
| Field Poppy | 80 | 100 | 85 | 100 | 80 | 90 | 85 | 85 | 70 | 65 | 75 | 55 | 50 | 55 |
| Field Violet | 85 | 85 | 100 | 80 | 100 | 65 | 85 | 75 | 98 | 90 | 90 | 95 | 95 | 85 |
| Foxtail, Green | 90 | 95 | 80 | 90 | 80 | 80 | 75 | 75 | 55 | 70 | 70 | 70 | 65 | 10 |
| *Galium* | 95 | 100 | 100 | 100 | 100 | 95 | 100 | 100 | 100 | 90 | 95 | 95 | 100 | 100 |
| *Geranium*, Cutleaf | — | — | — | — | — | — | — | — | 65 | — | — | — | — | 40 |
| *Kochia* | 100 | 85 | 95 | 75 | 95 | 65 | 90 | 55 | 100 | 95 | 95 | 100 | 100 | 80 |
| Lambs-quarters | 100 | 100 | 95 | 100 | 90 | 85 | 100 | 80 | 90 | 100 | 95 | 95 | 95 | 98 |
| Mustard, Wild | 50 | 60 | 35 | 25 | 50 | 25 | 35 | 20 | 95 | 75 | 25 | 75 | 85 | 80 |
| Oat, Wild | 98 | 90 | 90 | 85 | 95 | 85 | 95 | 95 | 90 | 90 | 85 | 95 | 95 | 70 |
| Oilseed Rape | 55 | 70 | 45 | 70 | 45 | 70 | 40 | 65 | 5 | 75 | 15 | 70 | 70 | 65 |
| Pigweed | 100 | 100 | 100 | 100 | 95 | 80 | 100 | 75 | 90 | 100 | 100 | 100 | 85 | 100 |
| Radish, Wild | 50 | 90 | 20 | 90 | 40 | 65 | 20 | 60 | 75 | 75 | 15 | 75 | 75 | 70 |
| Russian Thistle | 70 | 85 | 75 | 80 | 70 | 75 | 65 | 75 | 75 | 60 | 45 | 70 | 75 | 40 |
| Ryegrass, Italian | 95 | 90 | 85 | 85 | 95 | 85 | 95 | 90 | 90 | 95 | 85 | 90 | 85 | 90 |
| Speedwell | 75 | 80 | 75 | 70 | 70 | 70 | 75 | 65 | 100 | 35 | 50 | 65 | 60 | 65 |
| Wheat, Spring | 10 | 0 | 0 | 0 | 0 | 0 | 0 | 0 | 35 | 15 | 10 | 20 | 15 | 0 |
| Wheat, Winter | 0 | 0 | 0 | 0 | 0 | 0 | 0 | 10 | 35 | 15 | 5 | 15 | 15 | 0 |
| Windgrass | 90 | 80 | 75 | 85 | 75 | 70 | 85 | 80 | 50 | 75 | 70 | 70 | 65 | 20 |

| 62 g ai/ha Post-emergence | Compounds | |
|---|---|---|
| | 129 | 153 |
| Barley, Spring | 25 | 5 |
| Barley, Winter | 20 | 5 |
| Blackgrass | 45 | 70 |
| Bluegrass | 15 | 15 |
| Bromegrass, | 40 | 35 |

TABLE D-continued

|  |  |  |  |  |  |  |  |  |  |  |  |  |  |
|---|---|---|---|---|---|---|---|---|---|---|---|---|---|
| Downy Buckwheat, Wild |  |  |  | 100 |  |  |  |  | 95 |  |  |  |  |
| Canada Thistle |  |  |  | 100 |  |  |  |  | 98 |  |  |  |  |
| Canarygrass |  |  |  | 55 |  |  |  |  | 75 |  |  |  |  |
| Chamomile |  |  |  | 98 |  |  |  |  | 95 |  |  |  |  |
| Chickweed |  |  |  | 100 |  |  |  |  | 85 |  |  |  |  |
| Deadnettle |  |  |  | 40 |  |  |  |  | 75 |  |  |  |  |
| Field Poppy |  |  |  | 75 |  |  |  |  | 95 |  |  |  |  |
| Field Violet |  |  |  | 70 |  |  |  |  | 90 |  |  |  |  |
| Foxtail, Green |  |  |  | 80 |  |  |  |  | 80 |  |  |  |  |
| *Galium* |  |  |  | 100 |  |  |  |  | 100 |  |  |  |  |
| *Geranium*, Cutleaf |  |  |  | 70 |  |  |  |  | 90 |  |  |  |  |
| *Kochia* |  |  |  | 70 |  |  |  |  | 15 |  |  |  |  |
| Lambs-quarters |  |  |  | 90 |  |  |  |  | 65 |  |  |  |  |
| Mustard, Wild |  |  |  | 80 |  |  |  |  | 98 |  |  |  |  |
| Oat, Wild |  |  |  | 90 |  |  |  |  | 85 |  |  |  |  |
| Oilseed Rape |  |  |  | 5 |  |  |  |  | 85 |  |  |  |  |
| Pigweed |  |  |  | 98 |  |  |  |  | 75 |  |  |  |  |
| Radish, Wild |  |  |  | 75 |  |  |  |  | 85 |  |  |  |  |
| Russian Thistle |  |  |  | 80 |  |  |  |  | 20 |  |  |  |  |
| Ryegrass, Italian |  |  |  | 85 |  |  |  |  | 90 |  |  |  |  |
| Speedwell |  |  |  | 60 |  |  |  |  | 75 |  |  |  |  |
| Wheat, Spring |  |  |  | 35 |  |  |  |  | 30 |  |  |  |  |
| Wheat, Winter |  |  |  | 35 |  |  |  |  | 15 |  |  |  |  |
| Windgrass |  |  |  | 35 |  |  |  |  | 30 |  |  |  |  |

| 31 g ai/ha Post-emergence | Compounds |  |  |  |  |  |  |  |  |  |  |  |  |
|---|---|---|---|---|---|---|---|---|---|---|---|---|---|
|  | 1 | 2 | 11 | 20 | 21 | 22 | 25 | 27 | 28 | 34 | 35 | 36 | 41 | 42 |
| Barley, Spring | 0 | 0 | 0 | 0 | 0 | 0 | 0 | 0 | 5 | 0 | 0 | 0 | 0 | 0 |
| Barley, Winter | 5 | 10 | 20 | 0 | 0 | 0 | 0 | 0 | 0 | 0 | 0 | 0 | 0 | 0 |
| Blackgrass | 40 | 65 | 25 | 15 | 80 | 15 | 65 | 75 | 75 | 25 | 30 | 25 | 55 | 75 |
| Bluegrass | 0 | 5 | 5 | 10 | 20 | 10 | 10 | 15 | 20 | 10 | 35 | 10 | 15 | 15 |
| Bromegrass, Downy | 0 | 10 | 15 | 0 | 45 | 10 | 5 | 15 | 15 | 20 | 5 | 10 | 10 | 0 |
| Buckwheat, Wild | 70 | 85 | 45 | 80 | 100 | 90 | 80 | 100 | 100 | 100 | 95 | 100 | 80 | 80 |
| Canada Thistle | — | — | — | — | — | — | — | — | — | — | — | — | — | — |
| Canarygrass | 20 | 25 | 10 | 10 | 80 | 20 | 70 | 75 | 75 | 30 | 20 | 15 | 55 | 50 |
| Chamomile | 65 | 70 | 40 | 70 | 90 | 80 | 75 | 80 | 85 | 75 | 100 | 95 | 75 | 75 |
| Chickweed | 80 | 85 | 45 | 90 | 90 | 85 | 98 | 95 | 100 | 95 | 90 | 100 | 98 | 95 |
| Deadnettle | 35 | 60 | 75 | 25 | 90 | 10 | 5 | 5 | 10 | 95 | 15 | 80 | 85 | 5 |
| Field Poppy | 95 | 75 | 35 | 30 | 85 | 75 | 70 | 85 | 80 | 100 | 100 | 60 | 55 | 65 |
| Field Violet | 85 | 60 | 65 | 5 | 95 | 70 | 65 | 75 | 80 | 75 | 65 | 70 | 100 | 70 |
| Foxtail, Green | 50 | 70 | 5 | 15 | 70 | 15 | 60 | 70 | 65 | 40 | 75 | 35 | 45 | 35 |
| *Galium* | 80 | 85 | 85 | 70 | 100 | 90 | 100 | 100 | 100 | 95 | 98 | 100 | 100 | 100 |
| *Geranium*, Cutleaf | — | — | — | — | — | — | — | — | — | — | — | — | — | — |
| *Kochia* | 70 | 50 | 60 | 35 | 35 | 80 | 90 | 45 | 35 | 60 | 25 | 85 | 85 | 70 |
| Lambs-quarters | 75 | 90 | 60 | 85 | 80 | 80 | 90 | 80 | 80 | 90 | 75 | 95 | 70 | 80 |
| Mustard, Wild | 25 | 25 | 65 | 75 | 100 | 90 | 20 | 15 | 35 | 80 | 98 | 100 | 90 | 25 |
| Oat, Wild | 40 | 55 | 40 | 20 | 80 | 65 | 75 | 75 | 75 | 75 | 85 | 35 | 70 | 75 |
| Oilseed Rape | 0 | 20 | 0 | 0 | 80 | 30 | 5 | 55 | 65 | 65 | 95 | 75 | 0 | 10 |
| Pigweed | 80 | 70 | 35 | 80 | 80 | 85 | 80 | 75 | 75 | 100 | 80 | 100 | 75 | 85 |
| Radish, Wild | 10 | 25 | 50 | 50 | 95 | 85 | 15 | 65 | 85 | 65 | 85 | 80 | 90 | 5 |
| Russian Thistle | — | — | — | 70 | 70 | 65 | 70 | 65 | 70 | 70 | 70 | 80 | 70 | 70 |
| Ryegrass, Italian | 65 | 70 | 80 | 55 | 80 | 75 | 75 | 80 | 75 | 90 | 65 | 75 | 80 | 75 |
| Speedwell | 25 | 50 | 0 | 5 | 100 | 60 | 10 | 35 | 60 | 65 | 70 | 60 | 100 | 10 |
| Wheat, Spring | 0 | 0 | 15 | 0 | 20 | 5 | 0 | 0 | 0 | 0 | 15 | 0 | 15 | 0 |

TABLE D-continued

| | | | | | | | | | | | | | |
|---|---|---|---|---|---|---|---|---|---|---|---|---|---|
| Wheat, Winter | 0 | 0 | 10 | 0 | 20 | 5 | 0 | 0 | 5 | 5 | 10 | 0 | 10 | 0 |
| Windgrass | 10 | 10 | 10 | 25 | 70 | 15 | 70 | 75 | 70 | 40 | 25 | 40 | 40 | 70 |

| 31 g ai/ha Post-emergence | Compounds | | | | | | | | | | | | |
|---|---|---|---|---|---|---|---|---|---|---|---|---|---|
| | 47 | 52 | 54 | 57 | 59 | 60 | 66 | 67 | 69 | 72 | 73 | 75 | 79 | 80 |
| Barley, Spring | 0 | 0 | 0 | 10 | 25 | 15 | 0 | 0 | 0 | 5 | 10 | 0 | 0 | 0 |
| Barley, Winter | 10 | 0 | 0 | 20 | 20 | 10 | 0 | 0 | 0 | 10 | 15 | 0 | 0 | 0 |
| Blackgrass | 25 | 10 | 25 | 15 | 70 | 75 | 65 | 70 | 20 | 40 | 65 | 15 | 10 | 75 |
| Bluegrass | 5 | 5 | 10 | 5 | 25 | 15 | 0 | 5 | 0 | 20 | 15 | 10 | 5 | 15 |
| Bromegrass, Downy | 5 | 0 | 10 | 15 | 35 | 30 | 50 | 60 | 0 | 45 | 25 | 0 | 5 | 55 |
| Buckwheat, Wild | 60 | 100 | 100 | 80 | 65 | 90 | 95 | 100 | 60 | 95 | 95 | 100 | 70 | 100 |
| Canada Thistle | — | — | — | — | — | — | — | — | 85 | — | — | — | — | — |
| Canarygrass | 0 | 0 | 35 | 5 | 75 | 80 | 55 | 75 | 25 | 40 | 60 | 15 | 5 | 55 |
| Chamomile | — | 85 | 90 | 100 | 80 | 75 | 85 | 95 | 65 | 75 | 70 | 80 | 85 | 80 |
| Chickweed | 90 | 90 | 100 | 100 | 100 | 85 | 75 | 85 | 75 | 98 | 90 | 100 | 95 | 90 |
| Deadnettle | 20 | 35 | 100 | 70 | 80 | 70 | 15 | 40 | 20 | 85 | 75 | 75 | 5 | 35 |
| Field Poppy | 80 | 85 | 70 | 100 | 70 | 60 | 70 | 80 | 65 | 80 | 75 | 100 | 75 | 60 |
| Field Violet | — | 35 | 85 | 80 | 75 | 80 | 85 | 80 | 75 | 90 | 90 | 95 | 75 | 90 |
| Foxtail, Green | 50 | 5 | 55 | 75 | 65 | 35 | 75 | 80 | 10 | 60 | 65 | 0 | 20 | 70 |
| *Galium* | 65 | 90 | 100 | 90 | 100 | 100 | 85 | 90 | 75 | 95 | 95 | 90 | 95 | 90 |
| *Geranium*, Cutleaf | — | — | — | — | — | — | — | — | 15 | — | — | — | — | — |
| *Kochia* | 45 | 0 | 15 | 40 | 95 | 70 | 85 | 10 | 60 | 80 | 100 | 95 | 70 | 100 |
| Lambs-quarters | 45 | 75 | 95 | 75 | 90 | 80 | 95 | 90 | 75 | 80 | 95 | 100 | 85 | 95 |
| Mustard, Wild | 0 | 20 | 100 | 30 | 90 | 75 | 10 | 25 | 20 | 85 | 85 | 100 | 20 | 35 |
| Oat, Wild | 10 | 5 | 75 | 15 | 80 | 85 | 85 | 95 | 70 | 85 | 85 | 50 | 70 | 95 |
| Oilseed Rape | 20 | 0 | 75 | 20 | 60 | 65 | 0 | 70 | 0 | 65 | 65 | 70 | 0 | 15 |
| Pigweed | 75 | 35 | 100 | 85 | 80 | 75 | 95 | 75 | 80 | 95 | 100 | 100 | 100 | 100 |
| Radish, Wild | 5 | 35 | 80 | 40 | 95 | 65 | 5 | 55 | 0 | 75 | 75 | 95 | 0 | 10 |
| Russian Thistle | — | 20 | 80 | — | 80 | 80 | 75 | 55 | 15 | 70 | 75 | 80 | 50 | 70 |
| Ryegrass, Italian | 10 | 40 | 80 | 25 | 80 | 80 | 85 | 85 | 75 | 95 | 70 | 90 | 70 | 85 |
| Speedwell | 10 | 70 | 75 | 100 | 65 | 85 | 55 | 70 | 70 | 75 | 70 | 80 | 25 | 65 |
| Wheat, Spring | 10 | 0 | 0 | 0 | 40 | 30 | 0 | 0 | 0 | 40 | 45 | 0 | 0 | 0 |
| Wheat, Winter | 5 | 0 | 0 | 5 | 35 | 25 | 0 | 0 | 0 | 25 | 25 | 0 | 0 | 0 |
| Windgrass | 10 | 0 | 35 | 10 | 75 | 80 | 75 | 85 | 15 | 65 | 70 | 10 | 15 | 75 |

| 31 g ai/ha Post-emergence | Compounds | | | | | | | | | | | | |
|---|---|---|---|---|---|---|---|---|---|---|---|---|---|
| | 81 | 82 | 83 | 84 | 85 | 87 | 88 | 90 | 104 | 105 | 108 | 109 | 126 | 129 |
| Barley, Spring | 0 | 0 | 0 | 0 | 0 | 0 | 0 | 10 | 0 | 0 | 0 | 0 | 0 | 20 |
| Barley, Winter | 0 | 0 | 0 | 0 | 0 | 0 | 0 | 0 | 0 | 0 | 5 | 5 | 0 | 10 |
| Blackgrass | 65 | 45 | 65 | 65 | 75 | 65 | 75 | 15 | 35 | 15 | 20 | 20 | 15 | 35 |
| Bluegrass | 5 | 10 | 0 | 20 | 10 | 25 | 10 | 5 | 10 | 10 | 5 | 5 | 0 | 10 |
| Bromegrass, Downy | 15 | 55 | 25 | 40 | 30 | 45 | 15 | 20 | 20 | 10 | 25 | 30 | 5 | 25 |
| Buckwheat, Wild | 100 | 85 | 100 | 85 | 95 | 85 | 80 | 80 | 90 | 65 | 90 | 95 | 70 | 100 |
| Canada Thistle | — | — | — | — | — | — | — | 98 | — | — | — | — | 98 | 100 |
| Canarygrass | 75 | 50 | 50 | 50 | 75 | 55 | 65 | 25 | 45 | 40 | 40 | 40 | 20 | 30 |
| Chamomile | 100 | 90 | 95 | 95 | 75 | 90 | 85 | 70 | 80 | 80 | 75 | 80 | 70 | 100 |
| Chickweed | 100 | 80 | 100 | 85 | 90 | 85 | 85 | 80 | 95 | 90 | 90 | 100 | 80 | 100 |
| Deadnettle | 15 | 10 | 15 | 5 | 10 | 10 | 5 | 70 | 45 | 10 | 35 | 20 | 40 | 35 |
| Field Poppy | 100 | 70 | 100 | 70 | 70 | 70 | 70 | 65 | 15 | 70 | 20 | 45 | 25 | 70 |
| Field Violet | 75 | 95 | 90 | 85 | 65 | 80 | 75 | 90 | 85 | 85 | 90 | 90 | 85 | 65 |
| Foxtail, Green | 80 | 75 | 75 | 75 | 75 | 70 | 70 | 25 | 30 | 70 | 65 | 55 | 10 | 80 |
| *Galium* | 100 | 90 | 100 | 90 | 85 | 85 | 100 | 98 | 85 | 85 | 90 | 100 | 90 | 90 |
| *Geranium*, Cutleaf | — | — | — | — | — | — | — | 45 | — | — | — | — | 30 | 60 |

TABLE D-continued

| | | | | | | | | | | | | | | |
|---|---|---|---|---|---|---|---|---|---|---|---|---|---|---|
| *Kochia* | 60 | 90 | 70 | 85 | 40 | 85 | 45 | 85 | 95 | 85 | 90 | 95 | 75 | 60 |
| Lambsquarters | 95 | 95 | 95 | 90 | 80 | 95 | 80 | 90 | 95 | 85 | 90 | 90 | 90 | 75 |
| Mustard, Wild | 50 | 25 | 25 | 25 | 10 | 10 | 10 | 80 | 70 | 5 | 70 | 60 | 80 | 80 |
| Oat, Wild | 85 | 90 | 80 | 85 | 75 | 85 | 80 | 75 | 85 | 80 | 85 | 95 | 60 | 90 |
| Oilseed Rape | 70 | 25 | 65 | 10 | 65 | 15 | 65 | 0 | 70 | 0 | 45 | 65 | 60 | 5 |
| Pigweed | 100 | 90 | 100 | 95 | 75 | 95 | 75 | 80 | 100 | 85 | 95 | 85 | 98 | 98 |
| Radish, Wild | 75 | 25 | 75 | 20 | 60 | 15 | 35 | 65 | 70 | 5 | 75 | 75 | 40 | 60 |
| Russian Thistle | 75 | 65 | 75 | 70 | 65 | 60 | 75 | 30 | 55 | 40 | 65 | 60 | 30 | 70 |
| Ryegrass, Italian | 85 | 85 | 80 | 80 | 80 | 90 | 80 | 75 | 90 | 75 | 90 | 85 | 85 | 80 |
| Speedwell | 75 | 70 | 65 | 70 | 35 | 70 | 25 | 100 | 30 | 45 | 60 | 50 | 60 | 35 |
| Wheat, Spring | 0 | 0 | 0 | 0 | 0 | 0 | 0 | 25 | 10 | 0 | 15 | 5 | 0 | 25 |
| Wheat, Winter | 0 | 0 | 0 | 0 | 0 | 0 | 0 | 20 | 5 | 0 | 10 | 10 | 0 | 30 |
| Windgrass | 70 | 70 | 75 | 75 | 60 | 80 | 65 | 30 | 55 | 60 | 65 | 60 | 0 | 20 |

| 31 g ai/ha Post-emergence | | Compound 153 |
|---|---|---|
| | Barley, Spring | 5 |
| | Barley, Winter | 0 |
| | Blackgrass | 65 |
| | Bluegrass | 15 |
| | Bromegrass, Downy | 25 |
| | Buckwheat, Wild | 95 |
| | Canada Thistle | 98 |
| | Canarygrass | 75 |
| | Chamomile | 70 |
| | Chickweed | 80 |
| | Deadnettle | 70 |
| | Field Poppy | 75 |
| | Field Violet | 85 |
| | Foxtail, Green | 80 |
| | *Galium* | 100 |
| | *Geranium*, Cutleaf | 75 |
| | *Kochia* | 20 |
| | Lambsquarters | 75 |
| | Mustard, Wild | 98 |
| | Oat, Wild | 85 |
| | Oilseed Rape | 70 |
| | Pigweed | 80 |
| | Radish, Wild | 80 |
| | Russian Thistle | 25 |
| | Ryegrass, Italian | 80 |
| | Speedwell | 75 |
| | Wheat, Spring | 20 |
| | Wheat, Winter | 10 |
| | Windgrass | 25 |

| 250 g ai/ha Pre-emergence | Compounds | | | | | | | | | | | | | |
|---|---|---|---|---|---|---|---|---|---|---|---|---|---|---|
| | 1 | 2 | 11 | 20 | 22 | 25 | 27 | 28 | 34 | 35 | 36 | 41 | 42 | 47 |
| Barley, Spring | 15 | 0 | 15 | 0 | 0 | 0 | 0 | 0 | 20 | 0 | 0 | 60 | 5 | 15 |
| Barley, Winter | 0 | 0 | 20 | 0 | 0 | 20 | 15 | 15 | 65 | 0 | 0 | 30 | 15 | 10 |
| Blackgrass | 90 | 90 | 75 | 75 | 75 | 95 | 100 | 95 | 65 | 95 | 50 | 80 | 100 | 50 |
| Bluegrass | 50 | 50 | 55 | 35 | 40 | 75 | 80 | 75 | 60 | 45 | 15 | 90 | 80 | 20 |
| Bromegrass, Downy | 70 | 70 | 55 | 45 | 80 | 85 | 85 | 85 | 80 | 65 | 35 | 80 | 90 | 15 |

TABLE D-continued

| | | | | | | | | | | | | | | |
|---|---|---|---|---|---|---|---|---|---|---|---|---|---|---|
| Buckwheat, Wild | 100 | 100 | 25 | 100 | 95 | 25 | 80 | 100 | 0 | 35 | 10 | 75 | 60 | 85 |
| Canada Thistle | — | — | — | — | — | — | — | — | — | — | — | — | — | — |
| Canarygrass | 90 | 90 | 90 | 80 | 90 | 100 | 100 | 95 | 95 | 98 | 65 | 95 | 100 | 5 |
| Chamomile | 90 | 100 | — | — | 100 | 95 | 100 | 100 | — | 100 | — | — | 100 | 85 |
| Chickweed | 100 | 100 | 100 | 95 | 100 | 100 | 100 | 100 | 100 | 100 | 100 | 95 | 100 | 90 |
| Deadnettle | 60 | 55 | 100 | 20 | — | 50 | 80 | 5 | 95 | 80 | 85 | 100 | 15 | 65 |
| Field Poppy | 95 | 100 | 100 | 100 | 100 | 100 | 100 | 100 | 100 | 100 | 100 | 95 | 100 | 100 |
| Field Violet | 100 | 100 | 100 | 75 | 100 | 100 | 95 | 100 | 95 | 100 | 95 | 100 | 100 | 100 |
| Foxtail, Green | 100 | 100 | 65 | 85 | 20 | 100 | 100 | 100 | 75 | 100 | 75 | 100 | 100 | 100 |
| *Galium* | 100 | 100 | 100 | 85 | 85 | 100 | 100 | 100 | 85 | 100 | 85 | 100 | 100 | 100 |
| *Geranium*, Cutleaf | — | — | — | — | — | — | — | — | — | — | — | — | — | — |
| *Kochia* | 75 | 20 | 95 | 90 | 75 | 100 | 60 | 65 | 50 | 25 | 60 | 100 | 100 | 40 |
| Lambsquarters | 100 | 100 | 100 | 100 | 100 | 100 | 100 | 100 | 95 | 100 | 95 | 100 | 100 | 100 |
| Mustard, Wild | 25 | 40 | 100 | 100 | 95 | 60 | 65 | 55 | 100 | 100 | 90 | 95 | 25 | 65 |
| Oat, Wild | 100 | 100 | 85 | 95 | 95 | 100 | 95 | 100 | 90 | 95 | 85 | 95 | 95 | 40 |
| Oilseed Rape | 20 | 40 | 5 | 0 | 75 | 35 | 35 | 25 | 85 | 100 | 65 | 15 | 0 | 15 |
| Pigweed | 100 | 100 | 100 | 100 | 100 | 100 | 100 | 100 | 100 | 100 | 100 | 100 | 100 | 100 |
| Radish, Wild | 100 | 100 | 25 | 65 | 80 | 0 | 95 | 30 | 60 | 100 | 70 | 100 | 60 | 85 |
| Russian Thistle | — | — | — | 70 | 20 | 90 | 75 | 35 | 15 | 25 | 15 | 70 | 75 | — |
| Ryegrass, Italian | 100 | 100 | 100 | 100 | 100 | 100 | 100 | 100 | 100 | 100 | 70 | 100 | 100 | 70 |
| Speedwell | 95 | 100 | 100 | 90 | 100 | 100 | 100 | 100 | 100 | 100 | 100 | 100 | 100 | 100 |
| Wheat, Spring | 10 | 10 | 35 | 45 | 25 | 25 | 25 | 25 | 60 | 30 | 30 | 85 | 20 | 15 |
| Wheat, Winter | 5 | 5 | 30 | 25 | 5 | 20 | 5 | 0 | 40 | 10 | 0 | 75 | 15 | 10 |
| Windgrass | 100 | 100 | 75 | 60 | 80 | 100 | 100 | 100 | 70 | 100 | 65 | 95 | 100 | 75 |

| 250 g ai/ha Pre-emergence | Compounds | | | | | | | | | | | | | |
|---|---|---|---|---|---|---|---|---|---|---|---|---|---|---|
| | 52 | 54 | 57 | 59 | 60 | 66 | 67 | 69 | 72 | 73 | 75 | 79 | 80 | 81 |
| Barley, Spring | 0 | 5 | 10 | 60 | 60 | 10 | 0 | 0 | 60 | 60 | 0 | 0 | 0 | 5 |
| Barley, Winter | 0 | 0 | 5 | 45 | 65 | 10 | 0 | 0 | 75 | 75 | 0 | 10 | 45 | 45 |
| Blackgrass | 65 | 75 | 80 | 100 | 100 | 80 | 80 | 75 | 75 | 85 | 55 | 60 | 85 | 85 |
| Bluegrass | 35 | 25 | 65 | 80 | 80 | 30 | 50 | 65 | 50 | 30 | 35 | 35 | 75 | 60 |
| Bromegrass, Downy | 20 | 40 | 30 | 95 | 98 | 85 | 70 | 65 | 60 | 90 | 25 | 60 | 85 | 75 |
| Buckwheat, Wild | 100 | 80 | 100 | 95 | 60 | 0 | 0 | 15 | 10 | 30 | 50 | 100 | 20 | 15 |
| Canada Thistle | — | — | — | — | — | — | — | 95 | — | — | — | — | — | — |
| Canarygrass | 35 | 90 | 65 | 100 | 100 | 95 | 95 | 95 | 95 | 100 | 75 | 85 | 100 | 100 |
| Chamomile | 100 | — | — | 100 | 100 | 100 | 100 | 100 | — | — | — | — | 100 | — |
| Chickweed | 100 | 100 | 100 | 100 | 100 | 100 | 100 | 100 | 100 | 100 | 100 | 100 | 100 | 100 |
| Deadnettle | 25 | 95 | 45 | 100 | 100 | 55 | 60 | 98 | 70 | 100 | 100 | 90 | 75 | 55 |
| Field Poppy | 100 | 100 | 100 | 100 | 100 | 100 | 100 | 100 | 100 | 100 | 100 | 100 | 100 | 100 |
| Field Violet | 85 | 95 | 100 | 100 | 100 | 98 | 100 | 95 | 95 | 95 | 100 | 100 | 95 | 95 |
| Foxtail, Green | 35 | 100 | 100 | 100 | 100 | 70 | 85 | 55 | 85 | 100 | 100 | 95 | 100 | 100 |
| *Galium* | 95 | 100 | 100 | 100 | 100 | 75 | 70 | 90 | 85 | 90 | 80 | 100 | 90 | 95 |
| *Geranium*, Cutleaf | — | — | — | — | — | — | 10 | — | — | — | — | — | — | — |
| *Kochia* | 90 | 45 | 100 | 100 | 75 | 85 | 0 | 5 | 40 | 95 | 100 | 95 | 100 | 15 |
| Lambsquarters | 100 | 95 | 100 | 100 | 100 | 100 | 100 | 100 | 95 | 100 | 100 | 100 | 100 | 95 |
| Mustard, Wild | 98 | 100 | 30 | 100 | 90 | 0 | 0 | 80 | 80 | 100 | 95 | 10 | 0 | 50 |
| Oat, Wild | 30 | 95 | 60 | 100 | 100 | 90 | 90 | 95 | 95 | 100 | 85 | 90 | 95 | 95 |
| Oilseed Rape | 55 | 100 | 25 | 80 | 80 | 35 | 25 | 15 | 25 | 70 | 100 | 35 | 40 | 100 |
| Pigweed | 90 | 100 | 100 | 100 | 100 | 100 | 100 | 100 | 100 | 100 | 100 | 100 | 100 | 100 |
| Radish, Wild | 75 | 100 | 100 | 100 | 90 | 70 | 95 | 20 | 50 | 90 | 100 | 55 | 100 | — |
| Russian Thistle | 0 | 35 | — | 90 | 70 | 90 | 25 | 10 | 25 | 75 | 35 | 100 | 100 | 35 |
| Ryegrass, Italian | 98 | 100 | 95 | 100 | 100 | 95 | 90 | 100 | 90 | 100 | 0 | 100 | 100 | 100 |
| Speedwell | 100 | 100 | 100 | 100 | 100 | 100 | 100 | 100 | 100 | 100 | — | 100 | 100 | 100 |
| Wheat, Spring | 5 | 45 | 10 | 85 | 75 | 20 | 10 | 10 | 80 | 85 | 45 | 0 | 35 | 40 |

TABLE D-continued

| | | | | | | | | | | | | | |
|---|---|---|---|---|---|---|---|---|---|---|---|---|---|
| Wheat, Winter | 0 | 35 | 10 | 80 | 55 | 0 | 5 | 0 | 45 | 75 | 15 | 0 | 20 | 5 |
| Windgrass | 10 | 95 | 80 | 100 | 100 | 85 | 95 | 95 | 90 | 95 | 85 | 80 | 98 | 100 |

| 250 g ai/ha Pre-emergence | Compounds | | | | | | | | | | | | |
|---|---|---|---|---|---|---|---|---|---|---|---|---|---|
| | 82 | 83 | 84 | 85 | 87 | 88 | 90 | 104 | 105 | 108 | 109 | 126 | 129 | 153 |
| Barley, Spring | 10 | 5 | 5 | 5 | 5 | 0 | 35 | 15 | 20 | 0 | 5 | 0 | 20 | 40 |
| Barley, Winter | 25 | 40 | 35 | 15 | 25 | 25 | 30 | 20 | 25 | 20 | 10 | 5 | 10 | 40 |
| Blackgrass | 80 | 85 | 90 | 85 | 80 | 90 | 60 | 75 | 75 | 80 | 80 | 65 | 75 | 95 |
| Bluegrass | 80 | 35 | 80 | 75 | 70 | 80 | 65 | 75 | 75 | 75 | 60 | 40 | 60 | 75 |
| Bromegrass, Downy | 85 | 40 | 85 | 80 | 80 | 75 | 95 | 85 | 75 | 75 | 65 | 30 | 80 | 95 |
| Buckwheat, Wild | 0 | 25 | 20 | 100 | 60 | 80 | 80 | 95 | 25 | 35 | 75 | 25 | 85 | 85 |
| Canada Thistle | — | — | — | — | — | — | 100 | — | — | — | — | 95 | 100 | 100 |
| Canarygrass | 95 | 100 | 95 | 95 | 95 | 90 | 95 | 100 | 98 | 95 | 98 | 90 | 90 | 100 |
| Chamomile | 100 | — | 100 | — | 100 | — | 100 | — | — | — | — | 100 | 100 | 100 |
| Chickweed | 100 | 100 | 100 | 100 | 100 | 100 | 100 | 100 | 100 | 100 | 100 | 100 | 100 | 100 |
| Deadnettle | 70 | 100 | 75 | 35 | 70 | 85 | 98 | 100 | 65 | 100 | 95 | 80 | 95 | 100 |
| Field Poppy | 100 | 100 | 100 | 95 | 100 | 90 | 100 | 100 | 100 | 100 | 100 | 95 | 100 | 100 |
| Field Violet | 100 | 100 | 100 | 100 | 100 | 100 | 100 | 100 | 100 | 100 | 100 | 100 | 100 | 100 |
| Foxtail, Green | 85 | 100 | 100 | 100 | 95 | 100 | 95 | 100 | 100 | 100 | 95 | 45 | 95 | 100 |
| *Galium* | 85 | 85 | 90 | 100 | 80 | 100 | 95 | 100 | 100 | 100 | 100 | 98 | 95 | 98 |
| *Geranium*, Cutleaf | — | — | — | — | — | — | 90 | — | — | — | — | 15 | 95 | 90 |
| *Kochia* | 100 | 50 | 95 | 45 | 100 | 55 | 80 | 100 | 100 | 100 | 100 | 95 | 100 | 70 |
| Lambs-quarters | 100 | 100 | 100 | 100 | 100 | 100 | 100 | 100 | 100 | 100 | 100 | 100 | 100 | 100 |
| Mustard, Wild | 15 | 25 | 20 | 40 | 25 | 70 | 90 | 95 | 20 | 85 | 100 | 98 | 100 | 100 |
| Oat, Wild | 95 | 90 | 95 | 90 | 95 | 95 | 98 | 100 | 100 | 95 | 90 | 90 | 100 | 98 |
| Oilseed Rape | 60 | 10 | 35 | 30 | 45 | 25 | 0 | 55 | 50 | 40 | 85 | 90 | 100 | 100 |
| Pigweed | 100 | 100 | 100 | 100 | 100 | 100 | 100 | 100 | 100 | 100 | 100 | 100 | 98 | 100 |
| Radish, Wild | 100 | 90 | 65 | 100 | 95 | — | 95 | 100 | 55 | 90 | 95 | 90 | 100 | 100 |
| Russian Thistle | 65 | 0 | 95 | 75 | 100 | 25 | 60 | 75 | 90 | 100 | 50 | 15 | 100 | 100 |
| Ryegrass, Italian | 95 | 100 | 100 | 90 | 98 | 90 | 100 | 100 | 98 | 100 | 100 | 100 | 100 | 100 |
| Speedwell | 100 | 100 | 95 | 100 | 100 | 100 | 100 | — | — | — | — | 100 | 100 | 100 |
| Wheat, Spring | 40 | 35 | — | 40 | 20 | 30 | 70 | 45 | 40 | 40 | 40 | 0 | 75 | 85 |
| Wheat, Winter | 10 | 25 | 5 | 15 | 15 | 15 | 50 | 15 | 5 | 30 | 20 | 0 | 60 | 50 |
| Windgrass | 100 | 95 | 100 | 100 | 100 | 95 | 98 | 100 | 95 | 95 | 100 | 85 | 80 | 95 |

| 125 g ai/ha Pre-emergence | Compounds | | | | | | | | | | | | |
|---|---|---|---|---|---|---|---|---|---|---|---|---|---|
| | 1 | 2 | 11 | 20 | 22 | 25 | 27 | 28 | 34 | 35 | 36 | 41 | 42 | 47 |
| Barley, Spring | 10 | 0 | 10 | 0 | 0 | 0 | 0 | 0 | 0 | 0 | 0 | 30 | 0 | 15 |
| Barley, Winter | 0 | 0 | 5 | 0 | 0 | 5 | 10 | 15 | 0 | 0 | 0 | 25 | 5 | 5 |
| Blackgrass | 85 | 85 | 55 | 60 | 55 | 90 | 95 | 85 | 40 | 85 | 35 | 80 | 95 | 30 |
| Bluegrass | 35 | 30 | 30 | 25 | 30 | 40 | 70 | 65 | 50 | 35 | 10 | 80 | 65 | 20 |
| Bromegrass, Downy | 70 | 65 | 20 | 40 | 25 | 80 | 85 | 70 | 50 | 55 | 10 | 70 | 70 | 15 |
| Buckwheat, Wild | 65 | 100 | 15 | 100 | 85 | 20 | 45 | 20 | 0 | 20 | 10 | 65 | 80 | 70 |
| Canada Thistle | — | — | — | — | — | — | — | — | — | — | — | — | — | — |
| Canarygrass | 85 | 85 | 90 | 70 | 85 | 95 | 100 | 95 | 90 | 95 | 40 | 90 | 100 | 0 |
| Chamomile | 95 | 95 | — | — | 100 | 100 | 100 | 100 | — | 100 | — | — | 100 | 85 |
| Chickweed | 100 | 100 | 100 | 95 | 100 | 100 | 100 | 100 | 100 | 100 | 100 | 95 | 100 | 100 |
| Deadnettle | 0 | 0 | 50 | 10 | 15 | 0 | 55 | 5 | 50 | 55 | 50 | 100 | 25 | 10 |
| Field Poppy | 95 | 95 | 100 | 95 | 100 | 100 | 100 | 95 | 100 | 100 | 70 | — | 100 | 100 |
| Field Violet | 100 | 100 | 100 | 25 | 80 | 100 | 95 | 100 | 75 | 85 | 70 | 100 | 100 | 100 |
| Foxtail, Green | 75 | 100 | 15 | 75 | 0 | 95 | 100 | 100 | 60 | 65 | 70 | 100 | 100 | 60 |
| *Galium* | 100 | 100 | 100 | 75 | 75 | 95 | 85 | 85 | 80 | 95 | 75 | 95 | 95 | 100 |
| *Geranium*, Cutleaf | — | — | — | — | — | — | — | — | — | — | — | — | — | — |

TABLE D-continued

| | | | | | | | | | | | | | | |
|---|---|---|---|---|---|---|---|---|---|---|---|---|---|---|
| *Kochia* | 35 | 0 | 75 | 70 | 50 | 40 | 30 | 30 | 15 | 20 | 45 | 80 | 75 | 35 |
| Lambs-quarters | 100 | 100 | 100 | 100 | 100 | 98 | 100 | 100 | 95 | 100 | 75 | 100 | 100 | 100 |
| Mustard, Wild | 10 | 5 | 75 | 100 | 85 | 20 | 45 | 30 | 75 | 100 | 85 | 95 | 20 | 40 |
| Oat, Wild | 95 | 95 | 80 | 85 | 70 | 95 | 90 | 90 | 85 | 85 | 75 | 90 | 95 | 35 |
| Oilseed Rape | 5 | 20 | 5 | 0 | 0 | 0 | 0 | 10 | 50 | 65 | 55 | 25 | 0 | 10 |
| Pigweed | 100 | 65 | 98 | 100 | 98 | 100 | 100 | 100 | 100 | 100 | 100 | 100 | 100 | 100 |
| Radish, Wild | 15 | 15 | 20 | 50 | 70 | 0 | 60 | 35 | 60 | 100 | 50 | 95 | 15 | 100 |
| Russian Thistle | — | — | — | 40 | 0 | 40 | 65 | 15 | 10 | 0 | 10 | 40 | 65 | — |
| Ryegrass, Italian | 100 | 100 | 100 | 100 | 100 | 100 | 100 | 100 | 100 | 100 | 70 | 100 | 100 | 60 |
| Speedwell | — | 90 | 85 | 70 | 50 | 95 | 100 | 95 | 100 | 100 | 100 | 100 | 70 | 80 |
| Wheat, Spring | 0 | 5 | 25 | 25 | 10 | 10 | 5 | 5 | 25 | 5 | 0 | 70 | 0 | 15 |
| Wheat, Winter | 5 | 0 | 20 | 15 | 0 | 0 | 0 | 0 | 25 | 0 | 0 | 45 | 5 | 10 |
| Windgrass | 85 | 95 | 55 | 50 | 70 | 100 | 100 | 90 | 55 | 100 | 5 | 80 | 85 | 20 |

| 125 g ai/ha Pre-emergence | Compounds | | | | | | | | | | | | |
|---|---|---|---|---|---|---|---|---|---|---|---|---|---|
| | 52 | 54 | 57 | 59 | 60 | 66 | 67 | 69 | 72 | 73 | 75 | 79 | 80 | 81 |
| Barley, Spring | 0 | 0 | 10 | 40 | 45 | — | 0 | 0 | 0 | 0 | 0 | 0 | 5 | 0 |
| Barley, Winter | 0 | 0 | 5 | 40 | 50 | 0 | 0 | 0 | 50 | 60 | 0 | 0 | 15 | 45 |
| Blackgrass | 65 | 50 | 70 | 95 | 100 | 75 | 75 | 70 | 55 | 80 | 40 | 55 | 80 | 70 |
| Bluegrass | 25 | 15 | 25 | 75 | 65 | 25 | 20 | 35 | 25 | 35 | 10 | 25 | 75 | 20 |
| Bromegrass, Downy | 15 | 15 | 25 | 90 | 95 | 80 | 35 | 35 | 35 | 50 | 10 | 50 | 75 | 15 |
| Buckwheat, Wild | 55 | 70 | 10 | 100 | 50 | 0 | 0 | 5 | 15 | 60 | 0 | 25 | 20 | 0 |
| Canada Thistle | — | — | — | — | — | — | — | 95 | — | — | — | — | — | — |
| Canarygrass | 25 | 80 | 55 | 95 | 95 | 85 | 90 | 95 | 85 | 90 | 70 | 75 | 90 | 95 |
| Chamomile | 100 | — | — | 100 | 100 | 100 | 100 | 100 | — | — | — | — | 100 | — |
| Chickweed | 100 | 95 | 100 | 100 | 100 | 100 | 100 | 100 | 100 | 100 | 95 | 100 | 100 | 100 |
| Deadnettle | 10 | 70 | 25 | 90 | 85 | 55 | 55 | 75 | 65 | 70 | 90 | 100 | 70 | 5 |
| Field Poppy | 100 | 100 | 100 | 100 | 100 | 100 | 100 | 100 | 100 | 100 | 100 | 100 | 100 | 100 |
| Field Violet | 75 | 70 | 100 | 95 | 100 | 95 | 100 | 95 | 75 | 80 | 100 | 98 | 100 | 100 |
| Foxtail, Green | 15 | 65 | 100 | 85 | 95 | 65 | 85 | 50 | 60 | 50 | 55 | 65 | 100 | 100 |
| *Galium* | 90 | 85 | 100 | 100 | 95 | 65 | 35 | 90 | 70 | 80 | 60 | 100 | 80 | 85 |
| *Geranium*, Cutleaf | — | — | — | — | — | — | — | 0 | — | — | — | — | — | — |
| *Kochia* | 40 | 30 | 35 | 95 | 60 | 75 | 0 | 70 | 10 | 85 | 80 | 100 | 100 | 25 |
| Lambs-quarters | 100 | 95 | 100 | 100 | 100 | 100 | 100 | 100 | 95 | 95 | 100 | 100 | 100 | 70 |
| Mustard, Wild | 90 | 100 | 25 | 100 | 85 | 0 | 0 | 40 | 60 | 100 | 100 | 5 | 0 | 0 |
| Oat, Wild | 25 | 85 | 50 | 95 | 100 | 85 | 80 | 90 | 85 | 85 | 80 | 85 | 90 | 85 |
| Oilseed Rape | 0 | 85 | 0 | 50 | 40 | 35 | 25 | 15 | 15 | 0 | 100 | 40 | 35 | 50 |
| Pigweed | 65 | 100 | 98 | 100 | 100 | 100 | 100 | 100 | 95 | 100 | 100 | 100 | 100 | 100 |
| Radish, Wild | 55 | 100 | 25 | 95 | 95 | 75 | 75 | 20 | 50 | 100 | 100 | 45 | 100 | — |
| Russian Thistle | 0 | 25 | — | 80 | 35 | 60 | 0 | 0 | 15 | 40 | 25 | 75 | 95 | 15 |
| Ryegrass, Italian | 100 | 100 | 80 | 100 | 100 | 90 | 85 | 98 | 100 | 100 | 100 | 90 | 95 | 85 |
| Speedwell | 95 | 100 | 100 | 100 | 100 | 100 | 100 | 100 | — | 100 | 100 | — | 95 | 100 |
| Wheat, Spring | 0 | 0 | 5 | 80 | 65 | 5 | 0 | 0 | 65 | 70 | 35 | 0 | 25 | 0 |
| Wheat, Winter | 0 | 15 | 5 | 70 | 55 | 0 | 0 | 0 | 25 | 50 | 20 | 0 | 0 | 5 |
| Windgrass | 10 | 70 | 65 | 100 | 100 | 85 | 80 | 75 | 80 | 90 | 50 | 50 | 95 | 90 |

| 125 g ai/ha Pre-emergence | Compounds | | | | | | | | | | | | |
|---|---|---|---|---|---|---|---|---|---|---|---|---|---|
| | 82 | 83 | 84 | 85 | 87 | 88 | 90 | 104 | 105 | 108 | 109 | 126 | 129 | 153 |
| Barley, Spring | 0 | 0 | 0 | 0 | 0 | 0 | 20 | 5 | 0 | 0 | 5 | 0 | 0 | 25 |
| Barley, Winter | 5 | 0 | 5 | 0 | 10 | 0 | 15 | 10 | 10 | 10 | 0 | 0 | 0 | 25 |
| Blackgrass | 75 | 70 | 80 | 85 | 80 | 85 | 45 | 65 | 60 | 50 | 75 | 55 | 55 | 85 |

TABLE D-continued

| | | | | | | | | | | | | | | |
|---|---|---|---|---|---|---|---|---|---|---|---|---|---|---|
| Bluegrass | 65 | 35 | 65 | 65 | 45 | 75 | 65 | 70 | 60 | 35 | 30 | 30 | 25 | 75 |
| Bromegrass, Downy | 80 | 60 | 75 | 55 | 75 | 65 | 55 | 65 | 70 | 70 | 65 | 20 | 65 | 85 |
| Buckwheat, Wild | 15 | 0 | 25 | 80 | 0 | 50 | 40 | 55 | 5 | 20 | 30 | 10 | 85 | 85 |
| Canada Thistle | — | — | — | — | — | — | 100 | — | — | — | — | 95 | 100 | 100 |
| Canarygrass | 90 | 90 | 90 | 90 | 90 | 90 | 85 | 95 | 95 | 90 | 90 | 80 | 60 | 95 |
| Chamomile | 100 | — | 100 | — | 100 | — | 100 | — | — | — | — | 100 | 100 | 100 |
| Chickweed | 100 | 100 | 100 | 100 | 100 | 100 | 100 | 95 | 100 | 100 | 100 | 100 | 98 | 100 |
| Deadnettle | 25 | 15 | 65 | 10 | 65 | 65 | 90 | 80 | 15 | 95 | 80 | 70 | 75 | 100 |
| Field Poppy | 100 | 100 | 100 | — | 100 | 90 | 100 | 100 | 100 | 100 | 100 | 90 | 100 | 100 |
| Field Violet | 95 | 95 | 100 | 95 | 95 | 100 | 100 | 95 | 100 | 100 | 100 | 100 | 85 | 100 |
| Foxtail, Green | 90 | 100 | 75 | 100 | 95 | 100 | 70 | 100 | 65 | 100 | 75 | 25 | 80 | 100 |
| *Galium* | 80 | 40 | 75 | 75 | 60 | 75 | 85 | 100 | 85 | 95 | 100 | 85 | 90 | 95 |
| *Geranium*, Cutleaf | — | — | — | — | — | — | 65 | — | — | — | — | 0 | 70 | 85 |
| *Kochia* | 75 | 30 | 75 | 10 | 100 | 15 | 90 | 95 | 95 | 80 | 80 | 75 | 85 | 25 |
| Lambs-quarters | 100 | 100 | 95 | 100 | 100 | 100 | 85 | 100 | 100 | 100 | 100 | 75 | 100 | 100 |
| Mustard, Wild | 25 | 35 | 5 | 35 | 0 | 65 | 100 | 75 | 0 | 95 | 100 | 70 | 100 | 100 |
| Oat, Wild | 95 | 90 | 95 | 85 | 90 | 90 | 85 | 80 | 85 | 80 | 90 | 80 | 90 | 98 |
| Oilseed Rape | 35 | 10 | 35 | 20 | 30 | 0 | 0 | 55 | 50 | 75 | 75 | 15 | 55 | 90 |
| Pigweed | 100 | 100 | 100 | 100 | 100 | 100 | 100 | 100 | 100 | 100 | 100 | 100 | 100 | 100 |
| Radish, Wild | 60 | 90 | 35 | 100 | 75 | — | 90 | 95 | 35 | 100 | 90 | 75 | 100 | 98 |
| Russian Thistle | 65 | 15 | 95 | 25 | 85 | 15 | 35 | 55 | 70 | 70 | 35 | 5 | 100 | 60 |
| Ryegrass, Italian | 90 | 90 | 100 | 85 | 98 | 85 | 100 | 100 | 95 | 100 | 100 | 98 | 98 | 100 |
| Speedwell | 100 | 100 | 90 | 100 | 90 | 100 | 100 | — | — | — | — | 100 | 100 | 100 |
| Wheat, Spring | 15 | 10 | 15 | 15 | 15 | 25 | 60 | 35 | 0 | 25 | 20 | 0 | 60 | 70 |
| Wheat, Winter | 0 | 5 | 0 | 5 | 0 | 10 | 25 | 5 | 5 | 10 | 5 | 0 | 45 | 45 |
| Windgrass | 100 | 90 | 90 | 95 | 85 | 85 | 80 | 80 | 80 | 75 | 80 | 75 | 75 | 80 |

| 62 g ai/ha Pre-emergence | Compounds | | | | | | | | | | | | | |
|---|---|---|---|---|---|---|---|---|---|---|---|---|---|---|
| | 1 | 2 | 11 | 20 | 22 | 25 | 27 | 28 | 34 | 35 | 36 | 41 | 42 | 47 |
| Barley, Spring | 0 | 0 | 5 | 0 | 0 | 0 | 0 | 0 | 0 | 0 | 0 | 0 | 0 | 5 |
| Barley, Winter | 0 | 0 | 5 | 0 | 0 | 0 | 0 | 0 | 0 | 0 | 0 | 20 | 0 | 0 |
| Blackgrass | 70 | 75 | 30 | 40 | 45 | 90 | 90 | 85 | 20 | 85 | 30 | 75 | 80 | 20 |
| Bluegrass | 15 | 15 | 15 | 15 | 30 | 35 | 35 | 45 | 25 | 25 | 15 | 75 | 45 | 20 |
| Bromegrass, Downy | 25 | 50 | 5 | 35 | 5 | 65 | 55 | 55 | 50 | 30 | 0 | 55 | 55 | 10 |
| Buckwheat, Wild | 10 | 10 | 15 | 20 | 20 | 0 | 30 | 0 | 10 | 20 | 0 | 55 | 25 | 60 |
| Canada Thistle | — | — | — | — | — | — | — | — | — | — | — | — | — | — |
| Canarygrass | 60 | 60 | 55 | 35 | 35 | 80 | 95 | 85 | 50 | 85 | 45 | 90 | 95 | 0 |
| Chamomile | 95 | 100 | — | — | 100 | 100 | 100 | 95 | — | 100 | — | — | 100 | 80 |
| Chickweed | 90 | 100 | 100 | 95 | 100 | 100 | 100 | 100 | 95 | 95 | 95 | 95 | 100 | 95 |
| Deadnettle | 0 | 0 | 15 | 0 | 0 | 0 | 0 | 0 | 40 | 15 | 0 | 90 | 0 | 10 |
| Field Poppy | 95 | 95 | 75 | 70 | 0 | 100 | 100 | 95 | 100 | 85 | 50 | 95 | 100 | 100 |
| Field Violet | 100 | 100 | 100 | 15 | 65 | 100 | 90 | 85 | 25 | 75 | 10 | 90 | 95 | 100 |
| Foxtail, Green | 15 | 100 | 10 | 60 | 0 | 90 | 95 | 80 | 60 | 45 | 25 | 80 | 65 | 25 |
| *Galium* | 95 | 85 | 80 | 30 | 65 | 90 | 70 | 60 | 35 | 85 | 20 | 85 | 85 | 95 |
| *Geranium*, Cutleaf | — | — | — | — | — | — | — | — | — | — | — | — | — | — |
| *Kochia* | 0 | 0 | 40 | 25 | 35 | 10 | 20 | 20 | 10 | 0 | 25 | 75 | 60 | 10 |
| Lambs-quarters | 100 | 60 | 35 | 90 | 100 | 95 | 100 | 100 | 60 | 98 | 95 | 100 | 100 | 100 |
| Mustard, Wild | 0 | 0 | 20 | 35 | 65 | 0 | 40 | 15 | 25 | 100 | 85 | 90 | 15 | 20 |
| Oat, Wild | 70 | 90 | 70 | 65 | 55 | 90 | 85 | 85 | 75 | 80 | 45 | 90 | 90 | 20 |
| Oilseed Rape | 0 | 0 | 0 | 0 | 0 | 0 | 0 | 0 | 55 | 10 | 0 | 5 | 0 | 0 |
| Pigweed | 100 | 50 | 0 | 40 | 98 | 100 | 100 | 100 | 95 | 95 | 75 | 75 | 100 | 100 |
| Radish, Wild | 0 | 5 | 15 | 0 | 25 | 0 | 50 | 0 | 0 | 100 | 0 | 85 | — | 25 |
| Russian Thistle | — | — | — | 30 | 0 | 25 | 10 | 0 | 0 | 0 | 15 | 20 | 15 | — |
| Ryegrass, Italian | 100 | 95 | 90 | 100 | 90 | 100 | 100 | 95 | 95 | 85 | 65 | 100 | 100 | 30 |
| Speedwell | 50 | — | 15 | 70 | 0 | 80 | 100 | 95 | 100 | 75 | 100 | 95 | 75 | 25 |

TABLE D-continued

| | | | | | | | | | | | | | | |
|---|---|---|---|---|---|---|---|---|---|---|---|---|---|---|
| Wheat, Spring | 0 | 0 | 15 | 15 | 0 | 0 | 0 | 0 | 0 | 0 | 0 | 55 | 0 | 5 |
| Wheat, Winter | 0 | 0 | 0 | 0 | 0 | 0 | 0 | 0 | 0 | 0 | 0 | 20 | 0 | 5 |
| Windgrass | 60 | 75 | 35 | 40 | 20 | 85 | 85 | 75 | 25 | 95 | 5 | 75 | 85 | 5 |

| 62 g ai/ha Pre-emergence | Compounds | | | | | | | | | | | | | |
|---|---|---|---|---|---|---|---|---|---|---|---|---|---|---|
| | 52 | 54 | 57 | 59 | 60 | 66 | 67 | 69 | 72 | 73 | 75 | 79 | 80 | 81 |
| Barley, Spring | 0 | 0 | 10 | 25 | 10 | 0 | 0 | 0 | 0 | 10 | 0 | 0 | 0 | 0 |
| Barley, Winter | 0 | 0 | 0 | 25 | 30 | 0 | 0 | 0 | 25 | 40 | 0 | 0 | 0 | 0 |
| Blackgrass | 20 | 30 | 35 | 90 | 95 | 70 | 75 | 25 | 30 | 60 | 30 | 45 | 75 | 60 |
| Bluegrass | 10 | 10 | 20 | 50 | 45 | 15 | 0 | 0 | 25 | 35 | 15 | 10 | 55 | 10 |
| Bromegrass, Downy | 0 | 15 | 5 | 85 | 90 | 60 | 35 | 20 | 0 | 40 | 0 | 35 | 35 | 45 |
| Buckwheat, Wild | 20 | 5 | 10 | 65 | 25 | 0 | 0 | 0 | 0 | 0 | 0 | 90 | 25 | 15 |
| Canada Thistle | — | — | — | — | — | — | — | 90 | — | — | — | — | — | — |
| Canarygrass | 25 | 55 | 10 | 90 | 95 | 80 | 85 | 80 | 80 | 85 | 55 | 60 | 90 | 65 |
| Chamomile | 100 | — | — | 95 | 100 | 100 | 95 | 100 | — | — | — | — | 100 | — |
| Chickweed | 98 | 90 | 100 | 100 | 100 | 100 | 100 | 100 | 100 | 90 | 100 | 100 | 100 | 100 |
| Deadnettle | 0 | 60 | 20 | 90 | 90 | 40 | 30 | 55 | 15 | 0 | 55 | 10 | 65 | 0 |
| Field Poppy | 0 | 55 | 100 | 100 | 100 | 100 | 100 | 90 | 100 | 100 | 95 | 100 | 100 | 100 |
| Field Violet | 10 | 35 | 100 | 90 | 100 | 85 | 98 | 90 | 75 | 75 | 100 | 85 | 95 | 80 |
| Foxtail, Green | 0 | 60 | 70 | 75 | 80 | 35 | 80 | 50 | 30 | 20 | 35 | 60 | 80 | 65 |
| *Galium* | 100 | 45 | 100 | 95 | 85 | 20 | 10 | 70 | 60 | 80 | 50 | 90 | 40 | 65 |
| *Geranium*, Cutleaf | — | — | — | — | — | — | — | 0 | — | — | — | — | — | — |
| *Kochia* | 35 | 60 | 10 | 60 | 20 | 15 | 0 | 20 | 15 | 30 | 80 | 55 | 75 | 0 |
| Lambs-quarters | 90 | 65 | 100 | 100 | 100 | 100 | 100 | 100 | 100 | 95 | 95 | 100 | 100 | 95 |
| Mustard, Wild | 100 | 100 | 25 | 95 | 70 | 0 | 0 | 30 | 25 | 80 | 35 | 15 | 0 | 0 |
| Oat, Wild | 25 | 75 | 30 | 90 | 95 | 85 | 75 | 75 | 75 | 90 | 65 | 80 | 90 | 85 |
| Oilseed Rape | 0 | 50 | 0 | 30 | 15 | 35 | 20 | 15 | 15 | 5 | 75 | 35 | 35 | 0 |
| Pigweed | 55 | 100 | 75 | 100 | 100 | 100 | 95 | 100 | 85 | 100 | 100 | 100 | 100 | 100 |
| Radish, Wild | 15 | 100 | 10 | 85 | 90 | 70 | 60 | 0 | 0 | 75 | 70 | 25 | 75 | 50 |
| Russian Thistle | 0 | 0 | — | 50 | 20 | 20 | 0 | 0 | 10 | 25 | 0 | 70 | 95 | 0 |
| Ryegrass, Italian | 85 | 90 | 75 | 100 | 100 | 85 | 80 | 95 | 75 | 100 | 100 | 85 | 90 | 65 |
| Speedwell | 100 | 95 | 90 | 100 | 100 | 100 | 75 | 100 | 70 | 100 | 100 | — | 95 | 60 |
| Wheat, Spring | 0 | 0 | 5 | 65 | 55 | 0 | 0 | 0 | 35 | 55 | 25 | 0 | 0 | 0 |
| Wheat, Winter | 0 | 0 | 5 | 35 | 35 | 0 | 0 | 0 | 10 | 40 | 0 | 0 | 0 | 0 |
| Windgrass | 10 | 50 | 35 | 85 | 90 | 75 | 75 | 55 | 65 | 65 | 15 | 40 | 90 | 75 |

| 62 g ai/ha Pre-emergence | Compounds | | | | | | | | | | | | | |
|---|---|---|---|---|---|---|---|---|---|---|---|---|---|---|
| | 82 | 83 | 84 | 85 | 87 | 88 | 90 | 104 | 105 | 108 | 109 | 126 | 129 | 153 |
| Barley, Spring | 0 | 0 | 0 | 0 | 0 | 0 | 0 | 0 | 0 | 0 | 0 | 0 | 0 | 0 |
| Barley, Winter | 0 | 0 | 0 | 0 | 0 | 0 | 0 | 0 | 10 | 0 | 0 | 0 | 0 | 10 |
| Blackgrass | 75 | 60 | 75 | 80 | 75 | 85 | 35 | 60 | 50 | 35 | 25 | 45 | 15 | 80 |
| Bluegrass | 45 | 15 | 30 | 60 | 35 | 60 | 40 | 35 | 30 | 15 | 20 | 5 | 10 | 75 |
| Bromegrass, Downy | 65 | 30 | 55 | 35 | 65 | 45 | 20 | 65 | 65 | 25 | 30 | 0 | 15 | 75 |
| Buckwheat, Wild | 0 | 0 | 15 | 65 | 0 | 45 | — | 60 | 5 | 0 | 20 | 0 | 30 | 60 |
| Canada Thistle | — | — | — | — | — | — | 95 | — | — | — | — | 15 | 100 | 100 |
| Canarygrass | 85 | 85 | 85 | 90 | 90 | 90 | 75 | 85 | 95 | 80 | 75 | 50 | 15 | 90 |
| Chamomile | 100 | — | 100 | — | 95 | — | 100 | — | — | — | — | 100 | 100 | 100 |
| Chickweed | 100 | 100 | 100 | 100 | 100 | 100 | 198 | 100 | 100 | 100 | 100 | 98 | 100 | 100 |
| Deadnettle | 25 | 0 | 20 | 0 | 35 | 0 | 70 | 80 | 10 | 25 | 60 | 45 | 75 | 100 |
| Field Poppy | 100 | 100 | 95 | — | 100 | 95 | 100 | 100 | 100 | 10 | 100 | 45 | 98 | 100 |
| Field Violet | 90 | 80 | 100 | 70 | 85 | 95 | 95 | 100 | 100 | 100 | 100 | 85 | 85 | 100 |
| Foxtail, Green | 75 | 50 | 35 | 55 | 55 | 100 | 45 | 70 | 55 | 90 | 65 | 20 | 70 | 75 |
| *Galium* | 60 | 25 | 60 | 70 | 40 | 70 | 75 | 95 | 95 | 70 | 75 | 70 | 90 | 95 |

TABLE D-continued

| | | | | | | | | | | | | | | |
|---|---|---|---|---|---|---|---|---|---|---|---|---|---|---|
| *Geranium*, Cutleaf | — | — | — | — | — | — | 60 | — | — | — | — | 0 | 0 | 75 |
| *Kochia* | 15 | 0 | 15 | 10 | 55 | 10 | 65 | 75 | 50 | 95 | 70 | 20 | 55 | 50 |
| Lambs-quarters | 95 | 65 | 95 | 100 | 100 | 100 | 98 | 100 | 100 | 100 | 100 | 100 | 75 | 85 |
| Mustard, Wild | 0 | 0 | 0 | 25 | 0 | 55 | 98 | 70 | 0 | 60 | 75 | 70 | 100 | 100 |
| Oat, Wild | 85 | 85 | 90 | 75 | 85 | 85 | 80 | 80 | 80 | 80 | 80 | 70 | 75 | 95 |
| Oilseed Rape | 35 | 5 | 20 | 0 | 30 | 0 | 0 | 20 | 60 | 45 | 40 | 0 | 15 | 85 |
| Pigweed | 100 | 100 | 100 | 100 | 100 | 100 | 35 | 100 | 100 | 100 | 100 | 100 | 100 | 100 |
| Radish, Wild | 60 | 70 | 35 | 25 | 65 | 0 | 65 | 100 | 15 | 100 | 75 | 15 | 100 | 98 |
| Russian Thistle | 15 | 0 | 5 | 10 | 15 | 0 | 15 | 10 | 60 | 15 | 20 | 0 | 50 | 15 |
| Ryegrass, Italian | 80 | 75 | 90 | 80 | 95 | 85 | 100 | 100 | 90 | 98 | 95 | 90 | 80 | 100 |
| Speedwell | 75 | 75 | 75 | 90 | 85 | 100 | 100 | — | — | — | — | 100 | 100 | 100 |
| Wheat, Spring | 0 | 0 | 5 | 0 | 0 | 10 | 35 | 15 | 0 | 20 | 5 | 0 | 50 | 45 |
| Wheat, Winter | 0 | 0 | 0 | 0 | 0 | 0 | 10 | 0 | 0 | 0 | 0 | 0 | 35 | 20 |
| Windgrass | 80 | 75 | 80 | 70 | 80 | 75 | 65 | 75 | 80 | 50 | 60 | 35 | 45 | 80 |

| 31 g ai/ha Pre-emergence | Compounds | | | | | | | | | | | | | |
|---|---|---|---|---|---|---|---|---|---|---|---|---|---|---|
| | 1 | 2 | 11 | 20 | 22 | 25 | 27 | 28 | 34 | 35 | 36 | 41 | 42 | 47 |
| Barley, Spring | 0 | 0 | 5 | 0 | 0 | 0 | 0 | 0 | 0 | 0 | 0 | 0 | 0 | 0 |
| Barley, Winter | 0 | 0 | 5 | 0 | 0 | 0 | 0 | 0 | 0 | 0 | 0 | 0 | 0 | 0 |
| Blackgrass | 35 | 65 | 5 | 20 | 45 | 85 | 85 | 85 | 15 | 75 | 15 | 70 | 80 | 5 |
| Bluegrass | 5 | 0 | 10 | 10 | 0 | 25 | 25 | 30 | 0 | 25 | 0 | 70 | 35 | 0 |
| Bromegrass, Downy | 20 | 10 | 5 | 15 | 0 | 40 | 35 | 45 | 0 | 20 | 0 | 50 | 45 | 5 |
| Buckwheat, Wild | 5 | — | 20 | 15 | 20 | 0 | 25 | 0 | 0 | 15 | 0 | 35 | 20 | 70 |
| Canada Thistle | — | — | — | — | — | — | — | — | — | — | — | — | — | — |
| Canarygrass | 40 | 40 | 45 | 25 | 25 | 80 | 85 | 85 | 20 | 75 | 0 | 90 | 90 | 0 |
| Chamomile | 95 | 80 | — | — | 95 | 100 | 100 | 100 | — | 100 | — | — | 95 | 80 |
| Chickweed | 100 | 90 | 20 | 85 | 95 | 95 | 100 | 100 | 85 | 95 | 95 | 90 | 100 | 90 |
| Deadnettle | 0 | 0 | 10 | 0 | 0 | 0 | 0 | 0 | 0 | 0 | 0 | 35 | 0 | 0 |
| Field Poppy | 95 | 95 | 75 | 70 | 0 | 95 | 100 | 100 | — | 75 | — | 95 | 100 | 60 |
| Field Violet | 95 | 95 | 85 | 0 | 20 | 90 | 80 | 75 | 15 | 15 | 15 | 95 | 85 | 95 |
| Foxtail, Green | 10 | 65 | 10 | 25 | 0 | 35 | 95 | 70 | 55 | 50 | 45 | 45 | 30 | 0 |
| *Galium* | 75 | 100 | 70 | 10 | 10 | 70 | 60 | 15 | 0 | 80 | 0 | 75 | 70 | 85 |
| *Geranium*, Cutleaf | — | — | — | — | — | — | — | — | — | — | — | — | — | — |
| *Kochia* | 0 | 0 | 10 | 0 | 35 | 0 | 0 | 20 | 25 | 0 | 0 | 80 | 20 | 10 |
| Lambs-quarters | 20 | 15 | 25 | 75 | 100 | 80 | 100 | 100 | 60 | 70 | 75 | 25 | 98 | 100 |
| Mustard, Wild | 0 | 0 | 0 | 25 | 5 | 0 | 40 | 10 | 15 | 85 | 45 | 70 | 15 | 10 |
| Oat, Wild | 75 | 80 | 15 | 35 | 30 | 85 | 85 | 85 | 70 | 75 | 35 | 85 | 90 | 10 |
| Oilseed Rape | 0 | 0 | 5 | 0 | 0 | 0 | 0 | 0 | 10 | 0 | 0 | 0 | 0 | 0 |
| Pigweed | 70 | 25 | 0 | 30 | 100 | 100 | 100 | 90 | 50 | 25 | 55 | 25 | 90 | 70 |
| Radish, Wild | 0 | 0 | 10 | 0 | 0 | 0 | 0 | 0 | 0 | 35 | 0 | 25 | 0 | 20 |
| Russian Thistle | — | — | — | 0 | 0 | 10 | 0 | 0 | 0 | 0 | 0 | 25 | 10 | — |
| Ryegrass, Italian | 100 | 85 | 85 | 90 | 85 | 95 | 90 | 90 | 75 | 75 | 20 | 95 | 95 | 20 |
| Speedwell | 70 | 55 | 0 | 70 | 0 | 35 | 75 | 95 | 100 | 0 | 95 | 100 | 70 | 25 |
| Wheat, Spring | 0 | 0 | 5 | 0 | 0 | 0 | 0 | 0 | 0 | 0 | 0 | 40 | 0 | 5 |
| Wheat, Winter | 0 | 0 | 0 | 0 | 0 | 0 | 0 | 0 | 0 | 0 | 0 | 10 | 0 | 5 |
| Windgrass | 15 | 60 | 25 | 35 | 0 | 75 | 75 | 70 | 15 | 25 | 0 | 70 | 70 | 5 |

| 31 g ai/ha Pre-emergence | Compounds | | | | | | | | | | | | | |
|---|---|---|---|---|---|---|---|---|---|---|---|---|---|---|
| | 52 | 54 | 57 | 59 | 60 | 66 | 67 | 69 | 72 | 73 | 75 | 79 | 80 | 81 |
| Barley, Spring | 0 | 0 | 5 | 5 | 5 | 0 | 0 | 0 | 0 | 0 | 0 | 0 | 0 | 0 |
| Barley, Winter | 0 | 0 | 0 | 15 | 15 | 0 | 0 | 0 | 5 | 5 | 0 | 0 | 0 | 0 |
| Blackgrass | 20 | 15 | 25 | 85 | 90 | 25 | 75 | 15 | 15 | 50 | 15 | 20 | 70 | 55 |

TABLE D-continued

| Weed | | | | | | | | | | | | | | |
|---|---|---|---|---|---|---|---|---|---|---|---|---|---|---|
| Bluegrass | 0 | 0 | 0 | 30 | 35 | 10 | 0 | 5 | 10 | 15 | 15 | 10 | 20 | 0 |
| Bromegrass, Downy | 0 | 0 | 0 | 75 | 60 | 15 | 25 | 20 | 0 | 20 | 0 | 35 | 30 | 20 |
| Buckwheat, Wild | 20 | 0 | 0 | 20 | 0 | 0 | 0 | 0 | 0 | 0 | 0 | 0 | 0 | 15 |
| Canada Thistle | — | — | — | — | — | — | — | 30 | — | — | — | — | — | — |
| Canarygrass | 20 | 15 | 0 | 80 | 90 | 25 | 40 | 30 | 0 | 80 | 20 | 45 | 85 | 75 |
| Chamomile | 60 | — | — | 100 | 95 | 90 | 95 | 100 | — | — | — | — | 95 | — |
| Chickweed | 98 | 85 | 100 | 100 | 95 | 90 | 100 | 95 | 70 | 95 | 90 | 100 | 100 | 95 |
| Deadnettle | 0 | 0 | 0 | 50 | 35 | 15 | 15 | 15 | 5 | 0 | 30 | 0 | 55 | 0 |
| Field Poppy | 0 | 90 | 100 | 100 | 75 | 100 | 100 | 85 | 100 | 70 | 0 | 100 | 90 | 100 |
| Field Violet | 0 | 25 | 95 | 80 | 95 | 60 | 85 | 85 | 10 | 35 | 95 | 80 | 55 | 75 |
| Foxtail, Green | 0 | 50 | 10 | 55 | 70 | 15 | 15 | 50 | 20 | 15 | 15 | 55 | 20 | 75 |
| *Galium* | 70 | 0 | 85 | 95 | 75 | 0 | 0 | 45 | 20 | 40 | 15 | 80 | 25 | 25 |
| *Geranium*, Cutleaf | — | — | — | — | — | — | — | 0 | — | — | — | — | — | — |
| *Kochia* | 15 | 25 | 10 | 20 | 15 | 0 | 0 | 0 | 10 | 30 | 65 | 60 | 35 | 0 |
| Lambsquarters | 35 | 65 | 100 | 95 | 100 | 55 | 95 | 85 | 35 | 95 | 95 | 100 | 100 | 55 |
| Mustard, Wild | 85 | 50 | 0 | 95 | 45 | 0 | 0 | 0 | 0 | 65 | 55 | 0 | 0 | 0 |
| Oat, Wild | 25 | 75 | 15 | 90 | 90 | 75 | 70 | 60 | 65 | 75 | 55 | 80 | 85 | 85 |
| Oilseed Rape | 0 | 15 | 0 | 20 | 0 | 35 | 10 | 10 | 5 | 0 | 50 | 25 | 35 | 0 |
| Pigweed | 60 | 80 | 70 | 95 | 100 | 30 | 35 | 50 | 35 | 70 | 85 | 45 | 100 | 95 |
| Radish, Wild | 0 | 25 | 0 | — | 55 | 30 | 25 | 0 | 0 | 30 | 40 | 25 | 20 | 0 |
| Russian Thistle | 0 | 0 | — | 40 | 15 | 0 | 0 | 0 | 0 | 10 | 0 | 0 | 10 | 0 |
| Ryegrass, Italian | 85 | 35 | 55 | 100 | 100 | 80 | 75 | 90 | 55 | 95 | 95 | 80 | 90 | 55 |
| Speedwell | 50 | 100 | 25 | 100 | 100 | 75 | 80 | 98 | 5 | 100 | 95 | — | 65 | 55 |
| Wheat, Spring | 0 | 0 | 5 | 35 | 35 | 0 | 0 | 0 | 0 | 15 | 0 | 0 | 0 | 0 |
| Wheat, Winter | 0 | 0 | 5 | 10 | 10 | 0 | 0 | 0 | 5 | 15 | 0 | 0 | 0 | 0 |
| Windgrass | 10 | 0 | 20 | 85 | 85 | 70 | 30 | 35 | 25 | 40 | 0 | 25 | 75 | 60 |

| 31 g ai/ha Pre-emergence | Compounds | | | | | | | | | | | | | |
|---|---|---|---|---|---|---|---|---|---|---|---|---|---|---|
| | 82 | 83 | 84 | 85 | 87 | 88 | 90 | 104 | 105 | 108 | 109 | 126 | 129 | 153 |
| Barley, Spring | 0 | 0 | 0 | 0 | 0 | 0 | 0 | 0 | 0 | 0 | 0 | 0 | 0 | 0 |
| Barley, Winter | 0 | 0 | 0 | 0 | 0 | 0 | 0 | 5 | 0 | 0 | 0 | 0 | 0 | 0 |
| Blackgrass | 70 | 20 | 70 | 75 | 70 | 80 | 25 | 25 | 35 | 15 | 25 | 25 | 10 | 75 |
| Bluegrass | 15 | 15 | 15 | 40 | 25 | 35 | 0 | 35 | 25 | 10 | 10 | 5 | 0 | 70 |
| Bromegrass, Downy | 45 | 20 | 35 | 15 | 25 | 20 | 15 | 0 | 35 | 25 | 0 | 0 | 15 | 75 |
| Buckwheat, Wild | 35 | 0 | 10 | 20 | 0 | 0 | 15 | 0 | 15 | 0 | 0 | 0 | 0 | 40 |
| Canada Thistle | — | — | — | — | — | — | 50 | — | — | — | — | 0 | 80 | 100 |
| Canarygrass | 75 | 65 | 85 | 80 | 85 | 85 | 50 | 65 | 85 | 45 | 35 | 15 | 5 | 85 |
| Chamomile | 100 | — | 80 | — | 95 | — | 100 | — | — | — | — | 85 | 100 | 100 |
| Chickweed | 100 | 100 | 100 | 100 | 100 | 100 | 100 | 100 | 100 | 100 | 100 | 70 | 98 | 98 |
| Deadnettle | 10 | 0 | 25 | 0 | 25 | 5 | 15 | 65 | — | 0 | 0 | 0 | 60 | 98 |
| Field Poppy | 95 | 100 | 90 | — | 100 | — | 15 | 0 | 100 | 10 | 100 | 30 | 90 | 100 |
| Field Violet | 100 | 75 | 65 | 65 | 80 | 70 | 95 | 100 | 100 | 90 | 85 | 85 | 85 | 100 |
| Foxtail, Green | 35 | 15 | 30 | 25 | 10 | 30 | 25 | 20 | 45 | 30 | 0 | 20 | 35 | 75 |
| *Galium* | 60 | 0 | 20 | 30 | 15 | 25 | 75 | 65 | 80 | 60 | 40 | 50 | 75 | 85 |
| *Geranium*, Cutleaf | — | — | — | — | — | — | 0 | — | — | — | — | 0 | 0 | 35 |
| *Kochia* | 0 | 0 | 10 | 5 | 0 | 10 | 75 | 30 | 10 | 60 | 20 | 10 | 5 | 20 |
| Lambsquarters | 75 | 95 | 95 | 25 | 70 | 100 | 90 | 75 | 95 | 100 | 95 | 100 | 100 | 70 |
| Mustard, Wild | 0 | 0 | 0 | 25 | 0 | 20 | 35 | 10 | 10 | 5 | 5 | 60 | 75 | 100 |
| Oat, Wild | 80 | 80 | 90 | 75 | 80 | 80 | 75 | 75 | 80 | 80 | 75 | 65 | 75 | 80 |
| Oilseed Rape | 30 | 5 | 25 | 0 | 15 | 0 | 0 | 15 | 55 | 20 | 15 | 0 | 0 | 75 |
| Pigweed | 100 | 100 | 95 | 95 | 50 | 75 | 25 | 60 | 100 | 100 | 100 | 98 | 100 | 100 |
| Radish, Wild | 65 | 30 | — | 0 | 45 | 5 | 0 | 95 | — | 45 | 25 | 5 | 80 | 80 |
| Russian Thistle | 10 | 0 | 5 | 5 | 5 | 0 | 10 | 0 | 0 | 0 | 0 | 0 | 10 | 0 |
| Ryegrass, Italian | 75 | 40 | 80 | 55 | 90 | 75 | 100 | 100 | 85 | 80 | 80 | 75 | 70 | 100 |
| Speedwell | 75 | 70 | 70 | 50 | 80 | 95 | 100 | — | — | — | — | 70 | 90 | 100 |

TABLE D-continued

| | | | | | | | | | | | | | | |
|---|---|---|---|---|---|---|---|---|---|---|---|---|---|---|
| Wheat, Spring | 0 | 0 | 0 | 0 | 0 | 0 | 20 | 0 | 0 | 0 | 0 | 0 | 25 | 25 |
| Wheat, Winter | 0 | 0 | 0 | 0 | 0 | 0 | 0 | 0 | 0 | 0 | 0 | 0 | 10 | 5 |
| Windgrass | 75 | 15 | 75 | 55 | 80 | 60 | 50 | 70 | 75 | 25 | 55 | 25 | 35 | 75 |

Test E

Seeds of plant species selected from corn (*Zea mays*), soybean (*Glycine max*), velvetleaf (*Abutilon theophrasti*), lambsquarters (*Chenopodium album*), wild poinsettia (*Euphorbia heterophylla*), pigweed, palmer (palmer pigweed, *Amaranthus palmeri*), waterhemp (common waterhemp, *Amaranthus rudis*), surinam grass (*Brachiaria decumbens*), crabgrass, large (large crabgrass, *Digitaria sanguinalis*), crabgrass, Brazilian (Brazilian crabgrass, *Digitaria horizontalis*), panicum, fall (fall panicum, *Panicum dichotomiflorum*), foxtail, giant (giant foxtail, *Setaria faberii*), foxtail, green (green foxtail, *Setaria viridis*), goosegrass (*Eleusine indica*), johnsongrass (*Sorghum halepense*), ragweed (common ragweed, *Ambrosia elatior*), barnyardgrass (*Echinochloa crus-galli*), sandbur (southern sandbur, *Cenchrus echinatus*), arrowleaf sida (*Sida rhombifolia*), Italian ryegrass (*Lolium multiflorum*), dayflower (Virginia (VA) dayflower, *Commelina virginica*), field bindweed (*Convolvulus arvensis*), morningglory (*Ipomoea coccinea*), nightshade (eastern black nightshade, *Solanum ptycanthum*), kochia (*Kochia scoparia*), nutsedge, yellow (yellow nutsedge, *Cyperus esculentus*), horseweed (*Conyza canadensis*), and beggarticks (hairy beggarticks, *Bidens pilosa*), were planted into a silt loam soil and treated preemergence with test chemicals formulated in a non-phytotoxic solvent mixture which included a surfactant.

At the same time, plants from these crop and weed species and also waterhemp_RES1, (ALS & Triazine resistant common waterhemp, *Amaranthus rudis*), and waterhemp_RES2, (ALS & HPPD resistant common waterhemp, *Amaranthus rudis*) were planted in pots containing Redi-Earth® planting medium (Scotts Company, 14111 Scottslawn Road, Marysville, Ohio 43041) comprising spaghnum peat moss, vermiculite, wetting agent and starter nutrients were treated with postemergence applications of test chemicals formulated in the same manner. Plants ranged in height from 2 to 18 cm for postemergence treatments (1- to 4-leaf stage). Treated plants and controls were maintained in a greenhouse for 14 to 21 d, after which time all species were compared to controls and visually evaluated. Plant response ratings, summarized in Table E, are based on a scale of 0 to 100 where 0 is no effect and 100 is complete control. A dash (-) response means no test result.

TABLE E

| 250 g ai/ha Postemergence | Compounds | | | | | | | | | | | | | |
|---|---|---|---|---|---|---|---|---|---|---|---|---|---|---|
| | 1 | 2 | 20 | 25 | 28 | 34 | 41 | 42 | 47 | 57 | 69 | 72 | 75 | 79 |
| Arrowleaf Sida | 80 | 40 | 80 | 85 | 60 | 75 | 90 | 80 | 60 | 45 | 80 | 90 | 80 | 70 |
| Barnyardgrass | 35 | 35 | 80 | 50 | 60 | 40 | 60 | 35 | 60 | 90 | 30 | 50 | 30 | 20 |
| Beggarticks | 100 | 100 | 100 | 100 | 100 | 100 | 100 | 100 | 98 | 100 | 100 | 98 | 100 | 100 |
| Corn | 5 | 5 | 15 | 15 | 5 | 5 | 5 | 20 | 20 | 15 | 5 | 30 | 0 | 0 |
| Crabgrass, Brazil | 35 | 15 | 50 | 50 | 60 | 50 | 50 | 50 | 40 | 30 | 30 | 70 | 50 | 40 |
| Dayflower, VA | 50 | 65 | 50 | 65 | 80 | 90 | 90 | 70 | 10 | 30 | 80 | 80 | 65 | 65 |
| Field Bindweed | 95 | 80 | 95 | 90 | 80 | 95 | 95 | 90 | 90 | 95 | 90 | 90 | 85 | 95 |
| Horseweed | — | — | 85 | — | 80 | 90 | 70 | 85 | 75 | 80 | 90 | 70 | 50 | 90 |
| Kochia | — | — | 90 | 98 | 90 | 85 | 95 | 98 | 85 | 75 | 95 | 90 | 100 | 98 |
| Panicum, Fall | 85 | 90 | 50 | 90 | 90 | 60 | 50 | 95 | 70 | 80 | 50 | 85 | 60 | 75 |
| Pigweed, Palmer | 98 | 35 | 70 | 85 | 50 | 75 | 95 | 95 | 70 | 60 | 60 | 75 | 100 | 75 |
| Poinsettia, Wild | 35 | 15 | 30 | 60 | 40 | — | — | — | 30 | 20 | 0 | 75 | — | 10 |
| Ragweed | — | — | 80 | 95 | 75 | 100 | 95 | 90 | 95 | 95 | 95 | 95 | 90 | 100 |
| Ryegrass, Italian | 90 | 75 | 80 | 90 | 75 | 90 | 90 | 90 | 10 | 50 | 85 | 90 | 90 | 80 |
| Sandbur | 30 | 30 | 40 | 75 | 80 | 90 | 75 | 60 | 35 | 70 | 10 | 80 | 30 | 65 |
| Soybean | 20 | 0 | 30 | 75 | 60 | 60 | 75 | 50 | 30 | 10 | 20 | 50 | 75 | 10 |
| Waterhemp | 100 | 90 | 85 | 90 | 75 | 90 | 85 | 90 | 100 | 75 | 90 | 90 | 95 | 80 |
| Waterhemp_RES1 | 100 | 100 | 80 | 95 | 80 | 95 | 95 | 98 | 95 | 60 | 85 | 90 | 90 | 75 |
| Waterhemp_RES2 | 75 | 60 | 60 | 75 | 50 | 70 | 85 | 80 | 70 | 50 | 65 | 65 | 75 | 55 |

| 250 g ai/ha Postemergence | Compounds | | | | | | | | | |
|---|---|---|---|---|---|---|---|---|---|---|
| | 81 | 82 | 83 | 84 | 85 | 88 | 100 | 126 | 153 | 171 |
| Arrowleaf Sida | 60 | 90 | 60 | 80 | 50 | 60 | 75 | 85 | 40 | 95 |
| Barnyardgrass | 50 | 50 | 50 | 40 | 30 | 25 | 50 | 30 | 80 | 50 |
| Beggarticks | 100 | 98 | 100 | 100 | 100 | 100 | 100 | 100 | 100 | 100 |
| Corn | 5 | 0 | 10 | 0 | 5 | 5 | 0 | 5 | 0 | 0 |
| Crabgrass, Brazil | 50 | 50 | 50 | 20 | 50 | 50 | 50 | 50 | 50 | 60 |
| Dayflower, VA | 80 | 65 | 70 | 30 | 80 | 80 | 0 | 50 | 95 | 90 |
| Field Bindweed | 85 | 85 | 75 | 80 | 90 | 75 | 95 | 100 | 95 | 100 |
| Horseweed | 85 | 80 | 90 | 85 | 90 | 90 | 80 | 80 | 85 | 60 |
| Kochia | 75 | 98 | 65 | 100 | 80 | 90 | 100 | 100 | 70 | 100 |
| Panicum, Fall | 90 | 75 | 90 | 90 | 95 | 85 | 80 | 35 | 90 | 75 |
| Pigweed, Palmer | 50 | 65 | 60 | 70 | 80 | 50 | 50 | 80 | 40 | 70 |
| Poinsettia, Wild | 50 | 50 | — | 40 | — | — | 35 | 50 | 75 | 80 |
| Ragweed | 80 | 90 | 75 | 95 | 85 | 80 | 90 | 100 | 90 | 98 |
| Ryegrass, Italian | 80 | 80 | 85 | 85 | 80 | 85 | 85 | 90 | 95 | 90 |

TABLE E-continued

| | | | | | | | | | | |
|---|---|---|---|---|---|---|---|---|---|---|
| Sandbur | 75 | 75 | 70 | 65 | 70 | 70 | 50 | 40 | 70 | 60 |
| Soybean | 10 | 35 | 15 | 35 | 15 | 10 | 0 | 30 | 25 | 70 |
| Waterhemp | 75 | 90 | 60 | 95 | 90 | 70 | 90 | 90 | 75 | 90 |
| Waterhemp_RES1 | 65 | 95 | 70 | 95 | 80 | 85 | 90 | 100 | 60 | 90 |
| Waterhemp_RES2 | 50 | 60 | 50 | 70 | 50 | 50 | 70 | 85 | 50 | 60 |

| 125 g ai/ha | Compounds | | | | | | | | | | | | |
|---|---|---|---|---|---|---|---|---|---|---|---|---|---|
| Postemergence | 1 | 2 | 20 | 25 | 28 | 34 | 41 | 42 | 47 | 57 | 66 | 69 | 72 | 75 |
| Arrowleaf Sida | 70 | 35 | 70 | 80 | 60 | 70 | 95 | 70 | 60 | 40 | 70 | 70 | 80 | 80 |
| Barnyardgrass | 25 | 30 | 60 | 50 | 50 | 40 | 50 | 30 | 40 | 90 | 20 | 20 | 40 | 25 |
| Beggarticks | 100 | 100 | 98 | 100 | 100 | 98 | 98 | 95 | 100 | 98 | 100 | 100 | 98 | 100 |
| Corn | 5 | 5 | 0 | 20 | 5 | 0 | 0 | 15 | 5 | 15 | 15 | 0 | 20 | 0 |
| Crabgrass, Brazil | 20 | 10 | 20 | 50 | 50 | 50 | 30 | 40 | 25 | 20 | 40 | 30 | 60 | 50 |
| Dayflower, VA | 30 | 65 | 50 | 50 | 70 | 90 | 85 | 60 | 0 | 35 | 50 | 65 | 80 | 50 |
| Field Bindweed | 85 | 75 | 90 | 95 | 60 | 80 | 85 | 90 | 85 | 98 | 80 | 80 | 95 | 80 |
| Horseweed | — | — | 70 | — | 80 | 80 | 80 | 75 | 60 | 75 | 90 | 85 | 75 | 60 |
| Kochia | — | — | 75 | 100 | 75 | 85 | 95 | 95 | 80 | 60 | 95 | 80 | 90 | 100 |
| Panicum, Fall | 80 | 85 | 30 | 80 | 70 | 70 | 30 | 80 | 55 | 70 | 80 | 30 | 80 | 50 |
| Pigweed, Palmer | 75 | 5 | 55 | 100 | 50 | 65 | 90 | 60 | 30 | 30 | 80 | 40 | 60 | 100 |
| Poinsettia, Wild | 15 | 15 | 30 | 35 | 50 | — | — | — | 25 | 30 | — | 5 | 65 | — |
| Ragweed | — | — | 85 | 90 | 70 | 90 | 90 | 95 | 95 | 95 | 90 | 90 | 90 | 60 |
| Ryegrass, Italian | 65 | 65 | 70 | 85 | 75 | 85 | 85 | 85 | 0 | 20 | 50 | 90 | 85 | 85 |
| Sandbur | 30 | 20 | 30 | 70 | 60 | 85 | 70 | 60 | 25 | 65 | 60 | 5 | 75 | 20 |
| Soybean | 15 | 0 | 40 | 30 | 50 | 70 | 60 | 30 | 20 | 15 | 20 | 25 | 30 | 70 |
| Waterhemp | 98 | 75 | 80 | 85 | 70 | 85 | 90 | 100 | 85 | 30 | 80 | 80 | 80 | 90 |
| Waterhemp_RES1 | 98 | 70 | 80 | 85 | 60 | 90 | 90 | 70 | 80 | 40 | 80 | 85 | 80 | 95 |
| Waterhemp_RES2 | 70 | 5 | 50 | 70 | 50 | — | 80 | 70 | 60 | 20 | 50 | 50 | 50 | 60 |

| 125 g ai/ha | Compounds | | | | | | | | | | | | |
|---|---|---|---|---|---|---|---|---|---|---|---|---|---|
| Postemergence | 79 | 81 | 82 | 83 | 84 | 85 | 88 | 90 | 99 | 100 | 105 | 109 | 126 | 153 |
| Arrowleaf Sida | 60 | 30 | 80 | 60 | 70 | 50 | 50 | 90 | 60 | 70 | 70 | 80 | 100 | 40 |
| Barnyardgrass | 20 | 30 | 50 | 40 | 40 | 20 | 20 | 50 | 50 | 30 | 30 | 40 | 40 | 50 |
| Beggarticks | 100 | 100 | 98 | 100 | 95 | 100 | 100 | 100 | 95 | 90 | 100 | 100 | 100 | 100 |
| Corn | 0 | 5 | 0 | 0 | 0 | 0 | 5 | 0 | 0 | 0 | 20 | 20 | 5 | 0 |
| Crabgrass, Brazil | 25 | 50 | 50 | 50 | 15 | 50 | 30 | 70 | 20 | 40 | 50 | 50 | 40 | 40 |
| Dayflower, VA | 60 | 80 | 60 | 75 | 10 | 60 | 70 | 90 | 75 | 0 | 60 | 60 | 50 | 90 |
| Field Bindweed | 95 | 75 | 95 | 70 | 100 | 60 | 60 | 100 | 80 | 90 | 95 | 90 | 95 | 100 |
| Horseweed | 95 | 65 | 75 | 85 | 85 | 85 | 90 | 70 | 75 | 75 | — | 85 | 85 | 85 |
| Kochia | 90 | 70 | 95 | 75 | 100 | 80 | 80 | 100 | 70 | 80 | 100 | 100 | 100 | 55 |
| Panicum, Fall | 60 | 85 | 75 | 80 | 85 | 80 | 85 | 70 | 70 | 70 | 80 | 80 | 30 | 90 |
| Pigweed, Palmer | 40 | — | 75 | 50 | 80 | 80 | 50 | 60 | 50 | 40 | 70 | 100 | 50 | 30 |
| Poinsettia, Wild | 20 | 40 | 40 | — | 30 | — | — | 60 | 50 | 10 | 30 | 50 | 50 | 60 |
| Ragweed | 95 | 85 | 90 | 70 | 98 | 60 | 70 | 90 | 90 | 90 | 95 | 95 | 100 | 80 |
| Ryegrass, Italian | 70 | 75 | 75 | 80 | 75 | 75 | 80 | 85 | 80 | 70 | 80 | 85 | 85 | 90 |
| Sandbur | 50 | 70 | 70 | 65 | 60 | 70 | 70 | 50 | 40 | 40 | 50 | 70 | 40 | 60 |
| Soybean | 15 | 0 | 40 | 0 | 10 | 5 | 0 | 60 | 30 | 0 | 25 | 20 | 40 | 10 |
| Waterhemp | 70 | 60 | 85 | 40 | 90 | 65 | 60 | 90 | 75 | — | 90 | 90 | 90 | 50 |
| Waterhemp_RES1 | 70 | 60 | 85 | 80 | 80 | 75 | 65 | 80 | 75 | 85 | 100 | 90 | 90 | 50 |
| Waterhemp_RES2 | 15 | 50 | 60 | 40 | 70 | 40 | 50 | 70 | 60 | 65 | 70 | 60 | 70 | 30 |

| 125 g ai/ha | Compound |
|---|---|
| Postemergence | 171 |
| Arrowleaf Sida | 90 |
| Barnyardgrass | 50 |
| Beggarticks | 100 |
| Corn | 0 |
| Crabgrass, Brazil | 50 |
| Dayflower, VA | 70 |
| Field Bindweed | 100 |
| Horseweed | 70 |
| Kochia | 100 |
| Panicum, Fall | 60 |
| Pigweed, Palmer | 60 |
| Poinsettia, Wild | 40 |
| Ragweed | 90 |
| Ryegrass, Italian | 85 |
| Sandbur | 50 |
| Soybean | 50 |
| Waterhemp | 85 |
| Waterhemp_RES1 | 75 |
| Waterhemp_RES2 | 40 |

TABLE E-continued

| 62 g ai/ha | Compounds | | | | | | | | | | | | | |
|---|---|---|---|---|---|---|---|---|---|---|---|---|---|---|
| Postemergence | 1 | 2 | 20 | 25 | 34 | 41 | 42 | 47 | 57 | 66 | 69 | 72 | 75 | 79 |
| Arrowleaf Sida | 70 | 30 | 60 | 75 | 60 | 90 | 60 | 50 | 20 | 60 | 60 | 75 | 70 | 50 |
| Barnyardgrass | 20 | 25 | 50 | 50 | 40 | 35 | 30 | 30 | 85 | 25 | 25 | 40 | 30 | 15 |
| Beggarticks | 98 | 100 | 95 | 100 | 100 | 95 | 95 | 100 | 100 | 90 | 85 | 100 | 95 | 100 |
| Corn | 5 | 0 | 0 | 20 | 0 | 0 | 15 | 5 | 10 | 10 | 0 | 10 | 0 | 0 |
| Crabgrass, Brazil | 15 | 0 | 20 | 40 | 40 | 20 | 35 | 20 | 20 | 30 | 20 | 40 | 40 | 20 |
| Dayflower, VA | 0 | 15 | 10 | 40 | 80 | 40 | 50 | 5 | 15 | 60 | 50 | 65 | 50 | 50 |
| Field Bindweed | 70 | 65 | 85 | 95 | 80 | 90 | 85 | 75 | 95 | 80 | 85 | 80 | 90 | 95 |
| Horseweed | — | — | 80 | — | 75 | 80 | 75 | 40 | 75 | 90 | 75 | 60 | 75 | 95 |
| Kochia | — | — | 65 | 95 | 98 | 95 | 85 | 70 | 70 | 90 | 80 | 98 | 98 | 80 |
| Panicum, Fall | 75 | 70 | 15 | 50 | 65 | 25 | 50 | 55 | 60 | 70 | 20 | 80 | 40 | 60 |
| Pigweed, Palmer | 90 | 5 | 35 | 80 | 80 | 60 | 75 | 35 | 20 | 60 | 20 | 50 | 70 | 35 |
| Poinsettia, Wild | 15 | 0 | 20 | 30 | — | — | — | 15 | 10 | — | 0 | 40 | — | 10 |
| Ragweed | — | — | 75 | 90 | 85 | — | 85 | 90 | 60 | 80 | 80 | 90 | 70 | 98 |
| Ryegrass, Italian | 50 | 50 | 50 | 80 | 80 | 85 | 70 | 0 | 0 | 40 | 70 | 80 | 80 | 40 |
| Sandbur | 30 | 15 | 20 | 60 | 80 | 50 | 50 | 20 | 60 | 50 | 0 | 70 | 20 | 30 |
| Soybean | 10 | 0 | 20 | 20 | 40 | 40 | 20 | 25 | 0 | 20 | 10 | 30 | 70 | 10 |
| Waterhemp | 95 | 75 | 75 | 80 | 85 | 85 | 80 | 80 | 50 | 75 | 85 | 65 | 90 | 60 |
| Waterhemp_RES1 | 90 | 70 | 70 | 80 | 90 | 75 | 75 | 70 | 50 | 75 | 70 | 80 | 90 | 60 |
| Waterhemp_RES2 | 70 | 5 | 50 | 60 | 80 | 80 | 65 | 50 | 10 | 40 | 40 | 40 | 60 | 15 |

| 62 g ai/ha | Compounds | | | | | | | | | | | | | |
|---|---|---|---|---|---|---|---|---|---|---|---|---|---|---|
| Postemergence | 81 | 82 | 83 | 84 | 85 | 88 | 90 | 99 | 100 | 105 | 109 | 126 | 153 | 171 |
| Arrowleaf Sida | 40 | 70 | 50 | 60 | 50 | 50 | 90 | 50 | 60 | 60 | 60 | 80 | 50 | 80 |
| Barnyardgrass | 20 | 40 | 50 | 30 | 30 | 30 | 40 | 40 | 40 | 30 | 30 | 50 | 40 | 45 |
| Beggarticks | 100 | 90 | 100 | 100 | 100 | 100 | 98 | 100 | 80 | 100 | 85 | 100 | 100 | 95 |
| Corn | 0 | 0 | 0 | 0 | 0 | 0 | 5 | 0 | 5 | 15 | 10 | 10 | 0 | 0 |
| Crabgrass, Brazil | 40 | 30 | 40 | 10 | 30 | 15 | 50 | 10 | 50 | 40 | 30 | 25 | 30 | 50 |
| Dayflower, VA | 70 | 50 | 60 | 0 | 60 | 60 | 80 | 70 | 0 | 50 | 50 | 20 | 90 | 50 |
| Field Bindweed | 65 | 80 | 70 | 100 | 50 | 60 | 90 | 70 | 80 | 75 | 95 | 90 | 90 | 85 |
| Horseweed | 75 | 70 | 80 | 75 | 85 | 95 | 75 | 60 | 70 | 85 | 90 | 75 | 80 | 60 |
| Kochia | 70 | 98 | 60 | 98 | 70 | 70 | 95 | 60 | 80 | 90 | 95 | 100 | 50 | 95 |
| Panicum, Fall | 80 | 65 | 70 | 70 | 75 | 80 | 60 | 50 | 50 | 70 | 65 | 35 | 90 | 50 |
| Pigweed, Palmer | 20 | 60 | 40 | 75 | 80 | 55 | 50 | 30 | 30 | 70 | 65 | 50 | 20 | 50 |
| Poinsettia, Wild | 40 | 30 | — | 30 | — | — | 50 | 40 | 0 | 25 | 45 | 20 | 30 | 30 |
| Ragweed | 60 | 90 | 50 | 95 | 50 | 50 | 80 | 80 | 85 | 90 | 90 | 80 | 70 | 75 |
| Ryegrass, Italian | 70 | 70 | 60 | 65 | 60 | 65 | 85 | 70 | 60 | 70 | 90 | 80 | 90 | 75 |
| Sandbur | 60 | 60 | 50 | 50 | 60 | 60 | 50 | 40 | 40 | 45 | 60 | 30 | 85 | 50 |
| Soybean | 0 | 25 | 0 | 15 | 0 | 0 | 40 | 10 | 0 | 15 | 20 | 30 | 15 | 40 |
| Waterhemp | 60 | 80 | 50 | 85 | 50 | 60 | 80 | 60 | 75 | 80 | 80 | 90 | 40 | 80 |
| Waterhemp_RES1 | 60 | 75 | 65 | 85 | 75 | 70 | 50 | 70 | 80 | 75 | 90 | 95 | 30 | 70 |
| Waterhemp_RES2 | 20 | 50 | 40 | 65 | 50 | 50 | 60 | 40 | 60 | 60 | 50 | 70 | 40 | 30 |

| 31 g ai/ha | Compounds | | | | | | | | | | | | | |
|---|---|---|---|---|---|---|---|---|---|---|---|---|---|---|
| Postemergence | 1 | 2 | 20 | 25 | 34 | 41 | 42 | 47 | 57 | 66 | 69 | 72 | 75 | 79 |
| Arrowleaf Sida | 50 | 25 | 40 | 60 | 65 | 85 | 20 | 40 | 10 | 40 | 50 | 70 | 70 | 50 |
| Barnyardgrass | 15 | 20 | 30 | 40 | 30 | 20 | 20 | 10 | 80 | 15 | 20 | 30 | 20 | 15 |
| Beggarticks | 85 | 95 | 85 | 100 | 90 | 100 | 95 | 85 | 100 | 80 | 80 | 90 | 100 | 100 |
| Corn | 5 | 0 | 0 | 10 | 0 | 0 | 10 | 0 | 15 | 0 | 0 | 0 | 0 | 0 |
| Crabgrass, Brazil | 15 | 10 | 10 | 30 | 40 | 10 | 20 | 20 | 15 | 20 | 10 | 50 | 40 | 20 |
| Dayflower, VA | 0 | 20 | 0 | 10 | 60 | 50 | 30 | 0 | 10 | 25 | 20 | 60 | 30 | 50 |
| Field Bindweed | 65 | 60 | 75 | 90 | 70 | 80 | 90 | 70 | 85 | 60 | 70 | 70 | 85 | 80 |
| Horseweed | — | — | 70 | — | 85 | 75 | 75 | 40 | 60 | 80 | 70 | 60 | 40 | 90 |
| Kochia | — | — | 60 | 90 | 70 | 90 | 75 | 60 | 50 | 95 | 75 | 70 | 90 | 70 |
| Panicum, Fall | 75 | 70 | 0 | 50 | 50 | 15 | 60 | 40 | 40 | 70 | 20 | 75 | 50 | 55 |
| Pigweed, Palmer | 20 | 50 | 40 | 75 | 50 | 50 | 70 | 35 | 10 | 70 | 10 | 50 | 70 | 40 |
| Poinsettia, Wild | 10 | 0 | 0 | 35 | — | — | — | 10 | 10 | — | 5 | 30 | — | 10 |
| Ragweed | — | — | 65 | 90 | 90 | 80 | 90 | 80 | 50 | 80 | 70 | 85 | 55 | 90 |
| Ryegrass, Italian | 35 | 30 | 40 | 75 | 65 | 80 | 50 | 0 | 0 | 30 | 65 | 80 | 75 | 30 |
| Sandbur | 10 | 10 | 15 | 50 | 70 | 60 | 35 | 20 | 50 | 40 | 0 | 60 | 10 | 20 |
| Soybean | 0 | 0 | 20 | 0 | 35 | 30 | 10 | 20 | 10 | 0 | 5 | 25 | 70 | 0 |
| Waterhemp | 85 | 70 | 70 | 80 | 70 | 75 | 75 | 75 | 50 | 65 | 65 | 65 | 80 | 50 |
| Waterhemp_RES1 | 80 | 70 | 60 | 75 | 90 | 75 | 75 | 60 | 40 | 80 | 65 | 60 | 90 | 50 |
| Waterhemp_RES2 | 75 | 0 | 50 | 70 | 40 | 20 | 60 | 15 | 20 | 40 | 50 | 35 | 60 | 20 |

| 31 g ai/ha | Compounds | | | | | | | | | | | | | |
|---|---|---|---|---|---|---|---|---|---|---|---|---|---|---|
| Postemergence | 81 | 82 | 83 | 84 | 85 | 88 | 90 | 99 | 100 | 105 | 109 | 126 | 153 | 171 |
| Arrowleaf Sida | 40 | 65 | 50 | 50 | 40 | 60 | 80 | 30 | 50 | 60 | 65 | 75 | 40 | 80 |
| Barnyardgrass | 20 | 30 | 40 | 30 | 20 | 20 | 30 | 30 | 30 | 20 | 30 | 40 | 25 | 40 |
| Beggarticks | 90 | 90 | 98 | 95 | 90 | 100 | 90 | 80 | 75 | 90 | 90 | 100 | 100 | 80 |
| Corn | 0 | 0 | 0 | 0 | 0 | 0 | 0 | 0 | 0 | 5 | 0 | 0 | 0 | 0 |

TABLE E-continued

| | | | | | | | | | | | | | | |
|---|---|---|---|---|---|---|---|---|---|---|---|---|---|---|
| Crabgrass, Brazil | 40 | 20 | 30 | 10 | 15 | 15 | 55 | 10 | 25 | 20 | 40 | 10 | 20 | 40 |
| Dayflower, VA | 60 | 40 | 50 | 5 | 50 | 50 | 60 | 60 | 0 | 30 | 30 | 0 | 85 | 40 |
| Field Bindweed | 60 | 85 | 60 | 70 | 50 | 50 | 80 | 60 | 75 | 80 | 80 | 85 | 80 | 70 |
| Horseweed | 50 | 60 | 75 | 60 | 60 | 75 | 70 | 50 | 35 | 85 | 80 | 70 | 85 | 50 |
| Kochia | 60 | 90 | 40 | 80 | 60 | 60 | 90 | 50 | 60 | 80 | 95 | 100 | 50 | 90 |
| Panicum, Fall | 85 | 70 | 70 | 60 | 75 | 75 | 60 | 30 | 30 | 60 | 60 | 10 | 85 | 40 |
| Pigweed, Palmer | 30 | 50 | 40 | 70 | 65 | 50 | 65 | 10 | 20 | 70 | 50 | 40 | 20 | 50 |
| Poinsettia, Wild | 30 | 40 | — | 20 | — | — | 35 | 30 | 0 | 30 | 25 | 30 | 20 | 25 |
| Ragweed | 60 | 85 | 60 | 85 | 50 | 50 | 75 | 75 | 75 | — | 85 | 70 | 75 | 60 |
| Ryegrass, Italian | 50 | 50 | 60 | 60 | 50 | 50 | 80 | 50 | 50 | 50 | 75 | 70 | 85 | 65 |
| Sandbur | 60 | 50 | 40 | 50 | 40 | 40 | 40 | 30 | 20 | 40 | 40 | 0 | 50 | 30 |
| Soybean | 0 | 10 | 0 | 10 | 0 | 0 | 30 | 0 | 0 | 10 | 0 | 10 | 0 | 40 |
| Waterhemp | 50 | 70 | 40 | 70 | 50 | 70 | 70 | 45 | 80 | 70 | 75 | 75 | 50 | 80 |
| Waterhemp_RES1 | 50 | 60 | 70 | 60 | 80 | 60 | 50 | 50 | 80 | 80 | 70 | 75 | 50 | 50 |
| Waterhemp_RES2 | 10 | 50 | 30 | 55 | 40 | 40 | 50 | 50 | 50 | 50 | 50 | 55 | 10 | 15 |

| 16 g ai/ha | Compounds | | | | | | |
|---|---|---|---|---|---|---|---|
| Postemergence | 1 | 2 | 66 | 90 | 99 | 105 | 109 |
| Arrowleaf Sida | 30 | 0 | 30 | 70 | 10 | 50 | 50 |
| Barnyardgrass | 10 | 20 | 20 | 30 | 40 | 15 | 25 |
| Beggarticks | 70 | 85 | 75 | 85 | 70 | 80 | 80 |
| Corn | 0 | 0 | 0 | 5 | 0 | 0 | 0 |
| Crabgrass, Brazil | 0 | 0 | 10 | 50 | 5 | 5 | 10 |
| Dayflower, VA | 0 | 0 | 0 | 40 | 40 | 30 | 30 |
| Field Bindweed | 65 | 60 | 70 | 60 | 50 | 75 | 75 |
| Horseweed | — | — | 60 | 50 | 40 | 80 | 60 |
| Kochia | — | — | 90 | 90 | 55 | 80 | 80 |
| Panicum, Fall | 70 | 60 | 30 | 40 | 20 | 40 | 50 |
| Pigweed, Palmer | 70 | 0 | 50 | 40 | 5 | 75 | 60 |
| Poinsettia, Wild | 5 | 0 | — | 20 | 35 | 30 | 0 |
| Ragweed | — | — | 75 | 50 | 50 | 70 | 80 |
| Ryegrass, Italian | 20 | 20 | 20 | 75 | 40 | 30 | 50 |
| Sandbur | 0 | 5 | 25 | 40 | 20 | 30 | 60 |
| Soybean | 0 | 0 | 0 | 20 | 0 | 0 | 0 |
| Waterhemp | 70 | 70 | 70 | 50 | 65 | 60 | 60 |
| Waterhemp_RES1 | 75 | 65 | 70 | 50 | 50 | 80 | 60 |
| Waterhemp_RES2 | 0 | 0 | 40 | 50 | 50 | 40 | — |

| 250 g ai/ha | Compounds | | | | | | | | | | | | |
|---|---|---|---|---|---|---|---|---|---|---|---|---|---|
| Preemergence | 1 | 2 | 20 | 25 | 27 | 28 | 29 | 34 | 37 | 41 | 47 | 57 | 59 | 69 |
| Arrowleaf Sida | 80 | 5 | 95 | 95 | 35 | 70 | 98 | 80 | 98 | 100 | 90 | 40 | 98 | 80 |
| Barnyardgrass | 20 | 70 | 30 | 90 | 95 | 90 | 90 | 65 | 30 | 65 | 95 | 100 | 90 | 10 |
| Beggarticks | 100 | 100 | 98 | 100 | 100 | 100 | 100 | 100 | 100 | 100 | 100 | 100 | 100 | 100 |
| Corn | 0 | 0 | 0 | 0 | 0 | 0 | 0 | 0 | 0 | 25 | 0 | 0 | 20 | 10 |
| Crabgrass, Brazil | 100 | 100 | 90 | 95 | 95 | 90 | 90 | 80 | 95 | 80 | 60 | 70 | 100 | 60 |
| Crabgrass, Large | 65 | 60 | 30 | 85 | 90 | 90 | 65 | 20 | 90 | 60 | 35 | 0 | 95 | 20 |
| Dayflower, VA | 25 | 90 | 0 | 30 | 65 | 70 | 60 | 90 | 60 | 80 | 80 | 80 | 80 | 70 |
| Field Bindweed | 100 | 70 | 95 | 98 | 70 | 75 | 98 | 60 | 100 | 90 | 100 | 100 | 95 | 85 |
| Foxtail, Giant | 98 | 98 | 90 | 100 | 100 | 100 | 98 | 65 | 90 | 90 | 80 | 95 | 100 | 60 |
| Foxtail, Green | 90 | 98 | 70 | 100 | 100 | 100 | 100 | 65 | 80 | 75 | 70 | 100 | 100 | 30 |
| Goosegrass | 25 | 25 | 85 | 90 | 85 | 90 | 90 | 10 | 80 | 60 | 0 | 5 | 98 | 50 |
| Horseweed | — | — | 100 | 100 | 100 | 98 | 100 | — | 100 | 100 | — | — | 100 | — |
| Johnsongrass | 40 | 50 | 0 | 90 | 70 | 90 | 100 | 0 | 100 | 25 | 20 | 35 | 80 | 20 |
| Kochia | 85 | 40 | 100 | 100 | 100 | 100 | 70 | 85 | 65 | 100 | 100 | 100 | 100 | 95 |
| Lambsquarters | 100 | 100 | 100 | 100 | 100 | 98 | 98 | 98 | 100 | 100 | 100 | 100 | 100 | 90 |
| Morningglory | 100 | 100 | 95 | 100 | 100 | 100 | 95 | 90 | 65 | 95 | 100 | 100 | 100 | 85 |
| Nightshade | 100 | 100 | — | 98 | 98 | 100 | 90 | 95 | 98 | 98 | 100 | 98 | — | 90 |
| Nutsedge, Yellow | 70 | 70 | 95 | 65 | 80 | 95 | 70 | 80 | 70 | 85 | 35 | 70 | 70 | 60 |
| Panicum, Fall | 100 | 100 | 98 | 100 | 100 | 100 | 98 | 95 | 100 | 98 | 95 | 100 | 100 | 70 |
| Pigweed, Palmer | 100 | 100 | 70 | 100 | 85 | 98 | 100 | 90 | 100 | 85 | 65 | 60 | 100 | 70 |
| Poinsettia, Wild | 35 | 50 | — | — | — | — | — | — | — | 65 | 20 | 50 | — | 20 |
| Ragweed | 100 | 98 | 98 | 100 | 100 | 98 | 98 | 100 | 98 | 100 | 100 | 100 | 100 | 100 |
| Ryegrass, Italian | 100 | 100 | 100 | 100 | 100 | 100 | 100 | 100 | 100 | 100 | 50 | 80 | 100 | 100 |
| Sandbur | 70 | 75 | 75 | 85 | 90 | 85 | 90 | 70 | 65 | 80 | 70 | 80 | 90 | 60 |
| Soybean | 75 | 40 | — | 70 | 0 | 0 | 50 | 0 | 0 | 65 | 40 | 20 | 70 | 20 |
| Surinam Grass | 75 | 95 | 90 | 95 | 100 | 98 | 100 | 80 | 90 | 95 | 35 | 95 | 100 | 50 |
| Velvetleaf | 98 | 90 | 100 | 100 | 100 | 100 | 100 | 100 | 100 | 100 | 100 | 100 | 98 | 90 |
| Waterhemp | 100 | 98 | 100 | 100 | 95 | 100 | 100 | 100 | 100 | 100 | 100 | 80 | 100 | 100 |

| 250 g ai/ha | Compounds | | | | | | | | | | |
|---|---|---|---|---|---|---|---|---|---|---|---|
| Preemergence | 72 | 75 | 79 | 81 | 82 | 83 | 84 | 85 | 87 | 88 | 153 |
| Arrowleaf Sida | 65 | 98 | 75 | 70 | 95 | 65 | 100 | 70 | 80 | 50 | 75 |
| Barnyardgrass | 50 | 65 | 50 | 75 | 40 | 75 | 20 | 35 | 35 | 70 | 90 |
| Beggarticks | 100 | 100 | 100 | 100 | 100 | 100 | 100 | 100 | 100 | 100 | 100 |

TABLE E-continued

| | | | | | | | | | | | | |
|---|---|---|---|---|---|---|---|---|---|---|---|---|
| Corn | 0 | 35 | 20 | 0 | 5 | 0 | 15 | 0 | 15 | 0 | 20 | |
| Crabgrass, Brazil | 98 | 90 | 100 | 100 | 100 | 80 | 100 | 90 | 100 | 90 | 100 | |
| Crabgrass, Large | 90 | 30 | 30 | 98 | 90 | 20 | 75 | 25 | 65 | 20 | 80 | |
| Dayflower, VA | 50 | 75 | 70 | 65 | 35 | 65 | 50 | 75 | 35 | 70 | 90 | |
| Field Bindweed | 90 | 98 | 100 | 100 | 95 | 100 | 98 | 95 | 100 | 100 | 100 | |
| Foxtail, Giant | 80 | 75 | 90 | 100 | 95 | 100 | 90 | 100 | 95 | 100 | 100 | |
| Foxtail, Green | 70 | 90 | 90 | 100 | 90 | 70 | 100 | 100 | 80 | 100 | 95 | |
| Goosegrass | 80 | 5 | 65 | 80 | 90 | 25 | 35 | 20 | 75 | 0 | 75 | |
| Horseweed | 100 | — | 100 | 100 | 100 | — | 100 | — | — | — | 100 | |
| Johnsongrass | 35 | 15 | 65 | 100 | 50 | 20 | 0 | 0 | 75 | 0 | 60 | |
| Kochia | 98 | 100 | 100 | 100 | 100 | 75 | 100 | 98 | 100 | 98 | 90 | |
| Lambsquarters | 100 | 100 | 100 | 100 | 100 | 100 | 100 | 100 | 100 | 100 | 100 | |
| Morningglory | 95 | 100 | 100 | 100 | 100 | 100 | 95 | 100 | 90 | 100 | 100 | |
| Nightshade | 100 | 100 | 100 | 98 | 100 | 100 | 100 | 100 | 98 | 100 | 100 | |
| Nutsedge, Yellow | 35 | 65 | 75 | 90 | 65 | 75 | 40 | 65 | 60 | 65 | 95 | |
| Panicum, Fall | 98 | 90 | 90 | 100 | 100 | 98 | 100 | 100 | 98 | 100 | 100 | |
| Pigweed, Palmer | 90 | 100 | 75 | 100 | 100 | 80 | 100 | 90 | 90 | 100 | 95 | |
| Poinsettia, Wild | 20 | — | 55 | 60 | 20 | — | 30 | — | 20 | — | 75 | |
| Ragweed | 100 | 100 | 100 | 100 | 100 | 98 | 100 | 98 | 100 | 100 | 100 | |
| Ryegrass, Italian | 100 | 100 | 100 | 100 | 100 | 100 | 100 | 100 | 100 | 100 | 100 | |
| Sandbur | 70 | 70 | 75 | 90 | 75 | 80 | 75 | 90 | 85 | 85 | 90 | |
| Soybean | 15 | 70 | 50 | 0 | — | 0 | 0 | 0 | 0 | 0 | — | |
| Surinam Grass | 90 | 90 | 80 | 95 | 90 | 95 | 95 | 90 | 75 | 95 | 100 | |
| Velvetleaf | 90 | 98 | 100 | 95 | 98 | 100 | 90 | 95 | 95 | 100 | 100 | |
| Waterhemp | 100 | 100 | 100 | 90 | 100 | 75 | 100 | 85 | 100 | 100 | 100 | |

| 125 g ai/ha | Compounds | | | | | | | | | | | | |
|---|---|---|---|---|---|---|---|---|---|---|---|---|---|
| Preemergence | 1 | 2 | 20 | 21 | 25 | 27 | 28 | 29 | 34 | 37 | 41 | 47 | 57 | 59 |
| Arrowleaf Sida | 75 | 0 | 85 | 50 | 90 | 75 | 50 | 98 | 65 | 90 | 98 | 75 | 50 | 98 |
| Barnyardgrass | 0 | 25 | 10 | 90 | 60 | 80 | 65 | 65 | 35 | 0 | 40 | 50 | 75 | 60 |
| Beggarticks | 100 | 100 | 95 | 100 | 100 | 100 | 100 | 100 | 100 | 98 | 100 | 100 | 100 | 100 |
| Corn | 0 | 0 | 0 | 30 | 0 | 0 | 0 | 0 | 0 | 0 | 0 | 0 | 0 | 0 |
| Crabgrass, Brazil | 100 | 50 | 70 | 100 | 95 | 95 | 80 | 70 | 80 | 90 | 100 | 0 | 40 | 100 |
| Crabgrass, Large | 35 | 30 | 35 | 100 | 80 | 50 | 90 | 40 | 50 | 80 | 80 | 0 | 0 | 80 |
| Dayflower, VA | 15 | 25 | 0 | 80 | 15 | 30 | 65 | 10 | 70 | 40 | 70 | 0 | 30 | 80 |
| Field Bindweed | 95 | 35 | 85 | 98 | 60 | 70 | 90 | 95 | 40 | 85 | 75 | 90 | 98 | 95 |
| Foxtail, Giant | 95 | 98 | 75 | 100 | 98 | 100 | 100 | 95 | 40 | 80 | 70 | 40 | 95 | 98 |
| Foxtail, Green | 90 | 95 | 65 | 100 | 98 | 100 | 100 | 90 | 25 | 65 | 50 | 30 | 90 | 95 |
| Goosegrass | 35 | 25 | 50 | 95 | 80 | 80 | 75 | 50 | 10 | 75 | 50 | 0 | 5 | 98 |
| Horseweed | — | — | 100 | 100 | 100 | 100 | 100 | 100 | — | 100 | 100 | — | — | 100 |
| Johnsongrass | 30 | 35 | — | 60 | 80 | 75 | 80 | 65 | 0 | 100 | 0 | 0 | 30 | 80 |
| Kochia | 35 | 0 | 98 | 65 | 98 | 80 | 60 | 25 | 5 | 0 | 100 | 75 | 75 | 100 |
| Lambsquarters | 100 | 98 | 95 | 100 | 100 | 100 | 100 | 100 | 100 | 98 | 100 | 100 | 100 | 100 |
| Morningglory | 90 | 100 | 90 | 100 | 95 | 90 | 95 | 80 | 35 | 50 | 90 | 100 | 100 | 98 |
| Nightshade | 100 | 98 | — | — | 95 | 95 | 98 | 85 | 98 | 98 | 98 | 100 | 98 | — |
| Nutsedge, Yellow | 50 | 65 | 75 | 80 | 20 | 98 | 70 | 30 | 40 | 65 | 75 | 30 | 60 | 75 |
| Panicum, Fall | 95 | 98 | 65 | 100 | 100 | 100 | 98 | 98 | 90 | 100 | 95 | 80 | 100 | 100 |
| Pigweed, Palmer | 100 | 90 | 5 | 98 | 100 | 85 | 95 | 100 | 90 | 100 | 75 | 25 | 40 | 100 |
| Poinsettia, Wild | 30 | 30 | — | — | — | — | — | — | — | — | 40 | 0 | 25 | — |
| Ragweed | 100 | 98 | 70 | 100 | 98 | 100 | 95 | 70 | 100 | 95 | 90 | 98 | 100 | 100 |
| Ryegrass, Italian | 100 | 100 | 98 | 100 | 98 | 100 | 95 | 95 | 100 | 100 | 100 | 30 | 65 | 100 |
| Sandbur | 70 | 70 | 65 | 90 | 80 | 90 | 80 | 90 | 65 | 50 | 75 | 10 | 30 | 90 |
| Soybean | 40 | 15 | 20 | 35 | 0 | 0 | 0 | 70 | 15 | — | 20 | 0 | 0 | 30 |
| Surinam Grass | 80 | 90 | 85 | 100 | 90 | 100 | 100 | 95 | 95 | 75 | 75 | 35 | 85 | 100 |
| Velvetleaf | 90 | 80 | 80 | 90 | 98 | 95 | 70 | 100 | 100 | 70 | 95 | 75 | 95 | 95 |
| Waterhemp | 100 | 85 | 85 | 100 | 100 | 85 | 98 | 98 | 100 | 98 | 100 | 90 | 40 | 100 |

| 125 g ai/ha | Compounds | | | | | | | | | | | | |
|---|---|---|---|---|---|---|---|---|---|---|---|---|---|
| Preemergence | 66 | 69 | 72 | 75 | 79 | 80 | 81 | 82 | 83 | 84 | 85 | 87 | 88 | 105 |
| Arrowleaf Sida | 65 | 50 | 85 | 90 | 75 | 25 | 70 | 85 | 35 | 80 | 50 | 70 | 0 | 50 |
| Barnyardgrass | 15 | 15 | 50 | 35 | 40 | 20 | 35 | 30 | 35 | 10 | 30 | 10 | 30 | 35 |
| Beggarticks | 100 | 100 | 98 | 100 | 100 | 100 | 100 | 100 | 100 | 100 | 100 | 100 | 100 | 100 |
| Corn | 20 | 0 | 0 | 0 | 0 | 0 | 0 | 0 | 0 | 0 | 0 | 20 | 0 | 0 |
| Crabgrass, Brazil | 65 | 50 | 90 | 90 | 80 | 100 | 90 | 100 | 50 | 90 | 80 | 90 | 25 | 75 |
| Crabgrass, Large | 15 | 0 | 30 | 0 | 20 | 35 | 90 | 80 | 40 | 15 | 0 | 65 | 20 | 75 |
| Dayflower, VA | 20 | 70 | 50 | 60 | 65 | 10 | 35 | 5 | 25 | 35 | 30 | 10 | 10 | 10 |
| Field Bindweed | 40 | 95 | 65 | 100 | 100 | 100 | 75 | 100 | 35 | 100 | 20 | 95 | 65 | 70 |
| Foxtail, Giant | 90 | 50 | 70 | 35 | 85 | 85 | 98 | 50 | 100 | 85 | 95 | 70 | 100 | 75 |
| Foxtail, Green | 70 | 0 | 65 | 0 | 80 | 65 | 95 | 75 | 95 | 75 | 15 | 60 | 100 | 40 |
| Goosegrass | 10 | 30 | 60 | 0 | 60 | 20 | 70 | 70 | 5 | 30 | 5 | 60 | 5 | 10 |
| Horseweed | — | — | 100 | — | 100 | 100 | 100 | 100 | — | 100 | — | — | — | 100 |
| Johnsongrass | 0 | 0 | 35 | 10 | — | 80 | 65 | 35 | 0 | 0 | 0 | 70 | 0 | 20 |
| Kochia | 90 | 50 | 60 | 100 | 100 | 100 | 35 | 100 | 0 | 100 | 0 | 100 | 25 | 100 |
| Lambsquarters | 100 | — | 100 | 100 | 100 | 100 | 100 | 100 | 100 | 100 | 100 | 100 | 100 | 100 |
| Morningglory | 40 | 50 | 80 | 60 | 90 | 75 | 100 | 90 | 95 | 90 | 50 | 50 | 100 | 60 |
| Nightshade | 100 | 90 | 100 | 90 | 100 | 98 | 100 | 98 | 100 | 50 | 100 | 98 | 15 | 98 |

TABLE E-continued

| | | | | | | | | | | | | | | |
|---|---|---|---|---|---|---|---|---|---|---|---|---|---|---|
| Nutsedge, Yellow | 50 | 30 | 30 | 70 | 65 | 35 | 80 | 40 | 70 | 60 | 35 | 65 | 50 | 40 |
| Panicum, Fall | 98 | 75 | 90 | 80 | 80 | 98 | 100 | 98 | 100 | 95 | 98 | 100 | 100 | 98 |
| Pigweed, Palmer | 100 | 60 | 95 | 50 | 70 | 70 | 75 | 100 | 50 | 90 | 50 | 75 | 70 | 90 |
| Poinsettia, Wild | — | 20 | 10 | — | 60 | 40 | 30 | 0 | — | 10 | — | 15 | — | 10 |
| Ragweed | 100 | 95 | 90 | 80 | 100 | 100 | 100 | 100 | 95 | 100 | 90 | 98 | 100 | 98 |
| Ryegrass, Italian | 100 | 100 | 100 | 100 | 100 | 98 | 90 | 100 | 98 | 98 | 95 | 98 | 100 | 100 |
| Sandbur | 70 | 50 | 60 | 40 | 80 | 75 | 70 | 60 | 75 | 60 | 80 | 75 | 80 | 75 |
| Soybean | 0 | 10 | 0 | 40 | 40 | 0 | 0 | 0 | 0 | 0 | 0 | 0 | 0 | 75 |
| Surinam Grass | 50 | 20 | 75 | 60 | 60 | 75 | 95 | 85 | 85 | 90 | 70 | 80 | 90 | 70 |
| Velvetleaf | 80 | 60 | 80 | 100 | 95 | 90 | 90 | 95 | 70 | 70 | 70 | 90 | 70 | 95 |
| Waterhemp | 90 | 100 | 100 | 100 | 100 | 100 | 90 | 100 | 75 | 90 | 70 | 90 | 75 | 100 |

| 125 g ai/ha | Compounds | |
|---|---|---|
| Preemergence | 109 | 153 |
| Arrowleaf Sida | 35 | 60 |
| Barnyardgrass | 25 | 70 |
| Beggarticks | 100 | 100 |
| Corn | 0 | 10 |
| Crabgrass, Brazil | 70 | 100 |
| Crabgrass, Large | 35 | 75 |
| Dayflower, VA | 25 | 90 |
| Field Bindweed | 80 | 100 |
| Foxtail, Giant | 80 | 95 |
| Foxtail, Green | 60 | 90 |
| Goosegrass | 50 | 60 |
| Horseweed | 100 | 100 |
| Johnsongrass | 40 | — |
| Kochia | 100 | 50 |
| Lambsquarters | 98 | 100 |
| Morningglory | 65 | 90 |
| Nightshade | 98 | 95 |
| Nutsedge, Yellow | 40 | 80 |
| Panicum, Fall | 95 | 100 |
| Pigweed, Palmer | 85 | 60 |
| Poinsettia, Wild | 30 | 60 |
| Ragweed | 100 | 95 |
| Ryegrass, Italian | 98 | 100 |
| Sandbur | 75 | 85 |
| Soybean | 0 | 30 |
| Surinam Grass | 40 | 90 |
| Velvetleaf | 65 | 90 |
| Waterhemp | 98 | 85 |

| 62 g ai/ha | Compounds | | | | | | | | | | | | | |
|---|---|---|---|---|---|---|---|---|---|---|---|---|---|---|
| Preemergence | 1 | 2 | 20 | 21 | 25 | 27 | 28 | 29 | 34 | 37 | 41 | 47 | 57 | 59 |
| Arrowleaf Sida | 65 | 0 | 70 | 0 | 80 | 65 | 0 | 90 | 20 | 85 | 50 | 0 | 0 | 95 |
| Barnyardgrass | 0 | 0 | 0 | 70 | 60 | 50 | 20 | 25 | 0 | 0 | 25 | 0 | 0 | 25 |
| Beggarticks | 100 | 100 | 85 | 100 | 100 | 100 | 100 | 98 | 100 | 98 | 98 | 100 | 100 | 100 |
| Corn | 0 | 0 | 0 | 0 | 0 | 0 | 0 | 0 | 0 | 0 | 0 | 0 | 0 | 0 |
| Crabgrass, Brazil | 80 | 60 | 60 | 98 | 90 | 70 | 70 | 75 | 10 | 85 | 65 | 0 | 0 | 90 |
| Crabgrass, Large | 20 | 0 | 35 | 85 | 15 | 50 | 35 | 25 | 0 | 75 | 70 | 0 | 0 | 50 |
| Dayflower, VA | 20 | 20 | 0 | 60 | 5 | 10 | 10 | 0 | 35 | 5 | 40 | 0 | 25 | 40 |
| Field Bindweed | 80 | 15 | 65 | 95 | 98 | 40 | 0 | 50 | 90 | 70 | 50 | 95 | 75 |
| Foxtail, Giant | 35 | 95 | 20 | 98 | 95 | 98 | 100 | 80 | 40 | 70 | 65 | 0 | 35 | 95 |
| Foxtail, Green | 70 | 95 | 40 | 100 | 98 | 100 | 98 | 75 | 0 | 60 | 25 | 20 | 20 | 90 |
| Goosegrass | 5 | 5 | 10 | 95 | 65 | 75 | 60 | 20 | 5 | 35 | 0 | 0 | 0 | 95 |
| Horseweed | — | — | 100 | 100 | 100 | 100 | 100 | 100 | — | 100 | 100 | — | — | 100 |
| Johnsongrass | 0 | 20 | — | 20 | 60 | 75 | 80 | 70 | 0 | 0 | 0 | 0 | 30 | 25 |
| Kochia | 5 | 0 | 90 | 0 | 80 | 25 | 0 | 0 | 5 | 0 | 90 | 85 | 65 | 90 |
| Lambsquarters | 98 | 98 | 95 | 100 | 100 | 100 | 100 | 100 | 100 | 100 | 100 | 100 | 100 | 100 |
| Morningglory | 98 | 90 | 75 | 98 | 70 | 85 | 90 | 65 | 25 | 40 | 50 | 75 | 40 | 95 |
| Nightshade | 95 | 98 | — | — | 80 | 100 | 98 | 70 | 25 | 80 | 80 | 98 | 98 | — |
| Nutsedge, Yellow | 15 | 35 | 50 | 75 | 20 | 15 | 20 | 0 | 80 | 0 | 65 | — | 30 | 35 |
| Panicum, Fall | 90 | 95 | 35 | 100 | 100 | 100 | 95 | 95 | 80 | 100 | 90 | 50 | 98 | 98 |
| Pigweed, Palmer | 100 | 50 | 0 | 70 | 90 | 60 | 65 | 70 | 0 | 90 | 85 | 0 | 35 | 98 |
| Poinsettia, Wild | 30 | 30 | — | — | — | — | — | — | — | — | 40 | 0 | 20 | — |
| Ragweed | 75 | 75 | 65 | 98 | 95 | 95 | 90 | 85 | 75 | 90 | 70 | 95 | 100 | 95 |
| Ryegrass, Italian | 100 | 98 | 95 | 100 | 95 | 95 | 80 | 75 | 100 | 95 | 100 | 30 | 35 | 100 |
| Sandbur | 20 | 15 | 0 | 80 | 65 | 40 | 65 | 75 | 40 | 35 | 70 | 0 | 0 | 70 |
| Soybean | 15 | 0 | 0 | 35 | — | 0 | 0 | 50 | 35 | 0 | 35 | 0 | 0 | 30 |
| Surinam Grass | 50 | 75 | 65 | 100 | 80 | 95 | 98 | 95 | 75 | 75 | 75 | 0 | 70 | 90 |
| Velvetleaf | 75 | 60 | 65 | 90 | 100 | 80 | 35 | 95 | 90 | 50 | 85 | — | 65 | 95 |
| Waterhemp | 100 | 80 | 65 | 95 | 100 | 90 | 80 | 90 | 100 | 75 | 98 | 90 | 75 | 100 |

TABLE E-continued

| 62 g ai/ha | Compounds | | | | | | | | | | | | | |
|---|---|---|---|---|---|---|---|---|---|---|---|---|---|---|
| Preemergence | 66 | 69 | 72 | 75 | 79 | 80 | 81 | 82 | 83 | 84 | 85 | 87 | 88 | 105 |
| Arrowleaf Sida | 40 | 60 | 35 | 75 | 80 | 35 | 60 | 70 | 25 | 0 | 0 | 60 | 0 | 40 |
| Barnyardgrass | 20 | 10 | 30 | 20 | 30 | 20 | 25 | 15 | 30 | 0 | 0 | 0 | 0 | 20 |
| Beggarticks | 95 | 95 | 80 | 80 | 100 | 100 | 100 | 100 | 100 | 100 | 100 | 100 | 100 | 100 |
| Corn | 0 | 0 | 0 | 0 | 0 | 0 | 0 | 0 | 0 | 0 | 0 | 0 | 0 | 0 |
| Crabgrass, Brazil | 25 | 20 | 60 | 20 | 30 | 90 | 95 | 100 | 10 | 85 | 50 | 80 | 40 | 35 |
| Crabgrass, Large | 0 | 0 | 0 | 0 | 0 | 35 | 75 | 70 | 5 | 10 | 0 | 0 | 5 | 50 |
| Dayflower, VA | 0 | 60 | 15 | 10 | 70 | 0 | 15 | 5 | 10 | 20 | 0 | 0 | 5 | 0 |
| Field Bindweed | 50 | 40 | 0 | 5 | 90 | 70 | 0 | 50 | 5 | 90 | 5 | 98 | 5 | 50 |
| Foxtail, Giant | 40 | 50 | 65 | 5 | 70 | 80 | 98 | 65 | 98 | 35 | 65 | 65 | 98 | 35 |
| Foxtail, Green | 35 | 0 | 35 | 0 | 70 | 50 | 70 | 70 | 40 | 50 | 25 | 20 | 75 | 30 |
| Goosegrass | 10 | 10 | 40 | 0 | 60 | 30 | 40 | 25 | 0 | 30 | 5 | 0 | 0 | 0 |
| Horseweed | — | — | 100 | — | 100 | 100 | 100 | 100 | — | 100 | — | — | — | 100 |
| Johnsongrass | 0 | 0 | 0 | 0 | — | 80 | 90 | — | 0 | 0 | 0 | 65 | 0 | 20 |
| Kochia | 60 | — | 35 | 100 | 70 | 100 | 20 | 90 | 0 | 75 | 0 | 100 | 0 | 35 |
| Lambsquarters | 100 | — | 80 | 100 | 100 | 98 | 100 | 75 | 98 | 100 | 100 | 100 | 100 | 100 |
| Morningglory | 30 | 30 | 30 | 30 | 85 | 70 | 85 | 80 | 20 | 70 | 30 | 35 | 30 | 70 |
| Nightshade | 15 | 80 | 80 | 0 | 100 | 100 | 90 | 98 | 50 | 100 | 95 | 90 | 5 | 98 |
| Nutsedge, Yellow | 65 | 0 | 20 | 10 | 60 | 40 | 30 | 10 | 65 | 0 | 35 | 60 | 50 | 10 |
| Panicum, Fall | 95 | 20 | 80 | 50 | 70 | 95 | 100 | 95 | 95 | 90 | 85 | 90 | 98 | 90 |
| Pigweed, Palmer | 65 | 60 | 75 | 85 | 70 | 70 | 75 | 90 | 20 | 100 | 30 | 65 | 50 | 98 |
| Poinsettia, Wild | — | 25 | 15 | — | 60 | 0 | 5 | 0 | — | 0 | — | 15 | — | 10 |
| Ragweed | 90 | 85 | 90 | 65 | 100 | 100 | 100 | 80 | 75 | 98 | 80 | 95 | 85 | 95 |
| Ryegrass, Italian | 90 | 90 | 90 | 100 | 80 | 98 | 95 | 95 | 95 | 95 | 80 | 95 | 98 | 95 |
| Sandbur | 10 | 40 | 35 | 10 | 70 | 70 | 40 | 35 | 70 | 30 | 50 | 65 | 65 | 70 |
| Soybean | 0 | 15 | 0 | 35 | 50 | 0 | 0 | 0 | 0 | 0 | 0 | 0 | 0 | 0 |
| Surinam Grass | 5 | 5 | 40 | 35 | 50 | 20 | 90 | 65 | 60 | 65 | 70 | 15 | 75 | 10 |
| Velvetleaf | 20 | 20 | 40 | 85 | 80 | 70 | 70 | 75 | 35 | 70 | 30 | 60 | 65 | 70 |
| Waterhemp | 80 | 100 | 100 | 60 | 100 | 100 | 90 | 90 | 65 | 90 | 80 | 90 | 90 | 90 |

| 62 g ai/ha | Compounds | |
|---|---|---|
| Preemergence | 109 | 153 |
| Arrowleaf Sida | 30 | 70 |
| Barnyardgrass | 10 | 50 |
| Beggarticks | 100 | 100 |
| Corn | 0 | 0 |
| Crabgrass, Brazil | 40 | 70 |
| Crabgrass, Large | 40 | 70 |
| Dayflower, VA | 25 | 85 |
| Field Bindweed | 40 | 100 |
| Foxtail, Giant | 40 | 95 |
| Foxtail, Green | 40 | 75 |
| Goosegrass | 25 | 40 |
| Horseweed | 100 | 100 |
| Johnsongrass | 0 | 0 |
| Kochia | 85 | 30 |
| Lambsquarters | 100 | 100 |
| Morningglory | 20 | 90 |
| Nightshade | 65 | 85 |
| Nutsedge, Yellow | 40 | 70 |
| Panicum, Fall | 90 | 100 |
| Pigweed, Palmer | 100 | 60 |
| Poinsettia, Wild | 25 | 50 |
| Ragweed | 100 | 100 |
| Ryegrass, Italian | 98 | 100 |
| Sandbur | 65 | 85 |
| Soybean | — | 50 |
| Surinam Grass | 60 | 80 |
| Velvetleaf | 25 | 90 |
| Waterhemp | 70 | 70 |

| 31 g ai/ha | Compounds | | | | | | | | | | | | | |
|---|---|---|---|---|---|---|---|---|---|---|---|---|---|---|
| Preemergence | 1 | 2 | 20 | 21 | 25 | 27 | 28 | 29 | 34 | 37 | 41 | 47 | 57 | 59 |
| Arrowleaf Sida | 0 | 0 | 0 | 0 | 40 | 40 | — | 70 | 0 | 70 | 20 | 0 | 0 | 80 |
| Barnyardgrass | 0 | 0 | 0 | 40 | 20 | 15 | 20 | 0 | 0 | 0 | 10 | 0 | 0 | 0 |
| Beggarticks | 100 | 100 | 20 | 100 | 100 | 90 | 100 | 80 | 90 | 80 | 65 | 100 | 100 | 100 |
| Corn | 0 | 0 | 0 | 0 | 0 | 0 | 0 | 0 | 0 | 0 | 0 | 0 | 0 | 0 |
| Crabgrass, Brazil | 10 | 35 | 40 | 90 | 75 | 70 | 70 | 30 | 0 | 70 | 80 | 0 | 0 | 60 |
| Crabgrass, Large | 0 | 0 | 30 | 65 | — | 35 | — | 0 | 0 | 50 | 65 | 0 | 0 | 0 |
| Dayflower, VA | 0 | 15 | 0 | 80 | 0 | 0 | 5 | 0 | 35 | 0 | 15 | 0 | 0 | 10 |
| Field Bindweed | 20 | 0 | 35 | 35 | 80 | 0 | 0 | 80 | 5 | 75 | 30 | 50 | 70 | 65 |
| Foxtail, Giant | 50 | 75 | 5 | 95 | 80 | 95 | 85 | 70 | 5 | 65 | 30 | 0 | 5 | 85 |
| Foxtail, Green | 15 | 35 | 0 | 95 | 65 | 75 | 65 | 65 | 0 | 0 | 20 | 0 | 0 | 65 |

TABLE E-continued

| | | | | | | | | | | | | | | |
|---|---|---|---|---|---|---|---|---|---|---|---|---|---|---|
| Goosegrass | 15 | 0 | 20 | 90 | 20 | 35 | 35 | 0 | 5 | 35 | 0 | 0 | 10 | 90 |
| Horseweed | — | — | 100 | 100 | 100 | 100 | 100 | 100 | — | 100 | 100 | — | — | 100 |
| Johnsongrass | 0 | 35 | 0 | — | 75 | 70 | 70 | 70 | 0 | 0 | 0 | 0 | 0 | 0 |
| Kochia | 0 | 0 | 0 | 0 | 20 | 0 | 0 | 0 | 0 | 0 | 90 | 0 | 20 | 80 |
| Lambsquarters | 65 | 100 | 70 | 100 | 98 | 100 | 100 | 100 | 10 | 100 | 35 | 100 | 100 | 100 |
| Morningglory | 60 | 75 | 20 | 90 | 65 | 85 | 50 | 35 | 0 | 15 | 30 | 25 | 85 | 75 |
| Nightshade | 90 | 75 | — | — | 90 | 90 | 80 | 5 | 0 | 90 | 25 | 80 | 90 | — |
| Nutsedge, Yellow | 10 | 0 | 0 | 0 | 0 | 10 | 20 | 0 | 0 | 0 | 25 | 0 | 0 | 50 |
| Panicum, Fall | 75 | 85 | 0 | 100 | 95 | 100 | 90 | 85 | 70 | 90 | 80 | 50 | 95 | 95 |
| Pigweed, Palmer | 90 | 20 | 0 | 65 | 65 | — | 0 | 90 | 0 | 0 | 15 | 0 | 35 | 95 |
| Poinsettia, Wild | 30 | 25 | — | — | — | — | — | — | — | — | 15 | 0 | 0 | — |
| Ragweed | 70 | 35 | 30 | 95 | 75 | 95 | 95 | 90 | 70 | 50 | 5 | 80 | 90 | 100 |
| Ryegrass, Italian | 95 | 95 | 90 | 100 | 95 | 80 | 70 | 65 | 90 | 85 | 98 | 5 | 10 | 100 |
| Sandbur | 10 | 15 | 0 | 80 | 35 | 30 | 15 | 75 | 0 | 20 | 50 | 0 | 0 | 70 |
| Soybean | 0 | 0 | 0 | 35 | 0 | 0 | 0 | 70 | 0 | 0 | 0 | 0 | 0 | 35 |
| Surinam Grass | 25 | 35 | 10 | 95 | 65 | 85 | 85 | 75 | 5 | 50 | 10 | 0 | 5 | 85 |
| Velvetleaf | 75 | 30 | 0 | 80 | 60 | 50 | 0 | 70 | 20 | 30 | 20 | 0 | 30 | 90 |
| Waterhemp | 90 | 65 | 0 | 95 | 100 | 95 | 65 | 80 | 100 | 0 | 75 | 50 | 80 | 75 |

| 31 g ai/ha | Compounds | | | | | | | | | | | | | |
|---|---|---|---|---|---|---|---|---|---|---|---|---|---|---|
| Preemergence | 66 | 69 | 72 | 75 | 79 | 80 | 81 | 82 | 83 | 84 | 85 | 87 | 88 | 105 |
| Arrowleaf Sida | 0 | 20 | 20 | 50 | 75 | 0 | 40 | 20 | 15 | 0 | 0 | 0 | 0 | 0 |
| Barnyardgrass | 15 | 10 | 0 | 20 | 30 | 0 | 0 | 0 | 0 | 0 | 0 | 0 | 0 | — |
| Beggarticks | 70 | 90 | 70 | 35 | 100 | 85 | 80 | 100 | 100 | 90 | 90 | 90 | 85 | 80 |
| Corn | 0 | 0 | 0 | 0 | 0 | 0 | 0 | 0 | 0 | 0 | 0 | 0 | 0 | 0 |
| Crabgrass, Brazil | 25 | 0 | 50 | 0 | — | 75 | 65 | 75 | 0 | 80 | 10 | 60 | 15 | 0 |
| Crabgrass, Large | 0 | 0 | 0 | 0 | 0 | 0 | 50 | — | 0 | 0 | 0 | 0 | 0 | 0 |
| Dayflower, VA | 0 | 50 | 0 | 10 | 50 | 0 | 10 | 0 | 0 | 10 | 0 | 0 | 0 | 0 |
| Field Bindweed | 5 | 0 | 0 | 0 | 60 | 25 | 0 | 65 | 0 | 60 | — | 40 | 0 | 20 |
| Foxtail, Giant | 5 | 40 | 35 | 0 | 60 | 50 | 75 | 30 | 95 | 5 | 15 | 25 | 95 | 0 |
| Foxtail, Green | 0 | 0 | 30 | 0 | 55 | 15 | 20 | 20 | 0 | 10 | 0 | 20 | 50 | 0 |
| Goosegrass | 5 | 0 | 20 | 0 | 50 | 0 | 20 | 20 | 0 | 20 | 5 | 0 | 0 | 0 |
| Horseweed | — | — | 0 | — | 100 | 100 | 90 | 90 | — | 100 | — | — | — | 0 |
| Johnsongrass | 0 | 0 | 0 | 0 | 70 | 0 | 70 | 0 | 0 | 0 | 0 | — | 0 | 0 |
| Kochia | 0 | 0 | 25 | 98 | 50 | 90 | 0 | 20 | 0 | 0 | 0 | 65 | 0 | 0 |
| Lambsquarters | 90 | 10 | 90 | 100 | 100 | 100 | 98 | 98 | 100 | 15 | 70 | 100 | 100 | 0 |
| Morningglory | 0 | 20 | 20 | 0 | 60 | 65 | 60 | 70 | 25 | 20 | 25 | 20 | 25 | 20 |
| Nightshade | 0 | 70 | 0 | 0 | 80 | 75 | 80 | 90 | 35 | 80 | 95 | 50 | 0 | 50 |
| Nutsedge, Yellow | 5 | 0 | — | 0 | 50 | 10 | 35 | 0 | 65 | 0 | — | 0 | 10 | 0 |
| Panicum, Fall | 60 | 20 | 75 | 10 | 80 | 90 | 98 | 90 | 90 | 85 | 95 | 95 | 90 | 65 |
| Pigweed, Palmer | 0 | 40 | 35 | 30 | 75 | 35 | 35 | 90 | 0 | 75 | 25 | 0 | 65 | 0 |
| Poinsettia, Wild | — | 0 | 0 | — | 50 | 0 | 0 | 0 | — | 0 | — | 0 | — | 10 |
| Ragweed | 65 | 40 | 0 | 35 | 100 | 70 | 90 | 85 | 70 | 90 | 60 | 98 | 20 | 65 |
| Ryegrass, Italian | 65 | 80 | 90 | 100 | 75 | 70 | 75 | 75 | 80 | 80 | 80 | 75 | 95 | 90 |
| Sandbur | 0 | 50 | 0 | 0 | 60 | 65 | 10 | 0 | 20 | 0 | 0 | 25 | 10 | 15 |
| Soybean | 0 | 0 | 0 | 0 | 40 | 0 | 0 | 0 | 0 | 0 | 0 | 0 | 0 | 0 |
| Surinam Grass | 20 | 0 | 5 | 5 | 40 | 10 | 70 | 35 | 65 | 0 | 60 | 10 | 25 | 0 |
| Velvetleaf | 0 | 30 | 50 | 35 | 70 | 20 | 10 | 0 | 0 | 25 | 0 | 0 | 15 | 50 |
| Waterhemp | 65 | 50 | 90 | 50 | 75 | 70 | 60 | 85 | 65 | 85 | 35 | 75 | 60 | 80 |

| 31 g ai/ha | Compounds | |
|---|---|---|
| Preemergence | 109 | 153 |
| Arrowleaf Sida | 35 | 50 |
| Barnyardgrass | 0 | 20 |
| Beggarticks | 75 | 100 |
| Corn | 0 | 0 |
| Crabgrass, Brazil | 60 | 90 |
| Crabgrass, Large | 0 | 70 |
| Dayflower, VA | 25 | 80 |
| Field Bindweed | 0 | 90 |
| Foxtail, Giant | 35 | 75 |
| Foxtail, Green | 0 | 50 |
| Goosegrass | 20 | 40 |
| Horseweed | 100 | 90 |
| Johnsongrass | 0 | 0 |
| Kochia | 10 | 40 |
| Lambsquarters | 95 | 100 |
| Morningglory | 0 | 85 |
| Nightshade | 65 | 70 |
| Nutsedge, Yellow | 0 | 50 |
| Panicum, Fall | 80 | 100 |
| Pigweed, Palmer | 20 | 50 |
| Poinsettia, Wild | 10 | 40 |
| Ragweed | 5 | 100 |
| Ryegrass, Italian | 75 | 100 |
| Sandbur | 40 | 80 |

TABLE E-continued

| | | |
|---|---|---|
| Soybean | 0 | 30 |
| Surinam Grass | 30 | 50 |
| Velvetleaf | 0 | 85 |
| Waterhemp | 0 | 60 |

| 16 g ai/ha | Compounds | | | | | |
|---|---|---|---|---|---|---|
| Preemergence | 1 | 2 | 66 | 80 | 105 | 109 |
| Arrowleaf Sida | 0 | 0 | 0 | 0 | 0 | 40 |
| Barnyardgrass | 0 | 0 | 0 | 0 | 20 | 0 |
| Beggarticks | 100 | 90 | 65 | 100 | 90 | 20 |
| Corn | 0 | 0 | 0 | 0 | 0 | 0 |
| Crabgrass, Brazil | 0 | 0 | 0 | 65 | — | 70 |
| Crabgrass, Large | 0 | 0 | 0 | 0 | 0 | 0 |
| Dayflower, VA | 0 | 0 | 0 | 0 | 0 | 0 |
| Field Bindweed | 5 | 0 | 0 | 20 | 20 | 0 |
| Foxtail, Giant | 0 | 40 | 0 | 0 | 0 | 0 |
| Foxtail, Green | 0 | 0 | 0 | 0 | 0 | 0 |
| Goosegrass | 0 | 0 | 5 | 0 | 0 | 0 |
| Horseweed | — | — | — | 100 | 0 | 0 |
| Johnsongrass | 0 | 0 | 0 | — | 0 | 0 |
| Kochia | 0 | 0 | 0 | 25 | 0 | 0 |
| Lambsquarters | 65 | 50 | 5 | 65 | 0 | 0 |
| Morningglory | 20 | 0 | 0 | 0 | 40 | 0 |
| Nightshade | 80 | 35 | 0 | 75 | 0 | 25 |
| Nutsedge, Yellow | 0 | 0 | 0 | 5 | 0 | 0 |
| Panicum, Fall | 65 | 75 | 10 | 80 | 25 | 75 |
| Pigweed, Palmer | 20 | 0 | 0 | 20 | 0 | 0 |
| Poinsettia, Wild | 20 | 0 | — | 0 | 0 | 10 |
| Ragweed | 35 | 20 | 25 | 70 | 50 | 0 |
| Ryegrass, Italian | 70 | 50 | 40 | 50 | 75 | 60 |
| Sandbur | 0 | 0 | 0 | 0 | 0 | 0 |
| Soybean | 0 | 0 | 0 | 0 | 0 | 0 |
| Surinam Grass | 0 | 5 | 5 | 0 | 0 | 0 |
| Velvetleaf | 35 | 0 | 0 | 0 | 0 | 0 |
| Waterhemp | 35 | 65 | 0 | 0 | 70 | 0 |

Test F

This test evaluated the effect of mixtures of Compound 1 or Compound 2 with various commercial herbicides on multiple plant species. Seeds of multiple plant species selected were planted into Sandy Loam soil and treated either Post-emergence or Pre-emergence with test chemicals formulated in a non-phytotoxic solvent mixture. Plants were grown in a greenhouse using supplemental lighting to maintain a photoperiod of approximately 16 h; daytime and nighttime temperatures were approximately 24-30 and 19-21° C., respectively. Balanced fertilizer was applied through the watering system. Treated plants and controls were maintained in a greenhouse for 20 d, after which time all species were compared to controls and visually evaluated. Plant response ratings summarized in Tables F1 through F4 and are based on a scale of 0 to 100 where 0 is no effect and 100 is complete control. A dash (-) response means no test result. Application rates (i.e. "Rate") are expressed in grams of active ingredient per hectare (g a.i./ha). In the following tables KCHSC is kochia (*Kochia scoparia*), LOLMU in Italian Ryegrass (*Lolium multiflorum*), AMBEL is common ragweed (*Ambrosia elatior*), ECHCG is barnyardgrass (*Echinochloa crus-galli*), SETVI is giant foxtail (*Setaria faberii*), AMARE is redroot pigweed (*Amaranthus retroflexus*), ALOMY is blackgrass (*Alopecurus myosuroides*) and GALAP is galium (*Galium aparine*). "Obsd." is observed effect. "Exp." is expected effect calculated from Colby's Equation.

Colby's Equation was used to determine the herbicidal effects expected from the mixtures. Colby's Equation (Colby, S. R. "Calculating Synergistic and Antagonistic Responses of Herbicide Combinations," Weeds, 15(1), pp 20-22 (1967)) calculates the expected additive effect of herbicidal mixtures, and for two active ingredients is of the form:

$$P_{a+b} = P_a + P_b - (P_a P_b/100)$$

wherein $P_{a+b}$ is the percentage effect of the mixture expected from additive contribution of the individual components:

$P_a$ is the observed percentage effect of the first active ingredient at the same use rate as in the mixture, and $P_b$ is the observed percentage effect of the second active ingredient at the same use rate as in the mixture.

The results and additive effects expected from Colby's Equation are listed in Tables F1 through F4.

TABLE F1

Observed and Expected Results from Compound 1 Alone and in Combination with Mesotrione when applied Post-emergence.

| Treatment | Rate | KCHSC Obsd. | KCHSC Exp. | LOLMU Obsd. | LOLMU Exp. | AMBEL Obsd. | AMBEL Exp. | ECHCG Obsd. | ECHCG Exp. |
|---|---|---|---|---|---|---|---|---|---|
| 1 | 16 | 60.0 | | 65.0 | | 95.0 | | 0.0 | |
| 1 | 62 | 100.0 | | 100.0 | | 100.0 | | 0.0 | |
| mesotrione | 4 | 0.0 | | 0.0 | | 0.0 | | 0.0 | |
| mesotrione | 16 | 90.0 | | 0.0 | | 75.0 | | 20.0 | |
| 1 + mesotrione | 16 + 4 | 100.0 | 60.0 | 65.0 | 65.0 | 75.0 | 95.0 | 20.0 | 0.0 |
| 1 + mesotrione | 16 + 16 | 100.0 | 96.0 | 95.0 | 65.0 | 100.0 | 98.8 | 75.0 | 20.0 |
| 1 + mesotrione | 62 + 4 | 100.0 | 100.0 | 100.0 | 100.0 | 100.0 | 100.0 | 60.0 | 0.0 |
| 1 + mesotrione | 62 + 16 | 100.0 | 100.0 | 100.0 | 100.0 | 100.0 | 100.0 | 100.0 | 20.0 |

| Treatment | Rate | SETVI Obsd. | SETVI Exp. | AMARE Obsd. | AMARE Exp. | ALOMY Obsd. | ALOMY Exp. | GALAP Obsd. | GALAP Exp. |
|---|---|---|---|---|---|---|---|---|---|
| 1 | 16 | 0.0 | | 30.0 | | 0.0 | | 65.0 | |
| 1 | 62 | 40.0 | | 100.0 | | 35.0 | | 100.0 | |
| mesotrione | 4 | 0.0 | | 0.0 | | 0.0 | | 0.0 | |
| mesotrione | 16 | 0.0 | | 30.0 | | 0.0 | | 35.0 | |
| 1 + mesotrione | 16 + 4 | 0.0 | 0.0 | 100.0 | 30.0 | 0.0 | 0.0 | 100.0 | 65.0 |
| 1 + mesotrione | 16 + 16 | 20.0 | 0.0 | 100.0 | 51.0 | 50.0 | 0.0 | 100.0 | 77.3 |
| 1 + mesotrione | 62 + 4 | 70.0 | 40.0 | 100.0 | 100.0 | 65.0 | 35.0 | 100.0 | 100.0 |
| 1 + mesotrione | 62 + 16 | 95.0 | 40.0 | 100.0 | 100.0 | 75.0 | 35.0 | 100.0 | 100.0 |

As can be seen from the results listed in Table F1, most of the observed results for weed species were greater/equal than expected, thereby showing highly synergistic effect of Compound 1 and mesotrione on all above weed species in Post emergence herbicidal application.

TABLE F2

Observed and Expected Results from Compound 1 Alone and in Combination with Mesotrione when applied Pre-emergence.

| Treatment | Rate | KCHSC Obsd. | KCHSC Exp. | LOLMU Obsd. | LOLMU Exp. | AMBEL Obsd. | AMBEL Exp. |
|---|---|---|---|---|---|---|---|
| 1 | 16 | 0 | | 65 | | 65 | |
| 1 | 62 | 25 | | 100 | | 90 | |
| mesotrione | 4 | 0 | | 0 | | 0 | |
| mesotrione | 16 | 50 | | 0 | | 30 | |
| 1 + mesotrione | 16 + 4 | 50 | 0 | 65 | 65 | 85 | 65 |
| 1 + mesotrione | 16 + 6 | 100 | 25 | 100 | 100 | 100 | 90 |
| 1 + mesotrione | 62 + 4 | 50 | 50 | 80 | 65 | 100 | 76 |
| 1 + mesotrione | 62 + 16 | 100 | 63 | 100 | 100 | 100 | 93 |

TABLE F2-continued

Observed and Expected Results from Compound 1 Alone and in Combination with Mesotrione when applied Pre-emergence.

| Treatment | Rate | ECHCG Obsd. | ECHCG Exp. | SETVI Obsd. | SETVI Exp. | AMARE Obsd. | AMARE Exp. |
|---|---|---|---|---|---|---|---|
| 1 | 16 | 0 | | 0 | | 20 | |
| 1 | 62 | 20 | | 60 | | 90 | |
| mesotrione | 4 | 0 | | 0 | | 0 | |
| mesotrione | 16 | 0 | | 0 | | 20 | |
| 1 + mesotrione | 16 + 4 | 0 | 0 | 0 | 0 | 98 | 20 |
| 1 + mesotrione | 16 + 16 | 10 | 20 | 50 | 60 | 100 | 90 |
| 1 + mesotrione | 62 + 4 | 20 | 0 | 0 | 0 | 100 | 36 |
| 1 + mesotrione | 62 + 16 | 45 | 20 | 90 | 60 | 100 | 92 |

As can be seen from the results listed in Table F2, most of the observed results for weed species were greater/equal than expected, thereby showing highly synergistic effect of Compound 1 and mesotrione on all above weed species in Pre-emergence herbicidal application.

TABLE F3

Observed and Expected Results from Compoune 2 Alone and in Combination with Atrazine when applied Post-emergence

| Treatment | Rate | KCHSC Obsd. | KCHSC Exp. | LOLMU Obsd. | LOLMU Exp. | AMBEL Obsd. | AMBEL Exp. | ECHCG Obsd. | ECHCG Exp. |
|---|---|---|---|---|---|---|---|---|---|
| 2 | 16 | 16 | | 50 | | 75 | | 40 | 5 |
| 2 | 62 | 62 | | 75 | | 95 | | 80 | 20 |
| atrazine | 62 | 62 | | 100 | | 15 | | 10 | 20 |
| 2 + atrazine | 16 + 62 | 100 | 100 | 100 | 100 | 79 | 75 | 46 | 50 |
| 2 + atrazine | 62 + 62 | 100 | 100 | 100 | 100 | 96 | 100 | 82 | 100 |

| Treatment | Rate | SETVT Obsd. | SETVT Exp. | AMARE Obsd. | AMARE Exp. | ALOMY Obsd. | ALOMY Exp. | GALAP Obsd. | GALAP Exp. |
|---|---|---|---|---|---|---|---|---|---|
| 2 | 16 | 15 | | 25 | | 20 | | 100 | |
| 2 | 62 | 80 | | 80 | | 60 | | 100 | |

TABLE F3-continued

Observed and Expected Results from Compoune 2 Alone and in
Combination with Atrazine when applied Post-emergence

| atrazine | 62 | | 5 | | 75 | | 60 | | 50 |
|---|---|---|---|---|---|---|---|---|---|
| 2 + atrazine | 16 + 62 | 24 | 85 | 19 | 100 | 81 | 100 | 68 | 100 |
| 2 + atrazine | 62 + 62 | 36 | 95 | 81 | 100 | 95 | 100 | 84 | 100 |

As can be seen from the results listed in Table F3, most of the observed results for weed species were greater/equal than expected, thereby showing highly synergistic effect of Compound 2 and atrazine on all above weed species in Post emergence herbicidal application.

TABLE F4

Observed and Expected Results from Compound 2 Alone and in
Combination with Atrazine when applied Pre-emergence

| | | KCHSC | | LOLMU | | AMBEL | |
|---|---|---|---|---|---|---|---|
| Treatment | Rate | Obsd. | Exp. | Obsd. | Exp. | Obsd. | Exp. |
| 2 | 16 | 16 | 0 | | 0 | | 30 |
| 2 | 62 | 62 | 0 | | 50 | | 95 |
| atrazine | 62 | 62 | 100 | | 100 | | 10 |
| 2 + atrazine | 16 + 62 | 100 | 100 | 100 | 65 | 100 | 100 |
| 2 + atrazine | 62 + 62 | 100 | 100 | 100 | 100 | 100 | 100 |

| | | ECHCG | | SETVI | | AMARE | |
|---|---|---|---|---|---|---|---|
| Treatment | Rate | Obsd. | Exp. | Obsd. | Exp. | Obsd. | Exp. |
| 2 | 16 | | 0 | | 60 | | 25 |
| 2 | 62 | | 25 | | 98 | | 75 |
| atrazine | 62 | | 0 | | 5 | | 85 |
| 2 + atrazine | 16 + 62 | 37 | 25 | 0 | 70 | 62 | 100 |
| 2 + atrazine | 62 + 62 | 96 | 50 | 25 | 100 | 98 | 100 |

As can be seen from the results listed in Table F4, most of the observed results for weed species were greater/equal than expected, thereby showing synergistic/additive effect of Compound 2 and atrazine on all above weed species in Pre-emergence herbicidal application.

What is claimed is:

1. A compound selected from Formula 3, N-oxides and salts thereof,

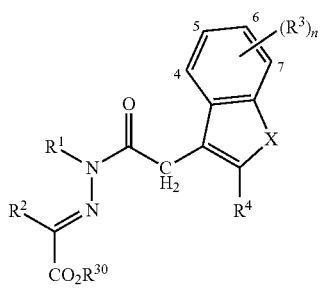

3 wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl; or a 5-, or 6-membered saturated or partially saturated heterocyclic ring containing ring members selected from carbon and up to 1 O and 1 S;

$R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio, $C_2$-$C_3$ alkoxycarbonyl; or phenyl optionally substituted by halogen, $C_1$-$C_4$ alkyl or $C_1$-$C_4$ haloalkyl;

X is O, S or $NR^5$; or

X is —C($R^6$)═C($R^7$)—, wherein the carbon atom bonded to $R^6$ is also bonded to the carbon atom bonded to $R^4$, and the carbon atom bonded to $R^7$ is also bonded to the phenyl ring moiety in Formula 3;

each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

$R^4$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;

$R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^5$ is H, $C_1$-$C_3$ alkyl or $C_1$-$C_3$ haloalkyl;

n is 0, 1, 2, 3 or 4; and $R^{30}$ is alkyl.

2. The compound of claim 1 wherein

X is O, S, —CH═CH—, —C($CH_3$)═CH—, —CH═CF—, —CH═CCl— or —CH═C($CH_3$)—;

$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl;

$R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy or $C_1$-$C_5$ alkylthio;

each $R^3$ is independently halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;
and
n is 0, 1, 2 or 3.

3. The compound of claim 2 wherein
X is —CH=CH—, —C(CH$_3$)=CH—, —CH=CF—, —CH=CCl— or —CH=C(CH$_3$)—;
$R^1$ is H, $C_1$-$C_7$ alkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl, $C_3$-$C_7$ alkylthioalkyl, $C_1$-$C_7$ alkoxy or benzyl;
$R^2$ is H, halogen, —CN, —CHO, $C_1$-$C_7$ alkyl, $C_2$-$C_4$ alkylcarbonyl, $C_2$-$C_7$ alkylcarbonyloxy, $C_4$-$C_7$ alkylcycloalkyl, $C_1$-$C_4$ alkylsulfinyl, $C_1$-$C_4$ alkylsulfonyl, $C_1$-$C_4$ alkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_2$-$C_7$ alkoxyalkyl or $C_1$-$C_7$ alkoxy;
each $R^3$ is independently halogen, —CN, $C_1$-$C_2$ alkyl, —CH=CH$_2$, —C≡CH, cyclopropyl, $C_1$-$C_2$ haloalkyl or $C_1$-$C_2$ alkoxy;
$R^4$ is halogen, —CN, $C_1$-$C_2$ alkyl, —CH=CH$_2$, —C≡CH, cyclopropyl, $C_1$-$C_2$ haloalkyl or $C_1$-$C_2$ alkoxy.

4. The compound of claim 3 wherein
X is —CH=CH—, —CH=CF—, —CH=CCl— or —CH=C(CH$_3$)—;
$R^1$ is methyl, ethyl, n-propyl or 2-methoxyethyl;
$R^2$ is H, methyl, ethyl, n-propyl, CF$_3$ or methoxy;
each $R^3$ is independently halogen, —CN, methyl, ethyl, —CH=CH$_2$, —C≡CH, cyclopropyl, CF$_3$, methoxy or ethoxy;
$R^4$ is halogen, —CN, methyl, ethyl, —CH=CH$_2$, —C≡CH, cyclopropyl, CF$_3$, methoxy or ethoxy;
n is 1 or 2; and
$R^{30}$ is methyl or ethyl.

5. The compound of claim 1 wherein
$R^{30}$ is Me, X is —CH=CH—, $R^1$ is Me, $R^2$ is Me, $R^4$ is Me, and n is 0;
$R^{30}$ is Me, X is —CH=CH—, $R^1$ is Me, $R^2$ is Me, $R^3$ is 5-Me, and $R^4$ is Me;
$R^{30}$ is Me, X is —CH=CH—, $R^1$ is Me, $R^2$ is Me, $R^3$ is 4,6-di-Me, and $R^4$ is Me;
$R^{30}$ is Me, X is —CH=CH—, $R^1$ is Me, $R^2$ is Me, $R^3$ is 5,7-di-Me, and $R^4$ is Me;
$R^{30}$ is Me, X is —CH=CH—, $R^1$ is Me, $R^2$ is Me, $R^4$ is Et, n is 0;
$R^{30}$ is Me, X is —CH=CH—, $R^1$ is Me, $R^2$ is Me, $R^3$ is 5-Me, and $R^4$ is Et;
$R^{30}$ is Me, X is —CH=CH—, $R^1$ is Me, $R^2$ is Me, $R^3$ is 4,6-di-Me, and $R^4$ is Et;
$R^{30}$ is Me, X is —CH=CH—, $R^1$ is Me, $R^2$ is Me, $R^3$ is 5,7-di-Me, and $R^4$ is Et;
$R^{30}$ is Me, X is —CH=CH—, $R^1$ is Me, $R^2$ is Et, $R^4$ is Me, and n is 0;
$R^{30}$ is Me, X is —CH=CH—, $R^1$ is Me, $R^2$ is Et, $R^3$ is 5-Me, and $R^4$ is Me;
$R^{30}$ is Me, X is —CH=CH—, $R^1$ is Me, $R^2$ is Et, $R^3$ is 4,6-di-Me, and $R^4$ is Me;
$R^{30}$ is Me, X is —CH=CH—, $R^1$ is Me, $R^2$ is Et, $R^3$ is 5,7-di-Me, and $R^4$ is Me;
$R^{30}$ is Me, X is —CH=CH—, $R^1$ is Me, $R^2$ is Et, $R^4$ is Et, n is 0;
$R^{30}$ is Me, X is —CH=CH—, $R^1$ is Me, $R^2$ is Et, $R^3$ is 5-Me, and $R^4$ is Et;
$R^{30}$ is Me, X is —CH=CH—, $R^1$ is Me, $R^2$ is Et, $R^3$ is 4,6-di-Me, and $R^4$ is Et; or
$R^{30}$ is Me, X is —CH=CH—, $R^1$ is Me, $R^2$ is Et, $R^3$ is 5,7-di-Me, and $R^4$ is Et.

6. The compound of claim 1 selected from
methyl 2-[2-[2-(2,5-dimethylbenzo[b]thien-3yl)acetyl]-2-methylhydrazinylidene]propanoate;
methyl 2-[2-[2-(2,5-dimethyl-3-benzofuranyl)acetyl]-2-methylhydrazinylidene]propanoate;
and 2,5,7-trimethyl-3-benzofuranacetic acid 2-(2-methoxy-1-methyl-2-oxoethylidene)-1-methylhydrazide.

7. A method for preparing a compound of Formula 1b

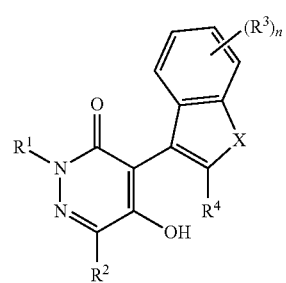

wherein
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl; or a 5-, or 6-membered saturated or partially saturated heterocyclic ring containing ring members selected from carbon and up to 1 O and 1 S;
$R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio, $C_2$-$C_3$ alkoxycarbonyl; or phenyl optionally substituted by halogen, $C_1$-$C_4$ alkyl or $C_1$-$C_4$ haloalkyl;
X is O, S or NR$^5$; or
X is —C(R$^6$)=C(R$^7$)—, wherein the carbon atom bonded to R$^6$ is also bonded to the carbon atom bonded to R$^4$, and the carbon atom bonded to R$^7$ is also bonded to the phenyl ring moiety in Formula 1b;
each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;
$R^4$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;

$R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^5$ is H, $C_1$-$C_3$ alkyl or $C_1$-$C_3$ haloalkyl; and n is 0, 1, 2, 3 or 4 comprising cyclizing the compound of Formula 3 in the presence of solvent and base

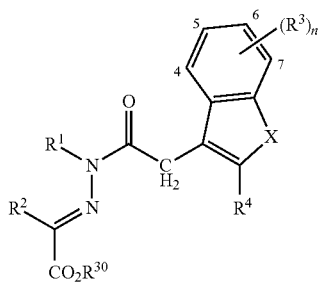

3 wherein
- $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl; or a 5-, or 6-membered saturated or partially saturated heterocyclic ring containing ring members selected from carbon and up to 1 O and 1 S;
- $R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio, $C_2$-$C_3$ alkoxycarbonyl; or phenyl optionally substituted by halogen, $C_1$-$C_4$ alkyl or $C_1$-$C_4$ haloalkyl;

X is O, S or $NR^5$; or

X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 3;

each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

$R^4$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;

$R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^5$ is H, $C_1$-$C_3$ alkyl or $C_1$-$C_3$ haloalkyl;

n is 0, 1, 2, 3 or 4; and $R^{30}$ is alkyl.

8. The method of claim 7 preparing a compound of Formula 1b wherein
- $R^1$ is methyl or ethyl;
- $R^2$ is methyl or ethyl;
- X is —C($R^6$)=C($R^7$)—;
- each $R^3$ is independently F, Cl, Br, methyl, ethyl or methoxy;
- $R^4$ is halogen, —CN, methyl, ethyl, —CH=$CH_2$, —C≡CH, cyclopropyl, $CF_3$, methoxy or ethoxy;
- $R^6$ and $R^7$ are H or halogen; and
- n is 0, 1 or 2 comprising cyclizing the compound of Formula 3 in the presence of solvent and base wherein
- $R^1$ is methyl or ethyl;
- $R^2$ is methyl or ethyl;
- X is —C($R^6$)=C($R^7$)—;
- each $R^3$ is independently F, Cl, Br, methyl, ethyl or methoxy;
- $R^4$ is halogen, —CN, methyl, ethyl, —CH=$CH_2$, —C≡CH, cyclopropyl, $CF_3$, methoxy or ethoxy;
- $R^6$ and $R^7$ are H or halogen;
- n is 0, 1 or 2; and
- $R^{30}$ is methyl or ethyl.

9. A method for preparing a compound of Formula 3

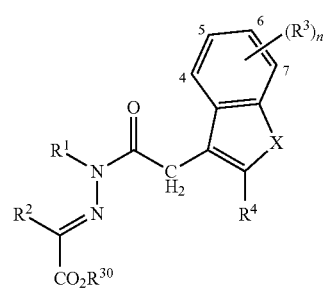

3 wherein
- $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl; or a 5-, or 6-membered saturated or partially saturated heterocyclic ring containing ring members selected from carbon and up to 1 O and 1 S;
- $R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio, $C_2$-$C_3$ alkoxycarbonyl; or phenyl optionally substituted by halogen, $C_1$-$C_4$ alkyl or $C_1$-$C_4$ haloalkyl;

X is O, S or $NR^5$; or

X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 3;

each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

$R^4$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;

$R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^5$ is H, $C_1$-$C_3$ alkyl or $C_1$-$C_3$ haloalkyl;

n is 0, 1, 2, 3 or 4; and $R^{30}$ is alkyl;

comprising reacting a hydrazine ester of Formula 4

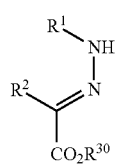

4 wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_3$-$C_7$ alkylthioalkyl, $C_1$-$C_7$ alkoxy, benzyl or phenyl; or a 5-, or 6-membered saturated or partially saturated heterocyclic ring containing ring members selected from carbon and up to 1 O and 1 S;

$R^2$ is H, halogen, —CN, —CHO, $C_1$-$C_7$ alkyl, $C_3$-$C_8$ alkylcarbonylalkyl, $C_3$-$C_8$ alkoxycarbonylalkyl, $C_2$-$C_4$ alkylcarbonyl, $C_2$-$C_7$ alkylcarbonyloxy, $C_4$-$C_7$ alkylcycloalkyl, $C_3$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_1$-$C_7$ alkoxy, $C_1$-$C_5$ alkylthio, $C_2$-$C_3$ alkoxycarbonyl; or phenyl optionally substituted by halogen, $C_1$-$C_4$ alkyl or $C_1$-$C_4$ haloalkyl; and $R^{30}$ is alkyl;

with an acid chloride of Formula 5

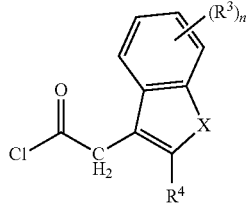

5 wherein

X is O, S or $NR^5$; or

X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 5;

each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

$R^4$ is halogen, —CN, $C_1$-$C_3$ alkyl, $C_2$-$C_4$ alkenyl, $C_2$-$C_4$ alkynyl, $C_3$-$C_4$ cycloalkyl, $C_1$-$C_3$ haloalkyl, $C_1$-$C_3$ alkoxy, $C_1$-$C_2$ haloalkoxy, $C_1$-$C_2$ alkylthio or $C_1$-$C_2$ haloalkylthio;

$R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

$R^5$ is H, $C_1$-$C_3$ alkyl or $C_1$-$C_3$ haloalkyl; and

A n is 0, 1, 2, 3 or 4 in the presence of solvent and base.

10. The method of claim 9 preparing a compound of Formula 3 wherein $R^1$ is methyl or ethyl;

$R^2$ is methyl or ethyl;

X is —C($R^6$)=C($R^7$)—;

each $R^3$ is independently F, Cl, Br, methyl, ethyl or methoxy;

$R^4$ is halogen, —CN, methyl, ethyl, —CH=$CH_2$, —C≡CH, cyclopropyl, $CF_3$, methoxy or ethoxy;

$R^6$ and $R^7$ are H or halogen;

n is 0, 1 or 2; and $R^{30}$ is methyl or ethyl comprising reacting a hydrazine ester of Formula 4 wherein $R^1$ is methyl or ethyl;

$R^2$ is methyl or ethyl; and $R^{30}$ is methyl or ethyl with an acid chloride of Formula 5 wherein X is —C($R^6$)=C($R^7$)—;

each $R^3$ is independently F, Cl, Br, methyl, ethyl or methoxy;

$R^4$ is halogen, —CN, methyl, ethyl, —CH=$CH_2$, —C≡CH, cyclopropyl, $CF_3$, methoxy or ethoxy;

$R^6$ and $R^7$ are H or halogen; and n is 0, 1 or 2 in the presence of solvent and base.

* * * * *